US009637795B2

(12) United States Patent
Agoulnik et al.

(10) Patent No.: US 9,637,795 B2

(45) Date of Patent: May 2, 2017

(54) METHODS AND COMPOSITIONS FOR PREDICTING RESPONSE TO ERIBULIN

(75) Inventors: Sergei I. Agoulnik, Andover, MA (US); Michael Chapman Byrne, Brookline, MA (US); Bruce A. Littlefield, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 146 days.

(21) Appl. No.: 14/001,737

(22) PCT Filed: Mar. 16, 2012

(86) PCT No.: PCT/US2012/029479

§ 371 (c)(1),
(2), (4) Date: May 2, 2014

(87) PCT Pub. No.: WO2012/129100

PCT Pub. Date: Sep. 27, 2012

(65) Prior Publication Data

US 2014/0235707 A1 Aug. 21, 2014

Related U.S. Application Data

(60) Provisional application No. 61/454,426, filed on Mar. 18, 2011.

(51) Int. Cl.

| | |
|---|---|
| *C12Q 1/68* | (2006.01) |
| *G01N 33/574* | (2006.01) |
| *A61K 31/35* | (2006.01) |

(52) U.S. Cl.

CPC ............ *C12Q 1/6886* (2013.01); *A61K 31/35* (2013.01); *G01N 33/57415* (2013.01); *C12Q 2600/106* (2013.01)

(58) Field of Classification Search

None

See application file for complete search history.

(56) References Cited

U.S. PATENT DOCUMENTS

| | | | |
|---|---|---|---|
| 4,683,202 A | 7/1987 | Mullis | |
| 5,075,216 A | 12/1991 | Innis et al. | |
| 5,445,934 A | 8/1995 | Fodor et al. | |
| 5,677,195 A | 10/1997 | Winkler et al. | |
| 5,744,305 A | 4/1998 | Fodor et al. | |
| 5,770,722 A | 6/1998 | Lockhart et al. | |
| 5,800,992 A | 9/1998 | Fodor et al. | |
| 5,854,033 A | 12/1998 | Lizardi | |
| 5,874,219 A | 2/1999 | Rava et al. | |
| 6,020,135 A | 2/2000 | Levine et al. | |
| 6,033,860 A | 3/2000 | Lockhart et al. | |
| 6,040,138 A | 3/2000 | Lockhart et al. | |
| 6,214,865 B1 | 4/2001 | Littlefield et al. | |
| 6,344,316 B1 | 2/2002 | Lockhart et al. | |
| 6,469,182 B1 | 10/2002 | Littlefield et al. | |
| 6,653,341 B1 | 11/2003 | Littlefield et al. | |
| 2006/0104984 A1 | 5/2006 | Littlefield et al. | |
| 2006/0154312 A1* | 7/2006 | Agoulnik ............ | A61K 31/353 435/7.23 |
| 2011/0217297 A1* | 9/2011 | Kao ................ | G01N 33/57415 424/133.1 |

FOREIGN PATENT DOCUMENTS

| | | |
|---|---|---|
| WO | WO-94/16101 A1 | 7/1994 |
| WO | WO-2005/032347 A2 | 4/2005 |

OTHER PUBLICATIONS

Nishidate et al (International J Oncology, 2004, 25:797-819).*

Hu et al (Mol Cancer Res, 2009, 7:511-522).*

Addou-Klouche et al (Molecular Cancer, 2010, 9:213, internet pp. 1-13).*

Jezequel et al (Breast Cancer Res treat, 2009, 116:509-520).*

Derso et al (PLoS One, 2014, 9:el 06131).*

GeneAnnot website probesets for TUBB6, printed Nov. 201.*

GeneAnnot website probesets for AIB3, printed Nov. 201.*

Cortes et al (The Lancet, Mar. 12, 2011, 377:914-923).*

GeneAnnot website probeset for NMU, printed Jun. 2016.*

BreastCancer.org (published Nov. 15, 2010, http://www.breastcancer.org/research-news/20101115b, internet pp. 1-2).*

Adam B.L., et al., "Serum Protein Fingerprinting with a Pattern-matching Algorithm Distinguishes Prostate Cancer for Bening Prostate Hyperplasia and Helathy Men," Cancer Res, vol. 2, pp. 3609-3614, 2002.

Agoulnik S. et al., "Sensitivity to halichondrin analog E7839 and herniasterlin analog E7974 correlates with beta.III tubulin isotype expression in human breast cancer cell lines," Journal of Clinical Oncology, vol. 23, pp. 1-2, 2005.

Aicher T.D. et al., "Total Synthesis of Halicondrin B and Norhalichondrin B," J. Am. Chem. Soc., vol. 114, pp. 3162-3164, 1992.

Barany Francis, "Genetic disease detection and DNA amplification using cloned thermostable ligase," Proc. Natl. Acad. Sci. USA, vol. 88, pp. 189-193, 1991.

Cigler T. et al., "Eribulin mesylate for the treatment of breast cancer," Expert Opinion on Pharmacotherapy, vol. 11, No. 9, pp. 1587-1593, Jun. 2010.

Cortes J. et al, "Phase II study of the halichondrin B analog eribulin mesylate in patients with locally advanced or metastatic breast cancer previously treated with an anthracycline, a taxane, and a capecitabine," Journal of Clincial Oncology, vol. 28, No. 25, pp. 3922-3928, 2010.

Cortes J. et al., "Eribulin monotherapy versus treatment of physician's choice in patients with metastatic breast cancer (Embrace): a phase 3 open-label randomised study," The Lancet, vol. 377, No. 9769, pp. 914-923, 2011.

(Continued)

*Primary Examiner* — Laura B Goddard

(74) *Attorney, Agent, or Firm* — McCarter & English, LLP; Maria Laccotripe Zacharakis; Maneesh Gulati

(57) ABSTRACT

The invention provides methods for predicting the efficacy of eribulin, an analog thereof, or a pharmaceutically acceptable salt thereof (e.g., eribulin mesylate), in the treatment of a subject suffering from breast cancer by determining the level of particular biomarkers in a sample derived from the subject.

20 Claims, 4 Drawing Sheets

(56) References Cited

OTHER PUBLICATIONS

Engelke D.R., et al., "Direct sequencing of enzymatically amplified human genomic DNA," Proc. Natl. Acad. Sci. USA, vol. 85, pp. 544-548, 1988.
Griffin H.G. et al., "DNA Sequencing Recent Innovations and Future Trends," vol. 38, pp. 147159, 1993.
Guatelli J.C., et al., "Isothermal, in vitro amplification of nucleic acids by a multienzyme reaction modeled after retroviral replication," *Proc. Natl. Acad. Sci. USA*, vol. 87, pp. 1874-1878, 1990.
Kim DS et al., "New Syntheses of E7389 C14-C35 and Halichondrin C14-C38 Building Blocks: Double-Inversion Approach," J. Am. Chem. Soc., vol. 131, pp. 15636-15641, 2009.
Kuznetzsov G, et al., "Antiproliferative effects of halichondrin B analog eribulin mesylate (E7389) against paclitaxel-resistant human cancer cells in vitro," AAR-NCI EORTC International Conference; Molecular Targets and Therapeutics, pp. 1-2, 2007.
Kwoh D.Y. et al., "Transcript-based amplification system and detection of amplified human immunodefiency virus type 1 with a bead-based sandwich hybridization format," *Proc. Natl. Acad. Sci. USA*, vol. 86, pp. 1173-1177, 1989.
Laronga C. et al., "Seldi-Tof serum profiling for prognostic and diagnostic classification of breast cancers," Disease Markers, vol. 19, pp. 229-238, 2003.
Li J. et al., "Proteomics and Bioinformatics Approaches for Identification of Serum Biomarkers to Detect Breast Cancer," Clinical Chemistry, vol. 48, No. 8, pp. 1296-1304, 2002.
Lizardi P.M. et al., "Exponential Amplification of Recombinant-RNA Hybridization probess," Bio/Technology, vol. 6, pp. 1197-1202, 1988.
Maxam A.M. and Gilbert W., "A new method for sequencing DNA," Proc. Natl. Acad. Sci. USA, vol. 74, No. 2, pp. 560-564, 1977.
Melton D.A. et al., "Efficient in vitro synthesis of biologically active RNA and RNA hybridization probes from plasmids containing a bacteriophage SP6 promoter," *Nucleic Acids Research*, vol. 12, No. 8, pp. 7035-7056, 1984.
Petricoin E.F., et al., "Use of proteomic patterns in serum to identify ovarian cancer," vol. 359, pp. 572-575, 2002.
Sanger F. et al., "DNA sequencing with chain-terminating inhibitors," Proc. Natl. Acad. Sci. USA, vol. 74, No. 12, pp. 5463-5467, 1977.
Tolson J. et al., "Serum protein profiling by SELDI mass spectromertry: detection of multiple variants of serum amyloid alpha in renal cancer patients," Laboratory Investigation, vol. 84, pp. 845-856, 2004.
Twelves C. et al., "Phase III trials of eribulin mesylate (E7389) in extensively pretreated patients with locally recurrent or metastatic breast cancer," Clinical Breast Cancer, vol. 10, No. 2, pp. 160-163, 2010.
Whitehurst A.W. et al., "Synthetic lethal screen identification of chemosensitizer loci in cancer cells," Nature, vol. 446, pp. 815-819, 2007.
Wong C. et al., "Chracterization of β-thalassaemia mutations using direct genomic sequencing of amplified single copy DNA," Nature, vol. 330, No. 26, pp. 384-386, 1987.
Wright, G.L. Jr., "SELDI proteinchip MS: a platform for biomaker discovery and cancer diagnosis," Expert Revoew of Molecular Diagnostics, vol. 2, No. 6, pp. 549-563, 2002.
Xiao Z. et al., "Quantitation of Serum Prostate-specific Membrane Antigen by a Novel Protein Biochip Immunoassay Discriminates Bening from Malignant Prostate Disease," Cancer Research, vol. 61, pp. 6029-6033, 2001.
Zhang L. et al., "Salivary Transcriptomic Biomarkers for Detection of Resectable Pancreatic Cancer," Gastroenterology, vol. 128, No. 3, pp. 949-957, 2010.
International Search Report and Written Opinion issued in International Application PCT/US2012/029479, dated Jul. 18, 2012.
International Preliminary Report on Patentability issued in International Application PCT/US2012/029479, dated Oct. 3, 2013.

* cited by examiner

Pre-Clinical Biomarker Studies

RNAi Screen In Breast Cancer Lines

Whole Human Genome RNAi Screen

Pre-Clinical Biomarker Studies
RNAi Screen In Breast Cancer Lines
Screen
1. Fold change compared to negative control (sensitization)
2. P value (<0.05)
18,500 siRNAs
364 primary hits
240 siRNAs
Excluded:
ORFs, hypothetical proteins,
zinc-finger proteins, others Pre-Clinical Biomarker Studies RNAi Screen In Breast Cancer Lines

Confirmation Assays

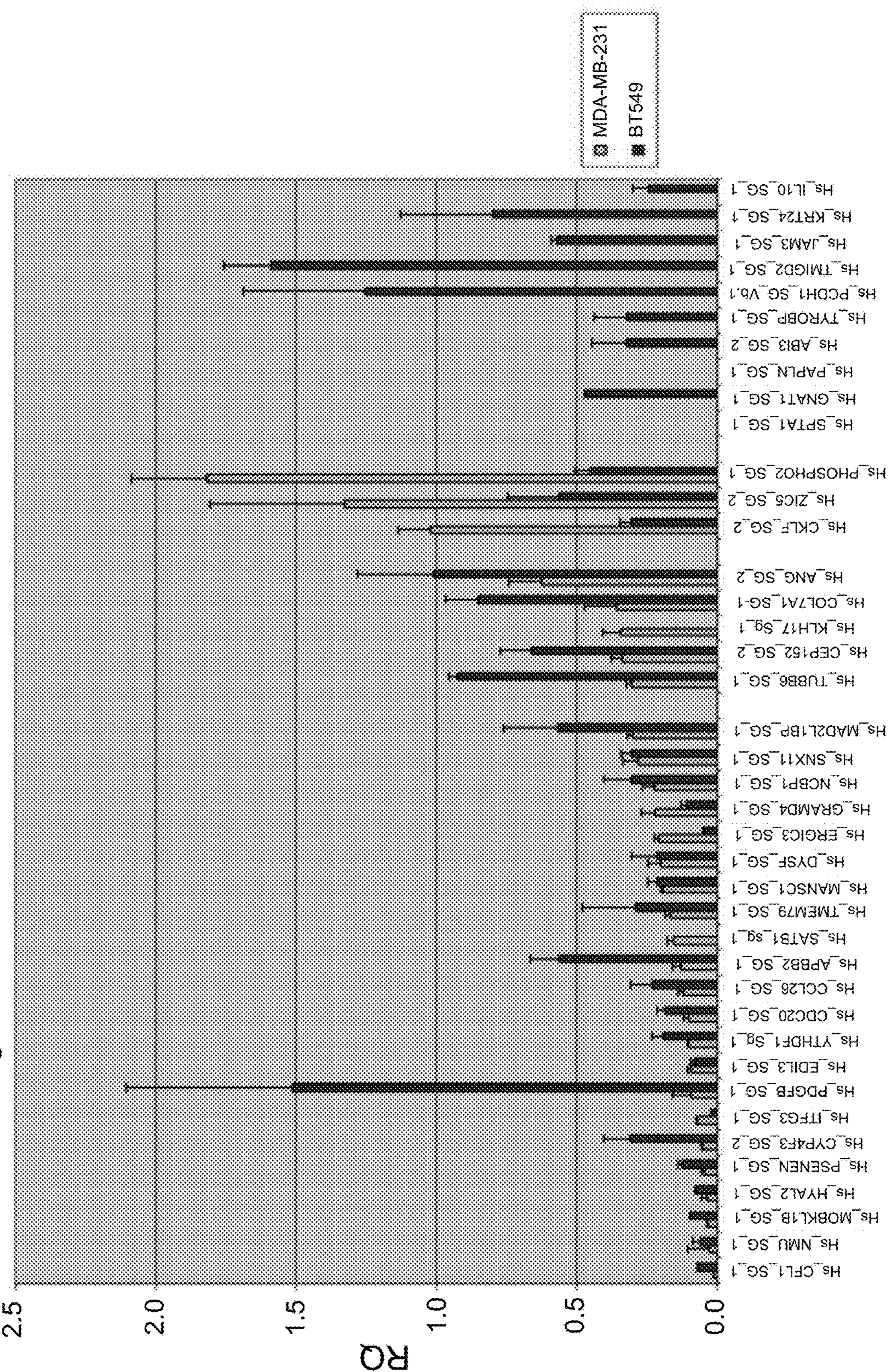
FIGURE 4
On-Target effects in MDA-MB-231 and BT549 cells
MDA-MB-231
BT549
RQ
0.0
0.5
1.0
1.5
2.0
2.5
Hs_CFL1_SG_1
Hs_NMU_SG_1
Hs_MOBKL1B_SG_1
Hs_HYAL2_SG_1
Hs_PSENEN_SG_1
Hs_CYP4F3_SG_2
Hs_ITFG3_SG_1
Hs_PDGFB_SG_1
Hs_EDIL3_SG_1
Hs_YTHDF1_Sg_1
Hs_CDC20_SG_1
Hs_CCL26_SG_1
Hs_APBB2_SG_1
Hs_SATB1_sg_1
Hs_TMEM79_SG_1
Hs_MANSC1_SG_1
Hs_DYSF_SG_1
Hs_ERGIC3_SG_1
Hs_GRAMD4_SG_1
Hs_NCBP1_SG_1
Hs_SNX11_SG_1
Hs_MAD2L1BP_SG_1
Hs_TUBB6_SG_1
Hs_CEP152_SG_2
Hs_KLH17_Sg_1
Hs_COL7A1_SG-1
Hs_ANG_SG_2
Hs_CKLF_SG_2
Hs_ZIC5_SG_2
Hs_PHOSPHO2_SG_1
Hs_SPTA1_SG_1
Hs_GNAT1_SG_1
Hs_PAPLN_SG_1
Hs_ABI3_SG_2
Hs_TYROBP_SG_1
Hs_PCDH1_SG_Vb.1
Hs_TMIGD2_SG_1
Hs_JAM3_SG_1
Hs_KRT24_SG_1
Hs_IL10_SG_1

METHODS AND COMPOSITIONS FOR PREDICTING RESPONSE TO ERIBULIN

RELATED APPLICATIONS

This application is a 35 U.S.C. §371 national stage filing of International Application No. PCT/US2012/029479, filed Mar. 16, 2012, which claims priority to U.S. Provisional Application No. 61/454,426, filed Mar. 18, 2011, the entire contents of each of which are hereby incorporated by reference herein.

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches involve the administration of chemotherapeutic drugs that interfere with the growth of rapidly dividing cells, such as cancer cells.

Halichondrin B is a structurally complex, macrocyclic compound that was originally isolated from the marine sponge *Halichondria okadai*, and subsequently was found in *Axinella* sp., *Phakellia carteri*, and *Lissodendoryx* sp. A total synthesis of halichondrin B was published in 1992 (Aicher et al., *J. Am. Chem. Soc.* 114:3162-3164, 1992). Halichondrin B has been shown to inhibit tubulin polymerization, microtubule assembly, beta-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

In particular, eribulin mesylate, a Halichondrin B analog, has been developed as an anticancer drug. Recently, eribulin mesylate was approved for the treatment of patients with metastatic breast cancer who have previously received at least two chemotherapeutic regimens for the treatment of metastatic disease, wherein prior therapy may have included an anthracycline and/or a taxane in either the adjuvant or metastatic setting. The ability to predict in advance of treatment whether a cancer patient is likely to be responsive to an anti-cancer agent can guide selection of appropriate treatment, and is beneficial to patients. Accordingly, there is a need for methods for and compositions useful in, assessing or predicting responsiveness to eribulin in patients having cancer and, in particular, breast cancer.

SUMMARY OF THE INVENTION

The invention is based, at least in part, on the observation that a low level of expression, e.g., the absence of expression, of the biomarkers identified herein is indicative of responsiveness to eribulin, an analog thereof, or a pharmaceutically acceptable salt thereof (e.g., eribulin mesylate). Specifically, the absence of expression or a low level of expression of these biomarkers, including, for example, one or more of those biomarkers set forth in Table 1, in a subject is indicative that the subject will be responsive to treatment with eribulin, an analog thereof, or a pharmaceutically acceptable salt thereof (e.g., eribulin mesylate).

Accordingly, in one aspect, the present invention provides a method for determining whether eribulin, an analog thereof, or a pharmaceutically acceptable salt thereof (e.g., eribulin mesylate), may be used to treat a subject having breast cancer, by assaying a sample derived from the subject to determine the level of expression in the sample of a biomarker selected from the group of biomarkers listed in Table 1, wherein a low level of expression of the biomarker is indicative that eribulin, an analog thereof, or a pharmaceutically acceptable salt thereof (e.g., eribulin mesylate), will be effective in treating the subject having breast cancer. In another aspect, the present invention provides a method for determining whether eribulin, an analog thereof, or a pharmaceutically acceptable salt thereof (e.g., eribulin mesylate), may be used to treat a subject having breast cancer, by determining the level of expression of a biomarker selected from the group of biomarkers listed in Table 1 in a sample derived from the subject, wherein a low level of expression of the biomarker is indicative that eribulin, an analog thereof, or a pharmaceutically acceptable salt thereof (e.g., eribulin mesylate), will be effective in treating the subject having breast cancer. In a further aspect, the present invention provides a method for predicting whether eribulin, an analog thereof, or a pharmaceutically acceptable salt thereof (e.g., eribulin mesylate), may be used to treat a subject having breast cancer, by determining the level of expression of a biomarker selected from the group of biomarkers listed in Table 1 in a sample derived from the subject, and predicting that eribulin, an analog thereof, or a pharmaceutically acceptable salt thereof (e.g., eribulin mesylate), will be effective in treating a subject having breast cancer when there is a low level of expression of the biomarker in the sample. In one embodiment of the foregoing aspects of the invention, the methods may further include obtaining a sample from a subject.

In yet another aspect, the present invention provides a method for determining the sensitivity of a breast tumor, for example, derived from a subject having breast cancer, to treatment with eribulin, an analog thereof, or a pharmaceutically acceptable salt thereof (e.g., eribulin mesylate), by determining the level of expression of a biomarker selected from the group of biomarkers listed in Table 1 in the tumor, wherein a low level of expression of the biomarker in the tumor indicates that the tumor is sensitive to treatment with eribulin, or an analog thereof. In yet another aspect, the present invention provides a method for determining the sensitivity of a breast tumor, for example, derived from a subject having breast cancer, to treatment with eribulin, an analog thereof, or a pharmaceutically acceptable salt thereof (e.g., eribulin mesylate), by determining the level of expression of a biomarker selected from the group of biomarkers listed in Table 1 in the tumor, and identifying the tumor as being sensitive to treatment with eribulin, an analog thereof, or a pharmaceutically acceptable salt thereof (e.g., eribulin mesylate), when the biomarker is expressed in the tumor at a low level.

In further aspects of the invention, methods are provided for treating a subject having breast cancer. The methods include identifying a subject having breast cancer in which a biomarker selected from the group of biomarkers listed in Table 1 is expressed at a low level, and administering a therapeutically effective amount of eribulin, an analog thereof, or a pharmaceutically acceptable salt thereof (e.g., eribulin mesylate), to the subject. In yet a further aspect, the present invention provides methods of treating a subject having breast cancer, by assaying a sample derived from the subject to determine the level of expression in the sample of a biomarker selected from the group of biomarkers listed in Table 1, and administering a therapeutically effective amount of eribulin, an analog thereof, or a pharmaceutically acceptable salt thereof (e.g., eribulin mesylate), to the subject when a low level of expression of the biomarker is detected in the sample. In one embodiment of the foregoing aspects of the invention, the methods may further include obtaining a sample from a subject.

In further aspects of the invention, methods are provided for treating a subject having breast cancer that is sensitive to eribulin, an analog thereof, or a pharmaceutically acceptable salt thereof. The methods include identifying a subject having breast cancer that is sensitive to eribulin, an analog thereof, or a pharmaceutically acceptable salt thereof, (e.g., a breast cancer in which a biomarker selected from the group of biomarkers listed in Table 1 is expressed at a low level), and administering a therapeutically effective amount of eribulin, an analog thereof, or a pharmaceutically acceptable salt thereof (e.g., eribulin mesylate), to the subject. In yet a further aspect, the present invention provides methods of treating a subject having breast cancer that is sensitive to eribulin, an analog thereof, or a pharmaceutically acceptable salt thereof, by assaying a sample derived from the subject to determine the level of expression in the sample of a biomarker selected from the group of biomarkers listed in Table 1, and administering a therapeutically effective amount of eribulin, an analog thereof, or a pharmaceutically acceptable salt thereof (e.g., eribulin mesylate), to the subject when a low level of expression of the biomarker is detected in the sample. In one embodiment of the foregoing aspects of the invention, the methods may further include obtaining a sample from a subject.

In various embodiments, the subject has not been previously treated with eribulin, an analog thereof, or a pharmaceutically acceptable salt thereof (e.g., eribulin mesylate). Alternatively, the subject has been previously treated with eribulin, an analog thereof, or a pharmaceutically acceptable salt thereof. In certain embodiments, the breast cancer is an Estrogen Receptor (ER) negative breast cancer and/or a Progesterone Receptor (PR) negative breast cancer and/or a Her-2 negative breast cancer.

In various embodiments, the level of expression of at least 2, at least 3, at least 4 or at least 5 biomarkers selected from the group of biomarkers listed in Table 1 is determined.

In particular embodiments, a predictive gene signature comprising a sub-combination of 2 or more biomarkers selected from the group of biomarkers listed in Table 1 is used. In various embodiments, the level of expression of at least 2, at least 3, at least 4 or at least 5 biomarkers selected from the group of biomarkers listed in Table 1 is determined. For example, the predictive gene signature may include at least 2 biomarkers, e.g., DYSF and EDIL3; GNAT1 and ERGIC3; KRT24 and PAPLN; MANSC1 and PDGFB; PCDH1 and PDGFB; or PHOSPHO2 and PSENEN. In another embodiment, the predictive gene signature may include at least 3 biomarkers, e.g., COL7A1, YTHDF1 and ZIC5; CKLF, IL10 and TUBB6; CDC20, CFL1 and TMEM79; HYAL2, NCBP1 and SNX11; or CEP152, NCBP1 and SATB1. In another embodiment, the predictive gene signature may include at least 4 biomarkers, e.g., APBB2, CCL26, PSENEN and SATB1; ANG, JAM3, KLHL17 and PAPLN; ITFG3, MAD2L1BP, NMU and PDGFB; SPTA1, TYROBP, SNX11 and PSENEN; GRAMD4, GNAT1, TMIGD2 and YTHDF1; or GRAMD4, HYAL2, PHOSPHO2 and TUBB6. In another embodiment, the predictive gene signature may include at least 5 biomarkers, e.g., CCL26, CDC20, ERGIC3, EDIL3 and PCDH1; DYSF, NMU, PHOSPHO2, PSENEN and SNX11; APBB2, CKLF, CYP4F3, TUBB6 and YTHDF1; or CEP152, MAD2L1BP, SPTA1, TMEM79 and ZIC5.

In particular embodiments, the predictive gene signature may include 2 or more of biomarkers ABI3, ANG, APBB2, CCL26, CDC20, CEP152, CFL1, CKLF, COL7A1, CYP4F3, DYSF, GNAT1, GRAMD4, HYAL2, IL10, ITFG3, JAM3, KLHL17, KRT24, MAD2L1BP, MANSC1, MOBKL1B, NCBP1, NMU, PCDH1, PHOSPHO2, SPTA1, TMIGD2, TYROBP, ZIC5, ERGIC3, PDGFB, PSENEN, SATB1, SNX11, TMEM79 and YTHDF1, e.g., ABI3 and ANG; APBB2 and CCL26; GNAT1 and GRAMD4; IL10 and ITFG3; MACSC1 and MOBKL1B; NMU and PCDH1; or TYROBP and ZIC5. In other embodiments, the predictive gene signature includes at least 3 of the previously recited biomarkers, e.g., ABI3, ANG and APBB2; CCL26, CKLF and COL7A1; DYSF, GNAT1 and HYAL2; JAM3, KLHL17 and KRT24; NCBP1, NMU and PCDH1; SPTA1, TMIGD2 and TYROBP; or ZIC5, MAD2L1BP and CDC20. In other embodiments, the predictive gene signature includes at least 4 of the previously recited biomarkers, e.g., ABI3, ANG, APBB2 and CCL26; CEP152, CFL1, CKLF and COL7A1; KRT24, MANSC1, MOBKL1B and SPTA1; TYROBP, TMIGD2, PHOSPHO2 and NMU; ABI3, GNATI, KLHL17 and SPTA1; or CEP152, HYAL2, PCDH1 and TMIGD2. In yet further embodiments, the predictive gene signature includes at least 5 of the previously recited biomarkers, e.g., CKLF, COL7A1, GRAMD4, JAM3 and PCDH1; APBB2, CEP152, DYSF, IL10 and TYROBP; CYP4F3, HYAL2, ITFG3, KLHL17 and KRT24; NCBP1, SPTA1, TMIGD2, IL10 and JAM3; or CCL26, PHOSPHO2, SPTA1, TMIGD2 and ZIC5.

In other embodiments, the predictive gene signature may include 2 or more of biomarkers ERGIC3, PDGFB, PSENEN, SATB1, SNX11, TMEM79 or YTHDF1, or any sub-combination thereof, e.g., ERGIC3 and PDGFB; ERGIC3 and PSENEN; ERGIC3 and SATB1; ERGIC3 and SNX11; ERGIC3 and TMEM79; ERGIC3 and YTHDF1; PDGFB and PSENEN; PDGFB and SATB1; PDGFB and SNX11; PDGFB and TMEM79; PDGFB and YTHDF1; PSENEN and SATB1; PSENEN and SNX11; PSENEN and TMEM79; PSENEN and YTHDF1; SATB1 and SNX11; SATB1 and TMEM79; SATB1 and YTHDF1; SNX11 and TMEM79; SNX11 and YTHDF1; or TMEM79 and YTHDF1. In other embodiments, the predictive gene signature includes at least 3 biomarkers, for example, ERGIC3, PDGFB and PSENEN; SATB1, SNX11 and TMEM79; SNX11, TMEM79 and YTHDF1; or ERGIC3, PDGFB and SATB1. In further embodiments, the predictive gene signature includes at least 4 biomarkers, for example, ERGIC3, PDGFB, PSENEN and SATB1; SNX11, TMEM79, YTHDF1 and ERGIC3; or ERGIC3, PDGFB, PSENEN and YTHDF1. In further embodiments, the predictive gene signature includes at least 5 biomarkers, for example, ERGIC3, PDGFB, PSENEN, SATB1 and SNX11; ERGIC3, PDGFB, PSENEN, SATB1 and TMEM79; or PSENEN, SATB1, SNX11, TMEM79 and YTHDF1. In yet further embodiments, the predictive gene signature includes at least 6 biomarkers, for example, ERGIC3, PDGFB, PSENEN, SATB1, SNX11 and TMEM79; PDGFB, PSENEN, SATB1, SNX11, TMEM79 and YTHDF1; or ERGIC3, PSENEN, SATB1, SNX11, TMEM79 and YTHDF1. In yet another embodiment, the predictive gene signature includes 7 biomarkers, for example, ERGIC3, PDGFB, PSENEN, SATB1, SNX11, TMEM79 and YTHDF1.

In various embodiments, the biomarker is not one or more of SPTA1, PAPLN, PCDH1, TMIGD2 and/or KRT24. In a particular embodiment, the biomarker is not SPTA1, PAPLN, PCDH1, TMIGD2 and KRT24. In one embodiment, the biomarker is not SPTA1. In another embodiment, the biomarker is not PAPLN. In another embodiment, the biomarker is not PCDH1. In another embodiment, the biomarker is not TMIGD2. In yet another embodiment, the biomarker is not KRT24.

In particular embodiments, the predictive gene signature may include 2 or more of biomarkers ABI3, ANG, APBB2, CCL26, CDC20, CEP152, CFL1, CKLF, COL7A1, CYP4F3, DYSF, GNAT1, GRAMD4, HYAL2, IL10, ITFG3, JAM3, KLHL17, MAD2L1BP, MANSC1, MOBKL1B, NCBP1, NMU, PHOSPHO2, TYROBP, ZIC5, ERGIC3, PDGFB, PSENEN, SATB1, SNX11, TMEM79, YTHDF1, EDIL3 and TUBB6, e.g., ABI3 and ANG; GRAMD4 and HYAL2; NMU and PHOSPHO2; ZIC5 and PSENEN; or SNX11 and MOBKL1B. In other embodiments, the predictive gene signature includes at least 3 of the previously recited biomarkers, e.g., APBB2, CDC20 and CKLF; COL7A1, DYSF and GNAT1; NCBP1, SATB1 and EDIL3; PSENEN, DYSF and GNAT1; MANSC1, ZIC5 and CFL1; or CKLF, GRAMD4 and NMU. In other embodiments, the predictive gene signature includes at least 4 of the previously recited biomarkers, e.g., ANG, CCL26, CEP152 and JAM3; APBB2, CYP4F3, ITFG3 and TYROBP; CYP4F3, MANSC1, PDGFB and YTHDF1; TUBB6, DYSF, PHOSPHO2 and CDC20; or CKLF, KLHL17, HYAL2 and ZIC5. In yet further embodiments, the predictive gene signature includes at least 5 of the previously recited biomarkers, e.g., IL10, CEP152, COL7A1, TYROBP and ERGIC3; TMEM79, SNX11, PSENEN, GNAT1 and GRAMD4; JAM3, SNX11, KLHL17, MOBKL1B and ERGIC3; or NMU, PHOSPHO2, PDGFB, CFL1 and ANG.

In various methods and or kits of the invention, the biomarker is not ABI3, is not ANG, is not APBB2, is not CCL26, is not CDC20, is not CEP152, is not CFL1, is not CKLF, is not COL7A1, is not CYP4F3, is not DYSF, is not GNAT1, is not GRAMD4, is not HYAL2, is not IL10, is not ITFG3, is not JAM3, is not KLHL17, is not KRT24, is not MAD2L1BP, is not MANSC1, is not MOBKL1B, is not NCBP1, is not NMU, is not PCDH1, is not PHOSPHO2, is not SPTA1, is not TMIGD2, is not TYROBP, is not ZIC5, is not ERGIC3, is not PDGFB, is not PSENEN, is not SATB1, is not SNX11, is not TMEM79, is not EDIL3, is not PAPLN, is not TUBB6 and/or is not YTHDF1.

In certain embodiments, the biomarker is not expressed at a detectable level. In another embodiment, the biomarker is expressed at a low level as compared to a control. Expression can be determined directly or indirectly by any suitable method. In certain embodiments, the level of expression of the biomarker is determined at the nucleic acid level using any suitable method. For example, the level of expression of the biomarker can be determined by detecting cDNA, mRNA or DNA. In particular embodiments, the level of expression of the biomarker is determined by using a technique selected from the group consisting of polymerase chain reaction (PCR) amplification reaction, reverse-transcriptase PCR analysis, quantitative reverse-transcriptase PCR analysis, Northern blot analysis, RNAase protection assay, digital RNA detection/quantitation (e.g., nanoString) and combinations or sub-combinations thereof.

In certain embodiments, the level of expression of the biomarker can be determined by detecting miRNA. Specifically, mRNA expression can be assessed indirectly by assessing levels of miRNA, wherein an elevated level of an miRNA which controls the expression of an mRNA is indicative of a low level of expression of the mRNA encoding the biomarker.

In other embodiments, the level of expression of the biomarker is determined at the protein level using any suitable method. For example, the presence or level of the protein can be detected using an antibody or antigen binding fragment thereof, which specifically binds to the protein. In particular embodiments, the antibody or antigen binding fragment thereof is selected from the group consisting of a murine antibody, a human antibody, a humanized antibody, a bispecific antibody, a chimeric antibody, a Fab, Fab', $F(ab')_2$, ScFv, SMIP, affibody, avimer, versabody, nanobody, and a domain antibody, or an antigen binding fragment of any of the foregoing. In particular embodiments, the antibody or antigen binding portion thereof is labeled, for example, with a label selected from the group consisting of a radio-label, a biotin-label, a chromophore-label, a fluorophore-label, and an enzyme-label. In certain embodiments, the level of expression of the biomarker is determined by using a technique selected from the group consisting of an immunoassay, a western blot analysis, a radioimmunoassay, immunofluorimetry, immunoprecipitation, equilibrium dialysis, immunodiffusion, electrochemiluminescence immunoassay (ECLIA), ELISA assay, immunopolymerase chain reaction and combinations or sub-combinations thereof. In particular embodiments, the immunoassay is a solution-based immunoassay selected from the group consisting of electrochemiluminescence, chemiluminescence, fluorogenic chemiluminescence, fluorescence polarization, and time-resolved fluorescence. In other embodiments, the immunoassay is a sandwich immunoassay selected from the group consisting of electrochemiluminescence, chemiluminescence, and fluorogenic chemiluminescence. Other assays which rely on agents capable of detecting the protein, such as those relying upon a suitable binding partner or enzymatic activity, can also be used (e.g., use of a ligand to detect a receptor molecule).

Samples can be obtained from a subject by any suitable method, and may optionally have undergone further processing step(s) (e.g., freezing, fractionation, fixation, guanidine treatment, etc). Any suitable sample derived from a subject can be used, such as any tissue (e.g., biopsy), cell, or fluid, as well as any component thereof, such as a fraction or extract. In various embodiments, the sample is a fluid obtained from the subject, or a component of such a fluid. For example, the fluid can be blood, plasma, serum, sputum, lymph, cystic fluid, nipple aspirate, urine, or fluid collected from a biopsy (e.g., lump biopsy). In other embodiments, the sample is a tissue or component thereof obtained from the subject. For example, the tissue can be tissue obtained from a biopsy (e.g., lump biopsy), breast tissue, connective tissue, and/or lymphatic tissue. In a particular embodiment, the tissue is breast tissue, or a component thereof (e.g., cells collected from the breast tissue). In a particular embodiment, the component of the breast tissue are breast tissue cells. In another embodiment, the component of the breast tissue are circulating breast tumor cells.

In one embodiment, the subject is a human.

In another aspect, the present invention provides a kit for predicting whether eribulin, an analog thereof, or a pharmaceutically acceptable salt thereof (e.g., eribulin mesylate), may be used to treat a subject having breast cancer, including reagents for determining the level of expression of a biomarker selected from the group of biomarkers listed in Table 1; and instructions for use of the kit to predict whether eribulin, an analog thereof, or a pharmaceutically acceptable salt thereof (e.g., eribulin mesylate), may be used to treat a subject having breast cancer. For example, the reagent for determining the level of expression of the biomarker can be a probe for identifying a null mutation in the biomarker. The reagent for determining the level of expression of the biomarker can be a probe for amplifying and/or detecting the biomarker. In yet another embodiment, the reagent for determining the level of expression of the biomarker can be an antibody, for example, an antibody specific for the product of the expression of the wild type or null mutant version of the biomarker.

In a particular embodiment, the kit further includes reagents for obtaining a biological sample from a subject. In another embodiment, the kit includes a control sample.

In another aspect, the present invention provides methods for determining whether eribulin, an analog thereof, or a pharmaceutically acceptable salt thereof (e.g., eribulin mesylate), may be used to treat a subject having breast cancer by determining and/or identifying whether the subject carries at least one gene, selected from the group of biomarkers set forth in Table 1, which contains a null mutation. In another aspect, the present invention provides methods for predicting whether eribulin, an analog thereof, or a pharmaceutically acceptable salt thereof (e.g., eribulin mesylate), may be used to treat a subject having breast cancer by assaying a sample derived from the subject to determine whether the subject carries at least one gene, selected from the group of biomarkers set forth in Table 1, which contains a null mutation. In a further aspect, the present invention provides methods for determining the sensitivity of a breast tumor to treatment with eribulin, an analog thereof, or a pharmaceutically acceptable salt thereof by determining and/or identifying whether said tumor is characterized by at least one gene, selected from the group of biomarkers set forth in Table 1, which contains a null mutation. In yet another aspect, the present invention is directed to methods for treating a subject having breast cancer with eribulin, an analog thereof, or a pharmaceutically acceptable salt thereof by identifying whether at least one gene, selected from the group of biomarkers set forth in Table 1, which contains a null mutation and administering a therapeutically effective amount of eribulin, an analog thereof, or a pharmaceutically acceptable salt thereof (e.g., eribulin mesylate) to the subject.

BRIEF DESCRIPTION OF THE DRAWINGS

FIG. 4 depicts the results of the QuantiTect SYBR Assays to determine the relative quantities of cDNAs after treatment with siRNA as set forth in Example 1.

DETAILED DESCRIPTION OF THE INVENTION

Figure 1:
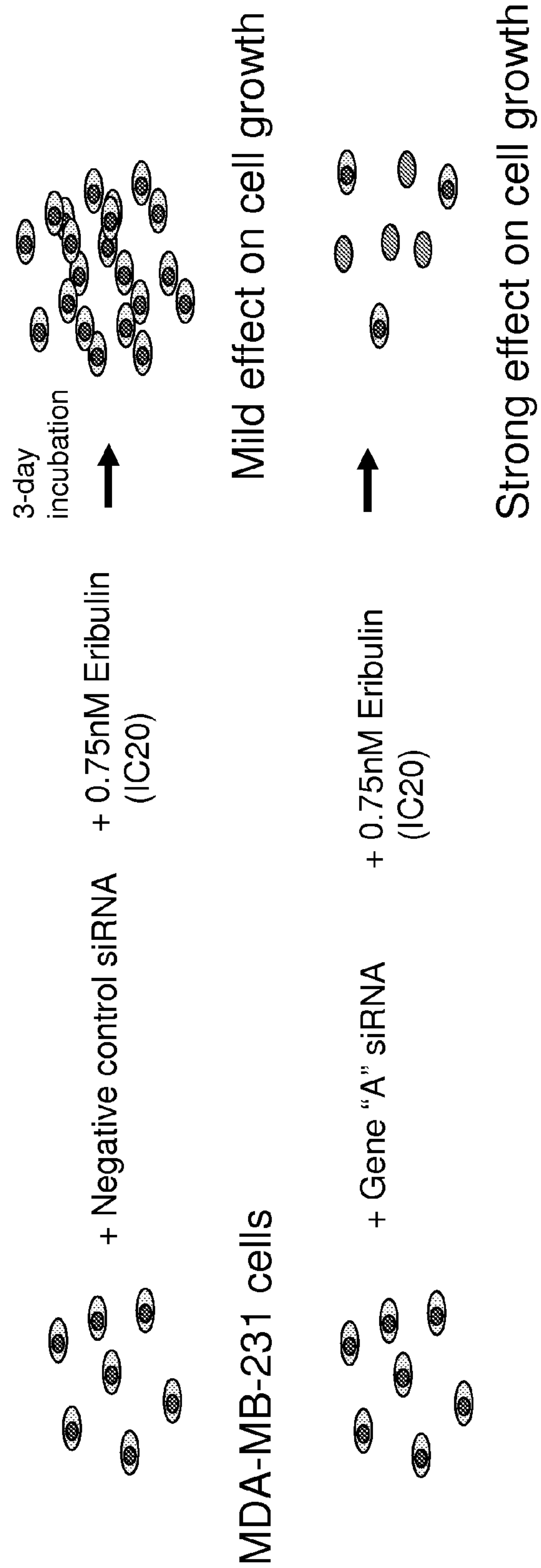
FIG. 1 depicts the high throughput siRNA screening methods in Breast Cancer Cell Lines performed as described in Example 1.

The present invention provides methods for determining whether eribulin, an analog thereof, or a pharmaceutically acceptable salt thereof (e.g., eribulin mesylate), may be used to treat a subject having breast cancer, methods for predicting whether eribulin, an analog thereof, or a pharmaceutically acceptable salt thereof (e.g., eribulin mesylate), may be used to treat a subject having breast cancer, methods for determining the sensitivity of a breast tumor to treatment with eribulin, an analog thereof, or a pharmaceutically acceptable salt thereof (e.g., eribulin mesylate), and methods of treating a subject having breast cancer. Generally, the methods involve determining the level of expression of at least one biomarker as set forth in Table 1 in a sample derived from the subject, wherein a low level of expression of the biomarker is an indication that eribulin, or an analog thereof may be used to treat breast cancer and/or that the breast tumor is sensitive to treatment with eribulin, an analog thereof, or a pharmaceutically acceptable salt thereof (e.g., eribulin mesylate).

The invention is based, at least in part, on the observation that a low level of expression, e.g., the absence of expression, of the biomarkers identified herein is indicative of responsiveness to eribulin, an analog thereof, or a pharmaceutically acceptable salt thereof (e.g., eribulin mesylate). As shown herein, siRNA techniques were employed to "knock down" expression of certain genes and assess the sensitivity of the resulting knock down cells to eribulin mesylate. Based on the findings from these studies, low levels of expression of each of the genes set forth in Table 1 was identified as being associated with the sensitivity of breast cancer cells to treatment with eribulin, an analog thereof, or a pharmaceutically acceptable salt thereof (e.g., eribulin mesylate).

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms, for example, those characterized by "a" or "an", shall include pluralities, e.g., one or more biomarkers. In this application, the use of "or" means "and/or", unless stated otherwise. Furthermore, the use of the term "including," as well as other forms of the term, such as "includes" and "included", is not limiting. Also, terms such as "element" or "component" encompass both elements and components comprising one unit and elements and components that comprise more than one unit unless specifically stated otherwise.

The phrase "determining whether eribulin, an analog thereof, or a pharmaceutically acceptable salt thereof (e.g., eribulin mesylate), may be used to treat a subject having breast cancer" refers to assessing the likelihood that treatment of a subject with eribulin, an analog thereof, or a pharmaceutically acceptable salt thereof (e.g., eribulin mesylate) will be effective (e.g., provide a therapeutic benefit to the subject) or will not be effective in the subject. Assessment of the likelihood that treatment will or will not be effective typically can be performed before treatment with eribulin, an analog thereof, or a pharmaceutically acceptable salt thereof (e.g., eribulin mesylate), has begun or before treatment is resumed. Alternatively or in combination, assessment of the likelihood of efficacious treatment can be performed during treatment, for example, to determine whether treatment should be continued or discontinued. For example, such an assessment can be performed (a) by determining the level of expression of a biomarker, for example, a biomarker selected from the group of biomarkers listed in Table 1, in a sample derived from said subject, wherein a low level of expression of the biomarker indicates that eribulin, an analog thereof, or a pharmaceutically acceptable salt thereof, may be used to treat said subject having breast cancer, or (b) by assaying a sample derived from said subject to determine the level of expression in said sample of a biomarker, for example, a biomarker selected from the group of biomarkers listed in Table 1, wherein a low level of expression of the biomarker indicates that eribulin, an analog thereof, or a pharmaceutically acceptable salt thereof, may be used to treat said subject having breast cancer.

The phrase "determining the sensitivity of a breast tumor to treatment with eribulin, an analog thereof, or a pharmaceutically acceptable salt thereof", as used herein, is intended to refer to assessing the susceptibility of a breast tumor, e.g., breast cancer cells, to treatment with eribulin, an analog thereof, or a pharmaceutically acceptable salt thereof (e.g., eribulin mesylate). Sensitivity of a tumor can include the ability of eribulin, an analog thereof, or a pharmaceutically acceptable salt thereof (e.g., eribulin mesylate), to kill tumor cells, to inhibit the spread and/or metastasis of tumor cells, and/or to inhibit the growth of tumor cells completely or partially (e.g., slow down the growth of tumor cells by at least 5%, 10%, 15%, 20%, 25%, 30%, 35%, 40%, 45%, 50%, 55%, 60%, 65%, 70%, 75%, 80%, 85%, 90%, or 95%). The assessment can be performed (i) before treatment with eribulin, an analog thereof, or a pharmaceutically acceptable salt thereof (e.g., eribulin mesylate), is begun; (ii) before treatment is resumed in the subject; and/or during treatment, for example, to determine whether treatment should be continued or discontinued. For example, such a determination can be performed (a) by determining the level of expression of a biomarker, e.g., a biomarker selected from the group of biomarkers listed in Table 1, in said tumor, wherein a low level of expression of the biomarker in said tumor indicates that said tumor is sensitive to treatment with eribulin, an analog thereof, or a pharmaceutically acceptable salt thereof, or (b) by determining the level of expression of a biomarker e.g., a biomarker selected from the group of biomarkers listed in Table 1, in said tumor, and identifying said tumor as being sensitive to treatment with eribulin, an analog thereof, or a pharmaceutically acceptable salt thereof, when said biomarker is expressed in said tumor at a low level.

The term "eribulin" as used herein refers to the art-recognized fully synthetic macrocyclic ketone analog of halichondrin B. As set forth in U.S. Pat. No. 6,214,865, the entire contents of which are incorporated herein by reference, eribulin has the following structure

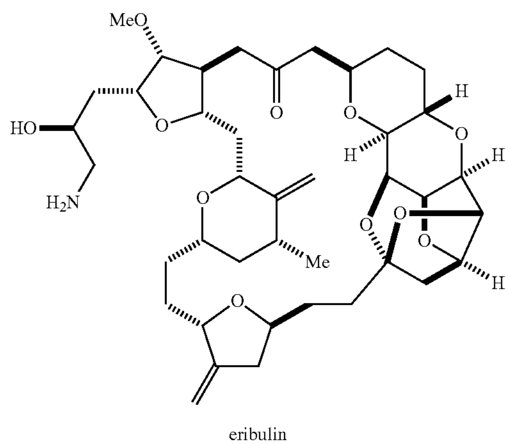

eribulin and can be generated using techniques as described therein or as described in Kim D S et al. (November 2009) *J. Am. Chem. Soc.* 131 (43): 15636-41, the entire contents of which are incorporated herein by reference. Eribulin is also known as ER-086526 and is identified by CAS number 253128-41-5. Eribulin mesylate is also known as E7389.

As used herein, the term "eribulin analog" includes compounds in which one or more atoms or functional groups of eribulin have been replaced with different atoms or functional groups. For example, eribulin analogs include compounds having the following formula (I), which also encompasses eribulin:

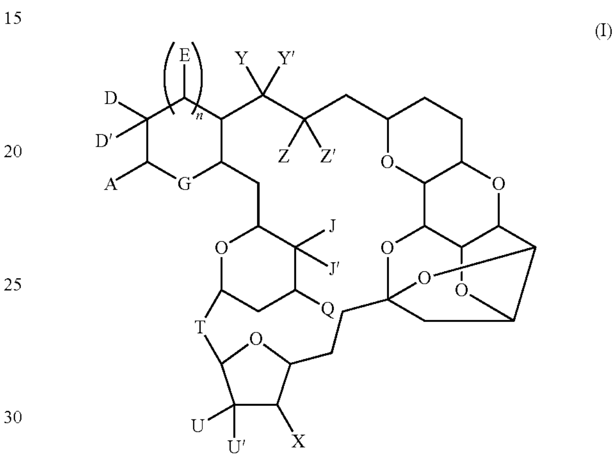

In formula (I), A is a $C_{1-6}$ saturated or $C_{2-6}$ unsaturated hydrocarbon skeleton, the skeleton being unsubstituted or having between 1 and 13 substituents, preferably between 1 and 10 substituents, e.g., at least one substituent selected from cyano, halo, azido, $Q_1$, and oxo. Each $Q_1$ is independently selected from $OR_1$, $SR_1$, $SO_2R_1$, $OSO_2R_1$, $NR_2$, $R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$. The number of substituents can be, for example, from 1 to 6, from 1 to 8, from 2 to 5, or from 1 to 4. Throughout the disclosure, numerical ranges are understood to be inclusive.

Each of $R_1$, $R_2$, $R_4$, $R_5$, and $R_6$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl (e.g., p-fluorophenyl or p-chlorophenyl), $C_{6-10}$ hydroxyaryl, $C_{1-4}$ alkoxy-$C_6$ aryl (e.g., $C_{1-3}$ alkoxy-$C_6$ aryl, p-methoxyphenyl, 3,4,5-trimethoxyphenyl, p-ethoxyphenyl, or 3,5-diethoxyphenyl), $C_{6-10}$ aryl-$C_{1-6}$ alkyl (e.g., benzyl or phenethyl), $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl. There may be more than one $R_1$, for example, if A is substituted with two different alkoxy ($OR_1$) groups such as butoxy and 2-aminoethoxy.

Examples of A include 2,3-dihydroxypropyl, 2-hydroxyethyl, 3-hydroxy-4-perfluorobutyl, 2,4,5-trihydroxypentyl, 3-amino-2-hydroxypropyl, 1,2-dihydroxyethyl, 2,3-dihydroxy-4-perfluorobutyl, 3-cyano-2-hydroxypropyl, 2-amino-1-hydroxy ethyl, 3-azido-2-hydroxypropyl, 3,3-difluoro-2,4-dihydroxybutyl, 2,4-dihydroxybutyl, 2-hydroxy-2(p-fluorophenyl)-ethyl, —$CH_2$(CO) (substituted or unsubstituted aryl), —$CH_2$(CO) (alkyl or substituted alkyl, such as haloalkyl or hydroxyalkyl) and 3,3-difluoro-2-hydroxypent-4-enyl.

Examples of $Q_1$ include —NH(CO)(CO)-(heterocyclic radical or heteroaryl), —$OSO_2$-(aryl or substituted aryl), —O(CO)NH-(aryl or substituted aryl), aminoalkyl, hydroxyalkyl, —NH(CO)(CO)-(aryl or substituted aryl), —NH(CO)(alkyl)(heteroaryl or heterocyclic radical), O(substituted or unsubstituted alkyl)(substituted or unsubstituted aryl), and —NH(CO)(alkyl)(aryl or substituted aryl).

Each of D and D' is independently selected from $R_3$ and $OR_3$, wherein $R_3$ is H, $C_{1-3}$ alkyl, or $C_{1-3}$ haloalkyl. Examples of D and D' are methoxy, methyl, ethoxy, and ethyl. In some embodiments, one of D and D' is H.

The value for n is 1 or preferably 0, thereby forming either a six-membered or five-membered ring. This ring can be unsubstituted or substituted, e.g., where E is $R_5$ or $OR_5$, and can be a heterocyclic radical or a cycloalkyl, e.g. where G is S, $CH_2$, $NR_6$, or preferably O.

Each of J and J' is independently H, $C_{1-6}$ alkoxy, or $C_{1-6}$ alkyl; or J and J' taken together are =$CH_2$ or —O-(straight or branched $C_{1-5}$ alkylene)-O—, such as exocyclic methylidene, isopropylidene, methylene, or ethylene.

Q is $C_{1-3}$ alkyl, and is preferably methyl.

T is ethylene or ethenylene, optionally substituted with $(CO)OR_7$, where $R_7$ is H or $C_{1-6}$ alkyl.

Each of U and U' is independently H, $C_{1-6}$ alkoxy, or $C_{1-6}$ alkyl; or U and U' taken together are =$CH_2$ or —O-(straight or branched $C_{1-5}$ alkylene)-O—.

X is H or $C_{1-6}$ alkoxy.

Each of Y and Y' is independently H or $C_{1-6}$ alkoxy; or Y and Y' taken together are =O, =$CH_2$, or —O-(straight or branched $C_{1-5}$ alkylene)-O—.

Each of Z and Z' is independently H or $C_{1-6}$ alkoxy; or Z and Z' taken together are =O, =$CH_2$, or —O-(straight or branched $C_{1-5}$ alkylene)-O—.

In certain embodiments, the eribulin analogs include compounds having the following formula (II):

(II)

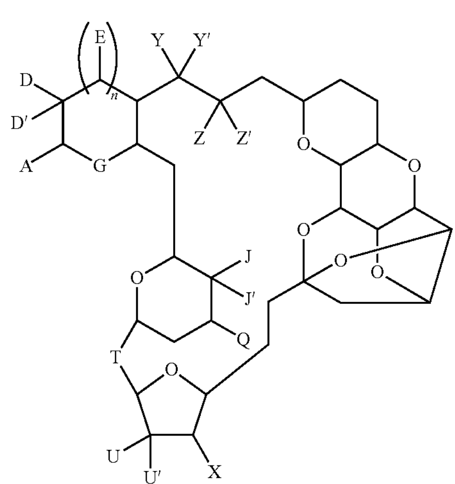

In formula (II), the substitutions are defined as follows:

A is a $C_{1-6}$ saturated or $C_{2-6}$ unsaturated hydrocarbon skeleton, said skeleton being unsubstituted or having between 1 and 10 substituents, inclusive, independently selected from cyano, halo, azido, oxo, and $Q_1$.

Each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$.

Each of $R_1$, $R_2$ and $R_4$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl, $C_{6-10}$ hydroxyaryl, $C_{1-3}$ alkoxy-$C_6$ aryl, $C_{6-10}$ aryl-$C_{1-6}$ alkyl, $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl.

Each of D and D' is independently selected from $R_3$ and $OR_3$, wherein $R_3$ is H, $C_{1-3}$ alkyl, or $C_{1-3}$ haloalkyl.

n is 0 or 1.

E is $R_5$ or $OR_5$, wherein $R_5$ is independently selected from H, $C_{1-6}$ alkyl, $C_{1-6}$ haloalkyl, $C_{1-6}$ hydroxyalkyl and $C_{1-6}$ aminoalkyl.

G is O.

Each of J and J' is independently H, $C_{1-6}$ alkoxy, or $C_{1-6}$ alkyl; or J and J' taken together are =$CH_2$.

Q is $C_{1-3}$ alkyl.

T is ethylene or ethenylene.

Each of U and U' is independently H, $C_{1-6}$ alkoxy, or $C_{1-6}$ alkyl; or U and U' taken together are =$CH_2$.

X is H or $C_{1-6}$ alkoxy.

Each of Y and Y' is independently H or $C_{1-6}$ alkoxy; or Y and Y' taken together are =O.

Each of Z and Z' is independently H or $C_{1-6}$ alkoxy; or Z and Z' taken together are =O.

In some embodiments, the eribulin analogs include compounds having the following formula (III):

(III)

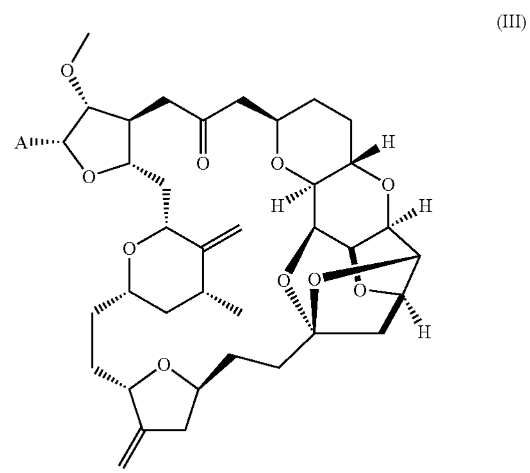

wherein A is a $C_{1-6}$ saturated or $C_{2-6}$ unsaturated hydrocarbon skeleton, the skeleton being unsubstituted or having between 1 and 13 substituents, e.g., between 1 and 10 substituents selected from cyano, halo, azido, $Q_1$, and oxo;

each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$; and each of $R_1$, $R_2$, and $R_4$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl, $C_{6-10}$ hydroxyaryl, $C_{1-4}$ alkoxy-$C_6$ aryl, $C_{6-10}$ aryl-$C_{1-6}$ alkyl, $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl.

Hydrocarbon skeletons contain carbon and hydrogen atoms and may be linear, branched, or cyclic. Unsaturated hydrocarbons include one, two, three or more C—C double bonds ($sp^2$) or C—C triple bonds (sp). Examples of unsaturated hydrocarbon radicals include ethynyl, 2-propynyl, 1-propenyl, 2-butenyl, 1,3-butadienyl, 2-pentenyl, vinyl (ethenyl), allyl, and isopropenyl. Examples of bivalent unsaturated hydrocarbon radicals include alkenylenes and alkylidenes such as methylidyne, ethylidene, ethylidyne, vinylidene, and isopropylidene. In general, compounds of the invention have hydrocarbon skeletons ("A" in formula (I)) that are substituted, e.g., with hydroxy, amino, cyano, azido, heteroaryl, aryl, and other moieties described herein. Hydrocarbon skeletons may have two geminal hydrogen atoms replaced with oxo, a bivalent carbonyl oxygen atom (═O), or a ring-forming substituent, such as —O-(straight or branched alkylene or alkylidene)-O— to form an acetal or ketal.

$C_{1-6}$ alkyl includes linear, branched, and cyclic hydrocarbons, such as methyl, ethyl, propyl, isopropyl, butyl, isobutyl, sec-butyl, tert-butyl, pentyl, isopentyl, sec-pentyl, neopentyl, tert-pentyl, cyclopentyl, hexyl, isohexyl, sec-hexyl, cyclohexyl, 2-methylpentyl, tert-hexyl, 2,3-dimethylbutyl, 3,3-dimethylbutyl, 1,3-dimethylbutyl, and 2,3-dimethyl but-2-yl. Alkoxy (—OR), alkylthio (—SR), and other alkyl-derived moieties (substituted, unsaturated, or bivalent) are analogous to alkyl groups (R). Alkyl groups, and alkyl-derived groups such as the representative alkoxy, haloalkyl, hydroxyalkyl, alkenyl, alkylidene, and alkylene groups, can be $C_{2-6}$, $C_{3-6}$, $C_{1-3}$, or $C_{2-4}$.

Alkyls substituted with halo, hydroxy, amino, cyano, azido, and so on can have 1, 2, 3, 4, 5 or more substituents, which are independently selected (may or may not be the same) and may or may not be on the same carbon atom. For example, haloalkyls are alkyl groups with at least one substituent selected from fluoro, chloro, bromo, and iodo. Haloalkyls may have two or more halo substituents which may or may not be the same halogen and may or may not be on the same carbon atom. Examples include chloromethyl, periodomethyl, 3,3-dichloropropyl, 1,3-difluorobutyl, and 1-bromo-2-chloropropyl.

Heterocyclic radicals and heteroaryls include furyl, pyranyl, isobenzofuranyl, chromenyl, xanthenyl, phenoxathienyl, 2H-pyrrolyl, pyrrolyl, imidazolyl (e.g., 1-, 2- or 4-imidazolyl), pyrazolyl, isothiazolyl, isoxazolyl, pyridyl (e.g., 1-, 2-, or 3-pyridyl), pyrazinyl, pyrimidinyl, pyridazinyl, indolizinyl, isoindolyl, 3H-indolyl, indolyl (e.g., 1-, 2-, or 3-indolyl), indazolyl, purinyl, 4H-quinolizinyl, isoquinolyl, quinolyl, phthalazinyl, naphthyridinyl, quinoxalinyl, quinazolinyl, cinnolinyl, pteridinyl, pyrrolinyl, pyrrolidinyl, imidazolidinyl, pyrazolidinyl, pyrazolinyl, piperidyl, piperazinyl, indolinyl, isoindolinyl, and morpholinyl. Heterocyclic radicals and heteroaryls may be linked to the rest of the molecule at any position along the ring. Heterocyclic radicals and heteroaryls can be $C_{2-9}$, or smaller, such as $C_{3-6}$, $C_{2-5}$, or $C_{3-7}$.

Aryl groups include phenyl, benzyl, naphthyl, tolyl, mesityl, xylyl, and cumenyl.

It is understood that "heterocyclic radical", "aryl", and "heteroaryl" include those having 1, 2, 3, 4, or more substituents independently selected from lower alkyl, lower alkoxy, amino, halo, cyano, nitro, azido, and hydroxyl. Heterocyclic radicals, heteroaryls, and aryls may also be bivalent substituents of hydrocarbon skeleton "A" in formula (I).

The term "eribulin analog" includes eribulin prodrugs. The term "eribulin prodrugs" includes eribulin that has been chemically modified to be inactive or less active until bioactivation (e.g., metabolism in vivo) by an enzyme which cleaves the chemically modified portion of the eribulin prodrug, thereby providing the active form of eribulin.

As used herein, the term "eribulin analog" includes all stereoisomers of eribulin and other compounds of formula (I), including diastereoisomers and enantiomers thereof "Stereoisomers" refers to isomers that differ only in the arrangement of the atoms in space. "Diastereoisomers" refers to stereoisomers that are not mirror images of each other. "Enantiomers" refers to stereoisomers that are non-superimposable mirror images of one another. For example, Formula (IV) encompasses eribulin and such stereoisomers:

(IV)

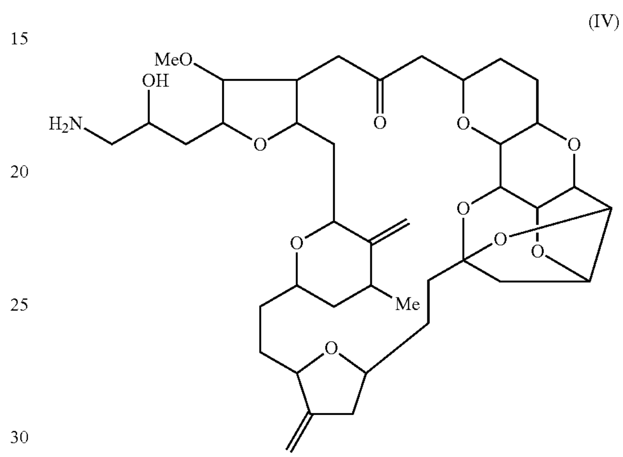

The phrase "pharmaceutically acceptable salt," as used herein, is a salt formed from an acid and a basic nitrogen group of Eribulin or an eribulin analog. Examples of such salts include acid addition salts and base addition salts, such as inorganic acid salts or organic acid salts (e.g., hydrochloric acid salt, sulfuric acid salt, citrate, hydrobromic acid salt, hydroiodic acid salt, nitric acid salt, bisulfate, phosphoric acid salt, super phosphoric acid salt, isonicotinic acid salt, acetic acid salt, lactic acid salt, salicylic acid salt, tartaric acid salt, pantothenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate)), as well as salts of aluminum, calcium, lithium, magnesium, calcium, sodium, zinc, and diethanolamine. It will be understood that reference to eribulin, an analog thereof, or a pharmaceutically acceptable salt thereof, includes pharmaceutically acceptable salts of eribulin as well as pharmaceutically acceptable salts of an analog thereof. Examples of such pharmaceutically acceptable salts include, but are not limited to, a pharmaceutically acceptable salt of Formula I, a pharmaceutically acceptable salt of Formula II, a pharmaceutically acceptable salt of Formula III or a pharmaceutically acceptable salt of Formula IV.

In a particular embodiment, eribulin mesylate, a pharmaceutically acceptable salt form of eribulin is utilized in the methods of the present invention. Eribulin mesylate is sold under the trade name HALAVEN®. The chemical name for eribulin mesylate is 11,15:18,21:24,28-Triepoxy-7,9-ethano-12,15-methano-9H,15H-furo[3,2-i]furo[2',3':5,6]pyrano[4,3-b][1,4]dioxacyclopentacosin-5(4H)-one, 2-[(2S)-3-amino-2-hydroxypropyl]hexacosahydro-3-methoxy-26-methyl-20,27-bis(methylene)-, (2R,3R,3aS,7R, 8aS,9S,10aR,11S,12R,13aR,13bS,15S,18S,21S,24S,26R, 28R,29aS)-methanesulfonate (salt). Eribulin mesylate has the following structure

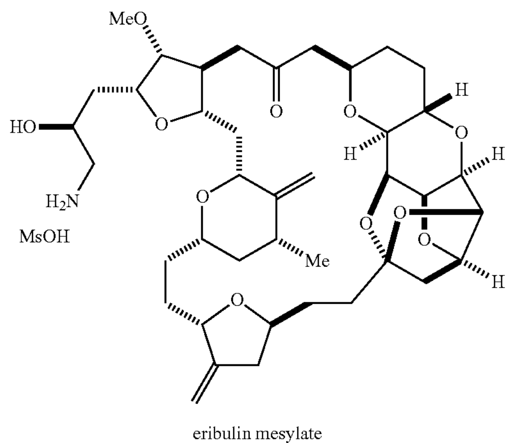

eribulin mesylate

Eribulin mesylate is label indicated for the treatment of patients with metastatic breast cancer who have previously received at least two chemotherapeutic regimens for the treatment of metastatic disease, including, for example, therapy with an anthracycline and a taxane in either the adjuvant or metastatic setting.

As used herein, the term "biomarker" is intended to encompass a substance that is used as an indicator of a biologic state and includes for example, genes (or portions thereof), mRNAs (or portions thereof), miRNAs (microRNAs), and proteins (or portions thereof). A "biomarker expression pattern" is intended to refer to a quantitative or qualitative summary of the expression of one or more biomarkers in a subject, such as in comparison to a standard or a control.

Various biomarkers which can be used in the methods described herein are summarized in Table 1. Table 1 provides gene abbreviations, Gene ID numbers and accession numbers for transcripts from which encoding nucleotide gene sequences can be identified. For example, gene ABI3 refers to a *Homo sapiens* ABI family, member 3. The nucleotide sequence for human ABI3 transcript variant 1 can be found at Accession Number NM_016428. Reference to a gene (e.g., ABI3) is intended to encompass naturally occurring or endogenous versions of the gene, including wild type, polymorphic or allelic variants or mutants (e.g., germline mutation, somatic mutation) of the gene, which can be found in a subject and/or tumor from a subject. In some embodiments, the sequence of the biomarker gene is at least about 80%, at least about 85%, at least about 90%, at least about 91%, at least about 92%, at least about 93%, at least about 94%, at least about 95%, at least about 96%, at least about 97%, at least about 98%, or at least about 99% identical to a sequence identified in Table 1 by Accession Number or Gene_ID number. For example, sequence identity can be determined by comparing sequences using NCBI BLAST (e.g., Megablast with default parameters).

As used herein, the phrase "predictive gene signature" refers to expression levels of two or more biomarkers of the present invention in a subject that are indicative of responsiveness to treatment with eribulin, or an eribulin analog. For example, the low level expression of at least 2, at least 3, at least 4, at least 5, at least 6, at least 7, at least 8, at least 9 or at least 10 biomarkers from Table 1 in a subject may constitute a gene signature that indicates that the subject will respond positively to treatment with eribulin, an analog thereof, or a pharmaceutically acceptable salt thereof (e.g., eribulin mesylate). Any sub-combination of 2 or more markers from Table 1 may constitute a predictive gene signature of the invention. In another example, the expression of at least 1, at least 2, at least 3, at least 4, at least 5, at least 6, at least 7, at least 8, at least 9 or at least 10 biomarkers from Table 1 under particular threshold levels, or any sub-combination thereof, constitutes a gene signature that indicates that the subject will respond positively to treatment with eribulin, an analog thereof, or a pharmaceutically acceptable salt thereof (e.g., eribulin mesylate).

A "low level of expression" of the biomarker, for example, a biomarker selected from the group of biomarkers listed in Table 1, refers to a level of expression of the biomarker in a test sample (e.g., a sample derived from a subject) that correlates with sensitivity to eribulin, an analog thereof, or a pharmaceutically acceptable salt thereof (e.g., eribulin mesylate). This can be determined by comparing the level of expression of the biomarker in the test sample with that of a suitable control. A "low level of expression" also includes a lack of detectable expression of the biomarker.

In some embodiments, the level of expression of the biomarker is determined relative to a control sample, such as the level of expression of the biomarker in normal tissue (e.g., a range determined from the levels of expression of the biomarker observed in normal tissue samples). In these embodiments, a low level of expression will fall below or within the lower levels of this range. In some embodiments, the level of expression of the biomarker is determined relative to a control sample, such as the level of expression of the biomarker in samples (e.g., tumor samples, circulating tumor cells) from other subjects. For example, the level of expression of the biomarker in samples from other subjects can be determined to define levels of expression which correlate with sensitivity to treatment with eribulin, an analog thereof, or a pharmaceutically acceptable salt thereof (e.g., eribulin mesylate), and the level of expression of the biomarker in the sample from the subject of interest is compared to these levels of expression, wherein a comparable or lower level of expression in the sample from the subject is indicative of a "low level of expression" of the biomarker in the sample. In another example, the level of expression of the biomarker in samples (e.g., tumor samples, circulating tumor cells) from other subjects can be determined to define levels of expression which correlate with resistance or non-responsiveness to treatment with eribulin, an analog thereof, or a pharmaceutically acceptable salt thereof (e.g., eribulin mesylate), and the level of expression of the biomarker in the sample from the subject of interest is compared to these levels of expression, wherein a lower level of expression in the sample from the subject is indicative of a "low level of expression" of the biomarker in the sample.

The term "known standard level" or "control level" can refer to an accepted or pre-determined expression level of the biomarker, for example, a biomarker selected from the group of biomarkers listed in Table 1 which is used to compare expression level of the biomarker in a sample derived from a subject. In one embodiment, the control expression level of the biomarker is the average expression level of the biomarker in samples derived from a population of subjects. For example, the control expression level can be the average expression level of the biomarker in breast cancer cells derived from a population of subjects with breast cancer. The population may be subjects who have not responded to treatment with eribulin, an analog thereof, or a pharmaceutically acceptable salt thereof (e.g., eribulin mesylate), or the population may be a group of subjects who express the respective biomarker at high or normal levels. In some embodiments, the control level may constitute a range of expression of the biomarker in normal tissue, as described above. For example, the control level may constitute a range of expression of the biomarker in tumor samples from a variety of subjects having breast cancer, as described above.

As further information becomes available as a result of routine performance of the methods described herein, population-average values for "control" level of expression of the biomarkers of the present invention may be used. In other embodiments, the "control" level of expression of the biomarkers may be determined by determining expression level of the respective biomarker in a subject sample obtained from a subject before the suspected onset of breast cancer in the subject, from archived subject samples, and the like.

Control levels of expression of biomarkers of the invention may be available from publicly available databases. In addition, Universal Reference Total RNA (Clontech Laboratories) and Universal Human Reference RNA (Stratagene) and the like can be used as controls. For example, qPCR can be used to determine the level of expression of a biomarker, and an increase in the number of cycles needed to detect expression of a biomarker in a sample from a subject, relative to the number of cycles needed for detection using such a control, is indicative of a low level of expression of the biomarker.

As used herein, the term "subject" or "patient" refers to human and non-human animals, e.g., veterinary patients. The term "non-human animal" includes vertebrates, e.g., mammals, such as non-human primates, mice, rabbits, sheep, dog, cat, horse, cow, or other rodent, ovine, canine, feline, equine or bovine species. In one embodiment, the subject is a human.

The term "sample" as used herein refers to cells, tissues or fluids isolated from a subject, as well as cells, tissues or fluids present within a subject. The term "sample" includes any body fluid (e.g., blood, lymph, cystic fluid, nipple aspirates, urine and fluids collected from a biopsy (e.g., lump biopsy)), tissue or a cell or collection of cells from a subject, as well as any component thereof, such as a fraction or extract. In one embodiment, the tissue or cell is removed from the subject. In another embodiment, the tissue or cell is present within the subject. Other samples include tears, plasma, serum, cerebrospinal fluid, feces, sputum and cell extracts. In one embodiment, the sample contains protein (e.g., proteins or peptides) from the subject. In another embodiment, the sample contains RNA (e.g., mRNA molecules) from the subject or DNA (e.g., genomic DNA molecules) from the subject.

As used herein, the term "breast cancer" refers generally to the uncontrolled growth of breast tissue and, more specifically, to a condition characterized by anomalous rapid proliferation of abnormal cells in one or both breasts of a subject. The abnormal cells often are referred to as malignant or "neoplastic cells," which are transformed cells that can form a solid tumor. The term "tumor" refers to an abnormal mass or population of cells (i.e., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize. In breast cancer, neoplastic cells may be identified in one or both breasts only and not in another tissue or organ, in one or both breasts and one or more adjacent tissues or organs (e.g. lymph node), or in a breast and one or more non-adjacent tissues or organs to which the breast cancer cells have metastasized.

Eribulin, an analog thereof, or pharmaceutically acceptable salt thereof, can be used to treat breast cancer, and, accordingly, the methods of the present invention can be used in breast cancer and in subjects having breast cancer.

In one embodiment, the breast cancer is Estrogen Receptor (ER) negative breast cancer, Progesterone Receptor (PR) negative breast cancer and/or HER-2 negative breast cancer. For example, the breast cancer may be Estrogen Receptor (ER) negative and Progesterone Receptor (PR) negative breast cancer; Estrogen Receptor (ER) negative and HER-2 negative breast cancer; Progesterone Receptor (PR) negative and HER-2 negative breast cancer; or Estrogen Receptor (ER) negative breast cancer, Progesterone Receptor (PR) negative breast cancer and HER-2 negative (triple negative) breast cancer. Assessment of ER, PR and HER-2 status can be done using any suitable method. For example, HER-2 status can be assessed by immunohistochemistry (IHC) and/or gene amplification by fluorescence in situ hybridization (FISH), for example, according to National Comprehensive Cancer Network [NCCN] guidelines.

The breast cancer can be for example, adenocarcinoma, inflammatory breast cancer, recurrent (e.g., locally recurrent) and/or metastatic breast cancer. In some embodiments, the breast cancer is endocrine refractory or hormone refractory. The terms "endocrine refractory" and "hormone refractory" refer to a cancer that is resistant to treatment with hormone therapy for breast cancer, e.g., aromatase inhibitors or tamoxifen. Breast cancers arise most commonly in the lining of the milk ducts of the breast (ductal carcinoma), or in the lobules where breast milk is produced (lobular carcinoma). Accordingly, in various embodiments of the invention, the breast cancer can be ductal carcinoma or lobular carcinoma. Cancerous cells from the breast(s) may invade or metastasize to any other organ or tissue of the body. For example, cancer cells often invade lymph node cells and/or metastasize to the liver, brain and/or bone.

In various embodiments of the present invention, the subject may be suffering from Stage I, Stage II, Stage III or Stage IV breast cancer. The stage of a breast cancer can be classified as a range of stages from Stage 0 to Stage IV based on its size and the extent to which it has spread. The following table summarizes the stages, which are well known to clinicians:

| STAGE | TUMOR SIZE | LYMPH NODE INVOLVEMENT | METASTASIS (SPREAD) |
|---|---|---|---|
| I | Less than 2 cm | No | No |
| II | Between 2-5 cm | No or in same side of breast | No |
| III | More than 5 cm | Yes, on same side of breast | No |
| IV | Not applicable | Not applicable | Yes |

Various aspects of the invention are described in further detail in the following subsections.

I. Prediction of Responsiveness to Eribulin, an Analog Thereof, or a Pharmaceutically Acceptable Salt Thereof (e.g., Eribulin Mesylate) in Subjects with Breast Cancer In one aspect, the invention provides a method for determining whether eribulin, an analog thereof, or a pharmaceutically acceptable salt thereof (e.g., eribulin mesylate), may be used to treat a subject having breast cancer and/or for determining the sensitivity of a breast tumor to treatment with eribulin, an analog thereof, or a pharmaceutically acceptable salt thereof (e.g., eribulin mesylate). The methods involve determining the expression level of at least one biomarker, for example, by assaying a sample derived from a subject having breast cancer. The identification of low levels of expression of at least one biomarker is indicative that eribulin, an analog thereof, or a pharmaceutically acceptable salt thereof (e.g., eribulin mesylate) may be used for treatment of the breast cancer and/or that the breast tumor is sensitive to the treatment with eribulin, an analog thereof, or a pharmaceutically acceptable salt thereof (e.g., eribulin mesylate).

In the methods of the invention, the expression level of at least one biomarker selected from the group of biomarkers set forth in Table 1 is assessed, which, as explained herein, can comprise determining the level of expression of one or more of these genes (e.g., ABI3, ANG) using various approaches, such as determining in a suitable sample the presence of certain DNA polymorphisms or null mutations, determining the level of RNA expressed from a gene, including an mRNA exemplified in Table 1 and/or other transcripts from the gene, or a protein product(s) of any of the foregoing.

TABLE 1

BIOMARKERS OF RESPONSIVENESS TO ERIBULIN, AN ANALOG THEREOF, OR A PHARMACEUTICALLY ACCEPTABLE SALT THEREOF (e.g., ERIBULIN MESYLATE)

| GENE NAME | GENE_ID | ACCESSION NO. | SEQ ID NO: | NAME |
|---|---|---|---|---|
| ABI3 | 51225 | NM_016428 | 1 & 2 | *Homo sapiens* ABI family, member 3 (ABI3), transcript variant 1, mRNA |
| ANG | 283 | NM_001097577 | 3 & 4 | *Homo sapiens* angiogenin, ribonuclease, RNase A family, 5 (ANG), transcript variant 2, mRNA |
| APBB2 | 323 | NM_173075 | 5 & 6 | *Homo sapiens* amyloid beta (A4) precursor protein-binding, family B, member 2 (APBB2), mRNA |
| CCL26 | 10344 | NM_006072 | 7 & 8 | *Homo sapiens* chemokine (C-C motif) ligand 26 (CCL26), mRNA |
| CDC20 | 991 | NM_001255 | 9 & 10 | *Homo sapiens* cell division cycle 20 homolog (*S. cerevisiae*) (CDC20), mRNA |
| CEP152 | 22995 | NM_014985 | 11 & 12 | *Homo sapiens* centrosomal protein 152 kDa (CEP152), mRNA |
| CFL1 | 1072 | NM_005507 | 13 & 14 | *Homo sapiens* cofilin 1 (non-muscle) (CFL1), mRNA |
| CKLF | 51192 | NM_016326 | 15 & 16 | *Homo sapiens* chemokine-like factor (CKLF), transcript variant 3, mRNA |
| COL7A1 | 1294 | NM_000094 | 17 & 18 | *Homo sapiens* collagen, type VII, alpha 1 (COL7A1), mRNA |
| CYP4F3 | 4051 | NM_000896 | 19 & 20 | *Homo sapiens* cytochrome P450, family 4, subfamily F, polypeptide 3 (CYP4F3), mRNA |
| DYSF | 8291 | NM_003494 | 21 & 22 | *Homo sapiens* dysferlin, limb girdle muscular dystrophy 2B (autosomal recessive) (DYSF), transcript variant 8, mRNA |
| EDIL3 | 10085 | NM_005711 | 23 & 24 | *Homo sapiens* EGF-like repeats and discoidin I-like domains 3 (EDIL3), mRNA |
| ERGIC3 | 51614 | NM_015966 | 25 & 26 | *Homo sapiens* ERGIC and golgi 3 (ERGIC3), transcript variant 2, mRNA |
| GNAT1 | 2779 | NM_000172 | 27 & 28 | *Homo sapiens* guanine nucleotide binding protein (G protein), alpha transducing activity polypeptide 1 (GNAT1), transcript variant 2, mRNA |
| GRAMD4 | 23151 | NM_015124 | 29 & 30 | *Homo sapiens* GRAM domain containing 4 (GRAMD4), mRNA |
| HYAL2 | 8692 | NM_003773 | 31 & 32 | *Homo sapiens* hyaluronoglucosaminidase 2 (HYAL2), transcript variant 1, mRNA |
| IL10 | 3586 | NM_000572 | 33 & 34 | *Homo sapiens* interleukin 10 (IL10), mRNA |
| ITFG3 | 83986 | NM_032039 | 35 & 36 | *Homo sapiens* integrin alpha FG-GAP repeat containing 3 (ITFG3), mRNA |
| JAM3 | 83700 | NM_032801 | 37 & 38 | *Homo sapiens* junctional adhesion molecule 3 (JAM3), mRNA |
| KLHL17 | 339451 | NM_198317 | 39 & 40 | *Homo sapiens* kelch-like 17 (*Drosophila*) (KLHL17), mRNA |
| KRT24 | 192666 | NM_019016 | 41 & 42 | *Homo sapiens* keratin 24 (KRT24), mRNA |
| MAD2L1BP | 9587 | NM_014628 | 43 & 44 | *Homo sapiens* MAD2L1 binding protein (MAD2L1BP), transcript variant 2, mRNA |
| MANSC1 | 54682 | NM_018050 | 45 & 46 | *Homo sapiens* MANSC domain containing 1 (MANSC1), mRNA |
| MOBKL1B | 55233 | NM_018221 | 47 & 48 | *Homo sapiens* MOB1, Mps One Binder kinase activator-like 1B (yeast) (MOBKL1B), mRNA |
| NCBP1 | 4686 | NM_002486 | 49 & 50 | *Homo sapiens* nuclear cap binding protein subunit 1, 80 kDa (NCBP1), mRNA |
| NMU | 10874 | NM_006681 | 51 & 52 | *Homo sapiens* neuromedin U (NMU), mRNA |

TABLE 1-continued

BIOMARKERS OF RESPONSIVENESS TO ERIBULIN, AN ANALOG THEREOF, OR A PHARMACEUTICALLY ACCEPTABLE SALT THEREOF (e.g., ERIBULIN MESYLATE)

| GENE NAME | GENE_ID | ACCESSION NO. | SEQ ID NO: | NAME |
|---|---|---|---|---|
| PAPLN | 89932 | NM_173462 | 53 & 54 | *Homo sapiens* papilin, proteoglycan-like sulfated glycoprotein (PAPLN), mRNA |
| PCDH1 | 5097 | NM_002587 | 55 & 56 | *Homo sapiens* protocadherin 1 (PCDH1), transcript variant 1, mRNA |
| PDGFB | 5155 | NM_002608 | 57 & 58 | *Homo sapiens* platelet-derived growth factor beta polypeptide (simian sarcoma viral (v-sis) oncogene homolog) (PDGFB), transcript variant 1, mRNA |
| PHOSPHO2 | 493911 | NM_001008489 | 59 & 60 | *Homo sapiens* phosphatase, orphan 2 (PHOSPHO2), mRNA |
| PSENEN | 55851 | NM_172341 | 61 & 62 | *Homo sapiens* presenilin enhancer 2 homolog (*C. elegans*) (PSENEN), mRNA |
| SATB1 | 6304 | NM_002971 | 63 & 64 | *Homo sapiens* SATB homeobox 1 (SATB1), transcript variant 1, mRNA |
| SNX11 | 29916 | NM_013323 | 65 & 66 | *Homo sapiens* sorting nexin 11 (SNX11), transcript variant 2, mRNA |
| SPTA1 | 6708 | NM_003126 | 67 & 68 | *Homo sapiens* spectrin, alpha, erythrocytic 1 (elliptocytosis 2) (SPTA1), mRNA |
| TMEM79 | 84283 | NM_032323 | 69 & 70 | *Homo sapiens* transmembrane protein 79 (TMEM79), transcript variant 1, mRNA |
| TMIGD2 | 126259 | NM_144615 | 71 & 72 | *Homo sapiens* transmembrane and immunoglobulin domain containing 2 (TMIGD2), mRNA |
| TUBB6 | 84617 | NM_032525 | 73 & 74 | *Homo sapiens* tubulin, beta 6 (TUBB6), mRNA |
| TYROBP | 7305 | NM_198125 | 75 & 76 | *Homo sapiens* TYRO protein tyrosine kinase binding protein (TYROBP), transcript variant 2, mRNA |
| YTHDF1 | 54915 | NM_017798 | 77 & 78 | *Homo sapiens* YTH domain family, member 1 (YTHDF1), mRNA |
| ZIC5 | 85416 | NM_033132 | 79 & 80 | *Homo sapiens* Zic family member 5 (odd-paired homolog, *Drosophila*) (ZIC5), mRNA |

Each of the accession numbers identified in Table 1, and their corresponding sequences, are hereby incorporated herein by reference.

In various embodiments, the level of expression of at least 2, 3, 4, 5, 6, 7, 8, 9 or 10 biomarkers selected from the group of biomarkers listed in Table 1 is determined.

In particular embodiments, a predictive gene signature comprising a sub-combination of 2 or more biomarkers selected from the group of biomarkers listed in Table 1 is used. In various embodiments, the level of expression of at least 2, at least 3, at least 4 or at least 5 biomarkers selected from the group of biomarkers listed in Table 1 is determined. For example, the predictive gene signature may include at least 2 biomarkers, e.g., DYSF and EDIL3; GNAT1 and ERGIC3; KRT24 and PAPLN; MANSC1 and PDGFB; PCDH1 and PDGFB; or PHOSPHO2 and PSENEN. In another embodiment, the predictive gene signature may include at least 3 biomarkers, e.g., COL7A1, YTHDF1 and ZIC5; CKLF, IL10 and TUBB6; CDC20, CFL1 and TMEM79; HYAL2, NCBP1 and SNX11; or CEP152, NCBP1 and SATB1. In another embodiment, the predictive gene signature may include at least 4 biomarkers, e.g., APBB2, CCL26, PSENEN and SATB1; ANG, JAM3, KLHL17 and PAPLN; ITFG3, MAD2L1BP, NMU and PDGFB; SPTA1, TYROBP, SNX11 and PSENEN; GRAMD4, GNAT1, TMIGD2 and YTHDF1; or GRAMD4, HYAL2, PHOSPHO2 and TUBB6. In another embodiment, the predictive gene signature may include at least 5 biomarkers, e.g., CCL26, CDC20, ERGIC3, EDIL3 and PCDH1; DYSF, NMU, PHOSPHO2, PSENEN and SNX11; APBB2, CKLF, CYP4F3, TUBB6 and YTHDF1; or CEP152, MAD2L1BP, SPTA1, TMEM79 and ZIC5.

In particular embodiments, the predictive gene signature may include 2 or more of biomarkers ABI3, ANG, APBB2, CCL26, CDC20, CEP152, CFL1, CKLF, COL7A1, CYP4F3, DYSF, GNAT1, GRAMD4, HYAL2, IL10, ITFG3, JAM3, KLHL17, KRT24, MAD2L1BP, MANSC1, MOBKL1B, NCBP1, NMU, PCDH1, PHOSPHO2, SPTA1, TMIGD2, TYROBP, ZIC5, ERGIC3, PDGFB, PSENEN, SATB1, SNX11, TMEM79 and YTHDF1, e.g., ABI3 and ANG; APBB2 and CCL26; GNAT1 and GRAMD4; IL10 and ITFG3; MACSC1 and MOBKL1B; NMU and PCDH1; or TYROBP and ZIC5. In other embodiments, the predictive gene signature includes at least 3 of the previously recited biomarkers, e.g., ABI3, ANG and APBB2; CCL26, CKLF and COL7A1; DYSF, GNAT1 and HYAL2; JAM3, KLHL17 and KRT24; NCBP1, NMU and PCDH1; SPTA1, TMIGD2 and TYROBP; or ZIC5, MAD2L1BP and CDC20. In other embodiments, the predictive gene signature includes at least 4 of the previously recited biomarkers, e.g., ABI3, ANG, APBB2 and CCL26; CEP152, CFL1, CKLF and COL7A1; KRT24, MANSC1, MOBKL1B and SPTA1; TYROBP, TMIGD2, PHOSPHO2 and NMU; ABI3, GNATI, KLHL17 and SPTA1; or CEP152, HYAL2, PCDH1 and TMIGD2. In yet further embodiments, the predictive gene signature includes at least 5 of the previously recited biomarkers, e.g., CKLF, COL7A1, GRAMD4, JAM3 and PCDH1; APBB2, CEP152, DYSF, IL10 and TYROBP; CYP4F3, HYAL2, ITFG3, KLHL17 and KRT24; NCBP1, SPTA1, TMIGD2, IL10 and JAM3; or CCL26, PHOSPHO2, SPTA1, TMIGD2 and ZIC5.

In other embodiments, the predictive gene signature may include 2 or more of biomarkers ERGIC3, PDGFB, PSENEN, SATB1, SNX11, TMEM79 or YTHDF1, or any sub-combination thereof, e.g., ERGIC3 and PDGFB; ERGIC3 and PSENEN; ERGIC3 and SATB1; ERGIC3 and SNX11; ERGIC3 and TMEM79; ERGIC3 and YTHDF1; PDGFB and PSENEN; PDGFB and SATB1; PDGFB and SNX11; PDGFB and TMEM79; PDGFB and YTHDF1; PSENEN and SATB1; PSENEN and SNX11; PSENEN and TMEM79; PSENEN and YTHDF1; SATB1 and SNX11; SATB1 and TMEM79; SATB1 and YTHDF1; SNX11 and TMEM79; SNX11 and YTHDF1; or TMEM79 and YTHDF1. In other embodiments, the predictive gene signature includes at least 3 biomarkers, for example, ERGIC3, PDGFB and PSENEN; SATB1, SNX11 and TMEM79; SNX11, TMEM79 and YTHDF1; or ERGIC3, PDGFB and SATB1. In further embodiments, the predictive gene signature includes at least 4 biomarkers, for example, ERGIC3, PDGFB, PSENEN and SATB1; SNX11, TMEM79, YTHDF1 and ERGIC3; or ERGIC3, PDGFB, PSENEN and YTHDF1. In further embodiments, the predictive gene signature includes at least 5 biomarkers, for example, ERGIC3, PDGFB, PSENEN, SATB1 and SNX11; ERGIC3, PDGFB, PSENEN, SATB1 and TMEM79; or PSENEN, SATB1, SNX11, TMEM79 and YTHDF1. In yet further embodiments, the predictive gene signature includes at least 6 biomarkers, for example, ERGIC3, PDGFB, PSENEN, SATB1, SNX11 and TMEM79; PDGFB, PSENEN, SATB1, SNX11, TMEM79 and YTHDF1; or ERGIC3, PSENEN, SATB1, SNX11, TMEM79 and YTHDF1. In yet another embodiment, the predictive gene signature includes 7 biomarkers, for example, ERGIC3, PDGFB, PSENEN, SATB1, SNX11, TMEM79 and YTHDF1.

In various embodiments, the biomarker is not one or more of SPTA1, PAPLN, PCDH1, TMIGD2 and/or KRT24. In a particular embodiment, the biomarker is not SPTA1, PAPLN, PCDH1, TMIGD2 and KRT24. In one embodiment, the biomarker is not SPTA1. In another embodiment, the biomarker is not PAPLN. In another embodiment, the biomarker is not PCDH1. In an alternative embodiment, the biomarker is not TMIGD2. In yet another embodiment, the biomarker is not KRT24.

In particular embodiments, the predictive gene signature may include 2 or more of biomarkers ABI3, ANG, APBB2, CCL26, CDC20, CEP152, CFL1, CKLF, COL7A1, CYP4F3, DYSF, GNAT1, GRAMD4, HYAL2, IL10, ITFG3, JAM3, KLHL17, MAD2L1BP, MANSC1, MOBKL1B, NCBP1, NMU, PHOSPHO2, TYROBP, ZIC5, ERGIC3, PDGFB, PSENEN, SATB1, SNX11, TMEM79, YTHDF1, EDIL3 and TUBB6, e.g., ABI3 and ANG; GRAMD4 and HYAL2; NMU and PHOSPHO2; ZIC5 and PSENEN; or SNX11 and MOBKL1B. In other embodiments, the predictive gene signature includes at least 3 of the previously recited biomarkers, e.g., APBB2, CDC20 and CKLF; COL7A1, DYSF and GNAT1; NCBP1, SATB1 and EDIL3; PSENEN, DYSF and GNAT1; MANSC1, ZIC5 and CFL1; or CKLF, GRAMD4 and NMU. In other embodiments, the predictive gene signature includes at least 4 of the previously recited biomarkers, e.g., ANG, CCL26, CEP152 and JAM3; APBB2, CYP4F3, ITFG3 and TYROBP; CYP4F3, MANSC1, PDGFB and YTHDF1; TUBB6, DYSF, PHOSPHO2 and CDC20; or CKLF, KLHL17, HYAL2 and ZIC5. In yet further embodiments, the predictive gene signature includes at least 5 of the previously recited biomarkers, e.g., IL10, CEP152, COL7A1, TYROBP and ERGIC3; TMEM79, SNX11, PSENEN, GNAT1 and GRAMD4; JAM3, SNX11, KLHL17, MOBKL1B and ERGIC3; or NMU, PHOSPHO2, PDGFB, CFL1 and ANG.

In various methods and or kits of the invention, the biomarker is not ABI3, is not ANG, is not APBB2, is not CCL26, is not CDC20, is not CEP152, is not CFL1, is not CKLF, is not COL7A1, is not CYP4F3, is not DYSF, is not GNAT1, is not GRAMD4, is not HYAL2, is not IL10, is not ITFG3, is not JAM3, is not KLHL17, is not KRT24, is not MAD2L1BP, is not MANSC1, is not MOBKL1B, is not NCBP1, is not NMU, is not PCDH1, is not PHOSPHO2, is not SPTA1, is not TMIGD2, is not TYROBP, is not ZIC5, is not ERGIC3, is not PDGFB, is not PSENEN, is not SATB1, is not SNX11, is not TMEM79, is not EDIL3, is not PAPLN, is not TUBB6 and/or is not YTHDF1.

Any suitable analytical method, can be utilized in the methods of the invention to assess (directly or indirectly) the level of expression of a biomarker in a sample. In some embodiments, a difference is observed between the level of expression of a biomarker, as compared to the control level of expression of the biomarker. In one embodiment, the difference is greater than the limit of detection of the method for determining the expression level of the biomarker. In further embodiments, the difference is greater than or equal to the standard error of the assessment method, and preferably the difference is at least about 2-, about 3-, about 4-, about 5-, about 6-, about 7-, about 8-, about 9-, about 10-, about 15-, about 20-, about 25-, about 100-, about 500- or about 1000-fold greater than the standard error of the assessment method. In some embodiments, the level of expression of the biomarker in a sample as compared to a control level of expression is assessed using parametric or nonparametric descriptive statistics, comparisons, regression analyses, and the like.

In some embodiments, a difference in the level of expression of the biomarker in the sample derived from the subject is detected relative to the control, and the difference is about 5%, about 10%, about 15%, about 20%, about 25%, about 30%, about 40%, about 50%, about 60%, about 70%, about 80%, or about 90% less than the expression level of the biomarker in the control sample.

The level of expression of a biomarker, for example, as set forth in Table 1, in a sample obtained from a subject may be assayed by any of a wide variety of techniques and methods, which transform the biomarker within the sample into a moiety that can be detected and/or quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, immunoblotting, Western blotting, Northern blotting, electron microscopy, mass spectrometry, e.g., MALDI-TOF and SELDI-TOF, immunoprecipitations, immunofluorescence, immunohistochemistry, enzyme linked immunosorbent assays (ELISAs), e.g., amplified ELISA, quantitative blood based assays, e.g., serum ELISA, quantitative urine based assays, flow cytometry, Southern hybridizations, array analysis, and the like, and combinations or sub-combinations thereof.

In one embodiment, the level of expression of the biomarker in a sample is determined by detecting a transcribed polynucleotide, or portion thereof, e.g., mRNA, or cDNA, of the biomarker gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, quantitative PCR analysis, RNase protection assays (Melton et al., *Nuc. Acids Res.* 12:7035), Northern blotting and in situ hybridization. Other suitable systems for mRNA sample analysis include microarray analysis (e.g., using Affymetrix's microarray system or Illumina's BeadArray Technology).

In one embodiment, the level of expression of the biomarker is determined using a nucleic acid probe. The term "probe", as used herein, refers to any molecule that is capable of selectively binding to a specific biomarker. Probes can be synthesized by one of skill in the art, or derived from appropriate biological preparations. Probes can be specifically designed to be labeled, by addition or incorporation of a label. Examples of molecules that can be utilized as probes include, but are not limited to, RNA, DNA, proteins, antibodies, and organic molecules.

As indicated above, isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to the biomarker mRNA. The nucleic acid probe can be, for example, a full-length cDNA, or a portion thereof, such as an oligonucleotide of at least about 7, 10, 15, 20, 25, 30, 35, 40, 45, 50, 100, 250 or about 500 nucleotides in length and sufficient to specifically hybridize under appropriate hybridization conditions to the biomarker genomic DNA. In a particular embodiment the probe will bind the biomarker genomic DNA under stringent conditions. Such stringent conditions, for example, hybridization in 6× sodium chloride/sodium citrate (SSC) at about 45° C., followed by one or more washes in 0.2×SSC, 0.1% SDS at 50-65° C., are known to those skilled in the art and can be found in Current Protocols in Molecular Biology, Ausubel et al., eds., John Wiley & Sons, Inc. (1995), sections 2, 4, and 6, the teachings of which are hereby incorporated by reference herein. Additional stringent conditions can be found in Molecular Cloning: A Laboratory Manual, Sambrook et al., Cold Spring Harbor Press, Cold Spring Harbor, N.Y. (1989), chapters 7, 9, and 11, the teachings of which are hereby incorporated by reference herein.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface, for example, in an Affymetrix gene chip array, and the probe(s) are contacted with mRNA. A skilled artisan can readily adapt mRNA detection methods for use in determining the level of the biomarker mRNA.

The level of expression of the biomarker in a sample can also be determined using methods that involve the use of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules. These approaches are especially useful for the detection of nucleic acid molecules if such molecules are present in very low numbers. In particular aspects of the invention, the level of expression of the biomarker is determined by quantitative fluorogenic RT-PCR (e.g., the TaqMan™ System). Such methods typically utilize pairs of oligonucleotide primers that are specific for the biomarker. Methods for designing oligonucleotide primers specific for a known sequence are well known in the art.

The expression levels of biomarker mRNA can be monitored using a membrane blot (such as used in hybridization analysis such as Northern, Southern, dot, and the like), or microwells, sample tubes, gels, beads or fibers (or any solid support comprising bound nucleic acids). See, for example, U.S. Pat. Nos. 5,770,722, 5,874,219, 5,744,305, 5,677,195 and 5,445,934, the contents of which as they relate to these assays are incorporated herein by reference. The determination of biomarker expression level may also comprise using nucleic acid probes in solution.

In one embodiment of the invention, microarrays are used to detect the level of expression of a biomarker. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138, 5,800,992 and 6,020,135, 6,033,860, and 6,344,316, the contents of which as they relate to these assays are incorporated herein by reference. High-density oligonucleotide arrays are particularly useful for determining the gene expression profile for a large number of RNA's in a sample.

Expression of a biomarker can also be assessed at the protein level, using a detection reagent that detects the protein product encoded by the mRNA of the biomarker, directly or indirectly. For example, if an antibody reagent is available that binds specifically to a biomarker protein product to be detected, then such an antibody reagent can be used to detect the expression of the biomarker in a sample from the subject, using techniques, such as immunohistochemistry, ELISA, FACS analysis, and the like.

Other known methods for detecting the biomarker at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitation reactions, immunodiffusion (single or double), immunoelectrophoresis, radioimmunoassay (RIA), enzyme-linked immunosorbent assays (ELISAs), immunofluorescent assays, and Western blotting.

Proteins from samples can be isolated using a variety of techniques, including those well known to those of skill in the art. The protein isolation methods employed can, for example, be those described in Harlow and Lane (Harlow and Lane, 1988, Antibodies: A Laboratory Manual, Cold Spring Harbor Laboratory Press, Cold Spring Harbor, N.Y.).

In one embodiment, antibodies, or antibody fragments, are used in methods such as Western blots or immunofluorescence techniques to detect the expressed proteins. Antibodies for determining the expression of the biomarkers of the invention are commercially available. For example, ERGIC-3 specific antibodies are commercially available from Santa Cruz Biotechnology, Inc. (ERGIC-3 (P-16)

Antibody and ERGIC-3 (Y-23) Antibody) and Sigma Aldrich (HPA015968, AV47209, HPA015242, SAB4502151). PDGFB specific antibodies are commercially available from Santa Cruz Biotechnology, Inc. (e.g., PDGF-B (C-5) Antibody and PDGF-B (H-55) Antibody) and Sigma Aldrich (e.g., HPA011972, SAB2101755 and SAB2900226). PSENEN specific antibodies are commercially available from Origene (e.g., Catalog No. TA306367) and Sigma Aldrich (e.g., PRS3981, WH0055851M1, PRS3979 and P5622). Further by way of example, SATB1 antibodies are commercially available from, for example, Abcam (Catalog No. ab49061, ab92307 and ab70004), Abnova Corporation (Catalog No. PAB13379), and Aviva Systems Biology (Catalog No. ARP33362_P050). SNX11 antibodies are commercially available from Abcam (Catalog Nos. ab4128, ab67578, ab76816 and ab76762) and Abnova Corporation (Catalog Nos. PAB6362 and H00029916-B01). TMEM79 Antibodies are commercially available from, for example, Abcam (Catalog No. ab81539) and Sigma Aldrich (Catalog No. SAB2102475). Finally, YTHDF1 antibodies are commercially available from, for example, Abnova Corporation (Catalog No. PAB17446), Aviva Systems Biology (Catalog No. ARP57032_P050) and Santa Cruz Biotechnology (Catalog No. sc-86026).

It is generally preferable to immobilize either the antibody or proteins on a solid support for Western blots and immunofluorescence techniques. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

Other standard methods include immunoassay techniques which are well known to one of ordinary skill in the art and may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays to determine the level of expression of the biomarker, may be labeled with a detectable label. The term "labeled", with regard to the probe or antibody, is intended to encompass direct labeling of the probe or antibody by incorporation of a label (e.g., a radioactive atom), coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In one embodiment, the antibody is labeled, e.g. a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair (e.g., biotin-streptavidin), or an antibody fragment (e.g. a single-chain antibody, or an isolated antibody hypervariable domain) which binds specifically with the biomarker is used.

In one embodiment of the invention, proteomic methods, e.g., mass spectrometry, are used. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., the biomarker) are ionized by different methods (e.g., by impacting them with an electron beam), resulting in the formation of charged particles (ions). The mass-to-charge ratio of the particles is then calculated from the motion of the ions as they transit through electromagnetic fields.

For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis biomarkers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to determine the expression level of a biomarker at the protein level.

Furthermore, in vivo techniques for determination of the expression level of the biomarker include introducing into a subject a labeled antibody directed against the biomarker, which binds to and transforms the biomarker into a detectable molecule. As discussed above, the presence, level, or even location of the detectable biomarker in a subject may be detected by standard imaging techniques.

In general, where a difference in the level of expression of a biomarker and the control is to be detected, it is preferable that the difference between the level of expression of the biomarker in a sample from a subject having breast cancer and being treated with eribulin, an analog thereof, or a pharmaceutically acceptable salt thereof (e.g., eribulin mesylate), or being considered for treatment with eribulin, an analog thereof, or a pharmaceutically acceptable salt thereof (e.g., eribulin mesylate), and the amount of the biomarker in a control sample, is as great as possible. Although this difference can be as small as the limit of detection of the method for determining the level of expression, it is preferred that the difference be greater than the limit of detection of the method or greater than the standard error of the assessment method, and preferably a difference of at least about 2-, about 3-, about 4-, about 5-, about 6-, about 7-, about 8-, about 9-, about 10-, about 15-, about 20-, about 25-, about 100-, about 500-, 1000-fold greater than the standard error of the assessment method.

In another aspect, the present invention provides methods for determining whether eribulin, an analog thereof, or a pharmaceutically acceptable salt thereof (e.g., eribulin mesylate), may be used to treat a subject having breast cancer by determining and/or identifying whether the subject carries at least one gene, selected from the group of biomarkers set forth in Table 1, which contains a polymorphism, for example, a mutation, that results in decreased expression and/or reduced function of the encoded protein, wherein the presence of a polymorphism in at least one gene is indicative that eribulin, an analog thereof, or a pharmaceutically acceptable salt there, will be effective in treating a subject. In another aspect, the present invention provides methods for predicting whether eribulin, an analog thereof, or a pharmaceutically acceptable salt thereof (e.g., eribulin mesylate), will be effective in treating a subject having breast cancer by assaying a sample derived from the subject to determine whether the subject carries at least one gene, selected from the group of biomarkers set forth in Table 1, which contains a polymorphism, for example, a mutation, that results in decreased expression and/or reduced function of the encoded protein, wherein the presence of the polymorphism in at least one gene in said sample is indicative that eribulin, an analog thereof, or a pharmaceutically acceptable salt there, may be used to treat said subject. In a further aspect, a method is provided for predicting whether eribulin, an analog thereof, or a pharmaceutically acceptable salt thereof, will be effective in treating a subject having breast cancer, the method comprising determining the presence of a polymorphism that results in reduced expression and/or function in a gene encoding a biomarker selected from the group of biomarkers listed in Table 1 in a sample derived from said subject, and predicting that eribulin, an analog thereof, or a pharmaceutically acceptable salt thereof, may be used to treat said subject based on the presence of the polymorphism.

In a further aspect, the present invention provides methods for determining the sensitivity of a breast tumor to treatment with eribulin, an analog thereof, or a pharmaceutically acceptable salt thereof by determining and/or identifying whether said tumor contains a polymorphism in at least one gene resulting in reduced expression and/or function of the encoded protein, wherein the gene is selected from the group of biomarkers set forth in Table 1. Identification and/or determination that the tumor contains such a polymorphism is indicative of sensitivity of said tumor to treatment with eribulin, an analog thereof, or a pharmaceutically acceptable salt thereof. In yet another aspect, the present invention is directed to methods for treating a subject having breast cancer with eribulin, an analog thereof, or a pharmaceutically acceptable salt thereof by identifying whether a sample derived from said subject has at least one gene, selected from the group of biomarkers set forth in Table 1, which contains a polymorphism resulting in reduced expression and/or function of the encoded protein and administering a therapeutically effective amount of eribulin, an analog thereof, or a pharmaceutically acceptable salt thereof (e.g., eribulin mesylate) to the subject when the polymorphism is identified.

In another aspect, the present invention provides methods for determining whether eribulin, an analog thereof, or a pharmaceutically acceptable salt thereof (e.g., eribulin mesylate), may be used to treat a subject having breast cancer by determining and/or identifying whether the subject carries at least one gene, selected from the group of biomarkers set forth in Table 1, which contains a null mutation, wherein the presence of a null mutation in at least one gene is indicative that eribulin, an analog thereof, or a pharmaceutically acceptable salt there, will be effective in treating the subject. In another aspect, the present invention provides methods for predicting whether eribulin, an analog thereof, or a pharmaceutically acceptable salt thereof (e.g., eribulin mesylate), may be used to treat a subject having breast cancer by assaying a sample derived from the subject to determine whether the subject carries at least one gene, selected from the group of biomarkers set forth in Table 1, which contains a null mutation, wherein the presence of a null mutation in at least one gene in said sample is indicative that eribulin, an analog thereof, or a pharmaceutically acceptable salt there, will be effective in treating the subject. In a further aspect, a method is provided for predicting whether eribulin, an analog thereof, or a pharmaceutically acceptable salt thereof, may be used to treat a subject having breast cancer, the method comprising determining the presence of a null mutation in a biomarker selected from the group of biomarkers listed in Table 1 in a sample derived from said subject, and predicting that eribulin, an analog thereof, or a pharmaceutically acceptable salt thereof, may be used to treat said subject based on the presence of said null mutation.

In a further aspect, the present invention provides methods for determining the sensitivity of a breast tumor to treatment with eribulin, an analog thereof, or a pharmaceutically acceptable salt thereof by determining and/or identifying whether said tumor contains a null mutation in at least one gene, selected from the group of biomarkers set forth in Table 1. Identification and/or determination that the tumor contains a null mutation is indicative of sensitivity of said tumor to treatment with eribulin, an analog thereof, or a pharmaceutically acceptable salt thereof. In yet another aspect, the present invention is directed to methods for treating a subject having breast cancer with eribulin, an analog thereof, or a pharmaceutically acceptable salt thereof by identifying whether a sample derived from said subject has at least one gene, selected from the group of biomarkers set forth in Table 1, which contains a null mutation and administering a therapeutically effective amount of eribulin, an analog thereof, or a pharmaceutically acceptable salt thereof (e.g., eribulin mesylate) to the subject when a null mutation is identified.

As used herein, the term "null mutation" refers to a mutation in a genomic DNA sequence that causes the product of the gene to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control the gene and/or the product of the gene so as to cause the gene product to be non-functional or largely absent. The null mutation may be a deletion of the native gene or a portion thereof. These sequence disruptions or modifications may include insertions, missense, frameshift, deletion, or substitutions, or replacements of DNA sequence, or any combination thereof. For example, the null mutation may result in the insertion of a premature stop codon. The null mutation results in functional inactivation of the gene product by, for example, inhibiting its production partially or completely; disrupting, inhibiting or curtailing the translation of the protein product, or resulting in a nonfunctional protein. The null mutation may be a pre-existing mutation in the subject or a mutation which arose in a tumor. The presence of a null mutation in a biomarker can be indicated by a lack of detectable expression of the biomarker. However, the presence of a null mutation can be determined by other methods. For example, in such embodiments, a sample of the subject's DNA may be sequenced in order to identify the presence of a null mutation. Any of the well-known methods for sequencing the biomarkers may be used in the methods of the invention, such as the methods described in, for example, U.S. Pat. No. 5,075,216, Engelke et al. (1988) *Proc. Natl. Acad. Sci. U.S.A.* 85, 544-548 and Wong et al. (1987) *Nature* 330, 384-386; Maxim and Gilbert (1977) *Proc. Natl. Acad. Sci. U.S.A.* 74:560; or Sanger (1977) *Proc. Natl. Acad. Sci. U.S.A.* 74:5463. In addition, any of a variety of automated sequencing procedures can be utilized see, e.g., Naeve, C. W et al. (1995) *Biotechniques* 19:448, including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159.

Determining the presence or absence of a null mutation in the sample may also be accomplished using various techniques such as polymerase chain reaction (PCR) amplification reaction, reverse-transcriptase PCR analysis, single-strand conformation polymorphism analysis (SSCP), mismatch cleavage detection, heteroduplex analysis, Southern blot analysis, Western blot analysis, deoxyribonucleic acid sequencing, restriction fragment length polymorphism analysis, haplotype analysis, serotyping, and combinations or sub-combinations thereof.

Any suitable sample obtained from a subject having breast cancer can be used to assess the level of expression, including a lack of expression, of the biomarker, for example, a biomarker provided in Table 1. For example, the sample may be any fluid or component thereof, such as a fraction or extract, e.g., blood, plasma, lymph, cystic fluid, urine, nipple aspirates, or fluids collected from a biopsy (e.g., lump biopsy), obtained from the subject. In a typical situation, the fluid may be blood, or a component thereof, obtained from the subject, including whole blood or components thereof, including, plasma, serum, and blood cells, such as red blood cells, white blood cells and platelets. The sample may also be any tissue or fragment or component thereof, e.g., breast tissue, connective tissue, lymph tissue or muscle tissue obtained from the subject.

Techniques or methods for obtaining samples from a subject are well known in the art and include, for example, obtaining samples by a mouth swab or a mouth wash; drawing blood; or obtaining a biopsy. Isolating components of fluid or tissue samples (e.g., cells or RNA or DNA) may be accomplished using a variety of techniques.

The sample from the cancer may be obtained by biopsy of the patient's cancer. In certain embodiments, more than one sample from the patient's tumor is obtained in order to acquire a representative sample of cells for further study. For example, a patient with breast cancer may have a needle biopsy to obtain a sample of cancer cells. Several biopsies of the tumor may be used to obtain a sample of cancer cells. In other embodiments, the sample may be obtained from surgical excision of the tumor. In this case, one or more samples may be taken from the excised tumor for analysis using the methods of the invention.

After the sample is obtained, it may be further processed. The cancer cells may be cultured, washed, or otherwise selected to remove normal tissue. The cells may be trypsinized to remove the cells from the tumor sample. The cells may be sorted by fluorescence activated cell sorting (FACS) or other cell sorting technique. The cells may be cultured to obtain a greater number of cells for study. In certain instances the cells may be immortalized. For some applications, the cells may be frozen or the cells may be embedded in paraffin.

II. Treatment with Eribulin, Analogs Thereof, or Pharmaceutically Acceptable Salts Thereof (e.g., Eribulin Mesylate)

Given the observation that the expression levels of certain biomarkers, for example, those set forth in Table 1, in a subject having breast cancer influences the responsiveness of the subject to eribulin, an analog thereof, or a pharmaceutically acceptable salt thereof (e.g., eribulin mesylate), a skilled artisan can select an appropriate treatment regimen for the subject based on the expression levels of the biomarkers in the subject. Accordingly, the present invention provides methods for treating a subject having breast cancer by (i) identifying a subject having breast cancer in which at least one biomarker selected from the group of biomarkers listed in Table 1 has a low level of expression and (ii) administering a therapeutically effective amount of eribulin, an analog thereof, or a pharmaceutically acceptable salt thereof (e.g., eribulin mesylate), to the subject. In another aspect, the present invention provides methods for treating a subject having breast cancer by (i) assaying a sample derived from the subject to determine the level of expression of at least one biomarker selected from the group of biomarkers listed in Table 1 and (ii) administering a therapeutically effective amount of eribulin, an analog thereof, or a pharmaceutically acceptable salt thereof (e.g., eribulin mesylate) to the subject when a low level of expression of the at least one biomarker is detected in the sample.

In various embodiments, the subject may have been previously treated with eribulin, an analog thereof, or a pharmaceutically acceptable salt thereof (e.g., eribulin mesylate). In other embodiments, the subject may be under consideration for treatment with eribulin, an analog thereof, or a pharmaceutically acceptable salt thereof (e.g., eribulin mesylate), for the first time. The level of expression of one or more, e.g., at least 1, 2, 3, 4, 5, 6, 7, 8, 9 or 10, biomarkers identified in Table 1 is determined. If level of expression of at least one biomarker (e.g., 1, 2, 3, 4, 5, 6, 7, 8, 9 or 10 biomarkers) is determined to be a low level of expression, treatment with eribulin, an analog thereof, or a pharmaceutically acceptable salt thereof (e.g., eribulin mesylate), is likely to be efficacious. However, it is not necessary that all of the biomarkers assayed have a low level of expression as compared to the respective control. For example, while certain biomarkers may be present at normal or high levels of expression, treatment with eribulin, an analog thereof, or a pharmaceutically acceptable salt thereof (e.g., eribulin mesylate), may be indicated when, for example, a low level of expression is present for at least 1, at least 2, at least 3, at least 4, at least 5, at least 6, at least 7, at least 8, at least 9 or at least 10 biomarkers.

When a low level of expression of one or more of the biomarkers of the invention is found (e.g., due to the presence of a null mutation in the biomarker gene) in a sample derived from a subject having breast cancer, the subject may be treated with eribulin, having the following the structure, with a pharmaceutically acceptable salt of eribulin, or with an eribulin analog or pharmaceutically acceptable thereof.

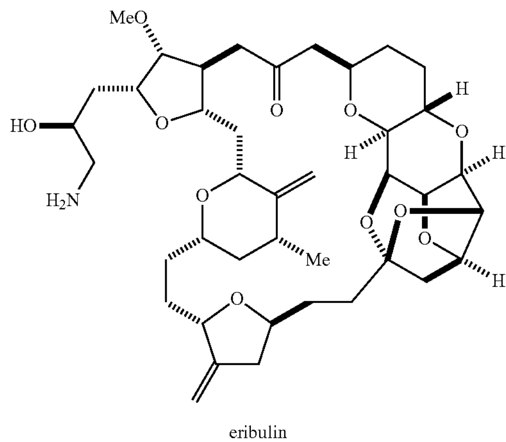

eribulin

In some embodiments, a pharmaceutically acceptable salt of eribulin is administered to the subject, such as eribulin mesylate.

The treatment regimen for eribulin, an analog thereof, or a pharmaceutically acceptable salt thereof (e.g., eribulin mesylate), that is selected typically includes at least one of the following parameters and more typically includes many or all of the following parameters: the dosage, the formulation, the route of administration and/or the frequency of administration. Selection of the particular parameters of the treatment regimen can be based on known treatment parameters for eribulin previously established in the art such as those described in the Dosage and Administration protocols set forth in the FDA Approved Label for HALAVEN®, the entire contents of which are incorporated herein by reference. For example, eribulin mesylate can be administered intravenously on Days 1 and 8 of a 21 day cycle, for example at a dose of 1.4 $mg/m^2$, or if a dose reduction is indicated (e.g., for hepatic or renal impairment), at a dose of 0.7 $mg/m^2$ or 1.1 $mg/m^2$. Various modifications to dosage, formulation, route of administration and/or frequency of administration can be made based on various factors including, for example, the disease, age, sex, and weight of the patient, as well as the severity or stage of cancer (see, for example, U.S. Pat. No. 6,653,341 and U.S. Pat. No. 6,469,182, the entire contents of each of which are hereby incorporated herein by reference).

As used herein, the term "therapeutically effective amount" means an amount of eribulin, an analog thereof, or a pharmaceutically acceptable salt thereof (e.g., eribulin mesylate) as described herein, that is capable of treating breast cancer. The dose of a compound to be administered according to this invention will, of course, be determined in light of the particular circumstances surrounding the case including, for example, the compound administered, the route of administration, condition of the patient, and the pathological condition being treated, for example, the stage of breast cancer.

For administration to a subject, eribulin, an analog thereof, or a pharmaceutically acceptable salt thereof (e.g., eribulin mesylate), typically is formulated into a pharmaceutical composition comprising eribulin, an analog thereof, or a pharmaceutically acceptable salt thereof, and a pharmaceutically acceptable carrier. Therapeutic compositions typically should be sterile and adequately stable under the conditions of manufacture and storage. Pharmaceutical compositions also can be administered in a combination therapy, i.e., combined with other agents, such as those agents set forth below (see, for example, U.S. Pat. No. 6,214,865 and U.S. Pat. No. 6,653,341, the entire contents of each of which are hereby incorporated herein by reference).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral (e.g., intravenous, intramuscular, subcutaneous, intrathecal) administration (e.g., by injection or infusion). Depending on the route of administration, the active compound may be coated in a material to protect the compound from the action of acids and other natural conditions that may inactivate the compound.

The pharmaceutical compositions may include one or more pharmaceutically acceptable salts, as defined above.

There are numerous types of anti-cancer approaches that can be used in conjunction with eribulin, an analog thereof, or a pharmaceutically acceptable salt thereof (e.g., eribulin mesylate) treatment, according to the invention. These include, for example, treatment with chemotherapeutic agents, biological agents (e.g., hormonal agents, cytokines (such as interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery, as described in more detail in U.S. Pat. No. 6,653,341 B1 and U.S. Publ. No. 2006/0104984 A1, the teachings of which are incorporated herein by reference in their entirety.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of eribulin, an analog thereof, or a pharmaceutically acceptable salt thereof (e.g., eribulin mesylate), with these approaches. For example, if a drug is normally administered as a sole therapeutic agent, when combined with eribulin, according to the invention, it may be desirable to decrease the dosage of the drug, as can be determined by those of skill in this art. Examples of the methods of the invention, as well as compositions that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with eribulin, an analog thereof, or a pharmaceutically acceptable salt thereof, according to the invention. Specific, non-limiting examples of these classes of drugs, as well as cancers that can be treated by their use, are as follows.

Numerous approaches for administering anti-cancer drugs are known in the art, and can readily be adapted for use in the present invention. In the case that one or more drugs are to be administered in conjunction with eribulin, an analog thereof, or a pharmaceutically acceptable salt thereof (e.g., eribulin mesylate), for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans.

Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug (or a subset of drugs).

Kits of the Invention

The invention also provides compositions and kits for predicting whether eribulin, an analog thereof, or a pharmaceutically acceptable salt thereof (e.g., eribulin mesylate), may be used to treat a subject having breast cancer. These kits include reagents for determining the level of expression of at least one, for example, 1, 2, 3, 4, 5, 6, 7, 8, 9 or 10, biomarker(s) selected form the group of biomarkers listed in Table 1 and instructions for use of the kit to predict whether eribulin, an analog thereof, or a pharmaceutically acceptable salt thereof (e.g., eribulin mesylate), may be used to treat a subject having breast cancer.

The kits of the invention may optionally comprise additional components useful for performing the methods of the invention. By way of example, the kits may comprise reagents for obtaining a biological sample from a subject, a control sample, and/or eribulin, an analog thereof, or a pharmaceutically acceptable salt thereof (e.g., eribulin mesylate).

In one embodiment, the reagents for determining the expression level of at least one biomarker in a biological sample from the subject comprises a nucleic acid preparation sufficient to detect expression of a nucleic acid, e.g., mRNA, encoding the biomarker. This nucleic acid preparation includes at least one, and may include more than one, nucleic acid probe or primer, the sequence(s) of which is designed such that the nucleic acid preparation can detect the expression of nucleic acid, e.g., mRNA, encoding the biomarker in the sample from the subject. A preferred nucleic acid preparation includes two or more PCR primers that allow for PCR amplification of a segment of the mRNA encoding the biomarker of interest. In other embodiments, the kit includes a nucleic acid preparation for each of at least 1, 2, 3, 4, 5, 6, 7, 8, 9 or 10 biomarkers provided in Table 1.

Alternatively, the reagents for detecting expression levels in the subject of one or more biomarkers predictive of responsiveness to eribulin, an analog thereof, or a pharmaceutically acceptable salt thereof (e.g., eribulin mesylate), can comprise a reagent that detects the gene product of the nucleic acid encoding the biomarker(s) of interest sufficient to distinguish it from other gene products in a sample from the subject. A non-limiting example of such a reagent is a monoclonal antibody preparation (comprising one or more monoclonal antibodies) sufficient to detect protein expression of at least one biomarker in a sample from the subject, such as a peripheral blood mononuclear cell sample.

The means for determining the expression level of the biomarkers of Table 1 can also include, for example, buffers or other reagents for use in an assay for evaluating expression (e.g., at either the nucleic acid or protein level).

In another embodiment, the kit can further comprise eribulin, an analog thereof, or a pharmaceutically acceptable salt thereof (e.g., eribulin mesylate), for treating breast cancer or another cancer, as described herein in the subject.

Preferably, the kit is designed for use with a human subject.

The present invention is further illustrated by the following examples which should not be construed as further limiting. The contents of all references, patents and published patent applications cited throughout this application, as well as the Figures and the Appendix of sequences provided herein, are expressly incorporated herein by reference in their entirety.

EXAMPLES

Example 1

Identification of Resistance Biomarkers for Treatment with Eribulin siRNA techniques were employed to "knock down" expression of certain genes and assess the sensitivity of the resulting knock down cells to eribulin. Based on these studies, the expression of those genes set forth in Table 1 were identified as being associated with the sensitivity of breast cancer cells to treatment with eribulin, an analog thereof, or a pharmaceutically acceptable salt thereof.

siRNA Transfection Optimization and Assay Development

Transfection conditions for human breast cancer cell lines MDA-MB-231 (ATCC Catalog No. HTB26™) and BT-549 (ATCC Catalog No. HTB122™) were optimized using transfection reagent DharmaFect 1 from Dharmacon. The MDA-MB-231 and BT-549 cell lines have been reported to be Estrogen Receptor (ER) negative, Progesterone Receptor (PR) negative and HER-2 negative (triple negative). As a non-targeting negative control we used Silencer Negative Control #1 siRNA from Applied Biosystems. The siGENOME TOX (siTOX) Transfection Control (Dharmacon), an RNA duplex designed to induce cell death, was used as a positive control for cell proliferation assays. A reverse transfection procedure in which siRNA was first mixed with transfection reagent and then cells were added to the well, was used in all experiments. Cell viability was compared in cells treated with medium, negative control siRNA and siTOX reagent combined with different amount of DharmaFect 1. Final selected transfection conditions were as follows: MDA-MB-231 cells at 0.035 μl of DharmaFect 1 per well, while BT-549 cells at 0.05 μl of DharmaFect 1 per well. Assays and library screening were performed at 50 nM final concentration of siRNAs. Efficacy of transfection was further confirmed by qPCR with control SMARTpool siRNA reagents targeting PPIA and GAPDH genes (Dharmacon).

High-Throughput siRNA Screening

The whole human genome siRNA library was purchased from Dharmacon. The library was diluted to 5 μM. Each well contained 4 SMARTpool siRNA reagents, each directed against a particular gene (four siRNAs targeting the same gene in a single well). More then 18,500 human genes were targeted with this library. 4 μl of each set of siRNAs from the library plates were transferred to 384-well master plates containing 36 μl OPTI-MEM medium per well. 40 μl of diluted DharmaFect 1 reagent were added to each well of the master plate and mixed. 10 μl of siRNA and transfection reagent mixture per well were distributed into five screening plates. After 10 min incubation, cells in 40 μl of growth medium were added to each well. Each screening plate included several replicates of negative control siRNA, positive control siTOX as well as medium plus transfection reagent (no siRNA) containing wells. After a 24 hour incubation, 3 screening plates received 10 μl of DMSO diluted in cell growth medium, while 2 repeats were treated with 10 μl of eribulin mesylate (E7389) in growth medium, yielding a final concentration corresponding to the $IC_{20}$ for E7389 for the cell line tested (0.75 nM E7389 for MDA-MB-231; eribulin was provided in a stock solution of DMSO and diluted in growth medium) (see FIG. 1). Cell viability was determined at 96 hours after transfection by CellTiter-Glo luminescent assay from Promega. 10 μl of CellTiter-Glo solution per well were used. Plates were mixed for 2 minutes on a horizontal shaker, incubated for 10 minutes and read on an EnVision® multilabel plate reader from PerkinElmer.

Identification of Primary Hits

Figure 2:
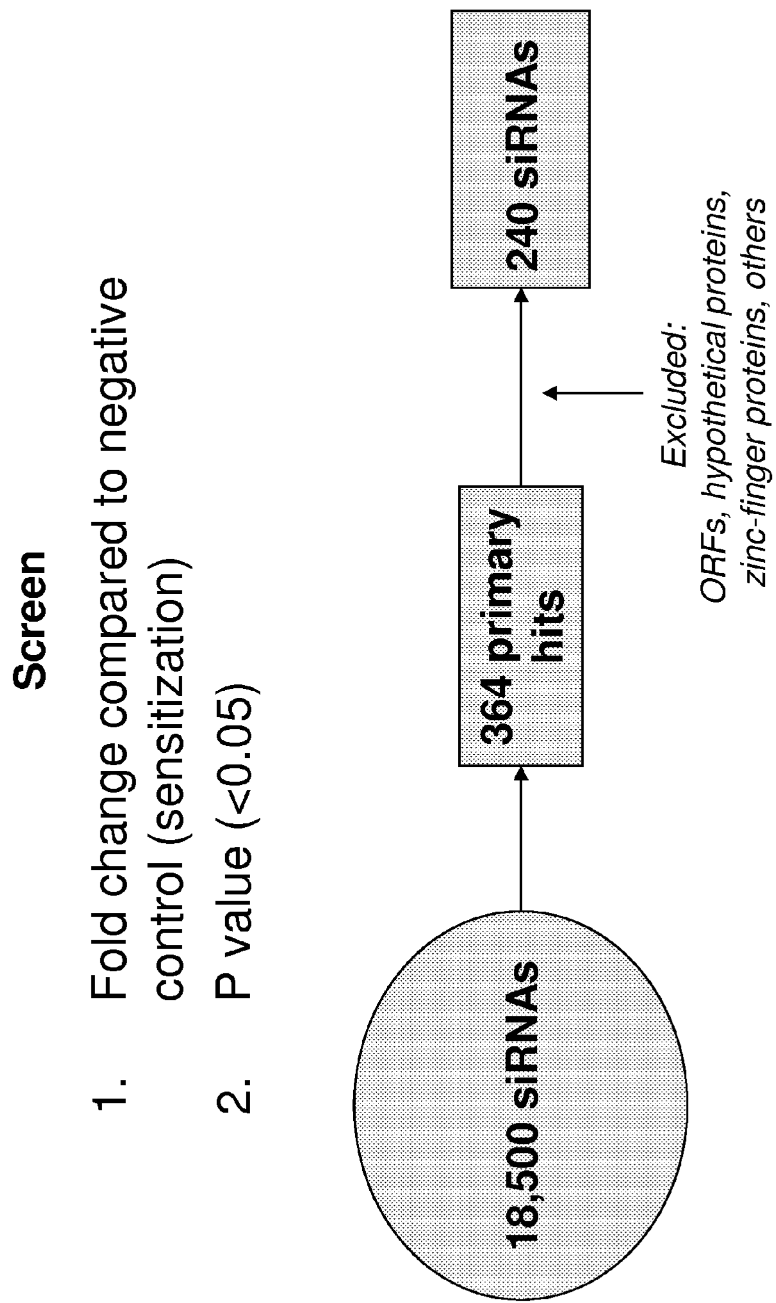
FIG. 2 depicts the identification and selection of certain genes for further consideration as biomarkers of efficacy of eribulin, an analog thereof, or a pharmaceutically acceptable salt thereof.
Figure 3:
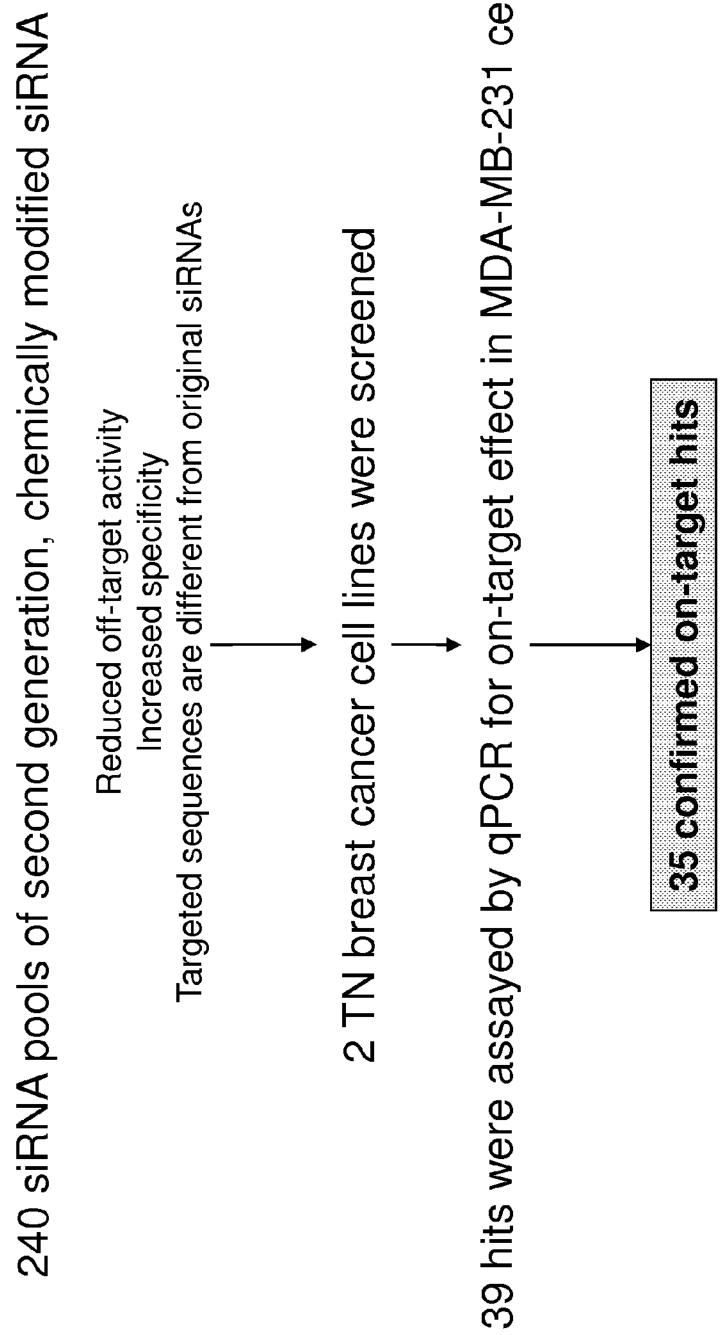
FIG. 3 depicts the confirmation assays performed as described in Example 1.

Identification of genes with a significant effect on cell sensitivity to E7389 was performed by a method that was similar to the method described for a paclitaxel siRNA screen (Whitehurst et al. (2007) *Nature* 446:815-819). Briefly, measurement of each well was normalized by average of medium plus transfection reagent containing reference wells on a plate (32 wells/plate). The biological replicates were averaged for DMSO and E7389-treated plates. For each gene, a two sample t-test was performed to identify significantly different values for wells treated with two different conditions. To narrow down the hit list, the magnitude of response was taken into account by arranging all data according to fold change ratio (average E7389/average DMSO) in ascending order. 364 genes with a fold change among the lowest 5 percentile of the distribution passed the cut-off level. Then, hypothetical open reading frames and genes encoding hypothetical proteins were excluded and the analysis was focused on the 240 remaining genes (see FIG. 2).

Confirmation Assays siRNA SMARTpools for the 240 selected genes were ordered in ON-TARGETplus format from Dharmacon. These reagents contain a modified sense strand to prevent interaction with RISC and favor antisense strand uptake. The antisense strand seed region is modified to decrease off-target activity and enhance target specificity. These reagents were used for confirmation secondary screening. To identify common genes influencing sensitivity of cancer cells to E7389, BT-549 breast cancer cells were screened with the 240 selected siRNA pools. The screening was performed using the same protocol as the primary screen with MDA-MB-231 cells, with the final concentration of eribulin mesylate (E7389) in each well corresponding to the $IC_{20}$ for BT-549 cells (0.25 nM E7389).

Data analysis showed that the treatment with 40 out of 240 siRNA pools caused significant differences when comparing E7389-treated wells to carrier-treated wells in both cell lines (Table 2).

To confirm specific down-regulation of 40 genes with siRNA pools, quantitative PCR analysis of targeted mRNAs was performed. MDA-MB-231 and BT-549 cells were transfected with 40 ON-TARGETplus siRNAs or non-targeting negative control siRNA according to the above protocol. 48 hours later cells were lysed and cDNAs were synthesized according to the manufacturer's instructions for use of the TaqMan® Gene Expression Cells-to-CT™ Kit (Applied Biosystems). Relative quantities of remaining cDNAs after the treatment with siRNAs were evaluated using QuantiTect SYBR Green PCR Kit with the gene-specific QuantiTect Primer Assays (Qiagen). Results of the analysis are shown in FIG. 4. The following 18 genes were down-regulated more than 50 percent in both tested cell lines: CFL1, NMU, MOBKL1B, HYAL2, PSENEN, CYP4F3, ITFG3, EDIL3, YTHDF1, CDC20, CCL26, TMEM79, MANSC1, DYSF, ERGIC3, GRAMD4, NCBP1, SNX11. 14 genes were down-regulated more than 50 percent in at least one cell line (PDGFB, APBB2, SATB1, MAD2L1BP, TUBB6, CEP152, KLH17, COL7A1, CKLF, PHOSPHO2, GNAT1, ABI3, TYROBP, IL10), while other 3 genes were down-regulated more than 35 percent in at least one cell line (ANG, ZIC5, JAM3). Expression of SPTA1, PAPLN, PCDH1, TMIGD2, and KRT24 was either not detectable by this method in MDA-MB-231 cells or didn't change after siRNA treatment in BT-549 cells. The foregoing results indicate that down-regulation of the 40 genes can lead to increased sensitivity to eribulin, an analog thereof, or pharmaceutically acceptable salt thereof.

TABLE 2

List of 40 overlapping genes from the screening of MDA-MB-231 and BT-549 cells. Fold changes (FC) compared to control and associated p-values are depicted.

| gene | Gene ID | MDA-MB-231 FC | MDA-MB-231 t-test | BT-549 FC | BT-549 t-test |
|---|---|---|---|---|---|
| PSENEN | 55851 | 0.70 | 0.03 | 0.39 | 0.00 |
| PHOSPHO2 | 493911 | 0.56 | 0.04 | 0.44 | 0.02 |
| CCL26 | 10344 | 0.71 | 0.02 | 0.45 | 0.03 |
| CDC20 | 991 | 0.47 | 0.03 | 0.47 | 0.03 |
| MAD2L1BP | 9587 | 0.47 | 0.00 | 0.48 | 0.01 |
| JAM3 | 83700 | 0.63 | 0.04 | 0.55 | 0.00 |
| KLHL17 | 339451 | 0.65 | 0.04 | 0.57 | 0.00 |
| PCDH1 | 5097 | 0.71 | 0.02 | 0.61 | 0.06 |
| ABI3 | 51225 | 0.66 | 0.04 | 0.62 | 0.04 |
| TMIGD2 | 126259 | 0.66 | 0.05 | 0.62 | 0.04 |
| NCBP1 | 4686 | 0.72 | 0.04 | 0.63 | 0.02 |
| IL10 | 3586 | 0.72 | 0.02 | 0.64 | 0.05 |
| ANG | 283 | 0.74 | 0.02 | 0.64 | 0.00 |
| KRT24 | 192666 | 0.69 | 0.01 | 0.65 | 0.00 |
| TMEM79 | 84283 | 0.66 | 0.01 | 0.67 | 0.02 |
| PDGFB | 5155 | 0.65 | 0.00 | 0.68 | 0.03 |
| SNX11 | 29916 | 0.68 | 0.05 | 0.68 | 0.05 |
| CFL1 | 1072 | 0.69 | 0.02 | 0.68 | 0.05 |
| CKLF | 51192 | 0.62 | 0.03 | 0.70 | 0.01 |
| TUBB6 | 84617 | 0.73 | 0.01 | 0.71 | 0.01 |
| HYAL2 | 8692 | 0.67 | 0.02 | 0.71 | 0.05 |
| TYROBP | 7305 | 0.73 | 0.04 | 0.71 | 0.01 |
| APBB2 | 323 | 0.70 | 0.00 | 0.71 | 0.02 |
| YTHDF1 | 54915 | 0.61 | 0.02 | 0.73 | 0.01 |
| CEP152 | 22995 | 0.46 | 0.03 | 0.74 | 0.05 |
| COL7A1 | 1294 | 0.73 | 0.03 | 0.75 | 0.05 |
| NMU | 10874 | 0.67 | 0.00 | 0.76 | 0.05 |
| SPTA1 | 6708 | 0.38 | 0.03 | 0.76 | 0.02 |
| ERGIC3 | 51614 | 0.70 | 0.05 | 0.76 | 0.05 |
| SATB1 | 6304 | 0.67 | 0.02 | 0.77 | 0.04 |
| MOBKL1B | 55233 | 0.74 | 0.03 | 0.77 | 0.01 |
| GNAT1 | 2779 | 0.66 | 0.04 | 0.78 | 0.03 |
| ITFG3 | 83986 | 0.73 | 0.05 | 0.78 | 0.05 |
| DYSF | 8291 | 0.26 | 0.01 | 0.78 | 0.05 |
| MANSC1 | 54682 | 0.65 | 0.03 | 0.78 | 0.05 |
| EDIL3 | 10085 | 0.65 | 0.01 | 0.79 | 0.05 |
| GRAMD4 | 23151 | 0.72 | 0.00 | 0.79 | 0.01 |
| ZIC5 | 85416 | 0.69 | 0.03 | 0.80 | 0.05 |
| PAPLN | 89932 | 0.71 | 0.03 | 0.80 | 0.01 |
| CYP4F3 | 4051 | 0.74 | 0.02 | 0.81 | 0.01 |

APPENDIX

NUCLEIC ACID AND AMINO ACID SEQUENCES OF BIOMARKERS

| Gener Name | Gene ID | Accession NO. | Name |
|---|---|---|---|
| ABI3 | 51225 | NM_016428 | *Homo sapiens* ABI family, member 3 (ABI3), transcript variant 1, mRNA |

mRNA Sequence

```
TCCTATCCACCCTCCACTCCCCTGTCCCTTGGTGACTCATCCCTGAGCTTCCCAAGGAAGCCCCCACCCT
CTGCCCTTTCCTCCCGCCTTCCATGAGTGGAAAATCCACCTCCGCCCCCTATAGCAGGCCAGCCCCCTTC
CTCCCCAGTCTCCGACCCCATCCCCCAGCCGACCAGTTTCCTCTCCAGGACCAGGGAGCAATCACAGCTG
CCCCGACCTTGGCTTCCTCTGCTGGGTGGGATTGGGGGCTGGGCCCCCAAATGGGCCCCTGGCTTCCCCC
```

APPENDIX-continued

NUCLEIC ACID AND AMINO ACID SEQUENCES OF BIOMARKERS

| Gener Name | Gene ID | Accession NO. | Name |
|---|---|---|---|

TTCCTCTGGGCAGGGGACAGAGAGACACAGGCTCGGGGAGCAGGACTGACTTCCTCTTGTCCCGGAATGA
GCATGCCTGCCCTTTGCAAGCAGGTTTGGGTCTCACGCAGAGGAAACCAAAAGCAATAAGAGGGAGGGAA
GGCAGAGCAACCAATCAAGGGCAGGGTGAGACTCAAAACGAGCGGGCTCCCTGGGGAGCCAGACAGAGGC
TGGGGGTGATGGCGGAGCTACAGCAGCTGCAGGAGTTTGAGATCCCCACTGGCCGGGAGGCTCTGAGGGG
CAACCACAGTGCCCTGCTGCGGGTCGCTGACTACTGCGAGGACAACTATGTGCAGGCCACAGACAAGCGG
AAGGCGCTGGAGGAGACCATGGCCTTCACTACCCAGGCACTGGCCAGCGTGGCCTACCAGGTGGGCAACC
TGGCCGGGCACACTCTGCGCATGTTGGACCTGCAGGGGGCCGCCCTGCGGCAGGTGGAAGCCCGTGTAAG
CACGCTGGGCCAGATGGTGAACATGCATATGGAGAAGGTGGCCCGAAGGGAGATCGGCACCTTAGCCACT
GTCCAGCGGCTGCCCCCCGGCCAGAAGGTCATCGCCCCAGAGAACCTACCCCCTCTCACGCCCTACTGCA
GGAGACCCCTCAACTTTGGCTGCCTGGACGACATTGGCCATGGGATCAAGGACCTCAGCACGCAGCTGTC
AAGAACAGGCACCCTGTCTCGAAAGAGCATCAAGGCCCCTGCCACACCCGCCTCCGCCACCTTGGGGAGA
CCACCCCGGATTCCCGAGCCAGTGCACCTGCCGGTGGTGCCCGACGGCAGACTCTCCGCCGCCTCCTCTG
CGTCTTCCCTGGCCTCGGCCGGCAGCGCCGAAGGTGTCGGTGGGGCCCCCACGCCCAAGGGGCAGGCAGC
ACCTCCAGCCCCACCTCTCCCCAGCTCCTTGGACCCACCTCCTCCACCAGCAGCCGTCGAGGTGTTCCAG
CGGCCTCCCACGCTGGAGGAGTTGTCCCCACCCCCACCGGACGAAGAGCTGCCCCTGCCACTGGACCTGC
CTCCTCCTCCACCCCTGGATGGAGATGAATTGGGGCTGCCTCCACCCCCACCAGGATTTGGGCCTGATGA
GCCCAGCTGGGTGCCTGCCTCATACTTGGAGAAAGTGGTGACACTGTACCCATACACCAGCCAGAAGGAC
AATGAGCTCTCCTTCTCTGAGGGCACTGTCATCTGTGTCACTCGCCGCTACTCCGATGGCTGGTGCGAGG
GCGTCAGCTCAGAGGGGACTGGATTCTTCCCTGGGAACTATGTGGAGCCCAGCTGCTGACAGCCCAGGGC
TCTCTGGGCAGCTGATGTCTGCACTGAGTGGGTTTCATGAGCCCCAAGCCAAAACCAGCTCCAGTCACAG
CTGGACTGGGTCTGCCCACCTCTTGGGCTGTGAGCTGTGTTCTGTCCTTCCTCCCATCGGAGGGAGAAGG
GGTCCTGGGGAGAGAGAATTTATCCAGAGGCCTGCTGCAGATGGGGAAGAGCTGGAAACCAAGAAGTTTG
TCAACAGAGGACCCCTACTCCATGCAGGACAGGGTCTCCTGCTGCAAGTCCCAACTTTGAATAAAACAGA
TGATGTCCTGTGACTGCCCCACAGAGATAAGGGGCCAGGAGGGATTGAAAGGCATCCCAGTTCTAAGGCT
GCTGCTAATTACAGCCCCCAACCTCCAACCCACCAGCTGACCTAGAAGCAGCATCTTCCCATTTCCTCAG
TACCCACAAAGTGCAGCCCACATTGGACCCCAGACACCCCTCTGCAGCCATTGACTGCAACTTGTTCTTT
TGCCCATTGAAAAAAAAAAAAAAAAAAAA (SEQ ID NO: 1)

Translated protein sequence

MAELQQLQEFEIPTGREALRGNHSALLRVADYCEDNYVQATDKRKALEETMAFTTQALASVAYQVGNLAG
HTLRMLDLQGAALRQVEARVSTLGQMVNMHMEKVARREIGTLATVQRLPPGQKVIAPENLPPLTPYCRRP
LNFGCLDDIGHGIKDLSTQLSRTGTLSRKSIKAPATPASATLGRPPRIPEPVHLPVVPDGRLSAASSASS
LASAGSAEGVGGAPTPKGQAAPPAPPLPSSLDPPPPPAAVEVFQRPPTLEELSPPPPDEELPLPLDLPPP
PPLDGDELGLPPPPPGFGPDEPSWVPASYLEKVVTLYPYTSQKDNELSFSEGTVICVTRRYSDGWCEGVS
SEGTGFFPGNYVEPSC (SEQ ID NO: 2)

| Gener Name | Gene ID | Accession NO. | Name |
|---|---|---|---|
| ANG | 283 | NM_001097577 | *Homo sapiens* angiogenin, ribonuclease, RNase A family, 5 (ANG), transcript variant 2, mRNA |

mRNA Sequence

TCCAGGTTCACACAACTGGAACCCATCTCCAGGAACAAACAGCTGGAACCCATCTCCCGTTGAAGGGAAA
CTGCCAGATTTTTGTAAGATTCTTCCTCCTGGGAGCCTGTGTTGGAAGAGATGGTGATGGGCCTGGGCGT
TTTGTTGTTGGTCTTCGTGCTGGGTCTGGGTCTGACCCCACCGACCCTGGCTCAGGATAACTCCAGGTAC
ACACACTTCCTGACCCAGCACTATGATGCCAAACCACAGGGCCGGGATGACAGATACTGTGAAAGCATCA
TGAGGAGACGGGGCCTGACCTCACCCTGCAAAGACATCAACACATTTATTCATGGCAACAAGCGCAGCAT
CAAGGCCATCTGTGAAAACAAGAATGGAAACCCTCACAGAGAAAACCTAAGAATAAGCAAGTCTTCTTTC
CAGGTCACCACTTGCAAGCTACATGGAGGTTCCCCCTGGCCTCCATGCCAGTACCGAGCCACAGCGGGGT
TCAGAAACGTTGTTGTTGCTTGTGAAAATGGCTTACCTGTCCACTTGGATCAGTCAATTTTCCGTCGTCC
GTAACCAGCGGGCCCCTGGTCAAGTGCTGGCTCTGCTGTCCTTGCCTTCCATTTCCCCTCTGCACCCAGA
ACAGTGGTGGCAACATTCATTGCCAAGGGCCCAAAGAAAGAGCTACCTGGACCTTTTGTTTTCTGTTTGA
CAACATGTTTAATAAATAAAAATGTCTTGATATCAGTAAGAA (SEQ ID NO: 3)

Translated protein sequence

MVMGLGVLLLVFVLGLGLTPPTLAQDNSRYTHFLTQHYDAKPQG
RDDRYCESIMRRRGLTSPCKDINTFIHGNKRSIKAICENKNGNPHRENLRISKSSFQV
TTCKLHGGSPWPPCQYRATAGFRNVVVACENGLPVHLDQSIFRRP (SEQ ID NO: 4)

| Gener Name | Gene ID | Accession NO. | Name |
|---|---|---|---|
| APBB2 | 323 | NM_173075 | *Homo sapiens* amyloid beta (A4) precursor protein-binding, family B, member 2 (APBB2), mRNA |

mRNA Sequence

GCCAAAGCCTGGAGAAGTGGAATCTCGTCAGCGCCGCTCCCTGCGCGGGACTCGCGGAACGGCACTGAGC
ATGCTCAGTTGCCGGAGCCCGTTCTGGTCTCAAGTAGGAAGCTAGTGCGCTGTAACCGCATCTGATCTGG
GCGCTCCGGGAAGGGCGAGACTGGAGCAGAGCCGCTGGGCGCCGGAGCCGAGGCGAGCGCCGCGCGCACC
ACTGGTTGGAGTTGCTGTGGGTGAGCTGCTGTGGTCTGTAGCCAAGCATGCTGTGGTCGGATCTGCCCAG
CCGTGGAACAGAAACATTTGCTGGATGGAAAATCCATAAAAGAAAGCTCCTGTGAAAAGCTGAGGCTGAC
AATAATTTAAGCAAAATCAGATCGATCTCTTTGGGCTGCCTGACCTCCTTGGGTGCTTGCTATTAATTAA
CAGACTTTGTGGGGAAAAAAAGGAGCTTGCCTTCTGAGCTTTGTACCAAAGACCTGGGAAAACTAACCAT
CTCAGTCTTTCCTGAGGACTTGGGAACTGCCGAGGCCTCTGCCAATGTGTTGACTGTCGCTATGGGCTCA
CTGTTGTCCAGGCAGCTCATATTTCAAATTATAACCTATTTCCTGCACCATTGCTGACGCCTGGTGATCC

APPENDIX-continued

NUCLEIC ACID AND AMINO ACID SEQUENCES OF BIOMARKERS

| Gener Name | Gene ID | Accession NO. | Name |
|---|---|---|---|

ATGTCAGAAGTACTTCCAGCTGACTCAGGTGTTGACACCTTGGCAGTGTTTATGGCCAGCAGCGGAACTA
CAGACGTCACAAATCGGAACAGCCCAGCCACACCACCAAACACCCTTAACCTCCGATCCTCCCACAATGA
ACTGTTGAACGCTGAAATAAAACACACAGAAACCAAGAACAGCACACCTCCCAAATGCAGGAAAAAATAT
GCACTAACTAACATCCAGGCGGCCATGGGCCTCTCGGATCCAGCTGCACAGCCCCTGCTGGGAAATGGCT
CTGCCAACATCAAGCTGGTGAAAAATGGGGAGAACCAGCTCCGTAAGGCTGCAGAGCAAGGGCAGCAGGA
CCCCAACAAAAACCTGAGCCCCACTGCAGTCATCAACATAACTTCTGAGAAGTTAGAGGGTAAAGAGCCC
CACCCACAGGATTCCTCGAGCTGTGAGATTTTACCCTCCCAGCCCAGGAGAACTAAGAGCTTCCTAAATT
ACTATGCAGATCTGGAAACCTCAGCCAGAGAACTAGAGCAGAACCGAGGCAATCACCATGGGACTGCGGA
AGAGAAATCCCAGCCAGTCCAGGGCCAGGCCTCCACCATCATTGGGAATGGCGATTTGCTGCTGCAGAAA
CCAAACAGACCCCAGTCCAGCCCTGAAGACGGCCAAGTAGCCACAGTGTCATCCAGCCCAGAAACCAAGA
AGGATCATCCGAAAACAGGGGCCAAAACCGACTGTGCACTGCACCGGATCCAGAACCTGGCACCGAGCGA
TGAGGAGTCCAGCTGGACAACGTTGTCCCAAGACAGTGCCTCACCCAGCTCCCCGGATGAAACAGATATA
TGGAGTGATCACTCATTTCAGACTGATCCAGATTTGCCGCCTGGCTGGAAAAGAGTCAGTGACATTGCCG
GGACCTATTATTGGCACATCCCAACAGGAACGACTCAGTGGGAACGGCCCGTCTCCATCCCAGCAGATCT
CCAGGGTTCTAGGAAAGGGTCACTTAGTTCTGTAACGCCATCTCCCACCCCAGAGAACGAGGATTTGCAT
GCAGCCACTGTTAACCCGGACCCCAGTTTAAAAGAGTTTGAAGGAGCAACCCTACGCTATGCATCTTTGA
AACTCAGAAATGCCCCACACCCTGATGATGATGATTCTTGTAGTATCAACAGTGACCCAGAAGCCAAGTG
TTTTGCTGTGCGTTCTCTGGGATGGGTAGAGATGGCAGAAGAGGACCTCGCCCCCGGTAAAAGTAGTGTT
GCGGTCAACAACTGCATCAGGCAACTTTCCTACTGCAAAAATGACATCCGAGACACAGTCGGGATTTGGG
GAGAGGGGAAAGACATGTACCTGATCCTGGAGAATGACATGCTCAGCCTGGTGGACCCCATGGACCGCAG
CGTGCTGCACTCGCAGCCCATCGTCAGCATCCGCGTGTGGGGCGTGGGCCGCGACAATGGCCGGGATTTT
GCTTATGTAGCAAGAGATAAAGATACAAGAATTTTGAAATGTCATGTATTTCGATGTGACACACCAGCAA
AAGCCATTGCCACAAGTCTCCACGAGATCTGCTCCAAGATTATGGCTGAACGGAAGAATGCCAAAGCGCT
GGCCTGCAGCTCCTTACAGGAAAGGGCCAATGTGAACCTCGATGTCCCTTTGCAAGATTTTCCAACACCA
AAGACTGAGCTGGTCCAGAAGTTCCACGTGCAGTACTTGGGCATGTTACCTGTAGACAAACCAGTCGGAA
TGGATATTTTGAACAGTGCCATAGAAAATCTTATGACCTCATCCAACAAGGAGGACTGGCTGTCAGTGAA
CATGAACGTGGCTGATGCCACTGTGACTGTCATCAGTGAAAAGAATGAAGAGGAAGTCTTAGTGGAATGT
CGTGTGCGATTCCTGTCCTTCATGGGTGTTGGGAAGGACGTCCACACATTTGCCTTCATCATGGACACGG
GGAACCAGCGCTTTGAGTGCCACGTTTTCTGGTGCGAGCCTAATGCTGGTAACGTGTCTGAGGCGGTGCA
GGCCGCCTGCATGTTACGATATCAGAAGTGCTTGGTAGCCAGGCCGCCTTCTCAGAAAGTTCGACCACCT
CCACCGCCAGCAGATTCAGTAACCAGAAGAGTCACAACCAATGTAAAACGAGGGGTCTTATCCCTCATTG
ACACTTTGAAACAGAAACGCCCTGTCACCGAAATGCCATAGCTGCACATGCAAAAGGACTCGGCTATTTA
CCTGAAGATTGACTAGCTACACTAAAGAAAATGAACTCCGCCATCCGACCTTCCATCCAGTTGCTGATGC
TTTGTCTTCAGAGAATTTACCCTTAACCAAGCAGTGTTAGACAAGCATGTTCTCTCGTCTTGCCACCATC
ATGTGATATGAAAAGAAGCATGAATAATTTTTTTGCTGTAAGTTACATCATGCGCAGTGGAAGGTCTTT
TTCTTATTGTAAATATTGTGAACATTACTTAACTTCACACACACACAGAGAAGAGTGTGGCCCCACCCCT
CCTAGTGAACTAACGCTGCGTCCTTGGAATGAATGATGCGTGAGTTAGTTTCACTGTCTTCTTGGCTGGA
CCTGTCACAAGCAACCTTTAAGTCCTACAGCACTTTGCCCTGTTTTCAACATTGGAGTAGGCACTGCATA
GCAGATACCATTGAATTGCTGTAAAAATAGGATGGCGAGTTTGTGTTTTAATTTTTCATAAAATTGAACC
TGTTGGTTGACAAAATTGGCTGTTGGCATCAGTATAGAAACCAACTGGCAGCTTTCCCTGACAAGCTCTT
TGACACATGGACACCATTTCATGTCTACAGCTGTTTGTGGGATGTTGGAAAAAAATGAAACTTCAAAATT
GATGAAAAACTAAATTCGAGGAATTAAAATCGAACAAAACATAGCCTTTCTTTTCCGATGGTTTTCAAAC
TGATTATTTTTAAAAGAGATTAATAAAATCATAATGCATTTTGGGTGGGACATATTTCAAACTTCTGCCT
TATATTGTACGGTGCAGCTAGAGAATTATAGTTCACTATGGCCATTCTCTACATAAACATTAAGATGAAA
TACTCCTCATCAGCCTTTCATCCTTAGTTTGAGAATTAGCTGATATGCAATTTGAAGTTGAGGAAATATC
ATTGATATTTCTATCATGCACGATTATTTTAGATTTCTACCACCGTGTGATTTTTGCTAGTCCATGTGCT
AGAGGTAAACGTTCTGCTGGAATTCTGCATCCAGCTCTATCCCCCTCTGATGCTTTTTGCCCAGAAAGCT
GTCTGTCCATCATGTATTGTCCATGGCAACAAATTACATTAGGTTGAACCTTTCCTTGATTTTATGTATT
TAATATTAGAATTTGTTGGACTCAACTAGATATATTTTTTAATTTATATTTTTTCCATTTTACTTTGAAG
ATTTGAAATGTTCATACCTGAGCAAAGTCTACACAGGAGTAATGGACTGTTTAACAAGTTTCCCAAAACA
GCATTTTCCTGCTCCTTCGTATGTAGGTGAGAAACTTAGCTGGAAAGACATACAAATTTAGACTCTCGTT
GACATTGTCGTTTTAAAAGGAAGTTGCTAAGGCGATCAATCTCAATATTAGTCTTGTTTACTTCTTCTTA
ATGTCAAAATTAACATTTACAACATCCAATTATAAAAGTAATGCTTTATGTTTATACACTGCTATGTACT
TGTCAAAATGGTTTCCACATTCTTATCACATCTGAGCCTTACCAGGTAGAGAAGGTACTAAATACACTTT
AGAAGTAAAAATATGAAGTACCGAGAGGCTAAACCCACTGGCCTAAGATCTCACCAAAGTTCATGAAAAC
CAGGACTAGGACCCACGGCTCCCAAAGCCCGTTCTTGCTGTGTTGTGCTGCCTCCATATCCGTCAGGAAG
AGCCTTTCCAGAATGATTCTGGGCATATACTAAGAAGAGCAGGTATGGAAAGATCTATTGTCAGGGAATC
TTAGAATTCCCTACACGAGTGGGAGAAAGATGTCCAAATTCCTTACGCAGTGGTATTCATGATGGTGCCC
TATCTAAGTCCAGGACTGTTTTCCTACAGCGTGCCTCAAAAGTGTTGTAGAGGGCAGGATTCTACATTCA
CAGCCTGTTCCATCTACGAGATTTTCCAGATGCTACTTGTGGTAGACATTCCTAACTCATGGTACTTAGC
CACCAGAGATCATGATGGAATGAGTGGGTGGCTTTTCTACCTGCCATTCCCTCAGAATTCATGAGGGGTG
GGGGACAGGGGGACCGGAATTGTCTTAGCACCCCAATGTTATGACAAAACTATGCTACTTTAGAAACGCA
GTCTGTTTTTCACCAATTGACATACTACTGATCTGAAGTAACCAGTGCCATCATAAGAAATTACTGCATT
AAGAAAATCCTTGCTGTGCCCTTTGAAAAGCTGTTCAGAAATCATTTACAGTGATCTTTCATCTCGGTCG
CTGTAGTGAAACATTTTAGTGTGATAAATTTCAAAATTCTAAACAAATTACCCACTTTTATATTGGAAAT
CTCTACCAGAACTCCCTCTTCATTTTTTAAGGCATACATTTGCTTGTTTTCAAGATCAAGAATTCTGAGC
TAGCTTTAAGTAGCAAACTGATTTATATGTGCAATTATAGGATGCATTAAGATGAATGATAGCCTTTACA
TATTGAAAACTTTGCAGACGTTTTGTTTTGAAAATGGCATTGTATAGTAAATGCAAATTAATTTTGTAAA
ATTATGTTAAAGAGTATGTTCAGACACTTTCTGCCATGGCCAAAAAGTATGTATGAAAGTATGTGTGTAT
TTGTTTGTAAAAGGATGCCAATGTTTTACCTGATATCTTAGTGACACTTCAGTTATCTATGCATTCTTTA
GATCTGTGATTCGGTAAACAGGCAGCCATGTTCACGATGCCTTCTATGTCTTACCATATTTTTAATTAAC
CTGTTAAATACAGCTTAAAATATTTTTATTTTATTTATTCTATTTTTACTGAAATATACTGCATTATTGT
GTTAATGTATTATCTTTCCTGGATATTATCTCCCAGTGTATCCAGATCTAAGTAATCTCAGTGAACTATA
CATTGCCTAAAAAGTGGTTTTGTAATGATTTGTAGTCACATTTCTATTGGGATATGTAGAAGAAAAGGCA
AAATGCTTAAAGTTCCTTTTATTTTTTAAAAGCAGCTAGATAGACACAGACTTGCCACCTCATACATCTG

APPENDIX-continued

NUCLEIC ACID AND AMINO ACID SEQUENCES OF BIOMARKERS

| Gener Name | Gene ID | Accession NO. | Name |
|---|---|---|---|

CTCCTTGGCAACATCAAGGGGAACGACTAGCCAACATGCCTATGGCTAAAAACTTTCCTTTGCAGACTAA
AGCACTGCTTGGTGCTTCGTTTTTCTACCCTTCACAACATGTGTGATTTCATCTAAGAGATATATACATG
TACACATGCCCTTTGTTTCCACCTGGATACAAGATCACTCATAGCTAATTAGGACCATTGTTTTTTGTTC
ATCTGTCTTGTTGCATGAAGGGACATTAGACCCATTTCCATTAAAATAAGTTCTTGGTGATAAACTGTGG
CACTGCTACTTCTTTTTAAATCCACTTTATGATTTCAAGATGGACACTTGTAAGATGACTCGACACAAGG
CCATTGCCTGGAAGCCCCAGAGCTTTCCTCTGTTTGTATGGCCCGTTCATGTCCCAGGCATTGCAACACA
AACTCCTCAAGATTTCACCACAACATGACAAGCATTTTCCTAACTGATATTAGCACAATTTAACTAATAA
GCCCCTTCGCTCTCTAGTTGGCCAGGCTTAACCTAATACACATCTAACGTGTGTGCCACACGGCCAGTAG
AAAGTTTAACTTCAGCTTCAGGGCAAAGATACCCACTCACACCGTGTCAACGCAAGCAGTAGTTCCTGGC
CTCCAGAGCAGCTTACTTCCCCTGAAAGAACGCTTTGTTTTCCTTTATGCCCTTTTCCTGTTGACCACTT
TTACACATTTAAATGTAATTTGTTGTGAGAATAAATTTAGCTGCATAAAACGTTCGGCTCATTTATCTGA
CATCTTAGTCACATATACAAGGAATAGAAATAGAAACTCGGTGTCTCTAGTTATTTTTAAATTATTCTTA
CCTCAGACTTCTTAGAAATCACTTTAGTAATGGAGCATTTTGCTTTGATTAGTTACTACATATTTCTGCC
TGGTAAGAACTAGGAAGTAACTTCAAATTTTGAGTAATCACCCTGTACTTATTTGGTGATCAGGAAGGCC
AGCTGGCCTTCCGGACATAGAAGCCTATTTAGTCACCAACTCGAGTCTTTTGTAAGCGGTCTTGCTAGGA
TTGTGATATTTTAGCACGAAGAAGTTTATCACTTCCTTTAAGAACCTGACATCAAAGAATAAAGAATAGA
GGTGTACACACACTAAATCCAAAATGAAAGGTAACTAGAGAAATCAGTTGAATCTGGTTTAGCTTAACTG
TTAGGCGCAGGAAGGCAGATAAACAGAATTTAAAGTATGTCCCCGCTTTTTGTTCATCTTGCACTTCCAC
AGTGGTTTCTCTCTAGTCAGTAACAAAATTTCATTATGGTTTCAGGCATTATATGGTGGTAAATAATTTC
AGATTAAAAATGTGTTTGCTATTGGAGTATCTGAATACTAGTAATTTCATTATTTAGAATTTTGCAGCAC
TTTTATCTCAAGAAGAAGTCCAAGAATGTAAAATGCCAAATGAAACATGTCAGTGGAATCAATATTCTCC
TTCATTAGAATTCCCTCATATTGCTTTTTTTTTTTTTCTTCAGACAGAGGAGTCTTACTCTGGAGTGCAG
TGGTGTAATTTCAGCTCACCACAACCTCCACCTCCCAAGTTCAAGCAATTCTCGCCTCAGCCTCCTGAGT
AGCTGGGATTACAGGCATGCACCGCCACGCCTGGCCAATTTGTATATTTTTAGTAGAGACAGGGTTTCGC
CACGTTGGCCAGGCTGGTCTCGAACTCCTGACCTCAGGTGATCCGCCCGCCCCAACCTCCCAAAGTATGT
GAGCCACCACGTCCGGCCTCATATTGCTTTTATCCAAAATTCTTTTCCCTTTTCACTCTACCAAAGTATT
TAAATAATCCTGTCCTTCATAGAAGATTCTCAAAGAAGAAAACTGCAGTGTAATTAATGAATGGTTTAAT
TCAGAATCTTCATATACTTCTAAAGAGAAAAATAATTTAGTGCCAAATGCATGTTAGGAGATAATCAATG
TAAGTGGCAACAAATTGTGACTTCACATGCTACTGTAGAGATCAGAAAATTATCCTAAACTATTCCATAA
CAATGAGACAACATCACAGAAAATACACTTGAAAATAAAAATCTCAAGACCAGCTACTTCTGGACAATGG
AATACTTTTCAGTCTGGTATGGTGGAGGGCCCGAAAAGGATAAGGGATTCTTATGATACACAATGGGATT
CTTTACTGAACAATATGTTAAATTAAGCTGCACCGCCTTCCTTGAGGCATGGACTACCCTAACCAACCAG
ATAGAAATCTGGGTGGGATAAGAGGATGAGCCACACGCTATAATTTTAGGGCAAGGAGATAGTGTTTGAT
TTTCAAAATCAGCAAAATAAGCTGAGCACTTTATATCTTTCTGTACAAGAGTGATAACATGAAGAATTCT
TCTTCAGGGATTTAAAATACAATAAGCCTGGTTCAACTATAAAAAGTCTTGTTTCCTTTCTTCATTGACA
CTTTTTTTTTTTTTTTTTTTTTTTTTGAGGCAAGGTCTCACTCTGCTTCCCAGGCTGGAGTGCAGTGGGGC
AATATTGGCTCACTGCAACCTGCACCTCCTGGACTCAAGAGATCCTCGTACCTCAGCCTCCTAAGTAGCT
GGGACTACAGGCGTGTCCCACCACACCCAGCTAATTTTTGTATTTTTTGTAGAGATGGGGTTTTGGGGTT
TCGCCATGTTGTCCAGGCTCGTCTGGAACTCCGGTGCTCAAGTGGCGTGCCCACCTCAGCCTCCCAAACT
GCTGAGATTACAGATGTGAGCCACTGCACCCAGCCCACTGACACGTTTTACTGATAAATGTAAATCTAAG
CTAAAATAAAAATAATGTATTACCGCTATAATACAATTCACCATTCTCTTTTCTCACTTCAAGTAAGAAA
GTAAAAATAGAATATCAGAGCTGAAGTAGACCTAAGTATTCATCTTGAAGAAGATAATATTCTAAAAATC
ATGCCACCTGAATTGAGCATTTAGGAATTTATGTAACATTTCTATACAACTGAATTGCAAAAATAAAACT
TTAAATTCAAACTTTAAAAAAAAAAAAAAAAAAAAAAAAAAAAAA (SEQ ID NO: 5)

Translated protein sequence

MSEVLPADSGVDTLAVFMASSGTTDVTNRNSPATPPNTLNLRSS
HNELLNAEIKHTETKNSTPPKCRKKYALTNIQAAMGLSDPAAQPLLGNGSANIKLVKN
GENQLRKAAEQGQQDPNKNLSPTAVINITSEKLEGKEPHPQDSSSCEILPSQPRRTKS
FLNYYADLETSARELEQNRGNHHGTAEEKSQPVQGQASTIIGNGDLLLQKPNRPQSSP
EDGQVATVSSSPETKKDHPKTGAKTDCALHRIQNLAPSDEESSWTTLSQDSASPSSPD
ETDIWSDHSFQTDPDLPPGWKRVSDIAGTYYWHIPTGTTQWERPVSIPADLQGSRKGS
LSSVTPSPTPENEDLHAATVNPDPSLKEFEGATLRYASLKLRNAPHPDDDDSCSINSD
PEAKCFAVRSLGWVEMAEEDLAPGKSSVAVNNCIRQLSYCKNDIRDTVGIWGEGKDMY
LILENDMLSLVDPMDRSVLHSQPIVSIRVWGVGRDNGRDFAYVARDKDTRILKCHVFR
CDTPAKAIATSLHEICSKIMAERKNAKALACSSLQERANVNLDVPLQDFPTPKTELVQ
KFHVQYLGMLPVDKPVGMDILNSAIENLMTSSNKEDWLSVNMNVADATVTVISEKNEE
EVLVECRVRFLSFMGVGKDVHTFAFIMDTGNQRFECHVFWCEPNAGNVSEAVQAACML
RYQKCLVARPPSQKVRPPPPPADSVTRRVTTNVKRGVLSLIDTLKQKRPVTEMP (SEQ ID NO: 6)

| CCL26 | 10344 | NM_006072 | *Homo sapiens* chemokine (C-C motif) ligand 26 (CCL26), mRNA |
|---|---|---|---|

mRNA Sequence

CTGGAATTGAGGCTGAGCCAAAGACCCCAGGGCCGTCTCAGTCTCATAAAAGGGGATCAGGCAGGAGGAG
TTTGGGAGAAACCTGAGAAGGGCCTGATTTGCAGCATCATGATGGGCCTCTCCTTGGCCTCTGCTGTGCT
CCTGGCCTCCCTCCTGAGTCTCCACCTTGGAACTGCCACACGTGGGAGTGACATATCCAAGACCTGCTGC
TTCCAATACAGCCACAAGCCCCTTCCCTGGACCTGGGTGCGAAGCTATGAATTCACCAGTAACAGCTGCT
CCCAGCGGGCTGTGATATTCACTACCAAAAGAGGCAAGAAAGTCTGTACCCATCCAAGGAAAAAATGGGT
GCAAAAATACATTTCTTTACTGAAAACTCCGAAACAATTGTGACTCAGCTGAATTTTCATCCGAGGACGC

APPENDIX-continued

NUCLEIC ACID AND AMINO ACID SEQUENCES OF BIOMARKERS

| Gener Name | Gene ID | Accession NO. | Name |
|---|---|---|---|

TTGGACCCCGCTCTTGGCTCTGCAGCCCTCTGGGGAGCCTGCGGAATCTTTTCTGAAGGCTACATGGACC
CGCTGGGGAGGAGAGGGTGTTTCCTCCCAGAGTTACTTTAATAAAGGTTGTTCATAGAGTTGACTTGTTC
AT (SEQ ID NO: 7)

Translated protein sequence

MMGLSLASAVLLASLLSLHLGTATRGSDISKTCCFQYSHKPLPW
TWVRSYEFTSNSCSQRAVIFTTKRGKKVCTHPRKKWVQKYISLLKTPKQL (SEQ ID NO: 8)

| Gener Name | Gene ID | Accession NO. | Name |
|---|---|---|---|
| CDC20 | 991 | NM_001255 | *Homo sapiens* cell division cycle 20 homolog (*S. cerevisiae*) (CDC20), mRNA |

mRNA Sequence

GAGGCGTAAGCCAGGCGTGTTAAAGCCGGTCGGAACTGCTCCGGAGGGCACGGGCTCCGTAGGCACCAAC
TGCAAGGACCCCTCCCCCTGCGGGCGCTCCCATGGCACAGTTCGCGTTCGAGAGTGACCTGCACTCGCTG
CTTCAGCTGGATGCACCCATCCCCAATGCACCCCCTGCGCGCTGGCAGCGCAAAGCCAAGGAAGCCGCAG
GCCCGGCCCCCTCACCCATGCGGGCCGCCAACCGATCCCACAGCGCCGGCAGGACTCCGGGCCGAACTCC
TGGCAAATCCAGTTCCAAGGTTCAGACCACTCCTAGCAAACCTGGCGGTGACCGCTATATCCCCCATCGC
AGTGCTGCCCAGATGGAGGTGGCCAGCTTCCTCCTGAGCAAGGAGAACCAGCCTGAAAACAGCCAGACGC
CCACCAAGAAGGAACATCAGAAAGCCTGGGCTTTGAACCTGAACGGTTTTGATGTAGAGGAAGCCAAGAT
CCTTCGGCTCAGTGGAAAACCACAAAATGCGCCAGAGGGTTATCAGAACAGACTGAAAGTACTCTACAGC
CAAAAGGCCACTCCTGGCTCCAGCCGGAAGACCTGCCGTTACATTCCTTCCCTGCCAGACCGTATCCTGG
ATGCGCCTGAAATCCGAAATGACTATTACCTGAACCTTGTGGATTGGAGTTCTGGGAATGTACTGGCCGT
GGCACTGGACAACAGTGTGTACCTGTGGAGTGCAAGCTCTGGTGACATCCTGCAGCTTTTGCAAATGGAG
CAGCCTGGGGAATATATATCCTCTGTGGCCTGGATCAAAGAGGGCAACTACTTGGCTGTGGGCACCAGCA
GTGCTGAGGTGCAGCTATGGGATGTGCAGCAGCAGAAACGGCTTCGAAATATGACCAGTCACTCTGCCCG
AGTGGGCTCCCTAAGCTGGAACAGCTATATCCTGTCCAGTGGTTCACGTTCTGGCCACATCCACCACCAT
GATGTTCGGGTAGCAGAACACCATGTGGCCACACTGAGTGGCCACAGCCAGGAAGTGTGTGGGCTGCGCT
GGGCCCCAGATGGACGACATTTGGCCAGTGGTGGTAATGATAACTTGGTCAATGTGTGGCCTAGTGCTCC
TGGAGAGGGTGGCTGGGTTCCTCTGCAGACATTCACCCAGCATCAAGGGGCTGTCAAGGCCGTAGCATGG
TGTCCCTGGCAGTCCAATGTCCTGGCAACAGGAGGGGGCACCAGTGATCGACACATTCGCATCTGGAATG
TGTGCTCTGGGGCCTGTCTGAGTGCCGTGGATGCCCATTCCCAGGTGTGCTCCATCCTCTGGTCTCCCCA
TTACAAGGAGCTCATCTCAGGCCATGGCTTTGCACAGAACCAGCTAGTTATTTGGAAGTACCCAACCATG
GCCAAGGTGGCTGAACTCAAAGGTCACACATCCCGGGTCCTGAGTCTGACCATGAGCCCAGATGGGGCCA
CAGTGGCATCCGCAGCAGCAGATGAGACCCTGAGGCTATGGCGCTGTTTTGAGTTGGACCCTGCGCGGCG
GCGGGAGCGGGAGAAGGCCAGTGCAGCCAAAAGCAGCCTCATCCACCAAGGCATCCGCTGAAGACCAACC
CATCACCTCAGTTGTTTTTATTTTTCTAATAAAGTCATGTCTCCCTTCATGTTTTTTTTTAAAAAAA
AAAAAAAAAAAAAAAAA (SEQ ID NO: 9)

Translated protein sequence

MAQFAFESDLHSLLQLDAPIPNAPPARWQRKAKEAAGPAPSPMR
AANRSHSAGRTPGRTPGKSSSKVQTTPSKPGGDRYIPHRSAAQMEVASFLLSKENQPE
NSQTPTKKEHQKAWALNLNGFDVEEAKILRLSGKPQNAPEGYQNRLKVLYSQKATPGS
SRKTCRYIPSLPDRILDAPEIRNDYYLNLVDWSSGNVLAVALDNSVYLWSASSGDILQ
LLQMEQPGEYISSVAWIKEGNYLAVGTSSAEVQLWDVQQQKRLRNMTSHSARVGSLSW
NSYILSSGSRSGHIHHHDVRVAEHHVATLSGHSQEVCGLRWAPDGRHLASGGNDNLVN
VWPSAPGEGGWVPLQTFTQHQGAVKAVAWCPWQSNVLATGGGTSDRHIRIWNVCSGAC
LSAVDAHSQVCSILWSPHYKELISGHGFAQNQLVIWKYPTMAKVAELKGHTSRVLSLT
MSPDGATVASAAADETLRLWRCFELDPARRREREKASAAKSSLIHQGIR (SEQ ID NO: 10)

| Gener Name | Gene ID | Accession NO. | Name |
|---|---|---|---|
| CEP152 | 22995 | NM_014985 | *Homo sapiens* centrosomal protein 152 kDa (CEP152), mRNA |

mRNA Sequence

GCCCACCGGGCGAGCTTCTAGTCGGCGATTGAAGGATGCGAGTGCTCCTTAAGGGCCTCCGCCCCGTGAG
TTCGGTTGTGACTAGGAAGGAGCTAGTGGACTAGAGCCAGGGTAAGGGGATCTGCTAGAAGTTGGTCTTC
CGCCAGGACTAGAGTTTCCTCGCGGTAACAGCCTCCGTGGCCTCCGGAGGACCATGTCATTAGACTTTGG
CAGTGTGGCACTACCAGTGCAAAATGAAGATGAAGAGTATGACGAAGAGGACTATGAAAGAGAGAAAGAG
TTGCAGCAGTTACTCACAGACCTTCCCCATGACATGCTGGATGACGACCTCTCCTCTCCAGAGCTCCAGT
ATTCGGACTGCAGCGAGGATGGCACAGACGGACAACCACATCATCCTGAGCAATTGGAGATGAGCTGGAA
TGAGCAAATGCTGCCCAAATCTCAAAGTGTAAATGGCTATAATGAAATTCAGAGTTTATATGCTGGAGAA
AAATGTGGTAATGTCTGGGAAGAAAATAGAAGTAAAACTGAAGACCGACATCCTGTGTACCATCCTGAAG
AAGGTGGAGATGAAGGTGGAAGTGGTTATAGTCCTCCAAGTAAATGTGAACAGACTGATTTATATCACCT
TCCTGAAAACTTTAGGCCATATACCAATGGTCAGAAGCAGGAATTTAATAACCAAGCAACCAATGTAATT
AAATTTTCAGATCCTCAATGGAACCATTTTCAGGGTCCCAGTTGTCAAGGTTTGGAACCGTATAATAAAG
TGACATATAAACCTTATCAGTCTTCTGCCCAGAATAATGGCTCACCAGCCCAGGAGATAACAGGAAGTGA
CACATTCGAAGGCCTGCAACAACAATTTTTAGGAGCTAATGAGAACTCTGCAGAAAATATGCAGATTATT
CAACTTCAGGTTCTTAACAAAGCAAAAGAGAGACAACTGGAGAACTTAATTGAAAAGTTAAATGAAAGTG
AACGTCAAATTCGATATCTGAATCACCAGCTTGTAATAATAAAAGATGAAAAGGATGGTTTGACTCTCAG
CCTTCGAGAATCACAGAAACTCTTTCAGAATGGAAAAGAAAGAGAGATACAGCTTGAAGCTCAAATAAAA
GCACTGGAGACTCAGATACAAGCATTAAAAGTCAATGAAGAACAGATGATCAAGAAGTCCAGAACAACTG
AAATGGCTCTGGAAAGCTTGAAGCAGCAGCTGGTGGACCTTCATCATTCTGAATCACTTCAACGAGCTAG

APPENDIX-continued

NUCLEIC ACID AND AMINO ACID SEQUENCES OF BIOMARKERS

| Gener Name | Gene ID | Accession NO. | Name |
|---|---|---|---|

AGAACAGCATGAGAGCATTGTTATGGGCCTCACAAAGAAGTACGAAGAGCAAGTATTGTCCTTACAAAAG
AATTTGGATGCCACAGTCACCGCACTTAAAGAACAGGAAGACATTTGCTCTCGTCTGAAAGATCACGTGA
AACAACTGGAAAGGAATCAAGAAGCAATCAAGTTAGAAAAGACTGAGATCATTAATAAGTTGACAAGAAG
TCTAGAGGAGAGTCAAAAGCAGTGTGCCCACTTGTTGCAGTCCGGGTCAGTACAAGAGGTGGCTCAGCTA
CAGTTCCAGCTGCAGCAAGCACAGAAGGCACATGCTATGAGTGCAAACATGAACAAGGCTTTGCAAGAAG
AATTAACAGAACTAAAAGATGAAATTTCTCTCTATGAATCTGCTGCAAAACTAGGAATACATCCAAGTGA
CTCAGAAGGAGAATTAAATATAGAACTCACTGAATCGTATGTGGATTTGGGTATTAAAAAGGTCAACTGG
AAAAAATCCAAAGTTACCAGCATTGTACAAGAAGAAGACCCAAATGAAGAGCTTTCAAAAGATGAGTTCA
TTCTGAAGTTAAAGGCAGAAGTACAGCGTTTGCTGGGTAGCAACTCAATGAAGCGTCATCTGGTGTCTCA
GTTACAAAATGACCTCAAAGACTGTCATAAGAAAATTGAAGATCTCCACCAAGTGAAGAAGGATGAAAAA
AGCATTGAGGTTGAGACTAAAACAGATACCTCAGAAAAACCAAAGAATCAATTATGGCCTGAGTCTTCTA
CTTCTGATGTTGTCAGAGATGATATTCTGCTGCTTAAAAATGAAATTCAAGTTTTACAACAACAAAATCA
GGAACTTAAAGAAACTGAAGGAAAACTGAGAAATACAAATCAAGACTTATGTAATCAAATGAGACAAATG
GTACAAGATTTTGACCATGACAAACAAGAAGCTGTGGATAGGTGTGAAAGGACTTATCAGCAGCACCATG
AAGCCATGAAAACTCAAATACGTGAAAGCCTATTAGCAAAGCATGCTTTGGAGAAGCAGCAGCTCTTTGA
GGCTTATGAGAGAACTCATTTGCAACTGAGGTCTGAGTTGGATAAGTTGAATAAGGAGGTGACTGCTGTG
CAGGAATGTTACCTAGAAGTGTGCAGAGAGAAGGATAATCTAGAATTGACTCTCAGGAAGACCACTGAAA
AGGAGCAACAGACTCAGGAGAAGATCAAAGAAAAACTCATTCAACAGCTTGAAAAGGAGTGGCAGTCTAA
GCTGGATCAAACTATAAAGGCAATGAAAAAGAAGACCTTAGATTGTGGCAGCCAAACTGACCAAGTAACC
ACCAGTGATGTTATTTCCAAGAAAGAGATGGCAATTATGATAGAAGAGCAGAAGTGCACAATCCAGCAAA
ACTTAGAACAAGAGAAGGACATAGCCATCAAGGGGGCTATGAAGAAACTCGAAATTGAATTGGAACTCAA
ACATTGTGAAAATATTACCAAACAGGTAGAAATAGCTGTGCAAAATGCTCATCAGCGATGGCTGGGAGAA
CTACCAGAGCTGGCAGAGTATCAAGCACTTGTGAAGGCAGAACAGAAAAAGTGGGAAGAACAGCATGAGG
TCTCTGTGAACAAAAGGATATCATTTGCTGTTTCTGAAGCTAAAGAGAAATGGAAGAGTGAGCTTGAAAA
TATGAGGAAAAATATACTTCCTGGAAAGGAATTGGAAGAGAAGATTCATTCTCTTCAGAAGGAACTTGAG
TTAAAGAACGAAGAAGTCCCTGTGGTCATCAGGGCTGAGTTAGCTAAGGCTCGGAGTGAATGGAACAAAG
AAAAGCAAGAAGAAATCCACAGAATCCAAGAACAAAATGAGCAAGATTACCGGCAATTTTTAGATGATCA
CCGAAATAAAATTAATGAGGTGCTTGCGGCAGCTAAAGAAGACTTTATGAAACAAAAAACTGAACTACTT
CTTCAGAAGGAGACAGAATTACAAACTTGTCTAGACCAGAGTCGTAGAGAATGGACTATGCAGGAAGCCA
AGCGGATCCAACTGGAAATCTATCAGTATGAGGAAGACATCCTGACTGTACTTGGGGTTCTTTTAAGTGA
TACCCAAAAGGAGCACATCAGTGATTCTGAGGACAAGCAGCTTTTGGAAATCATGTCGACTTGTTCTTCA
AAATGGATGTCTGTGCAATATTTTGAAAAACTAAAGGGCTGCATACAGAAAGCATTTCAAGATACACTTC
CTCTGCTTGTAGAAAACGCTGACCCAGAATGGAAAAAGAGAAATATGGCCGAGCTCTCTAAGGATTCTGC
CAGCCAGGGCACTGGCCAAGGAGACCCTGGACCTGCTGCTGGACACCATGCTCAGCCCTTGGCCTTACAA
GCAACAGAAGCAGAAGCTGAAGAGAATAATAAAGTTGTTGAAGAATTAATAGAAGAAAACAACGACATGA
AGAATAAATTGGAAGAATTGCAAACACTTTGTAAAACACCACCAAGGTCATTGTCAGCAGGGGCCATTGA
AAATGCTTGCCTGCCATGCAGTGGGGGAGCCTTGGAAGAACTTCGTGGGCAGTACATTAAAGCTGTAAAA
AAAATTAAATGTGACATGCTTCGTTATATTCAGGAGAGTAAGGAACGAGCTGCAGAAATGGTAAAAGCAG
AGGTACTGCGAGAACGTCAAGAAACCGCCCGAAAGATGCGCAAATATTATTTGATTTGCCTCCAACAGAT
TTTGCAGGATGATGGAAAAGAAGGGGCTGAGAAAAAGATTATGAATGCTGCTAGCAAACTTGCTACAATG
GCAAAATTACTGGAAACACCTATTTCTAGTAAGTCCCAAAGCAAAACTACACAGTCAGCACTGCCCCTAA
CTTCAGAGATGCTGATTGCAGTTAAAAAATCAAAAAGAAATGATGTGAATCAGAAAATACCATGTTGTAT
TGAAAGCAAATCAAATAGTGTAAACACCATCACCAGAACTCTGTGCGAACAAGCTCCCAAGAGGAGGGCA
GCTTGTAACTTACAAAGGCTGTTAGAGAACTCAGAGCATCAGAGCATAAAGCATGTGGGATCCAAAGAGA
CACATTTGGAATTCCAGTTTGGGGATGGTAGTTGCAAGCACCTAAACAGTTTGCCAAGGAATGTTTCTCC
TGAGTTTGTTCCTTGTGAAGGTGAAGGAGGCTTTGGTTTGCACAAGAAGAAAGACCTACTCAGTGATAAT
GGTTCTGAATCACTTCCGCATTCAGCTGCATACCCCTTTCTTGGAACCTTAGGAAATAAACCCTCACCTA
GATGTACCCCTGGTCCTTCTGAATCAGGATGCATGCATATAACCTTTCGCGATTCTAATGAAAGACTTGG
TTTAAAAGTATATAAATGCAATCCACTAATGGAAAGTGAAAATGCTGCATCTGAGAAAAGTCAAGGTTTG
GATGTTCAGGAACCTCCAGTAAAAGATGGAGGGGACCTTAGTGACTGCTTGGGCTGGCCTTCCAGCAGTG
CAACCTTATCCTTTGACAGTCGTGAAGCATCATTTGTACATGGTAGGCCACAAGGAACTTTGGAAATACC
AAGTGAATCTGTTAAATCCAAACAGTTTTCACCATCCGGTTATCTTTCAGATACAGAGGAAAGTAATATG
ATTTGTCAAACAATGAAATGTCAGCGTTATCAAACTCCATACCTGTCAGAAGAAACCACGTATTTGGAGC
CAGGAAAGATCAGTGTGAATTGTGGACACCCATCTCGTCATAAGGCTGATAGATTAAAGTCAGATTTCAA
AAAACTGAGCAGTACATTACCATCTTCAGTGTGTCAGCAGCCTTCAAGAAAATTAATTGTTCCGCTATCT
AGCCAACAAGATAGTGGCTTTGATAGCCCATTTGTTAATCTAGACTAATTATGGTACAGTATTTAAGAAG
AATCATTAATATATTAACAAAAATGGAAGGGAAGACCTCATACTGAAAAAAATTGTGAGCCCTGCCTCTT
TTGAGATGTTTTAATAACATCTGTTATATAAGTAAAGCATTCTTCTAAAATTGCTTGAGATATTTATGTT
GCCTTAATATTCCAAAGGCCTGATGGTGTATGTATAATCTGCTTTTGTGTGGTGCTTATTTTTGGTTTCT
AAACCATCTATTTTTATACTTATAAATTGACTCACTCTGCAGTGTTAACTTATTTAAATAAACTTGCATA
TGGTCTGTAAAAAAAAAA (SEQ ID NO: 11)

Translated protein sequence

MSLDFGSVALPVQNEDEEYDEEDYEREKELQQLLTDLPHDMLDD
DLSSPELQYSDCSEDGTDGQPHHPEQLEMSWNEQMLPKSQSVNGYNEIQSLYAGEKCG
NVWEENRSKTEDRHPVYHPEEGGDEGGSGYSPPSKCEQTDLYHLPENFRPYTNGQKQE
FNNQATNVIKFSDPQWNHFQGPSCQGLEPYNKVTYKPYQSSAQNNGSPAQEITGSDTF
EGLQQQFLGANENSAENMQIIQLQVLNKAKERQLENLIEKLNESERQIRYLNHQLVII
KDEKDGLTLSLRESQKLFQNGKEREIQLEAQIKALETQIQALKVNEEQMIKKSRTTEM
ALESLKQQLVDLHHSESLQRAREQHESIVMGLTKKYEEQVLSLQKNLDATVTALKEQE
DICSRLKDHVKQLERNQEAIKLEKTEIINKLTRSLEESQKQCAHLLQSGSVQEVAQLQ
FQLQQAQKAHAMSANMNKALQEELTELKDEISLYESAAKLGIHPSDSEGELNIELTES
YVDLGIKKVNWKKSKVTSIVQEEDPNEELSKDEFILKLKAEVQRLLGSNSMKRHLVSQ
LQNDLKDCHKKIEDLHQVKKDEKSIEVETKTDTSEKPKNQLWPESSTSDVVRDDILLL

APPENDIX-continued

NUCLEIC ACID AND AMINO ACID SEQUENCES OF BIOMARKERS

| Gener Name | Gene ID | Accession NO. | Name |
|---|---|---|---|

KNEIQVLQQQNQELKETEGKLRNTNQDLCNQMRQMVQDFDHDKQEAVDRCERTYQQHH
EAMKTQIRESLLAKHALEKQQLFEAYERTHLQLRSELDKLNKEVTAVQECYLEVCREK
DNLELTLRKTTEKEQQTQEKIKEKLIQQLEKEWQSKLDQTIKAMKKKTLDCGSQTDQV
TTSDVISKKEMAIMIEEQKCTIQQNLEQEKDIAIKGAMKKLEIELELKHCENITKQVE
IAVQNAHQRWLGELPELAEYQALVKAEQKKWEEQHEVSVNKRISFAVSEAKEKWKSEL
ENMRKNILPGKELEEKIHSLQKELELKNEEVPVVIRAELAKARSEWNKEKQEEIHRIQ
EQNEQDYRQFLDDHRNKINEVLAAAKEDFMKQKTELLLQKETELQTCLDQSRREWTMQ
EAKRIQLEIYQYEEDILTVLGVLLSDTQKEHISDSEDKQLLEIMSTCSSKWMSVQYFE
KLKGCIQKAFQDTLPLLVENADPEWKKRNMAELSKDSASQGTGQGDPGPAAGHHAQPL
ALQATEAEAEENNKVVEELIEENNDMKNKLEELQTLCKTPPRSLSAGAIENACLPCSG
GALEELRGQYIKAVKKIKCDMLRYIQESKERAAEMVKAEVLRERQETARKMRKYYLIC
LQQILQDDGKEGAEKKIMNAASKLATMAKLLETPISSKSQSKTTQSALPLTSEMLIAV
KKSKRNDVNQKIPCCIESKSNSVNTITRTLCEQAPKRRAACNLQRLLENSEHQSIKHV
GSKETHLEFQFGDGSCKHLNSLPRNVSPEFVPCEGEGGFGLHKKKDLLSDNGSESLPH
SAAYPFLGTLGNKPSPRCTPGPSESGCMHITFRDSNERLGLKVYKCNPLMESENAASE
KSQGLDVQEPPVKDGGDLSDCLGWPSSSATLSFDSREASFVHGRPQGTLEIPSESVKS
KQFSPSGYLSDTEESNMICQTMKCQRYQTPYLSEETTYLEPGKISVNCGHPSRHKADR
LKSDFKKLSSTLPSSVCQQPSRKLIVPLSSQQDSGFDSPFVNLD (SEQ ID NO: 12)

| | | | |
|---|---|---|---|
| CFL1 | 1072 | NM_005507 | *Homo sapiens* cofilin 1 (non-muscle) (CFL1), mRNA |

mRNA Sequence

GGCCGGCGGGAAGACTCCGTTACCCAGCGAGCGAGGCGGCGGCGCAGGGCCAGCGGACTCCATTTCCCGT
CGGCTCGCGGTGGGAGCGCCGGAAGCCCGCCCCACCCCTCATTGTGCGGCTCCTACTAAACGGAAGGGGC
CGGGAGAGGCCGCGTTCAGTCGGGTCCCGGCAGCGGCTGCAGCGCTCTCGTCTTCTGCGGCTCTCGGTGC
CCTCTCCTTTTCGTTTCCGGAAACATGGCCTCCGGTGTGGCTGTCTCTGATGGTGTCATCAAGGTGTTCA
ACGACATGAAGGTGCGTAAGTCTTCAACGCCAGAGGAGGTGAAGAAGCGCAAGAAGGCGGTGCTCTTCTG
CCTGAGTGAGGACAAGAAGAACATCATCCTGGAGGAGGGCAAGGAGATCCTGGTGGGCGATGTGGGCCAG
ACTGTCGACGACCCCTACGCCACCTTTGTCAAGATGCTGCCAGATAAGGACTGCCGCTATGCCCTCTATG
ATGCAACCTATGAGACCAAGGAGAGCAAGAAGGAGGATCTGGTGTTTATCTTCTGGGCCCCCGAGTCTGC
GCCCCTTAAGAGCAAAATGATTTATGCCAGCTCCAAGGACGCCATCAAGAAGAAGCTGACAGGGATCAAG
CATGAATTGCAAGCAAACTGCTACGAGGAGGTCAAGGACCGCTGCACCCTGGCAGAGAAGCTGGGGGGCA
GTGCCGTCATCTCCCTGGAGGGCAAGCCTTTGTGAGCCCCTTCTGGCCCCCTGCCTGGAGCATCTGGCAG
CCCCACACCTGCCCTTGGGGGTTGCAGGCTGCCCCCTTCCTGCCAGACCGGAGGGGCTGGGGGGATCCCA
GCAGGGGGAGGGCAATCCCTTCACCCCAGTTGCCAAACAGACCCCCCACCCCCTGGATTTTCCTTCTCCC
TCCATCCCTTGACGGTTCTGGCCTTCCCAAACTGCTTTTGATCTTTTGATTCCTCTTGGGCTGAAGCAGA
CCAAGTTCCCCCCAGGCACCCCAGTTGTGGGGGAGCCTGTATTTTTTTTAACAACATCCCCATTCCCCAC
CTGGTCCTCCCCCTTCCCATGCTGCCAACTTCTAACCGCAATAGTGACTCTGTGCTTGTCTGTTTAGTTC
TGTGTATAAATGGAATGTTGTGGAGATGACCCCTCCCTGTGCCGGCTGGTTCCTCTCCCTTTTCCCCTGG
TCACGGCTACTCATGGAAGCAGGACCAGTAAGGGACCTTCGATTAAAAAAAAAAAAAGACAATAATAAAAA (SEQ ID NO: 13)

Translated protein sequence

MASGVAVSDGVIKVFNDMKVRKSSTPEEVKKRKKAVLFCLSEDK
KNIILEEGKEILVGDVGQTVDDPYATFVKMLPDKDCRYALYDATYETKESKKEDLVFI
FWAPESAPLKSKMIYASSKDAIKKKLTGIKHELQANCYEEVKDRCTLAEKLGGSAVIS
LEGKPL (SEQ ID NO: 14)

| | | | |
|---|---|---|---|
| CKLF | 51192 | NM_016326 | *Homo sapiens* chemokine-like factor (CKLF), transcript variant 3, mRNA |

mRNA Sequence

ATGCGCGCAAGAGAGCGGGAAGCCGAGCTGGGCGAGAAGTAGGGGAGGGCGGTGCTCCGCCGCGGTGGCG
GTTGCTATCGCTTCGCAGAACCTACTCAGGCAGCCAGCTGAGAAGAGTTGAGGGAAAGTGCTGCTGCTGG
GTCTGCAGACGCGATGGATAACGTGCAGCCGAAAATAAAACATCGCCCCTTCTGCTTCAGTGTGAAAGGC
CACGTGAAGATGCTGCGGCTGGTGTTTGCACTTGTGACAGCAGTATGCTGTCTTGCCGACGGGGCCCTTA
TTTACCGGAAGCTTCTGTTCAATCCCAGCGGTCCTTACCAGAAAAAGCCTGTGCATGAAAAAAAAGAAGT
TTTGTAATTTTATATTACTTTTTAGTTTGATACTAAGTATTAAACATATTTCTGTATTCTTCCACATATT
TTCTGCAGTTATTTTAACTCAGTATAGGAGCTAGAGGAAGAGATTTCCGAAGTCTGCACCCCGCGCAGAG
CACTACTGTAACTTCCAAGGGAGCGCTGGGAGCAGCGGGATCGGGTTTTCCGGCACCCGGGCCTGGGTGG
CAGGGAAGAATGTGCCGGGATCCGCCTCAGGGATCTTTGAATCTCTTTACTGCCTGGCTGGCCGGCAGCT
CCG (SEQ ID NO: 15)

Translated protein sequence

MDNVQPKIKHRPFCFSVKGHVKMLRLVFALVTAVCCLADGALIY
RKLLFNPSGPYQKKPVHEKKEVL (SEQ ID NO: 16)

| | | | |
|---|---|---|---|
| COL7A1 | 1294 | NM_000094 | *Homo sapiens* collagen, type VII, alpha 1 (COL7A1), mRNA |

APPENDIX-continued

NUCLEIC ACID AND AMINO ACID SEQUENCES OF BIOMARKERS

| Gener Name | Gene ID | Accession NO. | Name |
|---|---|---|---|

mRNA Sequence

GATGACGCTGCGGCTTCTGGTGGCCGCGCTCTGCGCCGGGATCCTGGCAGAGGCGCCCCGAGTGCGAGCC
CAGCACAGGGAGAGAGTGACCTGCACGCGCCTTTACGCCGCTGACATTGTGTTCTTACTGGATGGCTCCT
CATCCATTGGCCGCAGCAATTTCCGCGAGGTCCGCAGCTTTCTCGAAGGGCTGGTGCTGCCTTTCTCTGG
AGCAGCCAGTGCACAGGGTGTGCGCTTTGCCACAGTGCAGTACAGCGATGACCCACGGACAGAGTTCGGC
CTGGATGCACTTGGCTCTGGGGGTGATGTGATCCGCGCCATCCGTGAGCTTAGCTACAAGGGGGGCAACA
CTCGCACAGGGGCTGCAATTCTCCATGTGGCTGACCATGTCTTCCTGCCCCAGCTGGCCCGACCTGGTGT
CCCCAAGGTCTGCATCCTGATCACAGACGGGAAGTCCCAGGACCTGGTGGACACAGCTGCCCAAAGGCTG
AAGGGGCAGGGGGTCAAGCTATTTGCTGTGGGGATCAAGAATGCTGACCCTGAGGAGCTGAAGCGAGTTG
CCTCACAGCCCACCAGTGACTTCTTCTTCTTCGTCAATGACTTCAGCATCTTGAGGACACTACTGCCCCT
CGTTTCCCGGAGAGTGTGCACGACTGCTGGTGGCGTGCCTGTGACCCGACCTCCGGATGACTCGACCTCT
GCTCCACGAGACCTGGTGCTGTCTGAGCCAAGCAGCCAATCCTTGAGAGTACAGTGGACAGCGGCCAGTG
GCCCTGTGACTGGCTACAAGGTCCAGTACACTCCTCTGACGGGGCTGGGACAGCCACTGCCGAGTGAGCG
GCAGGAGGTGAACGTCCCAGCTGGTGAGACCAGTGTGCGGCTGCGGGGTCTCCGGCCACTGACCGAGTAC
CAAGTGACTGTGATTGCCCTCTACGCCAACAGCATCGGGGAGGCTGTGAGCGGGACAGCTCGGACCACTG
CCCTAGAAGGGCCGGAACTGACCATCCAGAATACCACAGCCCACAGCCTCCTGGTGGCCTGGCGGAGTGT
GCCAGGTGCCACTGGCTACCGTGTGACATGGCGGGTCCTCAGTGGTGGGCCCACACAGCAGCAGGAGCTG
GGCCCTGGGCAGGGTTCAGTGTTGCTGCGTGACTTGGAGCCTGGCACGGACTATGAGGTGACCGTGAGCA
CCCTATTTGGCCGCAGTGTGGGGCCCGCCACTTCCCTGATGGCTCGCACTGACGCTTCTGTTGAGCAGAC
CCTGCGCCCGGTCATCCTGGGCCCCACATCCATCCTCCTTTCCTGGAACTTGGTGCCTGAGGCCCGTGGC
TACCGGTTGGAATGGCGGCGTGAGACTGGCTTGGAGCCACCGCAGAAGGTGGTACTGCCCTCTGATGTGA
CCCGCTACCAGTTGGATGGGCTGCAGCCGGGCACTGAGTACCGCCTCACACTCTACACTCTGCTGGAGGG
CCACGAGGTGGCCACCCCTGCAACCGTGGTTCCCACTGGACCAGAGCTGCCTGTGAGCCCTGTAACAGAC
CTGCAAGCCACCGAGCTGCCCGGGCAGCGGGTGCGAGTGTCCTGGAGCCCAGTCCCTGGTGCCACCCAGT
ACCGCATCATTGTGCGCAGCACCCAGGGGGTTGAGCGGACCCTGGTGCTTCCTGGGAGTCAGACAGCATT
CGACTTGGATGACGTTCAGGCTGGGCTTAGCTACACTGTGCGGGTGTCTGCTCGAGTGGGTCCCCGTGAG
GGCAGTGCCAGTGTCCTCACTGTCCGCCGGGAGCCGGAAACTCCACTTGCTGTTCCAGGGCTGCGGGTTG
TGGTGTCAGATGCAACGCGAGTGAGGGTGGCCTGGGGACCCGTCCCTGGAGCCAGTGGATTTCGGATTAG
CTGGAGCACAGGCAGTGGTCCGGAGTCCAGCCAGACACTGCCCCCAGACTCTACTGCCACAGACATCACA
GGGCTGCAGCCTGGAACCACCTACCAGGTGGCTGTGTCGGTACTGCGAGGCAGAGAGGAGGGCCCTGCTG
CAGTCATCGTGGCTCGAACGGACCCACTGGGCCCAGTGAGGACGGTCCATGTGACTCAGGCCAGCAGCTC
ATCTGTCACCATTACCTGGACCAGGGTTCCTGGCGCCACAGGATACAGGGTTTCCTGGCACTCAGCCCAC
GGCCCAGAGAAATCCCAGTTGGTTTCTGGGGAGGCCACGGTGGCTGAGCTGGATGGACTGGAGCCAGATA
CTGAGTATACGGTGCATGTGAGGGCCCATGTGGCTGGCGTGGATGGGCCCCCTGCCTCTGTGGTTGTGAG
GACTGCCCCTGAGCCTGTGGGTCGTGTGTCGAGGCTGCAGATCCTCAATGCTTCCAGCGACGTTCTACGG
ATCACCTGGGTAGGGGTCACTGGAGCCACAGCTTACAGACTGGCCTGGGGCCGGAGTGAAGGCGGCCCCA
TGAGGCACCAGATACTCCCAGGAAACACAGACTCTGCAGAGATCCGGGGTCTCGAAGGTGGAGTCAGCTA
CTCAGTGCGAGTGACTGCACTTGTCGGGGACCGCGAGGGCACACCTGTCTCCATTGTTGTCACTACGCCG
CCTGAGGCTCCGCCAGCCCTGGGGACGCTTCACGTGGTGCAGCGCGGGGAGCACTCGCTGAGGCTGCGCT
GGGAGCCGGTGCCCAGAGCGCAGGGCTTCCTTCTGCACTGGCAACCTGAGGGTGGCCAGGAACAGTCCCG
GGTCCTGGGGCCCGAGCTCAGCAGCTATCACCTGGACGGGCTGGAGCCAGCGACACAGTACCGCGTGAGG
CTGAGTGTCCTAGGGCCAGCTGGAGAAGGGCCCTCTGCAGAGGTGACTGCGCGCACTGAGTCACCTCGTG
TTCCAAGCATTGAACTACGTGTGGTGGACACCTCGATCGACTCGGTGACTTTGGCCTGGACTCCAGTGTC
CAGGGCATCCAGCTACATCCTATCCTGGCGGCCACTCAGAGGCCCTGGCCAGGAAGTGCCTGGGTCCCCG
CAGACACTTCCAGGGATCTCAAGCTCCCAGCGGGTGACAGGGCTAGAGCCTGGCGTCTCTTACATCTTCT
CCCTGACGCCTGTCCTGGATGGTGTGCGGGGTCCTGAGGCATCTGTCACACAGACGCCAGTGTGCCCCCG
TGGCCTGGCGGATGTGGTGTTCCTACCACATGCCACTCAAGACAATGCTCACCGTGCGGAGGCTACGAGG
AGGGTCCTGGAGCGTCTGGTGTTGGCACTTGGGCCTCTTGGGCCACAGGCAGTTCAGGTTGGCCTGCTGT
CTTACAGTCATCGGCCCTCCCCACTGTTCCCACTGAATGGCTCCCATGACCTTGGCATTATCTTGCAAAG
GATCCGTGACATGCCCTACATGGACCCAAGTGGGAACAACCTGGGCACAGCCGTGGTCACAGCTCACAGA
TACATGTTGGCACCAGATGCTCCTGGGCGCCGCCAGCACGTACCAGGGGTGATGGTTCTGCTAGTGGATG
AACCCTTGAGAGGTGACATATTCAGCCCCATCCGTGAGGCCCAGGCTTCTGGGCTTAATGTGGTGATGTT
GGGAATGGCTGGAGCGGACCCAGAGCAGCTGCGTCGCTTGGCGCCGGGTATGGACTCTGTCCAGACCTTC
TTCGCCGTGGATGATGGGCCAAGCCTGGACCAGGCAGTCAGTGGTCTGGCCACAGCCCTGTGTCAGGCAT
CCTTCACTACTCAGCCCCGGCCAGAGCCCTGCCCAGTGTATTGTCCAAAGGGCCAGAAGGGGGAACCTGG
AGAGATGGGCCTGAGAGGACAAGTTGGGCCTCCTGGCGACCCTGGCCTCCCGGGCAGGACCGGTGCTCCC
GGCCCCCAGGGGCCCCCTGGAAGTGCCACTGCCAAGGGCGAGAGGGGCTTCCCTGGAGCAGATGGGCGTC
CAGGCAGCCCTGGCCGCGCCGGGAATCCTGGGACCCCTGGAGCCCCTGGCCTAAAGGGCTCTCCAGGGTT
GCCTGGCCCTCGTGGGGACCCGGGAGAGCGAGGACCTCGAGGCCCAAAGGGGGAGCCGGGGGCTCCCGGA
CAAGTCATCGGAGGTGAAGGACCTGGGCTTCCTGGGCGGAAAGGGGACCCTGGACCATCGGGCCCCCCTG
GACCTCGTGGACCACTGGGGGACCCAGGACCCCGTGGCCCCCCAGGGCTTCCTGGAACAGCCATGAAGGG
TGACAAAGGCGATCGTGGGGAGCGGGGTCCCCCTGGACCAGGTGAAGGTGGCATTGCTCCTGGGGAGCCT
GGGCTGCCGGGTCTTCCCGGAAGCCCTGGACCCCAAGGCCCCGTTGGCCCCCCTGGAAAGAAAGGAGAAA
AAGGTGACTCTGAGGATGGAGCTCCAGGCCTCCCAGGACAACCTGGGTCTCCGGGTGAGCAGGGCCCACG
GGGACCTCCTGGAGCTATTGGCCCCAAAGGTGACCGGGGCTTTCCAGGGCCCCTGGGTGAGGCTGGAGAG
AAGGGCGAACGTGGACCCCCAGGCCCAGCGGGATCCCGGGGGCTGCCAGGGGTTGCTGGACGTCCTGGAG
CCAAGGGTCCTGAAGGGCCACCAGGACCCACTGGCCGCCAAGGAGAGAAGGGGGAGCCTGGTCGCCCTGG
GGACCCTGCAGTGGTGGGACCTGCTGTTGCTGGACCCAAAGGAGAAAAGGGAGATGTGGGGCCCGCTGGG
CCCAGAGGAGCTACCGGAGTCCAAGGGGAACGGGGCCCACCCGGCTTGGTTCTTCCTGGAGACCCTGGCC
CCAAGGGAGACCCTGGAGACCGGGGTCCCATTGGCCTTACTGGCAGAGCAGGACCCCCAGGTGACTCAGG
GCCTCCTGGAGAGAAGGGAGACCCTGGGCGGCCTGGCCCCCCAGGACCTGTTGGCCCCCGAGGACGAGAT
GGTGAAGTTGGAGAGAAAGGTGACGAGGGTCCTCCGGGTGACCCGGGTTTGCCTGGAAAAGCAGGCGAGC
GTGGCCTTCGGGGGGCACCTGGAGTTCGGGGGCCTGTGGGTGAAAAGGGAGACCAGGGAGATCCTGGAGA
GGATGGACGAAATGGCAGCCCTGGATCATCTGGACCCAAGGGTGACCGTGGGGAGCCGGGTCCCCCAGGA

APPENDIX-continued

NUCLEIC ACID AND AMINO ACID SEQUENCES OF BIOMARKERS

| Gener Name | Gene ID | Accession NO. | Name |
|---|---|---|---|

CCCCCGGGACGGCTGGTAGACACAGGACCTGGAGCCAGAGAGAAGGGAGAGCCTGGGGACCGCGGACAAG
AGGGTCCTCGAGGGCCCAAGGGTGATCCTGGCCTCCCTGGAGCCCCTGGGGAAAGGGGCATTGAAGGGTT
TCGGGGACCCCCAGGCCCACAGGGGGACCCAGGTGTCCGAGGCCCAGCAGGAGAAAAGGGTGACCGGGGT
CCCCCTGGGCTGGATGGCCGGAGCGGACTGGATGGGAAACCAGGAGCCGCTGGGCCCTCTGGGCCGAATG
GTGCTGCAGGCAAAGCTGGGGACCCAGGGAGAGACGGGCTTCCAGGCCTCCGTGGAGAACAGGGCCTCCC
TGGCCCCTCTGGTCCCCCTGGATTACCGGGAAAGCCAGGCGAGGATGGCAAACCTGGCCTGAATGGAAAA
AACGGAGAACCTGGGGACCCTGGAGAAGACGGGAGGAAGGGAGAGAAAGGAGATTCAGGCGCCTCTGGGA
GAGAAGGTCGTGATGGCCCCAAGGGTGAGCGTGGAGCTCCTGGTATCCTTGGACCCCAGGGGCCTCCAGG
CCTCCCAGGGCCAGTGGGCCCTCCTGGCCAGGGTTTTCCTGGTGTCCCAGGAGGCACGGGCCCCAAGGGT
GACCGTGGGGAGACTGGATCCAAAGGGGAGCAGGGCCTCCCTGGAGAGCGTGGCCTGCGAGGAGAGCCTG
GAAGTGTGCCGAATGTGGATCGGTTGCTGGAAACTGCTGGCATCAAGGCATCTGCCCTGCGGGAGATCGT
GGAGACCTGGGATGAGAGCTCTGGTAGCTTCCTGCCTGTGCCCGAACGGCGTCGAGGCCCCAAGGGGGAC
TCAGGCGAACAGGGCCCCCCAGGCAAGGAGGGCCCCATCGGCTTTCCTGGAGAACGCGGGCTGAAGGGCG
ACCGTGGAGACCCTGGCCCTCAGGGGCCACCTGGTCTGGCCCTTGGGGAGAGGGGCCCCCCCGGGCCTTC
CGGCCTTGCCGGGGAGCCTGGAAAGCCTGGTATTCCCGGGCTCCCAGGCAGGGCTGGGGGTGTGGGAGAG
GCAGGAAGGCCAGGAGAGAGGGGAGAACGGGGAGAGAAAGGAGAACGTGGAGAACAGGGCAGAGATGGCC
CTCCTGGACTCCCTGGAACCCCTGGGCCCCCCGGACCCCCTGGCCCCAAGGTGTCTGTGGATGAGCCAGG
TCCTGGACTCTCTGGAGAACAGGGACCCCCTGGACTCAAGGGTGCTAAGGGGGAGCCGGGCAGCAATGGT
GACCAAGGTCCCAAAGGAGACAGGGGTGTGCCAGGCATCAAAGGAGACCGGGGAGAGCCTGGACCGAGGG
GTCAGGACGGCAACCCGGGTCTACCAGGAGAGCGTGGTATGGCTGGGCCTGAAGGGAAGCCGGGTCTGCA
GGGTCCAAGAGGCCCCCCTGGCCCAGTGGGTGGTCATGGAGACCCTGGACCACCTGGTGCCCCGGGTCTT
GCTGGCCCTGCAGGACCCCAAGGACCTTCTGGCCTGAAGGGGGAGCCTGGAGAGACAGGACCTCCAGGAC
GGGGCCTGACTGGACCTACTGGAGCTGTGGGACTTCCTGGACCCCCCGGCCCTTCAGGCCTTGTGGGTCC
ACAGGGGTCTCCAGGTTTGCCTGGACAAGTGGGGGAGACAGGGAAGCCGGGAGCCCCAGGTCGAGATGGT
GCCAGTGGAAAAGATGGAGACAGAGGGAGCCCTGGTGTGCCAGGGTCACCAGGTCTGCCTGGCCCTGTCG
GACCTAAAGGAGAACCTGGCCCCACGGGGGCCCCTGGACAGGCTGTGGTCGGGCTCCCTGGAGCAAAGGG
AGAGAAGGGAGCCCCTGGAGGCCTTGCTGGAGACCTGGTGGGTGAGCCGGGAGCCAAAGGTGACCGAGGA
CTGCCAGGGCCGCGAGGCGAGAAGGGTGAAGCTGGCCGTGCAGGGGAGCCCGGAGACCCTGGGGAAGATG
GTCAGAAAGGGGCTCCAGGACCCAAAGGTTTCAAGGGTGACCCAGGAGTCGGGGTCCCGGGCTCCCCTGG
GCCTCCTGGCCCTCCAGGTGTGAAGGGAGATCTGGGCCTCCCTGGCCTGCCCGGTGCTCCTGGTGTTGTT
GGGTTCCCGGGTCAGACAGGCCCTCGAGGAGAGATGGGTCAGCCAGGCCCTAGTGGAGAGCGGGGTCTGG
CAGGCCCCCCAGGGAGAGAAGGAATCCCAGGACCCCTGGGGCCACCTGGACCACCGGGGTCAGTGGGACC
ACCTGGGGCCTCTGGACTCAAAGGAGACAAGGGAGACCCTGGAGTAGGGCTGCCTGGGCCCCGAGGCGAG
CGTGGGGAGCCAGGCATCCGGGGTGAAGATGGCCGCCCCGGCCAGGAGGGACCCCGAGGACTCACGGGGC
CCCCTGGCAGCAGGGGAGAGCGTGGGGAGAAGGGTGATGTTGGGAGTGCAGGACTAAAGGGTGACAAGGG
AGACTCAGCTGTGATCCTGGGGCCTCCAGGCCCACGGGGTGCCAAGGGGGACATGGGTGAACGAGGGCCT
CGGGGCTTGGATGGTGACAAAGGACCTCGGGGAGACAATGGGGACCCTGGTGACAAGGGCAGCAAGGGAG
AGCCTGGTGACAAGGGCTCAGCCGGGTTGCCAGGACTGCGTGGACTCCTGGGACCCCAGGGTCAACCTGG
TGCAGCAGGGATCCCTGGTGACCCGGGATCCCCAGGAAAGGATGGAGTGCCTGGTATCCGAGGAGAAAAA
GGAGATGTTGGCTTCATGGGTCCCCGGGGCCTCAAGGGTGAACGGGGAGTGAAGGGAGCCTGTGGCCTTG
ATGGAGAGAAGGGAGACAAGGGAGAAGCTGGTCCCCCAGGCCGCCCCGGGCTGGCAGGACACAAAGGAGA
GATGGGGGAGCCTGGTGTGCCGGGCCAGTCGGGGGCCCCTGGCAAGGAGGGCCTGATCGGTCCCAAGGGT
GACCGAGGCTTTGACGGGCAGCCAGGCCCCAAGGGTGACCAGGGCGAGAAAGGGGAGCGGGGAACCCCAG
GAATTGGGGGCTTCCCAGGCCCCAGTGGAAATGATGGCTCTGCTGGTCCCCCAGGGCCACCTGGCAGTGT
TGGTCCCAGAGGCCCCGAAGGACTTCAGGGCCAGAAGGGTGAGCGAGGTCCCCCCGGAGAGAGAGTGGTG
GGGGCTCCTGGGGTCCCTGGAGCTCCTGGCGAGAGAGGGGAGCAGGGGCGGCCAGGGCCTGCCGGTCCTC
GAGGCGAGAAGGGAGAAGCTGCACTGACGGAGGATGACATCCGGGGCTTTGTGCGCCAAGAGATGAGTCA
GCACTGTGCCTGCCAGGGCCAGTTCATCGCATCTGGATCACGACCCCTCCCTAGTTATGCTGCAGACACT
GCCGGCTCCCAGCTCCATGCTGTGCCTGTGCTCCGCGTCTCTCATGCAGAGGAGGAAGAGCGGGTACCCC
CTGAGGATGATGAGTACTCTGAATACTCCGAGTATTCTGTGGAGGAGTACCAGGACCCTGAAGCTCCTTG
GGATAGTGATGACCCCTGTTCCCTGCCACTGGATGAGGGCTCCTGCACTGCCTACACCCTGCGCTGGTAC
CATCGGGCTGTGACAGGCAGCACAGAGGCCTGTCACCCTTTTGTCTATGGTGGCTGTGGAGGGAATGCCA
ACCGTTTTGGGACCCGTGAGGCCTGCGAGCGCCGCTGCCCACCCCGGGTGGTCCAGAGCCAGGGGACAGG
TACTGCCCAGGACTGAGGCCCAGATAATGAGCTGAGATTCAGCATCCCCTGGAGGAGTCGGGGTCTCAGC
AGAACCCCACTGTCCCTCCCCTTGGTGCTAGAGGCTTGTGTGCACGTGAGCGTGCGTGTGCACGTCCGTT
ATTTCAGTGACTTGGTCCCGTGGGTCTAGCCTTCCCCCCTGTGGACAAACCCCCATTGTGGCTCCTGCCA
CCCTGGCAGATGACTCACTGTGGGGGGGTGGCTGTGGGCAGTGAGCGGATGTGACTGGCGTCTGACCCGC
CCCTTGACCCAAGCCTGTGATGACATGGTGCTGATTCTGGGGGGCATTAAAGCTGCTGTTTTAAAAGGC (SEQ
ID NO: 17)

Translated protein sequence

MTLRLLVAALCAGILAEAPRVRAQHRERVTCTRLYAADIVFLLD
GSSSIGRSNFREVRSFLEGLVLPFSGAASAQGVRFATVQYSDDPRTEFGLDALGSGGD
VIRAIRELSYKGGNTRTGAAILHVADHVFLPQLARPGVPKVCILITDGKSQDLVDTAA
QRLKGQGVKLFAVGIKNADPEELKRVASQPTSDFFFFVNDFSILRTLLPLVSRRVCTT
AGGVPVTRPPDDSTSAPRDLVLSEPSSQSLRVQWTAASGPVTGYKVQYTPLTGLGQPL
PSERQEVNVPAGETSVRLRGLRPLTEYQVTVIALYANSIGEAVSGTARTTALEGPELT
IQNTTAHSLLVAWRSVPGATGYRVTWRVLSGGPTQQQELGPGQGSVLLRDLEPGTDYE
VTVSTLFGRSVGPATSLMARTDASVEQTLRPVILGPTSILLSWNLVPEARGYRLEWRR
ETGLEPPQKVVLPSDVTRYQLDGLQPGTEYRLTLYTLLEGHEVATPATVVPTGPELPV
SPVTDLQATELPGQRVRVSWSPVPGATQYRIIVRSTQGVERTLVLPGSQTAFDLDDVQ
AGLSYTVRVSARVGPREGSASVLTVRREPETPLAVPGLRVVVSDATRVRVAWGPVPGA
SGFRISWSTGSGPESSQTLPPDSTATDITGLQPGTTYQVAVSVLRGREEGPAAVIVAR
TDPLGPVRTVHVTQASSSSVTITWTRVPGATGYRVSWHSAHGPEKSQLVSGEATVAEL

APPENDIX-continued

NUCLEIC ACID AND AMINO ACID SEQUENCES OF BIOMARKERS

| Gener Name | Gene ID | Accession NO. | Name |
|---|---|---|---|

DGLEPDTEYTVHVRAHVAGVDGPPASVVVRTAPEPVGRVSRLQILNASSDVLRITWVG
VTGATAYRLAWGRSEGGPMRHQILPGNTDSAEIRGLEGGVSYSVRVTALVGDREGTPV
SIVVTTPPEAPPALGTLHVVQRGEHSLRLRWEPVPRAQGFLLHWQPEGGQEQSRVLGP
ELSSYHLDGLEPATQYRVRLSVLGPAGEGPSAEVTARTESPRVPSIELRVVDTSIDSV
TLAWTPVSRASSYILSWRPLRGPGQEVPGSPQTLPGISSSQRVTGLEPGVSYIFSLTP
VLDGVRGPEASVTQTPVCPRGLADVVFLPHATQDNAHRAEATRRVLERLVLALGPLGP
QAVQVGLLSYSHRPSPLFPLNGSHDLGTTLQRIRDMPYMDPSGNNLGTAVVTAHRYML
APDAPGRRQHVPGVMVLLVDEPLRGDIFSPIREAQASGLNVVMLGMAGADPEQLRRLA
PGMDSVQTFFAVDDGPSLDQAVSGLATALCQASFTTQPRPEPCPVYCPKGQKGEPGEM
GLRGQVGPPGDPGLPGRTGAPGPQGPPGSATAKGERGFPGADGRPGSPGRAGNPGTPG
APGLKGSPGLPGPRGDPGERGPRGPKGEPGAPGQVIGGEGPGLPGRKGDPGPSGPPGP
RGPLGDPGPRGPPGLPGTAMKGDKGDRGERGPPGPGEGGIAPGEPGLPGLPGSPGPQG
PVGPPGKKGEKGDSEDGAPGLPGQPGSPGEQGPRGPPGAIGPKGDRGFPGPLGEAGEK
GERGPPGPAGSRGLPGVAGRPGAKGPEGPPGPTGRQGEKGEPGRPGDPAVVGPAVAGP
KGEKGDVGPAGPRGATGVQGERGPPGLVLPGDPGPKGDPGDRGPIGLTGRAGPPGDSG
PPGEKGDPGRPGPPGPVGPRGRDGEVGEKGDEGPPGDPGLPGKAGERGLRGAPGVRGP
VGEKGDQGDPGEDGRNGSPGSSGPKGDRGEPGPPGPPGRLVDTGPGAREKGEPGDRGQ
EGPRGPKGDPGLPGAPGERGIEGFRGPPGPQGDPGVRGPAGEKGDRGPPGLDGRSGLD
GKPGAAGPSGPNGAAGKAGDPGRDGLPGLRGEQGLPGPSGPPGLPGKPGEDGKPGLNG
KNGEPGDPGEDGRKGEKGDSGASGREGRDGPKGERGAPGILGPQGPPGLPGPVGPPGQ
GFPGVPGGTGPKGDRGETGSKGEQGLPGERGLRGEPGSVPNVDRLLETAGIKASALRE
IVETWDESSGSFLPVPERRRGPKGDSGEQGPPGKEGPIGFPGERGLKGDRGDPGPQGP
PGLALGERGPPGPSGLAGEPGKPGIPGLPGRAGGVGEAGRPGERGERGEKGERGEQGR
DGPPGLPGTPGPPGPPGPKVSVDEPGPGLSGEQGPPGLKGAKGEPGSNGDQGPKGDRG
VPGIKGDRGEPGPRGQDGNPGLPGERGMAGPEGKPGLQGPRGPPGPVGGHGDPGPPGA
PGLAGPAGPQGPSGLKGEPGETGPPGRGLTGPTGAVGLPGPPGPSGLVGPQGSPGLPG
QVGETGKPGAPGRDGASGKDGDRGSPGVPGSPGLPGPVGPKGEPGPTGAPGQAVVGLP
GAKGEKGAPGGLAGDLVGEPGAKGDRGLPGPRGEKGEAGRAGEPGDPGEDGQKGAPGP
KGFKGDPGVGVPGSPGPPGPPGVKGDLGLPGLPGAPGVVGFPGQTGPRGEMGQPGPSG
ERGLAGPPGREGIPGPLGPPGPPGSVGPPGASGLKGDKGDPGVGLPGPRGERGEPGIR
GEDGRPGQEGPRGLTGPPGSRGERGEKGDVGSAGLKGDKGDSAVILGPPGPRGAKGDM
GERGPRGLDGDKGPRGDNGDPGDKGSKGEPGDKGSAGLPGLRGLLGPQGQPGAAGIPG
DPGSPGKDGVPGIRGEKGDVGFMGPRGLKGERGVKGACGLDGEKGDKGEAGPPGRPGL
AGHKGEMGEPGVPGQSGAPGKEGLIGPKGDRGFDGQPGPKGDQGEKGERGTPGIGGFP
GPSGNDGSAGPPGPPGSVGPRGPEGLQGQKGERGPPGERVVGAPGVPGAPGERGEQGR
PGPAGPRGEKGEAALTEDDIRGFVRQEMSQHCACQGQFIASGSRPLPSYAADTAGSQL
HAVPVLRVSHAEEEERVPPEDDEYSEYSEYSVEEYQDPEAPWDSDDPCSLPLDEGSCT
AYTLRWYHRAVTGSTEACHPFVYGGCGGNANRFGTREACERRCPPRVVQSQGTGTAQD (SEQ ID NO: 18)

| | | | |
|---|---|---|---|
| CYP4F3 | 4051 | NM_000896 | *Homo sapiens* cytochrome P450, family 4, subfamily F, polypeptide 3 (CYP4F3), mRNA |

mRNA Sequence

AGAAGAAGGGGAGAGGAGGTTGTGTGGGACAAGGTGCTCCTGACAGAAGGATGCCACAGCTGAGCCTGTC
CTCGCTGGGCCTTTGGCCAATGGCAGCATCCCCGTGGCTGCTCCTGCTGCTGGTTGGGGCCTCCTGGCTC
CTGGCCCGCATCCTGGCCTGGACCTATACCTTCTATGACAACTGCTGCCGCCTCCGGTGTTTCCCGCAAC
CCCCGAAACGGAATTGGTTCTTGGGTCACCTGGGCCTGATTCACAGCTCGGAGGAAGGTCTCCTATACAC
ACAAAGCCTGGCATGCACCTTCGGTGATATGTGCTGCTGGTGGGTGGGGCCCTGGCACGCAATCGTCCGC
ATCTTCCACCCCACCTACATCAAGCCTGTGCTCTTTGCTCCAGCTGCCATTGTACCAAAGGACAAGGTCT
TCTACAGCTTCCTGAAGCCCTGGCTGGGGGATGGGCTCCTGCTGAGTGCTGGTGAAAAGTGGAGCCGCCA
CCGTCGGATGCTGACGCCTGCCTTCCATTTCAACATCCTGAAGCCCTATATGAAGATTTTCAATGAGAGT
GTGAACATCATGCATGCCAAGTGGCAGCTCCTGGCCTCAGAGGGTAGTGCCCGTCTGGACATGTTTGAGC
ACATCAGCCTCATGACCTTGGACAGTCTGCAGAAATGTGTCTTCAGCTTTGACAGCCATTGCCAGGAGAA
GCCCAGTGAATATATTGCCGCCATCTTGGAGCTCAGTGCCCTTGTGACAAAAAGACACCAGCAGATCCTC
CTGTACATAGACTTCCTGTATTATCTCACCCCTGATGGGCAGCGTTTCCGCAGGGCCTGCCGCCTGGTGC
ACGACTTCACAGATGCCGTCATCCAGGAGCGGCGCCGCACCCTCCCTAGCCAGGGTGTTGATGACTTCCT
CCAAGCCAAGGCCAAATCCAAGACTTTGGACTTCATTGATGTACTCCTGCTGAGCAAGGATGAAGATGGG
AAGAAGTTGTCCGATGAGGACATAAGAGCAGAAGCTGACACCTTTATGTTTGAGGGCCATGACACCACAG
CCAGTGGTCTCTCCTGGGTCCTGTACCACCTTGCAAAGCACCCGGAATACCAGGAGCGCTGTCGGCAGGA
GGTGCAAGAGCTTCTGAAGGACCGTGAGCCTAAAGAGATTGAATGGGACGACCTGGCCCAGCTGCCCTTC
CTGACCATGTGCATTAAGGAGAGCCTGAGGCTGCATCCCCCAGTCCCTGCCGTCTCTCGCTGCTGCACCC
AAGACATTGTGCTCCCAGACGGCCGGGTCATCCCCAAAGGCATTATCTGCCTCATCAGTGTTTTTGGAAC
CCATCACAACCCAGCCGTGTGGCCGGACCCTGAGGTCTATGACCCCTTTCGCTTTGACCCAAAGAACATC
AAGGAGAGGTCACCTCTGGCTTTTATTCCCTTCTCAGCAGGGCCCAGGAACTGCATCGGGCAGGCGTTCG
CGATGGCGGAGATGAAGGTGGTCCTGGGGCTCACGCTGCTGCGCTTCCGCGTCCTGCCTGACCACACCGA
GCCCCGCAGGAAGCCGGAGCTGGTCCTGCGCGCAGAGGGCGGACTTTGGCTGCGGGTGGAGCCCCTGAGC
TGAGTTCTGCAGAGACCCACTCTGACCCCACTAAAATGACCCCTGATTCATCAAAAGTGAGGCCTAGAAT
TACCCTAAGACCCTGTTCCACAGTCCTGTATTCCATCCTAGATATCTACTCAAAATAATTGAGACAAGTG
TTCAAACAGAAAGACGCTTGTGCGTGAATGTTCATGGCAGCCCTATTCACAGTAGCCAAACGATGAAAAC
AACCCCAAGCTATATATTACCAGATGAAAGGATAAACAAAATATGGTCCATCCATACAATGGAGTATTAC
ACAGCCATAAAAAGGAATGAAGCAGTGATCCCCACTACACTGTGGATGAACCTTGAATGCATGATACTGA
ATGAAAGACATCAGATGCAAAAGGTCACATAGTGTACTGTCCTTTTATATGAAATTTCCAGAACAGGCCA
ATCTGAAGAGATGTATAGTGGATTGGTGGCTTTCAGCAGCTGTGGGGAGGTGGGACTGAGGAGCGACTGC
TAATCAGGATGGGGTTTCCTCCTGGGATGGTGAAAATGTTCCGGACCTAGATAGTGATGAAGGTAGCACG

APPENDIX-continued

NUCLEIC ACID AND AMINO ACID SEQUENCES OF BIOMARKERS

| Gener Name | Gene ID | Accession NO. | Name |
|---|---|---|---|

ACACTGTGAGTGCACTAAATGCTATTGAATTGGACACTTTAGAATGGTTGAAATAGTGATTTTTATGTGA
ATTCTACCTAAACATGCTATTACAGCTCATATATACTTTTTCCATCTGGATTCTTCACAAAAGAATATGT
TGTGAGCATCTTTCCATGATATTAAATCATCTTAGGAAACATTATTTTGTGTTCTTCAAAATGTGCATGT
TAAGTATTCAAATCAGTCTTAAATTTTTAAAAATATGTAATTTTAGAAAATAATTTAAAAGGTTTTGTTT
CAGTTTGTAAGATTTCTTTTCTGGCACTTTAATGGCTTGAGGTATCATTATCAGTTACAAATTGAGTTAT
TCTTCATCAAATGACTTTTGGAGTAGAGATTTTATTTTTATAGCAATAGATGCACAGATATTCCTGTAAG
ATACAGGTGTGGTTAGACACTTTTCTAGAACAGGCATGCCCTGCAAACTCCACAGACACTGACTGTTTTT
GTCCTATTAAGAAGTAGACCACTGAGAAGGGAGAAGGTGACATTTTAGCTTTCCCAGGTAAAAGTGGTTT
TCATCCTCACACCAATTTTATGGACTGGACGTTAACTCTCTTGCTCAAGGTCACTCTGAGTGGAAGAGTG
GGGATAAATCTGGTTCGTTTGGCATCAGAGGCCATGACTTTTCCTACCACAGAAGTAATTTTCAAAGTAA
GTCTCTGCCCTAGGCACATCAGATCACCTGGGGACCACTCCAGAGTGAGTAGACAAGACTTTGACAGGGG
TGCCTAATTTTTTTTTTTTTTTGAGATGGAGTCTCGCTCTGTTGCCCA (SEQ ID NO: 19)

Translated protein sequence

MPQLSLSSLGLWPMAASPWLLLLLVGASWLLARILAWTYTFYDN
CCRLRCFPQPPKRNWFLGHLGLIHSSEEGLLYTQSLACTFGDMCCWWVGPWHAIVRIF
HPTYIKPVLFAPAAIVPKDKVFYSFLKPWLGDGLLLSAGEKWSRHRRMLTPAFHFNIL
KPYMKIFNESVNIMHAKWQLLASEGSARLDMFEHISLMTLDSLQKCVFSFDSHCQEKP
SEYIAAILELSALVTKRHQQILLYIDFLYYLTPDGQRFRRACRLVHDFTDAVIQERRR
TLPSQGVDDFLQAKAKSKTLDFIDVLLLSKDEDGKKLSDEDIRAEADTFMFEGHDTTA
SGLSWVLYHLAKHPEYQERCRQEVQELLKDREPKEIEWDDLAQLPFLTMCIKESLRLH
PPVPAVSRCCTQDIVLPDGRVIPKGIICLISVFGTHHNPAVWPDPEVYDPFRFDPKNI
KERSPLAFIPFSAGPRNCIGQAFAMAEMKVVLGLTLLRFRVLPDHTEPRRKPELVLRA
EGGLWLRVEPLS (SEQ ID NO: 20)

| DYSF | 8291 | NM_003494 | *Homo sapiens* dysferlin, limb girdle muscular dystrophy 2B (autosomal recessive) (DYSF), transcript variant 8, mRNA |
|---|---|---|---|

mRNA Sequence

GCGGCCGCCGCCCAGCCAGGTGCAAAATGCCGTGTCATTGGGAGACTCCGCAGCCGGAGCATTAGATTAC
AGCTCGACGGAGCTCGGGAAGGGCGGCGGGGGTGGAAGATGAGCAGAAGCCCCTGTTCTCGGAACGCCGG
CTGACAAGCGGGGTGAGCGCAGCCGGGGCGGGGACCCAGCCTAGCCCACTGGAGCAGCCGGGGGTGGCCC
GTTCCCCTTTAAGAGCAACTGCTCTAAGCCAGGAGCCAGAGATTCGAGCCGGCCTCGCCCAGCCAGCCCT
CTCCAGCGAGGGGACCCACAAGCGGCGCCTCGGCCCTCCCGACCTTTCCGAGCCCTCTTTGCGCCCTGGG
CGCACGGGGCCCTACACGCGCCAAGCATGCTGAGGGTCTTCATCCTCTATGCCGAGAACGTCCACACACC
CGACACCGACATCAGCGATGCCTACTGCTCCGCGGTGTTTGCAGGGGTGAAGAAGAGAACCAAAGTCATC
AAGAACAGCGTGAACCCTGTATGGAATGAGGGATTTGAATGGGACCTCAAGGGCATCCCCCTGGACCAGG
GCTCTGAGCTTCATGTGGTGGTCAAAGACCATGAGACGATGGGGAGGAACAGGTTCCTGGGGGAAGCCAA
GGTCCCACTCCGAGAGGTCCTCGCCACCCCTAGTCTGTCCGCCAGCTTCAATGCCCCCCTGCTGGACACC
AAGAAGCAGCCCACAGGGGCCTCGCTGGTCCTGCAGGTGTCCTACACACCGCTGCCTGGAGCTGTGCCCC
TGTTCCCGCCCCCTACTCCTCTGGAGCCCTCCCCGACTCTGCCTGACCTGGATGTAGTGGCAGACACAGG
AGGAGAGGAAGACACAGAGGACCAGGGACTCACTGGAGATGAGGCGGAGCCATTCCTGGATCAAAGCGGA
GGCCCGGGGGCTCCCACCACCCCAAGGAAACTACCTTCACGTCCTCCGCCCCACTACCCCGGGATCAAAA
GAAAGCGAAGTGCGCCTACATCTAGAAAGCTGCTGTCAGACAAACCGCAGGATTTCCAGATCAGGGTCCA
GGTGATCGAGGGGCGCCAGCTGCCGGGGGTGAACATCAAGCCTGTGGTCAAGGTTACCGCTGCAGGGCAG
ACCAAGCGGACGCGGATCCACAAGGGAAACAGCCCACTCTTCAATGAGACTCTTTTCTTCAACTTGTTTG
ACTCTCCTGGGGAGCTGTTTGATGAGCCCATCTTTATCACGGTGGTAGACTCTCGTTCTCTCAGGACAGA
TGCTCTCCTCGGGGAGTTCCGGATGGACGTGGGCACCATTTACAGAGAGCCCCGGCACGCCTATCTCAGG
AAGTGGCTGCTGCTCTCAGACCCTGATGACTTCTCTGCTGGGGCCAGAGGCTACCTGAAAACAAGCCTTT
GTGTGCTGGGGCCTGGGGACGAAGCGCCTCTGGAGAGAAAAGACCCCTCTGAAGACAAGGAGGACATTGA
AAGCAACCTGCTCCGGCCCACAGGCGTAGCCCTGCGAGGAGCCCACTTCTGCCTGAAGGTCTTCCGGGCC
GAGGACTTGCCGCAGATGGACGATGCCGTGATGGACAACGTGAAACAGATCTTTGGCTTCGAGAGTAACA
AGAAGAACTTGGTGGACCCCTTTGTGGAGGTCAGCTTTGCGGGGAAAATGCTGTGCAGCAAGATCTTGGA
GAAGACGGCCAACCCTCAGTGGAACCAGAACATCACACTGCCTGCCATGTTTCCCTCCATGTGCGAAAAA
ATGAGGATTCGTATCATAGACTGGGACCGCCTGACTCACAATGACATCGTGGCTACCACCTACCTGAGTA
TGTCGAAAATCTCTGCCCCTGGAGGAGAAATAGAAGAGGAGCCTGCAGGTGCTGTCAAGCCTTCGAAAGC
CTCAGACTTGGATGACTACCTGGGCTTCCTCCCCACTTTTGGGCCCTGCTACATCAACCTCTATGGCAGT
CCCAGAGAGTTCACAGGCTTCCCAGACCCCTACACAGAGCTCAACACAGGCAAGGGGGAAGGTGTGGCTT
ATCGTGGCCGGCTTCTGCTCTCCCTGGAGACCAAGCTGGTGGAGCACAGTGAACAGAAGGTGGAGGACCT
TCCTGCGGATGACATCCTCCGGGTGGAGAAGTACCTTAGGAGGCGCAAGTACTCCCTGTTTGCGGCCTTC
TACTCAGCCACCATGCTGCAGGATGTGGATGATGCCATCCAGTTTGAGGTCAGCATCGGGAACTACGGGA
ACAAGTTCGACATGACCTGCCTGCCGCTGGCCTCCACCACTCAGTACAGCCGTGCAGTCTTTGACGGGTG
CCACTACTACTACCTACCCTGGGGTAACGTGAAACCTGTGGTGGTGCTGTCATCCTACTGGGAGGACATC
AGCCATAGAATCGAGACTCAGAACCAGCTGCTTGGGATTGCTGACCGGCTGGAAGCTGGCCTGGAGCAGG
TCCACCTGGCCCTGAAGGCGCAGTGCTCCACGGAGGACGTGGACTCGCTGGTGGCTCAGCTGACGGATGA
GCTCATCGCAGGCTGCAGCCAGCCTCTGGGTGACATCCATGAGACACCCTCTGCCACCCACCTGGACCAG
TACCTGTACCAGCTGCGCACCCATCACCTGAGCCAAATCACTGAGGCTGCCCTGGCCCTGAAGCTCGGCC
ACAGTGAGCTCCCTGCAGCTCTGGAGCAGGCGGAGGACTGGCTCCTGCGTCTGCGTGCCCTGGCAGAGGA
GCCCCAGAACAGCCTGCCGGACATCGTCATCTGGATGCTGCAGGGAGACAAGCGTGTGGCATACCAGCGG
GTGCCCGCCCACCAAGTCCTCTTCTCCCGGCGGGGTGCCAACTACTGTGGCAAGAATTGTGGGAAGCTAC
AGACAATCTTTCTGAAATATCCGATGGAGAAGGTGCCTGGCGCCCGGATGCCAGTGCAGATACGGGTCAA
GCTGTGGTTTGGGCTCTCAGTGGATGAGAAGGAGTTCAACCAGTTTGCTGAGGGGAAGCTGTCTGTCTTT

APPENDIX-continued

NUCLEIC ACID AND AMINO ACID SEQUENCES OF BIOMARKERS

| Gener Name | Gene ID | Accession NO. | Name |
|---|---|---|---|

GCTGAAACCTATGAGAACGAGACTAAGTTGGCCCTTGTTGGGAACTGGGGCACAACGGGCCTCACCTACC
CCAAGTTTTCTGACGTCACGGGCAAGATCAAGCTACCCAAGGACAGCTTCCGCCCCTCGGCCGGCTGGAC
CTGGGCTGGAGATTGGTTCGTGTGTCCGGAGAAGACTCTGCTCCATGACATGGACGCCGGTCACCTGAGC
TTCGTGGAAGAGGTGTTTGAGAACCAGACCCGGCTTCCCGGAGGCCAGTGGATCTACATGAGTGACAACT
ACACCGATGTGAACGGGGAGAAGGTGCTTCCCAAGGATGACATTGAGTGCCCACTGGGCTGGAAGTGGGA
AGATGAGGAATGGTCCACAGACCTCAACCGGGCTGTCGATGAGCAAGGCTGGGAGTATAGCATCACCATC
CCCCCGGAGCGGAAGCCGAAGCACTGGGTCCCTGCTGAGAAGATGTACTACACACACCGACGGCGGCGCT
GGGTGCGCCTGCGCAGGAGGGATCTCAGCCAAATGGAAGCACTGAAAAGGCACAGGCAGGCGGAGGCGGA
GGGCGAGGGCTGGGAGTACGCCTCTCTTTTTGGCTGGAAGTTCCACCTCGAGTACCGCAAGACAGATGCC
TTCCGCCGCCGCCGCTGGCGCCGTCGCATGGAGCCACTGGAGAAGACGGGGCCTGCAGCTGTGTTTGCCC
TTGAGGGGGCCCTGGGCGGCGTGATGGATGACAAGAGTGAAGATTCCATGTCCGTCTCCACCTTGAGCTT
CGGTGTGAACAGACCCACGATTTCCTGCATATTCGACTATGGGAACCGCTACCATCTACGCTGCTACATG
TACCAGGCCCGGGACCTGGCTGCGATGGACAAGGACTCTTTTTCTGATCCCTATGCCATCGTCTCCTTCC
TGCACCAGAGCCAGAAGACGGTGGTGGTGAAGAACACCCTTAACCCCACCTGGGACCAGACGCTCATCTT
CTACGAGATCGAGATCTTTGGCGAGCCGGCCACAGTTGCTGAGCAACCGCCCAGCATTGTGGTGGAGCTG
TACGACCATGACACTTATGGTGCAGACGAGTTTATGGGTCGCTGCATCTGTCAACCGAGTCTGGAACGGA
TGCCACGGCTGGCCTGGTTCCCACTGACGAGGGGCAGCCAGCCGTCGGGGGAGCTGCTGGCCTCTTTTGA
GCTCATCCAGAGAGAGAAGCCGGCCATCCACCATATTCCTGGTTTTGAGGTGCAGGAGACATCAAGGATC
CTGGATGAGTCTGAGGACACAGACCTGCCCTACCCACCACCCCAGAGGGAGGCCAACATCTACATGGTTC
CTCAGAACATCAAGCCAGCGCTCCAGCGTACCGCCATCGAGATCCTGGCATGGGGCCTGCGGAACATGAA
GAGTTACCAGCTGGCCAACATCTCCTCCCCCAGCCTCGTGGTAGAGTGTGGGGGCCAGACGGTGCAGTCC
TGTGTCATCAGGAACCTCCGGAAGAACCCCAACTTTGACATCTGCACCCTCTTCATGGAAGTGATGCTGC
CCAGGGAGGAGCTCTACTGCCCCCCCATCACCGTCAAGGTCATCGATAACCGCCAGTTTGGCCGCCGGCC
TGTGGTGGGCCAGTGTACCATCCGCTCCCTGGAGAGCTTCCTGTGTGACCCCTACTCGGCGGAGAGTCCA
TCCCCACAGGGTGGCCCAGACGATGTGAGCCTACTCAGTCCTGGGGAAGACGTGCTCATCGACATTGATG
ACAAGGAGCCCCTCATCCCCATCCAGGAGGAAGAGTTCATCGATTGGTGGAGCAAATTCTTTGCCTCCAT
AGGGGAGAGGGAAAAGTGCGGCTCCTACCTGGAGAAGGATTTTGACACCCTGAAGGTCTATGACACACAG
CTGGAGAATGTGGAGGCCTTTGAGGGCCTGTCTGACTTTTGTAACACCTTCAAGCTGTACCGGGGCAAGA
CGCAGGAGGAGACAGAAGATCCATCTGTGATTGGTGAATTTAAGGGCCTCTTCAAAATTTATCCCCTCCC
AGAAGACCCAGCCATCCCCATGCCCCCAAGACAGTTCCACCAGCTGGCCGCCCAGGGACCCCAGGAGTGC
TTGGTCCGTATCTACATTGTCCGAGCATTTGGCCTGCAGCCCAAGGACCCCAATGGAAAGTGTGATCCTT
ACATCAAGATCTCCATAGGGAAGAAATCAGTGAGTGACCAGGATAACTACATCCCCTGCACGCTGGAGCC
CGTATTTGGAAAGATGTTCGAGCTGACCTGCACTCTGCCTCTGGAGAAGGACCTAAAGATCACTCTCTAT
GACTATGACCTCCTCTCCAAGGACGAAAAGATCGGTGAGACGGTCGTCGACCTGGAGAACAGGCTGCTGT
CCAAGTTTGGGGCTCGCTGTGGACTCCCACAGACCTACTGTGTCTCTGGACCGAACCAGTGGCGGGACCA
GCTCCGCCCCTCCCAGCTCCTCCACCTCTTCTGCCAGCAGCATAGAGTCAAGGCACCTGTGTACCGGACA
GACCGTGTAATGTTTCAGGATAAAGAATATTCCATTGAAGAGATAGAGGCTGGCAGGATCCCAAACCCAC
ACCTGGGCCCAGTGGAGGAGCGTCTGGCTCTGCATGTGCTTCAGCAGCAGGGCCTGGTCCCGGAGCACGT
GGAGTCACGGCCCCTCTACAGCCCCCTGCAGCCAGACATCGAGCAGGGGAAGCTGCAGATGTGGGTCGAC
CTATTTCCGAAGGCCCTGGGGCGGCCTGGACCTCCCTTCAACATCACCCCACGGAGAGCCAGAAGGTTTT
TCCTGCGTTGTATTATCTGGAATACCAGAGATGTGATCCTGGATGACCTGAGCCTCACGGGGGAGAAGAT
GAGCGACATTTATGTGAAAGGTTGGATGATTGGCTTTGAAGAACACAAGCAAAAGACAGACGTGCATTAT
CGTTCCCTGGGAGGTGAAGGCAACTTCAACTGGAGGTTCATTTTCCCCTTCGACTACCTGCCAGCTGAGC
AAGTCTGTACCATTGCCAAGAAGGATGCCTTCTGGAGGCTGGACAAGACTGAGAGCAAAATCCCAGCACG
AGTGGTGTTCCAGATCTGGGACAATGACAAGTTCTCCTTTGATGATTTTCTGGGCTCCCTGCAGCTCGAT
CTCAACCGCATGCCCAAGCCAGCCAAGACAGCCAAGAAGTGCTCCTTGGACCAGCTGGATGATGCTTTCC
ACCCAGAATGGTTTGTGTCCCTTTTTGAGCAGAAAACAGTGAAGGGCTGGTGGCCCTGTGTAGCAGAAGA
GGGTGAGAAGAAAATACTGGCGGGCAAGCTGGAAATGACCTTGGAGATTGTAGCAGAGAGTGAGCATGAG
GAGCGGCCTGCTGGCCAGGGCCGGGATGAGCCCAACATGAACCCTAAGCTTGAGGACCCAAGGCGCCCCG
ACACCTCCTTCCTGTGGTTTACCTCCCCATACAAGACCATGAAGTTCATCCTGTGGCGGCGTTTCCGGTG
GGCCATCATCCTCTTCATCATCCTCTTCATCCTGCTGCTGTTCCTGGCCATCTTCATCTACGCCTTCCCG
AACTATGCTGCCATGAAGCTGGTGAAGCCCTTCAGCTGAGGACTCTCCTGCCCTGTAGAAGGGGCCGTGG
GGTCCCCTCCAGCATGGGACTGGCCTGCCTCCTCCGCCCAGCTCGGCGAGCTCCTCCAGACCTCCTAGGC
CTGATTGTCCTGCCAGGGTGGGCAGACAGACAGATGGACCGGCCCACACTCCCAGAGTTGCTAACATGGA
GCTCTGAGATCACCCCACTTCCATCATTTCCTTCTCCCCCAACCCAACGCTTTTTTGGATCAGCTCAGAC
ATATTTCAGTATAAAACAGTTGGAACCACAAAAAAAAAAAAAAAAAAAAAAAAA (SEQ ID NO: 21)

Translated protein sequence

MLRVFILYAENVHTPDTDISDAYCSAVFAGVKKRTKVIKNSVNP
VWNEGFEWDLKGIPLDQGSELHVVVKDHETMGRNRFLGEAKVPLREVLATPSLSASFN
APLLDTKKQPTGASLVLQVSYTPLPGAVPLFPPPTPLEPSPTLPDLDVVADTGGEEDT
EDQGLTGDEAEPFLDQSGGPGAPTTPRKLPSRPPPHYPGIKRKRSAPTSRKLLSDKPQ
DFQIRVQVIEGRQLPGVNIKPWKVTAAGQTKRTRIHKGNSPLFNETLFFNLFDSPGE
LFDEPIFITVVDSRSLRTDALLGEFRMDVGTIYREPRHAYLRKWLLLSDPDDFSAGAR
GYLKTSLCVLGPGDEAPLERKDPSEDKEDIESNLLRPTGVALRGAHFCLKVFRAEDLP
QMDDAVMDNVKQIFGFESNKKNLVDPFVEVSFAGKMLCSKILEKTANPQWNQNITLPA
MFPSMCEKMRIRIIDWDRLTHNDIVATTYLSMSKISAPGGEIEEEPAGAVKPSKASDL
DDYLGFLPTFGPCYINLYGSPREFTGFPDPYTELNTGKGEGVAYRGRLLLSLETKLVE
HSEQKVEDLPADDILRVEKYLRRRKYSLFAAFYSATMLQDVDDAIQFEVSIGNYGNKF
DMTCLPLASTTQYSRAVFDGCHYYYLPWGNVKPVVVLSSYWEDISHRIETQNQLLGIA
DRLEAGLEQVHLALKAQCSTEDVDSLVAQLTDELIAGCSQPLGDIHETPSATHLDQYL
YQLRTHHLSQITEAALALKLGHSELPAALEQAEDWLLRLRALAEEPQNSLPDIVIWML
QGDKRVAYQRVPAHQVLFSRRGANYCGKNCGKLQTIFLKYPMEKVPGARMPVQIRVKL
WFGLSVDEKEFNQFAEGKLSVFAETYENETKLALVGNWGTTGLTYPKFSDVTGKIKLP

APPENDIX-continued

NUCLEIC ACID AND AMINO ACID SEQUENCES OF BIOMARKERS

| Gener Name | Gene ID | Accession NO. | Name |
|---|---|---|---|

KDSFRPSAGWTWAGDWFVCPEKTLLHDMDAGHLSFVEEVFENQTRLPGGQWIYMSDNY
TDVNGEKVLPKDDIECPLGWKWEDEEWSTDLNRAVDEQGWEYSITIPPERKPKHWVPA
EKMYYTHRRRRWVRLRRRDLSQMEALKRHRQAEAEGEGWEYASLFGWKFHLEYRKTDA
FRRRRWRRRMEPLEKTGPAAVFALEGALGGVMDDKSEDSMSVSTLSFGVNRPTISCIF
DYGNRYHLRCYMYQARDLAAMDKDSFSDPYAIVSFLHQSQKTVVVKNTLNPTWDQTLI
FYEIEIFGEPATVAEQPPSIVVELYDHDTYGADEFMGRCICQPSLERMPRLAWFPLTR
GSQPSGELLASFELIQREKPAIHHIPGFEVQETSRILDESEDTDLPYPPPQREANIYM
VPQNIKPALQRTAIEILAWGLRNMKSYQLANISSPSLVVECGGQTVQSCVIRNLRKNP
NFDICTLFMEVMLPREELYCPPITVKVIDNRQFGRRPVVGQCTIRSLESFLCDPYSAE
SPSPQGGPDDVSLLSPGEDVLIDIDDKEPLIPIQEEEFIDWWSKFFASIGEREKCGSY
LEKDFDTLKVYDTQLENVEAFEGLSDFCNTFKLYRGKTQEETEDPSVIGEFKGLFKIY
PLPEDPAIPMPPRQFHQLAAQGPQECLVRIYIVRAFGLQPKDPNGKCDPYIKISIGKK
SVSDQDNYIPCTLEPVFGKMFELTCTLPLEKDLKITLYDYDLLSKDEKIGETVVDLEN
RLLSKFGARCGLPQTYCVSGPNQWRDQLRPSQLLHLFCQQHRVKAPVYRTDRVMFQDK
EYSIEEIEAGRIPNPHLGPVEERLALHVLQQQGLVPEHVESRPLYSPLQPDIEQGKLQ
MWVDLFPKALGRPGPPFNITPRRARRFFLRCIIWNTRDVILDDLSLTGEKMSDIYVKG
WMIGFEEHKQKTDVHYRSLGGEGNFNWRFIFPFDYLPAEQVCTIAKKDAFWRLDKTES
KIPARVVFQIWDNDKFSFDDFLGSLQLDLNRMPKPAKTAKKCSLDQLDDAFHPEWFVS
LFEQKTVKGWWPCVAEEGEKKILAGKLEMTLEIVAESEHEERPAGQGRDEPNMNPKLE
DPRRPDTSFLWFTSPYKTMKFILWRRFRWAIILFIILFILLLFLAIFIYAFPNYAAMK
LVKPFS (SEQ ID NO: 22)

| | | | |
|---|---|---|---|
| EDIL3 | 10085 | NM_005711 | *Homo sapiens* EGF-like repeats and discoidin I-like domains 3 (EDIL3), mRNA |

mRNA Sequence

AGAAGCCCCGCAGCCGCCGCGCGGAGAACAGCGACAGCCGAGCGCCCGGTCCGCCTGTCTGCCGGTGGGT
CTGCCTGCCCGCGCAGCAGACCCGGGGCGGCCGCGGGAGCCCGCGCCCCGCCCGCCGCGCCTCTGCCGGG
ACCCACCCGCAGCGGAGGGCTGAGCCCGCCGGCGGCTCCCCGGAGCTCACCCACCTCCGCGCGCCGGAGC
GCAGGCAAAAGGGGAGGAAAGGCTCCTCTCTTTAGTCACCACTCTCGCCCTCTCCAAGAATTTGTTTAAC
AAAGCGCTGAGGAAAGAGAACGTCTTCTTGAATTCTTTAGTAGGGGCGGAGTCTGCTGCTGCCCTGCGCT
GCCACCTCGGCTACACTGCCCTCCGCGACGACCCCTGACCAGCCGGGGTCACGTCCGGGAGACGGGATCA
TGAAGCGCTCGGTAGCCGTCTGGCTCTTGGTCGGGCTCAGCCTCGGTGTCCCCCAGTTCGGCAAAGGTGA
TATTTGTGATCCCAATCCATGTGAAAATGGAGGTATCTGTTTGCCAGGATTGGCTGATGGTTCCTTTTCC
TGTGAGTGTCCAGATGGCTTCACAGACCCCAACTGTTCTAGTGTTGTGGAGGTTGCATCAGATGAAGAAG
AACCAACTTCAGCAGGTCCCTGCACTCCTAATCCATGCCATAATGGAGGAACCTGTGAAATAAGTGAAGC
ATACCGAGGGGATACATTCATAGGCTATGTTTGTAAATGTCCCCGAGGATTTAATGGGATTCACTGTCAG
CACAACATAAATGAATGCGAAGTTGAGCCTTGCAAAAATGGTGGAATATGTACAGATCTTGTTGCTAACT
ATTCCTGTGAGTGCCCAGGCGAATTTATGGGAAGAAATTGTCAATACAAATGCTCAGGCCCACTGGGAAT
TGAAGGTGGAATTATATCAAACCAGCAAATCACAGCTTCCTCTACTCACCGAGCTCTTTTTGGACTCCAA
AAATGGTATCCCTACTATGCACGTCTTAATAAGAAGGGGCTTATAAATGCGTGGACAGCTGCAGAAAATG
ACAGATGGCCGTGGATTCAGATAAATTTGCAAAGGAAAATGAGAGTTACTGGTGTGATTACCCAAGGAGC
CAAGAGGATTGGAAGCCCAGAGTATATAAAATCCTACAAAATTGCCTACAGTAATGATGGAAAGACTTGG
GCAATGTACAAAGTGAAAGGCACCAATGAAGACATGGTGTTTCGTGGAAACATTGATAACAACACTCCAT
ATGCTAACTCTTTCACACCCCCCATAAAAGCTCAGTATGTAAGACTCTATCCCCAAGTTTGTCGAAGACA
TTGCACTTTGCGAATGGAACTTCTTGGCTGTGAACTGTCGGGTTGTTCTGAGCCTCTGGGTATGAAATCA
GGACATATACAAGACTATCAGATCACTGCCTCCAGCATCTTCAGAACGCTCAACATGGACATGTTCACTT
GGGAACCAAGGAAAGCTCGGCTGGACAAGCAAGGCAAAGTGAATGCCTGGACCTCTGGCCACAATGACCA
GTCACAATGGTTACAGGTGGATCTTCTTGTTCCAACCAAAGTGACTGGCATCATTACACAAGGAGCTAAA
GATTTTGGTCATGTACAGTTTGTTGGCTCCTACAAACTGGCTTACAGCAATGATGGAGAACACTGGACTG
TATACCAGGATGAAAAGCAAAGAAAAGATAAGGTTTTCCAGGGAAATTTTGACAATGACACTCACAGAAA
AAATGTCATCGACCCTCCCATCTATGCACGACACATAAGAATCCTTCCTTGGTCCTGGTACGGGAGGATC
ACATTGCGGTCAGAGCTGCTGGGCTGCACAGAGGAGGAATGAGGGGAGGCTACATTTCACAACCCTCTTC
CCTATTTCCCTAAAAGTATCTCCATGGAATGAACTGTGCAAAATCTGTAGGAAACTGAATGGTTTTTTTT
TTTTTTTCATGAAAAAGTGCTCAAATTATGGTAGGCAACTAACGGTGTTTTTAAGGGGGTCTAAGCCTGC
CTTTTCAATGATTTAATTTGATTTTATTTTATCCGTCAAATCTCTTAAGTAACAACACATTAAGTGTGAA
TTACTTTTCTCTCATTGTTTCCTGAATTATTCGCATTGGTAGAAATATATTAGGGAAAGAAAGTAGCCTT
CTTTTTATAGCAAGAGTAAAAAAGTCTCAAAGTCATCAAATAAGAGCAAGAGTTGATAGAGCTTTTACAA
TCAATACTCACCTAATTCTGATAAAAGGAATACTGCAATGTTAGCAATAAGTTTTTTTCTTCTGTAATGA
CTCTACGTTATCCTGTTTCCCTGTGCCTACCAAACACTGTCAATGTTTATTACAAAATTTTAAAGAAGAA
TATGTAACATGCAGTACTGATATTATAATTCTCATTTTACTTTCATTATTTCTAATAAGAGATTATGTGA
CTTCTTTTTCTTTTAGTTCTATTCTACATTCTTAATATTGTATATTACCTGAATAATTCAATTTTTTTCT
AATTGAATTTCCTATTAGTTGACTAAAAGAAGTGTCATGTTTACTCATATATGTAGAACATGACTGCCTA
TCAGTAGATTGATCTGTATTTAATATTCGTTAATTAAATCTGCAGTTTTATTTTTGAAGGAAGCCATAAC
TATTTAATTTCCAAATAATTGCTTCATAAAGAATCCCATACTCTCAGTTTGCACAAAAGAACAAAAAATA
TATATGTCTCTTTAAATTTAAATCTTCATTTAGATGGTAATTACATATCCTTATATTTACTTTAAAAAAT
CGGCTTATTTGTTTATTTTATAAAAAATTTAGCAAAGAAATATTAATATAGTGCTGCATAGTTTGGCCAA
GCATACTCATCATTTCTTTGTTCAGCTCCACATTTCCTGTGAAACTAACATCTTATTGAGATTTGAAACT
GGTGGTAGTTTCCCAGGAAGGCACAGGTGGAGTT (SEQ ID NO: 23)

Translated protein sequence

MKRSVAVWLLVGLSLGVPQFGKGDICDPNPCENGGICLPGLADG
SFSCECPDGFTDPNCSSVVEVASDEEEPTSAGPCTPNPCHNGGTCEISEAYRGDTFIG

APPENDIX-continued

NUCLEIC ACID AND AMINO ACID SEQUENCES OF BIOMARKERS

| Gener Name | Gene ID | Accession NO. | Name |
|---|---|---|---|

YVCKCPRGFNGIHCQHNINECEVEPCKNGGICTDLVANYSCECPGEFMGRNCQYKCSG
PLGIEGGIISNQQITASSTHRALFGLQKWYPYYARLNKKGLINAWTAAENDRWPWIQI
NLQRKMRVTGVITQGAKRIGSPEYIKSYKIAYSNDGKTWAMYKVKGTNEDMVFRGNID
NNTPYANSFTPPIKAQYVRLYPQVCRRHCTLRMELLGCELSGCSEPLGMKSGHIQDYQ
ITASSIFRTLNMDMFTWEPRKARLDKQGKVNAWTSGHNDQSQWLQVDLLVPTKVTGII
TQGAKDFGHVQFVGSYKLAYSNDGEHWTVYQDEKQRKDKVFQGNFDNDTHRKNVIDPP
IYARHIRILPWSWYGRITLRSELLGCTEEE (SEQ ID NO: 24)

| ERGIC3 | 51614 | NM_015966 | *Homo sapiens* ERGIC and golgi 3 (ERGIC3), transcript variant 2, mRNA |
|---|---|---|---|

mRNA Sequence

GTGGCTCCAGGCCGGAAGAGGGAGTCTGTAGGGGCGGGCCGGCTGGCGTCCCCTTTCCGGCCGGTCCCCA
TGGAGGCGCTGGGGAAGCTGAAGCAGTTCGATGCCTACCCCAAGACTTTGGAGGACTTCCGGGTCAAGAC
CTGCGGGGGCGCCACCGTGACCATTGTCAGTGGCCTTCTCATGCTGCTACTGTTCCTGTCCGAGCTGCAG
TATTACCTCACCACGGAGGTGCATCCTGAGCTCTACGTGGACAAGTCGCGGGGAGATAAACTGAAGATCA
ACATCGATGTACTTTTTCCGCACATGCCTTGTGCCTATCTGAGTATTGATGCCATGGATGTGGCCGGAGA
ACAGCAGCTGGATGTGGAACACAACCTGTTCAAGCAACGACTAGATAAAGATGGCATCCCCGTGAGCTCA
GAGGCTGAGCGGCATGAGCTTGGGAAAGTCGAGGTGACGGTGTTTGACCCTGACTCCCTGGACCCTGATC
GCTGTGAGAGCTGCTATGGTGCTGAGGCAGAAGATATCAAGTGCTGTAACACCTGTGAAGATGTGCGGGA
GGCATATCGCCGTAGAGGCTGGGCCTTCAAGAACCCAGATACTATTGAGCAGTGCCGGCGAGAGGGCTTC
AGCCAGAAGATGCAGGAGCAGAAGAATGAAGGCTGCCAGGTGTATGGCTTCTTGGAAGTCAATAAGGTGG
CCGGAAACTTCCACTTTGCCCCTGGGAAGAGCTTCCAGCAGTCCCATGTGCACGTCCATGACTTGCAGAG
CTTTGGCCTTGACAACATCAACATGACCCACTACATCCAGCACCTGTCATTTGGGGAGGACTATCCAGGC
ATTGTGAACCCCCTGGACCACACCAATGTCACTGCGCCCCAAGCCTCCATGATGTTCCAGTACTTTGTGA
AGGTGGTGCCCACTGTGTACATGAAGGTGGACGGAGAGGTACTGAGGACAAATCAGTTCTCTGTGACCAG
ACATGAGAAGGTTGCCAATGGGCTGTTGGGCGACCAAGGCCTTCCCGGAGTCTTCGTCCTCTATGAGCTC
TCGCCCATGATGGTGAAGCTGACGGAGAAGCACAGGTCCTTCACCCACTTCCTGACAGGTGTGTGCGCCA
TCATTGGGGGCATGTTCACAGTGGCTGGACTCATCGATTCGCTCATCTACCACTCAGCACGAGCCATCCA
GAAGAAAATTGATCTAGGGAAGACAACGTAGTCACCCTCGGTGCTTCCTCTGTCTCCTCTTTCTCCCTGG
CCTGTGGTTGTCCCCCAGCCTCTGCCACCCTCCACCTCCTCGGTCAGCCCCAGCCCCAGGTTGATAAATC
TATTGATTGATTGTGATAGTAAAAAAAAAAAAAAAAAA (SEQ ID NO: 25)

Translated protein sequence

MEALGKLKQFDAYPKTLEDFRVKTCGGATVTIVSGLLMLLLFLS
ELQYYLTTEVHPELYVDKSRGDKLKINIDVLFPHMPCAYLSIDAMDVAGEQQLDVEHN
LFKQRLDKDGIPVSSEAERHELGKVEVTVFDPDSLDPDRCESCYGAEAEDIKCCNTCE
DVREAYRRRGWAFKNPDTIEQCRREGFSQKMQEQKNEGCQVYGFLEVNKVAGNFHFAP
GKSFQQSHVHVHDLQSFGLDNINMTHYIQHLSFGEDYPGIVNPLDHTNVTAPQASMMF
QYFVKVVPTVYMKVDGEVLRTNQFSVTRHEKVANGLLGDQGLPGVFVLYELSPMMVKL
TEKHRSFTHFLTGVCAIIGGMFTVAGLIDSLIYHSARAIQKKIDLGKTT (SEQ ID NO: 26)

| GNAT1 | 2779 | NM_000172 | *Homo sapiens* guanine nucleotide binding protein (G protein), alpha transducing activity polypeptide 1 (GNAT1), transcript variant 2, mRNA |
|---|---|---|---|

mRNA Sequence

AGTTGATTGCAGGTCCTCCTGGGGCCAGAAGGGTGCCTGGGAGGCCAGGTTCTGGGGATCCCCTCCATCC
AGAAGAACCACCTGCTCACTCTGTCCCTTCGCCTGCTGCTGGGACCATGGGGGCTGGGGCCAGTGCTGAG
GAGAAGCACTCCAGGGAGCTGGAAAAGAAGCTGAAAGAGGACGCTGAGAAGGATGCTCGAACCGTGAAGC
TGCTGCTTCTGGGTGCCGGTGAGTCCGGGAAGAGCACCATCGTCAAGCAGATGAAGATTATCCACCAGGA
CGGGTACTCGCTGGAAGAGTGCCTCGAGTTTATCGCCATCATCTACGGCAACACGTTGCAGTCCATCCTG
GCCATCGTACGCGCCATGACCACACTCAACATCCAGTACGGAGACTCTGCACGCCAGGACGACGCCCGGA
AGCTGATGCACATGGCAGACACTATCGAGGAGGGCACGATGCCCAAGGAGATGTCGGACATCATCCAGCG
GCTGTGGAAGGACTCCGGTATCCAGGCCTGTTTTGAGCGCGCCTCGGAGTACCAGCTCAACGACTCGGCG
GGCTACTACCTCTCCGACCTGGAGCGCCTGGTAACCCCGGGCTACGTGCCCACCGAGCAGGACGTGCTGC
GCTCGCGAGTCAAGACCACTGGCATCATCGAGACGCAGTTCTCCTTCAAGGATCTCAACTTCCGGATGTT
CGATGTGGGCGGGCAGCGCTCGGAGCGCAAGAAGTGGATCCACTGCTTCGAGGGCGTGACCTGCATCATC
TTCATCGCGGCGCTGAGCGCCTACGACATGGTGCTAGTGGAGGACGACGAAGTGAACCGCATGCACGAGA
GCCTGCACCTGTTCAACAGCATCTGCAACCACCGCTACTTCGCCACGACGTCCATCGTGCTCTTCCTTAA
CAAGAAGGACGTCTTCTTCGAGAAGATCAAGAAGGCGCACCTCAGCATCTGTTTCCCGGACTACGATGGA
CCCAACACCTACGAGGACGCCGGCAACTACATCAAGGTGCAGTTCCTCGAGCTCAACATGCGGCGCGACG
TGAAGGAGATCTATTCCCACATGACGTGCGCCACCGACACGCAGAACGTCAAATTTGTCTTCGACGCTGT
CACCGACATCATCATCAAGGAGAACCTCAAAGACTGTGGCCTCTTCTGAGGCCAGGGCCTGTGCTGCAGT
CGGGGACAAGGAGCTTCCGTCTGGCAAGGCCGGGGCACAATTTGCACTCCCCTCAGCTAGACGCACAGAC
TCAGCAATAAACCTTTGCATCAGGCTCCAGCTGTCCTTTCTTGGTGGAGGACTTAATTATCACAAGTCAT
GGGCATTTATTAAGTGCCCAGTGCTGGGTTGGGCATGAAGTGGGAAGATGGCCCCTCCCAGGAAGAAGTA
CCTGGCCTGACAAGGTGGGGCACTCTTGGGGGTATGGGACCAACTCATGGCTTTTCACGGGAGTTGAGGA
GAGAGGAGCTGTGGAAAATATTCACTGGGACAGTCTTGGATCAAGAGGGAGTTTTGAGGTGGAGGCTCAT
TCTGGCAGGGACCGTAGTGTCTACCAGCCCCAGAAACATGGGCTTATGGCCACAGGAGTTCAGTGGAGCA
AGAGCAGGGGAGGAGAGACGTGGACAGGTGCCCAAAGCCAGTCGGAGGGCCTGGGCTTTCTCAGAAGGTG

APPENDIX-continued

NUCLEIC ACID AND AMINO ACID SEQUENCES OF BIOMARKERS

| Gener Name | Gene ID | Accession NO. | Name |
|---|---|---|---|

ATGGAGAGTCTTGGAAGCCCTCGAGGCAGGAACATAATTGCAGGGCTGGGATTAGGGTGAGGGAAGTGAG
GCACACTCACCTTGGGTGCAACATTTAAGGCGATGCCAAAAAATTTAGTAACCAAGGTAAATAATATTAG
GATAATATTTTTAAAATCAAATGAATGCAAAACCCCACAATGAATGAAATATCAAAATCCAACAGAGGA
TCAAACAGAGGCATGCTAAGATATATTGGGGCTTGAAGCAAAGGGAAAACTATTTGTTGCTATATGTTTG
TAGGGATTTTTTGCCAGTTTTAAAAATACATGTATCATAAAGTTTACTATCTCAGCCACTTGCCGGTGTA
TAGTTTGGTGGTGTTAAGTACATTCATAATGTTGTACAACCACCGCAACTGTTCATCTCCAGAACTCCTT
TCCTCTTGTAAAACTGTAACTCTGTACCCATGAAAAAATAACCCCCCATTCCTGCCTTCCCCCGGCTCCT
GGCATCCACCATTCTACTTTCCATCTCTATGAATGTGACTGCTCTAAGTGCCTCAGATGTGTGGGTCCAT
GAAGTCTTTGTCTTTTTGCAACTGGCTTATTTCACTTAGCATCATGTCTTCAAGGTTTATTCATGTGTAG
CATATGGCAGAATCTCCTTCCTTTTTAAGGTTGAATAATATTCCATTGTATATATTCCACACTTTGTTTA
TTTATTCATCTATTGATGAATGGTTACATCTGCCTTTTGGCTATTGTGAATAATGCTGCTATGAACATGG
GTGTACAAATCTCTCAAAAAAAAAAAAAAAAAA (SEQ ID NO: 27)

Translated protein sequence

MGAGASAEEKHSRELEKKLKEDAEKDARTVKLLLLGAGESGKST
IVKQMKIIHQDGYSLEECLEFIAIIYGNTLQSILAIVRAMTTLNIQYGDSARQDDARK
LMHMADTIEEGTMPKEMSDIIQRLWKDSGIQACFERASEYQLNDSAGYYLSDLERLVT
PGYVPTEQDVLRSRVKTTGIIETQFSFKDLNFRMFDVGGQRSERKKWIHCFEGVTCII
FIAALSAYDMVLVEDDEVNRMHESLHLFNSICKHRYFATTSIVLFLNKKDVFFEKIKK
AHLSICFPDYDGPNTYEDAGNYIKVQFLELNMRRDVKEIYSHMTCATDTQNVKFVFDA
VTDIIIKENLKDCGLF (SEQ ID NO: 28)

| | | | |
|---|---|---|---|
| GRAMD4 | 23151 | NM_015124 | *Homo sapiens* GRAM domain containing 4 (GRAMD4), mRNA |

mRNA Sequence

CGTCATGTTAGGGTGAAGCAGAGGACCTCAGTGCTGAACATGCTAAGGAGGTTGGACAAAATCAGGTTCA
GAGGTCACAAGAGAGATGACTTCCTCGATCTAGCGGAGTCTCCAAATGCCTCGGACACCGAATGCAGCGA
CGAAATCCCCCTGAAGGTACCGCGGACCTCGCCCCGGGACAGCGAGGAGCTGAGGGACCCTGCTGGTCCA
GGGACCCTCATCATGGCCACAGGAGTCCAGGACTTTAACCGGACAGAGTTTGATCGACTGAATGAGATCA
AAGGTCACCTGGAAATTGCCTTATTGGAAAAACATTTCTTACAGGAGGAGCTCCGGAAGCTGCGAGAAGA
AACCAACGCGGAGATGCTGCGGCAGGAGCTGGACCGCGAGCGGCAGCGGCGGATGGAGCTGGAGCAGAAG
GTGCAGGAGGTGCTGAAGGCCAGAACCGAGGAGCAGATGGCTCAGCAGCCCCCAAAAGGGCAGGCCCAGG
CCAGCAATGGAGCAGAGCGCCGGAGCCAGGGGCTGTCCTCGCGCCTGCAGAAGTGGTTCTACGAGCGGTT
CGGGGAGTACGTGGAGGACTTCCGGTTCCAGCCCGAGGAGAACACTGTGGAGACAGAGGAACCCCTGAGC
GCCCGCAGGTTAACTGAAAATATGAGACGGCTCAAGCGCGGTGCCAAGCCGGTCACTAACTTTGTGAAGA
ACCTCTCTGCCTTATCCGACTGGTACTCCGTCTACACGTCTGCCATTGCCTTCACCGTGTACATGAATGC
CGTGTGGCATGGCTGGGCCATCCCATTGTTCTTATTTCTAGCAATTCTGAGGTTATCCCTCAATTACCTC
ATCGCCAGGGGGTGGCGGATACAGTGGAGCATCGTGCCCGAAGTGTCTGAGCCCGTGGAACCTCCAAAGG
AAGACCTGACTGTGTCTGAGAAGTTCCAGCTGGTGCTGGACGTCGCCCAGAAAGCCCAGAACCTTTTCGG
GAAGATGGCTGACATCCTGGAGAAGATCAAGAACTTGTTCATGTGGGTCCAGCCGGAGATCACACAGAAG
CTGTATGTGGCGCTCTGGGCTGCCTTCCTGGCCTCCTGCTTCTTCCCCTACCGCCTGGTGGGGCTTGCCG
TGGGACTCTATGCTGGTATCAAGTTCTTCCTCATTGATTTCATCTTTAAACGCTGCCCGAGGCTGCGCGC
CAAGTACGACACGCCCTATATCATCTGGAGGAGTCTCCCCACCGACCCGCAGCTCAAGGAGCGCTCCAGC
GCCGCAGTCTCACGCAGGCTGCAGACGACCTCGTCACGGAGCTACGTACCCAGCGCACCGGCCGGCCTGG
GTAAAGAGGAGGACGCCGGTCGCTTCCACAGCACCAAGAAGGGCAATTTCCACGAGATCTTCAATCTGAC
AGAAAACGAGCGTCCGCTGGCGGTGTGCGAGAATGGCTGGCGCTGCTGCCTCATCAACAGGGACCGGAAG
ATGCCCACGGACTACATCAGGAACGGGGTGCTCTACGTCACGGAGAATTACTTGTGCTTCGAAAGCTCCA
AATCTGGGTCCTCAAAGAGGAACAAAGTCATCAAGCTAGTGGACATCACGGACATCCAGAAGTACAAGGT
CCTGTCTGTCCTCCCAGGCTCAGGCATGGGGATTGCCGTGTCGACGCCATCCACCCAGAAACCGCTCGTG
TTTGGTGCCATGGTGCACAGGGATGAGGCCTTCGAGACCATTCTCAGCCAGTACATCAAGATCACCTCAG
CGGCAGCGTCTGGCGGGGACAGCTAGTATTGACTTGCCCAGGACGTTGCTGGAATTTTCTTTTTCTTTTT
CTTTTTCTTTTTTTTTTTTTACGATTTGGTAGTGGAAACAATTGGACATCCTCATGAGCTTTTGCAATAA
TTCTCCTGGACCTGTGGTTCTATTGTGTTGACCTCTGCGTTTTATCGACCAAGAAGGGGCCAGGGCTCAC
AGGGACGGGGGTGCCCCTCTCCCACAGGGCACGTCAGGTGCCTCTGAGGGCCACCCGCAGACTGGGGGAG
GGGGCAGAGGCCCTCGGGGGCCCGTGGAGAAGACACACAGGACCCCTGGCCCTGCCCTTCTCCGTTCCAG
CCTGGACAGAGAAACCTCTCCAGCCACCCCAAGAGGTTCTCGCAACCTTGTGTCCCGCTCTCCAGAGGCC
AGAAGCTCGTCCACCACCAAAGCCATAGCTGAAGAGTGCGGGGCCCTTCCTCCTGGGGACAGAAAGATGT
CGTCAAGGAGGGACATGGGGGCCTTTCACCAACCACCGAGAAACGGGCCTGGCGGCCCTCCTTCCTCTTA
CATGAGACCCTCCTGTGGCATTTGCCCTTGGTGCCGGGCTGGGGCCGGGCGCAGTGACCCTGCCTGCGCT
CCACACTCGCTCCACGGGAACAGAGAGGGTGAGAAGGGCCCACCCCTCGCCTGCCCTCAGTGTCTTTGGT
GGCACCTTCCTTGCTGGCCTCCAGGGCGCTCAGCACCGCGTCTGTAAGGGCCTGCCTGCTGCTCTCGGCC
TGACACGCCGGCCAGGAGGTCTGTAGCTGGGGACCAGTAAGGGCACAGGATGGTGCAGGTAAAAGCACAT
CTTTCTCACACTTTGCTCTTTGGAAGGCCCAGGAGAACATCCGCGAAGGCTGTTGGAGGTGCTCCGAGCA
CTGTGGCATGTCTGGCACATGGCCCCCAGGCTGCGGTTGCCTGGGTTGGTTGGGGGAGGAAGTGGGGAGG
AGTGTTCCGGGACCATGGTGGCCCAGGCTGCAGCCGCCTTTGGGCCATCCGAGAGGCTCTGGCAGCCCCT
GTGCTTTAGGGAGCAACCGTGAGCCGAGCCCAGAGGCCTGGGCCTGCACTGCCTGCAGCCGACATGCGAC
AGCGTTCCCTCCCCCGCGTGCCTAGCCGGTGCCGGTCCGGGCACAGACCCCCCCAGCCCCCGCCCTGCCC
CAGGGAAGCCTGGGCTTCCCGGGAACAAGGTGGCATTTGTGGAGGGAGCGCCCGCAGGCCTGGTCTGCTG
GGGCCGCCTGCGCTGGGCTGAAGGGAGGGAAAGGCGGCTTGGGCCTCCTGGAAGGAGGTGGCCACCCCGC
GGGCCTGCGTGTCTGCTGGGGCGGATCCCGCAGCTCCCTCAGCTTGTCCTGAGTCCCTTGGGTGTCGTTG
AGATTGTTGTTTTTTGAAGAAACAGAAGATTCTATTTTTTACAGCGAGCAAGCTGGTTTTCTTATTTTTG
TATCCTTTTTCAGATGTAATTTTTATCTTTGCTCCGATCCTCATTTGCTGGTGTGGGTGAGGGATCCGGC

APPENDIX-continued

NUCLEIC ACID AND AMINO ACID SEQUENCES OF BIOMARKERS

| Gener Name | Gene ID | Accession NO. | Name |
| --- | --- | --- | --- |

GGCATGGGCTGGTTTCACCCCCTTCACGAGGGGCCGCAGAGTCACACGCTGGTGCCGGGGGTGCTTTGGG
GGGAGCTGCGCCGATCACCAGATTAAGCACATGTCCTATCCCAGGCGGTGGAGCGGAGCCCCCGTGGCTC
TGGACTGCGCGGACGTTGGCGTCAGGATGACCACACGGCGGCCTTTCCCGAATGGGGACAGAACCCGCTC
TGAGCCGTGGGTCTGGCTCCTGTAGGGGACTGGCTCTCTTGGTGCACCAGGGGAGGGGGACATATCCCAG
TGAACCCCACCTTGGCGCCTGAGGCAACACAGGGTGGGCACTGACCCACCCCCAGGGGCGGCTGCAGAGG
CAGTGCCCGCAGACAATGGCCACACCTCTCTCCCCAGGGCCCGGCAGTGCCCAAGGATGGGTCCGGGGCC
TCGGGGCCAATGAGCGCCTCTTCCTAGGTGCTGGGATTCAGTCCCCAAACACAGCGGGAGGGGTCCCTGG
GGCAGATGGGGCTTTACCAGCGTCGGGTGGTTTAGTTCGAGTCCCTTTTGTGGAGAAAGGGAGATGAAAA
CTGACCACGTGCCAGGTGTGGCCGAAGCCCCCAGGGAGGGCCACATTCGGGGAGCGGGGGGTCGGGGGAG
GGCCACCGACTGGCTCTGCTGCCAGCACAGGCCCCTCCCTGGAAGTCCTCGGGAGCGGAGCGCGGATCGG
CACGGGCTCTGGGCTCCCCGTGGAGAGAAGCTGTAGTTTTTACCAAATTGTGTACATCTGGGCAGATGTT
TAATTTCTGTGACTAATCACTGAACTAGACGAATGTTAAATTTTTTATGTCTGAAGCCTGAGTCTATTTT
GGATCTGTAAATAATCATTGCCAGTGTGACTTTTGTTCAACAAAAGGATTGTACTGTATTAAGAACCGAT
GAAAAAAATTCTCCTGTAACATTTTTTTAAGAAAACTTTGTTTGTTTAAAGAAAAAGTATTGTATAAATT
ATAATTTTTATTTAAATAAACCTAAAATGCTTTGTGCTAAGGCTCAAAAAAAAAAAAAAAAAAAAA (SEQ ID NO: 29)

Translated protein sequence

MLRRLDKIRFRGHKRDDFLDLAESPNASDTECSDEIPLKVPRTS
PRDSEELRDPAGPGTLIMATGVQDFNRTEFDRLNEIKGHLEIALLEKHFLQEELRKLR
EETNAEMLRQELDRERQRRMELEQKVQEVLKARTEEQMAQQPPKGQAQASNGAERRSQ
GLSSRLQKWFYERFGEYVEDFRFQPEENTVETEEPLSARRLTENMRRLKRGAKPVTNF
VKNLSALSDWYSVYTSAIAFTVYMNAVWHGWAIPLFLFLAILRLSLNYLIARGWRIQW
SIVPEVSEPVEPPKEDLTVSEKFQLVLDVAQKAQNLFGKMADILEKIKNLFMWVQPEI
TQKLYVALWAAFLASCFFPYRLVGLAVGLYAGIKFFLIDFIFKRCPRLRAKYDTPYII
WRSLPTDPQLKERSSAAVSRRLQTTSSRSYVPSAPAGLGKEEDAGRFHSTKKGNFHEI
FNLTENERPLAVCENGWRCCLINRDRKMPTDYIRNGVLYVTENYLCFESSKSGSSKRN
KVIKLVDITDIQKYKVLSVLPGSGMGIAVSTPSTQKPLVFGAMVHRDEAFETILSQYI
KITSAAASGGDS (SEQ ID NO: 30)

| HYAL2 | 8692 | NM_003773 | *Homo sapiens* hyaluronoglucosaminidase 2 (HYAL2), transcript variant 1, mRNA |
| --- | --- | --- | --- |

mRNA Sequence

TTTCCTCTCAGGGGGCAGCAGGAAGTGAGGAGAAAGGGCTGGGATGGGAGGCGGGAGCGGATGGGAGGGA
ATGGGGTTTATCAAGTCCTCGGCGAGCTGCCCAACGGGCAGCAGCTGGCGCAAGTAGCCTAGCTGGAGAG
GCTCACCCCAGGAAGGAGGGAGGCCACCGACCTACTGGGCCGACGGACTCCCACACAGTTCCTGAGCTGG
TGCCAGGCAGGTGACACCTCCTGCAGCCCCCAGCATGCGGGCAGGCCCAGGCCCCACCGTTACATTGGCC
CTGGTGCTGGCGGTGTCATGGGCCATGGAGCTCAAGCCCACAGCACCACCCATCTTCACTGGCCGGCCCT
TTGTGGTAGCGTGGGACGTGCCCACACAGGACTGTGGCCCACGCCTCAAGGTGCCACTGGACCTGAATGC
CTTTGATGTGCAGGCCTCACCTAATGAGGGTTTTGTGAACCAGAATATTACCATCTTCTACCGCGACCGT
CTAGGCCTGTATCCACGCTTCGATTCTGCCGGAAGGTCTGTGCATGGTGGTGTGCCACAGAATGTCAGCC
TTTGGGCACACCGGAAGATGCTGCAGAAACGTGTGGAGCACTACATTCGGACACAGGAGTCTGCGGGGCT
GGCGGTCATCGACTGGGAGGACTGGCGACCTGTGTGGGTGCGCAACTGGCAGGACAAAGATGTGTATCGC
CGGTTATCACGCCAGCTAGTGGCCAGTCGTCACCCTGACTGGCCTCCAGACCGCATAGTCAAACAGGCAC
AATATGAGTTTGAGTTCGCAGCACAGCAGTTCATGCTGGAGACACTGCGTTATGTCAAGGCAGTGCGGCC
CCGGCACCTCTGGGGCTTCTACCTCTTTCCTGACTGCTACAATCATGATTATGTGCAGAACTGGGAGAGC
TACACAGGCCGCTGCCCTGATGTTGAGGTGGCCCGCAATGACCAGCTGGCCTGGCTGTGGGCTGAGAGCA
CGGCCCTCTTCCCGTCTGTCTACCTGGACGAGACACTTGCTTCCTCCCGCCATGGCCGCAACTTTGTGAG
CTTCCGTGTTCAGGAGGCCCTTCGTGTGGCTCGCACCCACCATGCCAACCATGCACTCCCAGTCTACGTC
TTCACACGACCCACCTACAGCCGCAGGCTCACGGGGCTTAGTGAGATGGACCTCATCTCTACCATTGGCG
AGAGTGCGGCCCTGGGCGCAGCTGGTGTCATCCTCTGGGGTGACGCGGGGTACACCACAAGCACGGAGAC
CTGCCAGTACCTCAAAGATTACCTGACACGGCTGCTGGTCCCCTACGTGGTCAATGTGTCCTGGGCCACC
CAATATTGCAGCCGGGCCCAGTGCCATGGCCATGGGCGCTGTGTGCGCCGCAACCCCAGTGCCAGTACCT
TCCTGCATCTCAGCACCAACAGTTTCCGCCTAGTGCCTGGCCATGCACCTGGTGAACCCCAGCTGCGACC
TGTGGGGGAGCTCAGTTGGGCCGACATTGACCACCTGCAGACACACTTCCGCTGCCAGTGCTACTTGGGC
TGGAGTGGTGAGCAATGCCAGTGGGACCATAGGCAGGCAGCTGGAGGTGCCAGCGAGGCCTGGGCTGGGT
CCCACCTCACCAGTCTGCTGGCTCTGGCAGCCCTGGCCTTTACCTGGACCTTGTAGGGGTCTCCTGCCTA
GCTGCCTAGCAAGCTGGCCTCTACCACAAGGGCTCTCTTAGGCATGTAGGACCCTGCAGGGGGTGGACAA
ACTGGAGTCTGGAGTGGGCAGAGCCCCCAGGAAGCCCAGGAGGGCATCCATACCAGCTCGCACCCCCCTG
TTCTAAGGGGGAGGGGAAGTCCCTGGGAGGCCCCTTCTCTCCCTGCCAGAGGGGAAGGAGGGTACAGCTG
GGCTGGGGAGGACCTGACCCTACTCCCTTGCCCTAGATAGTTTATTATTATTATTATTTGGGGTCTCTT
TTGTAAATTAAACATAAAACAATTGCTTCTCTGCTTGGATTTTGT (SEQ ID NO: 31)

Translated protein sequence

MRAGPGPTVTLALVLAVSWAMELKPTAPPIFTGRPFVVAWDVPT
QDCGPRLKVPLDLNAFDVQASPNEGFVNQNITIFYRDRLGLYPRFDSAGRSVHGGVPQ
NVSLWAHRKMLQKRVEHYIRTQESAGLAVIDWEDWRPVWVRNWQDKDVYRRLSRQLVA
SRHPDWPPDRIVKQAQYEFEFAAQQFMLETLRYVKAVRPRHLWGFYLFPDCYNHDYVQ
NWESYTGRCPDVEVARNDQLAWLWAESTALFPSVYLDETLASSRHGRNFVSFRVQEAL
RVARTHHANHALPVYVFTRPTYSRRLTGLSEMDLISTIGESAALGAAGVILWGDAGYT
TSTETCQYLKDYLTRLLVPYVVNVSWATQYCSRAQCHGHGRCVRRNPSASTFLHLSTN

APPENDIX-continued

| NUCLEIC ACID AND AMINO ACID SEQUENCES OF BIOMARKERS | | | |
|---|---|---|---|
| Gener Name | Gene ID | Accession NO. | Name |
| SFRLVPGHAPGEPQLRPVGELSWADIDHLQTHFRCQCYLGWSGEQCQWDHRQAAGGAS EAWAGSHLTSLLALAALAFTWTL (SEQ ID NO: 32) | | | |
| IL10 | 3586 | NM_000572 | *Homo sapiens* interleukin 10 (IL10), mRNA |

mRNA Sequence

ACACATCAGGGGCTTGCTCTTGCAAAACCAAACCACAAGACAGACTTGCAAAAGAAGGCATGCACAGCTC
AGCACTGCTCTGTTGCCTGGTCCTCCTGACTGGGGTGAGGGCCAGCCCAGGCCAGGGCACCCAGTCTGAG
AACAGCTGCACCCACTTCCCAGGCAACCTGCCTAACATGCTTCGAGATCTCCGAGATGCCTTCAGCAGAG
TGAAGACTTTCTTTCAAATGAAGGATCAGCTGGACAACTTGTTGTTAAAGGAGTCCTTGCTGGAGGACTT
TAAGGGTTACCTGGGTTGCCAAGCCTTGTCTGAGATGATCCAGTTTTACCTGGAGGAGGTGATGCCCCAA
GCTGAGAACCAAGACCCAGACATCAAGGCGCATGTGAACTCCCTGGGGGAGAACCTGAAGACCCTCAGGC
TGAGGCTACGGCGCTGTCATCGATTTCTTCCCTGTGAAAACAAGAGCAAGGCCGTGGAGCAGGTGAAGAA
TGCCTTTAATAAGCTCCAAGAGAAAGGCATCTACAAAGCCATGAGTGAGTTTGACATCTTCATCAACTAC
ATAGAAGCCTACATGACAATGAAGATACGAAACTGAGACATCAGGGTGGCGACTCTATAGACTCTAGGAC
ATAAATTAGAGGTCTCCAAAATCGGATCTGGGGCTCTGGGATAGCTGACCCAGCCCCTTGAGAAACCTTA
TTGTACCTCTCTTATAGAATATTTATTACCTCTGATACCTCAACCCCCATTTCTATTTATTTACTGAGCT
TCTCTGTGAACGATTTAGAAAGAAGCCCAATATTATAATTTTTTTCAATATTTATTATTTTCACCTGTTT
TTAAGCTGTTTCCATAGGGTGACACACTATGGTATTTGAGTGTTTTAAGATAAATTATAAGTTACATAAG
GGAGGAAAAAAAATGTTCTTTGGGGAGCCAACAGAAGCTTCCATTCCAAGCCTGACCACGCTTTCTAGCT
GTTGAGCTGTTTTCCCTGACCTCCCTCTAATTTATCTTGTCTCTGGGCTTGGGGCTTCCTAACTGCTACA
AATACTCTTAGGAAGAGAAACCAGGGAGCCCCTTTGATGATTAATTCACCTTCCAGTGTCTCGGAGGGAT
TCCCCTAACCTCATTCCCCAACCACTTCATTCTTGAAAGCTGTGGCCAGCTTGTTATTTATAACAACCTA
AATTTGGTTCTAGGCCGGGCGCGGTGGCTCACGCCTGTAATCCCAGCACTTTGGGAGGCTGAGGCGGGTG
GATCACTTGAGGTCAGGAGTTCCTAACCAGCCTGGTCAACATGGTGAAACCCCGTCTCTACTAAAAATAC
AAAAATTAGCCGGGCATGGTGGCGCGCACCTGTAATCCCAGCTACTTGGGAGGCTGAGGCAAGAGAATTG
CTTGAACCCAGGAGATGGAAGTTGCAGTGAGCTGATATCATGCCCCTGTACTCCAGCCTGGGTGACAGAG
CAAGACTCTGTCTCAAAAAATAAAAATAAAAATAAATTTGGTTCTAATAGAACTCAGTTTTAACTAGAAT
TTATTCAATTCCTCTGGGAATGTTACATTGTTTGTCTGTCTTCATAGCAGATTTTAATTTTGAATAAATA
AATGTATCTTATTCACATC (SEQ ID NO: 33)

Translated protein sequence

MHSSALLCCLVLLTGVRASPGQGTQSENSCTHFPGNLPNMLRDL
RDAFSRVKTFFQMKDQLDNLLLKESLLEDFKGYLGCQALSEMIQFYLEEVMPQAENQD
PDIKAHVNSLGENLKTLRLRLRRCHRFLPCENKSKAVEQVKNAFNKLQEKGIYKAMSE
FDIFINYIEAYMTMKIRN (SEQ ID NO: 34)

| Gener Name | Gene ID | Accession NO. | Name |
|---|---|---|---|
| ITFG3 | 83986 | NM_032039 | *Homo sapiens* integrin alpha FG-GAP repeat containing 3 (ITFG3), mRNA |

mRNA Sequence

AGTGACGCCAGGGGGCGGGGCCAGCGGCGCGGTCGGGTGAGAGGCCGCGGCGGCAGGTCCACCTGGGCTT
GCGAAGGCACAGATTCCCCGTCCACAGCTCACGACCAGATGCACCAGCAGGAGTCCACATCGAGGACGTC
CTCCGGGCACTCCCACGACCAGTGACCAGGAGTTAAACTTTGGGATGTGCCCGTGATGTTGGACCACAAG
GACTTAGAGGCCGAAATCCACCCCTTGAAAAATGAAGAAAGAAAATCGCAGGAAAATCTGGGAAATCCAT
CAAAAAATGAGGATAACGTGAAAAGCGCGCCTCCACAGTCCCGGCTCTCCCGGTGCCGAGCGGCGGCGTT
TTTTCTTTCATTGTTTCTCTGCCTTTTTGTGGTGTTCGTCGTCTCATTCGTCATCCCGTGTCCAGACCGG
CCGGCGTCACAGCGAATGTGGAGGATAGACTACAGTGCCGCTGTTATCTATGACTTTCTGGCTGTGGATG
ATATAAACGGGGACAGGATCCAAGATGTTCTTTTTCTTTATAAAAACACCAACAGCAGCAACAATTTCAG
CCGATCCTGTGTGGACGAAGGCTTTTCCTCTCCCTGCACCTTTGCAGCTGCTGTGTCGGGGGCCAACGGC
AGCACGCTCTGGGAGAGACCTGTGGCCCAAGACGTGGCCCTCGTGGAGTGTGCTGTGCCCCAGCCAAGAG
GCAGTGAGGCACCTTCTGCCTGCATCCTGGTGGGCAGACCCAGTTCTTTCATTGCAGTCAACTTGTTCAC
AGGGGAAACCCTGTGGAACCACAGCAGCAGCTTCAGCGGGAATGCGTCCATCCTGAGCCCTCTGCTGCAG
GTGCCTGATGTGGACGGCGATGGGGCCCCAGACCTGCTGGTTCTCACCCAGGAGCGGGAGGAGGTTAGTG
GCCACCTCTACTCCGGCAGCACCGGGCACCAGATTGGCCTCAGAGGCAGCCTTGGTGTGGACGGGGAAAG
TGGCTTCCTCCTTCACGTCACCAGGACAGGTGCCCACTACATCCTCTTTCCCTGCGCAAGCTCCCTCTGC
GGCTGCTCTGTGAAGGGTCTCTACGAGAAGGTGACCGGGAGCGGCGGCCCGTTCAAGAGTGACCCGCACT
GGGAGAGCATGCTCAATGCCACCACCCGCAGGATGCTTTCCCACAGCTCTGGAGCAGTGCGCTACCTGAT
GCATGTCCCAGGGAACGCCGGTGCAGATGTGCTTCTTGTGGGCTCAGAGGCCTTCGTGCTGCTGGACGGG
CAGGAGCTGACGCCTCGCTGGACACCCAAGGCAGCCCATGTCCTGAGAAAACCCATCTTCGGCCGCTACA
AACCAGACACCTTGGCTGTAGCCGTTGAAAACGGAACTGGCACCGACAGACAGATCCTGTTTCTGGACCT
TGGCACTGGAGCCGTCCTGTGTAGCCTAGCCCTCCCGAGCCTCCCTGGGGGTCCACTGTCCGCCAGCCTG
CCGACCGCAGACCACCGCTCAGCCTTCTTCTTCTGGGGCCTCCACGAGCTGGGGAGCACCAGCGAGACGG
AGACCGGGGAGGCCCGGCACAGCCTGTACATGTTCCACCCCACCCTGCCGCGCGTGCTGCTGGAGCTGGC
CAATGTCTCTACCCACATTGTCGCCTTTGACGCCGTCCTGTTTGAGCCAAGCCGCCACGCCGCCTACATC
CTTCTGACAGGCCCGGCAGACTCAGAGGCACCCGGCCTGGTCTCTGTGATCAAGCACAAGGTGCGGGACC
TTGTCCCAAGCAGCAGGGTGGTCCGCCTGGGTGAGGGTGGGCCAGACAGTGACCAAGCCATCAGGGACCG
GTTCTCCCGGCTGCGGTACCAGAGTGAGGCGTAGAGGCACGCCAGCCAGAGCCTGTGGAGAGACTCCGCC
TGCTGACACTAAACGTCCTGGGAAGTGGGCCCTTCCCTGGGTCTCTGCACTGACTCCCCCACTCCTGACC
CTGGTGATGGTCGCCACTGGGCAGCAGCAGCCTTACCAGTCCTCCATGATCACACCCAGGGACCTGCATG
GGTGAGGGGACACCCTGGGCCTCTCTCCCGCCCAGCATCCTCCCTGAGTCCCCACACAGGGCCTCACTCT
GCACCCCACCAGGGTCCCGCTCACACCAGGCAGCCTTCATAGTGGTCTCCCTGGCCACCTTGGGCAGAGC

APPENDIX-continued

| NUCLEIC ACID AND AMINO ACID SEQUENCES OF BIOMARKERS | | | |
|---|---|---|---|
| Gener Name | Gene ID | Accession NO. | Name |

TGGGTCATGCAGCACCCCATCCTTACCCGGTGCCCTCTCCTTGCCAGCTTCTCCCCAGGCCAGAGCGGCC
ATCGCGTAGAAAGAACCAGGGTGTCCCCGGGACAGGCCGTCCCCCACCCCATCCTGTAGAAGTCCATTCC
CCTTTTCCCTCCTGTGCTCTGTCCCCCAAGGAGTCATGGAACTCAGGGTACTGGGCCTCAACGGGAACCT
GAGACAGCTCCAGCTTCGCAGCCCTTCCCGGAGCTACAGGGGGATCCTCTAGCATGGGGGGTGTGACTTG
GTTCCTTTGACCAGGTCCTGTGAGGAAGCCTGGAGCAAGGGTCTCCCCCAGCAGGATGGGTGGGGCCTGC
TCTGGAGCTGAGCCCGTGGCCGCTCACAGGTGTCCTTAGTGGTGTTGCAGCTGTCTACTGGCTGCATGTG
CTGTGAATATCCCAAGGAACTGGCTGTGGAATGCGTGTTTGGGTCAGTCTGTGCCCTCTCAGTAGACACT
GGAGCTGCTCTGTCCCTGAAGAGGCCCCGTGCCCCAGGCATGGCAAGCGCCTGCCTCTCCCCTTCCGGTG
CTCACACGCCCACGCCGTGCCACCCGATGCAGGACTCACCTCTGTGCCTTGCTGCTCCTGAGGCCCAAGG
GCAGCCATGGTGCTCTGTACTGCTCGGGCCGCCCAGGTCACAGAGCCTGAGCTTCGTAGCCAAAGCAGCC
TGATGACCCACCCACCAAGGAAGAAAGCAGAATAAACATTTTTGCACTGCCTGAAAAACCCCGGTGGTCA
GGCGTGAGCCTAAAAAAAAAAAAAAAAAAA (SEQ ID NO: 35)

Translated protein sequence

MLDHKDLEAEIHPLKNEERKSQENLGNPSKNEDNVKSAPPQSRL
SRCRAAAFFLSLFLCLFVVFVVSFVIPCPDRPASQRMWRIDYSAAVIYDFLAVDDING
DRIQDVLFLYKNTNSSNNFSRSCVDEGFSSPCTFAAAVSGANGSTLWERPVAQDVALV
ECAVPQPRGSEAPSACILVGRPSSFIAVNLFTGETLWNHSSSFSGNASILSPLLQVPD
VDGDGAPDLLVLTQEREEVSGHLYSGSTGHQIGLRGSLGVDGESGFLLHVTRTGAHYI
LFPCASSLCGCSVKGLYEKVTGSGGPFKSDPHWESMLNATTRRMLSHSSGAVRYLMHV
PGNAGADVLLVGSEAFVLLDGQELTPRWTPKAAHVLRKPIFGRYKPDTLAVAVENGTG
TDRQILFLDLGTGAVLCSLALPSLPGGPLSASLPTADHRSAFFFWGLHELGSTSETET
GEARHSLYMFHPTLPRVLLELANVSTHIVAFDAVLFEPSRHAAYILLTGPADSEAPGL
VSVIKHKVRDLVPSSRVVRLGEGGPDSDQAIRDRFSRLRYQSEA (SEQ ID NO: 36)

| Gener Name | Gene ID | Accession NO. | Name |
|---|---|---|---|
| JAM3 | 83700 | NM_032801 | *Homo sapiens* junctional adhesion molecule 3 (JAM3), mRNA |

mRNA Sequence

TAGACCTCAGCTTCCTCTGTCACCATGGTGCCGGCTCGGCTGGGCCCGGCGGTCGCCATGGTAACTGGGG
CGGGTCGCAGGGTCCTGGCAGGCTGGGCGCATGCGCGCGGGGACTACAAGCCGCGCCGCGCTGCCGCTGG
CCCCTCAGCAACCCTCGACATGGCGCTGAGGCGGCCACCGCGACTCCGGCTCTGCGCTCGGCTGCCTGAC
TTCTTCCTGCTGCTGCTTTTCAGGGGCTGCCTGATAGGGGCTGTAAATCTCAAATCCAGCAATCGAACCC
CAGTGGTACAGGAATTTGAAAGTGTGGAACTGTCTTGCATCATTACGGATTCGCAGACAAGTGACCCCAG
GATCGAGTGGAAGAAAATTCAAGATGAACAAACCACATATGTGTTTTTTGACAACAAAATTCAGGGAGAC
TTGGCGGGTCGTGCAGAAATACTGGGGAAGACATCCCTGAAGATCTGGAATGTGACACGGAGAGACTCAG
CCCTTTATCGCTGTGAGGTCGTTGCTCGAAATGACCGCAAGGAAATTGATGAGATTGTGATCGAGTTAAC
TGTGCAAGTGAAGCCAGTGACCCCTGTCTGTAGAGTGCCGAAGGCTGTACCAGTAGGCAAGATGGCAACA
CTGCACTGCCAGGAGAGTGAGGGCCACCCCCGGCCTCACTACAGCTGGTATCGCAATGATGTACCACTGC
CCACGGATTCCAGAGCCAATCCCAGATTTCGCAATTCTTCTTTCCACTTAAACTCTGAAACAGGCACTTT
GGTGTTCACTGCTGTTCACAAGGACGACTCTGGGCAGTACTACTGCATTGCTTCCAATGACGCAGGCTCA
GCCAGGTGTGAGGAGCAGGAGATGGAAGTCTATGACCTGAACATTGGCGGAATTATTGGGGGGGTTCTGG
TTGTCCTTGCTGTACTGGCCCTGATCACGTTGGGCATCTGCTGTGCATACAGACGTGGCTACTTCATCAA
CAATAAACAGGATGGAGAAAGTTACAAGAACCCAGGGAAACCAGATGGAGTTAACTACATCCGCACTGAC
GAGGAGGGCGACTTCAGACACAAGTCATCGTTTGTGATCTGAGACCCGCGGTGTGGCTGAGAGCGCACAG
AGCGCACGTGCACATACCTCTGCTAGAAACTCCTGTCAAGGCAGCGAGAGCTGATGCACTCGGACAGAGC
TAGACACTCATTCAGAAGCTTTTCGTTTTGGCCAAAGTTGACCACTACTCTTCTTACTCTAACAAGCCAC
ATGAATAGAAGAATTTTCCTCAAGATGGACCCGGTAAATATAACCACAAGGAAGCGAAACTGGGTGCGTT
CACTGAGTTGGGTTCCTAATCTGTTTCTGGCCTGATTCCCGCATGAGTATTAGGGTGATCTTAAAGAGTT
TGCTCACGTAAACGCCCGTGCTGGGCCCTGTGAAGCCAGCATGTTCACCACTGGTCGTTCAGCAGCCACG
ACAGCACCATGTGAGATGGCGAGGTGGCTGGACAGCACCAGCAGCGCATCCCGGCGGGAACCCAGAAAAG
GCTTCTTACACAGCAGCCTTACTTCATCGGCCCACAGACACCACCGCAGTTTCTTCTTAAAGGCTCTGCT
GATCGGTGTTGCAGTGTCCATTGTGGAGAAGCTTTTTGGATCAGCATTTTGTAAAAACAACCAAAATCAG
GAAGGTAAATTGGTTGCTGGAAGAGGGATCTTGCCTGAGGAACCCTGCTTGTCCAACAGGGTGTCAGGAT
TTAAGGAAAACCTTCGTCTTAGGCTAAGTCTGAAATGGTACTGAAATATGCTTTTCTATGGGTCTTGTTT
ATTTTATAAAATTTTACATCTAAATTTTTGCTAAGGATGTATTTTGATTATTGAAAAGAAAATTTCTATT
TAAACTGTAAATATATTGTCATACAATGTTAAATAACCTATTTTTTTAAAAAAGTTCAACTTAAGGTAGA
AGTTCCAAGCTACTAGTGTTAAATTGGAAAATATCAATAATTAAGAGTATTTTACCCAAGGAATCCTCTC
ATGGAAGTTTACTGTGATGTTCCTTTTCTCACACAAGTTTTAGCCTTTTTCACAAGGGAACTCATACTGT
CTACACATCAGACCATAGTTGCTTAGGAAACCTTTAAAAATTCCAGTTAAGCAATGTTGAAATCAGTTTG
CATCTCTTCAAAAGAAACCTCTCAGGTTAGCTTTGAACTGCCTCTTCCTGAGATGACTAGGACAGTCTGT
ACCCAGAGGCCACCCAGAAGCCCTCAGATGTACATACACAGATGCCAGTCAGCTCCTGGGGTTGCGCCAG
GCGCCCCCGCTCTAGCTCACTGTTGCCTCGCTGTCTGCCAGGAGGCCCTGCCATCCTTGGGCCCTGGCAG
TGGCTGTGTCCCAGTGAGCTTTACTCACGTGGCCCTTGCTTCATCCAGCACAGCTCTCAGGTGGGCACTG
CAGGGACACTGGTGTCTTCCATGTAGCGTCCCAGCTTTGGGCTCCTGTAACAGACCTCTTTTTGGTTATG
GATGGCTCACAAAATAGGGCCCCCAATGCTATTTTTTTTTTTTAAGTTTGTTTAATTATTTGTTAAGATT
GTCTAAGGCCAAAGGCAATTGCGAAATCAAGTCTGTCAAGTACAATAACATTTTTAAAAGAAAATGGATC
CCACTGTTCCTCTTTGCCACAGAGAAAGCACCCAGACGCCACAGGCTCTGTCGCATTTCAAAACAAACCA
TGATGGAGTGGCGGCCAGTCCAGCCTTTTAAAGAACGTCAGGTGGAGCAGCCAGGTGAAAGGCCTGGCGG
GGAGGAAAGTGAAACGCCTGAATCAAAAGCAGTTTTCTAATTTTGACTTTAAATTTTTCATCCGCCGGAG
ACACTGCTCCCATTTGTGGGGGGACATTAGCAACATCACTCAGAAGCCTGTGTTCTTCAAGAGCAGGTGT
TCTCAGCCTCACATGCCCTGCCGTGCTGGACTCAGGACTGAAGTGCTGTAAAGCAAGGAGCTGCTGAGAA
GGAGCACTCCACTGTGTGCCTGGAGAATGGCTCTCACTACTCACCTTGTCTTTCAGCTTCCAGTGTCTTG

APPENDIX-continued

NUCLEIC ACID AND AMINO ACID SEQUENCES OF BIOMARKERS

| Gener Name | Gene ID | Accession NO. | Name |
|---|---|---|---|

GGTTTTTTATACTTTGACAGCTTTTTTTTAATTGCATACATGAGACTGTGTTGACTTTTTTTAGTTATGT
GAAACACTTTGCCGCAGGCCGCCTGGCAGAGGCAGGAAATGCTCCAGCAGTGGCTCAGTGCTCCCTGGTG
TCTGCTGCATGGCATCCTGGATGCTTAGCATGCAAGTTCCCTCCATCATTGCCACCTTGGTAGAGAGGGA
TGGCTCCCCACCCTCAGCGTTGGGGATTCACGCTCCAGCCTCCTTCTTGGTTGTCATAGTGATAGGGTAG
CCTTATTGCCCCCTCTTCTTATACCCTAAAACCTTCTACACTAGTGCCATGGGAACCAGGTCTGAAAAAG
TAGAGAGAAGTGAAAGTAGAGTCTGGGAAGTAGCTGCCTATAACTGAGACTAGACGGAAAAGGAATACTC
GTGTATTTTAAGATATGAATGTGACTCAAGACTCGAGGCCGATACGAGGCTGTGATTCTGCCTTTGGATG
GATGTTGCTGTACACAGATGCTACAGACTTGTACTAACACACCGTAATTTGGCATTTGTTTAACCTCATT
TATAAAAGCTTCAAAAAAACCCAAAAAAACCCAAA (SEQ ID NO: 37)

Translated protein sequence

MVPARLGPAVAMVTGAGRRVLAGWAHARGDYKPRRAAAGPSATL
DMALRRPPRLRLCARLPDFFLLLLFRGCLIGAVNLKSSNRTPVVQEFESVELSCIITD
SQTSDPRIEWKKIQDEQTTYVFFDNKIQGDLAGRAEILGKTSLKIWNVTRRDSALYRC
EVVARNDRKEIDEIVIELTVQVKPVTPVCRVPKAVPVGKMATLHCQESEGHPRPHYSW
YRNDVPLPTDSRANPRFRNSSFHLNSETGTLVFTAVHKDDSGQYYCIASNDAGSARCE
EQEMEVYDLNIGGIIGGVLVVLAVLALITLGICCAYRRGYFINNKQDGESYKNPGKPD
GVNYIRTDEEGDFRHKSSFVI (SEQ ID NO: 38)

| KLHL17 | 339451 | NM_198317 | *Homo sapiens* kelch-like 17 (Drosophila) (KLHL17), mRNA |
|---|---|---|---|

mRNA Sequence

AGTGAGCGACACAGAGCGGGCCGCCACCGCCGAGCAGCCCTCCGGCAGTCTCCGCGTCCGTTAAGCCCGC
GGGTCCTCCGCGAATCGGCGGTGGGTCCGGCAGCCGAATGCAGCCCCGCAGCGAGCGCCCGGCCGGCAGG
ACGCAGAGCCCGGAGCACGGCAGCCCGGGGCCCGGGCCCGAGGCGCCGCCGCCTCCACCGCCGCAGCCGC
CGGCCCCCGAGGCAGAGCGCACGCGGCCCCGGCAGGCTCGGCCCGCAGCCCCCATGGAGGGAGCCGTGCA
GCTGCTGAGCCGCGAGGGCCACAGCGTGGCCCACAACTCCAAGCGGCACTACCACGATGCCTTCGTGGCC
ATGAGCCGCATGCGCCAGCGCGGCCTCCTGTGCGACATCGTCCTGCACGTGGCTGCCAAGGAGATCCGTG
CGCACAAAGTGGTGCTGGCCTCCTGCAGCCCCTACTTCCACGCCATGTTCACAAATGAGATGAGCGAGAG
CCGCCAGACCCACGTGACGCTGCACGACATCGACCCTCAGGCCTTGGACCAGCTGGTGCAGTTTGCCTAC
ACGGCTGAGATTGTGGTGGGCGAGGGCAATGTGCAGACTCTGCTCCCAGCCGCCAGTCTCCTGCAGCTGA
ATGGCGTCCGAGACGCTTGCTGCAAGTTCCTACTGAGTCAGCTCGACCCCTCCAACTGCCTGGGTATCCG
GGGCTTTGCCGATGCGCACTCCTGCAGCGACCTGCTCAAGGCCGCCCACAGGTACGTGCTGCAGCACTTC
GTGGACGTGGCCAAGACCGAGGAGTTTATGCTGCTGCCCCTGAAACAGGTTCTGGAACTGGTCTCTAGCG
ACAGCCTGAACGTGCCTTCAGAGGAGGAGGTCTACCGAGCCGTCCTGAGCTGGGTGAAACACGACGTGGA
CGCCCGCAGGCAGCATGTCCCACGGCTCATGAAGTGTGTGCGGCTGCCCTTGCTGAGCCGCGACTTCCTG
CTGGGCCACGTGGATGCCGAGAGCCTGGTGAGGCACCACCCTGACTGCAAGGACCTCCTCATCGAGGCCC
TGAAGTTCCACCTGCTGCCTGAGCAGAGGGGCGTCCTAGGCACCAGCCGCACACGTCCCCGGCGCTGCGA
GGGGGCCGGGCCTGTGCTTTTTGCTGTGGGCGGCGGGAGCCTGTTTGCCATCCACGGAGACTGTGAGGCC
TACGACACGCGCACCGACCGCTGGCACGTGGTGGCCTCCATGTCCACGCGCCGGGCCCGGGTGGGAGTGG
CTGCGGTGGGGAACCGGCTCTATGCTGTGGGCGGCTATGATGGGACCTCAGACCTGGCTACCGTGGAGTC
CTACGACCCCGTGACTAACACGTGGCAGCCGGAGGTGTCCATGGGCACAAGGCGAAGCTGCCTGGGTGTG
GCCGCCTTGCATGGACTCCTGTACTCGGCCGGCGGCTATGACGGGGCCTCCTGCCTGAACAGTGCTGAAC
GCTACGACCCCCTGACCGGAACGTGGACGTCCGTCGCTGCCATGAGCACCCGGAGGCGCTATGTGCGAGT
GGCCACGCTTGATGGGAACCTGTATGCTGTGGGCGGCTACGACAGCTCCTCACACCTGGCCACTGTGGAG
AAGTATGAGCCCCAGGTGAACGTGTGGTCGCCCGTGGCGTCCATGCTGAGCCGACGCAGCTCAGCGGGCG
TGGCCGTGCTGGAGGGTGCCCTGTACGTGGCAGGGGGCAACGACGGCACCAGCTGCCTCAACTCGGTAGA
GAGATACAGTCCAAAGGCTGGAGCCTGGGAAAGCGTGGCGCCCATGAATATCCGCAGGAGCACGCATGAC
CTGGTGGCCATGGACGGATGGTTGTACGCCGTGGGGGGTAACGACGGTAGCTCCAGCCTCAACTCCATCG
AGAAGTACAACCCGAGGACCAACAAGTGGGTGGCCGCATCCTGCATGTTCACCCGGCGCAGCAGTGTGGG
TGTGGCGGTGCTGGAGCTGCTCAATTTCCCGCCGCCATCCTCCCCGACGCTGTCCGTGTCCTCCACCAGC
CTCTGACCCACCTACCACCAGAGGCCTGCAGCCTCCCACATGCCTTAAGGGGACCGTGGCCCCCACCAGG
GACGTCCTGCGCCATCCGTTCACGTCTCTGCATCCATTCCTTCATGTCTTTATTTAGTTGTTTATTTATT
TAGTTATTTATCTTATTTATTGAGGGGTGAGGAGTGCCACGGCTGCCCGTTTACACCTTTAGCGTCTGGT
CCTCCTGCGTGTCCTCCCCTCCACTGCCTGCATGGGGGGCGCGGGGAGTGACCAGGCGGGGGCCTCACCG
CCCCAGGGCCGTTGCCTGCTCAGACCTTGCAGGCTGTGGAGCAAGAGGCCCTGGGTCTCTCCAAGCAGCT
GCAGACCCCAGCTCGAATTTTGCACATGGCGGGGTCCCGGGAAGGGTGGGGAGCAGTTGTCCTTCCTGTC
GTCGTCTGCCGTGTGCCATCTTTCCTGGATCTTGTAGTGGGTGCACACGCGTGCACTGGACCCCACACA
GCAATACGAGTCCAACTTAATAAACACATTTCTGGGGTTCCTCAAAAAAAAAAAAAAAAAA (SEQ ID NO: 39)

Translated protein sequence

MQPRSERPAGRTQSPEHGSPGPGPEAPPPPPPQPPAPEAERTRP
RQARPAAPMEGAVQLLSREGHSVAHNSKRHYHDAFVAMSRMRQRGLLCDIVLHVAAKE
IRAHKVVLASCSPYFHAMFTNEMSESRQTHVTLHDIDPQALDQLVQFAYTAEIVVGEG
NVQTLLPAASLLQLNGVRDACCKFLLSQLDPSNCLGIRGFADAHSCSDLLKAAHRYVL
QHFVDVAKTEEFMLLPLKQVLELVSSDSLNVPSEEEVYRAVLSWVKHDVDARRQHVPR
LMKCVRLPLLSRDFLLGHVDAESLVRHHPDCKDLLIEALKFHLLPEQRGVLGTSRTRP
RRCEGAGPVLFAVGGGSLFAIHGDCEAYDTRTDRWHVVASMSTRRARVGVAAVGNRLY
AVGGYDGTSDLATVESYDPVTNTWQPEVSMGTRRSCLGVAALHGLLYSAGGYDGASCL
NSAERYDPLTGTWTSVAAMSTRRRYVRVATLDGNLYAVGGYDSSSHLATVEKYEPQVN
VWSPVASMLSRRSSAGVAVLEGALYVAGGNDGTSCLNSVERYSPKAGAWESVAPMNIR

APPENDIX-continued

NUCLEIC ACID AND AMINO ACID SEQUENCES OF BIOMARKERS

| Gener Name | Gene ID | Accession NO. | Name |
|---|---|---|---|
| RSTHDLVAMDGWLYAVGGNDGSSSLNSIEKYNPRTNKWVAASCMFTRRSSVGVAVLEL LNFPPPSSPTLSVSSTSL (SEQ ID NO: 40) | | | |
| KRT24 | 192666 | NM_019016 | *Homo sapiens* keratin 24 (KRT24), mRNA |

mRNA Sequence

ACTCTTCGTCATCACCTCTCCTATTCGCCTGGACAAGCTCATGTTTGCAGGAGCACCATGTCTTGCTCGT
CTCGCGCCTCCTCCTCCAGGGCTGGAGGCAGCAGCTCAGCCAGGGTGTCTGCTGGTGGAAGCAGCTTCAG
CAGTGGAAGCAGATGTGGTCTGGGGGGCAGCTCGGCCCAGGGCTTCCGAGGAGGAGCCAGCAGCTGCAGC
CTGAGTGGGGGGTCTAGCGGTGCTTTTGGGGGCAGCTTTGGAGGGGGCTTTGGTAGCTGCTCAGTAGGGG
GTGGTTTTGGGGGAGCTTCAGGCTCTGGGACAGGATTTGGTGGGGGTTCTAGCTTTGGCGGGGTCTCTGG
ATTTGGCAGGGGTTCTGGATTCTGTGGGAGTTCTAGATTCAGCAGTGGTGCTACTGGAGGCTTCTACAGC
TATGGTGGTGGTATGGGAGGTGGTGTTGGCGATGGGGGGCTTTTCTCTGGAGGGGAAAAGCAAACCATGC
AGAACCTCAATGACCGCTTGGCCAATTACCTAGACAAGGTCAGAGCCCTGGAGGAGGCTAACACTGATCT
GGAGAACAAAATCAAGGAGTGGTATGACAAATATGGGCCTGGGTCTGGAGACGGTGGATCGGGAAGAGAT
TATAGCAAATACTATTCAATAATTGAAGATCTCAGAAACCAGATCATTGCTGCCACTGTTGAAAATGCTG
GGATCATTTTGCACATTGACAATGCCAGATTGGCTGCTGATGACTTCAGACTGAAGTATGAGAACGAGCT
GTGTCTCCGGCAGAGCGTGGAGGCTGACATCAATGGCCTGCGGAAAGTCCTGGATGACCTGACTATGACC
CGCTCTGACCTGGAGATGCAGATTGAGAGTTTCACCGAGGAGCTAGCCTACCTGAGGAAGAACCACGAGG
AGGAAATGAAGAATATGCAAGGAAGCTCTGGAGGGGAGGTGACCGTAGAAATGAATGCTGCGCCAGGGAC
CGACCTGACCAAATTACTGAATGACATGAGGGCGCAGTACGAGGAGCTGGCTGAGCAAAACCGCCGAGAG
GCTGAGGAGCGGTTCAACAAGCAGAGCGCATCACTACAAGCACAAATCTCCACTGATGCTGGGGCAGCCA
CTTCTGCCAAGAATGAGATAACAGAACTAAAACGTACCCTGCAAGCCCTGGAAATTGAGCTTCAGTCCCA
ACTGGCCATGAAAAGCTCCCTGGAGGGAACCCTGGCTGACACAGAAGCTGGCTACGTGGCTCAGCTGTCA
GAAATTCAAACGCAGATCAGTGCCCTGGAGGAGGAGATCTGCCAGATCTGGGGTGAGACTAAATGCCAGA
ACGCAGAGTACAAGCAATTGCTGGACATCAAGACACGCCTGGAGGTGGAGATCGAGACCTACCGCCGCCT
GCTCGATGGAGAGGGAGGTGGTTCTAGTTTTGCAGAATTTGGTGGTAGAAACTCAGGATCTGTAAACATG
GGATCCAGGGATCTGGTATCTGGTGACTCAAGATCTGGAAGCTGTTCTGGTCAAGGACGAGATTCAAGCA
AGACTAGAGTGACTAAGACTATCGTAGAGGAGTTGGTGGATGGCAAGGTTGTCTCGTCTCAAGTCAGCAG
TATTTCTGAGGTGAAAGTTAAATAAGGAACTTCCAGATCAACAAAAGTGTCTTTCAAAGAAAAAAAAATC
AAGAAGGACACAAGCGAAGAAATGGCATCAATCTAGGCATCTTTCTGGATAATTTCAGGAAAAGCTTCAG
TCCAGAAATGGATGACTAGCCAACTTTTCTGCATCTTCTTATTTCCTCATTAGAATGCTCTTGAAATAGC
TGAATTAACAACTTTGCTTTAATTGTTTCTATGCTTCAATAAATTTACTTTTGCAAGTTAAAAAAAAAAA
AAAAAAA (SEQ ID NO: 41)

Translated protein sequence

MSCSSRASSSRAGGSSSARVSAGGSSFSSGSRCGLGGSSAQGFR
GGASSCSLSGGSSGAFGGSFGGGFGSCSVGGGFGGASGSGTGFGGGSSFGGVSGFGRG
SGFCGSSRFSSGATGGFYSYGGGMGGGVGDGGLFSGGEKQTMQNLNDRLANYLDKVRA
LEEANTDLENKIKEWYDKYGPGSGDGGSGRDYSKYYSIIEDLRNQIIAATVENAGIIL
HIDNARLAADDFRLKYENELCLRQSVEADINGLRKVLDDLTMTRSDLEMQIESFTEEL
AYLRKNHEEEMKNMQGSSGGEVTVEMNAAPGTDLTKLLNDMRAQYEELAEQNRREAEE
RFNKQSASLQAQISTDAGAATSAKNEITELKRTLQALEIELQSQLAMKSSLEGTLADT
EAGYVAQLSEIQTQISALEEEICQIWGETKCQNAEYKQLLDIKTRLEVEIETYRRLLD
GEGGGSSFAEFGGRNSGSVNMGSRDLVSGDSRSGSCSGQGRDSSKTRVTKTIVEELVD
GKVVSSQVSSISEVKVK (SEQ ID NO: 42)

| Gener Name | Gene ID | Accession NO. | Name |
|---|---|---|---|
| MAD2L1BP | 9587 | NM_014628 | *Homo sapiens* MAD2L1 binding protein (MAD2L1BP), transcript variant 2, mRNA |

mRNA Sequence

ATTCTAACCGCAAGGAGTAGCGGAGGGGAGGTCGTGATGGCGGCGCCGGAGGCGGAGGTTCTGTCCTCAG
CCGCAGTCCCTGATTTGGAGTGGTATGAGAAGTCCGAAGAAACTCACGCCTCCCAGATAGAACTACTTGA
GACAAGCTCTACGCAGGAACCTCTCAACGCTTCGGAGGCCTTTTGCCCAAGAGACTGCATGGTACCAGTG
GTGTTTCCTGGGCCTGTGAGCCAGGAAGGCTGCTGTCAGTTTACTTGTGAACTTCTAAAGCATATCATGT
ATCAACGCCAGCAGCTCCCTCTGCCCTATGAACAGCTTAAGCACTTTTACCGAAAACCTTCTCCCCAGGC
AGAGGAGATGCTGAAGAAGAAACCTCGGGCCACCACTGAGGTGAGCAGCAGGAAATGCCAACAAGCCCTG
GCAGAACTGGAGAGTGTCCTCAGCCACCTGGAGGACTTCTTTGCACGGACACTAGTACCGCGAGTGCTGA
TTCTCCTTGGGGGCAATGCCCTAAGCCCCAAGGAGTTCTATGAACTCGACTTGTCTCTGCTGGCCCCCTA
CAGCGTGGACCAGAGCCTGAGCACAGCAGCTTGTTTGCGCCGTCTCTTCCGAGCCATATTCATGGCTGAT
GCCTTTAGCGAGCTTCAGGCTCCTCCACTCATGGGCACCGTCGTCATGGCACAGGGACACCGCAACTGTG
GAGAAGATTGGTTTCGACCCAAGCTCAACTATCGAGTGCCCAGCCGGGGCCATAAACTGACTGTGACCCT
GTCATGTGGCAGACCTTCCATCCGAACCACGGCTTGGGAAGACTACATTTGGTTCCAGGCACCAGTGACA
TTTAAAGGCTTCCGCGAGTGAATGAGTGCTTCTTAATCCTAAAAACACAATGGCTGAATTATCTTTCTCC
ATGTGGCGCTGAATCACCCATCTGGTTTGGAGCTAGAGTTGCTTCCTGGTGAGAGAGGAAGCAACTCTCC
TTCTGGTTGTCTGCCTCCCCTCAGATTTCCTGATAGGCTGATGGCATGTGGCTGTGACTGTGACTGTAAT
CATTGCTGAACAACATCTCTTTGAATCAAAGGTTGATTTTCCCAGAGGGTGCTGGGTCAGGCATTTCTAT
TAGGAGTTGGAAAGCAAAAATGGGTCCATAGACACTCTATGGAGGTGTCCCTTTCTGCTCTTTGCTGTGT

APPENDIX-continued

NUCLEIC ACID AND AMINO ACID SEQUENCES OF BIOMARKERS

| Gener Name | Gene ID | Accession NO. | Name |
|---|---|---|---|

CCTTTCAGAATTTTTACCAGGAACATAATGTGGATGTGACTTATGAACTTAAATATAAAATAAATAGATT
CTTATTATATTTTCCTGAAAAAA (SEQ ID NO: 43)

Translated protein sequence

MAAPEAEVLSSAAVPDLEWYEKSEETHASQIELLETSSTQEPLN
ASEAFCPRDCMVPVVFPGPVSQEGCCQFTCELLKHIMYQRQQLPLPYEQLKHFYRKPS
PQAEEMLKKKPRATTEVSSRKCQQALAELESVLSHLEDFFARTLVPRVLILLGGNALS
PKEFYELDLSLLAPYSVDQSLSTAACLRRLFRAIFMADAFSELQAPPLMGTVVMAQGH
RNCGEDWFRPKLNYRVPSRGHKLTVTLSCGRPSIRTTAWEDYIWFQAPVTFKGFRE (SEQ ID NO: 44)

| MANSC1 | 54682 | NM_018050 | *Homo sapiens* MANSC domain containing 1 (MANSC1), mRNA |
|---|---|---|---|

mRNA Sequence

AACCACAAAACCCGCCAGGCCGGTGCGGGAGCTGCGGAGCATCCGCTGCGGTCCTCGCCGAGACCCCCGC
GCGGATTCGCCGGTCCTTCCCGCGGGCGCGACAGAGCTGTCCTCGCACCTGGATGGCAGCAGGGGCGCCG
GGGTCCTCTCGACGCCAGAGAGAAATCTCATCATCTGTGCAGCCTTCTTAAAGCAAACTAAGACCAGAGG
GAGGATTATCCTTGACCTTTGAAGACCAAAACTAAACTGAAATTTAAAATGTTCTTCGGGGGAGAAGGGA
GCTTGACTTACACTTTGGTAATAATTTGCTTCCTGACACTAAGGCTGTCTGCTAGTCAGAATTGCCTCAA
AAAGAGTCTAGAAGATGTTGTCATTGACATCCAGTCATCTCTTTCTAAGGGAATCAGAGGCAATGAGCCC
GTATATACTTCAACTCAAGAAGACTGCATTAATTCTTGCTGTTCAACAAAAAACATATCAGGGGACAAAG
CATGTAACTTGATGATCTTCGACACTCGAAAAACAGCTAGACAACCCAACTGCTACCTATTTTTCTGTCC
CAACGAGGAAGCCTGTCCATTGAAACCAGCAAAAGGACTTATGAGTTACAGGATAATTACAGATTTTCCA
TCTTTGACCAGAAATTTGCCAAGCCAAGAGTTACCCCAGGAAGATTCTCTCTTACATGGCCAATTTTCAC
AAGCAGTCACTCCCCTAGCCCATCATCACACAGATTATTCAAAGCCCACCGATATCTCATGGAGAGACAC
ACTTTCTCAGAAGTTTGGATCCTCAGATCACTTGGAGAAACTATTTAAGATGGATGAAGCAAGTGCCCAG
CTCCTTGCTTATAAGGAAAAAGGCCATTCTCAGAGTTCACAATTTTCCTCTGATCAAGAAATAGCTCATC
TGCTGCCTGAAAATGTGAGTGCGCTCCCAGCTACGGTGGCAGTTGCTTCTCCACATACCACCTCGGCTAC
TCCAAAGCCCGCCACCCTTCTACCCACCAATGCTTCAGTGACACCTTCTGGGACTTCCCAGCCACAGCTG
GCCACCACAGCTCCACCTGTAACCACTGTCACTTCTCAGCCTCCCACGACCCTCATTTCTACAGTTTTTA
CACGGGCTGCGGCTACACTCCAAGCAATGGCTACAACAGCAGTTCTGACTACCACCTTTCAGGCACCTAC
GGACTCGAAAGGCAGCTTAGAAACCATACCGTTTACAGAAATCTCCAACCTAACTTTGAACACAGGGAAT
GTGTATAACCCTACTGCACTTTCTATGTCAAATGTGGAGTCTTCCACTATGAATAAAACTGCTTCCTGGG
AAGGTAGGGAGGCCAGTCCAGGCAGTTCCTCCCAGGGCAGTGTTCCAGAAAATCAGTACGGCCTTCCATT
TGAAAAATGGCTTCTTATCGGGTCCCTGCTCTTTGGTGTCCTGTTCCTGGTGATAGGCCTCGTCCTCCTG
GGTAGAATCCTCTCGGAATCACTCCGCAGGAAACGTTACTCAAGACTGGATTATTTGATCAATGGGATCT
ATGTGGACATCTAAGGATGGAACTCGGTGTCTCTTAATTCATTTAGTAACCAGAAGCCCAAATGCAATGA
GTTTCTGCTGACTTGCTAGTCTTAGCAGGAGGTTGTATTTTGAAGACAGGAAAATGCCCCCTTCTGCTTT
CCTTTTTTTTTTTTGGAGACAGAGTCTTGCTTTGTTGCCCAGGCTGGAGTGCAGTAGCACGATCTCGGCT
CTCACCGCAACCTCCGTCTCCTGGGTTCAAGCGATTCTCCTGCCTCAGCCTCCTAAGTATCTGGGATTAC
AGGCATGTGCCACCACACCTGGGTGATTTTTGTATTTTTAGTAGAGACGGGGTTTCACCATGTTGGTCAG
GCTGGTCTCAAACTCCTGACCTAGTGATCCACCCTCCTCGGCCTCCCAAAGTGCTGGGATTACAGGCATG
AGCCACCACAGCTGGCCCCCTTCTGTTTTATGTTTGGTTTTTGAGAAGGAATGAAGTGGGAACCAAATTA
GGTAATTTTGGGTAATCTGTCTCTAAAATATTAGCTAAAAACAAAGCTCTATGTAAAGTAATAAAGTATA
ATTGCCATATAAATTTCAAAATTCAACTGGCTTTTATGCAAAGAAACAGGTTAGGACATCTAGGTTCCAA
TTCATTCACATTCTTGGTTCCAGATAAAATCAACTGTTTATATCAATTTCTAATGGATTTGCTTTTCTTT
TTATATGGATTCCTTTAAAACTTATTCCAGATGTAGTTCCTTCCAATTAAATATTTG (SEQ ID NO: 45)

Translated protein sequence

MFFGGEGSLTYTLVIICFLTLRLSASQNCLKKSLEDVVIDIQSS
LSKGIRGNEPVYTSTQEDCINSCCSTKNISGDKACNLMIFDTRKTARQPNCYLFFCPN
EEACPLKPAKGLMSYRIITDFPSLTRNLPSQELPQEDSLLHGQFSQAVTPLAHHHTDY
SKPTDISWRDTLSQKFGSSDHLEKLFKMDEASAQLLAYKEKGHSQSSQFSSDQEIAHL
LPENVSALPATVAVASPHTTSATPKPATLLPTNASVTPSGTSQPQLATTAPPVTTVTS
QPPTTLISTVFTRAAATLQAMATTAVLTTTFQAPTDSKGSLETIPFTEISNLTLNTGN
VYNPTALSMSNVESSTMNKTASWEGREASPGSSSQGSVPENQYGLPFEKWLLIGSLLF
GVLFLVIGLVLLGRILSESLRRKRYSRLDYLINGIYVDI (SEQ ID NO: 46)

| MOBKL1B | 55233 | NM_018221 | *Homo sapiens* MOB1, Mps One Binder kinase activator-like 1B (yeast) (MOBKL1B), mRNA |
|---|---|---|---|

mRNA Sequence

GCGAGGTGGGGTAGGCGGGCAAGGCGGGCGCCGAGGTTTGCAAAGGCTCGCAGCGGCCAGAAACCCGGCT
CCGAGCGGCGGCGGCCCGGCTTCCGCTGCCCGTGAGCTAAGGACGGTCCGCTCCCTCTAGCCAGCTCCGA
ATCCTGATCCAGGCGGGGGCCAGGGGCCCCTCGCCTCCCCTCTGAGGACCGAAGATGAGCTTCCTCTTCA
GCAGCCGCTCTTCTAAAACATTCAAACCAAAGAAGAATATCCCTGAAGGATCTCATCAGTATGAACTCTT
AAAACATGCAGAAGCAACTCTAGGAAGTGGGAATCTGAGACAAGCTGTTATGTTGCCTGAGGGAGAGGAT
CTCAATGAATGGATTGCTGTGAACACTGTGGATTTCTTTAACCAGATCAACATGTTATATGGAACTATTA
CAGAATTCTGCACTGAAGCAAGCTGTCCAGTCATGTCTGCAGGTCCGAGATATGAATATCACTGGGCAGA
TGGTACTAATATTAAAAAGCCAATCAAATGTTCTGCACCAAAATACATTGACTATTTGATGACTTGGGTT
CAAGATCAGCTTGATGATGAAACTCTTTTTCCTTCTAAGATTGGTGTCCCATTTCCCAAAAACTTTATGT

APPENDIX-continued

NUCLEIC ACID AND AMINO ACID SEQUENCES OF BIOMARKERS

| Gener Name | Gene ID | Accession NO. | Name |
|---|---|---|---|

CTGTGGCAAAGACTATTCTAAAGCGTCTGTTCAGGGTTTATGCCCATATTTATCACCAGCACTTTGATTC
TGTGATGCAGCTGCAAGAGGAGGCCCACCTCAACACCTCCTTTAAGCACTTTATTTTCTTTGTTCAGGAG
TTTAATCTGATTGATAGGCGTGAGCTGGCACCTCTTCAAGAATTAATAGAGAAACTTGGATCAAAAGACA
GATAAATGTTTCTTCTAGAACACAGTTACCCCCTTGCTTCATCTATTGCTAGAACTATCTCATTGCTATC
TGTTATAGACTAGTGATACAAACTTTAAGAAAACAGGATAAAAAGATACCCATTGCCTGTGTCTACTGAT
AAAATTATCCCAAAGGTAGGTTGGTGTGATAGTTTCCGAGTAAGACCTTAAGGACACAGCCAAATCTTAA
GTACTGTGTGACCACTCTTGTTGTTATCACATAGTCATACTTGGTTGTAATATGTGATGGTTAACCTGTA
GCTTATAAATTTACTTATTATTCTTTTACTCATTTACTCAGTCATTTCTTTACAAGAAAATGATTGAATC
TGTTTTAGGTGACAGCACAATGGACATTAAGAATTTCCATCAATAATTTATGAATAAGTTTCCAGAACAA
ATTTCCTAATAACACAATCAGATTGGTTTTATTCTTTTATTTTACGAATAAAAAATGTATTTTTCAGTAA
AAAAAA (SEQ ID NO: 47)

Translated protein sequence

MSFLFSSRSSKTFKPKKNIPEGSHQYELLKHAEATLGSGNLRQA
VMLPEGEDLNEWIAVNTVDFFNQINMLYGTITEFCTEASCPVMSAGPRYEYHWADGTN
IKKPIKCSAPKYIDYLMTWVQDQLDDETLFPSKIGVPFPKNFMSVAKTILKRLFRVYA
HIYHQHFDSVMQLQEEAHLNTSFKHFIFFVQEFNLIDRRELAPLQELIEKLGSKDR (SEQ ID NO: 48)

| | | | |
|---|---|---|---|
| NCBP1 | 4686 | NM_002486 | *Homo sapiens* nuclear cap binding protein subunit 1, 80 kDa (NCBP1), mRNA |

mRNA Sequence

ATTGAGAGGCCACCGGGAAACCATTGAGAAGCCCCGGAGGACCGGCCTGAGCGGAGGCGGAGACTAGAGC
GGCCGCCGGCACGACCCGCCTTCAGGCGTACGACGACCGCGGCCCGGGGGCTCTGAGTGGCCAAAGCGGC
GGCACTTTCTGCGTGGCCCCGGAAGGACATAGAGCGGAAGGCGGGAGAAAGAAGTAGCCGGCAGGCGGAG
GCAGCCCGAGGGGGCGGTTGCATGTGTGCCAGACGTTCGTAGCCCACTGAGCTTCCTCACGCCGGCTGTC
GCAGCGCCTAGCCCCACCCGGCGGCCTCTCCTGCGCTTCCGGGGCCGTGGCGAGCTAGTGCGCCTGCGTG
CCGGCCCATCCGCGCGCCTTGCAGCTGTCCTTGCGTCGGCCAGCGGCCAGACAGTTCCTGCAGCGCTTAC
CGCCTGGCCTCTCGGTTCCGCGGCGCACCGGAGGGCAGCATGTCGCGGCGGCGGCACAGCGACGAGAACG
ACGGTGGGCAGCCTCACAAAAGGAGAAAGACCTCTGATGCAAATGAAACTGAAGATCATTTGGAATCTTT
AATATGTAAAGTAGGAGAAAAGAGTGCCTGCTCTTTGGAGAGCAACCTAGAAGGCTTGGCTGGTGTTTTG
GAAGCTGATCTTCCTAACTACAAGAGCAAGATCTTAAGGCTTCTTTGTACAGTTGCACGCCTATTACCTG
AGAAGCTGACAATTTATACAACATTAGTTGGACTACTGAATGCCAGGAATTACAATTTTGGTGGAGAATT
TGTAGAAGCCATGATTCGTCAACTTAAAGAATCATTGAAAGCAAACAATTATAATGAAGCCGTGTATTTG
GTCCGTTTTTTATCTGATCTTGTGAATTGTCATGTGATTGCCGCCCCATCAATGGTTGCTATGTTTGAAA
ATTTTGTAAGCGTAACTCAGGAAGAAGATGTACCTCAGGTGCGACGAGATTGGTATGTGTATGCATTTCT
GTCATCTTTGCCCTGGGTTGGAAAGGAGTTGTACGAAAAGAAAGATGCAGAGATGGACCGCATCTTTGCC
AACACTGAAAGCTATCTTAAAAGACGCCAAAAGACTCATGTACCCATGTTACAGGTATGGACTGCTGATA
AACCACATCCACAAGAAGAGTATTTAGATTGCCTGTGGGCCCAGATTCAGAAATTGAAAAAGGATCGCTG
GCAGGAACGGCACATCCTAAGACCTTATCTTGCCTTTGACAGCATCCTGTGTGAAGCACTGCAGCACAAT
CTGCCTCCTTTTACACCACCTCCTCACACTGAAGATTCAGTGTACCCAATGCCAAGGGTCATCTTCAGAA
TGTTTGATTACACAGATGATCCCGAGGGTCCTGTCATGCCAGGGAGTCATTCAGTGGAAAGATTTGTAAT
AGAAGAGAATCTTCACTGCATCATTAAGTCCCACTGGAAGGAAAGGAAGACTTGTGCTGCACAGTTAGTG
AGCTATCCAGGGAAGAACAAGATCCCCTTGAACTACCACATAGTTGAGGTGATCTTTGCAGAGCTGTTTC
AACTTCCAGCACCCCCTCACATTGATGTGATGTACACAACACTCCTCATTGAACTGTGCAAACTTCAACC
TGGCTCTCTACCCCAAGTTCTTGCACAGGCAACTGAAATGCTATACATGCGTTTGGACACAATGAACACT
ACCTGTGTAGACAGGTTTATTAATTGGTTTTCTCATCATCTAAGTAACTTCCAGTTCCGTTGGAGCTGGG
AAGATTGGTCAGATTGTCTTAGTCAAGATCCTGAAAGTCCCAAACCGAAGTTTGTAAGAGAAGTTCTAGA
AAAATGTATGAGGTTGTCTTACCATCAGCGTATATTAGATATTGTTCCTCCTACCTTCTCAGCTCTGTGT
CCTGCAAACCCAACCTGCATTTACAAGTATGGAGATGAAAGTAGCAATTCTCTTCCTGGACATTCTGTTG
CCCTCTGTTTAGCTGTTGCCTTTAAAAGTAAGGCAACCAATGATGAAATCTTCAGCATTCTGAAAGATGT
ACCAAATCCTAACCAGGATGATGACGACGATGAAGGATTCAGTTTTAACCCATTGAAAATAGAAGTCTTT
GTACAGACTCTGCTACACTTGGCAGCCAAATCATTCAGCCACTCCTTCAGTGCTCTTGCAAAGTTTCATG
AAGTCTTCAAAACCCTAGCTGAAAGTGATGAAGGAAAGTTACATGTGCTAAGAGTTATGTTTGAGGTCTG
GAGGAACCATCCACAGATGATTGCTGTACTAGTGGATAAGATGATTCGTACACAAATAGTTGATTGTGCT
GCCGTAGCAAATTGGATCTTCTCTTCAGAACTATCTCGTGACTTTACCAGATTGTTTGTTTGGGAAATTT
TGCACTCTACAATTCGTAAGATGAACAAACATGTCCTGAAGATCCAGAAAGAGCTGGAAGAAGCTAAAGA
GAAACTTGCTAGGCAACACAAACGGCGAAGTGATGATGACGACAGAAGCAGTGACAGGAAAGACGGGGTT
CTTGAGGAACAAATAGAACGACTTCAGGAAAAAGTGGAATCTGCTCAGAGTGAACAAAAGAATCTTTTCC
TCGTTATATTTCAGCGGTTTATCATGATCTTGACCGAGCACCTAGTACGATGCGAAACTGATGGGACCAG
TGTATTAACACCATGGTATAAGAACTGTATAGAGAGGCTGCAGCAGATCTTCCTACAGCATCACCAAATA
ATCCAGCAGTACATGGTGACCCTGGAGAACCTTCTCTTCACTGCTGAATTAGACCCTCATATCTTGGCCG
TGTTCCAGCAGTTCTGTGCCCTGCAGGCCTAAGGGTCATTTTTTCCTCATGTCAAGGTTTTTTTTGATAT
CTTAAAATAATTTGTCTTATTTTTTGATGGTTTGAATGCTTGCTTTCTTGTAGTATCCTTTCACTTCTTA
AAGGAAACAAAGGGGAAGAGGACAGTGAATGAACATGGCATTACTTTTAATTGCCCTGAAAAGCAAATAC
TTCCTAACGGCAGTAATGTGACTATGACCATGATATATTATATATGTGACAGATACAAATTCTCTGTGAT
CAGTTTGTTATTTTTTTTCTCCTTAAGGCACAAAATAATTGGTTTGAGGTATGTGAAACACTAGAGGTCA
ACCTTACATAGTATATAGAACTGATGGGTTTACCCAGCTACCCAGTAGCATAACTTTTCACAGCTCGGGG
ATGAATTAACATGGCTGAAATAAAACTAAAGTATGGTTTTTAAACTTTGGCATTTCATGATTTATCATC
TCACTCTACTCTAAAACTGGTGGTTTCTTACTGAAGGTGTTCTCCATTTGAAATTTTATCTTCAAAGTAT
TTTTAAGTAGTATCTTTAAGACATGACTTGTTAGTAATAAAAGTGTTACTAGTTGGAAGAGTAGCTCTCA
AATTTGTCTTAATGTAAATCACCTGGGAATCTTTCAAGTTATTTTGAAATTTAAACCACCGTCTGGGGGT
GGAACGCAGACATCCTCAGTAATCCTTAAAGTTTCCCCAGGTGATTCCAGGTTTGGTCACCATTATCTTA

APPENDIX-continued

NUCLEIC ACID AND AMINO ACID SEQUENCES OF BIOMARKERS

| Gener Name | Gene ID | Accession NO. | Name |
|---|---|---|---|

GAGCATCTACTCACTTCCTCTAGCCTTGGGGTTATTTGTCCAAGGTCTTGTAGTGAGTTACAGAATACTA
AAGTGGATGTAGAAGTGGTCAGATTGACTGAAACTATACCCTGAATTAGATGTGAGTTTAGATTTTGTTT
ATATGGAACCTGATCCAAAAAACTACGAAGTCCTGAGCTTGTTTCCTGTATAGTACTGATGCTGAAATAA
GATGACAGCAGTTTGTAAAATAATACACAAATATGAGGAATTGTCTGACATTCCAAATTTCGAGGATTTT
TAGACTTTTTTCATTAAACCTTAGAAAAAAATTACCAGTAATCCTACAACTACTGGTAGTGTTGTTGTGC
ATTTGCACAAAATAGGTATAATTTTTTCTTATTACATCCCAAGTTTATGATGCATTAAGCGTTTTGCATA
TTTTGATATATTTTTGCTTTGGTTTACCATACATTTTAGTGGCTACAGAATGTAGTCTGCTTAATAAATG
GGAATTCCTAGAATGTTTAAATACCATACTATTTAAGACAAAATACAAAATATCCAGAAAAATCCAGGTT
GCGTGGCTGGTTAGTAAAGGACTAAAACCCAGGTTCTTGGCTAAATGTTTTCGTTTATACTGTTTATCTT
TCCCATTGCTTAAGCACAGCACAAACTATGTAATTATATATAATTACAGTTGACCCTTGAACAACATGGG
TTTGAACTGTGTGAGTCTCCTTACACACAGGTTTTCTTCCACCCCTGAGATGGCAAGACCAGCCCCTTGT
CTTCCTCAGCCTGCTCAACGTGAAGATGATGAGGATGAAGACCTTTATGATGATCCACTTCTACTTATTA
AATAGTAAATATATTTTTTTCTTATGATTTTATTTCTTTTCTCTAGCTTCATAAGAATATAGCATATGG
GCTGGGCGCAGTGGCTCACGCCTGTAATCCCAGCACTTTGGGAGGCTGAGGCGGGCGGATCACAAGGTCA
GGAGATTGAGACCATCCTGGCTAACACAGTGAAACCCTGTCTCTACTAAAAACACAAAAACTTAGCCAGG
CGTGGTGGTACATGGCTGTAGTCCCAGCTACTTGGGAGGCTGAGACAGGAGAATCGCTTGAACCTGGGAG
GTGGAGGTTTCAGTGAGCCAAGATTGTGCCACTGCACTCCAGCCTGGGTGATGGAGCGAGGCTCTGTCTC
AAAAAAGAAAAAAAATATATAGCATATAACATACAAAATGAGTTTATCAACTGTTTGTTATTGGTAAGTC
AGCAGTGGGCTATTGGTGGTTAAGTTTTGGGGGAGTCAAAAGTTACATGCAAATTTTTTACTGTGCGGGG
TGTCAGCATCCCTAACCCCATGTTGTTCAAGGGTCAACTGTAGTTTAAAATGACTCCTGTCTCAAAAAAC
CAAAGGATAACCTTTAAGGGATTGGTAACTTTGACTCAAAACTGCTTTGTAATCTTTTCACAATGTACTG
AAAAGTGTGGCTAGTTATGTTTGATCCACATTCTAGAGAAATTTGTAGGTTTTAATTTCTTTTCTCTTGG
TCCTCTCTTCATGTATAATGGTTGCTTTTAACAGCTGTTCGCTGATGTGGTCCTGCTCTGTCCCAGTCTA
GCAGCTTTAGTGTATGGAAAAATTGAACTAGGAATTGAGTTTTGAAGAAATAAAGGTGTAAGAGCAAACA
TTCAACAGTTGCTGTCCCCAGTAATGAAGTTCATACAGACAAAAGATGGCATGTCACTGTACATCATACC
TTGCAATAAATATTCTGTTAAATTGTGCTGGTGCAATTTAACATGCTTTTGTCAAAGTAAA (SEQ ID NO: 49)

Translated protein sequence

MSRRRHSDENDGGQPHKRRKTSDANETEDHLESLICKVGEKSAC
SLESNLEGLAGVLEADLPNYKSKILRLLCTVARLLPEKLTIYTTLVGLLNARNYNFGG
EFVEAMIRQLKESLKANNYNEAVYLVRFLSDLVNCHVIAAPSMVAMFENFVSVTQEED
VPQVRRDWYVYAFLSSLPWVGKELYEKKDAEMDRIFANTESYLKRRQKTHVPMLQVWT
ADKPHPQEEYLDCLWAQIQKLKKDRWQERHILRPYLAFDSILCEALQHNLPPFTPPPH
TEDSVYPMPRVIFRMFDYTDDPEGPVMPGSHSVERFVIEENLHCIIKSHWKERKTCAA
QLVSYPGKNKIPLNYHIVEVIFAELFQLPAPPHIDVMYTTLLIELCKLQPGSLPQVLA
QATEMLYMRLDTMNTTCVDRFINWFSHHLSNFQFRWSWEDWSDCLSQDPESPKPKFVR
EVLEKCMRLSYHQRILDIVPPTFSALCPANPTCIYKYGDESSNSLPGHSVALCLAVAF
KSKATNDEIFSILKDVPNPNQDDDDDEGFSFNPLKIEVFVQTLLHLAAKSFSHSFSAL
AKFHEVFKTLAESDEGKLHVLRVMFEVWRNHPQMIAVLVDKMIRTQIVDCAAVANWIF
SSELSRDFTRLFVWEILHSTIRKMNKHVLKIQKELEEAKEKLARQHKRRSDDDDRSSD
RKDGVLEEQIERLQEKVESAQSEQKNLFLVIFQRFIMILTEHLVRCETDGTSVLTPWY
KNCIERLQQIFLQHHQIIQQYMVTLENLLFTAELDPHILAVFQQFCALQA (SEQ ID NO: 50)

| Gener Name | Gene ID | Accession NO. | Name |
|---|---|---|---|
| NMU | 10874 | NM_006681 | *Homo sapiens* neuromedin U (NMU), mRNA |

mRNA Sequence

AGTCCTGTGTCCGGGCCCCGAGGCACAGCCAGGGCACCAGGTGGAGCACCAGCTACGCGTGGCGCAGCGC
AGCGTCCCTAGCACCGAGCCTCCCGCAGCCGCCGAGATGCTGCGAACAGAGAGCTGCCGCCCCAGGTCGC
CCGCCGGACAGGTGGCCGCGGCGTCCCCGCTCCTGCTGCTGCTGCTGCTCGCCTGGTGCGCGGGCGC
CTGCCGAGGTGCTCCAATATTACCTCAAGGATTACAGCCTGAACAACAGCTACAGTTGTGGAATGAGATA
GATGATACTTGTTCGTCTTTTCTGTCCATTGATTCTCAGCCTCAGGCATCCAACGCACTGGAGGAGCTTT
GCTTTATGATTATGGGAATGCTACCAAAGCCTCAGGAACAAGATGAAAAAGATAATACTAAAAGGTTCTT
ATTTCATTATTCGAAGACACAGAAGTTGGGCAAGTCAAATGTTGTGTCGTCAGTTGTGCATCCGTTGCTG
CAGCTCGTTCCTCACCTGCATGAGAGAAGAATGAAGAGATTCAGAGTGGACGAAGAATTCCAAAGTCCCT
TTGCAAGTCAAAGTCGAGGATATTTTTTATTCAGGCCACGGAATGGAAGAAGGTCAGCAGGGTTCATTTA
AAATGGATGCCAGCTAATTTTCCACAGAGCAATGCTATGGAATACAAAATGTACTGACATTTTGTTTTCT
TCTGAAAAAAATCCTTGCTAAATGTACTCTGTTGAAAATCCCTGTGTTGTCAATGTTCTCAGTTGTAACA
ATGTTGTAAATGTTCAATTTGTTGAAAATTAAAAAATCTAAAAATAAA (SEQ ID NO: 51)

Translated protein sequence

MLRTESCRPRSPAGQVAAASPLLLLLLLLAWCAGACRGAPILPQ
GLQPEQQLQLWNEIDDTCSSFLSIDSQPQASNALEELCFMIMGMLPKPQEQDEKDNTK
RFLFHYSKTQKLGKSNVVSSVVHPLLQLVPHLHERRMKRFRVDEEFQSPFASQSRGYF
LFRPRNGRRSAGFI (SEQ ID NO: 52)

| Gener Name | Gene ID | Accession NO. | Name |
|---|---|---|---|
| PAPLN | 89932 | NM_173462 | *Homo sapiens* papilin, proteoglycan-like sulfated glycoprotein (PAPLN), mRNA |

APPENDIX-continued

| NUCLEIC ACID AND AMINO ACID SEQUENCES OF BIOMARKERS | | | |
|---|---|---|---|
| Gener Name | Gene ID | Accession NO. | Name |
| mRNA Sequence | | | |

GCGTTCCTTGCGGCCCGGCCGACCTCGCGGGCTTGGGCCTGGGCGGGCACCGACGGAGCGGCCCTGGCTG
CAGCCTCCCGGCGCCAGCGAAGACAGGCTGAGATGCGGCTGCTCCTGCTCGTGCCGCTGCTGCTGGCTCC
AGCGCCCGGGTCCTCGGCTCCCAAGGTGAGGCGGCAGAGTGACACCTGGGGACCCTGGAGCCAGTGGAGC
CCCTGCAGCCGGACCTGTGGAGGGGGTGTCAGCTTCCGGGAGCGCCCCTGCTACTCCCAGAGGAGAGATG
GAGGCTCCAGCTGCGTGGGCCCCGCCCGGAGCCACCGCTCTTGTCGCACGGAGAGCTGCCCCGACGGCGC
CCGGGACTTCCGGGCCGAGCAGTGCGCGGAGTTCGACGGAGCGGAGTTCCAGGGGCGGCGGTATCGGTGG
CTGCCCTACTACAGCGCCCCAAACAAGTGTGAACTGAACTGCATTCCCAAGGGGGAGAACTTCTACTACA
AGCACAGGGAGGCTGTGGTTGATGGGACGCCCTGCGAGCCTGGCAAGAGGGATGTCTGTGTGGATGGCAG
CTGCCGGGTTGTCGGCTGTGATCACGAGCTGGACTCGTCCAAGCAGGAGGACAAGTGTCTGCGGTGTGGG
GGTGACGGCACGACCTGCTACCCCGTCGCAGGCACCTTTGACGCTAATGACCTCAGCCGAGCTGTGAAGA
ATGTTCGTGGGGAATACTACCTCAATGGGCACTGGACCATCGAGGCGGCCCGGGCCCTGCCAGCAGCCAG
CACCATCCTGCATTACGAGCGGGGTGCTGAGGGGGACCTGGCCCCTGAGCGACTCCATGCCCGGGGCCCC
ACCTCGGAGCCCCTGGTCATCGAGCTCATCAGCCAGGAGCCCAACCCCGGTGTGCACTATGAGTACCACC
TGCCCCTGCGCCGCCCCAGCCCCGGCTTCAGCTGGAGCCACGGCTCATGGAGTGACTGCAGCGCGGAGTG
TGGCGGAGGTCACCAGTCCCGCCTGGTGTTCTGCACCATCGACCATGAGGCCTACCCCGACCACATGTGC
CAGCGCCAGCCACGGCCAGCTGACCGGCGTTCCTGCAATCTTCACCCTTGCCCGGAGACCAAGCGCTGGA
AGGCAGGGCCATGGGCACCCTGCTCAGCCTCCTGTGGAGGAGGCTCCCAGTCCCGCTCCGTGTACTGCAT
CTCGTCTGACGGGGCCGGCATCCAGGAGGCCGTGGAGGAGGCTGAGTGTGCCGGGCTGCCTGGGAAGCCC
CCTGCCATTCAGGCCTGTAACCTGCAGCGCTGTGCAGCCTGGAGCCCGGAGCCCTGGGGAGAGTGTTCTG
TCAGTTGTGGCGTTGGCGTCCGGAAGCGGAGCGTTACTTGCCGGGGTGAAAGGGGTTCTTTGCTCCATAC
CGCAGCGTGCTCCTTGGAAGACCGGCCACCTCTGACTGAGCCCTGTGTGCATGAGGACTGCCCCCTCCTC
AGTGACCAGGCCTGGCATGTTGGCACCTGGGGTCTATGCTCCAAGAGCTGCAGCTCGGGCACTCGGAGGC
GACAGGTCATCTGTGCCATTGGGCCGCCCAGCCACTGCGGGAGCCTGCAGCACTCCAAGCCTGTGGATGT
GGAGCCTTGTAACACGCAGCCCTGTCATCTCCCCCAGGAGGTCCCCAGCATGCAGGATGTGCACACCCCT
GCCAGCAACCCCTGGATGCCGTTGGGCCCTCAGGAGTCCCCTGCCTCAGACTCCAGAGGCCAGTGGTGGG
CAGCCCAGGAACACCCCTCAGCCAGGGGTGACCACAGGGGAGAACGAGGTGACCCCAGGGGCGACCAAGG
CACCCACCTGTCAGCCCTGGGCCCCGCTCCCTCTCTGCAGCAGCCCCCATACCAGCAACCCCTGCGGTCG
GGCTCAGGGCCCCACGACTGCAGACACAGTCCTCACGGGTGCTGCCCCGATGGCCACACGGCATCTCTCG
GGCCTCAGTGGCAAGGCTGCCCTGGGGCCCCCTGTCAGCAGAGCAGGTACGGGTGCTGCCCTGACAGGGT
ATCTGTCGCTGAGGGGCCCCATCACGCTGGCTGCACAAAGTCGTATGGTGGTGACAGCACCGGGGGCATG
CCCAGGTCAAGGGCAGTGGCTTCTACAGTCCACAACACCCACCAGCCCCAGGCCCAGCAGAATGAGCCCA
GTGAGTGCCGGGGCTCCCAGTTTGGCTGTTGCTATGACAACGTGGCCACTGCAGCCGGTCCTCTTGGGGA
AGGCTGTGTGGGCCAGCCCAGCCATGCCTACCCCGTGCGGTGCCTGCTGCCCAGTGCCCATGGCTCTTGC
GCAGACTGGGCTGCCCGCTGGTACTTCGTTGCCTCTGTGGGCCAATGTAACCGCTTCTGGTATGGCGGCT
GCCATGGCAATGCCAATAACTTTGCCTCGGAGCAAGAGTGCATGAGCAGCTGCCAGGGATCTCTCCATGG
GCCCCGTCGTCCCCAGCCTGGGGCTTCTGGAAGGAGCACCCACACGGATGGTGGCGGCAGCAGTCCTGCA
GGCGAGCAGGAACCCAGCCAGCACAGGACAGGGGCCGCGGTGCAGAGAAAGCCCTGGCCTTCTGGTGGTC
TCTGGCGGCAAGACCAACAGCCTGGGCCAGGGGAGGCCCCCCACACCCAGGCCTTTGGAGAATGGCCATG
GGGGCAGGAGCTTGGGTCCAGGGCCCCTGGACTGGGTGGAGATGCCGGATCACCAGCGCCACCCTTCCAC
AGCTCCTCCTACAGGATTAGCTTGGCAGGTGTGGAGCCCTCGTTGGTGCAGGCAGCCCTGGGGCAGTTGG
TGCGGCTCTCCTGCTCAGACGACACTGCCCCGGAATCCCAGGCTGCCTGGCAGAAAGATGGCCAGCCCAT
CTCCTCTGACAGGCACAGGCTGCAGTTCGACGGATCCCTGATCATCCACCCCCTGCAGGCAGAGGACGCG
GGCACCTACAGCTGTGGCAGCACCCGGCCAGGCCGCGACTCCCAGAAGATCCAACTTCGCATCATAGGGG
GTGACATGGCCGTGCTGTCTGAGGCTGAGCTGAGCCGCTTCCCTCAGCCCAGGGACCCAGCTCAGGACTT
TGGCCAAGCGGGGGCTGCTGGGCCCCTGGGGGCCATCCCCTCTTCACACCCACAGCCTGCAAACAGGCTG
CGTTTGGACCAGAACCAGCCCCGGGTGGTGGATGCCAGTCCAGGCCAGCGGATCCGGATGACCTGCCGTG
CCGAAGGCTTCCCGCCCCCAGCCATCGAGTGGCAGAGAGATGGGCAGCCTGTCTCTTCTCCCAGACACCA
GCTGCAGCCTGATGGCTCCCTGGTCATTAGCCGAGTGGCTGTAGAAGATGGCGGCTTCTACACCTGTGTC
GCTTTCAATGGGCAGGACCGAGACCAGCGATGGGTCCAGCTCAGAGTTCTGGGGGAGCTGACAATCTCAG
GACTGCCCCCTACTGTGACAGTGCCAGAGGGTGATACGGCCAGGCTATTGTGTGTGGTAGCAGGAGAAAG
TGTGAACATCAGGTGGTCCAGGAACGGGCTACCTGTGCAGGCTGATGGCCACCGTGTCCACCAGTCCCCA
GATGGCACGCTGCTCATTTACAACTTGCGGGCCAGGGATGAGGGCTCCTACACGTGCAGTGCCTACCAGG
GGAGCCAGGCAGTCAGCCGCAGCACCGAGGTGAAGGTGGTCTCACCAGCACCCACCGCCCAGCCCAGGGA
CCCTGGCAGGGACTGCGTCGACCAGCCAGAGCTGGCCAACTGTGATTTGATCCTGCAGGCCCAGCTTTGT
GGCAATGAGTATTACTCCAGCTTCTGCTGTGCCAGCTGTTCACGTTTCCAGCCTCACGCTCAGCCCATCT
GGCAGTAGGGATGAAGGCTAGTTCCAGCCCCAGTCCAAAATAGTTCATAGGGCTAGGGAGAAAGGAAGAT
GGACTCTTGGCTTCCTCTCTCTGGCTGGCAAAGGGAGTTATCTTCTGGAATACATTAGCTCTTTCAAAAA
CCCACCCAGTGTTTAGCCTCAACGGCAGCCAGTTACCAGCTTCTCTCTGTAGCCTTCAGCAGTGTTTGCA
TCTCTGACATAACCACAGGCTGCTGTTTTCAAGAAGAGCAATCTGTTTGGATAAGAAAAACCTTTACTTT
ACAGCTTCCCTTTATAATTTGTTACACAGGAATAGTTAAATGCATTTGTTTGTTTGTTTTTGAGACAGA
GTTTCACTCTTGTTGCCCAGGCTGGAGGGCAATGGCGCGATCTCAGCTCACTGCAACCTCCGTCTCCTGG
GTTCTTGATTCTCCTGTGTCAGCCTTCTGAGTAGCTAGGATTACAGATGCCTATCACCATGCCTGGGTAA
TTTTTGTATTTTTAGTTGAGATGGGGTTTCACCATGTTGGCCAGGCTGGTCTCGAACTTCTGACCTCAGA
TGATCTGCCCGCCTCAGCCTCCCAAAGTGCTGGGATTACAGGCATGAGCCACCACGCCCAGCCATCAATG
CATTTTTTTTATTTTTTTTTTGAGACAGAGTTTCGCACTTCTTGCCCAGGCTGGAGTACAATGGTGCGAT
CTTGGCTCACTGCAACCTCCACCTCCTGGGTTCAAGCGCTTCTCCAGCCTCAGCCTCCTGAGTAGCTGGG
ATTACAGGTATGTGCCACCATGCCTGGCTAATTTTGTATTTTTAGTAGAGACGGGGTTTCTCCATGTTGG
TCAGACTGGTCTTGAACTCCCGACCTCAGGTAATCCGCCCGCCTCGGCCTCCCAAAATGCTGGGATTAGA
GGTGTGAGCCACTGTGCCCAGCCCATCAATGTGTTTTAAAGCTAGCTGTCAGGGTTCCACTTAATTTAAA
GCTGGGCAGGGAGATGTGTAATGATTTCAAAGTTAACACCTGTTTGTTTTCTAAAGGGCATGCCAAGTCC
TGCTGTATCAGGGAAGTATTCTGTGCTAAAATCAGCGATGGTTCATTGCTCTAGTCTCTCTCACCCTTCT
AGGCAGTGCATCAGTCAGCTCTAAATCTGGTGCAGAGGGTTAACAGCATAACCCTTGTTGGCAAAATGGA
ATAGATGTTAAGACCTCAAATAGGGATTTGGGATGAAACAGCTGCAGTTAGCACTGTTATCTGAGCATGA

APPENDIX-continued

NUCLEIC ACID AND AMINO ACID SEQUENCES OF BIOMARKERS

| Gener Name | Gene ID | Accession NO. | Name |
|---|---|---|---|

AAGAACTGGAAACGCTCCTTACGTCGAGATGTTGGACCTTGAAGCCCTCCTGAGGCCAACATGCAAATCT
GGCTGTGACGGTTCATCTGACACCTGTGTAAAGCTGACCAGCCTGCTCTGTACAGTGACAATGAGGAGCC
CCTCTCTTCCTTAAGTAGGAATCTGTGAAGCAAAATGTTTGCTGCCAAAGACAAATCAGACTGTCAGTCA
TTAAAAACAGCATTAGCAGGATGAGGATAGCAATGGGGAAGGGTTGTGGGCAATGCAGTAACAGGGAAAT
GGCTTCAGAAATGGTTTGAGTTGGAAGACAACATTCTTCATCTCTCAGGACTTCTAATTCCTTGATGCTA
AAAGAAGAGGCATGGATTCTATGAGCTTCCAAGTCCCTTTCCACTTTAACCTTCTACAAATCTTTCAGAG
GACTGCCTAGTAGCAAAGGTTATTCCTGGACACAGGAAAGACGGGCATTACAGGGACCAAAGCTCTGAAA
GGTGACTTTTATTACCAACACACTGGCTGGAAAAGGGACAAACCACATCACGGGTGAGTGATACTTCTCA
GTCTTCTCTACTCATTCAACAAAGGAAATGTGGGCTGGGGCAGAGGTCTTTTTTCATTTAATACTGGAAA
AATATTGAAGAGCATCCATGTTCACTTATGGCTGGTTTTGCTATAGAAATTGGAAAATAAAGGCCACTTT
TTTGAAATCCCCAGTTTAATTAAAAAAAAAAAAAAAAAA (SEQ ID NO: 53)

Translated protein sequence

MRLLLLVPLLLAPAPGSSAPKVRRQSDTWGPWSQWSPCSRTCGG
GVSFRERPCYSQRRDGGSSCVGPARSHRSCRTESCPDGARDFRAEQCAEFDGAEFQGR
RYRWLPYYSAPNKCELNCIPKGENFYYKHREAVVDGTPCEPGKRDVCVDGSCRVVGCD
HELDSSKQEDKCLRCGGDGTTCYPVAGTFDANDLSRAVKNVRGEYYLNGHWTIEAARA
LPAASTILHYERGAEGDLAPERLHARGPTSEPLVIELISQEPNPGVHYEYHLPLRRPS
PGFSWSHGSWSDCSAECGGGHQSRLVFCTIDHEAYPDHMCQRQPRPADRRSCNLHPCP
ETKRWKAGPWAPCSASCGGGSQSRSVYCISSDGAGIQEAVEEAECAGLPGKPPAIQAC
NLQRCAAWSPEPWGECSVSCGVGVRKRSVTCRGERGSLLHTAACSLEDRPPLTEPCVH
EDCPLLSDQAWHVGTWGLCSKSCSSGTRRRQVICAIGPPSHCGSLQHSKPVDVEPCNT
QPCHLPQEVPSMQDVHTPASNPWMPLGPQESPASDSRGQWWAAQEHPSARGDHRGERG
DPRGDQGTHLSALGPAPSLQQPPYQQPLRSGSGPHDCRHSPHGCCPDGHTASLGPQWQ
GCPGAPCQQSRYGCCPDRVSVAEGPHHAGCTKSYGGDSTGGMPRSRAVASTVHNTHQP
QAQQNEPSECRGSQFGCCYDNVATAAGPLGEGCVGQPSHAYPVRCLLPSAHGSCADWA
ARWYFVASVGQCNRFWYGGCHGNANNFASEQECMSSCQGSLHGPRRPQPGASGRSTHT
DGGGSSPAGEQEPSQHRTGAAVQRKPWPSGGLWRQDQQPGPGEAPHTQAFGEWPWGQE
LGSRAPGLGGDAGSPAPPFHSSSYRISLAGVEPSLVQAALGQLVRLSCSDDTAPESQA
AWQKDGQPISSDRHRLQFDGSLIIHPLQAEDAGTYSCGSTRPGRDSQKIQLRIIGGDM
AVLSEAELSRFPQPRDPAQDFGQAGAAGPLGAIPSSHPQPANRLRLDQNQPRVVDASP
GQRIRMTCRAEGFPPPAIEWQRDGQPVSSPRHQLQPDGSLVISRVAVEDGGFYTCVAF
NGQDRDQRWVQLRVLGELTISGLPPTVTVPEGDTARLLCVVAGESVNIRWSRNGLPVQ
ADGHRVHQSPDGTLLIYNLRARDEGSYTCSAYQGSQAVSRSTEVKVVSPAPTAQPRDP
GRDCVDQPELANCDLILQAQLCGNEYYSSFCCASCSRFQPHAQPIWQ (SEQ ID NO: 54)

| PCDH1 | 5097 | NM_002587 | *Homo sapiens* protocadherin 1 (PCDH1), transcript variant 1, mRNA |
|---|---|---|---|

mRNA Sequence

CGCAAAGCCGCCGGGCTGCTGCGCCCAGAGCCAGCCGGAGCCGGAGCCGGAGCCCGAACTGCAGCTCCAG
CCCCAGCCGTGCGGAGCCGCAGCCCAGGCCGGGGCCGGCGGCGGCTCATGGACAGCGGGGCGGGCGGCCG
GCGCTGCCCGGAGGCGGCCCTCCTGATTCTGGGGCCTCCCAGGATGGAGCACCTGAGGCACAGCCCAGGC
CCTGGGGGGCAACGGCTACTGCTGCCCTCCATGCTGCTAGCACTGCTGCTCCTGCTGGCTCCATCCCCAG
GCCACGCCACTCGGGTAGTGTACAAGGTGCCGGAGGAACAGCCACCCAACACCCTCATTGGGAGCCTCGC
AGCCGACTATGGTTTTCCAGATGTGGGGCACCTGTACAAGCTAGAGGTGGGTGCCCCGTACCTTCGCGTG
GATGGCAAGACAGGTGACATTTTCACCACCGAGACCTCCATCGACCGTGAGGGGCTCCGTGAATGCCAGA
ACCAGCTCCCTGGTGATCCCTGCATCCTGGAGTTTGAGGTATCTATCACAGACCTCGTGCAGAATGGCAG
CCCCCGGCTGCTAGAGGGCCAGATAGAAGTACAAGACATCAATGACAACACACCCAACTTCGCCTCACCA
GTCATCACTCTGGCCATCCCTGAGAACACCAACATCGGCTCACTCTTCCCCATCCCGCTGGCTTCAGACC
GTGATGCTGGTCCCAACGGTGTGGCATCCTATGAGCTGCAGGCTGGGCCTGAGGCCCAGGAGCTATTTGG
GCTGCAGGTGGCAGAGGACCAGGAGGAGAAGCAACCACAGCTCATTGTGATGGGCAACCTGGACCGTGAG
CGCTGGGACTCCTATGACCTCACCATCAAGGTGCAGGATGGCGGCAGCCCCCCACGCGCCAGCAGTGCCC
TGCTGCGTGTCACCGTGCTTGACACCAATGACAACGCCCCCAAGTTTGAGCGGCCCTCCTATGAGGCCGA
ACTATCTGAGAATAGCCCCATAGGCCACTCGGTCATCCAGGTGAAGGCCAATGACTCAGACCAAGGTGCC
AATGCAGAAATCGAATACACATTCCACCAGGCGCCCGAAGTTGTGAGGCGTCTTCTTCGACTGGACAGGA
ACACTGGACTTATCACTGTTCAGGGCCCGGTGGACCGTGAGGACCTAAGCACCCTGCGCTTCTCAGTGCT
TGCTAAGGACCGAGGCACCAACCCCAAGAGTGCCCGTGCCCAGGTGGTTGTGACCGTGAAGGACATGAAT
GACAATGCCCCCACCATTGAGATCCGGGGCATAGGGCTAGTGACTCATCAAGATGGGATGGCTAACATCT
CAGAGGATGTGGCAGAGGAGACAGCTGTGGCCCTGGTGCAGGTGTCTGACCGAGATGAGGGAGAGAATGC
AGCTGTCACCTGTGTGGTGGCAGGTGATGTGCCCTTCCAGCTGCGCCAGGCCAGTGAGACAGGCAGTGAC
AGCAAGAAGAAGTATTTCCTGCAGACTACCACCCCGCTAGACTACGAGAAGGTCAAAGACTACACCATTG
AGATTGTGGCTGTGGACTCTGGCAACCCCCCACTCTCCAGCACTAACTCCCTCAAGGTGCAGGTGGTGGA
CGTCAATGACAACGCACCTGTCTTCACTCAGAGTGTCACTGAGGTCGCCTTCCCGGAAAACAACAAGCCT
GGTGAAGTGATTGCTGAGATCACTGCCAGTGATGCTGACTCTGGCTCTAATGCTGAGCTGGTTTACTCTC
TGGAGCCTGAGCCGGCTGCTAAGGGCCTCTTCACCATCTCACCCGAGACTGGAGAGATCCAGGTGAAGAC
ATCTCTGGATCGGGAACAGCGGGAGAGCTATGAGTTGAAGGTGGTGGCAGCTGACCGGGGCAGTCCTAGC
CTCCAGGGCACAGCCACTGTCCTTGTCAATGTGCTGGACTGCAATGACAATGACCCCAAATTTATGCTGA
GTGGCTACAACTTCTCAGTGATGGAGAACATGCCAGCACTGAGTCCAGTGGGCATGGTGACTGTCATTGA
TGGAGACAAGGGGGAGAATGCCCAGGTGCAGCTCTCAGTGGAGCAGGACAACGGTGACTTTGTTATCCAG
AATGGCACAGGCACCATCCTATCCAGCCTGAGCTTTGATCGAGAGCAACAAAGCACCTACACCTTCCAGC
TGAAGGCAGTGGATGGTGGCGTCCCACCTCGCTCAGCTTACGTTGGTGTCACCATCAATGTGCTGGACGA
GAATGACAACGCACCCTATATCACTGCCCCTTCTAACACCTCTCACAAGCTGCTGACCCCCCAGACACGT

APPENDIX-continued

NUCLEIC ACID AND AMINO ACID SEQUENCES OF BIOMARKERS

| Gener Name | Gene ID | Accession NO. | Name |
|---|---|---|---|

CTTGGTGAGACGGTCAGCCAGGTGGCAGCCGAGGACTTTGACTCTGGTGTCAATGCTGAGCTGATCTACA
GCATTGCAGGTGGCAACCCTTATGGACTCTTCCAGATTGGGTCACATTCAGGTGCCATCACCCTGGAGAA
GGAGATTGAGCGGCGCCACCATGGGCTACACCGCCTGGTGGTGAAGGTCAGTGACCGCGGCAAGCCCCCA
CGCTATGGCACAGCCTTGGTCCATCTTTATGTCAATGAGACTCTGGCCAACCGCACGCTGCTGGAGACCC
TCCTGGGCCACAGCCTGGACACGCCGCTGGATATTGACATTGCTGGGGATCCAGAATATGAGCGCTCCAA
GCAGCGTGGCAACATTCTCTTTGGTGTGGTGGCTGGTGTGGTGGCCGTGGCCTTGCTCATCGCCCTGGCG
GTTCTTGTGCGCTACTGCAGACAGCGGGAGGCCAAAAGTGGTTACCAGGCTGGTAAGAAGGAGACCAAGG
ACCTGTATGCCCCCAAGCCCAGTGGCAAGGCCTCCAAGGGAAACAAAAGCAAAGGCAAGAAGAGCAAGTC
CCCAAAGCCCGTGAAGCCAGTGGAGGACGAGGATGAGGCCGGGCTGCAGAAGTCCCTCAAGTTCAACCTG
ATGAGCGATGCCCCTGGGGACAGTCCCCGCATCCACCTGCCCCTCAACTACCCACCAGGCAGCCCTGACC
TGGGCCGCCACTATCGCTCTAACTCCCCACTGCCTTCCATCCAGCTGCAGCCCCAGTCACCCTCAGCCTC
CAAGAAGCACCAGGTGGTACAGGACCTGCCACCTGCAAACACATTCGTGGGCACCGGGGACACCACGTCC
ACGGGCTCTGAGCAGTACTCCGACTACAGCTACCGCACCAACCCCCCCAAATACCCCAGCAAGCAGGTAG
GCCAGCCCTTTCAGCTCAGCACACCCCAGCCCCTACCCCACCCCTACCACGGAGCCATCTGGACCGAGGT
GTGGGAGTGATGGAGCAGGTTTACTGTGCCTGCCCGTGTTGGGGGCCAGCCTGAGCCAGCAGTGGGAGGT
GGGGCCTTAGTGCCTCACCGGGCACACGGATTAGGCTGAGTGAAGATTAAGGGAGGGTGTGCTCTGTGGT
CTCCTCCCTGCCCTCTCCCCACTGGGGAGAGACCTGTGATTTGCCAAGTCCCTGGACCCTGGACCAGCTA
CTGGGCCTTATGGGTTGGGGGTGGTAGGCAGGTGAGCGTAAGTGGGGAGGGAAATGGGTAAGAAGTCTAC
TCCAAACCTAGGTCTCTATGTCAGACCAGACCTAGGTGCTTCTCTAGGAGGGAAACAGGGAGACCTGGGG
TCCTGTGGATAACTGAGTGGGGAGTCTGCCAGGGGAGGGCACCTTCCCATTGTGCCTTCTGTGTGTATTG
TGCATTAACCTCTTCCTCACCACTAGGCTTCTGGGGCTGGGTCCCACATGCCCTTGACCCTGACAATAAA
GTTCTCTATTTTTGGAAAAAAAAAAAAAAAAAAAAAAAAAAAAAAAAAAAAAAAAAAAAAAAAAAAAAA
A (SEQ ID NO: 55)

Translated protein sequence

MDSGAGGRRCPEAALLILGPPRMEHLRHSPGPGGQRLLLPSMLL
ALLLLLAPSPGHATRVVYKVPEEQPPNTLIGSLAADYGFPDVGHLYKLEVGAPYLRVD
GKTGDIFTTETSIDREGLRECQNQLPGDPCILEFEVSITDLVQNGSPRLLEGQIEVQD
INDNTPNFASPVITLAIPENTNIGSLFPIPLASDRDAGPNGVASYELQAGPEAQELFG
LQVAEDQEEKQPQLIVMGNLDRERWDSYDLTIKVQDGGSPPRASSALLRVTVLDTNDN
APKFERPSYEAELSENSPIGHSVIQVKANDSDQGANAEIEYTFHQAPEVVRRLLRLDR
NTGLITVQGPVDREDLSTLRFSVLAKDRGTNPKSARAQVVVTVKDMNDNAPTIEIRGI
GLVTHQDGMANISEDVAEETAVALVQVSDRDEGENAAVTCVVAGDVPFQLRQASETGS
DSKKKYFLQTTTPLDYEKVKDYTIEIVAVDSGNPPLSSTNSLKVQVVDVNDNAPVFTQ
SVTEVAFPENNKPGEVIAEITASDADSGSNAELVYSLEPEPAAKGLFTISPETGEIQV
KTSLDREQRESYELKVVAADRGSPSLQGTATVLVNVLDCNDNDPKFMLSGYNFSVMEN
MPALSPVGMVTVIDGDKGENAQVQLSVEQDNGDFVIQNGTGTILSSLSFDREQQSTYT
FQLKAVDGGVPPRSAYVGVTINVLDENDNAPYITAPSNTSHKLLTPQTRLGETVSQVA
AEDFDSGVNAELIYSIAGGNPYGLFQIGSHSGAITLEKEIERRHHGLHRLVVKVSDRG
KPPRYGTALVHLYVNETLANRTLLETLLGHSLDTPLDIDIAGDPEYERSKQRGNILFG
VVAGVVAVALLIALAVLVRYCRQREAKSGYQAGKKETKDLYAPKPSGKASKGNKSKGK
KSKSPKPVKPVEDEDEAGLQKSLKFNLMSDAPGDSPRIHLPLNYPPGSPDLGRHYRSN
SPLPSIQLQPQSPSASKKHQVVQDLPPANTFVGTGDTTSTGSEQYSDYSYRTNPPKYP
SKQVGQPFQLSTPQPLPHPYHGAIWTEVWE (SEQ ID NO: 56)

| Gener Name | Gene ID | Accession NO. | Name |
|---|---|---|---|
| PDGFB | 5155 | NM_002608 | *Homo sapiens* platelet-derived growth factor beta polypeptide (simian sarcoma viral (v-sis) oncogene homolog) (PDGFB), transcript variant 1, mRNA |

mRNA Sequence

CCTGCCTGCCTCCCTGCGCACCCGCAGCCTCCCCCGCTGCCTCCCTAGGGCTCCCCTCCGGCCGCCAGCG
CCCATTTTTCATTCCCTAGATAGAGATACTTTGCGCGCACACACATACATACGCGCGCAAAAAGGAAAAA
AAAAAAAAAAAGCCCACCCTCCAGCCTCGCTGCAAAGAGAAAACCGGAGCAGCCGCAGCTCGCAGCTCGC
AGCTCGCAGCCCGCAGCCCGCAGAGGACGCCCAGAGCGGCGAGCGGGCGGGCAGACGGACCGACGGACTC
GCGCCGCGTCCACCTGTCGGCCGGGCCCAGCCGAGCGCGCAGCGGGCACGCCGCGCGCGCGGAGCAGCCG
TGCCCGCCGCCCGGGCCCCGCGCCAGGGCGCACACGCTCCCGCCCCCCTACCCGGCCCGGGCGGGAGTTT
GCACCTCTCCCTGCCCGGGTGCTCGAGCTGCCGTTGCAAAGCCAACTTTGGAAAAAGTTTTTTGGGGGAG
ACTTGGGCCTTGAGGTGCCCAGCTCCGCGCTTTCCGATTTTGGGGGCCTTTCCAGAAAATGTTGCAAAAA
AGCTAAGCCGGCGGGCAGAGGAAAACGCCTGTAGCCGGCGAGTGAAGACGAACCATCGACTGCCGTGTTC
CTTTTCCTCTTGGAGGTTGGAGTCCCCTGGGCGCCCCCACACGGCTAGACGCCTCGGCTGGTTCGCGACG
CAGCCCCCCGGCCGTGGATGCTCACTCGGGCTCGGGATCCGCCCAGGTAGCGGCCTCGGACCCAGGTCCT
GCGCCCAGGTCCTCCCCTGCCCCCCAGCGACGGAGCCGGGGCCGGGGGCGGCGGCGCCCGGGGGCCATGC
GGGTGAGCCGCGGCTGCAGAGGCCTGAGCGCCTGATCGCCGCGGACCCGAGCCGAGCCCACCCCCCTCCC
CAGCCCCCCACCCTGGCCGCGGGGGCGGCGCGCTCGATCTACGCGTCCGGGGCCCCGCGGGGCCGGGCCC
GGAGTCGGCATGAATCGCTGCTGGGCGCTCTTCCTGTCTCTCTGCTGCTACCTGCGTCTGGTCAGCGCCG
AGGGGGACCCCATTCCCGAGGAGCTTTATGAGATGCTGAGTGACCACTCGATCCGCTCCTTTGATGATCT
CCAACGCCTGCTGCACGGAGACCCCGGAGAGGAAGATGGGGCCGAGTTGGACCTGAACATGACCCGCTCC
CACTCTGGAGGCGAGCTGGAGAGCTTGGCTCGTGGAAGAAGGAGCCTGGGTTCCCTGACCATTGCTGAGC
CGGCCATGATCGCCGAGTGCAAGACGCGCACCGAGGTGTTCGAGATCTCCCGGCGCCTCATAGACCGCAC
CAACGCCAACTTCCTGGTGTGGCCGCCCTGTGTGGAGGTGCAGCGCTGCTCCGGCTGCTGCAACAACCGC
AACGTGCAGTGCCGCCCCACCCAGGTGCAGCTGCGACCTGTCCAGGTGAGAAAGATCGAGATTGTGCGGA
AGAAGCCAATCTTTAAGAAGGCCACGGTGACGCTGGAAGACCACCTGGCATGCAAGTGTGAGACAGTGGC

APPENDIX-continued

NUCLEIC ACID AND AMINO ACID SEQUENCES OF BIOMARKERS

| Gener Name | Gene ID | Accession NO. | Name |
|---|---|---|---|

AGCTGCACGGCCTGTGACCCGAAGCCCGGGGGGTTCCCAGGAGCAGCGAGCCAAAACGCCCCAAACTCGG
GTGACCATTCGGACGGTGCGAGTCCGCCGGCCCCCCAAGGGCAAGCACCGGAAATTCAAGCACACGCATG
ACAAGACGGCACTGAAGGAGACCCTTGGAGCCTAGGGGCATCGGCAGGAGAGTGTGTGGGCAGGGTTATT
TAATATGGTATTTGCTGTATTGCCCCCATGGGGTCCTTGGAGTGATAATATTGTTTCCCTCGTCCGTCTG
TCTCGATGCCTGATTCGGACGGCCAATGGTGCTTCCCCCACCCCTCCACGTGTCCGTCCACCCTTCCATC
AGCGGGTCTCCTCCCAGCGGCCTCCGGCGTCTTGCCCAGCAGCTCAAGAAGAAAAAGAAGGACTGAACTC
CATCGCCATCTTCTTCCCTTAACTCCAAGAACTTGGGATAAGAGTGTGAGAGAGACTGATGGGGTCGCTC
TTTGGGGGAAACGGGCTCCTTCCCCTGCACCTGGCCTGGGCCACACCTGAGCGCTGTGGACTGTCCTGAG
GAGCCCTGAGGACCTCTCAGCATAGCCTGCCTGATCCCTGAACCCCTGGCCAGCTCTGAGGGGAGGCACC
TCCAGGCAGGCCAGGCTGCCTCGGACTCCATGGCTAAGACCACAGACGGGCACACAGACTGGAGAAAACC
CCTCCCACGGTGCCCAAACACCAGTCACCTCGTCTCCCTGGTGCCTCTGTGCACAGTGGCTTCTTTTCGT
TTTCGTTTTGAAGACGTGGACTCCTCTTGGTGGGTGTGGCCAGCACACCAAGTGGCTGGGTGCCCTCTCA
GGTGGGTTAGAGATGGAGTTTGCTGTTGAGGTGGCTGTAGATGGTGACCTGGGTATCCCCTGCCTCCTGC
CACCCCTTCCTCCCCACACTCCACTCTGATTCACCTCTTCCTCTGGTTCCTTTCATCTCTCTACCTCCAC
CCTGCATTTTCCTCTTGTCCTGGCCCTTCAGTCTGCTCCACCAAGGGGCTCTTGAACCCCTTATTAAGGC
CCCAGATGATCCCAGTCACTCCTCTCTAGGGCAGAAGACTAGAGGCCAGGGCAGCAAGGGACCTGCTCAT
CATATTCCAACCCAGCCACGACTGCCATGTAAGGTTGTGCAGGGTGTGTACTGCACAAGGACATTGTATG
CAGGGAGCACTGTTCACATCATAGATAAAGCTGATTTGTATATTTATTATGACAATTTCTGGCAGATGTA
GGTAAAGAGGAAAAGGATCCTTTTCCTAATTCACACAAAGACTCCTTGTGGACTGGCTGTGCCCCTGATG
CAGCCTGTGGCTTGGAGTGGCCAAATAGGAGGGAGACTGTGGTAGGGGCAGGGAGGCAACACTGCTGTCC
ACATGACCTCCATTTCCCAAAGTCCTCTGCTCCAGCAACTGCCCTTCCAGGTGGGTGTGGGACACCTGGG
AGAAGGTCTCCAAGGGAGGGTGCAGCCCTCTTGCCCGCACCCCTCCCTGCTTGCACACTTCCCCATCTTT
GATCCTTCTGAGCTCCACCTCTGGTGGCTCCTCCTAGGAAACCAGCTCGTGGGCTGGGAATGGGGGAGAG
AAGGGAAAAGATCCCCAAGACCCCCTGGGGTGGGATCTGAGCTCCCACCTCCCTTCCCACCTACTGCACT
TTCCCCCTTCCCGCCTTCCAAAACCTGCTTCCTTCAGTTTGTAAAGTCGGTGATTATATTTTTGGGGGCT
TTCCTTTTATTTTTTAAATGTAAAATTTATTTATATTCCGTATTTAAAGTTGTAAAAAAAAATAACCACA
AAACAAAACCAAATGAAAAAAAAAAAAAAAAAA (SEQ ID NO: 57)

Translated protein sequence

MNRCWALFLSLCCYLRLVSAEGDPIPEELYEMLSDHSIRSFDDL
QRLLHGDPGEEDGAELDLNMTRSHSGGELESLARGRRSLGSLTIAEPAMIAECKTRTE
VFEISRRLIDRTNANFLVWPPCVEVQRCSGCCNNRNVQCRPTQVQLRPVQVRKIEIVR
KKPIFKKATVTLEDHLACKCETVAAARPVTRSPGGSQEQRAKTPQTRVTIRTVRVRRP
PKGKHRKFKHTHDKTALKETLGA (SEQ ID NO: 58)

| | | | |
|---|---|---|---|
| PHOSPHO2 | 493911 | NM_001008489 | *Homo sapiens* phosphatase, orphan 2 (PHOSPHO2), mRNA |

mRNA Sequence

AACAAGGGAGGTGCTGCAGTTGGCGGTCGGGCTAGAGAAGAGAGGCGCCTGCGCTTGCGAGCTGGGCTTG
TGAGTGGGGCTGCCGAGAGGGCAGGCGTGGGGCGAGGCCAAAGGACTGAACCCGCAGGAGCGTCACGGGC
GCCGGGGCGGCTGCCGACGGCGGGACTGGGTTTTCTATCAGATGTTCCACGTAATAATGCTGGAGTTAAG
AAGTTTCCATTATTTTGCTCCAAACCAGAAGACTCTGTTCCCTGTATATAGAATAGGAGTAATATTTGAA
AACAACTGGCTGATGTTTAAAACTGAAGATTGTCATGATTGTTTATCCTAATCCCAATGCTGAAGTAAGA
TTGTCTTGGAAATACTAAGTTGGGGTAATCCAAATCTATTTCTGGAACCATGAAAATTTTGCTAGTTTTT
GACTTTGACAATACAATCATAGATGACAATAGTGACACTTGGATTGTACAATGTGCTCCCAACAAAAAGC
TTCCTATTGAACTACGTGATTCTTATCGAAAAGGATTTTGGACAGAATTTATGGGCAGAGTCTTTAAGTA
TTTGGGAGATAAGGGTGTAAGAGAACATGAAATGAAAAGAGCAGTGACATCATTGCCTTTCACTCCAGGG
ATGGTGGAACTCTTCAACTTTATAAGAAAGAATAAGGATAAATTTGACTGCATTATTATTTCAGATTCAA
ATTCGGTCTTCATAGATTGGGTTTTAGAAGCTGCCAGTTTTCATGACATATTTGATAAAGTGTTTACAAA
TCCAGCAGCTTTTAATAGCAATGGTCATCTCACTGTTGAAAATTATCATACTCATTCTTGCAATAGATGC
CCAAAGAATCTTTGCAAAAAGGTAGTTTTGATAGAATTTGTAGATAAACAGTTACAACAGGGAGTGAATT
ATACACAAATTGTTTATATTGGTGATGGTGGAAATGATGTCTGTCCAGTCACCTTTTTAAAGAATGATGA
TGTTGCCATGCCACGGAAAGGATATACCTTACAGAAAACTCTTTCCAGAATGTCTCAAAATCTTGAGCCT
ATGGAATATTCTGTTGTAGTTTGGTCCTCAGGTGTTGATATAATTTCTCATTTACAATTTCTAATAAAGG
ATTAATATGTCAGCAAAAAAAAAAAAAAA (SEQ ID NO: 59)

Translated protein sequence

MKILLVFDFDNTIIDDNSDTWIVQCAPNKKLPIELRDSYRKGFW
TEFMGRVFKYLGDKGVREHEMKRAVTSLPFTPGMVELFNFIRKNKDKFDCIIISDSNS
VFIDWVLEAASFHDIFDKVFTNPAAFNSNGHLTVENYHTHSCNRCPKNLCKKVVLIEF
VDKQLQQGVNYTQIVYIGDGGNDVCPVTFLKNDDVAMPRKGYTLQKTLSRMSQNLEPM
EYSVVVWSSGVDIISHLQFLIKD (SEQ ID NO: 60)

| | | | |
|---|---|---|---|
| PSENEN | 55851 | NM_172341 | *Homo sapiens* presenilin enhancer 2 homolog (*C. elegans*) (PSENEN), mRNA |

mRNA Sequence

CTCGCCCAAAGAAGACTACAATCTCCAGGGAAACCTGGGGCGTCTCGCGCAAACGTCCATAACTGAAAGT
AGCTAAGGCACCCCAGCCGGAGGAAGTGAGCTCTCCTGGGGCGTGGTTGTTCGTGATCCTTGCATCTGTT
ACTTAGGGTCAAGGCTTGGGTCTTGCCCCGCAGACCCTTGGGACGACCCGGCCCCAGCGCAGCTATGAAC

APPENDIX-continued

NUCLEIC ACID AND AMINO ACID SEQUENCES OF BIOMARKERS

| Gener Name | Gene ID | Accession NO. | Name |
|---|---|---|---|

CTGGAGCGAGTGTCCAATGAGGAGAAATTGAACCTGTGCCGGAAGTACTACCTGGGGGGGTTTGCTTTCC
TGCCTTTTCTCTGGTTGGTCAACATCTTCTGGTTCTTCCGAGAGGCCTTCCTTGTCCCAGCCTACACAGA
ACAGAGCCAAATCAAAGGCTATGTCTGGCGCTCAGCTGTGGGCTTCCTCTTCTGGGTGATAGTGCTCACC
TCCTGGATCACCATCTTCCAGATCTACCGGCCCCGCTGGGGTGCCCTTGGGGACTACCTCTCCTTCACCA
TACCCCTGGGCACCCCCTGACAACTTCTGCACATACTGGGGCCCTGCTTATTCTCCCAGGACAGGCTCCT
TAAAGCAGAGGAGCCTGTCCTGGGAGCCCCTTCTCAAACTCCTAAGACTTGTTTTCATGTCCCACGTTCT
CTGCTGACATCCCCCAATAAAGGACCCTAACTTTCAAAAAAAAAAAAA (SEQ ID NO: 61)

Translated protein sequence

MNLERVSNEEKLNLCRKYYLGGFAFLPFLWLVNIFWFFREAFLV
PAYTEQSQIKGYVWRSAVGFLFWVIVLTSWITIFQIYRPRWGALGDYLSFTIPLGTP (SEQ ID NO: 62)

| | | | |
|---|---|---|---|
| SATB1 | 6304 | NM_002971 | *Homo sapiens* SATB homeobox 1 (SATB1), transcript variant 1, mRNA |

mRNA Sequence

TTTCTCGCTCGCTCCCGTTCCCCGGACGCGGCGGATGAGCCGGCCCCGCTGGGGAAGGCTCCGGGCGGCG
GCGGGCGGCCGGGAGGAGGCTGCGTGCTCGGGGCTGGGGCTGCGAGCGGGGTGATTTTGTATTAAAATGA
GGAGGAGGAAGAAGAGGCACCCACAGCGGCAGCGGCGGCGGCGGCGGCAGCAGCAGCAGGAGCAGCGGCG
GAGAGGGCTGCAGCCCGGGCGGACGCGCGGAGCCGAGCGGGGCACGGCGGCGGCAGCGACAGCGGCCGGG
ATGAGTCAACTAATAATTTAATGGGGGCAGAGACGGCAGCGAGGGGTAGAGCTAGCGAGGGAGAGAGCGA
GAGAAGCAGCCCCGTCCGGGGACTCGCGCTCACACTCACGCACACACACAAACACACACACACCTCTCCC
TGTGCCACCCAGCAACACCCGGCCTCGTCACAACAACAACAGCCGCGGCCGCCCTCTATCCTGCCCGGGG
GCCCAGCCGAAAGCCAGGGCGACTCTAGAGGACGCTGCCCGCCCCCCTCTTTCATTTCGGGAAACTCCTG
ATCAGTTTTGTCGGGGTTTCTGGGTTTCTTTTCCCCCAAAGTCCTAGTGCCATTGTGGTGCTCGTTGTTT
ACCTCGGACTCTGGACGAGTGAGAGCTTGGCGACTTTTTGGGGGGAGGGGGCGGGGAGTTTGTCGCTGCC
TAGGCGGTGGAGGTGGCTGGGGGTGCCTTCTGATCTTCCTCCTCCTCCCCCTCCCCCCGAACCTCTTCTC
TCCTCACTTGCTGGGACCCCAGACGCTCACAGCCCCGCGTCAATGGGCAGGGAGAGGGTCCTTGCGGCTG
TTGTCAGCGAGGGCAGAATCAAAAGTGGCATTTTAGTGCCTTTCCGGGGCTTTTCTCGCGACCCCCTGCC
CCCCACCCTCGCTGTCCCCCGCTAGATGCCCTCGTTGGGGGTGCGAGGCTGTGGGGAAAAGTTTAAGGTT
TGTTAATATTAGTCGCGATTGTTGGCGAGGGGGGTGGGGGTGATTGGAAGGGAGGCGAGGTGGCCTTCCC
AATGCGCGTTATTCGGGGTTATTGAAGAATAATATTGCAAGTGACAGCCAGAAGTAGACTTTCTGTCCTC
ACACCGAAGAACCCGAGTGAGCAGGAGGGAGGGAGAGACGCGAAGAGACCTTTTTTCCTTTTTGGAGACC
TTGTCCGCAGTGATTTTTTTTTTTTTAAGAGAATCCTCAGTCACCACGTCGTTTCCCCAGCACCATCACA
GTGTACAGCTCATAACGGGTTTTGCTTTGTTTTTACGATTTCCCCCCAACGAATCACTTGTCAGATCAAT
TTTATCTTCTTCCTCCTCCCTGCTTCCCACTCTCCCCTCCTCCCCATCGCAAACCCTGTTCTCTGAGGTT
AGACATTTTACAAACCCCTATATGTTGGTTTTCGAATTGTGATTTTTTTTTTAAACCCCTTTCTCATGGC
TACTCTTCTAGACGTTTATTTCTGCCCTTCCCCCGCTTAGGGGGGCGGGGGTAGGGGAAAGGAAAATAAT
ACAATTTCAGGGGAAGTCGCCTTCAGGTCTGCTGCTTTTTATTTTTTTTTTTTTAATTAAAAAAAAAAA
GGACATAGAAAACATCAGTCTTGAACTTCTCTTCAAGAACCCGGGCTGCAAAGGAAATCTCCTTTGTTTT
TGTTATTTATGTGCTGTCAAGTTTTGAAGTGGTGATCTTTAGACAGTGACTGAGTATGGATCATTTGAAC
GAGGCAACTCAGGGGAAAGAACATTCAGAAATGTCTAACAATGTGAGTGATCCGAAGGGTCCACCAGCCA
AGATTGCCCGCCTGGAGCAGAACGGGAGCCCGCTAGGAAGAGGAAGGCTTGGGAGTACAGGTGCAAAAAT
GCAGGGAGTGCCTTTAAAACACTCGGGCCATCTGATGAAAACCAACCTTAGGAAAGGAACCATGCTGCCA
GTTTTCTGTGTGGTGGAACATTATGAAAACGCCATTGAATATGATTGCAAGGAGGAGCATGCAGAATTTG
TGCTGGTGAGAAAGGATATGCTTTTCAACCAGCTGATCGAAATGGCATTGCTGTCTCTAGGTTATTCACA
TAGCTCTGCTGCCCAGGCCAAAGGGCTAATCCAGGTTGGAAAGTGGAATCCAGTTCCACTGTCTTACGTG
ACAGATGCCCCTGATGCTACAGTAGCAGATATGCTTCAAGATGTGTATCATGTGGTCACATTGAAAATTC
AGTTACACAGTTGCCCCAAACTAGAAGACTTGCCTCCCGAACAATGGTCGCACACCACAGTGAGGAATGC
TCTGAAGGACTTACTGAAAGATATGAATCAGAGTTCATTGGCCAAGGAGTGCCCCCTTTCACAGAGTATG
ATTTCTTCCATTGTGAACAGTACTTACTATGCAAATGTCTCAGCAGCAAAATGTCAAGAATTTGGAAGGT
GGTACAAACATTTCAAGAAGACAAAAGATATGATGGTTGAAATGGATAGTCTTTCTGAGCTATCCCAGCA
AGGCGCCAATCATGTCAATTTTGGCCAGCAACCAGTTCCAGGGAACACAGCCGAGCAGCCTCCATCCCCT
GCGCAGCTCTCCCATGGCAGCCAGCCCTCTGTCCGGACACCTCTTCCAAACCTGCACCCTGGGCTCGTAT
CAACACCTATCAGTCCTCAATTGGTCAACCAGCAGCTGGTGATGGCTCAGCTGCTGAACCAGCAGTATGC
AGTGAATAGACTTTTAGCCCAGCAGTCCTTAAACCAACAATACTTGAACCACCCTCCCCCTGTCAGTAGA
TCTATGAATAAGCCTTTGGAGCAACAGGTTTCGACCAACACAGAGGTGTCTTCCGAAATCTACCAGTGGG
TACGCGATGAACTGAAACGAGCAGGAATCTCCCAGGCGGTATTTGCACGTGTGGCTTTTAACAGAACTCA
GGGCTTGCTTTCAGAAATCCTCCGAAAGGAAGAGGACCCCAAGACTGCATCCCAGTCTTTGCTGGTAAAC
CTTCGGGCTATGCAGAATTTCTTGCAGTTACCGGAAGCTGAAAGAGACCGAATATACCAGGACGAAAGGG
AAAGGAGCTTGAATGCTGCCTCGGCCATGGGTCCTGCCCCCCTCATCAGCACACCACCCAGCCGTCCTCC
CCAGGTGAAAACAGCTACTATTGCCACTGAAAGGAATGGGAAACCAGAGAACAATACCATGAACATTAAT
GCTTCCATTTATGATGAGATTCAGCAGGAAATGAAGCGTGCTAAAGTGTCTCAAGCACTGTTTGCAAAGG
TTGCAGCAACCAAAAGCCAGGGATGGTTGTGCGAGCTGTTACGCTGGAAAGAAGATCCTTCTCCAGAAAA
CAGAACCCTGTGGGAGAACCTCTCCATGATCCGAAGGTTCCTCAGTCTTCCTCAGCCAGAACGTGATGCC
ATTTATGAACAGGAGAGCAACGCGGTGCATCACCATGGCGACAGGCCGCCCCACATTATCCATGTTCCAG
CAGAGCAGATTCAGCAACAGCAGCAGCAACAGCAACAGCAGCAGCAGCAGCAGCAGGCACCGCCGCCTCC
ACAGCCACAGCAGCAGCCACAGACAGGCCCTCGGCTCCCCCCACGGCAACCCACGGTGGCCTCTCCAGCA
GAGTCAGATGAGGAAAACCGACAGAAGACCCGGCCACGAACAAAAATTTCAGTGGAAGCCTTGGGAATCC
TCCAGAGTTTCATACAAGACGTGGGCCTGTACCCTGACGAAGAGGCCATCCAGACTCTGTCTGCCCAGCT
CGACCTTCCCAAGTACACCATCATCAAGTTCTTTCAGAACCAGCGGTACTATCTCAAGCACCACGGCAAA
CTGAAGGACAATTCCGGTTTAGAGGTCGATGTGGCAGAATATAAAGAAGAGGAGCTGCTGAAGGATTTGG
AAGAGAGTGTCCAAGATAAAAATACTAACACCCTTTTTTCAGTGAAACTAGAAGAAGAGCTGTCAGTGGA

APPENDIX-continued

NUCLEIC ACID AND AMINO ACID SEQUENCES OF BIOMARKERS

| Gener Name | Gene ID | Accession NO. | Name |
|---|---|---|---|

AGGAAACACAGACATTAATACTGATTTGAAAGACTGAGATAAAAGTATTTGTTTCGTTCAACAGTGCCAC
TGGTATTTACTAACAAAATGAAAAGTCCACCTTGTCTTCTCTCAGAAAACCTTTGTTGTTCATTGTTTGG
CCAATGAATCTTCAAAAACTTGCACAAACAGAAAAGTTGGAAAAGGATAATACAGACTGCACTAAATGTT
TTCCTCTGTTTTACAAACTGCTTGGCAGCCCCAGGTGAAGCATCAAGGATTGTTTGGTATTAAAATTTGT
GTTCACGGGATGCACCAAAGTGTGTACCCCGTAAGCATGAAACCAGTGTTTTTTGTTTTTTTTTTAGTTC
TTATTCCGGAGCCTCAAACAAGCATTATACCTTCTGTGATTATGATTTCCTCTCCTATAATTATTTCTGT
AGCACTCCACACTGATCTTTGGAAACTTGCCCCTTATTTAAAAAAAAAAAAGAAAAAAAAGAGTTTGTTA
CTCTATTGTATGTTACAAAAGAACTATAGACTGTGGAATGCAGTTTAAAGATGACATATGCCAACAAATG
CCTTGTATTATATGGCACTGCCGTAATTCAAATTTGTTTTTATTTTGGAAATAAAAGTTCACTGTACTTT
TTTTTCATTCTCATTGTTACATGATTTTTTAAAAAAAGGAAAAGAAAATGTGAAACACAATTTAGTCCTC
ATTATTTATTTGTAGATCCTGCAGCATCATGTTGTAATTAATTTTTTGGAAGTTTCCGTTAAATGTAATA
TTGCTTCTCTTGTTACCATACTGATTCTTTTCTATTTATAAATGTATTTTGATGGGCAGTAAAACAAAGT
GTCTTAAAAGTTTTAAATAGAGAAAATGTGCTTTACACAGTTGCCTATAAAAAGTGCTCTATGTTATCCA
AGCAATTCATACTATAAGCTTCACTCTTATTGTTGTATGCAATTTTTACTATCATGCAAATAAGCTTAGG
TAAATAAAACTAATAGATCACCTTAGAAAATTATGCAATTAATGTGAAAATAATTGATGTTTGCAATGTG
TCTTCCTTTGGTTTACAATCAATTTTAAAGCTACATCTGTATAAAATTTCTGTATAAAGGTGTATTTCTT
TTTTATGAGTTTATGGCTATGAAAACAGCTATTTTGTTACAGCTGGCTGTTTTTATAAGTGTATCACAAT
TTTCTTTATGCAGAAATGTTCTGACTAGGAGTGGTTATTGACTGTAACTACACAATTAAAATTGTTTGTA
TCGTATGACATGGTAGGGTTTGTCTGCTTATGTGAAGTAACTAAAGGAGTCAAAGGATGGCCCTCTCATT
TAGGTGCATGTTAATAACTTGTTATTTCACTGATTTTAAAAAGAGCAATTGACAAGTTACTTGAAACACT
GTAAATTTAAATCACAAACACATGCTCATTTTTAAATAGGTATGAAATTTCACAATGAAAATAACCTGTT
TGGTTAACATTTTGCTTAATAAGTAGAGATAGGATGGTCAAAAGACTCTCCGACAAAAACAAATCCAGTC
TCTAGCAGTTATGTTGTTAGAATGGA (SEQ ID NO: 63)

Translated protein sequence

MDHLNEATQGKEHSEMSNNVSDPKGPPAKIARLEQNGSPLGRGR
LGSTGAKMQGVPLKHSGHLMKTNLRKGTMLPVFCVVEHYENAIEYDCKEEHAEFVLVR
KDMLFNQLIEMALLSLGYSHSSAAQAKGLIQVGKWNPVPLSYVTDAPDATVADMLQDV
YHVVTLKIQLHSCPKLEDLPPEQWSHTTVRNALKDLLKDMNQSSLAKECPLSQSMISS
IVNSTYYANVSAAKCQEFGRWYKHFKKTKDMMVEMDSLSELSQQGANHVNFGQQPVPG
NTAEQPPSPAQLSHGSQPSVRTPLPNLHPGLVSTPISPQLVNQQLVMAQLLNQQYAVN
RLLAQQSLNQQYLNHPPPVSRSMNKPLEQQVSTNTEVSSEIYQWVRDELKRAGISQAV
FARVAFNRTQGLLSEILRKEEDPKTASQSLLVNLRAMQNFLQLPEAERDRIYQDERER
SLNAASAMGPAPLISTPPSRPPQVKTATIATERNGKPENNTMNINASIYDEIQQEMKR
AKVSQALFAKVAATKSQGWLCELLRWKEDPSPENRTLWENLSMIRRFLSLPQPERDAI
YEQESNAVHHHGDRPPHIIHVPAEQIQQQQQQQQQQQQQQAPPPPQPQQQPQTGPRL
PPRQPTVASPAESDEENRQKTRPRTKISVEALGILQSFIQDVGLYPDEEAIQTLSAQL
DLPKYTIIKFFQNQRYYLKHHGKLKDNSGLEVDVAEYKEEELLKDLEESVQDKNTNTL
FSVKLEEELSVEGNTDINTDLKD (SEQ ID NO: 64)

| Gener Name | Gene ID | Accession NO. | Name |
|---|---|---|---|
| SNX11 | 29916 | NM_013323 | *Homo sapiens* sorting nexin 11 (SNX11), transcript variant 2, mRNA |

mRNA Sequence

CCGGCGTCCCAAGTGAGTGGAGGGGGGATCCCGACTCCAGTCCGGGGCCTTGGCCAGCGGAGCCGCGCTA
TTCGGAAGCGGGAATCCCACTCAGAGCCCGGGCCTGTAGGGGCGGGGCGTCCCGGGCACCCGGGATTGGG
GCGTCTCCCGTCGTGCACCGGGGCACCGGCGACTCACCCGGAAGGAGAAGCCGTGATCTGGCTATATGGT
GGGGCGCGGGCGGTGTCGCTGTGGGGAGCTGGTGCTGTTCTCAGATGTTTCCTTCCAATGGCTTTTGGT
GTAGGATGTCGGAGAACCAAGAACAGGAGGAGGTGATTACAGTGCGTGTTCAGGACCCCCGAGTGCAGAA
TGAGGGCTCCTGGAACTCTTATGTGGATTATAAGATATTCCTCCATACCAACAGCAAAGCCTTTACTGCC
AAGACTTCCTGTGTGCGGCGCCGCTACCGTGAGTTCGTGTGGCTGAGAAAGCAGCTACAGAGAAATGCTG
GTTTGGTGCCTGTTCCTGAACTTCCTGGGAAGTCAACCTTCTTCGGCACCTCAGATGAGTTCATTGAGAA
GCGACGACAAGGTCTGCAGCACTTCCTTGAAAAGGTCCTGCAGAGTGTGGTTCTCCTGTCAGACAGCCAG
TTGCACCTATTCCTGCAAAGCCAGCTCTCGGTGCCTGAGATAGAAGCCTGTGTCCAGGGCCGAAGTACCA
TGACTGTGTCTGATGCCATTCTTCGATATGCTATGTCAAACTGTGGCTGGGCCCAGGAAGAGAGGCAGAG
CTCTTCTCACCTGGCTAAAGGAGACCAGCCTAAGAGTTGCTGCTTTCTTCCAAGATCGGGTAGGAGGAGC
TCTCCCTCACCGCCTCCCAGTGAAGAAAAGGACCATTTAGAAGTGTGGGCTCCAGTTGTTGACTCTGAGG
TTCCTTCCTTGGAAAGTCCCACTCTCCCACCCCTCTCCTCACCATTATGCTGTGATTTTGGAAGACCCAA
AGAGGGAACCTCCACTCTTCAGTCTGTGAGGAGGGCTGTGGGAGGAGATCATGCTGTGCCTTTGGACCCT
GGTCAGTTAGAAACAGTTTTGGAAAAGTGAGCTCTGGGTTCTGCTCTGAGATGGTCAGAGAAGATGCGGG
CCAGGAGACTTACTCAGGTGGGACTGGGCACAGGGCAGGTATGTGGGAGGCTGGGCTGCTTAGTGTCTTC
TAGTCACCTCTGCTTGGGCTGATTGACAGAGGTCAGTCATTACAGCCCCTTATGCCTCTTCCATGGGAAC
AAATACTGTGCAGATGTTTGTAAGTTAAACATAAGACACAGGGGCTGTTGCTTTTGAACAGAACCCTATA
TTACTCTCCTGGGATCTGAGTTTCTGCAGGTCATTTGTATGTAGGACCAGGAGTATCTCCTCAGGTGACC
AGTTTTGGGGACCCGTATGTGGCAAATTCTAAGCTGCCATATTGAACATCATCCCACTGGGAGTGGTTAT
GTTGTATCCCCATCTTGGCTGGCTTCAGTTTTTGCTGTAGCCCTAGAGCACTTTGTTTGTGGGAGGCTGG
CCTCTTGCCTACCTCCTTGCATGGACAGGGGGATGAATATTTACTTTCCCACCTCCTTGCTTTTTCTTTC
ACTGATACCACTGAATGGAACTGGTGCTGTGACTCCTGCTGCTGGGGATTTATGTCCCGAGACCTTAGCC
TGGCTGAGTGGAGCCTGAGACCTGCACAACAGCTCATGGTCATGCATGAGAGAGAAGTGGCTGGCCACAG
CCAGAGGGAACAGTAACAGCCCAGGGGCCTTTATTTTGGGAAAGGCTGTCCCGGGCTGTTACTGTCTCTT
CTGGTTATAAAGCAGACATGTGGCCATCTTTTCCGCAGGGTTAGAGTGGGCTCCTTTCTTTTTGGAATCC
TTTTCTTCTCCTTTGGTAGCAGCTCCCTGCCTCCAGGGCTTCCGCCACCAGCGTCTCTGCTGTGTTGCGC
AGTGCAGTGGGGTGCAAGGGCTTTGTTTCTGCCTGCCTGAAAGAGAGGGCTCTGGGGATGGAGATGAGAA

APPENDIX-continued

NUCLEIC ACID AND AMINO ACID SEQUENCES OF BIOMARKERS

| Gener Name | Gene ID | Accession NO. | Name |
|---|---|---|---|

ACAACACGCTCTCCTTCAGACAATGAGGCATTCTGTCCTCCTGCTGCCATTCTTCATCTCCACTGAGAGC
CAGAGCTGGTAGGAGCCGAGTGCCACAGGCATTCTGCATTGCTCTACTCTTAGGTTTGTGTGTGTGATCC
TTCCCCTCCCTGTCGCCCACTCCTCCCTCCTCTGGCTATCCTACCCTGTCTGTGGGCTCTTTTACTACCA
GCCTATGCTGTGGGACTGTCATGGCATTTAGTTCAGAGTGGAGGGGCTTTGGCCTGAAATAAAATGCAAG
TATTT (SEQ ID NO: 65)

Translated protein sequence

MGFWCRMSENQEQEEVITVRVQDPRVQNEGSWNSYVDYKIFLHT
NSKAFTAKTSCVRRRYREFVWLRKQLQRNAGLVPVPELPGKSTFFGTSDEFIEKRRQG
LQHFLEKVLQSVVLLSDSQLHLFLQSQLSVPEIEACVQGRSTMTVSDAILRYAMSNCG
WAQEERQSSSHLAKGDQPKSCCFLPRSGRRSSPSPPPSEEKDHLEVWAPVVDSEVPSL
ESPTLPPLSSPLCCDFGRPKEGTSTLQSVRRAVGGDHAVPLDPGQLETVLEK (SEQ ID NO: 66)

| | | | |
|---|---|---|---|
| 5PTA1 | 6708 | NM_003126 | *Homo sapiens* spectrin, alpha, erythrocytic 1 (elliptocytosis 2) (SPTA1), mRNA |

mRNA Sequence

TATGTCTTCTAAAGATAATGTCGATTGTGTATGGCTGATGGGATTCTAGGACCAAGCAAGAGGTTTTTTT
TTTTCCCCCACATACTTAACGTTTCTATATTTCTATTTGAATTCGACTGGACAGTTCCATTTGAATTATT
TCTCTCTCTCTCTCTCTGACACATTTTATCTTGCCAGGTTCTAAACCTTTAGGAAAAATGGAGCAATT
TCCAAAGGAAACCGTTGTGGAGAGCAGTGGGCCAAAGGTTTTGGAAACAGCAGAAGAGATCCAGGAGAGG
CGTCAGGAAGTGTTGACTCGGTATCAAAGTTTCAAGGAGCGGGTCGCTGAGAGGGGTCAGAAGCTTGAGG
ATTCCTATCACTTACAAGTTTTCAAGCGAGATGCAGATGATCTGGGGAAGTGGATCATGGAGAAAGTCAA
TATCTTAACCGATAAGAGCTATGAAGACCCAACTAATATACAGGGGAAATATCAGAAGCATCAATCCCTT
GAAGCAGAGGTGCAAACAAAATCAAGACTCATGTCTGAACTGGAAAAAACAAGGGAAGAACGATTTACCA
TGGGTCATTCTGCCCACGAAGAAACGAAGGCCCATATAGAGGAGCTACGCCACCTGTGGGACCTGCTGTT
AGAGCTGACCCTGGAGAAGGGTGACCAGTTGCTGCGGGCCCTGAAGTTCCAGCAGTATGTACAGGAGTGT
GCTGACATCTTAGAGTGGATTGGAGACAAGGAGGCTATAGCGACATCAGTGGAGCTAGGTGAAGACTGGG
AGCGCACCGAAGTTCTGCATAAGAAATTTGAAGACTTCCAAGTGGAGCTGGTAGCTAAAGAAGGGAGAGT
TGTTGAAGTGAACCAATATGCCAATGAGTGTGCCGAGGAAAACCATCCTGACCTACCCTTAATTCAGTCT
AAGCAAAATGAGGTGAATGCTGCCTGGGAGCGCCTTCGTGGTTTGGCTCTCCAGAGACAGAAAGCTCTGT
CCAATGCTGCAAACTTACAACGATTCAAAAGGGATGTGACTGAAGCCATCCAGTGGATCAAGGAGAAGGA
ACCTGTACTCACCTCTGAGGACTATGGCAAAGACCTTGTTGCCTCTGAAGGACTGTTTCACAGTCACAAG
GGACTTGAGAGAAATCTTGCTGTCATGAGTGACAAGGTGAAGGAGTTATGTGCTAAAGCAGAGAAGCTGA
CACTTTCCCATCCTTCAGATGCACCTCAGATCCAGGAGATGAAAGAAGATCTGGTCTCCAGCTGGGAGCA
TATTCGTGCCCTGGCCACCAGCAGATATGAAAAACTGCAGGCTACTTATTGGTACCATCGATTTTCATCT
GACTTTGATGAACTCTCAGGCTGGATGAACGAGAAGACTGCTGCGATCAATGCTGATGAGCTGCCAACAG
ATGTGGCTGGTGGAGAAGTTCTGCTGGACAGGCATCAGCAGCATAAGCATGAGATTGACTCTTACGATGA
CCGATTTCAATCTGCTGATGAGACTGGTCAAGACCTCGTGAATGCCAATCATGAAGCCTCTGATGAAGTT
CGGGAAAAGATGGAAATACTTGACAACAACTGGACTGCCCTGCTGGAACTGTGGGACGAGCGTCATCGTC
AGTATGAGCAGTGCTTGGACTTTCATCTCTTCTACAGAGACAGTGAGCAAGTGGACAGTTGGATGAGTAG
ACAAGAGGCCTTCCTGGAAAACGAGGATCTGGGAAACTCACTGGGCAGTGCAGAAGCCCTTCTTCAGAAG
CATGAAGACTTTGAGGAAGCCTTTACTGCCCAGGAAGAGAAGATCATAACTGTAGACAAGACTGCAACCA
AATTGATTGGTGATGACCATTATGATTCAGAGAACATCAAGGCTATCCGTGACGGGCTGTTAGCCCGGCG
GGATGCCCTACGTGAAAAGGCTGCCACTAGACGTAGATTGCTGAAGGAGTCATTGCTTCTGCAAAAACTG
TATGAGGACTCAGATGACCTAAAGAACTGGATCAACAAGAAGAAAAAGTTGGCAGATGATGAAGATTACA
AGGACATACAGAACTTGAAGAGCAGGGTTCAAAAGCAGCAAGTCTTTGAAAAGGAGTTGGCAGTTAATAA
GACCCAGCTGGAAAACATACAGAAAACTGGCCAAGAGATGATTGAGGGTGGTCACTATGCCTCTGACAAT
GTGACCACTCGTCTGAGTGAAGTTGCCAGCCTCTGGGAGGAGTTGCTGGAGGCTACAAAACAGAAAGGGA
CCCAGTTGCATGAGGCCAACCAGCAGCTGCAATTTGAAAATAATGCAGAAGATTTGCAGCGCTGGCTGGA
GGATGTTGAGTGGCAAGTCACCTCTGAGGATTATGGGAAAGGCCTGGCCGAGGTACAGAATCGACTCAGG
AAACACGGCCTCCTGGAGTCGGCTGTGGCTGCTCGTCAGGATCAGGTGGATATCCTTACAGACCTGGCTG
CATATTTTGAAGAAATAGGCCATCCTGATTCTAAGGATATAAGGGCAAGGCAAGAGTCCTTGGTATGCCG
ATTTGAAGCTCTGAAAGAGCCACTGGCCACCCGAAAGAAGAAGCTCTTAGACCTTCTCCATCTGCAGCTG
ATTTGTAGAGACACAGAGGATGAGGAGGCCTGGATCCAAGAGACTGAACCCTCAGCTACTTCCACCTACC
TTGGAAAGGACCTGATTGCTTCCAAAAAGCTTCTGAATAGGCATAGAGTCATCCTGGAGAACATTGCCAG
CCATGAACCACGCATTCAAGAGATAACAGAAAGGGGAAACAAAATGGTAGAGGAAGGACACTTTGCTGCA
GAAGATGTGGCCTCTAGGGTCAAGAGTTTGAACCAGAATATGGAGTCTCTCCGTGCTCGAGCTGCTAGGC
GACAAAATGATCTTGAAGCCAATGTCCAGTTCCAGCAGTACCTGGCTGACCTGCATGAAGCAGAAACATG
GATCAGAGAGAAGGAACCTATTGTAGATAATACTAACTATGGTGCTGATGAAGAAGCAGCTGGGGCTCTT
CTAAAGAAGCATGAGGCCTTTCTATTAGATCTCAATTCATTTGGAGACAGTATGAAAGCTCTGCGGAATC
AGGCAAACGCCTGCCAGCAACAACAGGCTGCACCAGTGGAGGGAGTTGCTGGAGAACAAAGGGTCATGGC
TTTATATGACTTCCAGGCCCGCAGCCCCCGAGAAGTCACCATGAAGAAAGGTGATGTCTTAACGCTGCTC
AGTTCCATCAATAAGGACTGGTGGAAGGTGGAAGCTGCTGATCATCAGGGCATTGTCCCAGCTGTCTATG
TCAGAAGACTGGCCCACGATGAGTTCCCGATGCTCCCACAGCGGCGACGAGAAGAGCCAGGAAACATCAC
CCAGCGCCAGGAGCAGATTGAGAACCAATACCGCTCCCTCTTGGATCGGGCAGAAGAACGCAGACGTCGT
CTATTGCAACGTTATAATGAATTTTTATTGGCCTATGAGGCAGGAGACATGCTGGAATGGATTCAAGAGA
AAAAGGCAGAAAACACTGGAGTGGAACTAGATGATGTTTGGGAGCTGCAGAAAAAGTTTGATGAGTTCCA
AAAGGATTTGAATACCAATGAGCCTCGGCTAAGGGATATCAACAAGGTAGCTGATGATCTACTATTTGAA
GGACTTCTAACACCAGAAGGAGCTCAAATCCGGCAGGAATTGAATTCCCGCTGGGGTTCTTTGCAGAGGC
TTGCAGATGAACAGCGGCAGCTGCTGGGCAGTGCCCATGCTGTTGAAGTGTTTCACAGAGAAGCAGATGA
CACGAAGGAGCAGATTGAGAAGAAATGCCAGGCCCTCAGTGCTGCAGACCCTGGCTCAGATCTGTTCAGT
GTTCAGGCTCTTCAGCGACGGCATGAGGGCTTTGAAAGGGACCTCGTACCCCTGGGAGATAAGGTGACCA

APPENDIX-continued

| NUCLEIC ACID AND AMINO ACID SEQUENCES OF BIOMARKERS | | | |
|---|---|---|---|
| Gener Name | Gene ID | Accession NO. | Name |

TACTGGGGGAGACAGCAGAGCGGCTCAGTGAGTCCCATCCAGATGCCACTGAGGACCTGCAGAGACAGAA
AATGGAGCTGAATGAGGCCTGGGAAGACCTGCAGGGGCGTACAAAGGATCGTAAGGAGAGCCTAAATGAG
GCCCAGAAATTCTACCTGTTCCTCAGCAAGGCCAGGGATCTGCAGAACTGGATCAGTAGCATTGGTGGCA
TGGTATCATCACAGGAGCTGGCCGAAGACTTAACTGGCATAGAGATCTTGCTGGAGAGACATCAGGAGCA
CCGTGCTGACATGGAGGCAGAGGCTCCCACCTTCCAGGCCTTAGAGGACTTCAGTGCAGAACTTATCGAC
AGTGGGCACCATGCTAGCCCTGAAATTGAAAAAAAGCTTCAAGCTGTCAAGCTAGAGAGAGATGATTTGG
AGAAGGCTTGGGAAAAACGCAAGAAGATCCTAGACCAGTGCCTGGAGTTGCAGATGTTCCAGGGGAACTG
TGATCAAGTTGAGAGCTGGATGGTGGCACGTGAGAATTCCCTGAGGTCAGATGACAAAAGTTCCTTAGAC
AGTCTGGAGGCTTTGATGAAGAAACGGGACGATTTGGACAAAGCAATCACTGCCCAGGAAGGGAAGATCA
CTGACCTAGAACATTTTGCTGAGAGCCTCATTGCTGATGAACACTATGCCAAAGAAGAGATTGCTACGCG
GCTCCAACGTGTACTAGACAGGTGGAAGGCTCTCAAAGCACAACTGATTGATGAGCGGACAAAGCTTGGA
GACTATGCCAACCTAAAACAATTCTACCGAGACCTTGAGGAGCTGGAAGAATGGATCAGTGAGATGCTGC
CCACAGCCTGTGATGAATCCTACAAAGACGCCACTAACATTCAGAGGAAATACCTGAAACACCAGACCTT
TGCACATGAAGTCGATGGCCGATCTGAGCAGGTGCATGGCGTCATCAACCTGGGGAACTCCCTGATTGAG
TGTAGCGCTTGTGATGGCAATGAAGAGGCCATGAAGGAGCAACTGGAACAGCTGAAGGAACATTGGGATC
ATCTGCTTGAGAGAACAAATGACAAAGGGAAGAAGCTCAATGAGGCCAGTCGTCAACAGAGGTTCAACAC
AAGCATCCGGGACTTTGAGTTCTGGCTCTCAGAGGCAGAGACATTGCTGGCCATGAAAGATCAGGCCAGG
GACTTGGCTTCAGCAGGAAACCTACTCAAGAAGCATCAGCTATTGGAGAGAGAGATGTTGGCTCGAGAGG
ATGCACTCAAGGACCTGAATACATTGGCTGAAGATTTGCTCTCCAGCGGGACTTTCAACGTTGATCAGAT
TGTGAAGAAAAAAGATAATGTCAACAAGCGTTTCCTGAATGTCCAAGAATTGGCAGCTGCACACCACGAA
AAATTGAAAGAGGCCTATGCCTTGTTCCAGTTCTTCCAGGATCTAGATGATGAGGAATCCTGGATAGAGG
AGAAGTTGATACGAGTGAGCTCCCAGGACTATGGGAGAGATCTTCAGGGGGTTCAGAACTTGCTGAAGAA
GCACAAACGCCTAGAGGGGGAGCTGGTGGCCCATGAGCCTGCCATCCAGAATGTGCTGGATATGGCAGAG
AAGCTGAAAGACAAGGCTGCTGTGGGGCAAGAGGAGATCCAGTTGCGGCTGGCTCAGTTTGTTGAACACT
GGGAGAAGCTCAAAGAGTTGGCCAAGGCCCGAGGACTTAAGTTGGAAGAATCCCTAGAATACTTGCAATT
CATGCAGAATGCTGAGGAAGAGGAAGCTTGGATCAATGAAAAGAATGCTTTGGCTGTCCGAGGAGATTGT
GGAGATACATTAGCTGCTACTCAGAGCTTGCTAATGAAGCATGAAGCTTTGGAAAATGACTTTGCTGTCC
ATGAGACCCGAGTACAAAATGTGTGTGCACAAGGAGAAGACATCCTAAATAAGGTGTTGCAGGAGGAAAG
TCAGAACAAAGAGATTTCTTCCAAGATAGAGGCTCTGAATGAAAAGACCCCTTCTCTGGCTAAGGCAATA
GCTGCTTGGAAGTTGCAATTGGAAGACGATTATGCCTTTCAGGAATTCAACTGGAAGGCTGATGTGGTAG
AGGCTTGGATAGCTGATAAGGAAACAAGCCTAAAGACCAATGGCAATGGTGCAGACCTTGGTGACTTCCT
CACTCTTCTGGCAAAACAGGACACTCTGGATGCCAGTCTGCAGAGTTTCCAGCAAGAGAGACTTCCCGAG
ATCACTGACCTGAAGGACAAACTGATTTCTGCTCAACACAACCAGTCTAAAGCCATTGAAGAGCGTTATG
CCGCTCTGCTGAAGCGCTGGGAACAGTTGCTGGAAGCCTCGGCAGTCCACAGACAGAAATTGCTGGAGAA
ACAGCTGCCTCTACAGAAGGCTGAGGACCTGTTCGTGGAATTTGCACATAAGGCTTCAGCTTTGAACAAC
TGGTGTGAAAAGATGGAAGAAAACTTGTCAGAGCCTGTGCACTGTGTCTCCCTGAATGAAATTCGGCAGC
TGCAGAAAGACCATGAGGACTTCTTGGCCTCCCTGGCTAGGGCTCAAGCAGACTTTAAATGTTTGCTGGA
GCTAGACCAGCAGATTAAGGCCTTAGGTGTGCCTTCCAGCCCTTATACCTGGTTAACAGTGGAGGTGCTG
GAAAGGACCTGGAAGCACCTATCTGACATCATTGAGGAACGGGAGCAGGAGCTGCAAAAGGAAGAGGCAA
GACAGGTCAAGAACTTTGAGATGTGTCAGGAGTTTGAACAGAATGCCAGTACCTTCCTTCAATGGATCCT
GGAAACCAGGGCTTACTTTCTGGATGGATCATTGCTCAAAGAAACAGGAACTCTGGAATCTCAGCTGGAA
GCAAATAAAAGAAAACAGAAGGAGATCCAGGCGATGAAGCGTCAACTAACCAAGATTGTGGACCTGGGGG
ACAACTTGGAAGACGCTCTGATCCTTGATATCAAATACAGCACCATTGGATTGGCTCAGCAGTGGGACCA
GCTCTACCAGCTTGGGTTGCGGATGCAACACAACCTGGAGCAACAGATCCAGGCCAAGGACATCAAAGGT
GTGAGTGAAGAGACTCTAAAGGAATTTAGCACAATCTATAAACACTTTGATGAGAATTTGACAGGGCGCC
TGACTCACAAAGAGTTCCGGTCCTGCCTGAGAGGACTCAATTACTACTTGCCCATGGTGGAGGAGGATGA
ACATGAGCCCAAGTTTGAGAAGTTCCTGGATGCTGTGGATCCAGGGAGGAAGGGCTATGTCTCACTGGAG
GACTATACTGCTTTCCTGATTGACAAGGAGTCAGAAAACATCAAGTCCAGTGATGAAATAGAGAATGCCT
TCCAAGCCCTGGCAGAGGGCAAGTCATATATTACCAAAGAAGACATGAAGCAGGCCCTTACCCCAGAGCA
AGTGTCATTCTGTGCCACACATATGCAGCAATATATGGACCCACGGGGTCGAAGCCATCTCTCTGGCTAT
GACTACGTTGGCTTCACCAATTCCTACTTTGGCAACTAATAAGCAGCTCCTCGTGGATCGTAGAAAATCT
TAGTGTCGTGGGAAATTTACTGGGGGGCAAAGAGTACAGGCAAATGTGGAAGATAAAGATGGCCTCGTGT
GTGTGTGTGTGTGTGTGTGTGTGTGTGTGTGCTTGTGTTTGTGTGCATATTACATTTATTGTAGGATCTT
AAAAAATCTCAAGGGTGGGAGATAGAAAGGTTAATAGAGTTGGAGGAGTGGAAGCTATTTTGTATGCAAC
TAGTCACTGCTGAGGGGTGTCAAAGTTTCTATTTTTATTTGTTCTGTTTTGCACGTCTTTATCATTTTGC
TTTATTCCGATTATAGAATAAAGTAATTCTTTTTAAAAATATTTTTTGGGGCAAAGTTAAGTAAAATGTT
GAGCTTCTATATTTCTGGGAACTGTACTCATATAAGAGTGGGCAGCTAATTTTACTGTAAAGAAGGGCCA
TGGTATAGTAGATAAATAAAATCCAAGGCAATTTTCAAACAATTTTTTTAAACTTTGGAATGTGTTTAAA
TTTAAATTTGAAAATAAAGATATTTGATTTTCTGGGG (SEQ ID NO: 67)

Translated protein sequence

MEQFPKETVVESSGPKVLETAEEIQERRQEVLTRYQSFKERVAE
RGQKLEDSYHLQVFKRDADDLGKWIMEKVNILTDKSYEDPTNIQGKYQKHQSLEAEVQ
TKSRLMSELEKTREERFTMGHSAHEETKAHIEELRHLWDLLLELTLEKGDQLLRALKF
QQYVQECADILEWIGDKEAIATSVELGEDWERTEVLHKKFEDFQVELVAKEGRVVEVN
QYANECAEENHPDLPLIQSKQNEVNAAWERLRGLALQRQKALSNAANLQRFKRDVTEA
IQWIKEKEPVLTSEDYGKDLVASEGLFHSHKGLERNLAVMSDKVKELCAKAEKLTLSH
PSDAPQIQEMKEDLVSSWEHIRALATSRYEKLQATYWYHRFSSDFDELSGWMNEKTAA
INADELPTDVAGGEVLLDRHQQHKHEIDSYDDRFQSADETGQDLVNANHEASDEVREK
MEILDNNWTALLELWDERHRQYEQCLDFHLFYRDSEQVDSWMSRQEAFLENEDLGNSL
GSAEALLQKHEDFEEAFTAQEEKIITVDKTATKLIGDDHYDSENIKAIRDGLLARRDA
LREKAATRRRLLKESLLLQKLYEDSDDLKNWINKKKKLADDEDYKDIQNLKSRVQKQQ
VFEKELAVNKTQLENIQKTGQEMIEGGHYASDNVTTRLSEVASLWEELLEATKQKGTQ
LHEANQQLQFENNAEDLQRWLEDVEWQVTSEDYGKGLAEVQNRLRKHGLLESAVAARQ

APPENDIX-continued

NUCLEIC ACID AND AMINO ACID SEQUENCES OF BIOMARKERS

| Gener Name | Gene ID | Accession NO. | Name |
|---|---|---|---|

DQVDILTDLAAYFEEIGHPDSKDIRARQESLVCRFEALKEPLATRKKKLLDLLHLQLI
CRDTEDEEAWIQETEPSATSTYLGKDLIASKKLLNRHRVILENIASHEPRIQEITERG
NKMVEEGHFAAEDVASRVKSLNQNMESLRARAARRQNDLEANVQFQQYLADLHEAETW
IREKEPIVDNTNYGADEEAAGALLKKHEAFLLDLNSFGDSMKALRNQANACQQQQAAP
VEGVAGEQRVMALYDFQARSPREVTMKKGDVLTLLSSINKDWWKVEAADHQGIVPAVY
VRRLAHDEFPMLPQRRREEPGNITQRQEQIENQYRSLLDRAEERRRRLLQRYNEFLLA
YEAGDMLEWIQEKKAENTGVELDDVWELQKKFDEFQKDLNTNEPRLRDINKVADDLLF
EGLLTPEGAQIRQELNSRWGSLQRLADEQRQLLGSAHAVEVFHREADDTKEQIEKKCQ
ALSAADPGSDLFSVQALQRRHEGFERDLVPLGDKVTILGETAERLSESHPDATEDLQR
QKMELNEAWEDLQGRTKDRKESLNEAQKFYLFLSKARDLQNWISSIGGMVSSQELAED
LTGIEILLERHQEHRADMEAEAPTFQALEDFSAELIDSGHHASPEIEKKLQAVKLERD
DLEKAWEKRKKILDQCLELQMFQGNCDQVESWMVARENSLRSDDKSSLDSLEALMKKR
DDLDKAITAQEGKITDLEHFAESLIADEHYAKEEIATRLQRVLDRWKALKAQLIDERT
KLGDYANLKQFYRDLEELEEWISEMLPTACDESYKDATNIQRKYLKHQTFAHEVDGRS
EQVHGVINLGNSLIECSACDGNEEAMKEQLEQLKEHWDHLLERTNDKGKKLNEASRQQ
RFNTSIRDFEFWLSEAETLLAMKDQARDLASAGNLLKKHQLLEREMLAREDALKDLNT
LAEDLLSSGTFNVDQIVKKKDNVNKRFLNVQELAAAHHEKLKEAYALFQFFQDLDDEE
SWIEEKLIRVSSQDYGRDLQGVQNLLKKHKRLEGELVAHEPAIQNVLDMAEKLKDKAA
VGQEEIQLRLAQFVEHWEKLKELAKARGLKLEESLEYLQFMQNAEEEEAWINEKNALA
VRGDCGDTLAATQSLLMKHEALENDFAVHETRVQNVCAQGEDILNKVLQEESQNKEIS
SKIEALNEKTPSLAKAIAAWKLQLEDDYAFQEFNWKADVVEAWIADKETSLKTNGNGA
DLGDFLTLLAKQDTLDASLQSFQQERLPEITDLKDKLISAQHNQSKAIEERYAALLKR
WEQLLEASAVHRQKLLEKQLPLQKAEDLFVEFAHKASALNNWCEKMEENLSEPVHCVS
LNEIRQLQKDHEDFLASLARAQADFKCLLELDQQIKALGVPSSPYTWLTVEVLERTWK
HLSDIIEEREQELQKEEARQVKNFEMCQEFEQNASTFLQWILETRAYFLDGSLLKETG
TLESQLEANKRKQKEIQAMKRQLTKIVDLGDNLEDALILDIKYSTIGLAQQWDQLYQL
GLRMQHNLEQQIQAKDIKGVSEETLKEFSTIYKHFDENLTGRLTHKEFRSCLRGLNYY
LPMVEEDEHEPKFEKFLDAVDPGRKGYVSLEDYTAFLIDKESENIKSSDEIENAFQAL
AEGKSYITKEDMKQALTPEQVSFCATHMQQYMDPRGRSHLSGYDYVGFTNSYFGN (SEQ ID NO: 68)

| TMEM79 | 84283 | NM_0323230 | *Homo sapiens*, transmembrane protein 79 (TMEM79), transcript variant 1, mRNA |
|---|---|---|---|

mRNA Sequence

AGGTTTTGAGACACAGGTAAAGGGAGGGAGACAGAGAGAAATACTTGCAGAGCCAGCAGGTAGCTGGGCA
GCTCCTTCCCGGACGGACGGATGGACAGACGCTGGGGACCCTCCACTCCATATGGAAAGATGACATGACC
TTGTGGTAGATCCCAGAACTGAGGCCCCAGGATGACAGAACAGGAGACCCTGGCCCTACTGGAAGTGAAG
AGGTCTGATTCCCCAGAGAAGAGCTCACCCCAGGCCTTGGTTCCCAATGGCCGGCAGCCAGAAGGGGAAG
GTGGGGCCGAATCCCCGGGAGCTGAGTCCCTCAGAGTGGGGTCTTCAGCTGGATCTCCCACAGCCATAGA
GGGGGCTGAGGATGGTCTAGACAGCACAGTAAGTGAGGCTGCCACCTTGCCCTGGGGGACTGGCCCTCAG
CCCAGTGCTCCGTTCCCGGATCCCCCTGGCTGGCGGGACATTGAACCAGAGCCCCCTGAGTCAGAACCAC
TTACCAAGCTAGAGGAGCTGCCCGAAGACGATGCCAACCTGCTGCCTGAGAAAGCGGCCCGTGCCTTCGT
GCCTATTGACCTACAGTGCATTGAGCGGCAGCCCCAAGAAGACCTTATCGTGCGCTGTGAGGCAGGCGAG
GGCGAGTGCCGAACCTTCATGCCCCCCCGGGTCACCCACCCCGACCCCACTGAGCGCAAGTGGGCTGAGG
CAGTGGTGAGGCCGCCTGGCTGTTCCTGTGGGGGCTGCGGGAGCTGTGGAGACCGTGAGTGGCTAAGGGC
TGTGGCCTCCGTGGGAGCCGCACTCATTCTCTTCCCTTGCCTACTATACGGGGCATATGCCTTCCTGCCG
TTTGATGTCCCACGGCTGCCCACCATGAGTTCCCGCCTGATCTACACACTGCGCTGCGGGGTCTTTGCCA
CCTTCCCCATTGTGCTGGGGATCCTGGTGTACGGGCTGAGCCTGTTATGCTTTTCTGCCCTTCGGCCCTT
TGGGGAGCCACGGCGGGAGGTGGAGATCCACCGGCGATATGTGGCCCAGTCGGTCCAGCTCTTTATTCTC
TACTTCTTCAACCTGGCCGTGCTTTCCACTTACCTGCCCCAGGATACCCTCAAACTGCTCCCTCTGCTCA
CTGGTCTCTTTGCCGTCTCCCGGCTGATCTACTGGCTGACCTTTGCCGTGGGCCGCTCCTTCCGAGGCTT
CGGCTACGGCCTGACGTTTCTGCCACTGCTGTCGATGCTGATGTGGAACCTCTACTACATGTTCGTGGTG
GAGCCGGAGCGCATGCTCACTGCCACCGAGAGCCGCCTGGACTACCCGGACCACGCCCGCTCGGCCTCCG
ACTACAGGCCCCGCCCCTGGGGCTGAGCCTCTCCGCCCTCGCCCTCGGAGTAGGGGGTAGCGGCTTGGGT
CTGACACATCTTTGAACCTTGTGGCCAGGCCTGGACTTCGCCCCCAGGCCTAGGACCGCGGTGGGTGGAA
CCCTGCTACTGCCCCAACAGGGACTCCAATCAATCGGAGTTCTCCCCTTGCCGGAGCTGCCCTTCACCTT
TGGGGCCCGAGACAGTCATAAGGGATGGACTTAGTTTTCTTGCAGGGAAAAAGGTGGACAGCCGTGTTTC
TTAAGGATGCTGAGGGCATGGGGCCAGGACCAGGGGAGAGGCACAGCTCCTTCCTGAGCAGCCTCTCACC
ACTGCCACAAGGCTCCCTAATGCTGGTCTCTGCTCCACTCCCCGGCTTCCCGTGAGGCAGGAGGCAGAGC
CACAGCCAAGGCCCTGACCACTTCTGTGCCAGTTGTCTAAGCAGAGCGCCTCAGGGACGCTGGAAATGCC
TTAAGGATAGAGGCTGGGCATCACATCAAATGGGACTGTGGTGTTTGGTGAAAACCTTCCTGAGGATCTG
GATTCAGGACCCTCCATGACTGGCCTATTTACTGTTTACAGCTGGCCAGTGCAGAGCTGCTGCTCTTTTA
CCTTTTTAGGCCCCTGTAACTTCCCACCTTTAAACTGCCCAGAAGGCATGCCTCTCCCACAGGAAGAGGG
GAGCAGACAGGGAAATCTGCCTACCAAGAGGGGTGTGTGTGTCTTTGTGCCCACACGTGGTGGCTGGGGA
GTGCCTGGATGGTGCGGTGGTTGATGTTAACCTAGTGTGTGTGTGTGTGTGTGTGTGTGTGTGTGTGTGT
GTGTGTGTGTAACAATAAATTACTACCAGTCAAAAAAAAAAAAAA (SEQ ID NO: 69)

Translated protein sequence

MTEQETLALLEVKRSDSPEKSSPQALVPNGRQPEGEGGAESPGA
ESLRVGSSAGSPTAIEGAEDGLDSTVSEAATLPWGTGPQPSAPFPDPPGWRDIEPEPP
ESEPLTKLEELPEDDANLLPEKAARAFVPIDLQCIERQPQEDLIVRCEAGEGECRTFM
PPRVTHPDPTERKWAEAVVRPPGCSCGGCGSCGDREWLRAVASVGAALILFPCLLYGA
YAFLPFDVPRLPTMSSRLIYTLRCGVFATFPIVLGILVYGLSLLCFSALRPFGEPRRE

APPENDIX-continued

NUCLEIC ACID AND AMINO ACID SEQUENCES OF BIOMARKERS

| Gener Name | Gene ID | Accession NO. | Name |
|---|---|---|---|

VEIHRRYVAQSVQLFILYFFNLAVLSTYLPQDTLKLLPLLTGLFAVSRLIYWLTFAVG
RSFRGFGYGLTFLPLLSMLMWNLYYMFVVEPERMLTATESRLDYPDHARSASDYRPRP
WG (SEQ ID NO: 70)

| Gener Name | Gene ID | Accession NO. | Name |
|---|---|---|---|
| TMIGD2 | 126259 | NM_144615 | *Homo sapiens* transmembrane and immunoglobulin domain containing 2 (TMIGD2), mRNA |

mRNA Sequence

GGAAGTCTGTCAACTGGGAGGGGGAGAGGGGGGTGATGGGCCAGGAATGGGGTCCCCGGGCATGGTGCTG
GGCCTCCTGGTGCAGATCTGGGCCCTGCAAGAAGCCTCAAGCCTGAGCGTGCAGCAGGGGCCCAACTTGC
TGCAGGTGAGGCAGGGCAGTCAGGCGACCCTGGTCTGCCAGGTGGACCAGGCCACAGCCTGGGAACGGCT
CCGTGTTAAGTGGACAAAGGATGGGGCCATCCTGTGTCAACCGTACATCACCAACGGCAGCCTCAGCCTG
GGGGTCTGCGGGCCCCAGGGACGGCTCTCCTGGCAGGCACCCAGCCATCTCACCCTGCAGCTGGACCCTG
TGAGCCTCAACCACAGCGGGGCGTACGTGTGCTGGGCGGCCGTAGAGATTCCTGAGTTGGAGGAGGCTGA
GGGCAACATAACAAGGCTCTTTGTGGACCCAGATGACCCCACACAGAACAGAAACCGGATCGCAAGCTTC
CCAGGATTCCTCTTCGTGCTGCTGGGGGTGGGAAGCATGGGTGTGGCTGCGATCGTGTGGGGTGCCTGGT
TCTGGGGCCGCCGCAGCTGCCAGCAAAGGGACTCAGGTAACAGCCCAGGAAATGCATTCTACAGCAACGT
CCTATACCGGCCCCGGGGGGCCCCAAAGAAGAGTGAGGACTGCTCTGGAGAGGGGAAGGACCAGAGGGGC
CAGAGCATTTATTCAACCTCCTTCCCGCAACCGGCCCCCCGCCAGCCGCACCTGGCGTCAAGACCCTGCC
CCAGCCCGAGACCCTGCCCCAGCCCCAGGCCCGGCCACCCCGTCTCTATGGTCAGGGTCTCTCCTAGACC
AAGCCCCACCCAGCAGCCGAGGCCAAAAGGGTTCCCCAAAGTGGGAGAGGAGTGAGAGATCCCAGGAGAC
CTCAACAGGACCCCACCCATAGGTACACACAAAAAAGGGGGGATCGAGGCCAGACACGGTGGCTCACGCC
TGTAATCCCAGCAGTTTGGGAAGCCGAGGCGGGTGGAACACTTGAGGTCAGGGGTTTGAGACCAGCCTGG
CTTGAACCTGGGAGGCGGAGGTTGCAGTGAGCCGAGATTGCGCCACTGCACTCCAGCCTGGGCGACAGAG
TGAGACTCCGTCTCAAAAAAAACAAAAAGCAGGAGGATTGGGAGCCTGTCAGCCCCATCCTGAGACCCCG
TCCTCATTTCTGTAATGATGGATCTCGCTCCCACTTTCCCCAAGAACCTAATAAAGGCTTGTGAAGAAA
AAGCAAAAAAAAAAAAAAAAAA (SEQ ID NO: 71)

Translated protein sequence

MGSPGMVLGLLVQIWALQEASSLSVQQGPNLLQVRQGSQATLVC
QVDQATAWERLRVKWTKDGAILCQPYITNGSLSLGVCGPQGRLSWQAPSHLTLQLDPV
SLNHSGAYVCWAAVEIPELEEAEGNITRLFVDPDDPTQNRNRIASFPGFLFVLLGVGS
MGVAAIVWGAWFWGRRSCQQRDSGNSPGNAFYSNVLYRPRGAPKKSEDCSGEGKDQRG
QSIYSTSFPQPAPRQPHLASRPCPSPRPCPSPRPGHPVSMVRVSPRPSPTQQPRPKGF
PKVGEE (SEQ ID NO: 72)

| Gener Name | Gene ID | Accession NO. | Name |
|---|---|---|---|
| TUBB6 | 84617 | NM_032525 | *Homo sapiens* tubulin, beta 6 (TUBB6), mRNA |

mRNA Sequence

GGGCACGAGGGCAGAGCCAGTTCCTAGCGCAGAGCCGCGCCCGCCATGAGGGAGATCGTGCACATCCAGG
CGGGCCAGTGCGGGAACCAGATCGGCACCAAGTTTTGGGAAGTGATCAGCGATGAGCACGGCATCGACCC
GGCCGGAGGCTACGTGGGAGACTCGGCGCTGCAGCTGGAGAGAATCAACGTCTACTACAATGAGTCATCG
TCTCAGAAATATGTGCCCAGGGCCGCCCTGGTGGACTTAGAGCCAGGCACCATGGACAGCGTGCGGTCTG
GGCCTTTTGGGCAGCTTTTCCGGCCTGACAACTTCATCTTTGGCCAGACGGGTGCAGGGAACAACTGGGC
GAAAGGGCACTACACGGAGGGCGCGGAGCTGGTGGACGCAGTGCTGGACGTGGTGCGGAAGGAGTGCGAG
CACTGCGACTGCCTGCAGGGCTTCCAGCTCACGCACTCGCTGGGCGGCGGCACGGGCTCAGGCATGGGCA
CGCTGCTCATCAGCAAGATCCGTGAGGAGTTCCCGGACCGCATCATGAACACCTTCAGCGTCATGCCCTC
GCCCAAGGTGTCGGACACGGTGGTGGAGCCCTACAATGCCACACTGTCGGTGCACCAGCTGGTGGAGAAT
ACAGACGAGACCTACTGCATCGACAACGAGGCGCTCTATGACATCTGCTTCCGCACTCTGAAGCTGACAA
CGCCCACCTACGGGGACCTCAACCACCTGGTGTCCGCCACCATGAGTGGGGTCACCACCTCGCTGCGCTT
CCCGGGCCAGCTCAATGCTGACCTGCGCAAGCTGGCGGTGAACATGGTGCCCTTCCCGCGCCTGCACTTC
TTCATGCCTGGCTTCGCGCCGCTCACCAGCCGCGGCAGCCAGCAGTACCGGGCCCTGACCGTGCCCGAGC
TCACCCAGCAGATGTTCGACGCCAGGAACATGATGGCCGCCTGCGATCCGCGCCATGGCCGCTACCTGAC
CGTGGCCACCGTGTTCCGCGGGCCCATGTCCATGAAGGAGGTGGACGAGCAGATGCTGGCCATCCAGAGT
AAGAACAGCAGCTACTTCGTGGAGTGGATTCCCAACAACGTGAAGGTGGCCGTGTGCGACATCCCGCCCC
GCGGCCTGAAGATGGCCTCCACCTTCATCGGCAACAGCACGGCCATCCAGGAGCTGTTCAAGCGCATCTC
CGAGCAGTTCTCAGCCATGTTCCGGCGCAAGGCCTTCCTGCACTGGTTCACGGGTGAGGGCATGGATGAA
ATGGAGTTCACCGAGGCGGAGAGCAACATGAACGACCTGGTATCCGAGTACCAGCAGTACCAGGATGCCA
CCGCCAATGACGGGGAGGAAGCTTTTGAGGATGAGGAAGAGGAGATCGATGGATAGTCGGAATAGAGCCG
CCCCAACTCAGATCCTACAACACGCAAGTTCCTTCTTGAACCCTGGTGCCTCCTACCCTATGGCCCTGAA
TGGTGCACTGGTTTAATTGTGTTGGTGTCGGCCCCTCACAAATGCAGCCAAGTCATGTAATTAGTCATCT
GGAACAAAGACTAAAAACAGCAGAGAATTGCGGGTTCTACCCAGTCAGAAGATCACACCATGGAGACTTT
CTACTAGAGGACTTGAAAGAGAACTGAGGGGCCACAAAATAAACTTCACCTTCCATTAAGTGTTCAAGCA
TGTCTGCAAATTAGGAGGGAGTTAGAAACAGTCTTTTTCATCCTTTGTGATGAAGCCTGAAATTGTGCCG
TGTTGCCTTATATGAATATGCAGTATGGGACTTTGAAATAATGATTCATAATAAAATACTAAACGTGTGT
CTTCAAAAAAAAAAAAAAAAAA (SEQ ID NO: 73)

Translated protein sequence

MREIVHIQAGQCGNQIGTKFWEVISDEHGIDPAGGYVGDSALQL
ERINVYYNESSSQKYVPRAALVDLEPGTMDSVRSGPFGQLFRPDNFIFGQTGAGNNWA
KGHYTEGAELVDAVLDVVRKECEHCDCLQGFQLTHSLGGGTGSGMGTLLISKIREEFP

APPENDIX-continued

NUCLEIC ACID AND AMINO ACID SEQUENCES OF BIOMARKERS

| Gener Name | Gene ID | Accession NO. | Name |
|---|---|---|---|

DRIMNTFSVMPSPKVSDTVVEPYNATLSVHQLVENTDETYCIDNEALYDICFRTLKLT
TPTYGDLNHLVSATMSGVTTSLRFPGQLNADLRKLAVNMVPFPRLHFFMPGFAPLTSR
GSQQYRALTVPELTQQMFDARNMMAACDPRHGRYLTVATVFRGPMSMKEVDEQMLAIQ
SKNSSYFVEWIPNNVKVAVCDIPPRGLKMASTFIGNSTAIQELFKRISEQFSAMFRRK
AFLHWFTGEGMDEMEFTEAESNMNDLVSEYQQYQDATANDGEEAFEDEEEEIDG (SEQ ID NO: 74)

| Gener Name | Gene ID | Accession NO. | Name |
|---|---|---|---|
| TYROBP | 7305 | NM_198125 | *Homo sapiens* TYRO protein tyrosine kinase binding protein (TYROBP), transcript variant 2, mRNA |

mRNA Sequence

AGACTTCCTCCTTCACTTGCCTGGACGCTGCGCCACATCCCACCGGCCCTTACACTGTGGTGTCCAGCAG
CATCCGGCTTCATGGGGGACTTGAACCCTGCAGCAGGCTCCTGCTCCTGCCTCTCCTGCTGGCTGTAAG
TGGTCTCCGTCCTGTCCAGGCCCAGGCCCAGAGCGATTGCAGTTGCTCTACGGTGAGCCCGGGCGTGCTG
GCAGGGATCGTGATGGGAGACCTGGTGCTGACAGTGCTCATTGCCCTGGCCGTGTACTTCCTGGGCCGGC
TGGTCCCTCGGGGGCGAGGGGCTGCGGAGGCGACCCGGAAACAGCGTATCACTGAGACCGAGTCGCCTTA
TCAGGAGCTCCAGGGTCAGAGGTCGGATGTCTACAGCGACCTCAACACACAGAGGCCGTATTACAAATGA
GCCCGAATCATGACAGTCAGCAACATGATACCTGGATCCAGCCATTCCTGAAGCCCACCCTGCACCTCAT
TCCAACTCCTACCGCGATACAGACCCACAGAGTGCCATCCCTGAGAGACCAGACCGCTCCCCAATACTCT
CCTAAAATAAACATGAAGCACAAAAACAAAAAAAAAAAAAAAAA (SEQ ID NO: 75)

Translated protein sequence

MGGLEPCSRLLLLPLLLAVSGLRPVQAQAQSDCSCSTVSPGVLA
GIVMGDLVLTVLIALAVYFLGRLVPRGRGAAEATRKQRITETESPYQELQGQRSDVYS
DLNTQRPYYK (SEQ ID NO: 76)

| Gener Name | Gene ID | Accession NO. | Name |
|---|---|---|---|
| YTHDF1 | 54915 | NM_017798 | *Homo sapiens* YTH domain family, member 1 (YTHDF1), mRNA |

mRNA Sequence

GCGTGCACGCTGACGCCGCGCAGTCTCGTCCCCTGCCGCCGCCGTCGCCGCTGCTGTCGCCGCCGCCGCC
GCCATTGGAGTCGACGCCTCCTCAGTGCGTCCGCGTCCCGGGCTCACCGCCGCTGCCGCCTCGCCAGGGG
CCCGCGCGCCCAGCAGCCGCCGCCGCCGCCCGGCCGGCGCCCGGGGAATTGGCGGCGGGGCCCGGGGCCG
CGCGAGCTAGGGTGACAGGCCCGGCCTCTAGGGGAGGCCCGAGCCGGCGGGCGCCCCGGCCCCGCGTCTA
GTTGTTCATGAAGCATGTCGGCCACCAGCGTGGACACCCAGAGAACAAAAGGACAAGATAATAAAGTACA
AAATGGTTCGTTACATCAGAAGGATACAGTTCATGACAATGACTTTGAGCCCTACCTTACTGGACAGTCA
AATCAGAGTAACAGTTACCCCTCAATGAGCGACCCCTACCTGTCCAGCTATTACCCGCCGTCCATTGGAT
TTCCTTACTCCCTCAATGAGGCTCCGTGGTCTACTGCAGGGGACCCTCCGATTCCATACCTCACCACCTA
CGGACAGCTCAGTAACGGAGACCATCATTTTATGCACGATGCTGTTTTTGGGCAGCCTGGGGGCCTGGGG
AACAACATCTATCAGCACAGGTTCAATTTTTTCCCTGAAAACCCTGCGTTCTCAGCATGGGGGACAAGTG
GGTCTCAAGGTCAGCAGACCCAGAGCTCCGCGTATGGGAGCAGCTACACCTACCCCCCGAGCTCCCTGGG
TGGCACGGTGGTTGATGGGCAGCCAGGCTTTCACAGCGACACCCTCAGCAAGGCCCCCGGGATGAACAGC
CTGGAGCAGGGCATGGTTGGCCTGAAGATTGGGGACGTCAGCTCCTCCGCCGTCAAGACGGTGGGCTCTG
TCGTCAGCAGCGTGGCACTGACTGGTGTCCTTTCTGGCAACGGTGGGACAAATGTGAACATGCCAGTTTC
AAAGCCGACCTCGTGGGCTGCCATTGCCAGCAAGCCTGCAAAACCACAGCCTAAAATGAAAACAAAGAGC
GGGCCTGTCATGGGGGGTGGGCTGCCCCCTCCACCCATAAAGCATAACATGGACATTGGCACCTGGGATA
ACAAGGGGCCTGTGCCGAAGGCCCCAGTCCCCCAGCAGGCACCCTCTCCACAGGCTGCCCCACAGCCCCA
GCAGGTGGCTCAGCCTCTCCCAGCACAGCCCCCAGCTTTGGCTCAACCGCAGTATCAGAGCCCTCAGCAG
CCACCCCAGACCCGCTGGGTTGCCCCACGCAACAGAAACGCGGCGTTTGGGCAGAGCGGAGGGGCTGGCA
GCGATAGCAACTCTCCTGGAAACGTCCAGCCTAATTCTGCCCCCAGCGTCGAATCCCACCCCGTCCTTGA
AAAACTGAAGGCTGCTCACAGCTACAACCCGAAAGAGTTTGAGTGGAATCTGAAAAGCGGGCGTGTGTTC
ATCATCAAGAGCTACTCTGAGGACGACATCCACCGCTCCATTAAGTACTCCATCTGGTGTAGCACAGAGC
ACGGCAACAAGCGCCTGGACAGCGCCTTCCGCTGCATGAGCAGCAAGGGGCCCGTCTACCTGCTCTTCAG
CGTCAATGGGAGTGGGCATTTTTGTGGGGTGGCCGAGATGAAGTCCCCCGTGGACTACGGCACCAGTGCC
GGGGTCTGGTCTCAGGACAAGTGGAAGGGGAAGTTTGATGTCCAGTGGATTTTTGTTAAGGATGTACCCA
ATAACCAGCTCCGGCACATCAGGCTGGAGAATAACGACAACAAACCGGTCACAAACTCCCGGGACACCCA
GGAGGTGCCCTTAGAAAAAGCCAAGCAAGTGCTGAAAATTATCAGTTCCTACAAGCACACAACCTCCATC
TTCGACGACTTTGCTCACTACGAGAAGCGCCAGGAGGAGGAGGAGGTGGTGCGCAAGGAACGGCAGAGTC
GAAACAAACAATGAGGGCGAACCAGTTTCTTACATGTTCTAACGTTTGACTTTGAAAACAGTTTAAAACA
CGTGTGCTTGGTCAGCTCCAGTGTGTCGTCCCGTGCGGGGGTTGAGTGTTGCATCTTTGCCTTTCTTGTC
GTTGATTTTTGCCCAGATGGATCTGCATTTATTTGTACTTTTTCTATGTATTATAATCCTGTAGAAGTCA
CTAATAAAGGAGTATTTTTTTTGTCAGCTTATCAATCAGACTGATCTAATGTGAAATGTAAGTATCCTTA
AAAACAAAGCATCTATTTTGGCAGAAATTGTGTTCTTAAATTCAGTCATTTGATATTCTGTGAGACTTCA
TATTTCTCATCCCTTTATTGCTTTTTAGCAAACATAAGAAACCATGAGTCATTTTGTCATTTAGAGTATT
CTGATAAAATCTCTTGAAAATACTGAAATCAAAAGGTTAATGATTTTTTGTTCATTCTGATTTGTCATTT
TATTATCTGTTATCGGTCTAAAGTGCTAATTTACCCATTTGATTTTTCTGCTAGACAGATAACTTTTAAT
TTTTCAAATTTGGCAGACACTTTTTTTTTTTTTTTGAAAATCTTTCCTTCCAGATCTGTTGCCCACTGAA
CAGCCACCCGTCCCTCACTGTCCTGGTGTCCGATTGGGCTGGATGGTGTTGGGGCATGATGTGTGGAGGA
ACTGGAAGGTGCTTTAGGTCTGGTTCAGGGTCGGGCATTCTTTGTTGTTTGCACATCTTTTTAAATTTTA
CACCTTTTCTTAAGAATTCTAATGCCGTCTTAAGTTTTTATACCAATAATGCTGAGCTTTAAGTGTAGGA
TCTGGTAGTACAGACAGTGTGATGGATGATGCTGCTGGTTGTAAATTTCATCGTGTGTGTCTAATTTTTT
TTCCTGTTGAATGGGTAAAAACAAAACAAAACTTTTTTTAGAAGATGAATTTGCTGTCATGTTTTGTGGA

APPENDIX-continued

NUCLEIC ACID AND AMINO ACID SEQUENCES OF BIOMARKERS

| Gener Name | Gene ID | Accession NO. | Name |
|---|---|---|---|

ATGAGGGACCGTTGAGCTCACTACCACCTGGAGTTTGAGTTGAAGCATGAAAATGGTGCCCATGCCTGAC
GCTCCAGCGCCTGGATCTGCACGTGCCCTTGTAGAGGATCCTTACCGTCCTAGAGAGCAGACGCTTTCTG
AAAACTACTTGCTCCAAAAGACCCTCTGAGTTAACGTTTCAGCTGTATCATTAGACTTGTATTTAGAGCG
TGTCACTTCCTCTGAACTGTTACTGCCTGAATGGAGTCCTGGACGACATTGGGTTTTTCCTCTAGGAGAA
TACAAGCCTTAATAAACAATACTATTTAGCAAAAAAAAAAAAAAAAAAAAAAAAAA (SEQ ID NO: 77)

Translated protein sequence

MSATSVDTQRTKGQDNKVQNGSLHQKDTVHDNDFEPYLTGQSNQ
SNSYPSMSDPYLSSYYPPSIGFPYSLNEAPWSTAGDPPIPYLTTYGQLSNGDHHFMHD
AVFGQPGGLGNNIYQHRFNFFPENPAFSAWGTSGSQGQQTQSSAYGSSYTYPPSSLGG
TVVDGQPGFHSDTLSKAPGMNSLEQGMVGLKIGDVSSSAVKTVGSVVSSVALTGVLSG
NGGTNVNMPVSKPTSWAAIASKPAKPQPKMKTKSGPVMGGGLPPPPIKHNMDIGTWDN
KGPVPKAPVPQQAPSPQAAPQPQQVAQPLPAQPPALAQPQYQSPQQPPQTRWVAPRNR
NAAFGQSGGAGSDSNSPGNVQPNSAPSVESHPVLEKLKAAHSYNPKEFEWNLKSGRVF
IIKSYSEDDIHRSIKYSIWCSTEHGNKRLDSAFRCMSSKGPVYLLFSVNGSGHFCGVA
EMKSPVDYGTSAGVWSQDKWKGKFDVQWIFVKDVPNNQLRHIRLENNDNKPVTNSRDT
QEVPLEKAKQVLKIISSYKHTTSIFDDFAHYEKRQEEEEVVRKERQSRNKQ (SEQ ID NO: 78)

| Z1C5 | 85416 | NM_033132 | *Homo sapiens* Zic family member 5 (odd-paired homolog, *Drosophila*) (ZIC5), mRNA |
|---|---|---|---|

mRNA Sequence

GCGGCCGCAAGCACGGGGGCGAATCCCCGCTGGGTCGAGGGCCTGAACGGGAGCCAATCGAGCAGCCGAG
GCTACTGCCAATCACGCGGCTCCCTCCAATCCCACCCGTGCCATTTCCAAAATCTCGGTCCCACTGTGCA
GCTCAAATGTGGTGTTCACTCTGCCAATCGCTGGAGGATAGAGTGGGAACAGGAATAAGCAGAGTTAAGA
GGCCAGGACAAAAGAAGTTAAAGAGCGCCCAATACATACATGTTTTTGAAGGCGGGCAGAGGGAATAAAG
TCCCCCCAGTGAGGGTCTATGGGCCTGATTGTGTAGTTCTGATGGAGCCCCCTTTGAGCAAGAGGAACCC
GCCAGCGCTGAGATTAGCGGATTTGGCAACGGCTCAGGTCCAGCCGCTTCAGAATATGACAGGCTTCCCG
GCGCTGGCCGGCCCGCCCGCCCACTCCCAACTCCGGGCCGCCGTCGCGCACCTCCGCCTGCGGGACCTGG
GCGCTGACCCCGGCGTGGCCACCACTCCGCTCGGACCCGAGCACATGGCCCAGGCGAGCACGCTGGGCCT
CAGCCCTCCCTCCCAGGCGTTCCCGGCACACCCGGAGGCTCCGGCAGCCGCCGCCCGTGCTGCAGCCTTG
GTCGCGCACCCCGGCGCGGGCAGCTACCCCTGCGGCGGGGGCAGCAGTGGCGCGCAGCCCTCCGCGCCCC
CGCCCCCAGCCCCTCCTCTTCCTCCCACCCCTTCACCCCCTCCCCCTCCCCCGCCTCCTCCTCCTCCTGC
CCTCTCGGGCTACACCACCACCAACAGTGGCGGCGGCGGCAGCAGCGGCAAAGGCCACAGCAGGGACTTC
GTCCTCCGGAGGGACCTTTCCGCCACGGCCCCCGCGGCGGCCATGCACGGGGCCCCGCTCGGAGGGGAGC
AGCGGTCCGGCACCGGCTCCCCCCAGCACCCGGCCCCGCCTCCCCACTCGGCCGGCATGTTCATCTCCGC
CAGCGGCACCTACGCGGGCCCGGACGGCAGCGGCGGCCCGGCGCTCTTCCCCGCGCTGCACGACACGCCG
GGGGCCCCAGGCGGCCACCCGCACCCGCTCAACGGCCAGATGCGCCTGGGGCTGGCGGCGGCAGCGGCAG
CCGCGGCGGCTGAGCTGTACGGCCGCGCCGAACCGCCCTTCGCGCCGCGCTCTGGGGACGCGCACTACGG
GGCGGTTGCGGCCGCAGCGGCGGCCGCCCTGCACGGCTACGGAGCCGTGAACTTAAACCTGAACCTGGCG
GCTGCGGCGGCCGCAGCAGCGGCCGGGCCCGGGCCCCACCTGCAGCACCACGCGCCGCCCCCGGCGCCGC
CGCCGCCGCCGGCGCCCGCGCAGCACCCGCACCAGCACCACCCCCACCTCCCAGGGGCGGCTGGGGCCTT
CCTGCGCTACATGCGGCAGCCAATCAAGCAGGAGCTCATCTGCAAGTGGATCGACCCCGACGAGCTGGCC
GGGCTGCCGCCGCCGCCGCCGCCGCCGCCGCCGCCGCCGCCGCCACCGCCCCCGGCCGGCGGCGCCAAGCCCT
GCTCCAAAACTTTCGGCACCATGCACGAGCTGGTGAATCACGTCACGGTGGAGCACGTGGGAGGCCCCGA
GCAGAGCAGCCACGTCTGCTTCTGGGAGGACTGTCCGCGCGAGGGCAAGCCCTTCAAGGCCAAATACAAG
CTCATCAACCACATCCGCGTGCACACCGGCGAGAAGCCCTTTCCCTGCCCTTTCCCCGGCTGCGGCAAGG
TCTTCGCGCGCTCCGAGAACCTCAAGATCCACAAGCGTACTCATACAGGGGAAAAGCCTTTCAAATGTGA
ATTTGATGGCTGTGACAGGAAGTTTGCCAATAGCAGTGATCGGAAGAAACATTCCCATGTCCACACCAGT
GACAAGCCCTACTACTGCAAGATTCGAGGCTGTGACAAATCCTACACTCACCCAAGCTCCCTGAGGAAGC
ACATGAAGATTCACTGCAAGTCCCCGCCACCTTCTCCAGGACCCCTTGGTTACTCATCAGTGGGGACTCC
AGTGGGCGCCCCCTTGTCCCCTGTGCTGGACCCAGCCAGGAGTCACTCCAGCACTCTGTCCCCTCAGGTG
ACCAACCTCAATGAGTGGTACGTTTGCCAGGCCAGTGGGGCCCCCAGCCACCTCCACACCCCTTCCAGCA
ACGGAACCACCTCTGAGACTGAAGATGAGGAAATTTACGGGAACCCTGAAGTTGTGCGGACGATACATTA
GAATTTATTATTAATAATAATAAGTGAAATAATAAGTGGGAGTCCTTGGACCACATCCTAACCTGAGACA
ATGCCGAGCCTGAGACAAACCCGTGACTCAGACTTGCCACCGGGTCTAATTAGCCCTATTTATTCAGTAT
GAAACCCTATGGTGTTTGTACATTTAATTAATTTAATTAAGATATTTGGGCTTTTTTTTTTTTTTTTCTT
AAAAAACAAACAAAAAACAACCAAGCTGGACTTGTACATTGCAGGAGGATGGGGCTGGGGGCAAATTGTA
CCAAGGAAAATGAATGGAGAGATTAGTTAATGGCGATACACACTGCCGATGCAATATATATATATATATA
TATATACATATATATATATATTATTTTTTTAAAAGGGGGAGAAAAAGAGCATTAAGTCAGAACTTAACA
CAGCACCAAGGCCCTCTGCATTTCCCAGAGTGCCTCTCAAATGCCTTTGACACCATACCATGGGCTGCTT
TTGAGCCTCCTTGTTGGACCCTAATTCTGCCAAGGCCTCTTGATTGTAAACCACACACCTGCTGCATTGC
CAACAGATCCTGTTCCGTACCTGTGTCCAAAAACATTTGTAAAAACCCTTTGAGTTTAATATTTGTAATT
TTTAATTTCCACTCTTTTATTACTGATCTTAGCTTAATACAATATTTTTATACAGGATTATTTCTTCAGT
ATCCTACTGTGTGATTTTAAAAAAAGATGCAGCAACCTTAATATATCTCCATATCTTGTGCTACTGTGAT
TGTTCAAGCAAAAGTGGAGAGAAGAAAAGCTGCTGCAAAAGACAACTGTGAAACTGTGATATTTTATAAA
ATAGAAGAAATTCAAGTGCTTTCTTTTTCCTATATGTTTTTTTTTTTTTTATCTGAATTCTCAGATACTGC
CTCCTAACTGTGTCCAAACTTCTTGTGTAATAAAGAGATTCTGTTTTCGATCCTAAGTTCTTTGGGATGC
CAACATTCACAGTCAAGTCTTGAGGAGGTGTGATGATGGCATCATGCCTATTTTTTTGGAAAGCTGTTGT
TTTTAAAACAGGCCAACACCTCTTTTATACTGTTGTATCAGCCTTTTAAAAAGTCTATTTTTCAATGCCT
GAAACTGCATTTTAATGCATTTTCTTCCACCTGAGCACTGAGCACACCAAACTGGAATCCATTTGAAAAT
GACAGTGTGTGAAGTGTATGATTTACATTAAAAGAGGGGAGGGAGTTGCCATACATATTAAAAATTTTTA
AAAGGTTTATAGTTACCACCAAACACTGATGAATGTGTGACCTTTGCCAGAGCTGTCAAGCTAGGATAAA

APPENDIX-continued

NUCLEIC ACID AND AMINO ACID SEQUENCES OF BIOMARKERS

| Gener Name | Gene ID | Accession NO. | Name |
|---|---|---|---|

AAAGGTCAAGGACCTAGGACAATAACTCTTAGTCGATTTATTTTCGGTTGGTACAACACATCTCCTGTGC
AAAATGTAGTCCATCAGAAACATCCTACAGATACACTAAAGAGCACTAATTTATCCTTAGAGACCCCGAA
GACACCCCCTCCCCAGGGTTTGTAGAAATTTGTTTTGTGTGCTGTGAGTGGTTGATGTAGTCTTGTCATT
GTTAATAACTTGTATGTGAACACTATTATTTGTACAGTTGAATTAATTTATTTTCAGACATCATCCTTTT
TTTTTTTCTTTCCTGGAAGAGTTCAAAGCACACCAAAGAATTATATTATACATTTTGGTGAAAGATTGTC
ATTTATGATCCATGGTTTATTTAAAAAAAAAAGGAAAGAAAATGGAAAAATATATTTTTAAGCTTACTTG
AATGAACAACGTAATGTGAAAACCAAGACTCTTCCTGCATGTCTTTTTTGCATTGTGTTGATAAGATTAT
ATATAGTTTATAGATATATTATATTACTAGTACAGTGCATGGTGCTGTCACTTGGAAAGCCTTTCAATGT
TGTCTTCAGATTGTTGTGATGAATATGAAACATGCAGACCCTCCTTTATAAAGAAAAAGACCTTAAAACT
TGAATATGAGATAATTTTACATTTTAAAAGTTTATTTGATTTTCATATTATTCACTTTCAAAGCCCTTTC
AAATAGAAAAGGTATGAACTTTTGGGGGGATAATTTATGTATCGTAAACTTATTAGAACAAAATATTCCT
GATGTATAATGAGTTGTTTTATTTATACAACTTTTTCAATGGTAGTTTGCACTATTCTTTATTATGCTAC
AGGTTTATTTATTATGAAACAAAGGAATATGTATTTTATGTATTTTACCATGCATAGGTTAACTCTTTGC
CACAGATTTATTGGTTCTTGATACACCTAAAATAAAAAAAAATGTGTACCTCCAATAGAGAGCAAGCAAG
AATGATTATGAAGTAACAAATTTAATAAAGGTATTCTTGTTATTATTAAAAAAAAAA (SEQ ID NO: 79)

Translated protein sequence

MFLKAGRGNKVPPVRVYGPDCVVLMEPPLSKRNPPALRLADLAT
AQVQPLQNMTGFPALAGPPAHSQLRAAVAHLRLRDLGADPGVATTPLGPEHMAQASTL
GLSPPSQAFPAHPEAPAAAARAAALVAHPGAGSYPCGGGSSGAQPSAPPPPAPPLPPT
PSPPPPPPPPPPPALSGYTTTNSGGGGSSGKGHSRDFVLRRDLSATAPAAAMHGAPLG
GEQRSGTGSPQHPAPPPHSAGMFISASGTYAGPDGSGGPALFPALHDTPGAPGGHPHP
LNGQMRLGLAAAAAAAAAELYGRAEPPFAPRSGDAHYGAVAAAAAAALHGYGAVNLNL
NLAAAAAAAAAGPGPHLQHHAPPPAPPPPPAPAQHPHQHHPHLPGAAGAFLRYMRQPI
KQELICKWIDPDELAGLPPPPPPPPPPPPPPPAGGAKPCSKTFGTMHELVNHVTVEHV
GGPEQSSHVCFWEDCPREGKPFKAKYKLINHIRVHTGEKPFPCPFPGCGKVFARSENL
KIHKRTHTGEKPFKCEFDGCDRKFANSSDRKKHSHVHTSDKPYYCKIRGCDKSYTHPS
SLRKHMKIHCKSPPPSPGPLGYSSVGTPVGAPLSPVLDPARSHSSTLSPQVTNLNEWY
VCQASGAPSHLHTPSSNGTTSETEDEEIYGNPEVVRTIH (SEQ ID NO: 80)

What is claimed is:

1. A method of treating a subject having breast cancer, the method comprising assaying a breast cancer sample derived from said subject to determine the level of expression in said sample of at least one biomarker selected from the group of biomarkers listed in Table 1, detecting no expression or a low level of expression of said at least one biomarker in said sample relative to a normal control; and administering a therapeutically effective amount of eribulin, an analog thereof, or a pharmaceutically acceptable salt thereof, to said subject.

2. The method of claim 1, wherein the pharmaceutically acceptable salt of eribulin is eribulin mesylate.

3. The method of claim 1, wherein said subject has not been previously treated with eribulin, an analog thereof, or a pharmaceutically acceptable salt thereof.

4. The method of claim 1, wherein said subject has been previously treated with eribulin, an analog thereof, or a pharmaceutically acceptable salt thereof.

5. The method of claim 1, wherein said breast cancer is an Estrogen Receptor (ER) negative breast cancer, a Progesterone Receptor (PR) negative breast cancer, and/or a HER-2 negative breast cancer.

6. The method of claim 1, wherein at least 2, 3, 4 or 5 biomarkers selected from the group of biomarkers listed in Table 1 have a low level of expression.

7. The method of claim 1, wherein there is a low level of expression of said biomarker as compared to a control.

8. The method of claim 7, where said biomarker is not expressed at a detectable level.

9. The method of claim 1, wherein the level of expression of said biomarker is determined at the nucleic acid level.

10. The method of claim 9, wherein the level of expression of said biomarker is determined by detecting cDNA, mRNA, miRNA or DNA.

11. The method claim 9, wherein the level of expression of said biomarker is determined by using a technique selected from the group consisting of polymerase chain reaction (PCR) amplification reaction, reverse-transcriptase PCR analysis, quantitative reverse-transcriptase PCR analysis, Northern blot analysis, RNAase protection assay, digital RNA detection/quantitation, and combinations or subcombinations thereof.

12. The method of claim 1, wherein the level of expression of said biomarker is determined at the protein level.

13. The method of claim 12, wherein the presence of the protein is detected using an antibody or antigen binding fragment thereof, which specifically binds to the protein.

14. The method of claim 13, wherein the antibody or antigen binding fragment thereof is selected from the group consisting of a murine antibody, a human antibody, a humanized antibody, a bispecific antibody, a chimeric antibody, a Fab, Fab', $F(ab')_2$, ScFv, SMIP, affibody, avimer, versabody, nanobody, a domain antibody, and an antigen binding fragment of any of the foregoing.

15. The method of claim 13, wherein the antibody or antigen binding fragment thereof is labeled.

16. The method of claim 15, wherein the antibody or antigen binding fragment thereof is labeled with a label selected from the group consisting of a radio-label, a biotin-label, a chromophore-label, a fluorophore-label, and an enzyme-label.

17. The method of claim 12, wherein the level of expression of said biomarker is determined by using a technique selected from the group consisting of an immunoassay, a western blot analysis, a radioimmunoassay, immunofluorimetry, immunoprecipitation, equilibrium dialysis, immunodiffusion, electrochemilummescence immunoassay (ECLIA), ELISA assay, immunopolymerase chain reaction and combinations or sub-combinations thereof.

18. The method of claim 17, wherein the immunoassay is (a) a solution-based immunoassay selected from the group consisting of electrochemilumninescence, chemiluminescence, fluorogenic chemiluminescence, fluorescence polarization, and time-resolved fluorescence; or (b) a sandwich immunoassay selected from the group consisting of electrochemiluminescence, chemiluminescence, and fluorogenic chemilumninescence.

19. The method of claim 1, wherein said sample is selected from the group consisting of a fluid, or component thereof, obtained from said subject, blood, lymph, serum, plasma, cystic fluid, nipple aspirates, urine, sputum, fluid collected from a biopsy, a tissue, or component thereof, obtained from said subject, breast tissue, connective tissue, lymphatic tissue, tissue obtained from a biopsy, tissue obtained from a lump biopsy, breast tissue cells, and circulating breast tumor cells.

20. The method of claim 1, wherein said subject is a human subject.

* * * * *

SEQUENCE LISTING

<160> NUMBER OF SEQ ID NOS: 80

<210> SEQ ID NO 1
<211> LENGTH: 2129
<212> TYPE: DNA
<213> ORGANISM: Homo sapiens

<400> SEQUENCE: 1
tcctatccac cctccactcc cctgtccctt ggtgactcat ccctgagctt cccaaggaag 60
cccccaccct ctgccctttc ctcccgcctt ccatgagtgg aaaatccacc tccgcccccct 120 atagcaggcc agccccttc ctccccagtc tccgacccca tcccccagcc gaccagtttc 180
ctctccagga ccagggagca atcacagctg ccccgacctt ggcttcctct gctgggtggg 240
attgggggct gggcccccaa atgggcccct ggcttccccc ttcctctggg caggggacag 300
agagacacag gctcggggag caggactgac ttcctcttgt cccggaatga gcatgcctgc 360
cctttgcaag caggtttggg tctcacgcag aggaaaccaa aagcaataag agggagggaa 420
ggcagagcaa ccaatcaagg gcagggtgag actcaaaacg agcgggctcc ctggggagcc 480
agacagaggc tgggggtgat ggcggagcta cagcagctgc aggagtttga gatccccact 540
ggccgggagg ctctgagggg caaccacagt gccctgctgc gggtcgctga ctactgcgag 600
gacaactatg tgcaggccac agacaagcgg aaggcgctgg aggagaccat ggccttcact 660
acccaggcac tggccagcgt ggcctaccag gtgggcaacc tggccgggca cactctgcgc 720
atgttggacc tgcagggggc cgccctgcgg caggtggaag cccgtgtaag cacgctgggc 780
cagatggtga acatgcatat ggagaaggtg gcccgaaggg agatcggcac cttagccact 840

```
gtccagcggc tgccccccgg ccagaaggtc atcgccccag agaacctacc ccctctcacg    900

ccctactgca ggagacccct caactttggc tgcctggacg acattggcca tgggatcaag    960

gacctcagca cgcagctgtc aagaacaggc accctgtctc gaaagagcat caaggcccct   1020

gccacacccg cctccgccac cttggggaga ccaccccgga ttcccgagcc agtgcacctg   1080

ccggtggtgc ccgacggcag actctccgcc gcctcctctg cgtcttccct ggcctcggcc   1140

ggcagcgccg aaggtgtcgg tggggccccc acgcccaagg ggcaggcagc acctccagcc   1200

ccacctctcc ccagctcctt ggacccacct cctccaccag cagccgtcga ggtgttccag   1260

cggcctccca cgctggagga gttgtcccca cccccaccgg acgaagagct gcccctgcca   1320

ctggacctgc ctcctcctcc accccctggat ggagatgaat tggggctgcc tccaccccca   1380

ccaggatttg ggcctgatga gcccagctgg gtgcctgcct catacttgga gaaagtggtg   1440

acactgtacc catacaccag ccagaaggac aatgagctct ccttctctga gggcactgtc   1500

atctgtgtca ctcgccgcta ctccgatggc tggtgcgagg gcgtcagctc agaggggact   1560

ggattcttcc ctgggaacta tgtggagccc agctgctgac agcccagggc tctctgggca   1620

gctgatgtct gcactgagtg ggtttcatga gccccaagcc aaaaccagct ccagtcacag   1680

ctggactggg tctgcccacc tcttgggctg tgagctgtgt tctgtccttc ctcccatcgg   1740

agggagaagg ggtcctgggg agagagaatt tatccagagg cctgctgcag atggggaaga   1800

gctggaaacc aagaagtttg tcaacagagg acccctactc catgcaggac agggtctcct   1860

gctgcaagtc ccaactttga ataaaacaga tgatgtcctg tgactgcccc acagagataa   1920

ggggccagga gggattgaaa ggcatcccag ttctaaggct gctgctaatt acagccccca   1980

acctccaacc caccagctga cctagaagca gcatcttccc atttcctcag tacccacaaa   2040

gtgcagccca cattggaccc cagacacccc tctgcagcca ttgactgcaa cttgttcttt   2100

tgcccattga aaaaaaaaaa aaaaaaaaa                                     2129
```

<210> SEQ ID NO 2
<211> LENGTH: 366
<212> TYPE: PRT
<213> ORGANISM: Homo sapiens

<400> SEQUENCE: 2

```
Met Ala Glu Leu Gln Gln Leu Gln Glu Phe Glu Ile Pro Thr Gly Arg
1               5                   10                  15

Glu Ala Leu Arg Gly Asn His Ser Ala Leu Leu Arg Val Ala Asp Tyr
            20                  25                  30

Cys Glu Asp Asn Tyr Val Gln Ala Thr Asp Lys Arg Lys Ala Leu Glu
        35                  40                  45

Glu Thr Met Ala Phe Thr Thr Gln Ala Leu Ala Ser Val Ala Tyr Gln
    50                  55                  60

Val Gly Asn Leu Ala Gly His Thr Leu Arg Met Leu Asp Leu Gln Gly
65                  70                  75                  80

Ala Ala Leu Arg Gln Val Glu Ala Arg Val Ser Thr Leu Gly Gln Met
                85                  90                  95

Val Asn Met His Met Glu Lys Val Ala Arg Arg Glu Ile Gly Thr Leu
            100                 105                 110

Ala Thr Val Gln Arg Leu Pro Pro Gly Gln Lys Val Ile Ala Pro Glu
        115                 120                 125

Asn Leu Pro Pro Leu Thr Pro Tyr Cys Arg Arg Pro Leu Asn Phe Gly
    130                 135                 140
```

```
Cys Leu Asp Asp Ile Gly His Gly Ile Lys Asp Leu Ser Thr Gln Leu
145                 150                 155                 160

Ser Arg Thr Gly Thr Leu Ser Arg Lys Ser Ile Lys Ala Pro Ala Thr
                165                 170                 175

Pro Ala Ser Ala Thr Leu Gly Arg Pro Pro Arg Ile Pro Glu Pro Val
            180                 185                 190

His Leu Pro Val Val Pro Asp Gly Arg Leu Ser Ala Ala Ser Ser Ala
        195                 200                 205

Ser Ser Leu Ala Ser Ala Gly Ser Ala Glu Gly Val Gly Gly Ala Pro
    210                 215                 220

Thr Pro Lys Gly Gln Ala Ala Pro Pro Ala Pro Pro Leu Pro Ser Ser
225                 230                 235                 240

Leu Asp Pro Pro Pro Pro Pro Ala Ala Val Glu Val Phe Gln Arg Pro
                245                 250                 255

Pro Thr Leu Glu Glu Leu Ser Pro Pro Pro Pro Asp Glu Glu Leu Pro
            260                 265                 270

Leu Pro Leu Asp Leu Pro Pro Pro Pro Pro Leu Asp Gly Asp Glu Leu
        275                 280                 285

Gly Leu Pro Pro Pro Pro Pro Gly Phe Gly Pro Asp Glu Pro Ser Trp
    290                 295                 300

Val Pro Ala Ser Tyr Leu Glu Lys Val Val Thr Leu Tyr Pro Tyr Thr
305                 310                 315                 320

Ser Gln Lys Asp Asn Glu Leu Ser Phe Ser Glu Gly Thr Val Ile Cys
                325                 330                 335

Val Thr Arg Arg Tyr Ser Asp Gly Trp Cys Glu Gly Val Ser Ser Glu
            340                 345                 350

Gly Thr Gly Phe Phe Pro Gly Asn Tyr Val Glu Pro Ser Cys
        355                 360                 365
```

<210> SEQ ID NO 3
<211> LENGTH: 742
<212> TYPE: DNA
<213> ORGANISM: Homo sapiens

<400> SEQUENCE: 3

```
tccaggttca cacaactgga acccatctcc aggaacaaac agctggaacc catctcccgt      60

tgaagggaaa ctgccagatt tttgtaagat tcttcctcct gggagcctgt gttggaagag     120

atggtgatgg gcctgggcgt tttgttgttg gtcttcgtgc tgggtctggg tctgacccca     180

ccgaccctgg ctcaggataa ctccaggtac acacacttcc tgacccagca ctatgatgcc     240

aaaccacagg gccgggatga cagatactgt gaaagcatca tgaggagacg gggcctgacc     300

tcaccctgca aagacatcaa cacatttatt catggcaaca agcgcagcat caaggccatc     360

tgtgaaaaca agaatggaaa ccctcacaga gaaaacctaa gaataagcaa gtcttctttc     420

caggtcacca cttgcaagct acatggaggt tccccctggc ctccatgcca gtaccgagcc     480

acagcggggt tcagaaacgt tgttgttgct tgtgaaaatg gcttacctgt ccacttggat     540

cagtcaattt tccgtcgtcc gtaaccagcg ggcccctggt caagtgctgg ctctgctgtc     600

cttgccttcc atttcccctc tgcacccaga acagtggtgg caacattcat tgccaagggc     660

ccaaagaaag agctacctgg accttttgtt ttctgtttga caacatgttt aataaataaa     720

aatgtcttga tatcagtaag aa                                              742
```

<210> SEQ ID NO 4
<211> LENGTH: 147

<212> TYPE: PRT
<213> ORGANISM: Homo sapiens

<400> SEQUENCE: 4

```
Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145
```

<210> SEQ ID NO 5
<211> LENGTH: 8935
<212> TYPE: DNA
<213> ORGANISM: Homo sapiens

<400> SEQUENCE: 5

```
gccaaagcct ggagaagtgg aatctcgtca gcgccgctcc ctgcgcggga ctcgcggaac      60

ggcactgagc atgctcagtt gccggagccc gttctggtct caagtaggaa gctagtgcgc     120

tgtaaccgca tctgatctgg gcgctccggg aagggcgaga ctggagcaga gccgctgggc     180

gccggagccg aggcgagcgc cgcgcgcacc actggttgga gttgctgtgg gtgagctgct     240

gtggtctgta gccaagcatg ctgtggtcgg atctgcccag ccgtggaaca gaaacatttg     300

ctggatggaa aatccataaa agaaagctcc tgtgaaaagc tgaggctgac aataatttaa     360

gcaaaatcag atcgatctct ttgggctgcc tgacctcctt gggtgcttgc tattaattaa     420

cagactttgt ggggaaaaaa aggagcttgc cttctgagct ttgtaccaaa gacctgggaa     480

aactaaccat ctcagtcttt cctgaggact tgggaactgc cgaggcctct gccaatgtgt     540

tgactgtcgc tatgggctca ctgttgtcca ggcagctcat atttcaaatt ataacctatt     600

tcctgcacca ttgctgacgc ctggtgatcc atgtcagaag tacttccagc tgactcaggt     660

gttgacacct tggcagtgtt tatggccagc agcggaacta cagacgtcac aaatcggaac     720

agcccagcca caccaccaaa caccccttaac ctccgatcct cccacaatga actgttgaac     780

gctgaaataa aacacacaga aaccaagaac agcacacctc ccaaatgcag gaaaaaatat     840

gcactaacta acatccaggc ggccatgggc ctctcggatc cagctgcaca gcccctgctg     900

ggaaatggct ctgccaacat caagctggtg aaaaatgggg agaaccagct ccgtaaggct     960

gcagagcaag ggcagcagga ccccaacaaa aacctgagcc ccactgcagt catcaacata    1020

acttctgaga agttagaggg taaagagccc cacccacagg attcctcgag ctgtgagatt    1080
```

```
ttaccctccc agcccaggag aactaagagc ttcctaaatt actatgcaga tctggaaacc   1140
tcagccagag aactagagca gaaccgaggc aatcaccatg ggactgcgga agagaaatcc   1200
cagccagtcc agggccaggc ctccaccatc attgggaatg gcgatttgct gctgcagaaa   1260
ccaaacagac cccagtccag ccctgaagac ggccaagtag ccacagtgtc atccagccca   1320
gaaaccaaga aggatcatcc gaaaacaggg gccaaaaccg actgtgcact gcaccggatc   1380
cagaacctgg caccgagcga tgaggagtcc agctggacaa cgttgtccca agacagtgcc   1440
tcacccagct ccccggatga aacagatata tggagtgatc actcatttca gactgatcca   1500
gatttgccgc ctggctggaa aagagtcagt gacattgccg ggacctatta ttggcacatc   1560
ccaacaggaa cgactcagtg ggaacggccc gtctccatcc cagcagatct ccagggttct   1620
aggaaagggt cacttagttc tgtaacgcca tctcccaccc cagagaacga ggatttgcat   1680
gcagccactg ttaacccgga ccccagttta aaagagtttg aaggagcaac cctacgctat   1740
gcatctttga aactcagaaa tgccccacac cctgatgatg atgattcttg tagtatcaac   1800
agtgacccag aagccaagtg ttttgctgtg cgttctctgg gatgggtaga gatggcagaa   1860
gaggacctcg cccccggtaa aagtagtgtt gcggtcaaca actgcatcag gcaactttcc   1920
tactgcaaaa atgacatccg agacacagtc gggatttggg gagaggggaa agacatgtac   1980
ctgatcctgg agaatgacat gctcagcctg gtggacccca tggaccgcag cgtgctgcac   2040
tcgcagccca tcgtcagcat ccgcgtgtgg ggcgtgggcc gcgacaatgg ccgggatttt   2100
gcttatgtag caagagataa agatacaaga attttgaaat gtcatgtatt tcgatgtgac   2160
acaccagcaa aagccattgc cacaagtctc cacgagatct gctccaagat tatggctgaa   2220
cggaagaatg ccaaagcgct ggcctgcagc tccttacagg aaagggccaa tgtgaacctc   2280
gatgtccctt tgcaagattt tccaacacca aagactgagc tggtccagaa gttccacgtg   2340
cagtacttgg gcatgttacc tgtagacaaa ccagtcggaa tggatatttt gaacagtgcc   2400
atagaaaatc ttatgacctc atccaacaag gaggactggc tgtcagtgaa catgaacgtg   2460
gctgatgcca ctgtgactgt catcagtgaa aagaatgaag aggaagtctt agtggaatgt   2520
cgtgtgcgat tcctgtcctt catgggtgtt gggaaggacg tccacacatt tgccttcatc   2580
atggacacgg ggaaccagcg ctttgagtgc cacgttttct ggtgcgagcc taatgctggt   2640
aacgtgtctg aggcggtgca ggccgcctgc atgttacgat atcagaagtg cttggtagcc   2700
aggccgcctt ctcagaaagt tcgaccacct ccaccgccag cagattcagt aaccagaaga   2760
gtcacaacca atgtaaaacg aggggtctta tccctcattg acactttgaa acagaaacgc   2820
cctgtcaccg aaatgccata gctgcacatg caaaaggact cggctattta cctgaagatt   2880
gactagctac actaaagaaa atgaactccg ccatccgacc ttccatccag ttgctgatgc   2940
tttgtcttca gagaatttac ccttaaccaa gcagtgttag acaagcatgt tctctcgtct   3000
tgccaccatc atgtgatatg aaaagaagca tgaataattt tttttgctgt aagttacatc   3060
atgcgcagtg gaaggtcttt ttcttattgt aaatattgtg aacattactt aacttcacac   3120
acacacagag aagagtgtgg ccccaccccct cctagtgaac taacgctgcg tccttggaat   3180
gaatgatgcg tgagttagtt tcactgtctt cttggctgga cctgtcacaa gcaaccttta   3240
agtcctacag cactttgccc tgttttcaac attggagtag gcactgcata gcagatacca   3300
ttgaattgct gtaaaaatag gatggcgagt ttgtgtttta atttttcata aaattgaacc   3360
tgttggttga caaaattggc tgttggcatc agtatagaaa ccaactggca gctttccctg   3420
acaagctctt tgacacatgg acaccatttc atgtctacag ctgtttgtgg gatgttggaa   3480
```

```
aaaaatgaaa cttcaaaatt gatgaaaaac taaattcgag gaattaaaat cgaacaaaac   3540
atagcctttc ttttccgatg gttttcaaac tgattatttt taaaagagat taataaaatc   3600
ataatgcatt ttgggtggga catatttcaa acttctgcct tatattgtac ggtgcagcta   3660
gagaattata gttcactatg gccattctct acataaacat taagatgaaa tactcctcat   3720
cagcctttca tccttagttt gagaattagc tgatatgcaa tttgaagttg aggaaatatc   3780
attgatattt ctatcatgca cgattatttt agatttctac caccgtgtga tttttgctag   3840
tccatgtgct agaggtaaac gttctgctgg aattctgcat ccagctctat ccccctctga   3900
tgctttttgc ccagaaagct gtctgtccat catgtattgt ccatggcaac aaattacatt   3960
aggttgaacc tttccttgat tttatgtatt taatattaga atttgttgga ctcaactaga   4020
tatatttttt aatttatatt ttttccattt tactttgaag atttgaaatg ttcatacctg   4080
agcaaagtct acacaggagt aatggactgt ttaacaagtt tcccaaaaca gcattttcct   4140
gctccttcgt atgtaggtga gaaacttagc tggaaagaca tacaaattta gactctcgtt   4200
gacattgtcg ttttaaaagg aagttgctaa ggcgatcaat ctcaatatta gtcttgttta   4260
cttcttctta atgtcaaaat taacatttac aacatccaat tataaaagta atgctttatg   4320
tttatacact gctatgtact tgtcaaaatg gtttccacat tcttatcaca tctgagcctt   4380
accaggtaga gaaggtacta aatacacttt agaagtaaaa atatgaagta ccgagaggct   4440
aaacccactg gcctaagatc tcaccaaagt tcatgaaaac caggactagg acccacggct   4500
cccaaagccc gttcttgctg tgttgtgctg cctccatatc cgtcaggaag agcctttcca   4560
gaatgattct gggcatatac taagaagagc aggtatggaa agatctattg tcagggaatc   4620
ttagaattcc ctacacgagt gggagaaaga tgtccaaatt ccttacgcag tggtattcat   4680
gatggtgccc tatctaagtc caggactgtt ttcctacagc gtgcctcaaa agtgttgtag   4740
agggcaggat tctacattca cagcctgttc catctacgag attttccaga tgctacttgt   4800
ggtagacatt cctaactcat ggtacttagc caccagagat catgatggaa tgagtgggtg   4860
gcttttctac ctgccattcc ctcagaattc atgaggggtg ggggacaggg ggaccggaat   4920
tgtcttagca ccccaatgtt atgacaaaac tatgctactt tagaaacgca gtctgttttt   4980
caccaattga catactactg atctgaagta accagtgcca tcataagaaa ttactgcatt   5040
aagaaaatcc ttgctgtgcc ctttgaaaag ctgttcagaa atcatttaca gtgatctttc   5100
atctcggtcg ctgtagtgaa acattttagt gtgataaatt tcaaaattct aaacaaatta   5160
cccactttta tattggaaat ctctaccaga actccctctt catttttaa ggcatacatt   5220
tgcttgtttt caagatcaag aattctgagc tagctttaag tagcaaactg atttatatgt   5280
gcaattatag gatgcattaa gatgaatgat agcctttaca tattgaaaac tttgcagacg   5340
ttttgttttg aaaatggcat tgtatagtaa atgcaaatta attttgtaaa attatgttaa   5400
agagtatgtt cagacacttt ctgccatggc caaaaagtat gtatgaaagt atgtgtgtat   5460
ttgtttgtaa aaggatgcca atgttttacc tgatatctta gtgacacttc agttatctat   5520
gcattcttta gatctgtgat tcggtaaaca ggcagccatg ttcacgatgc cttctatgtc   5580
ttaccatatt tttaattaac ctgttaaata cagcttaaaa tatttttatt ttatttattc   5640
tatttttact gaaatatact gcattattgt gttaatgtat tatctttcct ggatattatc   5700
tcccagtgta tccagatcta agtaatctca gtgaactata cattgcctaa aaagtggttt   5760
tgtaatgatt tgtagtcaca tttctattgg gatatgtaga agaaaaggca aaatgcttaa   5820
```

```
agttcctttt atttttttaaa agcagctaga tagacacaga cttgccacct catacatctg   5880
ctccttggca acatcaaggg gaacgactag ccaacatgcc tatggctaaa aactttcctt   5940
tgcagactaa agcactgctt ggtgcttcgt ttttctaccc ttcacaacat gtgtgatttc   6000
atctaagaga tatatacatg tacacatgcc ctttgtttcc acctggatac aagatcactc   6060
atagctaatt aggaccattg tttttgttc atctgtcttg ttgcatgaag ggacattaga   6120
cccatttcca ttaaaataag ttcttggtga taaactgtgg cactgctact tctttttaaa   6180
tccactttat gatttcaaga tggacacttg taagatgact cgacacaagg ccattgcctg   6240
gaagccccag agctttcctc tgtttgtatg gcccgttcat gtcccaggca ttgcaacaca   6300
aactcctcaa gatttcacca caacatgaca agcattttcc taactgatat tagcacaatt   6360
taactaataa gccccttcgc tctctagttg gccaggctta acctaataca catctaacgt   6420
gtgtgccaca cggccagtag aaagtttaac ttcagcttca gggcaaagat acccactcac   6480
accgtgtcaa cgcaagcagt agttcctggc ctccagagca gcttacttcc cctgaaagaa   6540
cgctttgttt tcctttatgc ccttttcctg ttgaccactt ttacacattt aaatgtaatt   6600
tgttgtgaga ataaatttag ctgcataaaa cgttcggctc atttatctga catcttagtc   6660
acatatacaa ggaatagaaa tagaaactcg gtgtctctag ttatttttaa attattctta   6720
cctcagactt cttagaaatc actttagtaa tggagcattt tgctttgatt agttactaca   6780
tatttctgcc tggtaagaac taggaagtaa cttcaaattt tgagtaatca ccctgtactt   6840
atttggtgat caggaaggcc agctggcctt ccggacatag aagcctattt agtcaccaac   6900
tcgagtcttt tgtaagcggt cttgctagga ttgtgatatt ttagcacgaa gaagtttatc   6960
acttccttta agaacctgac atcaaagaat aaagaataga ggtgtacaca cactaaatcc   7020
aaaatgaaag gtaactagag aaatcagttg aatctggttt agcttaactg ttaggcgcag   7080
gaaggcagat aaacagaatt taaagtatgt ccccgctttt tgttcatctt gcacttccac   7140
agtggtttct ctctagtcag taacaaaatt tcattatggt ttcaggcatt atatggtggt   7200
aaataatttc agattaaaaa tgtgtttgct attggagtat ctgaatacta gtaatttcat   7260
tatttagaat tttgcagcac ttttatctca agaagaagtc caagaatgta aaatgccaaa   7320
tgaaacatgt cagtggaatc aatattctcc ttcattagaa ttccctcata ttgctttttt   7380
ttttttcttt cagacagagg agtcttactc tggagtgcag tggtgtaatt tcagctcacc   7440
acaacctcca cctcccaagt tcaagcaatt ctcgcctcag cctcctgagt agctgggatt   7500
acaggcatgc accgccacgc ctggccaatt tgtatatttt tagtagagac agggtttcgc   7560
cacgttggcc aggctggtct cgaactcctg acctcaggtg atccgcccgc cccaacctcc   7620
caaagtatgt gagccaccac gtccggcctc atattgcttt tatccaaaat tcttttccct   7680
tttcactcta ccaaagtatt taaataatcc tgtccttcat agaagattct caaagaagaa   7740
aactgcagtg taattaatga atggtttaat tcagaatctt catatacttc taaagagaaa   7800
aataatttag tgccaaatgc atgttaggag ataatcaatg taagtggcaa caaattgtga   7860
cttcacatgc tactgtagag atcagaaaat tatcctaaac tattccataa caatgagaca   7920
acatcacaga aaatacactt gaaaataaaa atctcaagac cagctacttc tggacaatgg   7980
aatacttttc agtctggtat ggtggagggc ccgaaaagga taagggattc ttatgataca   8040
caatgggatt ctttactgaa caatatgtta aattaagctg caccgccttc cttgaggcat   8100
ggactaccct aaccaaccag atagaaatct gggtgggata agaggatgag ccacacgcta   8160
taattttagg gcaaggagat agtgtttgat tttcaaaatc agcaaaataa gctgagcact   8220
```

```
ttatatcttt ctgtacaaga gtgataacat gaagaattct tcttcaggga tttaaaatac   8280

aataagcctg gttcaactat aaaaagtctt gtttcctttc ttcattgaca cttttttttt   8340

tttttttttt tttttgaggc aaggtctcac tctgcttccc aggctggagt gcagtggggc   8400

aatattggct cactgcaacc tgcacctcct ggactcaaga gatcctcgta cctcagcctc   8460

ctaagtagct gggactacag gcgtgtccca ccacacccag ctaatttttg tatttttttgt   8520

agagatgggg ttttggggtt tcgccatgtt gtccaggctc gtctggaact ccggtgctca   8580

agtggcgtgc ccacctcagc ctcccaaact gctgagatta cagatgtgag ccactgcacc   8640

cagcccactg acacgtttta ctgataaatg taaatctaag ctaaaataaa aataatgtat   8700

taccgctata atacaattca ccattctctt ttctcacttc aagtaagaaa gtaaaaatag   8760

aatatcagag ctgaagtaga cctaagtatt catcttgaag aagataatat tctaaaaatc   8820

atgccacctg aattgagcat ttaggaattt atgtaacatt tctatacaac tgaattgcaa   8880

aaataaaact ttaaattcaa actttaaaaa aaaaaaaaaa aaaaaaaaaa aaaaa        8935
```

<210> SEQ ID NO 6
<211> LENGTH: 736
<212> TYPE: PRT
<213> ORGANISM: Homo sapiens

<400> SEQUENCE: 6

```
Met Ser Glu Val Leu Pro Ala Asp Ser Gly Val Asp Thr Leu Ala Val
1               5                   10                  15

Phe Met Ala Ser Ser Gly Thr Thr Asp Val Thr Asn Arg Asn Ser Pro
            20                  25                  30

Ala Thr Pro Pro Asn Thr Leu Asn Leu Arg Ser Ser His Asn Glu Leu
        35                  40                  45

Leu Asn Ala Glu Ile Lys His Thr Glu Thr Lys Asn Ser Thr Pro Pro
    50                  55                  60

Lys Cys Arg Lys Lys Tyr Ala Leu Thr Asn Ile Gln Ala Ala Met Gly
65                  70                  75                  80

Leu Ser Asp Pro Ala Ala Gln Pro Leu Leu Gly Asn Gly Ser Ala Asn
                85                  90                  95

Ile Lys Leu Val Lys Asn Gly Glu Asn Gln Leu Arg Lys Ala Ala Glu
            100                 105                 110

Gln Gly Gln Gln Asp Pro Asn Lys Asn Leu Ser Pro Thr Ala Val Ile
        115                 120                 125

Asn Ile Thr Ser Glu Lys Leu Glu Gly Lys Glu Pro His Pro Gln Asp
    130                 135                 140

Ser Ser Ser Cys Glu Ile Leu Pro Ser Gln Pro Arg Arg Thr Lys Ser
145                 150                 155                 160

Phe Leu Asn Tyr Tyr Ala Asp Leu Glu Thr Ser Ala Arg Glu Leu Glu
                165                 170                 175

Gln Asn Arg Gly Asn His His Gly Thr Ala Glu Glu Lys Ser Gln Pro
            180                 185                 190

Val Gln Gly Gln Ala Ser Thr Ile Ile Gly Asn Gly Asp Leu Leu Leu
        195                 200                 205

Gln Lys Pro Asn Arg Pro Gln Ser Ser Pro Glu Asp Gly Gln Val Ala
    210                 215                 220

Thr Val Ser Ser Ser Pro Glu Thr Lys Lys Asp His Pro Lys Thr Gly
225                 230                 235                 240

Ala Lys Thr Asp Cys Ala Leu His Arg Ile Gln Asn Leu Ala Pro Ser
```

```
                245                 250                 255

Asp Glu Glu Ser Ser Trp Thr Thr Leu Ser Gln Asp Ser Ala Ser Pro
            260                 265                 270

Ser Ser Pro Asp Glu Thr Asp Ile Trp Ser Asp His Ser Phe Gln Thr
        275                 280                 285

Asp Pro Asp Leu Pro Pro Gly Trp Lys Arg Val Ser Asp Ile Ala Gly
    290                 295                 300

Thr Tyr Tyr Trp His Ile Pro Thr Gly Thr Thr Gln Trp Glu Arg Pro
305                 310                 315                 320

Val Ser Ile Pro Ala Asp Leu Gln Gly Ser Arg Lys Gly Ser Leu Ser
                325                 330                 335

Ser Val Thr Pro Ser Pro Thr Pro Glu Asn Glu Asp Leu His Ala Ala
            340                 345                 350

Thr Val Asn Pro Asp Pro Ser Leu Lys Glu Phe Glu Gly Ala Thr Leu
        355                 360                 365

Arg Tyr Ala Ser Leu Lys Leu Arg Asn Ala Pro His Pro Asp Asp Asp
    370                 375                 380

Asp Ser Cys Ser Ile Asn Ser Asp Pro Glu Ala Lys Cys Phe Ala Val
385                 390                 395                 400

Arg Ser Leu Gly Trp Val Glu Met Ala Glu Glu Asp Leu Ala Pro Gly
                405                 410                 415

Lys Ser Ser Val Ala Val Asn Asn Cys Ile Arg Gln Leu Ser Tyr Cys
            420                 425                 430

Lys Asn Asp Ile Arg Asp Thr Val Gly Ile Trp Gly Glu Gly Lys Asp
        435                 440                 445

Met Tyr Leu Ile Leu Glu Asn Asp Met Leu Ser Leu Val Asp Pro Met
    450                 455                 460

Asp Arg Ser Val Leu His Ser Gln Pro Ile Val Ser Ile Arg Val Trp
465                 470                 475                 480

Gly Val Gly Arg Asp Asn Gly Arg Asp Phe Ala Tyr Val Ala Arg Asp
                485                 490                 495

Lys Asp Thr Arg Ile Leu Lys Cys His Val Phe Arg Cys Asp Thr Pro
            500                 505                 510

Ala Lys Ala Ile Ala Thr Ser Leu His Glu Ile Cys Ser Lys Ile Met
        515                 520                 525

Ala Glu Arg Lys Asn Ala Lys Ala Leu Ala Cys Ser Ser Leu Gln Glu
    530                 535                 540

Arg Ala Asn Val Asn Leu Asp Val Pro Leu Gln Asp Phe Pro Thr Pro
545                 550                 555                 560

Lys Thr Glu Leu Val Gln Lys Phe His Val Gln Tyr Leu Gly Met Leu
                565                 570                 575

Pro Val Asp Lys Pro Val Gly Met Asp Ile Leu Asn Ser Ala Ile Glu
            580                 585                 590

Asn Leu Met Thr Ser Ser Asn Lys Glu Asp Trp Leu Ser Val Asn Met
        595                 600                 605

Asn Val Ala Asp Ala Thr Val Thr Val Ile Ser Glu Lys Asn Glu Glu
    610                 615                 620

Glu Val Leu Val Glu Cys Arg Val Arg Phe Leu Ser Phe Met Gly Val
625                 630                 635                 640

Gly Lys Asp Val His Thr Phe Ala Phe Ile Met Asp Thr Gly Asn Gln
                645                 650                 655

Arg Phe Glu Cys His Val Phe Trp Cys Glu Pro Asn Ala Gly Asn Val
            660                 665                 670
```

```
Ser Glu Ala Val Gln Ala Ala Cys Met Leu Arg Tyr Gln Lys Cys Leu
        675                 680                 685

Val Ala Arg Pro Pro Ser Gln Lys Val Arg Pro Pro Pro Pro Ala
    690                 695                 700

Asp Ser Val Thr Arg Arg Val Thr Thr Asn Val Lys Arg Gly Val Leu
705                 710                 715                 720

Ser Leu Ile Asp Thr Leu Lys Gln Lys Arg Pro Val Thr Glu Met Pro
                725                 730                 735


<210> SEQ ID NO 7
<211> LENGTH: 562
<212> TYPE: DNA
<213> ORGANISM: Homo sapiens

<400> SEQUENCE: 7

ctggaattga ggctgagcca aagaccccag ggccgtctca gtctcataaa aggggatcag      60

gcaggaggag tttgggagaa acctgagaag ggcctgattt gcagcatcat gatgggcctc     120

tccttggcct ctgctgtgct cctggcctcc ctcctgagtc tccaccttgg aactgccaca     180

cgtgggagtg acatatccaa gacctgctgc ttccaataca gccacaagcc ccttccctgg     240

acctgggtgc gaagctatga attcaccagt aacagctgct cccagcgggc tgtgatattc     300

actaccaaaa gaggcaagaa agtctgtacc catccaagga aaaaatgggt gcaaaaatac     360

atttctttac tgaaaactcc gaaacaattg tgactcagct gaattttcat ccgaggacgc     420

ttggaccccg ctcttggctc tgcagccctc tggggagcct gcggaatctt ttctgaaggc     480

tacatggacc cgctggggag gagagggtgt ttcctcccag agttacttta ataaaggttg     540

ttcatagagt tgacttgttc at                                              562


<210> SEQ ID NO 8
<211> LENGTH: 94
<212> TYPE: PRT
<213> ORGANISM: Homo sapiens

<400> SEQUENCE: 8

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
            20                  25                  30

Cys Cys Phe Gln Tyr Ser His Lys Pro Leu Pro Trp Thr Trp Val Arg
        35                  40                  45

Ser Tyr Glu Phe Thr Ser Asn Ser Cys Ser Gln Arg Ala Val Ile Phe
    50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
                85                  90


<210> SEQ ID NO 9
<211> LENGTH: 1697
<212> TYPE: DNA
<213> ORGANISM: Homo sapiens

<400> SEQUENCE: 9

gaggcgtaag ccaggcgtgt taaagccggt cggaactgct ccggagggca cgggctccgt      60

aggcaccaac tgcaaggacc cctccccctg cgggcgctcc catggcacag ttcgcgttcg     120
```

-continued agagtgacct gcactcgctg cttcagctgg atgcacccat ccccaatgca ccccctgcgc 180
gctggcagcg caaagccaag gaagccgcag gcccggcccc ctcacccatg cgggccgcca 240
accgatccca cagcgccggc aggactccgg gccgaactcc tggcaaatcc agttccaagg 300
ttcagaccac tcctagcaaa cctggcggtg accgctatat cccccatcgc agtgctgccc 360
agatggaggt ggccagcttc ctcctgagca aggagaacca gcctgaaaac agccagacgc 420
ccaccaagaa ggaacatcag aaagcctggg ctttgaacct gaacggtttt gatgtagagg 480
aagccaagat ccttcggctc agtggaaaac cacaaaatgc gccagagggt tatcagaaca 540
gactgaaagt actctacagc caaaaggcca ctcctggctc cagccggaag acctgccgtt 600
acattccttc cctgccagac cgtatcctgg atgcgcctga aatccgaaat gactattacc 660
tgaaccttgt ggattggagt tctgggaatg tactggccgt ggcactggac aacagtgtgt 720
acctgtggag tgcaagctct ggtgacatcc tgcagctttt gcaaatggag cagcctgggg 780
aatatatatc ctctgtggcc tggatcaaag agggcaacta cttggctgtg ggcaccagca 840
gtgctgaggt gcagctatgg gatgtgcagc agcagaaacg gcttcgaaat atgaccagtc 900
actctgcccg agtgggctcc ctaagctgga acagctatat cctgtccagt ggttcacgtt 960
ctggccacat ccaccaccat gatgttcggg tagcagaaca ccatgtggcc acactgagtg 1020
gccacagcca ggaagtgtgt gggctgcgct gggccccaga tggacgacat ttggccagtg 1080
gtggtaatga taacttggtc aatgtgtggc ctagtgctcc tggagagggt ggctgggttc 1140
ctctgcagac attcacccag catcaagggg ctgtcaaggc cgtagcatgg tgtccctggc 1200
agtccaatgt cctggcaaca ggagggggca ccagtgatcg acacattcgc atctggaatg 1260
tgtgctctgg ggcctgtctg agtgccgtgg atgcccattc ccaggtgtgc tccatcctct 1320
ggtctcccca ttacaaggag ctcatctcag gccatggctt tgcacagaac cagctagtta 1380
tttggaagta cccaaccatg gccaaggtgg ctgaactcaa aggtcacaca tcccgggtcc 1440
tgagtctgac catgagccca gatggggcca cagtggcatc cgcagcagca gatgagaccc 1500
tgaggctatg gcgctgtttt gagttggacc ctgcgcggcg gcgggagcgg gagaaggcca 1560
gtgcagccaa aagcagcctc atccaccaag gcatccgctg aagaccaacc catcacctca 1620
gttgtttttt atttttctaa taaagtcatg tctcccttca tgtttttttt ttaaaaaaaa 1680
aaaaaaaaaa aaaaaaa 1697

<210> SEQ ID NO 10
<211> LENGTH: 499
<212> TYPE: PRT
<213> ORGANISM: Homo sapiens

<400> SEQUENCE: 10

Met Ala Gln Phe Ala Phe Glu Ser Asp Leu His Ser Leu Leu Gln Leu
1 5 10 15

Asp Ala Pro Ile Pro Asn Ala Pro Pro Ala Arg Trp Gln Arg Lys Ala
20 25 30

Lys Glu Ala Ala Gly Pro Ala Pro Ser Pro Met Arg Ala Ala Asn Arg
35 40 45

Ser His Ser Ala Gly Arg Thr Pro Gly Arg Thr Pro Gly Lys Ser Ser
50 55 60

Ser Lys Val Gln Thr Thr Pro Ser Lys Pro Gly Gly Asp Arg Tyr Ile
65 70 75 80

Pro His Arg Ser Ala Ala Gln Met Glu Val Ala Ser Phe Leu Leu Ser
85 90 95

```
Lys Glu Asn Gln Pro Glu Asn Ser Gln Thr Pro Thr Lys Lys Glu His
            100                 105                 110

Gln Lys Ala Trp Ala Leu Asn Leu Asn Gly Phe Asp Val Glu Glu Ala
        115                 120                 125

Lys Ile Leu Arg Leu Ser Gly Lys Pro Gln Asn Ala Pro Glu Gly Tyr
    130                 135                 140

Gln Asn Arg Leu Lys Val Leu Tyr Ser Gln Lys Ala Thr Pro Gly Ser
145                 150                 155                 160

Ser Arg Lys Thr Cys Arg Tyr Ile Pro Ser Leu Pro Asp Arg Ile Leu
                165                 170                 175

Asp Ala Pro Glu Ile Arg Asn Asp Tyr Tyr Leu Asn Leu Val Asp Trp
            180                 185                 190

Ser Ser Gly Asn Val Leu Ala Val Ala Leu Asp Asn Ser Val Tyr Leu
        195                 200                 205

Trp Ser Ala Ser Ser Gly Asp Ile Leu Gln Leu Leu Gln Met Glu Gln
    210                 215                 220

Pro Gly Glu Tyr Ile Ser Ser Val Ala Trp Ile Lys Glu Gly Asn Tyr
225                 230                 235                 240

Leu Ala Val Gly Thr Ser Ser Ala Glu Val Gln Leu Trp Asp Val Gln
                245                 250                 255

Gln Gln Lys Arg Leu Arg Asn Met Thr Ser His Ser Ala Arg Val Gly
            260                 265                 270

Ser Leu Ser Trp Asn Ser Tyr Ile Leu Ser Ser Gly Ser Arg Ser Gly
        275                 280                 285

His Ile His His His Asp Val Arg Val Ala Glu His His Val Ala Thr
    290                 295                 300

Leu Ser Gly His Ser Gln Glu Val Cys Gly Leu Arg Trp Ala Pro Asp
305                 310                 315                 320

Gly Arg His Leu Ala Ser Gly Gly Asn Asp Asn Leu Val Asn Val Trp
                325                 330                 335

Pro Ser Ala Pro Gly Glu Gly Gly Trp Val Pro Leu Gln Thr Phe Thr
            340                 345                 350

Gln His Gln Gly Ala Val Lys Ala Val Ala Trp Cys Pro Trp Gln Ser
        355                 360                 365

Asn Val Leu Ala Thr Gly Gly Gly Thr Ser Asp Arg His Ile Arg Ile
    370                 375                 380

Trp Asn Val Cys Ser Gly Ala Cys Leu Ser Ala Val Asp Ala His Ser
385                 390                 395                 400

Gln Val Cys Ser Ile Leu Trp Ser Pro His Tyr Lys Glu Leu Ile Ser
                405                 410                 415

Gly His Gly Phe Ala Gln Asn Gln Leu Val Ile Trp Lys Tyr Pro Thr
            420                 425                 430

Met Ala Lys Val Ala Glu Leu Lys Gly His Thr Ser Arg Val Leu Ser
        435                 440                 445

Leu Thr Met Ser Pro Asp Gly Ala Thr Val Ala Ser Ala Ala Ala Asp
    450                 455                 460

Glu Thr Leu Arg Leu Trp Arg Cys Phe Glu Leu Asp Pro Ala Arg Arg
465                 470                 475                 480

Arg Glu Arg Glu Lys Ala Ser Ala Ala Lys Ser Ser Leu Ile His Gln
                485                 490                 495

Gly Ile Arg
```

<210> SEQ ID NO 11
<211> LENGTH: 5478
<212> TYPE: DNA
<213> ORGANISM: Homo sapiens

<400> SEQUENCE: 11

```
gcccaccggg cgagcttcta gtcggcgatt gaaggatgcg agtgctcctt aagggcctcc     60
gccccgtgag ttcggttgtg actaggaagg agctagtgga ctagagccag ggtaagggga    120
tctgctagaa gttggtcttc cgccaggact agagtttcct cgcggtaaca gcctccgtgg    180
cctccggagg accatgtcat tagactttgg cagtgtggca ctaccagtgc aaaatgaaga    240
tgaagagtat gacgaagagg actatgaaag agagaaagag ttgcagcagt tactcacaga    300
ccttccccat gacatgctgg atgacgacct ctcctctcca gagctccagt attcggactg    360
cagcgaggat ggcacagacg gacaaccaca tcatcctgag caattggaga tgagctggaa    420
tgagcaaatg ctgcccaaat ctcaaagtgt aaatggctat aatgaaattc agagtttata    480
tgctggagaa aaatgtggta atgtctggga agaaaataga agtaaaactg aagaccgaca    540
tcctgtgtac catcctgaag aaggtggaga tgaaggtgga agtggttata gtcctccaag    600
taaatgtgaa cagactgatt tatatcacct tcctgaaaac tttaggccat ataccaatgg    660
tcagaagcag gaatttaata accaagcaac caatgtaatt aaattttcag atcctcaatg    720
gaaccatttt cagggtccca gttgtcaagg tttggaaccg tataataaag tgacatataa    780
accttatcag tcttctgccc agaataatgg ctcaccagcc caggagataa caggaagtga    840
cacattcgaa ggcctgcaac aacaattttt aggagctaat gagaactctg cagaaaatat    900
gcagattatt caacttcagg ttcttaacaa agcaaaagag agacaactgg agaacttaat    960
tgaaaagtta aatgaaagtg aacgtcaaat tcgatatctg aatcaccagc ttgtaataat   1020
aaaagatgaa aaggatggtt tgactctcag ccttcgagaa tcacagaaac tctttcagaa   1080
tggaaaagaa agagagatac agcttgaagc tcaaataaaa gcactggaga ctcagataca   1140
agcattaaaa gtcaatgaag aacagatgat caagaagtcc agaacaactg aaatggctct   1200
ggaaagcttg aagcagcagc tggtggacct tcatcattct gaatcacttc aacgagctag   1260
agaacagcat gagagcattg ttatgggcct cacaaagaag tacgaagagc aagtattgtc   1320
cttacaaaag aatttggatg ccacagtcac cgcacttaaa gaacaggaag acatttgctc   1380
tcgtctgaaa gatcacgtga aacaactgga aaggaatcaa gaagcaatca agttagaaaa   1440
gactgagatc attaataagt tgacaagaag tctagaggag agtcaaaagc agtgtgccca   1500
cttgttgcag tccgggtcag tacaagaggt ggctcagcta cagttccagc tgcagcaagc   1560
acagaaggca catgctatga gtgcaaacat gaacaaggct ttgcaagaag aattaacaga   1620
actaaaagat gaaatttctc tctatgaatc tgctgcaaaa ctaggaatac atccaagtga   1680
ctcagaagga gaattaaata tagaactcac tgaatcgtat gtggatttgg gtattaaaaa   1740
ggtcaactgg aaaaaatcca aagttaccag cattgtacaa gaagaagacc caaatgaaga   1800
gctttcaaaa gatgagttca ttctgaagtt aaaggcagaa gtacagcgtt tgctgggtag   1860
caactcaatg aagcgtcatc tggtgtctca gttacaaaat gacctcaaag actgtcataa   1920
gaaaattgaa gatctccacc aagtgaagaa ggatgaaaaa agcattgagg ttgagactaa   1980
aacagatacc tcagaaaaac caaagaatca attatggcct gagtcttcta cttctgatgt   2040
tgtcagagat gatattctgc tgcttaaaaa tgaaattcaa gttttacaac aacaaaatca   2100
ggaacttaaa gaaactgaag gaaaactgag aaatacaaat caagacttat gtaatcaaat   2160
```

-continued

```
gagacaaatg gtacaagatt ttgaccatga caaacaagaa gctgtggata ggtgtgaaag   2220
gacttatcag cagcaccatg aagccatgaa aactcaaata cgtgaaagcc tattagcaaa   2280
gcatgctttg gagaagcagc agctctttga ggcttatgag agaactcatt tgcaactgag   2340
gtctgagttg gataagttga ataaggaggt gactgctgtg caggaatgtt acctagaagt   2400
gtgcagagag aaggataatc tagaattgac tctcaggaag accactgaaa aggagcaaca   2460
gactcaggag aagatcaaag aaaaactcat tcaacagctt gaaaaggagt ggcagtctaa   2520
gctggatcaa actataaagg caatgaaaaa gaagacctta gattgtggca gccaaactga   2580
ccaagtaacc accagtgatg ttatttccaa gaaagagatg gcaattatga tagaagagca   2640
gaagtgcaca atccagcaaa acttagaaca agagaaggac atagccatca agggggctat   2700
gaagaaactc gaaattgaat tggaactcaa acattgtgaa aatattacca aacaggtaga   2760
aatagctgtg caaaatgctc atcagcgatg gctgggagaa ctaccagagc tggcagagta   2820
tcaagcactt gtgaaggcag aacagaaaaa gtgggaagaa cagcatgagg tctctgtgaa   2880
caaaaggata tcatttgctg tttctgaagc taaagagaaa tggaagagtg agcttgaaaa   2940
tatgaggaaa aatatacttc ctggaaagga attggaagag aagattcatt ctcttcagaa   3000
ggaacttgag ttaaagaacg aagaagtccc tgtggtcatc agggctgagt tagctaaggc   3060
tcggagtgaa tggaacaaag aaaagcaaga agaaatccac agaatccaag aacaaaatga   3120
gcaagattac cggcaatttt tagatgatca ccgaaataaa attaatgagg tgcttgcggc   3180
agctaaagaa gactttatga aacaaaaaac tgaactactt cttcagaagg agacagaatt   3240
acaaacttgt ctagaccaga gtcgtagaga atggactatg caggaagcca agcggatcca   3300
actggaaatc tatcagtatg aggaagacat cctgactgta cttggggttc ttttaagtga   3360
tacccaaaag gagcacatca gtgattctga ggacaagcag cttttggaaa tcatgtcgac   3420
ttgttcttca aaatggatgt ctgtgcaata ttttgaaaaa ctaaagggct gcatacagaa   3480
agcatttcaa gatacacttc ctctgcttgt agaaaacgct gacccagaat ggaaaaagag   3540
aaatatggcc gagctctcta aggattctgc cagccagggc actggccaag gagaccctgg   3600
acctgctgct ggacaccatg ctcagccctt ggccttacaa gcaacagaag cagaagctga   3660
agagaataat aaagttgttg aagaattaat agaagaaaac aacgacatga agaataaatt   3720
ggaagaattg caaacacttt gtaaaacacc accaaggtca ttgtcagcag ggccattga    3780
aaatgcttgc ctgccatgca gtgggggagc cttggaagaa cttcgtgggc agtacattaa   3840
agctgtaaaa aaaattaaat gtgacatgct tcgttatatt caggagagta aggaacgagc   3900
tgcagaaatg gtaaaagcag aggtactgcg agaacgtcaa gaaaccgccc gaaagatgcg   3960
caaatattat ttgatttgcc tccaacagat tttgcaggat gatggaaaag aaggggctga   4020
gaaaaagatt atgaatgctg ctagcaaact tgctacaatg gcaaaattac tggaaacacc   4080
tatttctagt aagtcccaaa gcaaaactac acagtcagca ctgcccctaa cttcagagat   4140
gctgattgca gttaaaaaat caaaaagaaa tgatgtgaat cagaaaatac catgttgtat   4200
tgaaagcaaa tcaaatagtg taaacaccat caccagaact ctgtgcgaac aagctcccaa   4260
gaggagggca gcttgtaact tacaaaggct gttagagaac tcagagcatc agagcataaa   4320
gcatgtggga tccaaagaga cacatttgga attccagttt ggggatggta gttgcaagca   4380
cctaaacagt ttgccaagga atgtttctcc tgagtttgtt ccttgtgaag gtgaaggagg   4440
ctttggtttg cacaagaaga aagacctact cagtgataat ggttctgaat cacttccgca   4500
ttcagctgca taccccttc ttggaacctt aggaaataaa ccctcaccta gatgtacccc    4560
```

-continued

```
tggtccttct gaatcaggat gcatgcatat aacctttcgc gattctaatg aaagacttgg   4620

tttaaaagta tataaatgca atccactaat ggaaagtgaa aatgctgcat ctgagaaaag   4680

tcaaggtttg gatgttcagg aacctccagt aaaagatgga ggggacctta gtgactgctt   4740

gggctggcct tccagcagtg caaccttatc ctttgacagt cgtgaagcat catttgtaca   4800

tggtaggcca caaggaactt tggaaatacc aagtgaatct gttaaatcca aacagttttc   4860

accatccggt tatctttcag atacagagga aagtaatatg atttgtcaaa caatgaaatg   4920

tcagcgttat caaactccat acctgtcaga agaaaccacg tatttggagc caggaaagat   4980

cagtgtgaat tgtggacacc catctcgtca taaggctgat agattaaagt cagatttcaa   5040

aaaactgagc agtacattac catcttcagt gtgtcagcag ccttcaagaa aattaattgt   5100

tccgctatct agccaacaag atagtggctt tgatagccca tttgttaatc tagactaatt   5160

atggtacagt atttaagaag aatcattaat atattaacaa aaatggaagg gaagacctca   5220

tactgaaaaa aattgtgagc cctgcctctt ttgagatgtt ttaataacat ctgttatata   5280

agtaaagcat tcttctaaaa ttgcttgaga tatttatgtt gccttaatat tccaaaggcc   5340

tgatggtgta tgtataatct gcttttgtgt ggtgcttatt tttggtttct aaaccatcta   5400

tttttatact tataaattga ctcactctgc agtgttaact tatttaaata aacttgcata   5460

tggtctgtaa aaaaaaaa                                                 5478
```

<210> SEQ ID NO 12
<211> LENGTH: 1654
<212> TYPE: PRT
<213> ORGANISM: Homo sapiens

<400> SEQUENCE: 12

```
Met Ser Leu Asp Phe Gly Ser Val Ala Leu Pro Val Gln Asn Glu Asp
1               5                   10                  15

Glu Glu Tyr Asp Glu Glu Asp Tyr Glu Arg Glu Lys Glu Leu Gln Gln
            20                  25                  30

Leu Leu Thr Asp Leu Pro His Asp Met Leu Asp Asp Asp Leu Ser Ser
        35                  40                  45

Pro Glu Leu Gln Tyr Ser Asp Cys Ser Glu Asp Gly Thr Asp Gly Gln
    50                  55                  60

Pro His His Pro Glu Gln Leu Glu Met Ser Trp Asn Glu Gln Met Leu
65                  70                  75                  80

Pro Lys Ser Gln Ser Val Asn Gly Tyr Asn Glu Ile Gln Ser Leu Tyr
                85                  90                  95

Ala Gly Glu Lys Cys Gly Asn Val Trp Glu Glu Asn Arg Ser Lys Thr
            100                 105                 110

Glu Asp Arg His Pro Val Tyr His Pro Glu Glu Gly Gly Asp Glu Gly
        115                 120                 125

Gly Ser Gly Tyr Ser Pro Pro Ser Lys Cys Glu Gln Thr Asp Leu Tyr
    130                 135                 140

His Leu Pro Glu Asn Phe Arg Pro Tyr Thr Asn Gly Gln Lys Gln Glu
145                 150                 155                 160

Phe Asn Asn Gln Ala Thr Asn Val Ile Lys Phe Ser Asp Pro Gln Trp
                165                 170                 175

Asn His Phe Gln Gly Pro Ser Cys Gln Gly Leu Glu Pro Tyr Asn Lys
            180                 185                 190

Val Thr Tyr Lys Pro Tyr Gln Ser Ser Ala Gln Asn Asn Gly Ser Pro
        195                 200                 205
```

```
Ala Gln Glu Ile Thr Gly Ser Asp Thr Phe Glu Gly Leu Gln Gln Gln
    210                 215                 220

Phe Leu Gly Ala Asn Glu Asn Ser Ala Glu Asn Met Gln Ile Ile Gln
225                 230                 235                 240

Leu Gln Val Leu Asn Lys Ala Lys Glu Arg Gln Leu Glu Asn Leu Ile
                245                 250                 255

Glu Lys Leu Asn Glu Ser Glu Arg Gln Ile Arg Tyr Leu Asn His Gln
            260                 265                 270

Leu Val Ile Ile Lys Asp Glu Lys Asp Gly Leu Thr Leu Ser Leu Arg
        275                 280                 285

Glu Ser Gln Lys Leu Phe Gln Asn Gly Lys Glu Arg Glu Ile Gln Leu
    290                 295                 300

Glu Ala Gln Ile Lys Ala Leu Glu Thr Gln Ile Gln Ala Leu Lys Val
305                 310                 315                 320

Asn Glu Glu Gln Met Ile Lys Lys Ser Arg Thr Thr Glu Met Ala Leu
                325                 330                 335

Glu Ser Leu Lys Gln Gln Leu Val Asp Leu His His Ser Glu Ser Leu
            340                 345                 350

Gln Arg Ala Arg Glu Gln His Glu Ser Ile Val Met Gly Leu Thr Lys
        355                 360                 365

Lys Tyr Glu Glu Gln Val Leu Ser Leu Gln Lys Asn Leu Asp Ala Thr
    370                 375                 380

Val Thr Ala Leu Lys Glu Gln Glu Asp Ile Cys Ser Arg Leu Lys Asp
385                 390                 395                 400

His Val Lys Gln Leu Glu Arg Asn Gln Glu Ala Ile Lys Leu Glu Lys
                405                 410                 415

Thr Glu Ile Ile Asn Lys Leu Thr Arg Ser Leu Glu Glu Ser Gln Lys
            420                 425                 430

Gln Cys Ala His Leu Leu Gln Ser Gly Ser Val Gln Glu Val Ala Gln
        435                 440                 445

Leu Gln Phe Gln Leu Gln Gln Ala Gln Lys Ala His Ala Met Ser Ala
    450                 455                 460

Asn Met Asn Lys Ala Leu Gln Glu Glu Leu Thr Glu Leu Lys Asp Glu
465                 470                 475                 480

Ile Ser Leu Tyr Glu Ser Ala Ala Lys Leu Gly Ile His Pro Ser Asp
                485                 490                 495

Ser Glu Gly Glu Leu Asn Ile Glu Leu Thr Glu Ser Tyr Val Asp Leu
            500                 505                 510

Gly Ile Lys Lys Val Asn Trp Lys Lys Ser Lys Val Thr Ser Ile Val
        515                 520                 525

Gln Glu Glu Asp Pro Asn Glu Glu Leu Ser Lys Asp Glu Phe Ile Leu
    530                 535                 540

Lys Leu Lys Ala Glu Val Gln Arg Leu Leu Gly Ser Asn Ser Met Lys
545                 550                 555                 560

Arg His Leu Val Ser Gln Leu Gln Asn Asp Leu Lys Asp Cys His Lys
                565                 570                 575

Lys Ile Glu Asp Leu His Gln Val Lys Lys Asp Glu Lys Ser Ile Glu
            580                 585                 590

Val Glu Thr Lys Thr Asp Thr Ser Glu Lys Pro Lys Asn Gln Leu Trp
        595                 600                 605

Pro Glu Ser Ser Thr Ser Asp Val Val Arg Asp Asp Ile Leu Leu Leu
    610                 615                 620
```

```
Lys Asn Glu Ile Gln Val Leu Gln Gln Gln Asn Gln Glu Leu Lys Glu
625                 630                 635                 640

Thr Glu Gly Lys Leu Arg Asn Thr Asn Gln Asp Leu Cys Asn Gln Met
                645                 650                 655

Arg Gln Met Val Gln Asp Phe Asp His Asp Lys Gln Glu Ala Val Asp
            660                 665                 670

Arg Cys Glu Arg Thr Tyr Gln Gln His His Glu Ala Met Lys Thr Gln
        675                 680                 685

Ile Arg Glu Ser Leu Leu Ala Lys His Ala Leu Glu Lys Gln Gln Leu
    690                 695                 700

Phe Glu Ala Tyr Glu Arg Thr His Leu Gln Leu Arg Ser Glu Leu Asp
705                 710                 715                 720

Lys Leu Asn Lys Glu Val Thr Ala Val Gln Glu Cys Tyr Leu Glu Val
                725                 730                 735

Cys Arg Glu Lys Asp Asn Leu Glu Leu Thr Leu Arg Lys Thr Thr Glu
            740                 745                 750

Lys Glu Gln Gln Thr Gln Glu Lys Ile Lys Glu Lys Leu Ile Gln Gln
        755                 760                 765

Leu Glu Lys Glu Trp Gln Ser Lys Leu Asp Gln Thr Ile Lys Ala Met
    770                 775                 780

Lys Lys Lys Thr Leu Asp Cys Gly Ser Gln Thr Asp Gln Val Thr Thr
785                 790                 795                 800

Ser Asp Val Ile Ser Lys Lys Glu Met Ala Ile Met Ile Glu Glu Gln
                805                 810                 815

Lys Cys Thr Ile Gln Gln Asn Leu Glu Gln Glu Lys Asp Ile Ala Ile
            820                 825                 830

Lys Gly Ala Met Lys Lys Leu Glu Ile Glu Leu Glu Leu Lys His Cys
        835                 840                 845

Glu Asn Ile Thr Lys Gln Val Glu Ile Ala Val Gln Asn Ala His Gln
    850                 855                 860

Arg Trp Leu Gly Glu Leu Pro Glu Leu Ala Glu Tyr Gln Ala Leu Val
865                 870                 875                 880

Lys Ala Glu Gln Lys Lys Trp Glu Glu Gln His Glu Val Ser Val Asn
                885                 890                 895

Lys Arg Ile Ser Phe Ala Val Ser Glu Ala Lys Glu Lys Trp Lys Ser
            900                 905                 910

Glu Leu Glu Asn Met Arg Lys Asn Ile Leu Pro Gly Lys Glu Leu Glu
        915                 920                 925

Glu Lys Ile His Ser Leu Gln Lys Glu Leu Glu Leu Lys Asn Glu Glu
    930                 935                 940

Val Pro Val Val Ile Arg Ala Glu Leu Ala Lys Ala Arg Ser Glu Trp
945                 950                 955                 960

Asn Lys Glu Lys Gln Glu Glu Ile His Arg Ile Gln Glu Gln Asn Glu
                965                 970                 975

Gln Asp Tyr Arg Gln Phe Leu Asp Asp His Arg Asn Lys Ile Asn Glu
            980                 985                 990

Val Leu Ala Ala Ala Lys Glu Asp  Phe Met Lys Gln Lys  Thr Glu Leu
        995                 1000                1005

Leu Leu  Gln Lys Glu Thr Glu  Leu Gln Thr Cys Leu  Asp Gln Ser
    1010                1015                1020

Arg Arg  Glu Trp Thr Met Gln  Glu Ala Lys Arg Ile  Gln Leu Glu
    1025                1030                1035

Ile Tyr  Gln Tyr Glu Glu Asp  Ile Leu Thr Val Leu  Gly Val Leu
```

```
    1040                1045                1050

Leu Ser  Asp Thr Gln Lys Glu  His Ile Ser Asp Ser  Glu Asp Lys
    1055                1060                1065

Gln Leu  Leu Glu Ile Met Ser  Thr Cys Ser Ser Lys  Trp Met Ser
    1070                1075                1080

Val Gln  Tyr Phe Glu Lys Leu  Lys Gly Cys Ile Gln  Lys Ala Phe
    1085                1090                1095

Gln Asp  Thr Leu Pro Leu Leu  Val Glu Asn Ala Asp  Pro Glu Trp
    1100                1105                1110

Lys Lys  Arg Asn Met Ala Glu  Leu Ser Lys Asp Ser  Ala Ser Gln
    1115                1120                1125

Gly Thr  Gly Gln Gly Asp Pro  Gly Pro Ala Ala Gly  His His Ala
    1130                1135                1140

Gln Pro  Leu Ala Leu Gln Ala  Thr Glu Ala Glu Ala  Glu Glu Asn
    1145                1150                1155

Asn Lys  Val Val Glu Glu Leu  Ile Glu Glu Asn Asn  Asp Met Lys
    1160                1165                1170

Asn Lys  Leu Glu Glu Leu Gln  Thr Leu Cys Lys Thr  Pro Pro Arg
    1175                1180                1185

Ser Leu  Ser Ala Gly Ala Ile  Glu Asn Ala Cys Leu  Pro Cys Ser
    1190                1195                1200

Gly Gly  Ala Leu Glu Glu Leu  Arg Gly Gln Tyr Ile  Lys Ala Val
    1205                1210                1215

Lys Lys  Ile Lys Cys Asp Met  Leu Arg Tyr Ile Gln  Glu Ser Lys
    1220                1225                1230

Glu Arg  Ala Ala Glu Met Val  Lys Ala Glu Val Leu  Arg Glu Arg
    1235                1240                1245

Gln Glu  Thr Ala Arg Lys Met  Arg Lys Tyr Tyr Leu  Ile Cys Leu
    1250                1255                1260

Gln Gln  Ile Leu Gln Asp Asp  Gly Lys Glu Gly Ala  Glu Lys Lys
    1265                1270                1275

Ile Met  Asn Ala Ala Ser Lys  Leu Ala Thr Met Ala  Lys Leu Leu
    1280                1285                1290

Glu Thr  Pro Ile Ser Ser Lys  Ser Gln Ser Lys Thr  Thr Gln Ser
    1295                1300                1305

Ala Leu  Pro Leu Thr Ser Glu  Met Leu Ile Ala Val  Lys Lys Ser
    1310                1315                1320

Lys Arg  Asn Asp Val Asn Gln  Lys Ile Pro Cys Cys  Ile Glu Ser
    1325                1330                1335

Lys Ser  Asn Ser Val Asn Thr  Ile Thr Arg Thr Leu  Cys Glu Gln
    1340                1345                1350

Ala Pro  Lys Arg Arg Ala Ala  Cys Asn Leu Gln Arg  Leu Leu Glu
    1355                1360                1365

Asn Ser  Glu His Gln Ser Ile  Lys His Val Gly Ser  Lys Glu Thr
    1370                1375                1380

His Leu  Glu Phe Gln Phe Gly  Asp Gly Ser Cys Lys  His Leu Asn
    1385                1390                1395

Ser Leu  Pro Arg Asn Val Ser  Pro Glu Phe Val Pro  Cys Glu Gly
    1400                1405                1410

Glu Gly  Gly Phe Gly Leu His  Lys Lys Lys Asp Leu  Leu Ser Asp
    1415                1420                1425

Asn Gly  Ser Glu Ser Leu Pro  His Ser Ala Ala Tyr  Pro Phe Leu
    1430                1435                1440
```

```
Gly Thr  Leu Gly Asn Lys Pro  Ser Pro Arg Cys Thr  Pro Gly Pro
    1445                 1450                 1455

Ser Glu  Ser Gly Cys Met His  Ile Thr Phe Arg Asp  Ser Asn Glu
    1460                 1465                 1470

Arg Leu  Gly Leu Lys Val Tyr  Lys Cys Asn Pro Leu  Met Glu Ser
    1475                 1480                 1485

Glu Asn  Ala Ala Ser Glu Lys  Ser Gln Gly Leu Asp  Val Gln Glu
    1490                 1495                 1500

Pro Pro  Val Lys Asp Gly Gly  Asp Leu Ser Asp Cys  Leu Gly Trp
    1505                 1510                 1515

Pro Ser  Ser Ser Ala Thr Leu  Ser Phe Asp Ser Arg  Glu Ala Ser
    1520                 1525                 1530

Phe Val  His Gly Arg Pro Gln  Gly Thr Leu Glu Ile  Pro Ser Glu
    1535                 1540                 1545

Ser Val  Lys Ser Lys Gln Phe  Ser Pro Ser Gly Tyr  Leu Ser Asp
    1550                 1555                 1560

Thr Glu  Glu Ser Asn Met Ile  Cys Gln Thr Met Lys  Cys Gln Arg
    1565                 1570                 1575

Tyr Gln  Thr Pro Tyr Leu Ser  Glu Glu Thr Thr Tyr  Leu Glu Pro
    1580                 1585                 1590

Gly Lys  Ile Ser Val Asn Cys  Gly His Pro Ser Arg  His Lys Ala
    1595                 1600                 1605

Asp Arg  Leu Lys Ser Asp Phe  Lys Lys Leu Ser Ser  Thr Leu Pro
    1610                 1615                 1620

Ser Ser  Val Cys Gln Gln Pro  Ser Arg Lys Leu Ile  Val Pro Leu
    1625                 1630                 1635

Ser Ser  Gln Gln Asp Ser Gly  Phe Asp Ser Pro Phe  Val Asn Leu
    1640                 1645                 1650

Asp
```

<210> SEQ ID NO 13
<211> LENGTH: 1260
<212> TYPE: DNA
<213> ORGANISM: Homo sapiens

<400> SEQUENCE: 13

```
ggccggcggg aagactccgt tacccagcga gcgaggcggc ggcgcagggc cagcggactc     60

catttcccgt cggctcgcgg tgggagcgcc ggaagcccgc cccacccctc attgtgcggc    120

tcctactaaa cggaaggggc cgggagaggc cgcgttcagt cgggtcccgg cagcggctgc    180

agcgctctcg tcttctgcgg ctctcggtgc cctctccttt tcgtttccgg aaacatggcc    240

tccggtgtgg ctgtctctga tggtgtcatc aaggtgttca acgacatgaa ggtgcgtaag    300

tcttcaacgc cagaggaggt gaagaagcgc aagaaggcgg tgctcttctg cctgagtgag    360

gacaagaaga acatcatcct ggaggagggc aaggagatcc tggtgggcga tgtgggccag    420

actgtcgacg acccctacgc cacctttgtc aagatgctgc cagataagga ctgccgctat    480

gccctctatg atgcaaccta tgagaccaag gagagcaaga aggaggatct ggtgtttatc    540

ttctgggccc ccgagtctgc gccccttaag agcaaaatga tttatgccag ctccaaggac    600

gccatcaaga agaagctgac agggatcaag catgaattgc aagcaaactg ctacgaggag    660

gtcaaggacc gctgcaccct ggcagagaag ctgggggca gtgccgtcat ctccctggag    720

ggcaagcctt tgtgagcccc ttctggcccc ctgcctggag catctggcag ccccacacct    780
```

gcccttgggg gttgcaggct gccccccttcc tgccagaccg gaggggctgg ggggatccca 840
gcagggggag ggcaatccct tcaccccagt tgccaaacag accccccacc ccctggattt 900
tccttctccc tccatccctt gacggttctg gccttcccaa actgcttttg atcttttgat 960
tcctcttggg ctgaagcaga ccaagttccc cccaggcacc ccagttgtgg gggagcctgt 1020 attttttta acaacatccc cattccccac ctggtcctcc cccttcccat gctgccaact 1080
tctaaccgca atagtgactc tgtgcttgtc tgtttagttc tgtgtataaa tggaatgttg 1140
tggagatgac ccctccctgt gccggctggt tcctctccct tttcccctgg tcacggctac 1200
tcatggaagc aggaccagta agggaccttc gattaaaaaa aaaaaagaca ataataaaaa 1260

<210> SEQ ID NO 14
<211> LENGTH: 166
<212> TYPE: PRT
<213> ORGANISM: Homo sapiens

<400> SEQUENCE: 14

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 15
<211> LENGTH: 633
<212> TYPE: DNA
<213> ORGANISM: Homo sapiens

<400> SEQUENCE: 15
atgcgcgcaa gagagcggga agccgagctg ggcgagaagt aggggagggc ggtgctccgc 60
cgcggtggcg gttgctatcg cttcgcagaa cctactcagg cagccagctg agaagagttg 120
agggaaagtg ctgctgctgg gtctgcagac gcgatggata acgtgcagcc gaaaataaaa 180
catcgcccct tctgcttcag tgtgaaaggc cacgtgaaga tgctgcggct ggtgtttgca 240
cttgtgacag cagtatgctg tcttgccgac ggggccctta tttaccggaa gcttctgttc 300
aatcccagcg gtccttacca gaaaaagcct gtgcatgaaa aaaaagaagt tttgtaattt 360
tatattactt tttagtttga tactaagtat taaacatatt tctgtattct tccacatatt 420

```
ttctgcagtt attttaactc agtataggag ctagaggaag agatttccga agtctgcacc    480

ccgcgcagag cactactgta acttccaagg gagcgctggg agcagcggga tcgggttttc    540

cggcacccgg gcctgggtgg cagggaagaa tgtgccggga tccgcctcag ggatctttga    600

atctctttac tgcctggctg gccggcagct ccg                                 633


<210> SEQ ID NO 16
<211> LENGTH: 67
<212> TYPE: PRT
<213> ORGANISM: Homo sapiens

<400> SEQUENCE: 16

Met Asp Asn Val Gln Pro Lys Ile Lys His Arg Pro Phe Cys Phe Ser
1               5                   10                  15

Val Lys Gly His Val Lys Met Leu Arg Leu Val Phe Ala Leu Val Thr
            20                  25                  30

Ala Val Cys Cys Leu Ala Asp Gly Ala Leu Ile Tyr Arg Lys Leu Leu
        35                  40                  45

Phe Asn Pro Ser Gly Pro Tyr Gln Lys Lys Pro Val His Glu Lys Lys
    50                  55                  60

Glu Val Leu
65


<210> SEQ ID NO 17
<211> LENGTH: 9169
<212> TYPE: DNA
<213> ORGANISM: Homo sapiens

<400> SEQUENCE: 17

gatgacgctg cggcttctgg tggccgcgct ctgcgccggg atcctggcag aggcgccccg     60

agtgcgagcc cagcacaggg agagagtgac ctgcacgcgc ctttacgccg ctgacattgt    120

gttcttactg gatggctcct catccattgg ccgcagcaat ttccgcgagg tccgcagctt    180

tctcgaaggg ctggtgctgc ctttctctgg agcagccagt gcacagggtg tgcgctttgc    240

cacagtgcag tacagcgatg acccacggac agagttcggc ctggatgcac ttggctctgg    300

gggtgatgtg atccgcgcca tccgtgagct tagctacaag gggggcaaca ctcgcacagg    360

ggctgcaatt ctccatgtgg ctgaccatgt cttcctgccc cagctggccc gacctggtgt    420

ccccaaggtc tgcatcctga tcacagacgg gaagtcccag gacctggtgg acacagctgc    480

ccaaaggctg aaggggcagg gggtcaagct atttgctgtg gggatcaaga atgctgaccc    540

tgaggagctg aagcgagttg cctcacagcc caccagtgac ttcttcttct tcgtcaatga    600

cttcagcatc ttgaggacac tactgcccct cgtttcccgg agagtgtgca cgactgctgg    660

tggcgtgcct gtgacccgac ctccggatga ctcgacctct gctccacgag acctggtgct    720

gtctgagcca agcagccaat ccttgagagt acagtggaca gcggccagtg gccctgtgac    780

tggctacaag gtccagtaca ctcctctgac ggggctggga cagccactgc cgagtgagcg    840

gcaggaggtg aacgtcccag ctggtgagac cagtgtgcgg ctgcggggtc tccggccact    900

gaccgagtac caagtgactg tgattgccct ctacgccaac agcatcgggg aggctgtgag    960

cgggacagct cggaccactg ccctagaagg gccggaactg accatccaga ataccacagc   1020

ccacagcctc ctggtggcct ggcggagtgt gccaggtgcc actggctacc gtgtgacatg   1080

gcgggtcctc agtggtgggc ccacacagca gcaggagctg ggccctgggc agggttcagt   1140

gttgctgcgt gacttggagc ctggcacgga ctatgaggtg accgtgagca ccctatttgg   1200
```

```
ccgcagtgtg gggcccgcca cttccctgat ggctcgcact gacgcttctg ttgagcagac   1260
cctgcgcccg gtcatcctgg gccccacatc catcctcctt tcctggaact tggtgcctga   1320
ggcccgtggc taccggttgg aatggcggcg tgagactggc ttggagccac cgcagaaggt   1380
ggtactgccc tctgatgtga cccgctacca gttggatggg ctgcagccgg gcactgagta   1440
ccgcctcaca ctctacactc tgctggaggg ccacgaggtg gccacccctg caaccgtggt   1500
tcccactgga ccagagctgc ctgtgagccc tgtaacagac ctgcaagcca ccgagctgcc   1560
cgggcagcgg gtgcgagtgt cctggagccc agtccctggt gccacccagt accgcatcat   1620
tgtgcgcagc acccaggggg ttgagcggac cctggtgctt cctgggagtc agacagcatt   1680
cgacttggat gacgttcagg ctgggcttag ctacactgtg cgggtgtctg ctcgagtggg   1740
tccccgtgag ggcagtgcca gtgtcctcac tgtccgccgg gagccggaaa ctccacttgc   1800
tgttccaggg ctgcgggttg tggtgtcaga tgcaacgcga gtgagggtgg cctggggacc   1860
cgtccctgga gccagtggat ttcggattag ctggagcaca ggcagtggtc cggagtccag   1920
ccagacactg cccccagact ctactgccac agacatcaca gggctgcagc ctggaaccac   1980
ctaccaggtg gctgtgtcgg tactgcgagg cagagaggag ggccctgctg cagtcatcgt   2040
ggctcgaacg gacccactgg gcccagtgag gacggtccat gtgactcagg ccagcagctc   2100
atctgtcacc attacctgga ccagggttcc tggcgccaca ggatacaggg tttcctggca   2160
ctcagcccac ggcccagaga aatcccagtt ggtttctggg gaggccacgg tggctgagct   2220
ggatggactg gagccagata ctgagtatac ggtgcatgtg agggcccatg tggctggcgt   2280
ggatgggccc cctgcctctg tggttgtgag gactgcccct gagcctgtgg gtcgtgtgtc   2340
gaggctgcag atcctcaatg cttccagcga cgttctacgg atcacctggg taggggtcac   2400
tggagccaca gcttacagac tggcctgggg ccggagtgaa ggcggcccca tgaggcacca   2460
gatactccca ggaaacacag actctgcaga gatccggggt ctcgaaggtg gagtcagcta   2520
ctcagtgcga gtgactgcac ttgtcgggga ccgcgagggc acacctgtct ccattgttgt   2580
cactacgccg cctgaggctc cgccagccct ggggacgctt cacgtggtgc agcgcgggga   2640
gcactcgctg aggctgcgct gggagccggt gcccagagcg cagggcttcc ttctgcactg   2700
gcaacctgag ggtggccagg aacagtcccg ggtcctgggg cccgagctca gcagctatca   2760
cctggacggg ctggagccag cgacacagta ccgcgtgagg ctgagtgtcc tagggccagc   2820
tggagaaggg ccctctgcag aggtgactgc gcgcactgag tcacctcgtg ttccaagcat   2880
tgaactacgt gtggtggaca cctcgatcga ctcggtgact ttggcctgga ctccagtgtc   2940
cagggcatcc agctacatcc tatcctggcg gccactcaga ggccctggcc aggaagtgcc   3000
tgggtccccg cagacacttc cagggatctc aagctcccag cgggtgacag ggctagagcc   3060
tggcgtctct tacatcttct ccctgacgcc tgtcctggat ggtgtgcggg gtcctgaggc   3120
atctgtcaca cagacgccag tgtgcccccg tggcctggcg gatgtggtgt tcctaccaca   3180
tgccactcaa gacaatgctc accgtgcgga ggctacgagg agggtcctgg agcgtctggt   3240
gttggcactt gggcctcttg ggccacaggc agttcaggtt ggcctgctgt cttacagtca   3300
tcggccctcc ccactgttcc cactgaatgg ctcccatgac cttggcatta tcttgcaaag   3360
gatccgtgac atgccctaca tggacccaag tgggaacaac ctgggcacag ccgtggtcac   3420
agctcacaga tacatgttgg caccagatgc tcctgggcgc cgccagcacg taccaggggt   3480
gatggttctg ctagtggatg aacccttgag aggtgacata ttcagcccca tccgtgaggc   3540
ccaggcttct gggcttaatg tggtgatgtt gggaatggct ggagcggacc cagagcagct   3600
```

```
gcgtcgcttg gcgccgggta tggactctgt ccagaccttc ttcgccgtgg atgatgggcc   3660
aagcctggac caggcagtca gtggtctggc cacagccctg tgtcaggcat ccttcactac   3720
tcagccccgg ccagagccct gcccagtgta ttgtccaaag ggccagaagg gggaacctgg   3780
agagatgggc ctgagaggac aagttgggcc tcctggcgac cctggcctcc cgggcaggac   3840
cggtgctccc ggcccccagg ggccccctgg aagtgccact gccaagggcg agaggggctt   3900
ccctggagca gatgggcgtc caggcagccc tggccgcgcc gggaatcctg ggacccctgg   3960
agcccctggc ctaaagggct ctccagggtt gcctggccct cgtggggacc cgggagagcg   4020
aggacctcga ggcccaaagg gggagccggg ggctcccgga caagtcatcg gaggtgaagg   4080
acctgggctt cctgggcgga aaggggaccc tggaccatcg ggccccccctg gacctcgtgg   4140
accactgggg gacccaggac cccgtggccc cccagggctt cctggaacag ccatgaaggg   4200
tgacaaaggc gatcgtgggg agcggggtcc ccctggacca ggtgaaggtg gcattgctcc   4260
tggggagcct gggctgccgg gtcttcccgg aagccctgga ccccaaggcc ccgttggccc   4320
ccctggaaag aaaggagaaa aaggtgactc tgaggatgga gctccaggcc tcccaggaca   4380
acctgggtct ccgggtgagc agggcccacg gggacctcct ggagctattg gccccaaagg   4440
tgaccggggc tttccagggc ccctgggtga ggctggagag aagggcgaac gtggaccccc   4500
aggcccagcg ggatcccggg ggctgccagg ggttgctgga cgtcctggag ccaagggtcc   4560
tgaagggcca ccaggaccca ctggccgcca aggagagaag ggggagcctg gtcgccctgg   4620
ggaccctgca gtggtgggac ctgctgttgc tggacccaaa ggagaaaagg gagatgtggg   4680
gcccgctggg cccagaggag ctaccggagt ccaaggggaa cggggcccac ccggcttggt   4740
tcttcctgga gaccctggcc ccaagggaga ccctggagac cggggtccca ttggccttac   4800
tggcagagca ggacccccag gtgactcagg gcctcctgga gagaagggag accctgggcg   4860
gcctggcccc ccaggacctg ttggcccccg aggacgagat ggtgaagttg gagagaaagg   4920
tgacgagggt cctccgggtg acccgggttt gcctggaaaa gcaggcgagc gtggccttcg   4980
gggggcacct ggagttcggg ggcctgtggg tgaaaaggga gaccagggag atcctggaga   5040
ggatggacga aatggcagcc ctggatcatc tggacccaag ggtgaccgtg gggagccggg   5100
tcccccagga cccccgggac ggctggtaga cacaggacct ggagccagag agaagggaga   5160
gcctggggac cgcggacaag agggtcctcg agggcccaag ggtgatcctg gcctccctgg   5220
agcccctggg gaaaggggca ttgaagggtt tcggggaccc ccaggcccac agggggaccc   5280
aggtgtccga ggcccagcag gagaaaaggg tgaccggggt ccccctgggc tggatggccg   5340
gagcggactg gatgggaaac caggagccgc tgggccctct gggccgaatg gtgctgcagg   5400
caaagctggg gacccaggga gagacgggct tccaggcctc cgtggagaac agggcctccc   5460
tggcccctct ggtccccctg gattaccggg aaagccaggc gaggatggca aacctggcct   5520
gaatggaaaa aacggagaac ctggggaccc tggagaagac gggaggaagg gagagaaagg   5580
agattcaggc gcctctggga gagaaggtcg tgatggcccc aagggtgagc gtggagctcc   5640
tggtatcctt ggaccccagg ggcctccagg cctcccaggg ccagtgggcc ctcctggcca   5700
gggttttcct ggtgtcccag gaggcacggg ccccaagggt gaccgtgggg agactggatc   5760
caaaggggag cagggcctcc ctggagagcg tggcctgcga ggagagcctg gaagtgtgcc   5820
gaatgtggat cggttgctgg aaactgctgg catcaaggca tctgccctgc gggagatcgt   5880
ggagacctgg gatgagagct ctggtagctt cctgcctgtg cccgaacggc gtcgaggccc   5940
```

caaggggggac tcaggcgaac agggcccccc aggcaaggag ggccccatcg gctttcctgg 6000
agaacgcggg ctgaagggcg accgtggaga ccctggccct caggggccac ctggtctggc 6060
ccttggggag aggggccccc ccgggccttc cggccttgcc ggggagcctg gaaagcctgg 6120
tattcccggg ctcccaggca gggctggggg tgtgggagag gcaggaaggc caggagagag 6180
gggagaacgg ggagagaaag gagaacgtgg agaacagggc agagatggcc ctcctggact 6240
ccctggaacc cctgggcccc ccggaccccc tggccccaag gtgtctgtgg atgagccagg 6300
tcctggactc tctggagaac agggaccccc tggactcaag ggtgctaagg gggagccggg 6360
cagcaatggt gaccaaggtc ccaaaggaga caggggtgtg ccaggcatca aaggagaccg 6420
gggagagcct ggaccgaggg gtcaggacgg caacccgggt ctaccaggag agcgtggtat 6480
ggctgggcct gaagggaagc cggtctgca gggtccaaga ggccccccctg gcccagtggg 6540 tggtcatgga gaccctggac cacctggtgc cccgggtctt gctggccctg caggacccca 6600
aggaccttct ggcctgaagg gggagcctgg agagacagga cctccaggac ggggcctgac 6660
tggacctact ggagctgtgg gacttcctgg acccccccggc ccttcaggcc ttgtgggtcc 6720
acaggggtct ccaggtttgc ctggacaagt gggggagaca gggaagccgg gagccccagg 6780
tcgagatggt gccagtggaa aagatggaga cagagggagc cctggtgtgc caggtcacc 6840 aggtctgcct ggccctgtcg gacctaaagg agaacctggc cccacggggg cccctggaca 6900
ggctgtggtc gggctccctg gagcaaaggg agagaaggga gcccctggag gccttgctgg 6960
agacctggtg ggtgagccgg gagccaaagg tgaccgagga ctgccagggc cgcgaggcga 7020
gaagggtgaa gctggccgtg caggggagcc cggagaccct ggggaagatg gtcagaaagg 7080
ggctccagga cccaaaggtt tcaagggtga cccaggagtc ggggtcccgg gctcccctgg 7140
gcctcctggc cctccaggtg tgaagggaga tctgggcctc cctggcctgc ccggtgctcc 7200
tggtgttgtt gggttcccgg gtcagacagg ccctcgagga gagatgggtc agccaggccc 7260
tagtggagag cggggtctgg caggcccccc agggagagaa ggaatcccag gacccctggg 7320
gccacctgga ccaccggggt cagtgggacc acctggggcc tctggactca aaggagacaa 7380
gggagaccct ggagtagggc tgcctgggcc ccgaggcgag cgtggggagc caggcatccg 7440
gggtgaagat ggccgccccg gccaggaggg accccgagga ctcacggggc cccctggcag 7500
caggggagag cgtggggaga agggtgatgt tgggagtgca ggactaaagg gtgacaaggg 7560
agactcagct gtgatcctgg ggcctccagg cccacggggt gccaaggggg acatgggtga 7620
acgagggcct cggggcttgg atggtgacaa aggacctcgg ggagacaatg ggaccctgg 7680 tgacaagggc agcaagggag agcctggtga caagggctca gccgggttgc caggactgcg 7740
tggactcctg ggaccccagg gtcaacctgg tgcagcaggg atccctggtg acccgggatc 7800
cccaggaaag gatggagtgc ctggtatccg aggagaaaaa ggagatgttg gcttcatggg 7860
tccccggggc ctcaagggtg aacggggagt gaagggagcc tgtggccttg atggagagaa 7920
gggagacaag ggagaagctg gtcccccagg ccgccccggg ctggcaggac acaaaggaga 7980
gatgggggag cctggtgtgc cgggccagtc gggggcccct ggcaaggagg gcctgatcgg 8040
tcccaagggt gaccgaggct ttgacgggca gccaggcccc aagggtgacc agggcgagaa 8100
aggggagcgg ggaaccccag gaattggggg cttcccaggc cccagtggaa atgatggctc 8160
tgctggtccc ccagggccac ctggcagtgt tggtcccaga ggccccgaag gacttcaggg 8220
ccagaagggt gagcgaggtc cccccggaga gagagtggtg ggggctcctg ggtccctgg 8280 agctcctggc gagagagggg agcaggggcg gccagggcct gccggtcctc gaggcgagaa 8340

```
gggagaagct gcactgacgg aggatgacat ccggggcttt gtgcgccaag agatgagtca   8400

gcactgtgcc tgccagggcc agttcatcgc atctggatca cgacccctcc ctagttatgc   8460

tgcagacact gccggctccc agctccatgc tgtgcctgtg ctccgcgtct ctcatgcaga   8520

ggaggaagag cgggtacccc ctgaggatga tgagtactct gaatactccg agtattctgt   8580

ggaggagtac caggaccctg aagctccttg ggatagtgat gacccctgtt ccctgccact   8640

ggatgagggc tcctgcactg cctacaccct gcgctggtac catcgggctg tgacaggcag   8700

cacagaggcc tgtcaccctt ttgtctatgg tggctgtgga gggaatgcca accgttttgg   8760

gacccgtgag gcctgcgagc gccgctgccc accccgggtg gtccagagcc aggggacagg   8820

tactgcccag gactgaggcc cagataatga gctgagattc agcatcccct ggaggagtcg   8880

gggtctcagc agaaccccac tgtccctccc cttggtgcta gaggcttgtg tgcacgtgag   8940

cgtgcgtgtg cacgtccgtt atttcagtga cttggtcccg tgggtctagc cttccccccct   9000

gtggacaaac ccccattgtg gctcctgcca ccctggcaga tgactcactg tgggggggtg   9060

gctgtgggca gtgagcggat gtgactggcg tctgacccgc cccttgaccc aagcctgtga   9120

tgacatggtg ctgattctgg ggggcattaa agctgctgtt ttaaaaggc              9169
```

<210> SEQ ID NO 18
<211> LENGTH: 2944
<212> TYPE: PRT
<213> ORGANISM: Homo sapiens

<400> SEQUENCE: 18

```
Met Thr Leu Arg Leu Leu Val Ala Ala Leu Cys Ala Gly Ile Leu Ala
1               5                   10                  15

Glu Ala Pro Arg Val Arg Ala Gln His Arg Glu Arg Val Thr Cys Thr
            20                  25                  30

Arg Leu Tyr Ala Ala Asp Ile Val Phe Leu Leu Asp Gly Ser Ser Ser
        35                  40                  45

Ile Gly Arg Ser Asn Phe Arg Glu Val Arg Ser Phe Leu Glu Gly Leu
    50                  55                  60

Val Leu Pro Phe Ser Gly Ala Ala Ser Ala Gln Gly Val Arg Phe Ala
65                  70                  75                  80

Thr Val Gln Tyr Ser Asp Asp Pro Arg Thr Glu Phe Gly Leu Asp Ala
                85                  90                  95

Leu Gly Ser Gly Gly Asp Val Ile Arg Ala Ile Arg Glu Leu Ser Tyr
            100                 105                 110

Lys Gly Gly Asn Thr Arg Thr Gly Ala Ala Ile Leu His Val Ala Asp
        115                 120                 125

His Val Phe Leu Pro Gln Leu Ala Arg Pro Gly Val Pro Lys Val Cys
    130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220
```

```
Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
    370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
    450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
        515                 520                 525

Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
        595                 600                 605

Ser Asp Ala Thr Arg Val Arg Val Ala Trp Gly Pro Val Pro Gly Ala
    610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
```

```
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro  Gly Ser Pro Gln Thr  Leu Pro Gly
        995                 1000                1005

Ile Ser  Ser Ser Gln Arg Val  Thr Gly Leu Glu Pro  Gly Val Ser
    1010                 1015                 1020

Tyr Ile  Phe Ser Leu Thr Pro  Val Leu Asp Gly Val  Arg Gly Pro
    1025                 1030                 1035

Glu Ala  Ser Val Thr Gln Thr  Pro Val Cys Pro Arg  Gly Leu Ala
    1040                 1045                 1050

Asp Val  Val Phe Leu Pro His  Ala Thr Gln Asp Asn  Ala His Arg
    1055                 1060                 1065
```

```
Ala Glu  Ala Thr Arg Arg Val  Leu Glu Arg Leu Val  Leu Ala Leu
    1070                 1075                 1080

Gly Pro  Leu Gly Pro Gln Ala  Val Gln Val Gly Leu  Leu Ser Tyr
    1085                 1090                 1095

Ser His  Arg Pro Ser Pro Leu  Phe Pro Leu Asn Gly  Ser His Asp
    1100                 1105                 1110

Leu Gly  Ile Ile Leu Gln Arg  Ile Arg Asp Met Pro  Tyr Met Asp
    1115                 1120                 1125

Pro Ser  Gly Asn Asn Leu Gly  Thr Ala Val Val Thr  Ala His Arg
    1130                 1135                 1140

Tyr Met  Leu Ala Pro Asp Ala  Pro Gly Arg Arg Gln  His Val Pro
    1145                 1150                 1155

Gly Val  Met Val Leu Leu Val  Asp Glu Pro Leu Arg  Gly Asp Ile
    1160                 1165                 1170

Phe Ser  Pro Ile Arg Glu Ala  Gln Ala Ser Gly Leu  Asn Val Val
    1175                 1180                 1185

Met Leu  Gly Met Ala Gly Ala  Asp Pro Glu Gln Leu  Arg Arg Leu
    1190                 1195                 1200

Ala Pro  Gly Met Asp Ser Val  Gln Thr Phe Phe Ala  Val Asp Asp
    1205                 1210                 1215

Gly Pro  Ser Leu Asp Gln Ala  Val Ser Gly Leu Ala  Thr Ala Leu
    1220                 1225                 1230

Cys Gln  Ala Ser Phe Thr Thr  Gln Pro Arg Pro Glu  Pro Cys Pro
    1235                 1240                 1245

Val Tyr  Cys Pro Lys Gly Gln  Lys Gly Glu Pro Gly  Glu Met Gly
    1250                 1255                 1260

Leu Arg  Gly Gln Val Gly Pro  Pro Gly Asp Pro Gly  Leu Pro Gly
    1265                 1270                 1275

Arg Thr  Gly Ala Pro Gly Pro  Gln Gly Pro Pro Gly  Ser Ala Thr
    1280                 1285                 1290

Ala Lys  Gly Glu Arg Gly Phe  Pro Gly Ala Asp Gly  Arg Pro Gly
    1295                 1300                 1305

Ser Pro  Gly Arg Ala Gly Asn  Pro Gly Thr Pro Gly  Ala Pro Gly
    1310                 1315                 1320

Leu Lys  Gly Ser Pro Gly Leu  Pro Gly Pro Arg Gly  Asp Pro Gly
    1325                 1330                 1335

Glu Arg  Gly Pro Arg Gly Pro  Lys Gly Glu Pro Gly  Ala Pro Gly
    1340                 1345                 1350

Gln Val  Ile Gly Gly Glu Gly  Pro Gly Leu Pro Gly  Arg Lys Gly
    1355                 1360                 1365

Asp Pro  Gly Pro Ser Gly Pro  Pro Gly Pro Arg Gly  Pro Leu Gly
    1370                 1375                 1380

Asp Pro  Gly Pro Arg Gly Pro  Pro Gly Leu Pro Gly  Thr Ala Met
    1385                 1390                 1395

Lys Gly  Asp Lys Gly Asp Arg  Gly Glu Arg Gly Pro  Pro Gly Pro
    1400                 1405                 1410

Gly Glu  Gly Gly Ile Ala Pro  Gly Glu Pro Gly Leu  Pro Gly Leu
    1415                 1420                 1425

Pro Gly  Ser Pro Gly Pro Gln  Gly Pro Val Gly Pro  Pro Gly Lys
    1430                 1435                 1440

Lys Gly  Glu Lys Gly Asp Ser  Glu Asp Gly Ala Pro  Gly Leu Pro
    1445                 1450                 1455
```

```
Gly Gln Pro Gly Ser Pro Gly Glu Gln Gly Pro Arg Gly Pro Pro
    1460                1465                1470

Gly Ala Ile Gly Pro Lys Gly Asp Arg Gly Phe Pro Gly Pro Leu
    1475                1480                1485

Gly Glu Ala Gly Glu Lys Gly Glu Arg Gly Pro Pro Gly Pro Ala
    1490                1495                1500

Gly Ser Arg Gly Leu Pro Gly Val Ala Gly Arg Pro Gly Ala Lys
    1505                1510                1515

Gly Pro Glu Gly Pro Pro Gly Pro Thr Gly Arg Gln Gly Glu Lys
    1520                1525                1530

Gly Glu Pro Gly Arg Pro Gly Asp Pro Ala Val Val Gly Pro Ala
    1535                1540                1545

Val Ala Gly Pro Lys Gly Glu Lys Gly Asp Val Gly Pro Ala Gly
    1550                1555                1560

Pro Arg Gly Ala Thr Gly Val Gln Gly Glu Arg Gly Pro Pro Gly
    1565                1570                1575

Leu Val Leu Pro Gly Asp Pro Gly Pro Lys Gly Asp Pro Gly Asp
    1580                1585                1590

Arg Gly Pro Ile Gly Leu Thr Gly Arg Ala Gly Pro Pro Gly Asp
    1595                1600                1605

Ser Gly Pro Pro Gly Glu Lys Gly Asp Pro Gly Arg Pro Gly Pro
    1610                1615                1620

Pro Gly Pro Val Gly Pro Arg Gly Arg Asp Gly Glu Val Gly Glu
    1625                1630                1635

Lys Gly Asp Glu Gly Pro Pro Gly Asp Pro Gly Leu Pro Gly Lys
    1640                1645                1650

Ala Gly Glu Arg Gly Leu Arg Gly Ala Pro Gly Val Arg Gly Pro
    1655                1660                1665

Val Gly Glu Lys Gly Asp Gln Gly Asp Pro Gly Glu Asp Gly Arg
    1670                1675                1680

Asn Gly Ser Pro Gly Ser Ser Gly Pro Lys Gly Asp Arg Gly Glu
    1685                1690                1695

Pro Gly Pro Pro Gly Pro Pro Gly Arg Leu Val Asp Thr Gly Pro
    1700                1705                1710

Gly Ala Arg Glu Lys Gly Glu Pro Gly Asp Arg Gly Gln Glu Gly
    1715                1720                1725

Pro Arg Gly Pro Lys Gly Asp Pro Gly Leu Pro Gly Ala Pro Gly
    1730                1735                1740

Glu Arg Gly Ile Glu Gly Phe Arg Gly Pro Pro Gly Pro Gln Gly
    1745                1750                1755

Asp Pro Gly Val Arg Gly Pro Ala Gly Glu Lys Gly Asp Arg Gly
    1760                1765                1770

Pro Pro Gly Leu Asp Gly Arg Ser Gly Leu Asp Gly Lys Pro Gly
    1775                1780                1785

Ala Ala Gly Pro Ser Gly Pro Asn Gly Ala Ala Gly Lys Ala Gly
    1790                1795                1800

Asp Pro Gly Arg Asp Gly Leu Pro Gly Leu Arg Gly Glu Gln Gly
    1805                1810                1815

Leu Pro Gly Pro Ser Gly Pro Pro Gly Leu Pro Gly Lys Pro Gly
    1820                1825                1830

Glu Asp Gly Lys Pro Gly Leu Asn Gly Lys Asn Gly Glu Pro Gly
    1835                1840                1845

Asp Pro Gly Glu Asp Gly Arg Lys Gly Glu Lys Gly Asp Ser Gly
```

```
    1850                1855                1860

Ala Ser  Gly Arg Glu Gly Arg  Asp Gly Pro Lys Gly  Glu Arg Gly
    1865                1870                1875

Ala Pro  Gly Ile Leu Gly Pro  Gln Gly Pro Pro Gly  Leu Pro Gly
    1880                1885                1890

Pro Val  Gly Pro Pro Gly Gln  Gly Phe Pro Gly Val  Pro Gly Gly
    1895                1900                1905

Thr Gly  Pro Lys Gly Asp Arg  Gly Glu Thr Gly Ser  Lys Gly Glu
    1910                1915                1920

Gln Gly  Leu Pro Gly Glu Arg  Gly Leu Arg Gly Glu  Pro Gly Ser
    1925                1930                1935

Val Pro  Asn Val Asp Arg Leu  Leu Glu Thr Ala Gly  Ile Lys Ala
    1940                1945                1950

Ser Ala  Leu Arg Glu Ile Val  Glu Thr Trp Asp Glu  Ser Ser Gly
    1955                1960                1965

Ser Phe  Leu Pro Val Pro Glu  Arg Arg Arg Gly Pro  Lys Gly Asp
    1970                1975                1980

Ser Gly  Glu Gln Gly Pro Pro  Gly Lys Glu Gly Pro  Ile Gly Phe
    1985                1990                1995

Pro Gly  Glu Arg Gly Leu Lys  Gly Asp Arg Gly Asp  Pro Gly Pro
    2000                2005                2010

Gln Gly  Pro Pro Gly Leu Ala  Leu Gly Glu Arg Gly  Pro Pro Gly
    2015                2020                2025

Pro Ser  Gly Leu Ala Gly Glu  Pro Gly Lys Pro Gly  Ile Pro Gly
    2030                2035                2040

Leu Pro  Gly Arg Ala Gly Gly  Val Gly Glu Ala Gly  Arg Pro Gly
    2045                2050                2055

Glu Arg  Gly Glu Arg Gly Glu  Lys Gly Glu Arg Gly  Glu Gln Gly
    2060                2065                2070

Arg Asp  Gly Pro Pro Gly Leu  Pro Gly Thr Pro Gly  Pro Pro Gly
    2075                2080                2085

Pro Pro  Gly Pro Lys Val Ser  Val Asp Glu Pro Gly  Pro Gly Leu
    2090                2095                2100

Ser Gly  Glu Gln Gly Pro Pro  Gly Leu Lys Gly Ala  Lys Gly Glu
    2105                2110                2115

Pro Gly  Ser Asn Gly Asp Gln  Gly Pro Lys Gly Asp  Arg Gly Val
    2120                2125                2130

Pro Gly  Ile Lys Gly Asp Arg  Gly Glu Pro Gly Pro  Arg Gly Gln
    2135                2140                2145

Asp Gly  Asn Pro Gly Leu Pro  Gly Glu Arg Gly Met  Ala Gly Pro
    2150                2155                2160

Glu Gly  Lys Pro Gly Leu Gln  Gly Pro Arg Gly Pro  Pro Gly Pro
    2165                2170                2175

Val Gly  Gly His Gly Asp Pro  Gly Pro Pro Gly Ala  Pro Gly Leu
    2180                2185                2190

Ala Gly  Pro Ala Gly Pro Gln  Gly Pro Ser Gly Leu  Lys Gly Glu
    2195                2200                2205

Pro Gly  Glu Thr Gly Pro Pro  Gly Arg Gly Leu Thr  Gly Pro Thr
    2210                2215                2220

Gly Ala  Val Gly Leu Pro Gly  Pro Pro Gly Pro Ser  Gly Leu Val
    2225                2230                2235

Gly Pro  Gln Gly Ser Pro Gly  Leu Pro Gly Gln Val  Gly Glu Thr
    2240                2245                2250
```

```
Gly Lys  Pro Gly Ala Pro Gly  Arg Asp Gly Ala Ser  Gly Lys Asp
    2255                 2260                 2265

Gly Asp  Arg Gly Ser Pro Gly  Val Pro Gly Ser Pro  Gly Leu Pro
    2270                 2275                 2280

Gly Pro  Val Gly Pro Lys Gly  Glu Pro Gly Pro Thr  Gly Ala Pro
    2285                 2290                 2295

Gly Gln  Ala Val Val Gly Leu  Pro Gly Ala Lys Gly  Glu Lys Gly
    2300                 2305                 2310

Ala Pro  Gly Gly Leu Ala Gly  Asp Leu Val Gly Glu  Pro Gly Ala
    2315                 2320                 2325

Lys Gly  Asp Arg Gly Leu Pro  Gly Pro Arg Gly Glu  Lys Gly Glu
    2330                 2335                 2340

Ala Gly  Arg Ala Gly Glu Pro  Gly Asp Pro Gly Glu  Asp Gly Gln
    2345                 2350                 2355

Lys Gly  Ala Pro Gly Pro Lys  Gly Phe Lys Gly Asp  Pro Gly Val
    2360                 2365                 2370

Gly Val  Pro Gly Ser Pro Gly  Pro Pro Gly Pro Pro  Gly Val Lys
    2375                 2380                 2385

Gly Asp  Leu Gly Leu Pro Gly  Leu Pro Gly Ala Pro  Gly Val Val
    2390                 2395                 2400

Gly Phe  Pro Gly Gln Thr Gly  Pro Arg Gly Glu Met  Gly Gln Pro
    2405                 2410                 2415

Gly Pro  Ser Gly Glu Arg Gly  Leu Ala Gly Pro Pro  Gly Arg Glu
    2420                 2425                 2430

Gly Ile  Pro Gly Pro Leu Gly  Pro Pro Gly Pro Pro  Gly Ser Val
    2435                 2440                 2445

Gly Pro  Pro Gly Ala Ser Gly  Leu Lys Gly Asp Lys  Gly Asp Pro
    2450                 2455                 2460

Gly Val  Gly Leu Pro Gly Pro  Arg Gly Glu Arg Gly  Glu Pro Gly
    2465                 2470                 2475

Ile Arg  Gly Glu Asp Gly Arg  Pro Gly Gln Glu Gly  Pro Arg Gly
    2480                 2485                 2490

Leu Thr  Gly Pro Pro Gly Ser  Arg Gly Glu Arg Gly  Glu Lys Gly
    2495                 2500                 2505

Asp Val  Gly Ser Ala Gly Leu  Lys Gly Asp Lys Gly  Asp Ser Ala
    2510                 2515                 2520

Val Ile  Leu Gly Pro Pro Gly  Pro Arg Gly Ala Lys  Gly Asp Met
    2525                 2530                 2535

Gly Glu  Arg Gly Pro Arg Gly  Leu Asp Gly Asp Lys  Gly Pro Arg
    2540                 2545                 2550

Gly Asp  Asn Gly Asp Pro Gly  Asp Lys Gly Ser Lys  Gly Glu Pro
    2555                 2560                 2565

Gly Asp  Lys Gly Ser Ala Gly  Leu Pro Gly Leu Arg  Gly Leu Leu
    2570                 2575                 2580

Gly Pro  Gln Gly Gln Pro Gly  Ala Ala Gly Ile Pro  Gly Asp Pro
    2585                 2590                 2595

Gly Ser  Pro Gly Lys Asp Gly  Val Pro Gly Ile Arg  Gly Glu Lys
    2600                 2605                 2610

Gly Asp  Val Gly Phe Met Gly  Pro Arg Gly Leu Lys  Gly Glu Arg
    2615                 2620                 2625

Gly Val  Lys Gly Ala Cys Gly  Leu Asp Gly Glu Lys  Gly Asp Lys
    2630                 2635                 2640
```

```
Gly Glu  Ala Gly Pro Pro Gly  Arg Pro Gly Leu Ala  Gly His Lys
    2645                 2650                 2655

Gly Glu  Met Gly Glu Pro Gly  Val Pro Gly Gln Ser  Gly Ala Pro
    2660                 2665                 2670

Gly Lys  Glu Gly Leu Ile Gly  Pro Lys Gly Asp Arg  Gly Phe Asp
    2675                 2680                 2685

Gly Gln  Pro Gly Pro Lys Gly  Asp Gln Gly Glu Lys  Gly Glu Arg
    2690                 2695                 2700

Gly Thr  Pro Gly Ile Gly Gly  Phe Pro Gly Pro Ser  Gly Asn Asp
    2705                 2710                 2715

Gly Ser  Ala Gly Pro Pro Gly  Pro Pro Gly Ser Val  Gly Pro Arg
    2720                 2725                 2730

Gly Pro  Glu Gly Leu Gln Gly  Gln Lys Gly Glu Arg  Gly Pro Pro
    2735                 2740                 2745

Gly Glu  Arg Val Val Gly Ala  Pro Gly Val Pro Gly  Ala Pro Gly
    2750                 2755                 2760

Glu Arg  Gly Glu Gln Gly Arg  Pro Gly Pro Ala Gly  Pro Arg Gly
    2765                 2770                 2775

Glu Lys  Gly Glu Ala Ala Leu  Thr Glu Asp Asp Ile  Arg Gly Phe
    2780                 2785                 2790

Val Arg  Gln Glu Met Ser Gln  His Cys Ala Cys Gln  Gly Gln Phe
    2795                 2800                 2805

Ile Ala  Ser Gly Ser Arg Pro  Leu Pro Ser Tyr Ala  Ala Asp Thr
    2810                 2815                 2820

Ala Gly  Ser Gln Leu His Ala  Val Pro Val Leu Arg  Val Ser His
    2825                 2830                 2835

Ala Glu  Glu Glu Glu Arg Val  Pro Pro Glu Asp Asp  Glu Tyr Ser
    2840                 2845                 2850

Glu Tyr  Ser Glu Tyr Ser Val  Glu Glu Tyr Gln Asp  Pro Glu Ala
    2855                 2860                 2865

Pro Trp  Asp Ser Asp Asp Pro  Cys Ser Leu Pro Leu  Asp Glu Gly
    2870                 2875                 2880

Ser Cys  Thr Ala Tyr Thr Leu  Arg Trp Tyr His Arg  Ala Val Thr
    2885                 2890                 2895

Gly Ser  Thr Glu Ala Cys His  Pro Phe Val Tyr Gly  Gly Cys Gly
    2900                 2905                 2910

Gly Asn  Ala Asn Arg Phe Gly  Thr Arg Glu Ala Cys  Glu Arg Arg
    2915                 2920                 2925

Cys Pro  Pro Arg Val Val Gln  Ser Gln Gly Thr Gly  Thr Ala Gln
    2930                 2935                 2940

Asp
```

```
<210> SEQ ID NO 19
<211> LENGTH: 2988
<212> TYPE: DNA
<213> ORGANISM: Homo sapiens

<400> SEQUENCE: 19

agaagaaggg gagaggaggt tgtgtgggac aaggtgctcc tgacagaagg atgccacagc     60

tgagcctgtc ctcgctgggc ctttggccaa tggcagcatc cccgtggctg ctcctgctgc    120

tggttggggc ctcctggctc ctggcccgca tcctggcctg gacctatacc ttctatgaca    180

actgctgccg cctccggtgt ttcccgcaac ccccgaaacg gaattggttc ttgggtcacc    240

tgggcctgat tcacagctcg gaggaaggtc tcctatacac acaaagcctg gcatgcacct    300
```

```
tcggtgatat gtgctgctgg tgggtggggc cctggcacgc aatcgtccgc atcttccacc    360
ccacctacat caagcctgtg ctctttgctc cagctgccat tgtaccaaag gacaaggtct    420
tctacagctt cctgaagccc tggctggggg atgggctcct gctgagtgct ggtgaaaagt    480
ggagccgcca ccgtcggatg ctgacgcctg ccttccattt caacatcctg aagccctata    540
tgaagatttt caatgagagt gtgaacatca tgcatgccaa gtggcagctc ctggcctcag    600
agggtagtgc ccgtctggac atgtttgagc acatcagcct catgaccttg gacagtctgc    660
agaaatgtgt cttcagcttt gacagccatt gccaggagaa gcccagtgaa tatattgccg    720
ccatcttgga gctcagtgcc cttgtgacaa aaagacacca gcagatcctc ctgtacatag    780
acttcctgta ttatctcacc cctgatgggc agcgtttccg cagggcctgc cgcctggtgc    840
acgacttcac agatgccgtc atccaggagc ggcgccgcac cctccctagc cagggtgttg    900
atgacttcct ccaagccaag gccaaatcca agactttgga cttcattgat gtactcctgc    960
tgagcaagga tgaagatggg aagaagttgt ccgatgagga cataagagca gaagctgaca   1020
cctttatgtt tgagggccat gacaccacag ccagtggtct ctcctgggtc ctgtaccacc   1080
ttgcaaagca cccggaatac caggagcgct gtcggcagga ggtgcaagag cttctgaagg   1140
accgtgagcc taaagagatt gaatgggacg acctggccca gctgcccttc ctgaccatgt   1200
gcattaagga gagcctgagg ctgcatcccc cagtccctgc cgtctctcgc tgctgcaccc   1260
aagacattgt gctcccagac ggccgggtca tccccaaagg cattatctgc ctcatcagtg   1320
tttttggaac ccatcacaac ccagccgtgt ggccggaccc tgaggtctat gacccctttc   1380
gctttgaccc aaagaacatc aaggagaggt cacctctggc ttttattccc ttctcagcag   1440
ggcccaggaa ctgcatcggg caggcgttcg cgatggcgga gatgaaggtg gtcctggggc   1500
tcacgctgct gcgcttccgc gtcctgcctg accacaccga gccccgcagg aagccggagc   1560
tggtcctgcg cgcagagggc ggactttggc tgcgggtgga gcccctgagc tgagttctgc   1620
agagacccac tctgacccca ctaaaatgac ccctgattca tcaaaagtga ggcctagaat   1680
taccctaaga ccctgttcca cagtcctgta ttccatccta gatatctact caaaataatt   1740
gagacaagtg ttcaaacaga aagacgcttg tgcgtgaatg ttcatggcag ccctattcac   1800
agtagccaaa cgatgaaaac aaccccaagc tatatattac cagatgaaag gataaacaaa   1860
atatggtcca tccatacaat ggagtattac acagccataa aaaggaatga agcagtgatc   1920
cccactacac tgtggatgaa ccttgaatgc atgatactga atgaaagaca tcagatgcaa   1980
aaggtcacat agtgtactgt ccttttatat gaaatttcca gaacaggcca atctgaagag   2040
atgtatagtg gattggtggc tttcagcagc tgtggggagg tgggactgag gagcgactgc   2100
taatcaggat ggggtttcct cctgggatgg tgaaaatgtt ccggacctag atagtgatga   2160
aggtagcacg acactgtgag tgcactaaat gctattgaat tggacacttt agaatggttg   2220
aaatagtgat ttttatgtga attctaccta aacatgctat tacagctcat atatactttt   2280
tccatctgga ttcttcacaa aagaatatgt tgtgagcatc tttccatgat attaaatcat   2340
cttaggaaac attattttgt gttcttcaaa atgtgcatgt taagtattca aatcagtctt   2400
aaatttttaa aaatatgtaa ttttagaaaa taatttaaaa ggttttgttt cagtttgtaa   2460
gatttctttt ctggcacttt aatggcttga ggtatcatta tcagttacaa attgagttat   2520
tcttcatcaa atgacttttg gagtagagat tttattttta tagcaataga tgcacagata   2580
ttcctgtaag atacaggtgt ggttagacac ttttctagaa caggcatgcc ctgcaaactc   2640
```

```
cacagacact gactgttttt gtcctattaa gaagtagacc actgagaagg gagaaggtga   2700

cattttagct ttcccaggta aaagtggttt tcatcctcac accaatttta tggactggac   2760

gttaactctc ttgctcaagg tcactctgag tggaagagtg gggataaatc tggttcgttt   2820

ggcatcagag gccatgactt ttcctaccac agaagtaatt ttcaaagtaa gtctctgccc   2880

taggcacatc agatcacctg gggaccactc cagagtgagt agacaagact ttgacagggg   2940

tgcctaattt tttttttttt ttgagatgga gtctcgctct gttgccca                2988


<210> SEQ ID NO 20
<211> LENGTH: 520
<212> TYPE: PRT
<213> ORGANISM: Homo sapiens

<400> SEQUENCE: 20

Met Pro Gln Leu Ser Leu Ser Ser Leu Gly Leu Trp Pro Met Ala Ala
1               5                   10                  15

Ser Pro Trp Leu Leu Leu Leu Leu Val Gly Ala Ser Trp Leu Leu Ala
            20                  25                  30

Arg Ile Leu Ala Trp Thr Tyr Thr Phe Tyr Asp Asn Cys Cys Arg Leu
        35                  40                  45

Arg Cys Phe Pro Gln Pro Pro Lys Arg Asn Trp Phe Leu Gly His Leu
    50                  55                  60

Gly Leu Ile His Ser Ser Glu Glu Gly Leu Leu Tyr Thr Gln Ser Leu
65                  70                  75                  80

Ala Cys Thr Phe Gly Asp Met Cys Cys Trp Trp Val Gly Pro Trp His
                85                  90                  95

Ala Ile Val Arg Ile Phe His Pro Thr Tyr Ile Lys Pro Val Leu Phe
            100                 105                 110

Ala Pro Ala Ala Ile Val Pro Lys Asp Lys Val Phe Tyr Ser Phe Leu
        115                 120                 125

Lys Pro Trp Leu Gly Asp Gly Leu Leu Leu Ser Ala Gly Glu Lys Trp
    130                 135                 140

Ser Arg His Arg Arg Met Leu Thr Pro Ala Phe His Phe Asn Ile Leu
145                 150                 155                 160

Lys Pro Tyr Met Lys Ile Phe Asn Glu Ser Val Asn Ile Met His Ala
                165                 170                 175

Lys Trp Gln Leu Leu Ala Ser Glu Gly Ser Ala Arg Leu Asp Met Phe
            180                 185                 190

Glu His Ile Ser Leu Met Thr Leu Asp Ser Leu Gln Lys Cys Val Phe
        195                 200                 205

Ser Phe Asp Ser His Cys Gln Glu Lys Pro Ser Glu Tyr Ile Ala Ala
    210                 215                 220

Ile Leu Glu Leu Ser Ala Leu Val Thr Lys Arg His Gln Gln Ile Leu
225                 230                 235                 240

Leu Tyr Ile Asp Phe Leu Tyr Tyr Leu Thr Pro Asp Gly Gln Arg Phe
                245                 250                 255

Arg Arg Ala Cys Arg Leu Val His Asp Phe Thr Asp Ala Val Ile Gln
            260                 265                 270

Glu Arg Arg Arg Thr Leu Pro Ser Gln Gly Val Asp Asp Phe Leu Gln
        275                 280                 285

Ala Lys Ala Lys Ser Lys Thr Leu Asp Phe Ile Asp Val Leu Leu Leu
    290                 295                 300

Ser Lys Asp Glu Asp Gly Lys Lys Leu Ser Asp Glu Asp Ile Arg Ala
305                 310                 315                 320
```

```
Glu Ala Asp Thr Phe Met Phe Glu Gly His Asp Thr Thr Ala Ser Gly
                325                 330                 335

Leu Ser Trp Val Leu Tyr His Leu Ala Lys His Pro Glu Tyr Gln Glu
            340                 345                 350

Arg Cys Arg Gln Glu Val Gln Glu Leu Leu Lys Asp Arg Glu Pro Lys
        355                 360                 365

Glu Ile Glu Trp Asp Asp Leu Ala Gln Leu Pro Phe Leu Thr Met Cys
    370                 375                 380

Ile Lys Glu Ser Leu Arg Leu His Pro Pro Val Pro Ala Val Ser Arg
385                 390                 395                 400

Cys Cys Thr Gln Asp Ile Val Leu Pro Asp Gly Arg Val Ile Pro Lys
                405                 410                 415

Gly Ile Ile Cys Leu Ile Ser Val Phe Gly Thr His His Asn Pro Ala
            420                 425                 430

Val Trp Pro Asp Pro Glu Val Tyr Asp Pro Phe Arg Phe Asp Pro Lys
        435                 440                 445

Asn Ile Lys Glu Arg Ser Pro Leu Ala Phe Ile Pro Phe Ser Ala Gly
    450                 455                 460

Pro Arg Asn Cys Ile Gly Gln Ala Phe Ala Met Ala Glu Met Lys Val
465                 470                 475                 480

Val Leu Gly Leu Thr Leu Leu Arg Phe Arg Val Leu Pro Asp His Thr
                485                 490                 495

Glu Pro Arg Arg Lys Pro Glu Leu Val Leu Arg Ala Glu Gly Gly Leu
            500                 505                 510

Trp Leu Arg Val Glu Pro Leu Ser
        515                 520
```

<210> SEQ ID NO 21
<211> LENGTH: 6914
<212> TYPE: DNA
<213> ORGANISM: Homo sapiens

<400> SEQUENCE: 21

```
gcggccgccg cccagccagg tgcaaaatgc cgtgtcattg ggagactccg cagccggagc      60
attagattac agctcgacgg agctcgggaa gggcggcggg ggtggaagat gagcagaagc     120
ccctgttctc ggaacgccgg ctgacaagcg gggtgagcgc agccggggcg gggacccagc     180
ctagcccact ggagcagccg gggtggccc gttcccctttt aagagcaact gctctaagcc     240
aggagccaga gattcgagcc ggcctcgccc agccagccct ctccagcgag gggacccaca     300
agcggcgcct cggccctccc gacctttccg agccctcttt gcgccctggg cgcacggggc     360
cctacacgcg ccaagcatgc tgagggtctt catcctctat gccgagaacg tccacacacc     420
cgacaccgac atcagcgatg cctactgctc cgcggtgttt gcaggggtga agaagagaac     480
caaagtcatc aagaacagcg tgaaccctgt atggaatgag ggatttgaat gggacctcaa     540
gggcatcccc ctggaccagg gctctgagct tcatgtggtg gtcaaagacc atgagacgat     600
ggggaggaac aggttcctgg gggaagccaa ggtcccactc cgagaggtcc tcgccacccc     660
tagtctgtcc gccagcttca atgcccccct gctggacacc aagaagcagc ccacaggggc     720
ctcgctggtc ctgcaggtgt cctacacacc gctgcctgga gctgtgcccc tgttcccgcc     780
ccctactcct ctggagccct ccccgactct gcctgacctg gatgtagtgg cagacacagg     840
aggagaggaa gacacagagg accagggact cactggagat gaggcggagc cattcctgga     900
tcaaagcgga ggcccggggg ctcccaccac cccaaggaaa ctaccttcac gtcctccgcc     960
```

```
ccactacccc gggatcaaaa gaaagcgaag tgcgcctaca tctagaaagc tgctgtcaga   1020
caaaccgcag gatttccaga tcagggtcca ggtgatcgag ggcgccagc tgccgggggt    1080
gaacatcaag cctgtggtca aggttaccgc tgcagggcag accaagcgga cgcggatcca   1140
caagggaaac agcccactct tcaatgagac tcttttcttc aacttgtttg actctcctgg   1200
ggagctgttt gatgagccca tctttatcac ggtggtagac tctcgttctc tcaggacaga   1260
tgctctcctc ggggagttcc ggatggacgt gggcaccatt tacagagagc cccggcacgc   1320
ctatctcagg aagtggctgc tgctctcaga ccctgatgac ttctctgctg ggccagaggg   1380
ctacctgaaa acaagccttt gtgtgctggg gcctggggac gaagcgcctc tggagagaaa   1440
agacccctct gaagacaagg aggacattga aagcaacctg ctccggccca caggcgtagc   1500
cctgcgagga gcccacttct gcctgaaggt cttccgggcc gaggacttgc cgcagatgga   1560
cgatgccgtg atggacaacg tgaaacagat ctttggcttc gagagtaaca agaagaactt   1620
ggtggacccc tttgtggagg tcagctttgc ggggaaaatg ctgtgcagca agatcttgga   1680
gaagacggcc aaccctcagt ggaaccagaa catcacactg cctgccatgt ttccctccat   1740
gtgcgaaaaa atgaggattc gtatcataga ctgggaccgc ctgactcaca atgacatcgt   1800
ggctaccacc tacctgagta tgtcgaaaat ctctgcccct ggaggagaaa tagaagagga   1860
gcctgcaggt gctgtcaagc cttcgaaagc ctcagacttg gatgactacc tgggcttcct   1920
ccccactttt gggccctgct acatcaacct ctatggcagt cccagagagt tcacaggctt   1980
cccagacccc tacacagagc tcaacacagg caaggggaa ggtgtggctt atcgtggccg    2040
gcttctgctc tccctggaga ccaagctggt ggagcacagt gaacagaagg tggaggacct   2100
tcctgcggat gacatcctcc gggtggagaa gtaccttagg aggcgcaagt actccctgtt   2160
tgcggccttc tactcagcca ccatgctgca ggatgtggat gatgccatcc agtttgaggt   2220
cagcatcggg aactacggga acaagttcga catgacctgc ctgccgctgg cctccaccac   2280
tcagtacagc cgtgcagtct ttgacgggtg ccactactac tacctaccct ggggtaacgt   2340
gaaacctgtg gtggtgctgt catcctactg ggaggacatc agccatagaa tcgagactca   2400
gaaccagctg cttgggattg ctgaccggct ggaagctggc ctggagcagg tccacctggc   2460
cctgaaggcg cagtgctcca cggaggacgt ggactcgctg gtggctcagc tgacggatga   2520
gctcatcgca ggctgcagcc agcctctggg tgacatccat gagacaccct ctgccaccca   2580
cctggaccag tacctgtacc agctgcgcac ccatcacctg agccaaatca ctgaggctgc   2640
cctggccctg aagctcggcc acagtgagct ccctgcagct ctggagcagg cggaggactg   2700
gctcctgcgt ctgcgtgccc tggcagagga gccccagaac agcctgccgg acatcgtcat   2760
ctggatgctg cagggagaca agcgtgtggc ataccagcgg gtgcccgccc accaagtcct   2820
cttctcccgg cggggtgcca actactgtgg caagaattgt gggaagctac agacaatctt   2880
tctgaaatat ccgatggaga aggtgcctgg cgcccggatg ccagtgcaga tacgggtcaa   2940
gctgtggttt gggctctcag tggatgagaa ggagttcaac cagtttgctg aggggaagct   3000
gtctgtcttt gctgaaacct atgagaacga gactaagttg gcccttgttg ggaactgggg   3060
cacaacgggc ctcacctacc ccaagttttc tgacgtcacg ggcaagatca agctacccaa   3120
ggacagcttc cgcccctcgg ccggctggac ctgggctgga gattggttcg tgtgtccgga   3180
gaagactctg ctccatgaca tggacgccgg tcacctgagc ttcgtggaag aggtgtttga   3240
gaaccagacc cggcttcccg gaggccagtg gatctacatg agtgacaact acaccgatgt   3300
```

```
gaacggggag aaggtgcttc ccaaggatga cattgagtgc ccactgggct ggaagtggga   3360
agatgaggaa tggtccacag acctcaaccg ggctgtcgat gagcaaggct gggagtatag   3420
catcaccatc cccccggagc ggaagccgaa gcactgggtc cctgctgaga agatgtacta   3480
cacacaccga cggcggcgct gggtgcgcct gcgcaggagg gatctcagcc aaatggaagc   3540
actgaaaagg cacaggcagg cggaggcgga gggcgagggc tgggagtacg cctctctttt   3600
tggctggaag ttccacctcg agtaccgcaa gacagatgcc ttccgccgcc gccgctggcg   3660
ccgtcgcatg gagccactgg agaagacggg gcctgcagct gtgtttgccc ttgagggggc   3720
cctgggcggc gtgatggatg acaagagtga agattccatg tccgtctcca ccttgagctt   3780
cggtgtgaac agacccacga tttcctgcat attcgactat gggaaccgct accatctacg   3840
ctgctacatg taccaggccc gggacctggc tgcgatggac aaggactctt tttctgatcc   3900
ctatgccatc gtctccttcc tgcaccagag ccagaagacg gtggtggtga agaacaccct   3960
taaccccacc tgggaccaga cgctcatctt ctacgagatc gagatctttg gcgagccggc   4020
cacagttgct gagcaaccgc ccagcattgt ggtggagctg tacgaccatg acacttatgg   4080
tgcagacgag tttatgggtc gctgcatctg tcaaccgagt ctggaacgga tgccacggct   4140
ggcctggttc ccactgacga ggggcagcca gccgtcgggg gagctgctgg cctcttttga   4200
gctcatccag agagagaagc cggccatcca ccatattcct ggttttgagg tgcaggagac   4260
atcaaggatc ctggatgagt ctgaggacac agacctgccc tacccaccac cccagaggga   4320
ggccaacatc tacatggttc ctcagaacat caagccagcg ctccagcgta ccgccatcga   4380
gatcctggca tggggcctgc ggaacatgaa gagttaccag ctggccaaca tctcctcccc   4440
cagcctcgtg gtagagtgtg gggccagac ggtgcagtcc tgtgtcatca ggaacctccg   4500
gaagaacccc aactttgaca tctgcaccct cttcatggaa gtgatgctgc ccagggagga   4560
gctctactgc ccccccatca ccgtcaaggt catcgataac cgccagtttg gccgccggcc   4620
tgtggtgggc cagtgtacca tccgctccct ggagagcttc ctgtgtgacc cctactcggc   4680
ggagagtcca tccccacagg gtggcccaga cgatgtgagc ctactcagtc ctggggaaga   4740
cgtgctcatc gacattgatg acaaggagcc cctcatcccc atccaggagg aagagttcat   4800
cgattggtgg agcaaattct ttgcctccat aggggagagg gaaaagtgcg gctcctacct   4860
ggagaaggat tttgacaccc tgaaggtcta tgacacacag ctggagaatg tggaggcctt   4920
tgagggcctg tctgactttt gtaacacctt caagctgtac cggggcaaga cgcaggagga   4980
gacagaagat ccatctgtga ttggtgaatt taagggcctc ttcaaaattt atcccctccc   5040
agaagaccca gccatcccca tgcccccaag acagttccac cagctggccg cccagggacc   5100
ccaggagtgc ttggtccgta tctacattgt ccgagcattt ggcctgcagc ccaaggaccc   5160
caatggaaag tgtgatcctt acatcaagat ctccataggg aagaaatcag tgagtgacca   5220
ggataactac atcccctgca cgctggagcc cgtatttgga aagatgttcg agctgacctg   5280
cactctgcct ctggagaagg acctaaagat cactctctat gactatgacc tcctctccaa   5340
ggacgaaaag atcggtgaga cggtcgtcga cctggagaac aggctgctgt ccaagtttgg   5400
ggctcgctgt ggactcccac agacctactg tgtctctgga ccgaaccagt ggcgggacca   5460
gctccgcccc tcccagctcc tccacctctt ctgccagcag catagagtca aggcacctgt   5520
gtaccggaca gaccgtgtaa tgtttcagga taaagaatat tccattgaag agatagaggc   5580
tggcaggatc ccaaacccac acctgggccc agtggaggag cgtctggctc tgcatgtgct   5640
tcagcagcag ggcctggtcc cggagcacgt ggagtcacgg cccctctaca gcccccctgca   5700
```

```
gccagacatc gagcagggga agctgcagat gtgggtcgac ctatttccga aggccctggg   5760

gcggcctgga cctcccttca acatcacccc acggagagcc agaaggtttt tcctgcgttg   5820

tattatctgg aataccagag atgtgatcct ggatgacctg agcctcacgg gggagaagat   5880

gagcgacatt tatgtgaaag gttggatgat tggctttgaa gaacacaagc aaaagacaga   5940

cgtgcattat cgttccctgg gaggtgaagg caacttcaac tggaggttca ttttcccctt   6000

cgactacctg ccagctgagc aagtctgtac cattgccaag aaggatgcct tctggaggct   6060

ggacaagact gagagcaaaa tcccagcacg agtggtgttc cagatctggg acaatgacaa   6120

gttctccttt gatgattttc tgggctccct gcagctcgat ctcaaccgca tgcccaagcc   6180

agccaagaca gccaagaagt gctccttgga ccagctggat gatgctttcc acccagaatg   6240

gtttgtgtcc ctttttgagc agaaaacagt gaagggctgg tggccctgtg tagcagaaga   6300

gggtgagaag aaaatactgg cgggcaagct ggaaatgacc ttggagattg tagcagagag   6360

tgagcatgag gagcggcctg ctggccaggg ccgggatgag cccaacatga accctaagct   6420

tgaggaccca aggcgccccg acacctcctt cctgtggttt acctccccat acaagaccat   6480

gaagttcatc ctgtggcggc gtttccggtg ggccatcatc ctcttcatca tcctcttcat   6540

cctgctgctg ttcctggcca tcttcatcta cgccttcccg aactatgctg ccatgaagct   6600

ggtgaagccc ttcagctgag gactctcctg ccctgtagaa ggggccgtgg ggtcccctcc   6660

agcatgggac tggcctgcct cctccgccca gctcggcgag ctcctccaga cctcctaggc   6720

ctgattgtcc tgccagggtg ggcagacaga cagatggacc ggcccacact cccagagttg   6780

ctaacatgga gctctgagat caccccactt ccatcatttc cttctccccc aacccaacgc   6840

tttttggat cagctcagac atatttcagt ataaaacagt tggaaccaca aaaaaaaaaa   6900

aaaaaaaaaa aaaa                                                     6914
```

<210> SEQ ID NO 22
<211> LENGTH: 2080
<212> TYPE: PRT
<213> ORGANISM: Homo sapiens

<400> SEQUENCE: 22

```
Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Pro Thr Pro Leu Glu Pro Ser Pro Thr
    130                 135                 140

Leu Pro Asp Leu Asp Val Val Ala Asp Thr Gly Gly Glu Glu Asp Thr
```

-continued

```
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
            340                 345                 350

Glu Arg Lys Asp Pro Ser Glu Asp Lys Glu Asp Ile Glu Ser Asn Leu
        355                 360                 365

Leu Arg Pro Thr Gly Val Ala Leu Arg Gly Ala His Phe Cys Leu Lys
    370                 375                 380

Val Phe Arg Ala Glu Asp Leu Pro Gln Met Asp Asp Ala Val Met Asp
385                 390                 395                 400

Asn Val Lys Gln Ile Phe Gly Phe Glu Ser Asn Lys Lys Asn Leu Val
                405                 410                 415

Asp Pro Phe Val Glu Val Ser Phe Ala Gly Lys Met Leu Cys Ser Lys
            420                 425                 430

Ile Leu Glu Lys Thr Ala Asn Pro Gln Trp Asn Gln Asn Ile Thr Leu
        435                 440                 445

Pro Ala Met Phe Pro Ser Met Cys Glu Lys Met Arg Ile Arg Ile Ile
    450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
                485                 490                 495

Ala Gly Ala Val Lys Pro Ser Lys Ala Ser Asp Leu Asp Asp Tyr Leu
            500                 505                 510

Gly Phe Leu Pro Thr Phe Gly Pro Cys Tyr Ile Asn Leu Tyr Gly Ser
        515                 520                 525

Pro Arg Glu Phe Thr Gly Phe Pro Asp Pro Tyr Thr Glu Leu Asn Thr
    530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
                565                 570                 575
```

```
Ala Asp Asp Ile Leu Arg Val Glu Lys Tyr Leu Arg Arg Arg Lys Tyr
            580                 585                 590

Ser Leu Phe Ala Ala Phe Tyr Ser Ala Thr Met Leu Gln Asp Val Asp
        595                 600                 605

Asp Ala Ile Gln Phe Glu Val Ser Ile Gly Asn Tyr Gly Asn Lys Phe
    610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Tyr Leu Pro Trp Gly Asn Val Lys
                645                 650                 655

Pro Val Val Val Leu Ser Ser Tyr Trp Glu Asp Ile Ser His Arg Ile
            660                 665                 670

Glu Thr Gln Asn Gln Leu Leu Gly Ile Ala Asp Arg Leu Glu Ala Gly
        675                 680                 685

Leu Glu Gln Val His Leu Ala Leu Lys Ala Gln Cys Ser Thr Glu Asp
    690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
            740                 745                 750

Glu Ala Ala Leu Ala Leu Lys Leu Gly His Ser Glu Leu Pro Ala Ala
        755                 760                 765

Leu Glu Gln Ala Glu Asp Trp Leu Leu Arg Leu Arg Ala Leu Ala Glu
    770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
            820                 825                 830

Thr Ile Phe Leu Lys Tyr Pro Met Glu Lys Val Pro Gly Ala Arg Met
        835                 840                 845

Pro Val Gln Ile Arg Val Lys Leu Trp Phe Gly Leu Ser Val Asp Glu
    850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
            900                 905                 910

Leu Pro Lys Asp Ser Phe Arg Pro Ser Ala Gly Trp Thr Trp Ala Gly
        915                 920                 925

Asp Trp Phe Val Cys Pro Glu Lys Thr Leu Leu His Asp Met Asp Ala
    930                 935                 940

Gly His Leu Ser Phe Val Glu Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
            980                 985                 990
```

```
Lys Trp Glu Asp Glu Glu Trp Ser  Thr Asp Leu Asn Arg  Ala Val Asp
        995                 1000                1005

Glu Gln  Gly Trp Glu Tyr Ser  Ile Thr Ile Pro Pro  Glu Arg Lys
    1010                 1015                 1020

Pro Lys  His Trp Val Pro Ala  Glu Lys Met Tyr Tyr  Thr His Arg
    1025                 1030                 1035

Arg Arg  Arg Trp Val Arg Leu  Arg Arg Arg Asp Leu  Ser Gln Met
    1040                 1045                 1050

Glu Ala  Leu Lys Arg His Arg  Gln Ala Glu Ala Glu  Gly Glu Gly
    1055                 1060                 1065

Trp Glu  Tyr Ala Ser Leu Phe  Gly Trp Lys Phe His  Leu Glu Tyr
    1070                 1075                 1080

Arg Lys  Thr Asp Ala Phe Arg  Arg Arg Arg Trp Arg  Arg Arg Met
    1085                 1090                 1095

Glu Pro  Leu Glu Lys Thr Gly  Pro Ala Ala Val Phe  Ala Leu Glu
    1100                 1105                 1110

Gly Ala  Leu Gly Gly Val Met  Asp Asp Lys Ser Glu  Asp Ser Met
    1115                 1120                 1125

Ser Val  Ser Thr Leu Ser Phe  Gly Val Asn Arg Pro  Thr Ile Ser
    1130                 1135                 1140

Cys Ile  Phe Asp Tyr Gly Asn  Arg Tyr His Leu Arg  Cys Tyr Met
    1145                 1150                 1155

Tyr Gln  Ala Arg Asp Leu Ala  Ala Met Asp Lys Asp  Ser Phe Ser
    1160                 1165                 1170

Asp Pro  Tyr Ala Ile Val Ser  Phe Leu His Gln Ser  Gln Lys Thr
    1175                 1180                 1185

Val Val  Val Lys Asn Thr Leu  Asn Pro Thr Trp Asp  Gln Thr Leu
    1190                 1195                 1200

Ile Phe  Tyr Glu Ile Glu Ile  Phe Gly Glu Pro Ala  Thr Val Ala
    1205                 1210                 1215

Glu Gln  Pro Pro Ser Ile Val  Val Glu Leu Tyr Asp  His Asp Thr
    1220                 1225                 1230

Tyr Gly  Ala Asp Glu Phe Met  Gly Arg Cys Ile Cys  Gln Pro Ser
    1235                 1240                 1245

Leu Glu  Arg Met Pro Arg Leu  Ala Trp Phe Pro Leu  Thr Arg Gly
    1250                 1255                 1260

Ser Gln  Pro Ser Gly Glu Leu  Leu Ala Ser Phe Glu  Leu Ile Gln
    1265                 1270                 1275

Arg Glu  Lys Pro Ala Ile His  His Ile Pro Gly Phe  Glu Val Gln
    1280                 1285                 1290

Glu Thr  Ser Arg Ile Leu Asp  Glu Ser Glu Asp Thr  Asp Leu Pro
    1295                 1300                 1305

Tyr Pro  Pro Pro Gln Arg Glu  Ala Asn Ile Tyr Met  Val Pro Gln
    1310                 1315                 1320

Asn Ile  Lys Pro Ala Leu Gln  Arg Thr Ala Ile Glu  Ile Leu Ala
    1325                 1330                 1335

Trp Gly  Leu Arg Asn Met Lys  Ser Tyr Gln Leu Ala  Asn Ile Ser
    1340                 1345                 1350

Ser Pro  Ser Leu Val Val Glu  Cys Gly Gly Gln Thr  Val Gln Ser
    1355                 1360                 1365

Cys Val  Ile Arg Asn Leu Arg  Lys Asn Pro Asn Phe  Asp Ile Cys
    1370                 1375                 1380

Thr Leu  Phe Met Glu Val Met  Leu Pro Arg Glu Glu  Leu Tyr Cys
```

```
    1385                1390                1395

Pro Pro  Ile Thr Val Lys Val  Ile Asp Asn Arg Gln  Phe Gly Arg
    1400                1405                1410

Arg Pro  Val Val Gly Gln Cys  Thr Ile Arg Ser Leu  Glu Ser Phe
    1415                1420                1425

Leu Cys  Asp Pro Tyr Ser Ala  Glu Ser Pro Ser Pro  Gln Gly Gly
    1430                1435                1440

Pro Asp  Asp Val Ser Leu Leu  Ser Pro Gly Glu Asp  Val Leu Ile
    1445                1450                1455

Asp Ile  Asp Asp Lys Glu Pro  Leu Ile Pro Ile Gln  Glu Glu Glu
    1460                1465                1470

Phe Ile  Asp Trp Trp Ser Lys  Phe Phe Ala Ser Ile  Gly Glu Arg
    1475                1480                1485

Glu Lys  Cys Gly Ser Tyr Leu  Glu Lys Asp Phe Asp  Thr Leu Lys
    1490                1495                1500

Val Tyr  Asp Thr Gln Leu Glu  Asn Val Glu Ala Phe  Glu Gly Leu
    1505                1510                1515

Ser Asp  Phe Cys Asn Thr Phe  Lys Leu Tyr Arg Gly  Lys Thr Gln
    1520                1525                1530

Glu Glu  Thr Glu Asp Pro Ser  Val Ile Gly Glu Phe  Lys Gly Leu
    1535                1540                1545

Phe Lys  Ile Tyr Pro Leu Pro  Glu Asp Pro Ala Ile  Pro Met Pro
    1550                1555                1560

Pro Arg  Gln Phe His Gln Leu  Ala Ala Gln Gly Pro  Gln Glu Cys
    1565                1570                1575

Leu Val  Arg Ile Tyr Ile Val  Arg Ala Phe Gly Leu  Gln Pro Lys
    1580                1585                1590

Asp Pro  Asn Gly Lys Cys Asp  Pro Tyr Ile Lys Ile  Ser Ile Gly
    1595                1600                1605

Lys Lys  Ser Val Ser Asp Gln  Asp Asn Tyr Ile Pro  Cys Thr Leu
    1610                1615                1620

Glu Pro  Val Phe Gly Lys Met  Phe Glu Leu Thr Cys  Thr Leu Pro
    1625                1630                1635

Leu Glu  Lys Asp Leu Lys Ile  Thr Leu Tyr Asp Tyr  Asp Leu Leu
    1640                1645                1650

Ser Lys  Asp Glu Lys Ile Gly  Glu Thr Val Val Asp  Leu Glu Asn
    1655                1660                1665

Arg Leu  Leu Ser Lys Phe Gly  Ala Arg Cys Gly Leu  Pro Gln Thr
    1670                1675                1680

Tyr Cys  Val Ser Gly Pro Asn  Gln Trp Arg Asp Gln  Leu Arg Pro
    1685                1690                1695

Ser Gln  Leu Leu His Leu Phe  Cys Gln Gln His Arg  Val Lys Ala
    1700                1705                1710

Pro Val  Tyr Arg Thr Asp Arg  Val Met Phe Gln Asp  Lys Glu Tyr
    1715                1720                1725

Ser Ile  Glu Glu Ile Glu Ala  Gly Arg Ile Pro Asn  Pro His Leu
    1730                1735                1740

Gly Pro  Val Glu Glu Arg Leu  Ala Leu His Val Leu  Gln Gln Gln
    1745                1750                1755

Gly Leu  Val Pro Glu His Val  Glu Ser Arg Pro Leu  Tyr Ser Pro
    1760                1765                1770

Leu Gln  Pro Asp Ile Glu Gln  Gly Lys Leu Gln Met  Trp Val Asp
    1775                1780                1785
```

```
Leu Phe  Pro Lys Ala Leu Gly  Arg Pro Gly Pro Pro  Phe Asn Ile
    1790                 1795                 1800

Thr Pro  Arg Arg Ala Arg Arg  Phe Phe Leu Arg Cys  Ile Ile Trp
    1805                 1810                 1815

Asn Thr  Arg Asp Val Ile Leu  Asp Asp Leu Ser Leu  Thr Gly Glu
    1820                 1825                 1830

Lys Met  Ser Asp Ile Tyr Val  Lys Gly Trp Met Ile  Gly Phe Glu
    1835                 1840                 1845

Glu His  Lys Gln Lys Thr Asp  Val His Tyr Arg Ser  Leu Gly Gly
    1850                 1855                 1860

Glu Gly  Asn Phe Asn Trp Arg  Phe Ile Phe Pro Phe  Asp Tyr Leu
    1865                 1870                 1875

Pro Ala  Glu Gln Val Cys Thr  Ile Ala Lys Lys Asp  Ala Phe Trp
    1880                 1885                 1890

Arg Leu  Asp Lys Thr Glu Ser  Lys Ile Pro Ala Arg  Val Val Phe
    1895                 1900                 1905

Gln Ile  Trp Asp Asn Asp Lys  Phe Ser Phe Asp Asp  Phe Leu Gly
    1910                 1915                 1920

Ser Leu  Gln Leu Asp Leu Asn  Arg Met Pro Lys Pro  Ala Lys Thr
    1925                 1930                 1935

Ala Lys  Lys Cys Ser Leu Asp  Gln Leu Asp Asp Ala  Phe His Pro
    1940                 1945                 1950

Glu Trp  Phe Val Ser Leu Phe  Glu Gln Lys Thr Val  Lys Gly Trp
    1955                 1960                 1965

Trp Pro  Cys Val Ala Glu Glu  Gly Glu Lys Lys Ile  Leu Ala Gly
    1970                 1975                 1980

Lys Leu  Glu Met Thr Leu Glu  Ile Val Ala Glu Ser  Glu His Glu
    1985                 1990                 1995

Glu Arg  Pro Ala Gly Gln Gly  Arg Asp Glu Pro Asn  Met Asn Pro
    2000                 2005                 2010

Lys Leu  Glu Asp Pro Arg Arg  Pro Asp Thr Ser Phe  Leu Trp Phe
    2015                 2020                 2025

Thr Ser  Pro Tyr Lys Thr Met  Lys Phe Ile Leu Trp  Arg Arg Phe
    2030                 2035                 2040

Arg Trp  Ala Ile Ile Leu Phe  Ile Ile Leu Phe Ile  Leu Leu Leu
    2045                 2050                 2055

Phe Leu  Ala Ile Phe Ile Tyr  Ala Phe Pro Asn Tyr  Ala Ala Met
    2060                 2065                 2070

Lys Leu  Val Lys Pro Phe Ser
    2075                 2080


<210> SEQ ID NO 23
<211> LENGTH: 2974
<212> TYPE: DNA
<213> ORGANISM: Homo sapiens

<400> SEQUENCE: 23

agaagccccg cagccgccgc gcggagaaca gcgacagccg agcgcccggt ccgcctgtct     60

gccggtgggt ctgcctgccc gcgcagcaga cccggggcgg ccgcgggagc ccgcgccccg    120

cccgccgcgc ctctgccggg acccacccgc agcggagggc tgagcccgcc ggcggctccc    180

cggagctcac ccacctccgc gcgccggagc gcaggcaaaa ggggaggaaa ggctcctctc    240

tttagtcacc actctcgccc tctccaagaa tttgtttaac aaagcgctga ggaaagagaa    300
```

```
cgtcttcttg aattctttag taggggcgga gtctgctgct gccctgcgct gccacctcgg    360
ctacactgcc ctccgcgacg acccctgacc agccggggtc acgtccggga gacgggatca    420
tgaagcgctc ggtagccgtc tggctcttgg tcgggctcag cctcggtgtc cccagttcg     480
gcaaaggtga tatttgtgat cccaatccat gtgaaaatgg aggtatctgt ttgccaggat    540
tggctgatgg ttccttttcc tgtgagtgtc cagatggctt cacagacccc aactgttcta    600
gtgttgtgga ggttgcatca gatgaagaag aaccaacttc agcaggtccc tgcactccta    660
atccatgcca taatggagga acctgtgaaa taagtgaagc ataccgaggg gatacattca    720
taggctatgt ttgtaaatgt ccccgaggat ttaatgggat tcactgtcag cacaacataa    780
atgaatgcga agttgagcct tgcaaaaatg gtggaatatg tacagatctt gttgctaact    840
attcctgtga gtgcccaggc gaatttatgg gaagaaattg tcaatacaaa tgctcaggcc    900
cactgggaat tgaaggtgga attatatcaa accagcaaat cacagcttcc tctactcacc    960
gagctctttt tggactccaa aaatggtatc cctactatgc acgtcttaat aagaaggggc   1020
ttataaatgc gtggacagct gcagaaaatg acagatggcc gtggattcag ataaatttgc   1080
aaaggaaaat gagagttact ggtgtgatta cccaaggagc caagaggatt ggaagcccag   1140
agtatataaa atcctacaaa attgcctaca gtaatgatgg aaagacttgg gcaatgtaca   1200
aagtgaaagg caccaatgaa gacatggtgt ttcgtggaaa cattgataac aacactccat   1260
atgctaactc tttcacaccc cccataaaag ctcagtatgt aagactctat ccccaagttt   1320
gtcgaagaca ttgcactttg cgaatggaac ttcttggctg tgaactgtcg ggttgttctg   1380
agcctctggg tatgaaatca ggacatatac aagactatca gatcactgcc tccagcatct   1440
tcagaacgct caacatggac atgttcactt gggaaccaag gaaagctcgg ctggacaagc   1500
aaggcaaagt gaatgcctgg acctctggcc acaatgacca gtcacaatgg ttacaggtgg   1560
atcttcttgt tccaaccaaa gtgactggca tcattacaca aggagctaaa gattttggtc   1620
atgtacagtt tgttggctcc tacaaactgg cttacagcaa tgatggagaa cactggactg   1680
tataccagga tgaaaagcaa agaaaagata aggttttcca gggaaatttt gacaatgaca   1740
ctcacagaaa aaatgtcatc gaccctccca tctatgcacg acacataaga atccttcctt   1800
ggtcctggta cgggaggatc acattgcggt cagagctgct gggctgcaca gaggaggaat   1860
gaggggaggc tacatttcac aaccctcttc cctatttccc taaaagtatc tccatggaat   1920
gaactgtgca aaatctgtag gaaactgaat ggtttttttt tttttttcat gaaaaagtgc   1980
tcaaattatg gtaggcaact aacggtgttt ttaagggggt ctaagcctgc cttttcaatg   2040
atttaatttg attttatttt atccgtcaaa tctcttaagt aacaacacat taagtgtgaa   2100
ttacttttct ctcattgttt cctgaattat tcgcattggt agaaatatat tagggaaaga   2160
aagtagcctt ctttttatag caagagtaaa aaagtctcaa agtcatcaaa taagagcaag   2220
agttgataga gcttttacaa tcaatactca cctaattctg ataaaaggaa tactgcaatg   2280
ttagcaataa gtttttttct tctgtaatga ctctacgtta tcctgtttcc ctgtgcctac   2340
caaacactgt caatgtttat tacaaaattt taaagaagaa tatgtaacat gcagtactga   2400
tattataatt ctcattttac tttcattatt tctaataaga gattatgtga cttctttttc   2460
ttttagttct attctacatt cttaatattg tatattacct gaataattca atttttttct   2520
aattgaattt cctattagtt gactaaaaga agtgtcatgt ttactcatat atgtagaaca   2580
tgactgccta tcagtagatt gatctgtatt taatattcgt taattaaatc tgcagtttta   2640
tttttgaagg aagccataac tatttaattt ccaaataatt gcttcataaa gaatcccata   2700
```

ctctcagttt gcacaaaaga acaaaaaata tatatgtctc tttaaattta aatcttcatt 2760
tagatggtaa ttacatatcc ttatatttac tttaaaaaat cggcttattt gtttatttta 2820
taaaaaattt agcaaagaaa tattaatata gtgctgcata gtttggccaa gcatactcat 2880
catttctttg ttcagctcca catttcctgt gaaactaaca tcttattgag atttgaaact 2940
ggtggtagtt tcccaggaag gcacaggtgg agtt 2974

<210> SEQ ID NO 24
<211> LENGTH: 480
<212> TYPE: PRT
<213> ORGANISM: Homo sapiens

<400> SEQUENCE: 24

Met Lys Arg Ser Val Ala Val Trp Leu Leu Val Gly Leu Ser Leu Gly
1               5                   10                  15

Val Pro Gln Phe Gly Lys Gly Asp Ile Cys Asp Pro Asn Pro Cys Glu
            20                  25                  30

Asn Gly Gly Ile Cys Leu Pro Gly Leu Ala Asp Gly Ser Phe Ser Cys
        35                  40                  45

Glu Cys Pro Asp Gly Phe Thr Asp Pro Asn Cys Ser Ser Val Val Glu
    50                  55                  60

Val Ala Ser Asp Glu Glu Glu Pro Thr Ser Ala Gly Pro Cys Thr Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Val Glu Pro Cys
        115                 120                 125

Lys Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
                165                 170                 175

Ser Ser Thr His Arg Ala Leu Phe Gly Leu Gln Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Asp Met Val Phe Arg
            260                 265                 270

Gly Asn Ile Asp Asn Asn Thr Pro Tyr Ala Asn Ser Phe Thr Pro Pro
        275                 280                 285

Ile Lys Ala Gln Tyr Val Arg Leu Tyr Pro Gln Val Cys Arg Arg His
    290                 295                 300

Cys Thr Leu Arg Met Glu Leu Leu Gly Cys Glu Leu Ser Gly Cys Ser
305                 310                 315                 320

```
Glu Pro Leu Gly Met Lys Ser Gly His Ile Gln Asp Tyr Gln Ile Thr
                325                 330                 335

Ala Ser Ser Ile Phe Arg Thr Leu Asn Met Asp Met Phe Thr Trp Glu
            340                 345                 350

Pro Arg Lys Ala Arg Leu Asp Lys Gln Gly Lys Val Asn Ala Trp Thr
        355                 360                 365

Ser Gly His Asn Asp Gln Ser Gln Trp Leu Gln Val Asp Leu Leu Val
    370                 375                 380

Pro Thr Lys Val Thr Gly Ile Ile Thr Gln Gly Ala Lys Asp Phe Gly
385                 390                 395                 400

His Val Gln Phe Val Gly Ser Tyr Lys Leu Ala Tyr Ser Asn Asp Gly
                405                 410                 415

Glu His Trp Thr Val Tyr Gln Asp Glu Lys Gln Arg Lys Asp Lys Val
            420                 425                 430

Phe Gln Gly Asn Phe Asp Asn Asp Thr His Arg Lys Asn Val Ile Asp
        435                 440                 445

Pro Pro Ile Tyr Ala Arg His Ile Arg Ile Leu Pro Trp Ser Trp Tyr
    450                 455                 460

Gly Arg Ile Thr Leu Arg Ser Glu Leu Leu Gly Cys Thr Glu Glu Glu
465                 470                 475                 480


<210> SEQ ID NO 25
<211> LENGTH: 1368
<212> TYPE: DNA
<213> ORGANISM: Homo sapiens

<400> SEQUENCE: 25

gtggctccag gccggaagag ggagtctgta ggggcgggcc ggctggcgtc ccctttccgg      60

ccggtcccca tggaggcgct ggggaagctg aagcagttcg atgcctaccc caagactttg     120

gaggacttcc gggtcaagac ctgcgggggc gccaccgtga ccattgtcag tggccttctc     180

atgctgctac tgttcctgtc cgagctgcag tattacctca ccacggaggt gcatcctgag     240

ctctacgtgg acaagtcgcg gggagataaa ctgaagatca acatcgatgt actttttccg     300

cacatgcctt gtgcctatct gagtattgat gccatggatg tggccggaga acagcagctg     360

gatgtggaac acaacctgtt caagcaacga ctagataaag atggcatccc cgtgagctca     420

gaggctgagc ggcatgagct tgggaaagtc gaggtgacgg tgtttgaccc tgactccctg     480

gaccctgatc gctgtgagag ctgctatggt gctgaggcag aagatatcaa gtgctgtaac     540

acctgtgaag atgtgcggga ggcatatcgc cgtagaggct gggccttcaa gaacccagat     600

actattgagc agtgccggcg agagggcttc agccagaaga tgcaggagca gaagaatgaa     660

ggctgccagg tgtatggctt cttggaagtc aataaggtgg ccggaaactt ccactttgcc     720

cctgggaaga gcttccagca gtcccatgtg cacgtccatg acttgcagag ctttggcctt     780

gacaacatca acatgaccca ctacatccag cacctgtcat ttggggagga ctatccaggc     840

attgtgaacc ccctggacca caccaatgtc actgcgcccc aagcctccat gatgttccag     900

tactttgtga aggtggtgcc cactgtgtac atgaaggtgg acggagaggt actgaggaca     960

aatcagttct ctgtgaccag acatgagaag gttgccaatg ggctgttggg cgaccaaggc    1020

cttcccggag tcttcgtcct ctatgagctc tcgcccatga tggtgaagct gacggagaag    1080

cacaggtcct tcacccactt cctgacaggt gtgtgcgcca tcattggggg catgttcaca    1140

gtggctggac tcatcgattc gctcatctac cactcagcac gagccatcca gaagaaaatt    1200

gatctaggga agacaacgta gtcaccctcg gtgcttcctc tgtctcctct ttctccctgg    1260
```

```
cctgtggttg tcccccagcc tctgccaccc tccacctcct cggtcagccc cagccccagg   1320

ttgataaatc tattgattga ttgtgatagt aaaaaaaaaa aaaaaaaa                1368


<210> SEQ ID NO 26
<211> LENGTH: 383
<212> TYPE: PRT
<213> ORGANISM: Homo sapiens

<400> SEQUENCE: 26

Met Glu Ala Leu Gly Lys Leu Lys Gln Phe Asp Ala Tyr Pro Lys Thr
1               5                   10                  15

Leu Glu Asp Phe Arg Val Lys Thr Cys Gly Gly Ala Thr Val Thr Ile
            20                  25                  30

Val Ser Gly Leu Leu Met Leu Leu Leu Phe Leu Ser Glu Leu Gln Tyr
        35                  40                  45

Tyr Leu Thr Thr Glu Val His Pro Glu Leu Tyr Val Asp Lys Ser Arg
    50                  55                  60

Gly Asp Lys Leu Lys Ile Asn Ile Asp Val Leu Phe Pro His Met Pro
65                  70                  75                  80

Cys Ala Tyr Leu Ser Ile Asp Ala Met Asp Val Ala Gly Glu Gln Gln
                85                  90                  95

Leu Asp Val Glu His Asn Leu Phe Lys Gln Arg Leu Asp Lys Asp Gly
            100                 105                 110

Ile Pro Val Ser Ser Glu Ala Glu Arg His Glu Leu Gly Lys Val Glu
        115                 120                 125

Val Thr Val Phe Asp Pro Asp Ser Leu Asp Pro Asp Arg Cys Glu Ser
    130                 135                 140

Cys Tyr Gly Ala Glu Ala Glu Asp Ile Lys Cys Cys Asn Thr Cys Glu
145                 150                 155                 160

Asp Val Arg Glu Ala Tyr Arg Arg Arg Gly Trp Ala Phe Lys Asn Pro
                165                 170                 175

Asp Thr Ile Glu Gln Cys Arg Arg Glu Gly Phe Ser Gln Lys Met Gln
            180                 185                 190

Glu Gln Lys Asn Glu Gly Cys Gln Val Tyr Gly Phe Leu Glu Val Asn
        195                 200                 205

Lys Val Ala Gly Asn Phe His Phe Ala Pro Gly Lys Ser Phe Gln Gln
    210                 215                 220

Ser His Val His Val His Asp Leu Gln Ser Phe Gly Leu Asp Asn Ile
225                 230                 235                 240

Asn Met Thr His Tyr Ile Gln His Leu Ser Phe Gly Glu Asp Tyr Pro
                245                 250                 255

Gly Ile Val Asn Pro Leu Asp His Thr Asn Val Thr Ala Pro Gln Ala
            260                 265                 270

Ser Met Met Phe Gln Tyr Phe Val Lys Val Val Pro Thr Val Tyr Met
        275                 280                 285

Lys Val Asp Gly Glu Val Leu Arg Thr Asn Gln Phe Ser Val Thr Arg
    290                 295                 300

His Glu Lys Val Ala Asn Gly Leu Leu Gly Asp Gln Gly Leu Pro Gly
305                 310                 315                 320

Val Phe Val Leu Tyr Glu Leu Ser Pro Met Met Val Lys Leu Thr Glu
                325                 330                 335

Lys His Arg Ser Phe Thr His Phe Leu Thr Gly Val Cys Ala Ile Ile
            340                 345                 350
```

Gly Gly Met Phe Thr Val Ala Gly Leu Ile Asp Ser Leu Ile Tyr His
355 360 365

Ser Ala Arg Ala Ile Gln Lys Lys Ile Asp Leu Gly Lys Thr Thr
370 375 380

<210> SEQ ID NO 27
<211> LENGTH: 2483
<212> TYPE: DNA
<213> ORGANISM: Homo sapiens

<400> SEQUENCE: 27
agttgattgc aggtcctcct ggggccagaa gggtgcctgg gaggccaggt tctggggatc 60
ccctccatcc agaagaacca cctgctcact ctgtcccttc gcctgctgct gggaccatgg 120
gggctggggc cagtgctgag gagaagcact ccagggagct ggaaaagaag ctgaaagagg 180
acgctgagaa ggatgctcga accgtgaagc tgctgcttct gggtgccggt gagtccggga 240
agagcaccat cgtcaagcag atgaagatta tccaccagga cgggtactcg ctggaagagt 300
gcctcgagtt tatcgccatc atctacggca acacgttgca gtccatcctg gccatcgtac 360
gcgccatgac cacactcaac atccagtacg gagactctgc acgccaggac gacgcccgga 420
agctgatgca catggcagac actatcgagg agggcacgat gcccaaggag atgtcggaca 480
tcatccagcg gctgtggaag gactccggta tccaggcctg ttttgagcgc gcctcggagt 540
accagctcaa cgactcggcg ggctactacc tctccgacct ggagcgcctg gtaaccccgg 600
gctacgtgcc caccgagcag gacgtgctgc gctcgcgagt caagaccact ggcatcatcg 660
agacgcagtt ctccttcaag gatctcaact tccggatgtt cgatgtgggc gggcagcgct 720
cggagcgcaa gaagtggatc cactgcttcg agggcgtgac ctgcatcatc ttcatcgcgg 780
cgctgagcgc ctacgacatg gtgctagtgg aggacgacga agtgaaccgc atgcacgaga 840
gcctgcacct gttcaacagc atctgcaacc accgctactt cgccacgacg tccatcgtgc 900
tcttccttaa caagaaggac gtcttcttcg agaagatcaa gaaggcgcac ctcagcatct 960
gtttcccgga ctacgatgga cccaacacct acgaggacgc cggcaactac atcaaggtgc 1020
agttcctcga gctcaacatg cggcgcgacg tgaaggagat ctattcccac atgacgtgcg 1080
ccaccgacac gcagaacgtc aaatttgtct tcgacgctgt caccgacatc atcatcaagg 1140
agaacctcaa agactgtggc ctcttctgag gccagggcct gtgctgcagt cggggacaag 1200
gagcttccgt ctggcaaggc cggggcacaa tttgcactcc cctcagctag acgcacagac 1260
tcagcaataa acctttgcat caggctccag ctgtcctttc ttggtggagg acttaattat 1320
cacaagtcat gggcatttat taagtgccca gtgctgggtt gggcatgaag tgggaagatg 1380
gcccctccca ggaagaagta cctggcctga caaggtgggg cactcttggg ggtatgggac 1440
caactcatgg cttttcacgg gagttgagga gagaggagct gtggaaaata ttcactggga 1500
cagtcttgga tcaagaggga gttttgaggt ggaggctcat tctggcaggg accgtagtgt 1560
ctaccagccc cagaaacatg ggcttatggc cacaggagtt cagtggagca agagcagggg 1620
aggagagacg tggacaggtg cccaaagcca gtcggagggc ctgggctttc tcagaaggtg 1680
atggagagtc ttggaagccc tcgaggcagg aacataattg cagggctggg attagggtga 1740
gggaagtgag gcacactcac cttgggtgca acatttaagg cgatgccaaa aaatttagta 1800
accaaggtaa ataatattag gataatattt ttaaaaatca aatgaatgca aaaccccaca 1860
atgaatgaaa tatcaaaatc caacagagga tcaaacagag gcatgctaag atatattggg 1920
gcttgaagca aagggaaaac tatttgttgc tatatgtttg tagggatttt ttgccagttt 1980

```
taaaaataca tgtatcataa agtttactat ctcagccact tgccggtgta tagtttggtg   2040

gtgttaagta cattcataat gttgtacaac caccgcaact gttcatctcc agaactcctt   2100

tcctcttgta aaactgtaac tctgtaccca tgaaaaaata accccccatt cctgccttcc   2160

cccggctcct ggcatccacc attctacttt ccatctctat gaatgtgact gctctaagtg   2220

cctcagatgt gtgggtccat gaagtctttg tctttttgca actggcttat ttcacttagc   2280

atcatgtctt caaggtttat tcatgtgtag catatggcag aatctccttc ctttttaagg   2340

ttgaataata ttccattgta tatattccac actttgttta tttattcatc tattgatgaa   2400

tggttacatc tgccttttgg ctattgtgaa taatgctgct atgaacatgg gtgtacaaat   2460

ctctcaaaaa aaaaaaaaaa aaa                                           2483


<210> SEQ ID NO 28
<211> LENGTH: 350
<212> TYPE: PRT
<213> ORGANISM: Homo sapiens

<400> SEQUENCE: 28

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Glu Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
    210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
```

```
        275                 280                 285

Pro Asn Thr Tyr Glu Asp Ala Gly Asn Tyr Ile Lys Val Gln Phe Leu
    290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350


<210> SEQ ID NO 29
<211> LENGTH: 4337
<212> TYPE: DNA
<213> ORGANISM: Homo sapiens

<400> SEQUENCE: 29

cgtcatgtta gggtgaagca gaggacctca gtgctgaaca tgctaaggag gttggacaaa      60

atcaggttca gaggtcacaa gagagatgac ttcctcgatc tagcggagtc tccaaatgcc     120

tcggacaccg aatgcagcga cgaaatcccc ctgaaggtac cgcggacctc gccccgggac     180

agcgaggagc tgagggaccc tgctggtcca gggaccctca tcatggccac aggagtccag     240

gactttaacc ggacagagtt tgatcgactg aatgagatca aaggtcacct ggaaattgcc     300

ttattggaaa aacatttctt acaggaggag ctccggaagc tgcgagaaga aaccaacgcg     360

gagatgctgc ggcaggagct ggaccgcgag cggcagcggc ggatggagct ggagcagaag     420

gtgcaggagg tgctgaaggc cagaaccgag gagcagatgg ctcagcagcc cccaaaaggg     480

caggcccagg ccagcaatgg agcagagcgc cggagccagg ggctgtcctc gcgcctgcag     540

aagtggttct acgagcggtt cggggagtac gtggaggact tccggttcca gcccgaggag     600

aacactgtgg agacagagga acccctgagc gcccgcaggt taactgaaaa tatgagacgg     660

ctcaagcgcg gtgccaagcc ggtcactaac tttgtgaaga acctctctgc cttatccgac     720

tggtactccg tctacacgtc tgccattgcc ttcaccgtgt acatgaatgc cgtgtggcat     780

ggctgggcca tcccattgtt cttatttcta gcaattctga ggttatccct caattacctc     840

atcgccaggg ggtggcggat acagtggagc atcgtgcccg aagtgtctga gcccgtggaa     900

cctccaaagg aagacctgac tgtgtctgag aagttccagc tggtgctgga cgtcgcccag     960

aaagcccaga accttttcgg gaagatggct gacatcctgg agaagatcaa gaacttgttc    1020

atgtgggtcc agccggagat cacacagaag ctgtatgtgg cgctctgggc tgccttcctg    1080

gcctcctgct tcttccccta ccgcctggtg gggcttgccg tgggactcta tgctggtatc    1140

aagttcttcc tcattgattt catctttaaa cgctgcccga ggctgcgcgc caagtacgac    1200

acgccctata tcatctggag gagtctcccc accgacccgc agctcaagga gcgctccagc    1260

gccgcagtct cacgcaggct gcagacgacc tcgtcacgga gctacgtacc cagcgcaccg    1320

gccggcctgg gtaaagagga ggacgccggt cgcttccaca gcaccaagaa gggcaatttc    1380

cacgagatct tcaatctgac agaaaacgag cgtccgctgg cggtgtgcga gaatggctgg    1440

cgctgctgcc tcatcaacag ggaccggaag atgcccacgg actacatcag gaacggggtg    1500

ctctacgtca cggagaatta cttgtgcttc gaaagctcca aatctgggtc ctcaaagagg    1560

aacaaagtca tcaagctagt ggacatcacg gacatccaga agtacaaggt cctgtctgtc    1620

ctcccaggct caggcatggg gattgccgtg tcgacgccat ccacccagaa accgctcgtg    1680

tttggtgcca tggtgcacag ggatgaggcc ttcgagacca ttctcagcca gtacatcaag    1740
```

```
atcacctcag cggcagcgtc tggcggggac agctagtatt gacttgccca ggacgttgct   1800
ggaattttct ttttcttttt ctttttcttt tttttttttt acgatttggt agtggaaaca   1860
attggacatc ctcatgagct tttgcaataa ttctcctgga cctgtggttc tattgtgttg   1920
acctctgcgt tttatcgacc aagaaggggc cagggctcac agggacgggg gtgcccctct   1980
cccacagggc acgtcaggtg cctctgaggg ccacccgcag actgggggag ggggcagagg   2040
ccctcggggg cccgtggaga agacacacag gacccctggc cctgcccttc tccgttccag   2100
cctggacaga gaaacctctc cagccacccc aagaggttct cgcaaccttg tgtcccgctc   2160
tccagaggcc agaagctcgt ccaccaccaa agccatagct gaagagtgcg gggcccttcc   2220
tcctggggac agaaagatgt cgtcaaggag ggacatgggg gcctttcacc aaccaccgag   2280
aaacgggcct ggcggccctc cttcctctta catgagaccc tcctgtggca tttgcccttg   2340
gtgccgggct ggggccgggc gcagtgaccc tgcctgcgct ccacactcgc tccacgggaa   2400
cagagagggt gagaagggcc caccccctcgc ctgccctcag tgtctttggt ggcaccttcc   2460
ttgctggcct ccagggcgct cagcaccgcg tctgtaaggg cctgcctgct gctctcggcc   2520
tgacacgccg gccaggaggt ctgtagctgg ggaccagtaa gggcacagga tggtgcaggt   2580
aaaagcacat ctttctcaca ctttgctctt tggaaggccc aggagaacat ccgcgaaggc   2640
tgttggaggt gctccgagca ctgtggcatg tctggcacat ggcccccagg ctgcggttgc   2700
ctgggttggt tgggggagga agtggggagg agtgttccgg gaccatggtg gcccaggctg   2760
cagccgcctt tgggccatcc gagaggctct ggcagcccct gtgctttagg gagcaaccgt   2820
gagccgagcc cagaggcctg ggcctgcact gcctgcagcc gacatgcgac agcgttccct   2880
cccccgcgtg cctagccggt gccggtccgg gcacagaccc ccccagcccc cgccctgccc   2940
cagggaagcc tgggcttccc gggaacaagg tggcatttgt ggagggagcg cccgcaggcc   3000
tggtctgctg gggccgcctg cgctgggctg aagggaggga aaggcggctt gggcctcctg   3060
gaaggaggtg gccaccccgc gggcctgcgt gtctgctggg gcggatcccg cagctccctc   3120
agcttgtcct gagtcccttg ggtgtcgttg agattgttgt tttttgaaga aacagaagat   3180
tctatttttt acagcgagca agctggtttt cttatttttg tatccttttt cagatgtaat   3240
ttttatcttt gctccgatcc tcatttgctg gtgtgggtga gggatccggc ggcatgggct   3300
ggtttcaccc ccttcacgag gggccgcaga gtcacacgct ggtgccgggg gtgctttggg   3360
gggagctgcg ccgatcacca gattaagcac atgtcctatc ccaggcggtg gagcggagcc   3420
cccgtggctc tggactgcgc ggacgttggc gtcaggatga ccacacggcg gcctttcccg   3480
aatggggaca gaacccgctc tgagccgtgg gtctggctcc tgtaggggac tggctctctt   3540
ggtgcaccag gggagggggga catatcccag tgaaccccac cttggcgcct gaggcaacac   3600
agggtgggca ctgacccacc cccaggggcg gctgcagagg cagtgcccgc agacaatggc   3660
cacacctctc tccccaggc ccggcagtgc ccaaggatgg gtccggggcc tcggggccaa   3720
tgagcgcctc ttcctaggtg ctgggattca gtccccaaac acagcgggag gggtccctgg   3780
ggcagatggg gctttaccag cgtcgggtgg tttagttcga gtccctttttg tggagaaagg   3840
gagatgaaaa ctgaccacgt gccaggtgtg gccgaagccc ccagggaggg ccacattcgg   3900
ggagcggggg gtcgggggag ggccaccgac tggctctgct gccagcacag gcccctccct   3960
ggaagtcctc gggagcggag cgcggatcgg cacgggctct gggctccccg tggagagaag   4020
ctgtagtttt taccaaattg tgtacatctg ggcagatgtt taatttctgt gactaatcac   4080
```

```
tgaactagac gaatgttaaa ttttttatgt ctgaagcctg agtctatttt ggatctgtaa   4140

ataatcattg ccagtgtgac ttttgttcaa caaaaggatt gtactgtatt aagaaccgat   4200

gaaaaaaatt ctcctgtaac attttttttaa gaaaactttg tttgtttaaa gaaaaagtat   4260

tgtataaatt ataattttta tttaaataaa cctaaaatgc tttgtgctaa ggctcaaaaa   4320

aaaaaaaaaa aaaaaaa                                                  4337


<210> SEQ ID NO 30
<211> LENGTH: 578
<212> TYPE: PRT
<213> ORGANISM: Homo sapiens

<400> SEQUENCE: 30

Met Leu Arg Arg Leu Asp Lys Ile Arg Phe Arg Gly His Lys Arg Asp
1               5                   10                  15

Asp Phe Leu Asp Leu Ala Glu Ser Pro Asn Ala Ser Asp Thr Glu Cys
            20                  25                  30

Ser Asp Glu Ile Pro Leu Lys Val Pro Arg Thr Ser Pro Arg Asp Ser
        35                  40                  45

Glu Glu Leu Arg Asp Pro Ala Gly Pro Gly Thr Leu Ile Met Ala Thr
    50                  55                  60

Gly Val Gln Asp Phe Asn Arg Thr Glu Phe Asp Arg Leu Asn Glu Ile
65                  70                  75                  80

Lys Gly His Leu Glu Ile Ala Leu Leu Glu Lys His Phe Leu Gln Glu
                85                  90                  95

Glu Leu Arg Lys Leu Arg Glu Glu Thr Asn Ala Glu Met Leu Arg Gln
            100                 105                 110

Glu Leu Asp Arg Glu Arg Gln Arg Arg Met Glu Leu Glu Gln Lys Val
        115                 120                 125

Gln Glu Val Leu Lys Ala Arg Thr Glu Glu Gln Met Ala Gln Gln Pro
    130                 135                 140

Pro Lys Gly Gln Ala Gln Ala Ser Asn Gly Ala Glu Arg Arg Ser Gln
145                 150                 155                 160

Gly Leu Ser Ser Arg Leu Gln Lys Trp Phe Tyr Glu Arg Phe Gly Glu
                165                 170                 175

Tyr Val Glu Asp Phe Arg Phe Gln Pro Glu Glu Asn Thr Val Glu Thr
            180                 185                 190

Glu Glu Pro Leu Ser Ala Arg Arg Leu Thr Glu Asn Met Arg Arg Leu
        195                 200                 205

Lys Arg Gly Ala Lys Pro Val Thr Asn Phe Val Lys Asn Leu Ser Ala
    210                 215                 220

Leu Ser Asp Trp Tyr Ser Val Tyr Thr Ser Ala Ile Ala Phe Thr Val
225                 230                 235                 240

Tyr Met Asn Ala Val Trp His Gly Trp Ala Ile Pro Leu Phe Leu Phe
                245                 250                 255

Leu Ala Ile Leu Arg Leu Ser Leu Asn Tyr Leu Ile Ala Arg Gly Trp
            260                 265                 270

Arg Ile Gln Trp Ser Ile Val Pro Glu Val Ser Glu Pro Val Glu Pro
        275                 280                 285

Pro Lys Glu Asp Leu Thr Val Ser Glu Lys Phe Gln Leu Val Leu Asp
    290                 295                 300

Val Ala Gln Lys Ala Gln Asn Leu Phe Gly Lys Met Ala Asp Ile Leu
305                 310                 315                 320

Glu Lys Ile Lys Asn Leu Phe Met Trp Val Gln Pro Glu Ile Thr Gln
```

```
                325                 330                 335

Lys Leu Tyr Val Ala Leu Trp Ala Ala Phe Leu Ala Ser Cys Phe Phe
            340                 345                 350

Pro Tyr Arg Leu Val Gly Leu Ala Val Gly Leu Tyr Ala Gly Ile Lys
        355                 360                 365

Phe Phe Leu Ile Asp Phe Ile Phe Lys Arg Cys Pro Arg Leu Arg Ala
    370                 375                 380

Lys Tyr Asp Thr Pro Tyr Ile Ile Trp Arg Ser Leu Pro Thr Asp Pro
385                 390                 395                 400

Gln Leu Lys Glu Arg Ser Ser Ala Ala Val Ser Arg Arg Leu Gln Thr
                405                 410                 415

Thr Ser Ser Arg Ser Tyr Val Pro Ser Ala Pro Ala Gly Leu Gly Lys
            420                 425                 430

Glu Glu Asp Ala Gly Arg Phe His Ser Thr Lys Lys Gly Asn Phe His
        435                 440                 445

Glu Ile Phe Asn Leu Thr Glu Asn Glu Arg Pro Leu Ala Val Cys Glu
    450                 455                 460

Asn Gly Trp Arg Cys Cys Leu Ile Asn Arg Asp Arg Lys Met Pro Thr
465                 470                 475                 480

Asp Tyr Ile Arg Asn Gly Val Leu Tyr Val Thr Glu Asn Tyr Leu Cys
                485                 490                 495

Phe Glu Ser Ser Lys Ser Gly Ser Ser Lys Arg Asn Lys Val Ile Lys
            500                 505                 510

Leu Val Asp Ile Thr Asp Ile Gln Lys Tyr Lys Val Leu Ser Val Leu
        515                 520                 525

Pro Gly Ser Gly Met Gly Ile Ala Val Ser Thr Pro Ser Thr Gln Lys
    530                 535                 540

Pro Leu Val Phe Gly Ala Met Val His Arg Asp Glu Ala Phe Glu Thr
545                 550                 555                 560

Ile Leu Ser Gln Tyr Ile Lys Ile Thr Ser Ala Ala Ala Ser Gly Gly
                565                 570                 575

Asp Ser
```

<210> SEQ ID NO 31
<211> LENGTH: 2005
<212> TYPE: DNA
<213> ORGANISM: Homo sapiens

<400> SEQUENCE: 31

```
tttcctctca gggggcagca ggaagtgagg agaaagggct gggatgggag gcgggagcgg      60

atgggaggga atggggttta tcaagtcctc ggcgagctgc ccaacgggca gcagctggcg     120

caagtagcct agctggagag gctcacccca ggaaggaggg aggccaccga cctactgggc     180

cgacggactc ccacacagtt cctgagctgg tgccaggcag gtgacacctc ctgcagcccc     240

cagcatgcgg gcaggcccag gccccaccgt tacattggcc ctggtgctgg cggtgtcatg     300

ggccatggag ctcaagccca cagcaccacc catcttcact ggccggccct ttgtggtagc     360

gtgggacgtg cccacacagg actgtggccc acgcctcaag gtgccactgg acctgaatgc     420

ctttgatgtg caggcctcac ctaatgaggg ttttgtgaac cagaatatta ccatcttcta     480

ccgcgaccgt ctaggcctgt atccacgctt cgattctgcc ggaaggtctg tgcatggtgg     540

tgtgccacag aatgtcagcc tttgggcaca ccggaagatg ctgcagaaac gtgtggagca     600

ctacattcgg acacaggagt ctgcggggct ggcggtcatc gactgggagg actggcgacc     660
```

```
tgtgtgggtg cgcaactggc aggacaaaga tgtgtatcgc cggttatcac gccagctagt    720
ggccagtcgt caccctgact ggcctccaga ccgcatagtc aaacaggcac aatatgagtt    780
tgagttcgca gcacagcagt tcatgctgga gacactgcgt tatgtcaagg cagtgcggcc    840
ccggcacctc tggggcttct acctctttcc tgactgctac aatcatgatt atgtgcagaa    900
ctgggagagc tacacaggcc gctgccctga tgttgaggtg gcccgcaatg accagctggc    960
ctggctgtgg gctgagagca cggccctctt cccgtctgtc tacctggacg agacacttgc   1020
ttcctcccgc catggccgca actttgtgag cttccgtgtt caggaggccc ttcgtgtggc   1080
tcgcacccac catgccaacc atgcactccc agtctacgtc ttcacacgac ccacctacag   1140
ccgcaggctc acggggctta gtgagatgga cctcatctct accattggcg agagtgcggc   1200
cctgggcgca gctggtgtca tcctctgggg tgacgcgggg tacaccacaa gcacggagac   1260
ctgccagtac ctcaaagatt acctgacacg gctgctggtc ccctacgtgg tcaatgtgtc   1320
ctgggccacc caatattgca gccgggccca gtgccatggc catgggcgct gtgtgcgccg   1380
caaccccagt gccagtacct tcctgcatct cagcaccaac agtttccgcc tagtgcctgg   1440
ccatgcacct ggtgaacccc agctgcgacc tgtgggggag ctcagttggg ccgacattga   1500
ccacctgcag acacacttcc gctgccagtg ctacttgggc tggagtggtg agcaatgcca   1560
gtgggaccat aggcaggcag ctggaggtgc cagcgaggcc tgggctgggt cccacctcac   1620
cagtctgctg gctctggcag ccctggcctt tacctggacc ttgtaggggt ctcctgccta   1680
gctgcctagc aagctggcct ctaccacaag ggctctctta ggcatgtagg accctgcagg   1740
gggtggacaa actggagtct ggagtgggca gagcccccag gaagcccagg agggcatcca   1800
taccagctcg caccccccctg ttctaagggg gaggggaagt ccctgggagg cccccttctct   1860
ccctgccaga ggggaaggag ggtacagctg ggctggggag gacctgaccc tactcccttg   1920
ccctagatag tttattatta ttattatttt ggggtctctt ttgtaaatta aacataaaac   1980
aattgcttct ctgcttggat tttgt                                         2005
```

<210> SEQ ID NO 32
<211> LENGTH: 473
<212> TYPE: PRT
<213> ORGANISM: Homo sapiens

<400> SEQUENCE: 32

```
Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
```

```
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470


<210> SEQ ID NO 33
<211> LENGTH: 1629
<212> TYPE: DNA
<213> ORGANISM: Homo sapiens

<400> SEQUENCE: 33

acacatcagg ggcttgctct tgcaaaacca aaccacaaga cagacttgca aaagaaggca      60

tgcacagctc agcactgctc tgttgcctgg tcctcctgac tggggtgagg gccagcccag     120

gccagggcac ccagtctgag aacagctgca cccacttccc aggcaacctg cctaacatgc     180
```

```
ttcgagatct ccgagatgcc ttcagcagag tgaagacttt ctttcaaatg aaggatcagc    240

tggacaactt gttgttaaag gagtccttgc tggaggactt taagggttac ctgggttgcc    300

aagccttgtc tgagatgatc cagttttacc tggaggaggt gatgccccaa gctgagaacc    360

aagacccaga catcaaggcg catgtgaact ccctggggga gaacctgaag accctcaggc    420

tgaggctacg gcgctgtcat cgatttcttc cctgtgaaaa caagagcaag gccgtggagc    480

aggtgaagaa tgcctttaat aagctccaag agaaaggcat ctacaaagcc atgagtgagt    540

ttgacatctt catcaactac atagaagcct acatgacaat gaagatacga aactgagaca    600

tcagggtggc gactctatag actctaggac ataaattaga ggtctccaaa atcggatctg    660

gggctctggg atagctgacc cagccccttg agaaacctta ttgtacctct cttatagaat    720

atttattacc tctgatacct caacccccat ttctatttat ttactgagct tctctgtgaa    780

cgatttagaa agaagcccaa tattataatt tttttcaata tttattattt tcacctgttt    840

ttaagctgtt tccatagggt gacacactat ggtatttgag tgttttaaga taaattataa    900

gttacataag ggaggaaaaa aaatgttctt tggggagcca acagaagctt ccattccaag    960

cctgaccacg ctttctagct gttgagctgt ttccctgac ctccctctaa tttatcttgt    1020

ctctgggctt ggggcttcct aactgctaca aatactctta ggaagagaaa ccagggagcc   1080

cctttgatga ttaattcacc ttccagtgtc tcggagggat tcccctaacc tcattcccca   1140

accacttcat tcttgaaagc tgtggccagc ttgttattta taacaaccta aatttggttc   1200

taggccgggc gcggtggctc acgcctgtaa tcccagcact ttgggaggct gaggcgggtg   1260

gatcacttga ggtcaggagt tcctaaccag cctggtcaac atggtgaaac cccgtctcta   1320

ctaaaaatac aaaaattagc cgggcatggt ggcgcgcacc tgtaatccca gctacttggg   1380

aggctgaggc aagagaattg cttgaaccca ggagatggaa gttgcagtga gctgatatca   1440

tgcccctgta ctccagcctg ggtgacagag caagactctg tctcaaaaaa taaaaataaa   1500

aataaatttg gttctaatag aactcagttt taactagaat ttattcaatt cctctgggaa   1560

tgttacattg tttgtctgtc ttcatagcag attttaattt tgaataaata aatgtatctt   1620

attcacatc                                                           1629
```

<210> SEQ ID NO 34
<211> LENGTH: 178
<212> TYPE: PRT
<213> ORGANISM: Homo sapiens

<400> SEQUENCE: 34

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110
```

```
Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 35
<211> LENGTH: 2970
<212> TYPE: DNA
<213> ORGANISM: Homo sapiens

<400> SEQUENCE: 35

```
agtgacgcca gggggcgggg ccagcggcgc ggtcgggtga gaggccgcgg cggcaggtcc     60

acctgggctt gcgaaggcac agattccccg tccacagctc acgaccagat gcaccagcag    120

gagtccacat cgaggacgtc ctccgggcac tcccacgacc agtgaccagg agttaaactt    180

tgggatgtgc ccgtgatgtt ggaccacaag gacttagagg ccgaaatcca cccccttgaaa   240

aatgaagaaa gaaaatcgca ggaaaatctg ggaaatccat caaaaaatga ggataacgtg    300

aaaagcgcgc ctccacagtc ccggctctcc cggtgccgag cggcggcgtt ttttctttca    360

ttgtttctct gcctttttgt ggtgttcgtc gtctcattcg tcatcccgtg tccagaccgg    420

ccggcgtcac agcgaatgtg gaggatagac tacagtgccg ctgttatcta tgactttctg    480

gctgtggatg atataaacgg ggacaggatc caagatgttc tttttcttta taaaaacacc    540

aacagcagca acaatttcag ccgatcctgt gtggacgaag gcttttcctc tccctgcacc    600

tttgcagctg ctgtgtcggg ggccaacggc agcacgctct gggagagacc tgtggcccaa    660

gacgtggccc tcgtggagtg tgctgtgccc cagccaagag gcagtgaggc accttctgcc    720

tgcatcctgg tgggcagacc cagttctttc attgcagtca acttgttcac aggggaaacc    780

ctgtggaacc acagcagcag cttcagcggg aatgcgtcca tcctgagccc tctgctgcag    840

gtgcctgatg tggacggcga tggggcccca gacctgctgg ttctcaccca ggagcgggag    900

gaggttagtg gccacctcta ctccggcagc accgggcacc agattggcct cagaggcagc    960

cttggtgtgg acggggaaag tggcttcctc cttcacgtca ccaggacagg tgcccactac   1020

atcctctttc cctgcgcaag ctccctctgc ggctgctctg tgaagggtct ctacgagaag   1080

gtgaccggga gcggcggccc gttcaagagt gacccgcact gggagagcat gctcaatgcc   1140

accacccgca ggatgctttc ccacagctct ggagcagtgc gctacctgat gcatgtccca   1200

gggaacgccg gtgcagatgt gcttcttgtg ggctcagagg ccttcgtgct gctggacggg   1260

caggagctga cgcctcgctg gacacccaag gcagcccatg tcctgagaaa acccatcttc   1320

ggccgctaca aaccagacac cttggctgta gccgttgaaa acggaactgg caccgacaga   1380

cagatcctgt ttctggacct tggcactgga gccgtcctgt gtagcctagc cctcccgagc   1440

ctccctgggg gtccactgtc cgccagcctg ccgaccgcag accaccgctc agccttcttc   1500

ttctggggcc tccacgagct ggggagcacc agcgagacgg agaccgggga ggcccggcac   1560

agcctgtaca tgttccaccc caccctgccg cgcgtgctgc tggagctggc caatgtctct   1620

acccacattg tcgcctttga cgccgtcctg tttgagccaa gccgccacgc cgcctacatc   1680

cttctgacag gcccggcaga ctcagaggca cccggcctgg tctctgtgat caagcacaag   1740
```

```
gtgcgggacc ttgtcccaag cagcagggtg gtccgcctgg gtgagggtgg gccagacagt   1800
gaccaagcca tcagggaccg gttctcccgg ctgcggtacc agagtgaggc gtagaggcac   1860
gccagccaga gcctgtggag agactccgcc tgctgacact aaacgtcctg ggaagtgggc   1920
ccttccctgg gtctctgcac tgactccccc actcctgacc ctggtgatgg tcgccactgg   1980
gcagcagcag ccttaccagt cctccatgat cacacccagg gacctgcatg ggtgagggga   2040
caccctgggc ctctctcccg cccagcatcc tccctgagtc cccacacagg gcctcactct   2100
gcaccccacc agggtcccgc tcacaccagg cagccttcat agtggtctcc ctggccacct   2160
tgggcagagc tgggtcatgc agcaccccat ccttacccgg tgccctctcc ttgccagctt   2220
ctccccaggc cagagcggcc atcgcgtaga aagaaccagg gtgtccccgg gacaggccgt   2280
cccccacccc atcctgtaga agtccattcc ccttttccct cctgtgctct gtcccccaag   2340
gagtcatgga actcagggta ctgggcctca acgggaacct gagacagctc cagcttcgca   2400
gcccttcccg gagctacagg gggatcctct agcatggggg gtgtgacttg gttcctttga   2460
ccaggtcctg tgaggaagcc tggagcaagg gtctccccca gcaggatggg tggggcctgc   2520
tctggagctg agcccgtggc cgctcacagg tgtccttagt ggtgttgcag ctgtctactg   2580
gctgcatgtg ctgtgaatat cccaaggaac tggctgtgga atgcgtgttt gggtcagtct   2640
gtgccctctc agtagacact ggagctgctc tgtccctgaa gaggccccgt gccccaggca   2700
tggcaagcgc ctgcctctcc ccttccggtg ctcacacgcc cacgccgtgc cacccgatgc   2760
aggactcacc tctgtgcctt gctgctcctg aggcccaagg gcagccatgg tgctctgtac   2820
tgctcgggcc gcccaggtca cagagcctga gcttcgtagc caaagcagcc tgatgaccca   2880
cccaccaagg aagaaagcag aataaacatt tttgcactgc ctgaaaaacc ccggtggtca   2940
ggcgtgagcc taaaaaaaaa aaaaaaaaaa                                    2970
```

<210> SEQ ID NO 36
<211> LENGTH: 552
<212> TYPE: PRT
<213> ORGANISM: Homo sapiens

<400> SEQUENCE: 36

```
Met Leu Asp His Lys Asp Leu Glu Ala Glu Ile His Pro Leu Lys Asn
1               5                   10                  15

Glu Glu Arg Lys Ser Gln Glu Asn Leu Gly Asn Pro Ser Lys Asn Glu
            20                  25                  30

Asp Asn Val Lys Ser Ala Pro Pro Gln Ser Arg Leu Ser Arg Cys Arg
        35                  40                  45

Ala Ala Ala Phe Phe Leu Ser Leu Phe Leu Cys Leu Phe Val Val Phe
    50                  55                  60

Val Val Ser Phe Val Ile Pro Cys Pro Asp Arg Pro Ala Ser Gln Arg
65                  70                  75                  80

Met Trp Arg Ile Asp Tyr Ser Ala Ala Val Ile Tyr Asp Phe Leu Ala
                85                  90                  95

Val Asp Asp Ile Asn Gly Asp Arg Ile Gln Asp Val Leu Phe Leu Tyr
            100                 105                 110

Lys Asn Thr Asn Ser Ser Asn Asn Phe Ser Arg Ser Cys Val Asp Glu
        115                 120                 125

Gly Phe Ser Ser Pro Cys Thr Phe Ala Ala Ala Val Ser Gly Ala Asn
    130                 135                 140

Gly Ser Thr Leu Trp Glu Arg Pro Val Ala Gln Asp Val Ala Leu Val
```

```
145                 150                 155                 160

Glu Cys Ala Val Pro Gln Pro Arg Gly Ser Glu Ala Pro Ser Ala Cys
                165                 170                 175

Ile Leu Val Gly Arg Pro Ser Ser Phe Ile Ala Val Asn Leu Phe Thr
            180                 185                 190

Gly Glu Thr Leu Trp Asn His Ser Ser Ser Phe Ser Gly Asn Ala Ser
        195                 200                 205

Ile Leu Ser Pro Leu Leu Gln Val Pro Asp Val Asp Gly Asp Gly Ala
    210                 215                 220

Pro Asp Leu Leu Val Leu Thr Gln Glu Arg Glu Glu Val Ser Gly His
225                 230                 235                 240

Leu Tyr Ser Gly Ser Thr Gly His Gln Ile Gly Leu Arg Gly Ser Leu
                245                 250                 255

Gly Val Asp Gly Glu Ser Gly Phe Leu Leu His Val Thr Arg Thr Gly
            260                 265                 270

Ala His Tyr Ile Leu Phe Pro Cys Ala Ser Ser Leu Cys Gly Cys Ser
        275                 280                 285

Val Lys Gly Leu Tyr Glu Lys Val Thr Gly Ser Gly Gly Pro Phe Lys
    290                 295                 300

Ser Asp Pro His Trp Glu Ser Met Leu Asn Ala Thr Thr Arg Arg Met
305                 310                 315                 320

Leu Ser His Ser Ser Gly Ala Val Arg Tyr Leu Met His Val Pro Gly
                325                 330                 335

Asn Ala Gly Ala Asp Val Leu Leu Val Gly Ser Glu Ala Phe Val Leu
            340                 345                 350

Leu Asp Gly Gln Glu Leu Thr Pro Arg Trp Thr Pro Lys Ala Ala His
        355                 360                 365

Val Leu Arg Lys Pro Ile Phe Gly Arg Tyr Lys Pro Asp Thr Leu Ala
    370                 375                 380

Val Ala Val Glu Asn Gly Thr Gly Thr Asp Arg Gln Ile Leu Phe Leu
385                 390                 395                 400

Asp Leu Gly Thr Gly Ala Val Leu Cys Ser Leu Ala Leu Pro Ser Leu
                405                 410                 415

Pro Gly Gly Pro Leu Ser Ala Ser Leu Pro Thr Ala Asp His Arg Ser
            420                 425                 430

Ala Phe Phe Phe Trp Gly Leu His Glu Leu Gly Ser Thr Ser Glu Thr
        435                 440                 445

Glu Thr Gly Glu Ala Arg His Ser Leu Tyr Met Phe His Pro Thr Leu
    450                 455                 460

Pro Arg Val Leu Leu Glu Leu Ala Asn Val Ser Thr His Ile Val Ala
465                 470                 475                 480

Phe Asp Ala Val Leu Phe Glu Pro Ser Arg His Ala Ala Tyr Ile Leu
                485                 490                 495

Leu Thr Gly Pro Ala Asp Ser Glu Ala Pro Gly Leu Val Ser Val Ile
            500                 505                 510

Lys His Lys Val Arg Asp Leu Val Pro Ser Ser Arg Val Val Arg Leu
        515                 520                 525

Gly Glu Gly Gly Pro Asp Ser Asp Gln Ala Ile Arg Asp Arg Phe Ser
    530                 535                 540

Arg Leu Arg Tyr Gln Ser Glu Ala
545                 550
```

<210> SEQ ID NO 37

<211> LENGTH: 3675
<212> TYPE: DNA
<213> ORGANISM: Homo sapiens

<400> SEQUENCE: 37

```
tagacctcag cttcctctgt caccatggtg ccggctcggc tgggcccggc ggtcgccatg     60
gtaactgggg cgggtcgcag ggtcctggca ggctgggcgc atgcgcgcgg ggactacaag    120
ccgcgccgcg ctgccgctgg cccctcagca accctcgaca tggcgctgag gcggccaccg    180
cgactccggc tctgcgctcg gctgcctgac ttcttcctgc tgctgctttt caggggctgc    240
ctgatagggg ctgtaaatct caaatccagc aatcgaaccc cagtggtaca ggaatttgaa    300
agtgtggaac tgtcttgcat cattacggat tcgcagacaa gtgaccccag gatcgagtgg    360
aagaaaattc aagatgaaca aaccacatat gtgtttttg acaacaaaat tcagggagac    420
ttggcgggtc gtgcagaaat actggggaag acatccctga agatctggaa tgtgacacgg    480
agagactcag ccctttatcg ctgtgaggtc gttgctcgaa atgaccgcaa ggaaattgat    540
gagattgtga tcgagttaac tgtgcaagtg aagccagtga cccctgtctg tagagtgccg    600
aaggctgtac cagtaggcaa gatggcaaca ctgcactgcc aggagagtga gggccacccc    660
cggcctcact acagctggta tcgcaatgat gtaccactgc ccacggattc cagagccaat    720
cccagatttc gcaattcttc tttccactta aactctgaaa caggcacttt ggtgttcact    780
gctgttcaca aggacgactc tggccagtac tactgcattg cttccaatga cgcaggctca    840
gccaggtgtg aggagcagga gatggaagtc tatgacctga acattggcgg aattattggg    900
ggggttctgg ttgtccttgc tgtactggcc ctgatcacgt tgggcatctg ctgtgcatac    960
agacgtggct acttcatcaa caataaacag gatggagaaa gttacaagaa cccagggaaa   1020
ccagatggag ttaactacat ccgcactgac gaggagggcg acttcagaca caagtcatcg   1080
tttgtgatct gagacccgcg gtgtggctga gagcgcacag agcgcacgtg cacataccte   1140
tgctagaaac tcctgtcaag gcagcgagag ctgatgcact cggacagagc tagacactca   1200
ttcagaagct tttcgttttg gccaaagttg accactactc ttcttactct aacaagccac   1260
atgaatagaa gaattttcct caagatggac ccggtaaata taaccacaag gaagcgaaac   1320
tgggtgcgtt cactgagttg ggttcctaat ctgtttctgg cctgattccc gcatgagtat   1380
tagggtgatc ttaaagagtt tgctcacgta aacgcccgtg ctgggccctg tgaagccagc   1440
atgttcacca ctggtcgttc agcagccacg acagcaccat gtgagatggc gaggtggctg   1500
gacagcacca gcagcgcatc ccggcgggaa cccagaaaag gcttcttaca cagcagcctt   1560
acttcatcgg cccacagaca ccaccgcagt ttcttcttaa aggctctgct gatcggtgtt   1620
gcagtgtcca ttgtggagaa gctttttgga tcagcatttt gtaaaaacaa ccaaaatcag   1680
gaaggtaaat tggttgctgg aagagggatc ttgcctgagg aaccctgctt gtccaacagg   1740
gtgtcaggat ttaaggaaaa ccttcgtctt aggctaagtc tgaaatggta ctgaaatatg   1800
cttttctatg ggtcttgttt attttataaa attttacatc taaatttttg ctaaggatgt   1860
attttgatta ttgaaaagaa aatttctatt taaactgtaa atatattgtc atacaatgtt   1920
aaataaccta tttttttaaa aaagttcaac ttaaggtaga agttccaagc tactagtgtt   1980
aaattggaaa atatcaataa ttaagagtat tttacccaag gaatcctctc atggaagttt   2040
actgtgatgt tccttttctc acacaagttt tagccttttt cacaagggaa ctcatactgt   2100
ctacacatca gaccatagtt gcttaggaaa cctttaaaaa ttccagttaa gcaatgttga   2160
aatcagtttg catctcttca aaagaaacct ctcaggttag ctttgaactg cctcttcctg   2220
```

```
agatgactag gacagtctgt acccagaggc cacccagaag ccctcagatg tacatacaca   2280
gatgccagtc agctcctggg gttgcgccag gcgcccccgc tctagctcac tgttgcctcg   2340
ctgtctgcca ggaggccctg ccatccttgg gccctggcag tggctgtgtc ccagtgagct   2400
ttactcacgt ggcccttgct tcatccagca cagctctcag gtgggcactg cagggacact   2460
ggtgtcttcc atgtagcgtc ccagctttgg gctcctgtaa cagacctctt tttggttatg   2520
gatggctcac aaaatagggc ccccaatgct attttttttt tttaagtttg tttaattatt   2580
tgttaagatt gtctaaggcc aaaggcaatt gcgaaatcaa gtctgtcaag tacaataaca   2640
tttttaaaag aaaatggatc ccactgttcc tctttgccac agagaaagca cccagacgcc   2700
acaggctctg tcgcatttca aaacaaacca tgatggagtg gcggccagtc cagcctttta   2760
aagaacgtca ggtggagcag ccaggtgaaa ggcctggcgg ggaggaaagt gaaacgcctg   2820
aatcaaaagc agttttctaa ttttgacttt aaatttttca tccgccggag acactgctcc   2880
catttgtggg gggacattag caacatcact cagaagcctg tgttcttcaa gagcaggtgt   2940
tctcagcctc acatgccctg ccgtgctgga ctcaggactg aagtgctgta aagcaaggag   3000
ctgctgagaa ggagcactcc actgtgtgcc tggagaatgg ctctcactac tcaccttgtc   3060
tttcagcttc cagtgtcttg ggttttttat actttgacag ctttttttta attgcataca   3120
tgagactgtg ttgacttttt ttagttatgt gaaacacttt gccgcaggcc gcctggcaga   3180
ggcaggaaat gctccagcag tggctcagtg ctccctggtg tctgctgcat ggcatcctgg   3240
atgcttagca tgcaagttcc ctccatcatt gccaccttgg tagagaggga tggctcccca   3300
ccctcagcgt tggggattca cgctccagcc tccttcttgg ttgtcatagt gatagggtag   3360
ccttattgcc ccctcttctt ataccctaaa accttctaca ctagtgccat gggaaccagg   3420
tctgaaaaag tagagagaag tgaaagtaga gtctgggaag tagctgccta taactgagac   3480
tagacggaaa aggaatactc gtgtatttta agatatgaat gtgactcaag actcgaggcc   3540
gatacgaggc tgtgattctg cctttggatg gatgttgctg tacacagatg ctacagactt   3600
gtactaacac accgtaattt ggcatttgtt taacctcatt tataaaagct tcaaaaaaac   3660
ccaaaaaaac ccaaa                                                    3675
```

<210> SEQ ID NO 38
<211> LENGTH: 355
<212> TYPE: PRT
<213> ORGANISM: Homo sapiens

<400> SEQUENCE: 38

```
Met Val Pro Ala Arg Leu Gly Pro Ala Val Ala Met Val Thr Gly Ala
1               5                   10                  15

Gly Arg Arg Val Leu Ala Gly Trp Ala His Ala Arg Gly Asp Tyr Lys
            20                  25                  30

Pro Arg Arg Ala Ala Ala Gly Pro Ser Ala Thr Leu Asp Met Ala Leu
        35                  40                  45

Arg Arg Pro Pro Arg Leu Arg Leu Cys Ala Arg Leu Pro Asp Phe Phe
    50                  55                  60

Leu Leu Leu Leu Phe Arg Gly Cys Leu Ile Gly Ala Val Asn Leu Lys
65                  70                  75                  80

Ser Ser Asn Arg Thr Pro Val Val Gln Glu Phe Glu Ser Val Glu Leu
                85                  90                  95

Ser Cys Ile Ile Thr Asp Ser Gln Thr Ser Asp Pro Arg Ile Glu Trp
            100                 105                 110
```

```
Lys Lys Ile Gln Asp Glu Gln Thr Thr Tyr Val Phe Phe Asp Asn Lys
        115                 120                 125

Ile Gln Gly Asp Leu Ala Gly Arg Ala Glu Ile Leu Gly Lys Thr Ser
    130                 135                 140

Leu Lys Ile Trp Asn Val Thr Arg Arg Asp Ser Ala Leu Tyr Arg Cys
145                 150                 155                 160

Glu Val Val Ala Arg Asn Asp Arg Lys Glu Ile Asp Glu Ile Val Ile
                165                 170                 175

Glu Leu Thr Val Gln Val Lys Pro Val Thr Pro Val Cys Arg Val Pro
            180                 185                 190

Lys Ala Val Pro Val Gly Lys Met Ala Thr Leu His Cys Gln Glu Ser
        195                 200                 205

Glu Gly His Pro Arg Pro His Tyr Ser Trp Tyr Arg Asn Asp Val Pro
    210                 215                 220

Leu Pro Thr Asp Ser Arg Ala Asn Pro Arg Phe Arg Asn Ser Ser Phe
225                 230                 235                 240

His Leu Asn Ser Glu Thr Gly Thr Leu Val Phe Thr Ala Val His Lys
                245                 250                 255

Asp Asp Ser Gly Gln Tyr Tyr Cys Ile Ala Ser Asn Asp Ala Gly Ser
            260                 265                 270

Ala Arg Cys Glu Glu Gln Glu Met Glu Val Tyr Asp Leu Asn Ile Gly
        275                 280                 285

Gly Ile Ile Gly Gly Val Leu Val Val Leu Ala Val Leu Ala Leu Ile
    290                 295                 300

Thr Leu Gly Ile Cys Cys Ala Tyr Arg Arg Gly Tyr Phe Ile Asn Asn
305                 310                 315                 320

Lys Gln Asp Gly Glu Ser Tyr Lys Asn Pro Gly Lys Pro Asp Gly Val
                325                 330                 335

Asn Tyr Ile Arg Thr Asp Glu Glu Gly Asp Phe Arg His Lys Ser Ser
            340                 345                 350

Phe Val Ile
        355
```

<210> SEQ ID NO 39
<211> LENGTH: 2581
<212> TYPE: DNA
<213> ORGANISM: Homo sapiens

<400> SEQUENCE: 39

```
agtgagcgac acagagcggg ccgccaccgc cgagcagccc tccggcagtc tccgcgtccg      60

ttaagcccgc gggtcctccg cgaatcggcg gtgggtccgg cagccgaatg cagccccgca     120

gcgagcgccc ggccggcagg acgcagagcc cggagcacgg cagcccgggg cccgggcccg     180

aggcgccgcc gcctccaccg ccgcagccgc cggcccccga ggcagagcgc acgcggcccc     240

ggcaggctcg gcccgcagcc cccatggagg gagccgtgca gctgctgagc cgcgagggcc     300

acagcgtggc ccacaactcc aagcggcact accacgatgc cttcgtggcc atgagccgca     360

tgcgccagcg cggcctcctg tgcgacatcg tcctgcacgt ggctgccaag gagatccgtg     420

cgcacaaagt ggtgctggcc tcctgcagcc cctacttcca cgccatgttc acaaatgaga     480

tgagcgagag ccgccagacc cacgtgacgc tgcacgacat cgaccctcag gccttggacc     540

agctggtgca gtttgcctac acggctgaga ttgtggtggg cgagggcaat gtgcagactc     600

tgctcccagc cgccagtctc ctgcagctga atggcgtccg agacgcttgc tgcaagtttc     660
```

```
tactgagtca gctcgacccc tccaactgcc tgggtatccg gggctttgcc gatgcgcact    720

cctgcagcga cctgctcaag gccgcccaca ggtacgtgct gcagcacttc gtggacgtgg    780

ccaagaccga ggagtttatg ctgctgcccc tgaaacaggt tctggaactg gtctctagcg    840

acagcctgaa cgtgccttca gaggaggagg tctaccgagc cgtcctgagc tgggtgaaac    900

acgacgtgga cgcccgcagg cagcatgtcc cacggctcat gaagtgtgtg cggctgccct    960

tgctgagccg cgacttcctg ctgggccacg tggatgccga gagcctggtg aggcaccacc   1020

ctgactgcaa ggacctcctc atcgaggccc tgaagttcca cctgctgcct gagcagaggg   1080

gcgtcctagg caccagccgc acacgtcccc ggcgctgcga gggggccggg cctgtgcttt   1140

ttgctgtggg cggcgggagc ctgtttgcca tccacggaga ctgtgaggcc tacgacacgc   1200

gcaccgaccg ctggcacgtg gtggcctcca tgtccacgcg ccgggcccgg gtgggagtgg   1260

ctgcggtggg gaaccggctc tatgctgtgg gcggctatga tgggacctca gacctggcta   1320

ccgtggagtc ctacgacccc gtgactaaca cgtggcagcc ggaggtgtcc atgggcacaa   1380

ggcgaagctg cctgggtgtg gccgccttgc atggactcct gtactcggcc ggcggctatg   1440

acggggcctc ctgcctgaac agtgctgaac gctacgaccc cctgaccgga acgtggacgt   1500

ccgtcgctgc catgagcacc cggaggcgct atgtgcgagt ggccacgctt gatgggaacc   1560

tgtatgctgt gggcggctac gacagctcct cacacctggc cactgtggag aagtatgagc   1620

cccaggtgaa cgtgtggtcg cccgtggcgt ccatgctgag ccgacgcagc tcagcgggcg   1680

tggccgtgct ggagggtgcc ctgtacgtgg caggggggcaa cgacggcacc agctgcctca   1740

actcggtaga gagatacagt ccaaaggctg gagcctggga aagcgtggcg cccatgaata   1800

tccgcaggag cacgcatgac ctggtggcca tggacggatg gttgtacgcc gtgggggggta   1860

acgacggtag ctccagcctc aactccatcg agaagtacaa cccgaggacc aacaagtggg   1920

tggccgcatc ctgcatgttc acccggcgca gcagtgtggg tgtggcggtg ctggagctgc   1980

tcaatttccc gccgccatcc tccccgacgc tgtccgtgtc ctccaccagc ctctgaccca   2040

cctaccacca gaggcctgca gcctcccaca tgccttaagg ggaccgtggc ccccaccagg   2100

gacgtcctgc gccatccgtt cacgtctctg catccattcc ttcatgtctt tatttagttg   2160

tttatttatt tagttattta tcttatttat tgaggggtga ggagtgccac ggctgcccgt   2220

ttacaccttt agcgtctggt cctcctgcgt gtcctcccct ccactgcctg catggggggc   2280

gcggggagtg accaggcggg ggcctcaccg ccccagggcc gttgcctgct cagaccttgc   2340

aggctgtgga gcaagaggcc ctgggtctct ccaagcagct gcagacccca gctcgaattt   2400

tgcacatggc ggggtcccgg gaagggtggg gagcagttgt ccttcctgtc gtcgtctgcc   2460

gtgtgccatc tttcctggat cttgtagtgg gtgcacacgc gtgcactggg accccacaca   2520

gcaatacgag tccaacttaa taaacacatt tctggggttc ctcaaaaaaa aaaaaaaaaa   2580

a                                                                   2581
```

```
<210> SEQ ID NO 40
<211> LENGTH: 642
<212> TYPE: PRT
<213> ORGANISM: Homo sapiens

<400> SEQUENCE: 40

Met Gln Pro Arg Ser Glu Arg Pro Ala Gly Arg Thr Gln Ser Pro Glu
1               5                   10                  15

His Gly Ser Pro Gly Pro Gly Pro Glu Ala Pro Pro Pro Pro Pro Pro
            20                  25                  30
```

```
Gln Pro Pro Ala Pro Glu Ala Glu Arg Thr Arg Pro Arg Gln Ala Arg
        35                  40                  45

Pro Ala Ala Pro Met Glu Gly Ala Val Gln Leu Leu Ser Arg Glu Gly
    50                  55                  60

His Ser Val Ala His Asn Ser Lys Arg His Tyr His Asp Ala Phe Val
65                  70                  75                  80

Ala Met Ser Arg Met Arg Gln Arg Gly Leu Leu Cys Asp Ile Val Leu
                85                  90                  95

His Val Ala Ala Lys Glu Ile Arg Ala His Lys Val Val Leu Ala Ser
            100                 105                 110

Cys Ser Pro Tyr Phe His Ala Met Phe Thr Asn Glu Met Ser Glu Ser
        115                 120                 125

Arg Gln Thr His Val Thr Leu His Asp Ile Asp Pro Gln Ala Leu Asp
    130                 135                 140

Gln Leu Val Gln Phe Ala Tyr Thr Ala Glu Ile Val Val Gly Glu Gly
145                 150                 155                 160

Asn Val Gln Thr Leu Leu Pro Ala Ala Ser Leu Leu Gln Leu Asn Gly
                165                 170                 175

Val Arg Asp Ala Cys Cys Lys Phe Leu Leu Ser Gln Leu Asp Pro Ser
            180                 185                 190

Asn Cys Leu Gly Ile Arg Gly Phe Ala Asp Ala His Ser Cys Ser Asp
        195                 200                 205

Leu Leu Lys Ala Ala His Arg Tyr Val Leu Gln His Phe Val Asp Val
    210                 215                 220

Ala Lys Thr Glu Glu Phe Met Leu Leu Pro Leu Lys Gln Val Leu Glu
225                 230                 235                 240

Leu Val Ser Ser Asp Ser Leu Asn Val Pro Ser Glu Glu Glu Val Tyr
                245                 250                 255

Arg Ala Val Leu Ser Trp Val Lys His Asp Val Asp Ala Arg Arg Gln
            260                 265                 270

His Val Pro Arg Leu Met Lys Cys Val Arg Leu Pro Leu Leu Ser Arg
        275                 280                 285

Asp Phe Leu Leu Gly His Val Asp Ala Glu Ser Leu Val Arg His His
    290                 295                 300

Pro Asp Cys Lys Asp Leu Leu Ile Glu Ala Leu Lys Phe His Leu Leu
305                 310                 315                 320

Pro Glu Gln Arg Gly Val Leu Gly Thr Ser Arg Thr Arg Pro Arg Arg
                325                 330                 335

Cys Glu Gly Ala Gly Pro Val Leu Phe Ala Val Gly Gly Gly Ser Leu
            340                 345                 350

Phe Ala Ile His Gly Asp Cys Glu Ala Tyr Asp Thr Arg Thr Asp Arg
        355                 360                 365

Trp His Val Val Ala Ser Met Ser Thr Arg Arg Ala Arg Val Gly Val
    370                 375                 380

Ala Ala Val Gly Asn Arg Leu Tyr Ala Val Gly Gly Tyr Asp Gly Thr
385                 390                 395                 400

Ser Asp Leu Ala Thr Val Glu Ser Tyr Asp Pro Val Thr Asn Thr Trp
                405                 410                 415

Gln Pro Glu Val Ser Met Gly Thr Arg Arg Ser Cys Leu Gly Val Ala
            420                 425                 430

Ala Leu His Gly Leu Leu Tyr Ser Ala Gly Gly Tyr Asp Gly Ala Ser
        435                 440                 445
```

```
Cys Leu Asn Ser Ala Glu Arg Tyr Asp Pro Leu Thr Gly Thr Trp Thr
    450                 455                 460

Ser Val Ala Ala Met Ser Thr Arg Arg Arg Tyr Val Arg Val Ala Thr
465                 470                 475                 480

Leu Asp Gly Asn Leu Tyr Ala Val Gly Gly Tyr Asp Ser Ser Ser His
                485                 490                 495

Leu Ala Thr Val Glu Lys Tyr Glu Pro Gln Val Asn Val Trp Ser Pro
            500                 505                 510

Val Ala Ser Met Leu Ser Arg Arg Ser Ser Ala Gly Val Ala Val Leu
        515                 520                 525

Glu Gly Ala Leu Tyr Val Ala Gly Gly Asn Asp Gly Thr Ser Cys Leu
    530                 535                 540

Asn Ser Val Glu Arg Tyr Ser Pro Lys Ala Gly Ala Trp Glu Ser Val
545                 550                 555                 560

Ala Pro Met Asn Ile Arg Arg Ser Thr His Asp Leu Val Ala Met Asp
                565                 570                 575

Gly Trp Leu Tyr Ala Val Gly Gly Asn Asp Gly Ser Ser Ser Leu Asn
            580                 585                 590

Ser Ile Glu Lys Tyr Asn Pro Arg Thr Asn Lys Trp Val Ala Ala Ser
        595                 600                 605

Cys Met Phe Thr Arg Arg Ser Ser Val Gly Val Ala Val Leu Glu Leu
    610                 615                 620

Leu Asn Phe Pro Pro Pro Ser Ser Pro Thr Leu Ser Val Ser Ser Thr
625                 630                 635                 640

Ser Leu
```

```
<210> SEQ ID NO 41
<211> LENGTH: 1897
<212> TYPE: DNA
<213> ORGANISM: Homo sapiens

<400> SEQUENCE: 41

actcttcgtc atcacctctc ctattcgcct ggacaagctc atgtttgcag gagcaccatg      60

tcttgctcgt ctcgcgcctc ctcctccagg gctggaggca gcagctcagc cagggtgtct     120

gctggtggaa gcagcttcag cagtggaagc agatgtggtc tggggggcag ctcggcccag     180

ggcttccgag gaggagccag cagctgcagc ctgagtgggg ggtctagcgg tgcttttggg     240

ggcagctttg gagggggctt tggtagctgc tcagtagggg gtggttttgg gggagcttca     300

ggctctggga caggatttgg tgggggttct agctttggcg gggtctctgg atttggcagg     360

ggttctggat tctgtgggag ttctagattc agcagtggtg ctactggagg cttctacagc     420

tatggtggtg gtatgggagg tggtgttggc gatgggggc ttttctctgg aggggaaaag      480

caaaccatgc agaacctcaa tgaccgcttg gccaattacc tagacaaggt cagagccctg     540

gaggaggcta acactgatct ggagaacaaa atcaaggagt ggtatgacaa atatgggcct     600

gggtctggag acggtggatc gggaagagat tatagcaaat actattcaat aattgaagat     660

ctcagaaacc agatcattgc tgccactgtt gaaaatgctg ggatcatttt gcacattgac     720

aatgccagat tggctgctga tgacttcaga ctgaagtatg agaacgagct gtgtctccgg     780

cagagcgtgg aggctgacat caatggcctg cggaaagtcc tggatgacct gactatgacc     840

cgctctgacc tggagatgca gattgagagt ttcaccgagg agctagccta cctgaggaag     900

aaccacgagg aggaaatgaa gaatatgcaa ggaagctctg gaggggaggt gaccgtagaa     960

atgaatgctg cgccagggac cgacctgacc aaattactga atgacatgag ggcgcagtac    1020
```

```
gaggagctgg ctgagcaaaa ccgccgagag gctgaggagc ggttcaacaa gcagagcgca   1080

tcactacaag cacaaatctc cactgatgct ggggcagcca cttctgccaa gaatgagata   1140

acagaactaa aacgtaccct gcaagccctg gaaattgagc ttcagtccca actggccatg   1200

aaaagctccc tggagggaac cctggctgac acagaagctg gctacgtggc tcagctgtca   1260

gaaattcaaa cgcagatcag tgccctggag gaggagatct gccagatctg gggtgagact   1320

aaatgccaga acgcagagta caagcaattg ctggacatca agacacgcct ggaggtggag   1380

atcgagacct accgccgcct gctcgatgga gagggaggtg gttctagttt tgcagaattt   1440

ggtggtagaa actcaggatc tgtaaacatg ggatccaggg atctggtatc tggtgactca   1500

agatctggaa gctgttctgg tcaaggacga gattcaagca agactagagt gactaagact   1560

atcgtagagg agttggtgga tggcaaggtt gtctcgtctc aagtcagcag tatttctgag   1620

gtgaaagtta aataaggaac ttccagatca acaaaagtgt ctttcaaaga aaaaaaaatc   1680

aagaaggaca caagcgaaga aatggcatca atctaggcat ctttctggat aatttcagga   1740

aaagcttcag tccagaaatg gatgactagc caacttttct gcatcttctt atttcctcat   1800

tagaatgctc ttgaaatagc tgaattaaca actttgcttt aattgtttct atgcttcaat   1860

aaatttactt ttgcaagtta aaaaaaaaaa aaaaaaa                            1897
```

<210> SEQ ID NO 42
<211> LENGTH: 525
<212> TYPE: PRT
<213> ORGANISM: Homo sapiens

<400> SEQUENCE: 42

```
Met Ser Cys Ser Ser Arg Ala Ser Ser Ser Arg Ala Gly Gly Ser Ser
1               5                   10                  15

Ser Ala Arg Val Ser Ala Gly Gly Ser Ser Phe Ser Ser Gly Ser Arg
            20                  25                  30

Cys Gly Leu Gly Gly Ser Ser Ala Gln Gly Phe Arg Gly Gly Ala Ser
        35                  40                  45

Ser Cys Ser Leu Ser Gly Gly Ser Ser Gly Ala Phe Gly Gly Ser Phe
    50                  55                  60

Gly Gly Gly Phe Gly Ser Cys Ser Val Gly Gly Gly Phe Gly Gly Ala
65                  70                  75                  80

Ser Gly Ser Gly Thr Gly Phe Gly Gly Gly Ser Ser Phe Gly Gly Val
                85                  90                  95

Ser Gly Phe Gly Arg Gly Ser Gly Phe Cys Gly Ser Ser Arg Phe Ser
            100                 105                 110

Ser Gly Ala Thr Gly Gly Phe Tyr Ser Tyr Gly Gly Gly Met Gly Gly
        115                 120                 125

Gly Val Gly Asp Gly Gly Leu Phe Ser Gly Gly Glu Lys Gln Thr Met
    130                 135                 140

Gln Asn Leu Asn Asp Arg Leu Ala Asn Tyr Leu Asp Lys Val Arg Ala
145                 150                 155                 160

Leu Glu Glu Ala Asn Thr Asp Leu Glu Asn Lys Ile Lys Glu Trp Tyr
                165                 170                 175

Asp Lys Tyr Gly Pro Gly Ser Gly Asp Gly Gly Ser Gly Arg Asp Tyr
            180                 185                 190

Ser Lys Tyr Tyr Ser Ile Ile Glu Asp Leu Arg Asn Gln Ile Ile Ala
        195                 200                 205

Ala Thr Val Glu Asn Ala Gly Ile Ile Leu His Ile Asp Asn Ala Arg
```

```
    210                 215                 220

Leu Ala Ala Asp Asp Phe Arg Leu Lys Tyr Glu Asn Glu Leu Cys Leu
225                 230                 235                 240

Arg Gln Ser Val Glu Ala Asp Ile Asn Gly Leu Arg Lys Val Leu Asp
                245                 250                 255

Asp Leu Thr Met Thr Arg Ser Asp Leu Glu Met Gln Ile Glu Ser Phe
            260                 265                 270

Thr Glu Glu Leu Ala Tyr Leu Arg Lys Asn His Glu Glu Glu Met Lys
        275                 280                 285

Asn Met Gln Gly Ser Ser Gly Gly Glu Val Thr Val Glu Met Asn Ala
    290                 295                 300

Ala Pro Gly Thr Asp Leu Thr Lys Leu Leu Asn Asp Met Arg Ala Gln
305                 310                 315                 320

Tyr Glu Glu Leu Ala Glu Gln Asn Arg Arg Glu Ala Glu Glu Arg Phe
                325                 330                 335

Asn Lys Gln Ser Ala Ser Leu Gln Ala Gln Ile Ser Thr Asp Ala Gly
            340                 345                 350

Ala Ala Thr Ser Ala Lys Asn Glu Ile Thr Glu Leu Lys Arg Thr Leu
        355                 360                 365

Gln Ala Leu Glu Ile Glu Leu Gln Ser Gln Leu Ala Met Lys Ser Ser
    370                 375                 380

Leu Glu Gly Thr Leu Ala Asp Thr Glu Ala Gly Tyr Val Ala Gln Leu
385                 390                 395                 400

Ser Glu Ile Gln Thr Gln Ile Ser Ala Leu Glu Glu Glu Ile Cys Gln
                405                 410                 415

Ile Trp Gly Glu Thr Lys Cys Gln Asn Ala Glu Tyr Lys Gln Leu Leu
            420                 425                 430

Asp Ile Lys Thr Arg Leu Glu Val Glu Ile Glu Thr Tyr Arg Arg Leu
        435                 440                 445

Leu Asp Gly Glu Gly Gly Gly Ser Ser Phe Ala Glu Phe Gly Gly Arg
    450                 455                 460

Asn Ser Gly Ser Val Asn Met Gly Ser Arg Asp Leu Val Ser Gly Asp
465                 470                 475                 480

Ser Arg Ser Gly Ser Cys Ser Gly Gln Gly Arg Asp Ser Ser Lys Thr
                485                 490                 495

Arg Val Thr Lys Thr Ile Val Glu Glu Leu Val Asp Gly Lys Val Val
            500                 505                 510

Ser Ser Gln Val Ser Ser Ile Ser Glu Val Lys Val Lys
        515                 520                 525
```

<210> SEQ ID NO 43
<211> LENGTH: 1283
<212> TYPE: DNA
<213> ORGANISM: Homo sapiens

<400> SEQUENCE: 43

```
attctaaccg caaggagtag cggaggggag gtcgtgatgg cggcgccgga ggcggaggtt      60

ctgtcctcag ccgcagtccc tgatttggag tggtatgaga agtccgaaga aactcacgcc     120

tcccagatag aactacttga gacaagctct acgcaggaac ctctcaacgc ttcggaggcc     180

ttttgcccaa gagactgcat ggtaccagtg gtgtttcctg ggcctgtgag ccaggaaggc     240

tgctgtcagt ttacttgtga acttctaaag catatcatgt atcaacgcca gcagctccct     300

ctgccctatg aacagcttaa gcacttttac cgaaaacctt ctccccaggc agaggagatg     360
```

```
ctgaagaaga aacctcgggc caccactgag gtgagcagca ggaaatgcca acaagccctg     420

gcagaactgg agagtgtcct cagccacctg gaggacttct ttgcacggac actagtaccg     480

cgagtgctga ttctccttgg gggcaatgcc ctaagcccca aggagttcta tgaactcgac     540

ttgtctctgc tggcccccta cagcgtggac cagagcctga gcacagcagc ttgtttgcgc     600

cgtctcttcc gagccatatt catggctgat gcctttagcg agcttcaggc tcctccactc     660

atgggcaccg tcgtcatggc acagggacac cgcaactgtg gagaagattg gtttcgaccc     720

aagctcaact atcgagtgcc cagccggggc cataaactga ctgtgaccct gtcatgtggc     780

agaccttcca tccgaaccac ggcttgggaa gactacattt ggttccaggc accagtgaca     840

tttaaaggct tccgcgagtg aatgagtgct tcttaatcct aaaaacacaa tggctgaatt     900

atctttctcc atgtggcgct gaatcaccca tctggtttgg agctagagtt gcttcctggt     960

gagagaggaa gcaactctcc ttctggttgt ctgcctcccc tcagatttcc tgataggctg    1020

atggcatgtg gctgtgactg tgactgtaat cattgctgaa caacatctct ttgaatcaaa    1080

ggttgatttt cccagagggt gctgggtcag gcatttctat taggagttgg aaagcaaaaa    1140

tgggtccata gacactctat ggaggtgtcc ctttctgctc tttgctgtgt cctttcagaa    1200

tttttaccag gaacataatg tggatgtgac ttatgaactt aaatataaaa taaatagatt    1260

cttattatat tttcctgaaa aaa                                            1283
```

<210> SEQ ID NO 44
<211> LENGTH: 274
<212> TYPE: PRT
<213> ORGANISM: Homo sapiens

<400> SEQUENCE: 44

```
Met Ala Ala Pro Glu Ala Glu Val Leu Ser Ser Ala Ala Val Pro Asp
1               5                   10                  15

Leu Glu Trp Tyr Glu Lys Ser Glu Glu Thr His Ala Ser Gln Ile Glu
            20                  25                  30

Leu Leu Glu Thr Ser Ser Thr Gln Glu Pro Leu Asn Ala Ser Glu Ala
        35                  40                  45

Phe Cys Pro Arg Asp Cys Met Val Pro Val Val Phe Pro Gly Pro Val
    50                  55                  60

Ser Gln Glu Gly Cys Cys Gln Phe Thr Cys Glu Leu Leu Lys His Ile
65                  70                  75                  80

Met Tyr Gln Arg Gln Gln Leu Pro Leu Pro Tyr Glu Gln Leu Lys His
                85                  90                  95

Phe Tyr Arg Lys Pro Ser Pro Gln Ala Glu Glu Met Leu Lys Lys Lys
            100                 105                 110

Pro Arg Ala Thr Thr Glu Val Ser Ser Arg Lys Cys Gln Gln Ala Leu
        115                 120                 125

Ala Glu Leu Glu Ser Val Leu Ser His Leu Glu Asp Phe Phe Ala Arg
    130                 135                 140

Thr Leu Val Pro Arg Val Leu Ile Leu Leu Gly Gly Asn Ala Leu Ser
145                 150                 155                 160

Pro Lys Glu Phe Tyr Glu Leu Asp Leu Ser Leu Leu Ala Pro Tyr Ser
                165                 170                 175

Val Asp Gln Ser Leu Ser Thr Ala Ala Cys Leu Arg Arg Leu Phe Arg
            180                 185                 190

Ala Ile Phe Met Ala Asp Ala Phe Ser Glu Leu Gln Ala Pro Pro Leu
        195                 200                 205
```

```
Met Gly Thr Val Val Met Ala Gln Gly His Arg Asn Cys Gly Glu Asp
    210                 215                 220

Trp Phe Arg Pro Lys Leu Asn Tyr Arg Val Pro Ser Arg Gly His Lys
225                 230                 235                 240

Leu Thr Val Thr Leu Ser Cys Gly Arg Pro Ser Ile Arg Thr Thr Ala
                245                 250                 255

Trp Glu Asp Tyr Ile Trp Phe Gln Ala Pro Val Thr Phe Lys Gly Phe
            260                 265                 270

Arg Glu


<210> SEQ ID NO 45
<211> LENGTH: 2297
<212> TYPE: DNA
<213> ORGANISM: Homo sapiens

<400> SEQUENCE: 45

aaccacaaaa cccgccaggc cggtgcggga gctgcggagc atccgctgcg gtcctcgccg     60

agacccccgc gcggattcgc cggtccttcc cgcgggcgcg acagagctgt cctcgcacct    120

ggatggcagc aggggcgccg gggtcctctc gacgccagag agaaatctca tcatctgtgc    180

agccttctta aagcaaacta agaccagagg gaggattatc cttgaccttt gaagaccaaa    240

actaaactga aatttaaaat gttcttcggg ggagaaggga gcttgactta cactttggta    300

ataatttgct tcctgacact aaggctgtct gctagtcaga attgcctcaa aaagagtcta    360

gaagatgttg tcattgacat ccagtcatct ctttctaagg gaatcagagg caatgagccc    420

gtatatactt caactcaaga agactgcatt aattcttgct gttcaacaaa aaacatatca    480

ggggacaaag catgtaactt gatgatcttc gacactcgaa aaacagctag acaacccaac    540

tgctacctat tttctgtcc caacgaggaa gcctgtccat tgaaaccagc aaaaggactt     600

atgagttaca ggataattac agattttcca tctttgacca gaaatttgcc aagccaagag    660

ttaccccagg aagattctct cttacatggc caattttcac aagcagtcac tcccctagcc    720

catcatcaca cagattattc aaagcccacc gatatctcat ggagagacac actttctcag    780

aagtttggat cctcagatca cttggagaaa ctatttaaga tggatgaagc aagtgcccag    840

ctccttgctt ataaggaaaa aggccattct cagagttcac aattttcctc tgatcaagaa    900

atagctcatc tgctgcctga aaatgtgagt gcgctcccag ctacggtggc agttgcttct    960

ccacatacca cctcggctac tccaaagccc gccacccttc tacccaccaa tgcttcagtg   1020

acaccttctg ggacttccca gccacagctg gccaccacag ctccacctgt aaccactgtc   1080

acttctcagc ctcccacgac cctcatttct acagtttta cacgggctgc ggctacactc    1140

caagcaatgg ctacaacagc agttctgact accacctttc aggcacctac ggactcgaaa   1200

ggcagcttag aaaccatacc gtttacagaa atctccaacc taactttgaa cacagggaat   1260

gtgtataacc ctactgcact ttctatgtca aatgtggagt cttccactat gaataaaact   1320

gcttcctggg aaggtaggga ggccagtcca ggcagttcct cccagggcag tgttccagaa   1380

aatcagtacg gccttccatt tgaaaaatgg cttcttatcg ggtccctgct ctttggtgtc   1440

ctgttcctgg tgataggcct cgtcctcctg ggtagaatcc tctcggaatc actccgcagg   1500

aaacgttact caagactgga ttatttgatc aatgggatct atgtggacat ctaaggatgg   1560

aactcggtgt ctcttaattc atttagtaac cagaagccca aatgcaatga gtttctgctg   1620

acttgctagt cttagcagga ggttgtattt tgaagacagg aaaatgcccc cttctgcttt   1680

cctttttttt ttttggagac agagtcttgc tttgttgccc aggctggagt gcagtagcac   1740
```

```
gatctcggct ctcaccgcaa cctccgtctc ctgggttcaa gcgattctcc tgcctcagcc   1800

tcctaagtat ctgggattac aggcatgtgc caccacacct gggtgatttt tgtattttta   1860

gtagagacgg ggtttcacca tgttggtcag gctggtctca aactcctgac ctagtgatcc   1920

accctcctcg gcctcccaaa gtgctgggat tacaggcatg agccaccaca gctggccccc   1980

ttctgtttta tgtttggttt ttgagaagga atgaagtggg aaccaaatta ggtaattttg   2040

ggtaatctgt ctctaaaata ttagctaaaa acaaagctct atgtaaagta ataaagtata   2100

attgccatat aaatttcaaa attcaactgg cttttatgca aagaaacagg ttaggacatc   2160

taggttccaa ttcattcaca ttcttggttc cagataaaat caactgttta tatcaatttc   2220

taatggattt gcttttcttt ttatatggat tcctttaaaa cttattccag atgtagttcc   2280

ttccaattaa atatttg                                                  2297


<210> SEQ ID NO 46
<211> LENGTH: 431
<212> TYPE: PRT
<213> ORGANISM: Homo sapiens

<400> SEQUENCE: 46

Met Phe Phe Gly Gly Glu Gly Ser Leu Thr Tyr Thr Leu Val Ile Ile
1               5                   10                  15

Cys Phe Leu Thr Leu Arg Leu Ser Ala Ser Gln Asn Cys Leu Lys Lys
            20                  25                  30

Ser Leu Glu Asp Val Val Ile Asp Ile Gln Ser Ser Leu Ser Lys Gly
        35                  40                  45

Ile Arg Gly Asn Glu Pro Val Tyr Thr Ser Thr Gln Glu Asp Cys Ile
    50                  55                  60

Asn Ser Cys Cys Ser Thr Lys Asn Ile Ser Gly Asp Lys Ala Cys Asn
65                  70                  75                  80

Leu Met Ile Phe Asp Thr Arg Lys Thr Ala Arg Gln Pro Asn Cys Tyr
                85                  90                  95

Leu Phe Phe Cys Pro Asn Glu Glu Ala Cys Pro Leu Lys Pro Ala Lys
            100                 105                 110

Gly Leu Met Ser Tyr Arg Ile Ile Thr Asp Phe Pro Ser Leu Thr Arg
        115                 120                 125

Asn Leu Pro Ser Gln Glu Leu Pro Gln Glu Asp Ser Leu Leu His Gly
    130                 135                 140

Gln Phe Ser Gln Ala Val Thr Pro Leu Ala His His His Thr Asp Tyr
145                 150                 155                 160

Ser Lys Pro Thr Asp Ile Ser Trp Arg Asp Thr Leu Ser Gln Lys Phe
                165                 170                 175

Gly Ser Ser Asp His Leu Glu Lys Leu Phe Lys Met Asp Glu Ala Ser
            180                 185                 190

Ala Gln Leu Leu Ala Tyr Lys Glu Lys Gly His Ser Gln Ser Ser Gln
        195                 200                 205

Phe Ser Ser Asp Gln Glu Ile Ala His Leu Leu Pro Glu Asn Val Ser
    210                 215                 220

Ala Leu Pro Ala Thr Val Ala Val Ala Ser Pro His Thr Thr Ser Ala
225                 230                 235                 240

Thr Pro Lys Pro Ala Thr Leu Leu Pro Thr Asn Ala Ser Val Thr Pro
                245                 250                 255

Ser Gly Thr Ser Gln Pro Gln Leu Ala Thr Thr Ala Pro Pro Val Thr
            260                 265                 270
```

```
Thr Val Thr Ser Gln Pro Pro Thr Thr Leu Ile Ser Thr Val Phe Thr
        275                 280                 285

Arg Ala Ala Ala Thr Leu Gln Ala Met Ala Thr Thr Ala Val Leu Thr
    290                 295                 300

Thr Thr Phe Gln Ala Pro Thr Asp Ser Lys Gly Ser Leu Glu Thr Ile
305                 310                 315                 320

Pro Phe Thr Glu Ile Ser Asn Leu Thr Leu Asn Thr Gly Asn Val Tyr
                325                 330                 335

Asn Pro Thr Ala Leu Ser Met Ser Asn Val Glu Ser Ser Thr Met Asn
            340                 345                 350

Lys Thr Ala Ser Trp Glu Gly Arg Glu Ala Ser Pro Gly Ser Ser Ser
        355                 360                 365

Gln Gly Ser Val Pro Glu Asn Gln Tyr Gly Leu Pro Phe Glu Lys Trp
    370                 375                 380

Leu Leu Ile Gly Ser Leu Leu Phe Gly Val Leu Phe Leu Val Ile Gly
385                 390                 395                 400

Leu Val Leu Leu Gly Arg Ile Leu Ser Glu Ser Leu Arg Arg Lys Arg
                405                 410                 415

Tyr Ser Arg Leu Asp Tyr Leu Ile Asn Gly Ile Tyr Val Asp Ile
            420                 425                 430
```

<210> SEQ ID NO 47
<211> LENGTH: 1336
<212> TYPE: DNA
<213> ORGANISM: Homo sapiens

<400> SEQUENCE: 47

```
gcgaggtggg gtaggcgggc aaggcgggcg ccgaggtttg caaaggctcg cagcggccag      60

aaacccggct ccgagcggcg gcggcccggc ttccgctgcc cgtgagctaa ggacggtccg     120

ctccctctag ccagctccga atcctgatcc aggcgggggc caggggcccc tcgcctcccc     180

tctgaggacc gaagatgagc ttcctcttca gcagccgctc ttctaaaaca ttcaaaccaa     240

agaagaatat ccctgaagga tctcatcagt atgaactctt aaaacatgca gaagcaactc     300

taggaagtgg gaatctgaga caagctgtta tgttgcctga gggagaggat ctcaatgaat     360

ggattgctgt gaacactgtg gatttcttta accagatcaa catgttatat ggaactatta     420

cagaattctg cactgaagca agctgtccag tcatgtctgc aggtccgaga tatgaatatc     480

actgggcaga tggtactaat attaaaaagc caatcaaatg ttctgcacca aaatacattg     540

actatttgat gacttgggtt caagatcagc ttgatgatga aactcttttt ccttctaaga     600

ttggtgtccc atttcccaaa aactttatgt ctgtggcaaa gactattcta aagcgtctgt     660

tcagggttta tgcccatatt tatcaccagc actttgattc tgtgatgcag ctgcaagagg     720

aggcccacct caacacctcc tttaagcact ttattttctt tgttcaggag tttaatctga     780

ttgataggcg tgagctggca cctcttcaag aattaataga gaaacttgga tcaaaagaca     840

gataaatgtt tcttctagaa cacagttacc cccttgcttc atctattgct agaactatct     900

cattgctatc tgttatagac tagtgataca aactttaaga aaacaggata aaaagatacc     960

cattgcctgt gtctactgat aaaattatcc caaaggtagg ttggtgtgat agtttccgag    1020

taagacctta aggacacagc caaatcttaa gtactgtgtg accactcttg ttgttatcac    1080

atagtcatac ttggttgtaa tatgtgatgg ttaacctgta gcttataaat ttacttatta    1140

ttcttttact catttactca gtcatttctt tacaagaaaa tgattgaatc tgttttaggt    1200
```

```
gacagcacaa tggacattaa gaatttccat caataattta tgaataagtt tccagaacaa   1260

atttcctaat aacacaatca gattggtttt attcttttat tttacgaata aaaaatgtat   1320

ttttcagtaa aaaaaa                                                   1336


<210> SEQ ID NO 48
<211> LENGTH: 216
<212> TYPE: PRT
<213> ORGANISM: Homo sapiens

<400> SEQUENCE: 48

Met Ser Phe Leu Phe Ser Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30

Glu Ala Thr Leu Gly Ser Gly Asn Leu Arg Gln Ala Val Met Leu Pro
        35                  40                  45

Glu Gly Glu Asp Leu Asn Glu Trp Ile Ala Val Asn Thr Val Asp Phe
    50                  55                  60

Phe Asn Gln Ile Asn Met Leu Tyr Gly Thr Ile Thr Glu Phe Cys Thr
65                  70                  75                  80

Glu Ala Ser Cys Pro Val Met Ser Ala Gly Pro Arg Tyr Glu Tyr His
                85                  90                  95

Trp Ala Asp Gly Thr Asn Ile Lys Lys Pro Ile Lys Cys Ser Ala Pro
            100                 105                 110

Lys Tyr Ile Asp Tyr Leu Met Thr Trp Val Gln Asp Gln Leu Asp Asp
        115                 120                 125

Glu Thr Leu Phe Pro Ser Lys Ile Gly Val Pro Phe Pro Lys Asn Phe
    130                 135                 140

Met Ser Val Ala Lys Thr Ile Leu Lys Arg Leu Phe Arg Val Tyr Ala
145                 150                 155                 160

His Ile Tyr His Gln His Phe Asp Ser Val Met Gln Leu Gln Glu Glu
                165                 170                 175

Ala His Leu Asn Thr Ser Phe Lys His Phe Ile Phe Phe Val Gln Glu
            180                 185                 190

Phe Asn Leu Ile Asp Arg Arg Glu Leu Ala Pro Leu Gln Glu Leu Ile
        195                 200                 205

Glu Lys Leu Gly Ser Lys Asp Arg
    210                 215


<210> SEQ ID NO 49
<211> LENGTH: 5381
<212> TYPE: DNA
<213> ORGANISM: Homo sapiens

<400> SEQUENCE: 49

attgagaggc caccgggaaa ccattgagaa gccccggagg accggcctga gcggaggcgg     60

agactagagc ggccgccggc acgacccgcc ttcaggcgta cgacgaccgc ggcccggggg    120

ctctgagtgg ccaaagcggc ggcactttct gcgtggcccc ggaaggacat agagcggaag    180

gcgggagaaa gaagtagccg gcaggcggag gcagcccgag gggcggttg catgtgtgcc    240

agacgttcgt agcccactga gcttcctcac gccggctgtc gcagcgccta gccccacccg    300

gcggcctctc ctgcgcttcc ggggccgtgg cgagctagtg cgcctgcgtg ccggcccatc    360

cgcgcgcctt gcagctgtcc ttgcgtcggc cagcggccag acagttcctg cagcgcttac    420

cgcctggcct ctcggttccg cggcgcaccg gagggcagca tgtcgcggcg gcggcacagc    480
```

```
gacgagaacg acggtgggca gcctcacaaa aggagaaaga cctctgatgc aaatgaaact    540
gaagatcatt tggaatcttt aatatgtaaa gtaggagaaa agagtgcctg ctctttggag    600
agcaacctag aaggcttggc tggtgttttg gaagctgatc ttcctaacta caagagcaag    660
atcttaaggc ttctttgtac agttgcacgc ctattacctg agaagctgac aatttataca    720
acattagttg gactactgaa tgccaggaat tacaattttg gtggagaatt tgtagaagcc    780
atgattcgtc aacttaaaga atcattgaaa gcaaacaatt ataatgaagc cgtgtatttg    840
gtccgttttt tatctgatct tgtgaattgt catgtgattg ccgccccatc aatggttgct    900
atgtttgaaa attttgtaag cgtaactcag gaagaagatg tacctcaggt gcgacgagat    960
tggtatgtgt atgcatttct gtcatctttg ccctgggttg gaaaggagtt gtacgaaaag   1020
aaagatgcag agatggaccg catctttgcc aacactgaaa gctatcttaa aagacgccaa   1080
aagactcatg tacccatgtt acaggtatgg actgctgata aaccacatcc acaagaagag   1140
tatttagatt gcctgtgggc ccagattcag aaattgaaaa aggatcgctg gcaggaacgg   1200
cacatcctaa gaccttatct tgcctttgac agcatcctgt gtgaagcact gcagcacaat   1260
ctgcctcctt ttacaccacc tcctcacact gaagattcag tgtacccaat gccaagggtc   1320
atcttcagaa tgtttgatta cacagatgat cccgagggtc ctgtcatgcc agggagtcat   1380
tcagtggaaa gatttgtaat agaagagaat cttcactgca tcattaagtc ccactggaag   1440
gaaaggaaga cttgtgctgc acagttagtg agctatccag ggaagaacaa gatccccttg   1500
aactaccaca tagttgaggt gatctttgca gagctgtttc aacttccagc acccccctcac  1560
attgatgtga tgtacacaac actcctcatt gaactgtgca aacttcaacc tggctctcta   1620
ccccaagttc ttgcacaggc aactgaaatg ctatacatgc gtttggacac aatgaacact   1680
acctgtgtag acaggtttat taattggttt tctcatcatc taagtaactt ccagttccgt   1740
tggagctggg aagattggtc agattgtctt agtcaagatc ctgaaagtcc caaaccgaag   1800
tttgtaagag aagttctaga aaaatgtatg aggttgtctt accatcagcg tatattagat   1860
attgttcctc ctaccttctc agctctgtgt cctgcaaacc caacctgcat ttacaagtat   1920
ggagatgaaa gtagcaattc tcttcctgga cattctgttg ccctctgttt agctgttgcc   1980
tttaaaagta aggcaaccaa tgatgaaatc ttcagcattc tgaaagatgt accaaatcct   2040
aaccaggatg atgacgacga tgaaggattc agttttaacc cattgaaaat agaagtcttt   2100
gtacagactc tgctacactt ggcagccaaa tcattcagcc actccttcag tgctcttgca   2160
aagtttcatg aagtcttcaa aaccctagct gaaagtgatg aaggaaagtt acatgtgcta   2220
agagttatgt ttgaggtctg gaggaaccat ccacagatga ttgctgtact agtggataag   2280
atgattcgta cacaaatagt tgattgtgct gccgtagcaa attggatctt ctcttcagaa   2340
ctatctcgtg actttaccag attgtttgtt tgggaaattt tgcactctac aattcgtaag   2400
atgaacaaac atgtcctgaa gatccagaaa gagctggaag aagctaaaga gaaacttgct   2460
aggcaacaca aacggcgaag tgatgatgac gacagaagca gtgacaggaa agacggggtt   2520
cttgaggaac aaatagaacg acttcaggaa aaagtggaat ctgctcagag tgaacaaaag   2580
aatcttttcc tcgttatatt tcagcggttt atcatgatct tgaccgagca cctagtacga   2640
tgcgaaactg atgggaccag tgtattaaca ccatggtata agaactgtat agagaggctg   2700
cagcagatct tcctacagca tcaccaaata atccagcagt acatggtgac cctggagaac   2760
cttctcttca ctgctgaatt agaccctcat atcttggccg tgttccagca gttctgtgcc   2820
```

```
ctgcaggcct aagggtcatt ttttcctcat gtcaaggttt tttttgatat cttaaaataa   2880
tttgtcttat tttttgatgg tttgaatgct tgctttcttg tagtatcctt tcacttctta   2940
aaggaaacaa aggggaagag gacagtgaat gaacatggca ttacttttaa ttgccctgaa   3000
aagcaaatac ttcctaacgg cagtaatgtg actatgacca tgatatatta tatatgtgac   3060
agatacaaat tctctgtgat cagtttgtta ttttttttct ccttaaggca caaaataatt   3120
ggtttgaggt atgtgaaaca ctagaggtca accttacata gtatatagaa ctgatgggtt   3180
tacccagcta cccagtagca taacttttca cagctcgggg atgaattaac atggctgaaa   3240
taaaactaaa agtatggttt ttaaactttg gcatttcatg atttatcatc tcactctact   3300
ctaaaactgg tggtttctta ctgaaggtgt tctccatttg aaatttttatc ttcaaagtat  3360
ttttaagtag tatctttaag acatgacttg ttagtaataa aagtgttact agttggaaga   3420
gtagctctca aatttgtctt aatgtaaatc acctgggaat ctttcaagtt attttgaaat   3480
ttaaaccacc gtctgggggt ggaacgcaga catcctcagt aatccttaaa gtttccccag   3540
gtgattccag gtttggtcac cattatctta gagcatctac tcacttcctc tagccttggg   3600
gttatttgtc caaggtcttg tagtgagtta cagaatacta aagtggatgt agaagtggtc   3660
agattgactg aaactatacc ctgaattaga tgtgagttta gattttgttt atatggaacc   3720
tgatccaaaa aactacgaag tcctgagctt gtttcctgta tagtactgat gctgaaataa   3780
gatgacagca gtttgtaaaa taatacacaa atatgaggaa ttgtctgaca ttccaaattt   3840
cgaggatttt tagacttttt tcattaaacc ttagaaaaaa attaccagta atcctacaac   3900
tactggtagt gttgttgtgc atttgcacaa aataggtata attttttctt attacatccc   3960
aagtttatga tgcattaagc gttttgcata ttttgatata tttttgcttt ggtttaccat   4020
acattttagt ggctacagaa tgtagtctgc ttaataaatg ggaattccta gaatgtttaa   4080
ataccatact atttaagaca aaatacaaaa tatccagaaa aatccaggtt gcgtggctgg   4140
ttagtaaagg actaaaaccc aggttcttgg ctaaatgttt tcgtttatac tgtttatctt   4200
tcccattgct taagcacagc acaaactatg taattatata taattacagt tgacccttga   4260
acaacatggg tttgaactgt gtgagtctcc ttacacacag gttttcttcc acccctgaga   4320
tggcaagacc agccccttgt cttcctcagc ctgctcaacg tgaagatgat gaggatgaag   4380
acctttatga tgatccactt ctacttatta aatagtaaat atattttttt cttatgattt   4440
tattttcttt tctctagctt cataagaata tagcatatgg gctgggcgca gtggctcacg   4500
cctgtaatcc cagcactttg ggaggctgag gcgggcggat cacaaggtca ggagattgag   4560
accatcctgg ctaacacagt gaaaccctgt ctctactaaa aacacaaaaa cttagccagg   4620
cgtggtggta catggctgta gtcccagcta cttgggaggc tgagacagga gaatcgcttg   4680
aacctgggag gtggaggttt cagtgagcca agattgtgcc actgcactcc agcctgggtg   4740
atggagcgag gctctgtctc aaaaaagaaa aaaaatatat agcatataac atacaaaatg   4800
agtttatcaa ctgtttgtta ttggtaagtc agcagtgggc tattggtggt taagttttgg   4860
gggagtcaaa agttacatgc aaattttta ctgtgcgggg tgtcagcatc cctaacccca   4920
tgttgttcaa gggtcaactg tagtttaaaa tgactcctgt ctcaaaaaac caaaggataa   4980
cctttaaggg attggtaact ttgactcaaa actgctttgt aatcttttca caatgtactg   5040
aaaagtgtgg ctagttatgt ttgatccaca ttctagagaa atttgtaggt tttaatttct   5100
tttctcttgg tcctctcttc atgtataatg gttgctttta acagctgttc gctgatgtgg   5160
tcctgctctg tcccagtcta gcagctttag tgtatggaaa aattgaacta ggaattgagt   5220
```

```
tttgaagaaa taaaggtgta agagcaaaca ttcaacagtt gctgtcccca gtaatgaagt   5280

tcatacagac aaaagatggc atgtcactgt acatcatacc ttgcaataaa tattctgtta   5340

aattgtgctg gtgcaattta acatgctttt gtcaaagtaa a                       5381


<210> SEQ ID NO 50
<211> LENGTH: 790
<212> TYPE: PRT
<213> ORGANISM: Homo sapiens

<400> SEQUENCE: 50

Met Ser Arg Arg Arg His Ser Asp Glu Asn Asp Gly Gly Gln Pro His
1               5                   10                  15

Lys Arg Arg Lys Thr Ser Asp Ala Asn Glu Thr Glu Asp His Leu Glu
            20                  25                  30

Ser Leu Ile Cys Lys Val Gly Glu Lys Ser Ala Cys Ser Leu Glu Ser
        35                  40                  45

Asn Leu Glu Gly Leu Ala Gly Val Leu Glu Ala Asp Leu Pro Asn Tyr
    50                  55                  60

Lys Ser Lys Ile Leu Arg Leu Leu Cys Thr Val Ala Arg Leu Leu Pro
65                  70                  75                  80

Glu Lys Leu Thr Ile Tyr Thr Thr Leu Val Gly Leu Leu Asn Ala Arg
                85                  90                  95

Asn Tyr Asn Phe Gly Gly Glu Phe Val Glu Ala Met Ile Arg Gln Leu
            100                 105                 110

Lys Glu Ser Leu Lys Ala Asn Asn Tyr Asn Glu Ala Val Tyr Leu Val
        115                 120                 125

Arg Phe Leu Ser Asp Leu Val Asn Cys His Val Ile Ala Ala Pro Ser
    130                 135                 140

Met Val Ala Met Phe Glu Asn Phe Val Ser Val Thr Gln Glu Glu Asp
145                 150                 155                 160

Val Pro Gln Val Arg Arg Asp Trp Tyr Val Tyr Ala Phe Leu Ser Ser
                165                 170                 175

Leu Pro Trp Val Gly Lys Glu Leu Tyr Glu Lys Lys Asp Ala Glu Met
            180                 185                 190

Asp Arg Ile Phe Ala Asn Thr Glu Ser Tyr Leu Lys Arg Arg Gln Lys
        195                 200                 205

Thr His Val Pro Met Leu Gln Val Trp Thr Ala Asp Lys Pro His Pro
    210                 215                 220

Gln Glu Glu Tyr Leu Asp Cys Leu Trp Ala Gln Ile Gln Lys Leu Lys
225                 230                 235                 240

Lys Asp Arg Trp Gln Glu Arg His Ile Leu Arg Pro Tyr Leu Ala Phe
                245                 250                 255

Asp Ser Ile Leu Cys Glu Ala Leu Gln His Asn Leu Pro Pro Phe Thr
            260                 265                 270

Pro Pro Pro His Thr Glu Asp Ser Val Tyr Pro Met Pro Arg Val Ile
        275                 280                 285

Phe Arg Met Phe Asp Tyr Thr Asp Asp Pro Glu Gly Pro Val Met Pro
    290                 295                 300

Gly Ser His Ser Val Glu Arg Phe Val Ile Glu Glu Asn Leu His Cys
305                 310                 315                 320

Ile Ile Lys Ser His Trp Lys Glu Arg Lys Thr Cys Ala Ala Gln Leu
                325                 330                 335

Val Ser Tyr Pro Gly Lys Asn Lys Ile Pro Leu Asn Tyr His Ile Val
```

```
            340                 345                 350

Glu Val Ile Phe Ala Glu Leu Phe Gln Leu Pro Ala Pro Pro His Ile
        355                 360                 365

Asp Val Met Tyr Thr Thr Leu Leu Ile Glu Leu Cys Lys Leu Gln Pro
    370                 375                 380

Gly Ser Leu Pro Gln Val Leu Ala Gln Ala Thr Glu Met Leu Tyr Met
385                 390                 395                 400

Arg Leu Asp Thr Met Asn Thr Thr Cys Val Asp Arg Phe Ile Asn Trp
                405                 410                 415

Phe Ser His His Leu Ser Asn Phe Gln Phe Arg Trp Ser Trp Glu Asp
            420                 425                 430

Trp Ser Asp Cys Leu Ser Gln Asp Pro Glu Ser Pro Lys Pro Lys Phe
        435                 440                 445

Val Arg Glu Val Leu Glu Lys Cys Met Arg Leu Ser Tyr His Gln Arg
    450                 455                 460

Ile Leu Asp Ile Val Pro Pro Thr Phe Ser Ala Leu Cys Pro Ala Asn
465                 470                 475                 480

Pro Thr Cys Ile Tyr Lys Tyr Gly Asp Glu Ser Ser Asn Ser Leu Pro
                485                 490                 495

Gly His Ser Val Ala Leu Cys Leu Ala Val Ala Phe Lys Ser Lys Ala
            500                 505                 510

Thr Asn Asp Glu Ile Phe Ser Ile Leu Lys Asp Val Pro Asn Pro Asn
        515                 520                 525

Gln Asp Asp Asp Asp Asp Glu Gly Phe Ser Phe Asn Pro Leu Lys Ile
    530                 535                 540

Glu Val Phe Val Gln Thr Leu Leu His Leu Ala Ala Lys Ser Phe Ser
545                 550                 555                 560

His Ser Phe Ser Ala Leu Ala Lys Phe His Glu Val Phe Lys Thr Leu
                565                 570                 575

Ala Glu Ser Asp Glu Gly Lys Leu His Val Leu Arg Val Met Phe Glu
            580                 585                 590

Val Trp Arg Asn His Pro Gln Met Ile Ala Val Leu Val Asp Lys Met
        595                 600                 605

Ile Arg Thr Gln Ile Val Asp Cys Ala Ala Val Ala Asn Trp Ile Phe
    610                 615                 620

Ser Ser Glu Leu Ser Arg Asp Phe Thr Arg Leu Phe Val Trp Glu Ile
625                 630                 635                 640

Leu His Ser Thr Ile Arg Lys Met Asn Lys His Val Leu Lys Ile Gln
                645                 650                 655

Lys Glu Leu Glu Glu Ala Lys Glu Lys Leu Ala Arg Gln His Lys Arg
            660                 665                 670

Arg Ser Asp Asp Asp Asp Arg Ser Ser Asp Arg Lys Asp Gly Val Leu
        675                 680                 685

Glu Glu Gln Ile Glu Arg Leu Gln Glu Lys Val Glu Ser Ala Gln Ser
    690                 695                 700

Glu Gln Lys Asn Leu Phe Leu Val Ile Phe Gln Arg Phe Ile Met Ile
705                 710                 715                 720

Leu Thr Glu His Leu Val Arg Cys Glu Thr Asp Gly Thr Ser Val Leu
                725                 730                 735

Thr Pro Trp Tyr Lys Asn Cys Ile Glu Arg Leu Gln Gln Ile Phe Leu
            740                 745                 750

Gln His His Gln Ile Ile Gln Gln Tyr Met Val Thr Leu Glu Asn Leu
        755                 760                 765
```

```
Leu Phe Thr Ala Glu Leu Asp Pro His Ile Leu Ala Val Phe Gln Gln
    770                 775                 780

Phe Cys Ala Leu Gln Ala
785                 790


<210> SEQ ID NO 51
<211> LENGTH: 818
<212> TYPE: DNA
<213> ORGANISM: Homo sapiens

<400> SEQUENCE: 51

agtcctgtgt ccgggccccg aggcacagcc agggcaccag gtggagcacc agctacgcgt      60

ggcgcagcgc agcgtcccta gcaccgagcc tcccgcagcc gccgagatgc tgcgaacaga     120

gagctgccgc cccaggtcgc ccgccggaca ggtggccgcg gcgtccccgc tcctgctgct     180

gctgctgctg ctcgcctggt gcgcgggcgc ctgccgaggt gctccaatat tacctcaagg     240

attacagcct gaacaacagc tacagttgtg gaatgagata gatgatactt gttcgtcttt     300

tctgtccatt gattctcagc ctcaggcatc caacgcactg gaggagcttt gctttatgat     360

tatgggaatg ctaccaaagc ctcaggaaca agatgaaaaa gataatacta aaaggttctt     420

atttcattat tcgaagacac agaagttggg caagtcaaat gttgtgtcgt cagttgtgca     480

tccgttgctg cagctcgttc ctcacctgca tgagagaaga atgaagagat tcagagtgga     540

cgaagaattc caaagtccct ttgcaagtca aagtcgagga tattttttat tcaggccacg     600

gaatggaaga aggtcagcag ggttcattta aaatggatgc cagctaattt tccacagagc     660

aatgctatgg aatacaaaat gtactgacat tttgttttct tctgaaaaaa atccttgcta     720

aatgtactct gttgaaaatc cctgtgttgt caatgttctc agttgtaaca atgttgtaaa     780

tgttcaattt gttgaaaatt aaaaaatcta aaaataaa                             818


<210> SEQ ID NO 52
<211> LENGTH: 174
<212> TYPE: PRT
<213> ORGANISM: Homo sapiens

<400> SEQUENCE: 52

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Leu Ala Trp Cys
            20                  25                  30

Ala Gly Ala Cys Arg Gly Ala Pro Ile Leu Pro Gln Gly Leu Gln Pro
        35                  40                  45

Glu Gln Gln Leu Gln Leu Trp Asn Glu Ile Asp Asp Thr Cys Ser Ser
    50                  55                  60

Phe Leu Ser Ile Asp Ser Gln Pro Gln Ala Ser Asn Ala Leu Glu Glu
65                  70                  75                  80

Leu Cys Phe Met Ile Met Gly Met Leu Pro Lys Pro Gln Glu Gln Asp
                85                  90                  95

Glu Lys Asp Asn Thr Lys Arg Phe Leu Phe His Tyr Ser Lys Thr Gln
            100                 105                 110

Lys Leu Gly Lys Ser Asn Val Val Ser Ser Val Val His Pro Leu Leu
        115                 120                 125

Gln Leu Val Pro His Leu His Glu Arg Arg Met Lys Arg Phe Arg Val
    130                 135                 140

Asp Glu Glu Phe Gln Ser Pro Phe Ala Ser Gln Ser Arg Gly Tyr Phe
```

145 150 155 160

Leu Phe Arg Pro Arg Asn Gly Arg Arg Ser Ala Gly Phe Ile
165 170

<210> SEQ ID NO 53
<211> LENGTH: 5849
<212> TYPE: DNA
<213> ORGANISM: Homo sapiens

<400> SEQUENCE: 53
gcgttccttg cggcccggcc gacctcgcgg gcttgggcct gggcgggcac cgacggagcg 60
gccctggctg cagcctcccg gcgccagcga agacaggctg agatgcggct gctcctgctc 120
gtgccgctgc tgctggctcc agcgcccggg tcctcggctc ccaaggtgag gcggcagagt 180
gacacctggg gaccctggag ccagtggagc ccctgcagcc ggacctgtgg agggggtgtc 240
agcttccggg agcgcccctg ctactcccag aggagagatg gaggctccag ctgcgtgggc 300
cccgcccgga gccaccgctc ttgtcgcacg gagagctgcc ccgacggcgc ccgggacttc 360
cgggccgagc agtgcgcgga gttcgacgga gcggagttcc aggggcggcg gtatcggtgg 420
ctgccctact acagcgcccc aaacaagtgt gaactgaact gcattcccaa gggggagaac 480
ttctactaca agcacaggga ggctgtggtt gatgggacgc cctgcgagcc tggcaagagg 540
gatgtctgtg tggatggcag ctgccgggtt gtcggctgtg atcacgagct ggactcgtcc 600
aagcaggagg acaagtgtct gcggtgtggg ggtgacggca cgacctgcta ccccgtcgca 660
ggcacctttg acgctaatga cctcagccga gctgtgaaga atgttcgtgg ggaatactac 720
ctcaatgggc actggaccat cgaggcggcc cgggccctgc cagcagccag caccatcctg 780
cattacgagc ggggtgctga gggggacctg gcccctgagc gactccatgc ccggggcccc 840
acctcggagc ccctggtcat cgagctcatc agccaggagc ccaaccccgg tgtgcactat 900
gagtaccacc tgcccctgcg ccgccccagc cccggcttca gctggagcca cggctcatgg 960
agtgactgca gcgcggagtg tggcggaggt caccagtccc gcctggtgtt ctgcaccatc 1020
gaccatgagg cctaccccga ccacatgtgc cagcgccagc cacggccagc tgaccggcgt 1080
tcctgcaatc ttcacccttg cccggagacc aagcgctgga aggcagggcc atgggcaccc 1140
tgctcagcct cctgtggagg aggctcccag tcccgctccg tgtactgcat ctcgtctgac 1200
ggggccggca tccaggaggc cgtggaggag gctgagtgtg ccgggctgcc tgggaagccc 1260
cctgccattc aggcctgtaa cctgcagcgc tgtgcagcct ggagcccgga gccctgggga 1320
gagtgttctg tcagttgtgg cgttggcgtc cggaagcgga gcgttacttg ccggggtgaa 1380
aggggttctt tgctccatac cgcagcgtgc tccttggaag accggccacc tctgactgag 1440
ccctgtgtgc atgaggactg ccccctcctc agtgaccagg cctggcatgt tggcacctgg 1500
ggtctatgct ccaagagctg cagctcgggc actcggaggc gacaggtcat ctgtgccatt 1560
gggccgccca gccactgcgg gagcctgcag cactccaagc ctgtggatgt ggagccttgt 1620
aacacgcagc cctgtcatct cccccaggag gtccccagca tgcaggatgt gcacacccct 1680
gccagcaacc cctggatgcc gttgggccct caggagtccc ctgcctcaga ctccagaggc 1740
cagtggtggg cagcccagga acacccctca gccaggggtg accacagggg agaacgaggt 1800
gaccccaggg gcgaccaagg cacccacctg tcagccctgg gccccgctcc ctctctgcag 1860
cagcccccat accagcaacc cctgcggtcg ggctcagggc cccacgactg cagacacagt 1920
cctcacgggt gctgccccga tggccacacg gcatctctcg ggcctcagtg gcaaggctgc 1980

```
cctggggccc cctgtcagca gagcaggtac gggtgctgcc ctgacagggt atctgtcgct   2040

gaggggcccc atcacgctgg ctgcacaaag tcgtatggtg gtgacagcac cgggggcatg   2100

cccaggtcaa gggcagtggc ttctacagtc cacaacaccc accagcccca ggcccagcag   2160

aatgagccca gtgagtgccg gggctcccag tttggctgtt gctatgacaa cgtggccact   2220

gcagccggtc ctcttgggga aggctgtgtg ggccagccca gccatgccta ccccgtgcgg   2280

tgcctgctgc ccagtgccca tggctcttgc gcagactggg ctgcccgctg gtacttcgtt   2340

gcctctgtgg gccaatgtaa ccgcttctgg tatggcggct gccatggcaa tgccaataac   2400

tttgcctcgg agcaagagtg catgagcagc tgccagggat ctctccatgg gccccgtcgt   2460

ccccagcctg gggcttctgg aaggagcacc cacacggatg gtggcggcag cagtcctgca   2520

ggcgagcagg aacccagcca gcacaggaca ggggccgcgg tgcagagaaa gccctggcct   2580

tctggtggtc tctggcggca agaccaacag cctgggccag gggaggcccc ccacacccag   2640

gcctttggag aatggccatg gggcaggag cttgggtcca gggcccctgg actgggtgga   2700

gatgccggat caccagcgcc acccttccac agctcctcct acaggattag cttggcaggt   2760

gtggagccct cgttggtgca ggcagccctg gggcagttgg tgcggctctc ctgctcagac   2820

gacactgccc cggaatccca ggctgcctgg cagaaagatg gccagcccat ctcctctgac   2880

aggcacaggc tgcagttcga cggatccctg atcatccacc ccctgcaggc agaggacgcg   2940

ggcacctaca gctgtggcag cacccggcca ggccgcgact cccagaagat ccaacttcgc   3000

atcatagggg gtgacatggc cgtgctgtct gaggctgagc tgagccgctt ccctcagccc   3060

agggacccag ctcaggactt tggccaagcg ggggctgctg ggcccctggg ggccatcccc   3120

tcttcacacc cacagcctgc aaacaggctg cgtttggacc agaaccagcc ccgggtggtg   3180

gatgccagtc caggccagcg gatccggatg acctgccgtg ccgaaggctt cccgcccccca   3240

gccatcgagt ggcagagaga tgggcagcct gtctcttctc ccagacacca gctgcagcct   3300

gatggctccc tggtcattag ccgagtggct gtagaagatg gcggcttcta cacctgtgtc   3360

gctttcaatg ggcaggaccg agaccagcga tgggtccagc tcagagttct gggggagctg   3420

acaatctcag gactgccccc tactgtgaca gtgccagagg gtgatacggc caggctattg   3480

tgtgtggtag caggagaaag tgtgaacatc aggtggtcca ggaacgggct acctgtgcag   3540

gctgatggcc accgtgtcca ccagtcccca gatggcacgc tgctcattta caacttgcgg   3600

gccagggatg agggctccta cacgtgcagt gcctaccagg ggagccaggc agtcagccgc   3660

agcaccgagg tgaaggtggt ctcaccagca cccaccgccc agcccaggga ccctggcagg   3720

gactgcgtcg accagccaga gctggccaac tgtgatttga tcctgcaggc ccagctttgt   3780

ggcaatgagt attactccag cttctgctgt gccagctgtt cacgtttcca gcctcacgct   3840

cagcccatct ggcagtaggg atgaaggcta gttccagccc cagtccaaaa tagttcatag   3900

ggctagggag aaaggaagat ggactcttgg cttcctctct ctggctggca aagggagtta   3960

tcttctggaa tacattagct ctttcaaaaa cccacccagt gtttagcctc aacggcagcc   4020

agttaccagc ttctctctgt agccttcagc agtgtttgca tctctgacat aaccacaggc   4080

tgctgttttc aagaagagca atctgtttgg ataagaaaaa cctttacttt acagcttccc   4140

tttataattt gttacacagg aatagttaaa tgcatttgtt tgtttgtttt ttgagacaga   4200

gtttcactct tgttgcccag gctggagggc aatggcgcga tctcagctca ctgcaacctc   4260

cgtctcctgg gttcttgatt ctcctgtgtc agccttctga gtagctagga ttacagatgc   4320

ctatcaccat gcctgggtaa tttttgtatt tttagttgag atggggtttc accatgttgg   4380
```

```
ccaggctggt ctcgaacttc tgacctcaga tgatctgccc gcctcagcct cccaaagtgc   4440
tgggattaca ggcatgagcc accacgccca gccatcaatg cattttttt atttttttt   4500
tgagacagag tttcgcactt cttgcccagg ctggagtaca atggtgcgat cttggctcac   4560
tgcaacctcc acctcctggg ttcaagcgct tctccagcct cagcctcctg agtagctggg   4620
attacaggta tgtgccacca tgcctggcta attttgtatt tttagtagag acggggtttc   4680
tccatgttgg tcagactggt cttgaactcc cgacctcagg taatccgccc gcctcggcct   4740
cccaaaatgc tgggattaga ggtgtgagcc actgtgccca gcccatcaat gtgttttaaa   4800
gctagctgtc agggttccac ttaatttaaa gctgggcagg gagatgtgta atgatttcaa   4860
agttaacacc tgtttgtttt ctaaagggca tgccaagtcc tgctgtatca gggaagtatt   4920
ctgtgctaaa atcagcgatg gttcattgct ctagtctctc tcacccttct aggcagtgca   4980
tcagtcagct ctaaatctgg tgcagagggt taacagcata acccttgttg gcaaaatgga   5040
atagatgtta agacctcaaa tagggatttg ggatgaaaca gctgcagtta gcactgttat   5100
ctgagcatga aagaactgga aacgctcctt acgtcgagat gttggacctt gaagccctcc   5160
tgaggccaac atgcaaatct ggctgtgacg gttcatctga cacctgtgta aagctgacca   5220
gcctgctctg tacagtgaca atgaggagcc cctctcttcc ttaagtagga atctgtgaag   5280
caaaatgttt gctgccaaag acaaatcaga ctgtcagtca ttaaaaacag cattagcagg   5340
atgaggatag caatggggaa gggttgtggg caatgcagta acagggaaat ggcttcagaa   5400
atggtttgag ttggaagaca acattcttca tctctcagga cttctaattc cttgatgcta   5460
aaagaagagg catggattct atgagcttcc aagtcccttt ccactttaac cttctacaaa   5520
tctttcagag gactgcctag tagcaaaggt tattcctgga cacaggaaag acgggcatta   5580
cagggaccaa agctctgaaa ggtgactttt attaccaaca cactggctgg aaaagggaca   5640
aaccacatca cgggtgagtg atacttctca gtcttctcta ctcattcaac aaaggaaatg   5700
tgggctgggg cagaggtctt ttttcattta atactggaaa aatattgaag agcatccatg   5760
ttcacttatg gctggttttg ctatagaaat tggaaaataa aggccacttt tttgaaatcc   5820
ccagtttaat taaaaaaaaa aaaaaaaaa                                       5849
```

<210> SEQ ID NO 54
<211> LENGTH: 1251
<212> TYPE: PRT
<213> ORGANISM: Homo sapiens

<400> SEQUENCE: 54

```
Met Arg Leu Leu Leu Leu Val Pro Leu Leu Leu Ala Pro Ala Pro Gly
1               5                   10                  15

Ser Ser Ala Pro Lys Val Arg Arg Gln Ser Asp Thr Trp Gly Pro Trp
            20                  25                  30

Ser Gln Trp Ser Pro Cys Ser Arg Thr Cys Gly Gly Gly Val Ser Phe
        35                  40                  45

Arg Glu Arg Pro Cys Tyr Ser Gln Arg Arg Asp Gly Gly Ser Ser Cys
    50                  55                  60

Val Gly Pro Ala Arg Ser His Arg Ser Cys Arg Thr Glu Ser Cys Pro
65                  70                  75                  80

Asp Gly Ala Arg Asp Phe Arg Ala Glu Gln Cys Ala Glu Phe Asp Gly
                85                  90                  95

Ala Glu Phe Gln Gly Arg Arg Tyr Arg Trp Leu Pro Tyr Tyr Ser Ala
            100                 105                 110
```

```
Pro Asn Lys Cys Glu Leu Asn Cys Ile Pro Lys Gly Glu Asn Phe Tyr
        115                 120                 125

Tyr Lys His Arg Glu Ala Val Val Asp Gly Thr Pro Cys Glu Pro Gly
    130                 135                 140

Lys Arg Asp Val Cys Val Asp Gly Ser Cys Arg Val Val Gly Cys Asp
145                 150                 155                 160

His Glu Leu Asp Ser Ser Lys Gln Glu Asp Lys Cys Leu Arg Cys Gly
                165                 170                 175

Gly Asp Gly Thr Thr Cys Tyr Pro Val Ala Gly Thr Phe Asp Ala Asn
            180                 185                 190

Asp Leu Ser Arg Ala Val Lys Asn Val Arg Gly Glu Tyr Tyr Leu Asn
        195                 200                 205

Gly His Trp Thr Ile Glu Ala Ala Arg Ala Leu Pro Ala Ala Ser Thr
    210                 215                 220

Ile Leu His Tyr Glu Arg Gly Ala Glu Gly Asp Leu Ala Pro Glu Arg
225                 230                 235                 240

Leu His Ala Arg Gly Pro Thr Ser Glu Pro Leu Val Ile Glu Leu Ile
                245                 250                 255

Ser Gln Glu Pro Asn Pro Gly Val His Tyr Glu Tyr His Leu Pro Leu
            260                 265                 270

Arg Arg Pro Ser Pro Gly Phe Ser Trp Ser His Gly Ser Trp Ser Asp
        275                 280                 285

Cys Ser Ala Glu Cys Gly Gly Gly His Gln Ser Arg Leu Val Phe Cys
    290                 295                 300

Thr Ile Asp His Glu Ala Tyr Pro Asp His Met Cys Gln Arg Gln Pro
305                 310                 315                 320

Arg Pro Ala Asp Arg Arg Ser Cys Asn Leu His Pro Cys Pro Glu Thr
                325                 330                 335

Lys Arg Trp Lys Ala Gly Pro Trp Ala Pro Cys Ser Ala Ser Cys Gly
            340                 345                 350

Gly Gly Ser Gln Ser Arg Ser Val Tyr Cys Ile Ser Ser Asp Gly Ala
        355                 360                 365

Gly Ile Gln Glu Ala Val Glu Glu Ala Glu Cys Ala Gly Leu Pro Gly
    370                 375                 380

Lys Pro Pro Ala Ile Gln Ala Cys Asn Leu Gln Arg Cys Ala Ala Trp
385                 390                 395                 400

Ser Pro Glu Pro Trp Gly Glu Cys Ser Val Ser Cys Gly Val Gly Val
                405                 410                 415

Arg Lys Arg Ser Val Thr Cys Arg Gly Glu Arg Gly Ser Leu Leu His
            420                 425                 430

Thr Ala Ala Cys Ser Leu Glu Asp Arg Pro Pro Leu Thr Glu Pro Cys
        435                 440                 445

Val His Glu Asp Cys Pro Leu Leu Ser Asp Gln Ala Trp His Val Gly
    450                 455                 460

Thr Trp Gly Leu Cys Ser Lys Ser Cys Ser Ser Gly Thr Arg Arg Arg
465                 470                 475                 480

Gln Val Ile Cys Ala Ile Gly Pro Pro Ser His Cys Gly Ser Leu Gln
                485                 490                 495

His Ser Lys Pro Val Asp Val Glu Pro Cys Asn Thr Gln Pro Cys His
            500                 505                 510

Leu Pro Gln Glu Val Pro Ser Met Gln Asp Val His Thr Pro Ala Ser
        515                 520                 525
```

```
Asn Pro Trp Met Pro Leu Gly Pro Gln Glu Ser Pro Ala Ser Asp Ser
    530                 535                 540

Arg Gly Gln Trp Trp Ala Ala Gln Glu His Pro Ser Ala Arg Gly Asp
545                 550                 555                 560

His Arg Gly Glu Arg Gly Asp Pro Arg Gly Asp Gln Gly Thr His Leu
                565                 570                 575

Ser Ala Leu Gly Pro Ala Pro Ser Leu Gln Gln Pro Pro Tyr Gln Gln
            580                 585                 590

Pro Leu Arg Ser Gly Ser Gly Pro His Asp Cys Arg His Ser Pro His
        595                 600                 605

Gly Cys Cys Pro Asp Gly His Thr Ala Ser Leu Gly Pro Gln Trp Gln
    610                 615                 620

Gly Cys Pro Gly Ala Pro Cys Gln Gln Ser Arg Tyr Gly Cys Cys Pro
625                 630                 635                 640

Asp Arg Val Ser Val Ala Glu Gly Pro His His Ala Gly Cys Thr Lys
                645                 650                 655

Ser Tyr Gly Gly Asp Ser Thr Gly Gly Met Pro Arg Ser Arg Ala Val
            660                 665                 670

Ala Ser Thr Val His Asn Thr His Gln Pro Gln Ala Gln Gln Asn Glu
        675                 680                 685

Pro Ser Glu Cys Arg Gly Ser Gln Phe Gly Cys Cys Tyr Asp Asn Val
    690                 695                 700

Ala Thr Ala Ala Gly Pro Leu Gly Glu Gly Cys Val Gly Gln Pro Ser
705                 710                 715                 720

His Ala Tyr Pro Val Arg Cys Leu Leu Pro Ser Ala His Gly Ser Cys
                725                 730                 735

Ala Asp Trp Ala Ala Arg Trp Tyr Phe Val Ala Ser Val Gly Gln Cys
            740                 745                 750

Asn Arg Phe Trp Tyr Gly Gly Cys His Gly Asn Ala Asn Asn Phe Ala
        755                 760                 765

Ser Glu Gln Glu Cys Met Ser Ser Cys Gln Gly Ser Leu His Gly Pro
    770                 775                 780

Arg Arg Pro Gln Pro Gly Ala Ser Gly Arg Ser Thr His Thr Asp Gly
785                 790                 795                 800

Gly Gly Ser Ser Pro Ala Gly Glu Gln Glu Pro Ser Gln His Arg Thr
                805                 810                 815

Gly Ala Ala Val Gln Arg Lys Pro Trp Pro Ser Gly Gly Leu Trp Arg
            820                 825                 830

Gln Asp Gln Gln Pro Gly Pro Gly Glu Ala Pro His Thr Gln Ala Phe
        835                 840                 845

Gly Glu Trp Pro Trp Gly Gln Glu Leu Gly Ser Arg Ala Pro Gly Leu
    850                 855                 860

Gly Gly Asp Ala Gly Ser Pro Ala Pro Pro Phe His Ser Ser Ser Tyr
865                 870                 875                 880

Arg Ile Ser Leu Ala Gly Val Glu Pro Ser Leu Val Gln Ala Ala Leu
                885                 890                 895

Gly Gln Leu Val Arg Leu Ser Cys Ser Asp Asp Thr Ala Pro Glu Ser
            900                 905                 910

Gln Ala Ala Trp Gln Lys Asp Gly Gln Pro Ile Ser Ser Asp Arg His
        915                 920                 925

Arg Leu Gln Phe Asp Gly Ser Leu Ile Ile His Pro Leu Gln Ala Glu
    930                 935                 940

Asp Ala Gly Thr Tyr Ser Cys Gly Ser Thr Arg Pro Gly Arg Asp Ser
```

```
945                 950                 955                 960

Gln Lys Ile Gln Leu Arg Ile Ile Gly Gly Asp Met Ala Val Leu Ser
                965                 970                 975

Glu Ala Glu Leu Ser Arg Phe Pro Gln Pro Arg Asp Pro Ala Gln Asp
            980                 985                 990

Phe Gly Gln Ala Gly Ala Ala Gly  Pro Leu Gly Ala Ile  Pro Ser Ser
        995                 1000                1005

His Pro  Gln Pro Ala Asn Arg  Leu Arg Leu Asp Gln  Asn Gln Pro
    1010                 1015                 1020

Arg Val  Val Asp Ala Ser Pro  Gly Gln Arg Ile Arg  Met Thr Cys
    1025                 1030                 1035

Arg Ala  Glu Gly Phe Pro Pro  Pro Ala Ile Glu Trp  Gln Arg Asp
    1040                 1045                 1050

Gly Gln  Pro Val Ser Ser Pro  Arg His Gln Leu Gln  Pro Asp Gly
    1055                 1060                 1065

Ser Leu  Val Ile Ser Arg Val  Ala Val Glu Asp Gly  Gly Phe Tyr
    1070                 1075                 1080

Thr Cys  Val Ala Phe Asn Gly  Gln Asp Arg Asp Gln  Arg Trp Val
    1085                 1090                 1095

Gln Leu  Arg Val Leu Gly Glu  Leu Thr Ile Ser Gly  Leu Pro Pro
    1100                 1105                 1110

Thr Val  Thr Val Pro Glu Gly  Asp Thr Ala Arg Leu  Leu Cys Val
    1115                 1120                 1125

Val Ala  Gly Glu Ser Val Asn  Ile Arg Trp Ser Arg  Asn Gly Leu
    1130                 1135                 1140

Pro Val  Gln Ala Asp Gly His  Arg Val His Gln Ser  Pro Asp Gly
    1145                 1150                 1155

Thr Leu  Leu Ile Tyr Asn Leu  Arg Ala Arg Asp Glu  Gly Ser Tyr
    1160                 1165                 1170

Thr Cys  Ser Ala Tyr Gln Gly  Ser Gln Ala Val Ser  Arg Ser Thr
    1175                 1180                 1185

Glu Val  Lys Val Val Ser Pro  Ala Pro Thr Ala Gln  Pro Arg Asp
    1190                 1195                 1200

Pro Gly  Arg Asp Cys Val Asp  Gln Pro Glu Leu Ala  Asn Cys Asp
    1205                 1210                 1215

Leu Ile  Leu Gln Ala Gln Leu  Cys Gly Asn Glu Tyr  Tyr Ser Ser
    1220                 1225                 1230

Phe Cys  Cys Ala Ser Cys Ser  Arg Phe Gln Pro His  Ala Gln Pro
    1235                 1240                 1245

Ile Trp  Gln
    1250


<210> SEQ ID NO 55
<211> LENGTH: 3851
<212> TYPE: DNA
<213> ORGANISM: Homo sapiens

<400> SEQUENCE: 55

cgcaaagccg ccgggctgct gcgcccagag ccagccggag ccggagccgg agcccgaact     60

gcagctccag ccccagccgt gcggagccgc agcccaggcc ggggccggcg gcggctcatg    120

gacagcgggg cgggcggccg gcgctgcccg gaggcggccc tcctgattct ggggcctccc    180

aggatggagc acctgaggca cagcccaggc cctgggggc aacggctact gctgccctcc     240

atgctgctag cactgctgct cctgctggct ccatccccag gccacgccac tcgggtagtg    300
```

```
tacaaggtgc cggaggaaca gccacccaac accctcattg ggagcctcgc agccgactat    360
ggttttccag atgtggggca cctgtacaag ctagaggtgg gtgccccgta ccttcgcgtg    420
gatggcaaga caggtgacat tttcaccacc gagacctcca tcgaccgtga ggggctccgt    480
gaatgccaga accagctccc tggtgatccc tgcatcctgg agtttgaggt atctatcaca    540
gacctcgtgc agaatggcag cccccggctg ctagagggcc agatagaagt acaagacatc    600
aatgacaaca cacccaactt cgcctcacca gtcatcactc tggccatccc tgagaacacc    660
aacatcggct cactcttccc catcccgctg gcttcagacc gtgatgctgg tcccaacggt    720
gtggcatcct atgagctgca ggctgggcct gaggcccagg agctatttgg gctgcaggtg    780
gcagaggacc aggaggagaa gcaaccacag ctcattgtga tgggcaacct ggaccgtgag    840
cgctgggact cctatgacct caccatcaag gtgcaggatg gcggcagccc cccacgcgcc    900
agcagtgccc tgctgcgtgt caccgtgctt gacaccaatg acaacgcccc caagtttgag    960
cggccctcct atgaggccga actatctgag aatagcccca taggccactc ggtcatccag   1020
gtgaaggcca atgactcaga ccaaggtgcc aatgcagaaa tcgaatacac attccaccag   1080
gcgcccgaag ttgtgaggcg tcttcttcga ctggacagga acactggact tatcactgtt   1140
cagggcccgg tggaccgtga ggacctaagc accctgcgct tctcagtgct tgctaaggac   1200
cgaggcacca accccaagag tgcccgtgcc caggtggttg tgaccgtgaa ggacatgaat   1260
gacaatgccc ccaccattga gatccggggc atagggctag tgactcatca agatgggatg   1320
gctaacatct cagaggatgt ggcagaggag acagctgtgg ccctggtgca ggtgtctgac   1380
cgagatgagg gagagaatgc agctgtcacc tgtgtggtgg caggtgatgt gcccttccag   1440
ctgcgccagg ccagtgagac aggcagtgac agcaagaaga agtatttcct gcagactacc   1500
accccgctag actacgagaa ggtcaaagac tacaccattg agattgtggc tgtggactct   1560
ggcaaccccc cactctccag cactaactcc ctcaaggtgc aggtggtgga cgtcaatgac   1620
aacgcacctg tcttcactca gagtgtcact gaggtcgcct tcccggaaaa caacaagcct   1680
ggtgaagtga ttgctgagat cactgccagt gatgctgact ctggctctaa tgctgagctg   1740
gtttactctc tggagcctga gccggctgct aagggcctct tcaccatctc acccgagact   1800
ggagagatcc aggtgaagac atctctggat cgggaacagc gggagagcta tgagttgaag   1860
gtggtggcag ctgaccgggg cagtcctagc ctccagggca cagccactgt ccttgtcaat   1920
gtgctggact gcaatgacaa tgaccccaaa tttatgctga gtggctacaa cttctcagtg   1980
atggagaaca tgccagcact gagtccagtg ggcatggtga ctgtcattga tggagacaag   2040
ggggagaatg cccaggtgca gctctcagtg gagcaggaca acggtgactt tgttatccag   2100
aatggcacag gcaccatcct atccagcctg agctttgatc gagagcaaca aagcacctac   2160
accttccagc tgaaggcagt ggatggtggc gtcccacctc gctcagctta cgttggtgtc   2220
accatcaatg tgctggacga gaatgacaac gcaccctata tcactgcccc ttctaacacc   2280
tctcacaagc tgctgacccc ccagacacgt cttggtgaga cggtcagcca ggtggcagcc   2340
gaggactttg actctggtgt caatgctgag ctgatctaca gcattgcagg tggcaaccct   2400
tatggactct tccagattgg gtcacattca ggtgccatca ccctggagaa ggagattgag   2460
cggcgccacc atgggctaca ccgcctggtg gtgaaggtca gtgaccgcgg caagccccca   2520
cgctatggca cagccttggt ccatctttat gtcaatgaga ctctggccaa ccgcacgctg   2580
ctggagaccc tcctgggcca cagcctggac acgccgctgg atattgacat tgctggggat   2640
```

```
ccagaatatg agcgctccaa gcagcgtggc aacattctct ttggtgtggt ggctggtgtg   2700
gtggccgtgg ccttgctcat cgccctggcg gttcttgtgc gctactgcag acagcgggag   2760
gccaaaagtg gttaccaggc tggtaagaag gagaccaagg acctgtatgc ccccaagccc   2820
agtggcaagg cctccaaggg aaacaaaagc aaaggcaaga agagcaagtc cccaaagccc   2880
gtgaagccag tggaggacga ggatgaggcc gggctgcaga agtccctcaa gttcaacctg   2940
atgagcgatg cccctgggga cagtccccgc atccacctgc cctcaacta cccaccaggc    3000
agccctgacc tgggccgcca ctatcgctct aactccccac tgccttccat ccagctgcag   3060
ccccagtcac cctcagcctc caagaagcac caggtggtac aggacctgcc acctgcaaac   3120
acattcgtgg gcaccgggga caccacgtcc acgggctctg agcagtactc cgactacagc   3180
taccgcacca acccccccaa ataccccagc aagcaggtag gccagccctt tcagctcagc   3240
acaccccagc cctaccccca cccctaccac ggagccatct ggaccgaggt gtgggagtga   3300
tggagcaggt ttactgtgcc tgcccgtgtt gggggccagc ctgagccagc agtgggaggt   3360
ggggccttag tgcctcaccg ggcacacgga ttaggctgag tgaagattaa gggagggtgt   3420
gctctgtggt ctcctccctg ccctctcccc actggggaga gacctgtgat ttgccaagtc   3480
cctggaccct ggaccagcta ctgggcctta tgggttgggg gtggtaggca ggtgagcgta   3540
agtggggagg gaaatgggta agaagtctac tccaaaccta ggtctctatg tcagaccaga   3600
cctaggtgct tctctaggag ggaaacaggg agacctgggg tcctgtggat aactgagtgg   3660
ggagtctgcc aggggagggc accttcccat tgtgccttct gtgtgtattg tgcattaacc   3720
tcttcctcac cactaggctt ctggggctgg gtcccacatg cccttgaccc tgacaataaa   3780
gttctctatt tttggaaaaa aaaaaaaaaa aaaaaaaaaa aaaaaaaaaa aaaaaaaaaa   3840
aaaaaaaaaa a                                                        3851
```

```
<210> SEQ ID NO 56
<211> LENGTH: 1060
<212> TYPE: PRT
<213> ORGANISM: Homo sapiens

<400> SEQUENCE: 56

Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro
            20                  25                  30

Gly Gly Gln Arg Leu Leu Leu Pro Ser Met Leu Leu Ala Leu Leu Leu
        35                  40                  45

Leu Leu Ala Pro Ser Pro Gly His Ala Thr Arg Val Val Tyr Lys Val
    50                  55                  60

Pro Glu Glu Gln Pro Pro Asn Thr Leu Ile Gly Ser Leu Ala Ala Asp
65                  70                  75                  80

Tyr Gly Phe Pro Asp Val Gly His Leu Tyr Lys Leu Glu Val Gly Ala
                85                  90                  95

Pro Tyr Leu Arg Val Asp Gly Lys Thr Gly Asp Ile Phe Thr Thr Glu
            100                 105                 110

Thr Ser Ile Asp Arg Glu Gly Leu Arg Glu Cys Gln Asn Gln Leu Pro
        115                 120                 125

Gly Asp Pro Cys Ile Leu Glu Phe Glu Val Ser Ile Thr Asp Leu Val
    130                 135                 140

Gln Asn Gly Ser Pro Arg Leu Leu Glu Gly Gln Ile Glu Val Gln Asp
145                 150                 155                 160
```

```
Ile Asn Asp Asn Thr Pro Asn Phe Ala Ser Pro Val Ile Thr Leu Ala
                165                 170                 175

Ile Pro Glu Asn Thr Asn Ile Gly Ser Leu Phe Pro Ile Pro Leu Ala
            180                 185                 190

Ser Asp Arg Asp Ala Gly Pro Asn Gly Val Ala Ser Tyr Glu Leu Gln
        195                 200                 205

Ala Gly Pro Glu Ala Gln Glu Leu Phe Gly Leu Gln Val Ala Glu Asp
    210                 215                 220

Gln Glu Glu Lys Gln Pro Gln Leu Ile Val Met Gly Asn Leu Asp Arg
225                 230                 235                 240

Glu Arg Trp Asp Ser Tyr Asp Leu Thr Ile Lys Val Gln Asp Gly Gly
                245                 250                 255

Ser Pro Pro Arg Ala Ser Ser Ala Leu Leu Arg Val Thr Val Leu Asp
            260                 265                 270

Thr Asn Asp Asn Ala Pro Lys Phe Glu Arg Pro Ser Tyr Glu Ala Glu
        275                 280                 285

Leu Ser Glu Asn Ser Pro Ile Gly His Ser Val Ile Gln Val Lys Ala
    290                 295                 300

Asn Asp Ser Asp Gln Gly Ala Asn Ala Glu Ile Glu Tyr Thr Phe His
305                 310                 315                 320

Gln Ala Pro Glu Val Val Arg Arg Leu Leu Arg Leu Asp Arg Asn Thr
                325                 330                 335

Gly Leu Ile Thr Val Gln Gly Pro Val Asp Arg Glu Asp Leu Ser Thr
            340                 345                 350

Leu Arg Phe Ser Val Leu Ala Lys Asp Arg Gly Thr Asn Pro Lys Ser
        355                 360                 365

Ala Arg Ala Gln Val Val Val Thr Val Lys Asp Met Asn Asp Asn Ala
    370                 375                 380

Pro Thr Ile Glu Ile Arg Gly Ile Gly Leu Val Thr His Gln Asp Gly
385                 390                 395                 400

Met Ala Asn Ile Ser Glu Asp Val Ala Glu Glu Thr Ala Val Ala Leu
                405                 410                 415

Val Gln Val Ser Asp Arg Asp Glu Gly Glu Asn Ala Ala Val Thr Cys
            420                 425                 430

Val Val Ala Gly Asp Val Pro Phe Gln Leu Arg Gln Ala Ser Glu Thr
        435                 440                 445

Gly Ser Asp Ser Lys Lys Lys Tyr Phe Leu Gln Thr Thr Thr Pro Leu
    450                 455                 460

Asp Tyr Glu Lys Val Lys Asp Tyr Thr Ile Glu Ile Val Ala Val Asp
465                 470                 475                 480

Ser Gly Asn Pro Pro Leu Ser Ser Thr Asn Ser Leu Lys Val Gln Val
                485                 490                 495

Val Asp Val Asn Asp Asn Ala Pro Val Phe Thr Gln Ser Val Thr Glu
            500                 505                 510

Val Ala Phe Pro Glu Asn Asn Lys Pro Gly Glu Val Ile Ala Glu Ile
        515                 520                 525

Thr Ala Ser Asp Ala Asp Ser Gly Ser Asn Ala Glu Leu Val Tyr Ser
    530                 535                 540

Leu Glu Pro Glu Pro Ala Ala Lys Gly Leu Phe Thr Ile Ser Pro Glu
545                 550                 555                 560

Thr Gly Glu Ile Gln Val Lys Thr Ser Leu Asp Arg Glu Gln Arg Glu
                565                 570                 575
```

```
Ser Tyr Glu Leu Lys Val Val Ala Ala Asp Arg Gly Ser Pro Ser Leu
            580                 585                 590

Gln Gly Thr Ala Thr Val Leu Val Asn Val Leu Asp Cys Asn Asp Asn
        595                 600                 605

Asp Pro Lys Phe Met Leu Ser Gly Tyr Asn Phe Ser Val Met Glu Asn
    610                 615                 620

Met Pro Ala Leu Ser Pro Val Gly Met Val Thr Val Ile Asp Gly Asp
625                 630                 635                 640

Lys Gly Glu Asn Ala Gln Val Gln Leu Ser Val Glu Gln Asp Asn Gly
                645                 650                 655

Asp Phe Val Ile Gln Asn Gly Thr Gly Thr Ile Leu Ser Ser Leu Ser
            660                 665                 670

Phe Asp Arg Glu Gln Gln Ser Thr Tyr Thr Phe Gln Leu Lys Ala Val
        675                 680                 685

Asp Gly Gly Val Pro Pro Arg Ser Ala Tyr Val Gly Val Thr Ile Asn
    690                 695                 700

Val Leu Asp Glu Asn Asp Asn Ala Pro Tyr Ile Thr Ala Pro Ser Asn
705                 710                 715                 720

Thr Ser His Lys Leu Leu Thr Pro Gln Thr Arg Leu Gly Glu Thr Val
                725                 730                 735

Ser Gln Val Ala Ala Glu Asp Phe Asp Ser Gly Val Asn Ala Glu Leu
            740                 745                 750

Ile Tyr Ser Ile Ala Gly Gly Asn Pro Tyr Gly Leu Phe Gln Ile Gly
        755                 760                 765

Ser His Ser Gly Ala Ile Thr Leu Glu Lys Glu Ile Glu Arg Arg His
    770                 775                 780

His Gly Leu His Arg Leu Val Val Lys Val Ser Asp Arg Gly Lys Pro
785                 790                 795                 800

Pro Arg Tyr Gly Thr Ala Leu Val His Leu Tyr Val Asn Glu Thr Leu
                805                 810                 815

Ala Asn Arg Thr Leu Leu Glu Thr Leu Leu Gly His Ser Leu Asp Thr
            820                 825                 830

Pro Leu Asp Ile Asp Ile Ala Gly Asp Pro Glu Tyr Glu Arg Ser Lys
        835                 840                 845

Gln Arg Gly Asn Ile Leu Phe Gly Val Val Ala Gly Val Val Ala Val
    850                 855                 860

Ala Leu Leu Ile Ala Leu Ala Val Leu Val Arg Tyr Cys Arg Gln Arg
865                 870                 875                 880

Glu Ala Lys Ser Gly Tyr Gln Ala Gly Lys Lys Glu Thr Lys Asp Leu
                885                 890                 895

Tyr Ala Pro Lys Pro Ser Gly Lys Ala Ser Lys Gly Asn Lys Ser Lys
            900                 905                 910

Gly Lys Lys Ser Lys Ser Pro Lys Pro Val Lys Pro Val Glu Asp Glu
        915                 920                 925

Asp Glu Ala Gly Leu Gln Lys Ser Leu Lys Phe Asn Leu Met Ser Asp
    930                 935                 940

Ala Pro Gly Asp Ser Pro Arg Ile His Leu Pro Leu Asn Tyr Pro Pro
945                 950                 955                 960

Gly Ser Pro Asp Leu Gly Arg His Tyr Arg Ser Asn Ser Pro Leu Pro
                965                 970                 975

Ser Ile Gln Leu Gln Pro Gln Ser Pro Ser Ala Ser Lys Lys His Gln
            980                 985                 990

Val Val Gln Asp Leu Pro Pro Ala  Asn Thr Phe Val Gly  Thr Gly Asp
```

```
        995                 1000                1005

Thr Thr  Ser Thr Gly Ser Glu  Gln Tyr Ser Asp Tyr  Ser Tyr Arg
    1010                 1015                 1020

Thr Asn  Pro Pro Lys Tyr Pro  Ser Lys Gln Val Gly  Gln Pro Phe
    1025                 1030                 1035

Gln Leu  Ser Thr Pro Gln Pro  Leu Pro His Pro Tyr  His Gly Ala
    1040                 1045                 1050

Ile Trp  Thr Glu Val Trp Glu
    1055                 1060


<210> SEQ ID NO 57
<211> LENGTH: 3393
<212> TYPE: DNA
<213> ORGANISM: Homo sapiens

<400> SEQUENCE: 57

cctgcctgcc tccctgcgca cccgcagcct cccccgctgc ctccctaggg ctcccctccg     60

gccgccagcg cccatttttc attccctaga tagagatact ttgcgcgcac acacatacat    120

acgcgcgcaa aaaggaaaaa aaaaaaaaaa agcccaccct ccagcctcgc tgcaaagaga    180

aaaccggagc agccgcagct cgcagctcgc agctcgcagc ccgcagcccg cagaggacgc    240

ccagagcggc gagcgggcgg gcagacggac cgacggactc gcgccgcgtc cacctgtcgg    300

ccgggcccag ccgagcgcgc agcgggcacg ccgcgcgcgc ggagcagccg tgcccgccgc    360

ccgggccccg cgccagggcg cacacgctcc cgccccccta cccggcccgg gcgggagttt    420

gcacctctcc ctgcccgggt gctcgagctg ccgttgcaaa gccaactttg gaaaaagttt    480

tttgggggag acttgggcct tgaggtgccc agctccgcgc tttccgattt tgggggcctt    540

tccagaaaat gttgcaaaaa agctaagccg gcgggcagag gaaaacgcct gtagccggcg    600

agtgaagacg aaccatcgac tgccgtgttc cttttcctct tggaggttgg agtcccctgg    660

gcgcccccac acggctagac gcctcggctg gttcgcgacg cagccccccg gccgtggatg    720

ctcactcggg ctcgggatcc gcccaggtag cggcctcgga cccaggtcct gcgcccaggt    780

cctcccctgc cccccagcga cggagccggg gccgggggcg gcggcgcccg ggggccatgc    840

gggtgagccg cggctgcaga ggcctgagcg cctgatcgcc gcggacccga gccgagccca    900

ccccctccc cagcccccca ccctggccgc gggggcggcg cgctcgatct acgcgtccgg    960

ggccccgcgg ggccgggccc ggagtcggca tgaatcgctg ctgggcgctc ttcctgtctc   1020

tctgctgcta cctgcgtctg gtcagcgccg agggggaccc cattcccgag gagctttatg   1080

agatgctgag tgaccactcg atccgctcct ttgatgatct ccaacgcctg ctgcacggag   1140

accccggaga ggaagatggg gccgagttgg acctgaacat gacccgctcc cactctggag   1200

gcgagctgga gagcttggct cgtggaagaa ggagcctggg ttccctgacc attgctgagc   1260

cggccatgat cgccgagtgc aagacgcgca ccgaggtgtt cgagatctcc cggcgcctca   1320

tagaccgcac caacgccaac ttcctggtgt ggccgccctg tgtggaggtg cagcgctgct   1380

ccggctgctg caacaaccgc aacgtgcagt gccgccccac ccaggtgcag ctgcgacctg   1440

tccaggtgag aaagatcgag attgtgcgga agaagccaat ctttaagaag gccacggtga   1500

cgctggaaga ccacctggca tgcaagtgtg agacagtggc agctgcacgg cctgtgaccc   1560

gaagcccggg gggttcccag gagcagcgag ccaaaacgcc ccaaactcgg gtgaccattc   1620

ggacggtgcg agtccgccgg ccccccaagg gcaagcaccg gaaattcaag cacacgcatg   1680

acaagacggc actgaaggag acccttggag cctaggggca tcggcaggag agtgtgtggg   1740
```

```
cagggttatt taatatggta tttgctgtat tgcccccatg gggtccttgg agtgataata   1800
ttgtttccct cgtccgtctg tctcgatgcc tgattcggac ggccaatggt gcttccccca   1860
cccctccacg tgtccgtcca cccttccatc agcgggtctc ctcccagcgg cctccggcgt   1920
cttgcccagc agctcaagaa gaaaaagaag gactgaactc catcgccatc ttcttccctt   1980
aactccaaga acttgggata agagtgtgag agagactgat ggggtcgctc tttgggggaa   2040
acgggctcct tcccctgcac ctggcctggg ccacacctga gcgctgtgga ctgtcctgag   2100
gagccctgag gacctctcag catagcctgc ctgatccctg aacccctggc cagctctgag   2160
gggaggcacc tccaggcagg ccaggctgcc tcggactcca tggctaagac cacagacggg   2220
cacacagact ggagaaaacc cctcccacgg tgcccaaaca ccagtcacct cgtctccctg   2280
gtgcctctgt gcacagtggc ttcttttcgt tttcgttttg aagacgtgga ctcctcttgg   2340
tgggtgtggc cagcacacca agtggctggg tgccctctca ggtgggttag agatggagtt   2400
tgctgttgag gtggctgtag atggtgacct gggtatcccc tgcctcctgc caccccttcc   2460
tccccacact ccactctgat tcacctcttc ctctggttcc tttcatctct ctacctccac   2520
cctgcatttt cctcttgtcc tggcccttca gtctgctcca ccaaggggct cttgaacccc   2580
ttattaaggc cccagatgat cccagtcact cctctctagg gcagaagact agaggccagg   2640
gcagcaaggg acctgctcat catattccaa cccagccacg actgccatgt aaggttgtgc   2700
agggtgtgta ctgcacaagg acattgtatg cagggagcac tgttcacatc atagataaag   2760
ctgatttgta tatttattat gacaatttct ggcagatgta ggtaaagagg aaaaggatcc   2820
ttttcctaat tcacacaaag actccttgtg gactggctgt gcccctgatg cagcctgtgg   2880
cttggagtgg ccaaatagga gggagactgt ggtaggggca gggaggcaac actgctgtcc   2940
acatgacctc catttcccaa agtcctctgc tccagcaact gcccttccag gtgggtgtgg   3000
gacacctggg agaaggtctc caagggaggg tgcagccctc ttgcccgcac ccctccctgc   3060
ttgcacactt ccccatcttt gatccttctg agctccacct ctggtggctc ctcctaggaa   3120
accagctcgt gggctgggaa tgggggagag aagggaaaag atccccaaga ccccctgggg   3180
tgggatctga gctcccacct cccttcccac ctactgcact ttccccccttc ccgccttcca   3240
aaacctgctt ccttcagttt gtaaagtcgg tgattatatt tttgggggct ttcctttttat   3300
tttttaaatg taaaatttat ttatattccg tatttaaagt tgtaaaaaaa aataaccaca   3360
aaacaaaacc aaatgaaaaa aaaaaaaaaa aaa                                 3393
```

<210> SEQ ID NO 58
<211> LENGTH: 241
<212> TYPE: PRT
<213> ORGANISM: Homo sapiens

<400> SEQUENCE: 58

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80
```

```
Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```

<210> SEQ ID NO 59
<211> LENGTH: 1149
<212> TYPE: DNA
<213> ORGANISM: Homo sapiens

<400> SEQUENCE: 59

```
aacaagggag gtgctgcagt tggcggtcgg gctagagaag agaggcgcct gcgcttgcga     60

gctgggcttg tgagtggggc tgccgagagg gcaggcgtgg ggcgaggcca aaggactgaa    120

cccgcaggag cgtcacgggc gccggggcgg ctgccgacgg cgggactggg ttttctatca    180

gatgttccac gtaataatgc tggagttaag aagtttccat tattttgctc caaaccagaa    240

gactctgttc cctgtatata gaataggagt aatatttgaa aacaactggc tgatgtttaa    300

aactgaagat tgtcatgatt gtttatccta atcccaatgc tgaagtaaga ttgtcttgga    360

aatactaagt tggggtaatc caaatctatt tctggaacca tgaaaatttt gctagttttt    420

gactttgaca atacaatcat agatgacaat agtgacactt ggattgtaca atgtgctccc    480

aacaaaaagc ttcctattga actacgtgat tcttatcgaa aaggattttg gacagaattt    540

atgggcagag tctttaagta tttgggagat aagggtgtaa gagaacatga aatgaaaaga    600

gcagtgacat cattgccttt cactccaggg atggtggaac tcttcaactt tataagaaag    660

aataaggata aatttgactg cattattatt tcagattcaa attcggtctt catagattgg    720

gttttagaag ctgccagttt tcatgacata tttgataaag tgtttacaaa tccagcagct    780

tttaatagca atggtcatct cactgttgaa aattatcata ctcattcttg caatagatgc    840

ccaaagaatc tttgcaaaaa ggtagttttg atagaatttg tagataaaca gttacaacag    900

ggagtgaatt atacacaaat tgtttatatt ggtgatggtg gaaatgatgt ctgtccagtc    960

accttttttaa agaatgatga tgttgccatg ccacggaaag gatataccttt acagaaaact   1020

ctttccagaa tgtctcaaaa tcttgagcct atggaatatt ctgttgtagt ttggtcctca   1080

ggtgttgata taatttctca tttacaattt ctaataaagg attaatatgt cagcaaaaaa   1140
```

aaaaaaaaa 1149

<210> SEQ ID NO 60
<211> LENGTH: 241
<212> TYPE: PRT
<213> ORGANISM: Homo sapiens

<400> SEQUENCE: 60

```
Met Lys Ile Leu Leu Val Phe Asp Phe Asp Asn Thr Ile Ile Asp Asp
1               5                   10                  15

Asn Ser Asp Thr Trp Ile Val Gln Cys Ala Pro Asn Lys Lys Leu Pro
            20                  25                  30

Ile Glu Leu Arg Asp Ser Tyr Arg Lys Gly Phe Trp Thr Glu Phe Met
        35                  40                  45

Gly Arg Val Phe Lys Tyr Leu Gly Asp Lys Gly Val Arg Glu His Glu
    50                  55                  60

Met Lys Arg Ala Val Thr Ser Leu Pro Phe Thr Pro Gly Met Val Glu
65                  70                  75                  80

Leu Phe Asn Phe Ile Arg Lys Asn Lys Asp Lys Phe Asp Cys Ile Ile
                85                  90                  95

Ile Ser Asp Ser Asn Ser Val Phe Ile Asp Trp Val Leu Glu Ala Ala
            100                 105                 110

Ser Phe His Asp Ile Phe Asp Lys Val Phe Thr Asn Pro Ala Ala Phe
        115                 120                 125

Asn Ser Asn Gly His Leu Thr Val Glu Asn Tyr His Thr His Ser Cys
    130                 135                 140

Asn Arg Cys Pro Lys Asn Leu Cys Lys Lys Val Val Leu Ile Glu Phe
145                 150                 155                 160

Val Asp Lys Gln Leu Gln Gln Gly Val Asn Tyr Thr Gln Ile Val Tyr
                165                 170                 175

Ile Gly Asp Gly Gly Asn Asp Val Cys Pro Val Thr Phe Leu Lys Asn
            180                 185                 190

Asp Asp Val Ala Met Pro Arg Lys Gly Tyr Thr Leu Gln Lys Thr Leu
        195                 200                 205

Ser Arg Met Ser Gln Asn Leu Glu Pro Met Glu Tyr Ser Val Val Val
    210                 215                 220

Trp Ser Ser Gly Val Asp Ile Ile Ser His Leu Gln Phe Leu Ile Lys
225                 230                 235                 240

Asp
```

<210> SEQ ID NO 61
<211> LENGTH: 678
<212> TYPE: DNA
<213> ORGANISM: Homo sapiens

<400> SEQUENCE: 61

```
ctcgcccaaa gaagactaca atctccaggg aaacctgggg cgtctcgcgc aaacgtccat     60

aactgaaagt agctaaggca ccccagccgg aggaagtgag ctctcctggg gcgtggttgt    120

tcgtgatcct tgcatctgtt acttagggtc aaggcttggg tcttgccccg cagacccttg    180

ggacgacccg gccccagcgc agctatgaac ctggagcgag tgtccaatga ggagaaattg    240

aacctgtgcc ggaagtacta cctggggggg tttgctttcc tgccttttct ctggttggtc    300

aacatcttct ggttcttccg agaggccttc cttgtcccag cctacacaga acagagccaa    360

atcaaaggct atgtctggcg ctcagctgtg ggcttcctct tctgggtgat agtgctcacc    420
```

```
tcctggatca ccatcttcca gatctaccgg ccccgctggg gtgcccttgg ggactacctc    480

tccttcacca taccccctggg caccccctga caacttctgc acatactggg gccctgctta    540

ttctcccagg acaggctcct taaagcagag gagcctgtcc tgggagcccc ttctcaaact    600

cctaagactt gttttcatgt cccacgttct ctgctgacat cccccaataa aggaccctaa    660

ctttcaaaaa aaaaaaaa                                                    678
```

<210> SEQ ID NO 62
<211> LENGTH: 101
<212> TYPE: PRT
<213> ORGANISM: Homo sapiens

<400> SEQUENCE: 62

```
Met Asn Leu Glu Arg Val Ser Asn Glu Glu Lys Leu Asn Leu Cys Arg
1               5                   10                  15

Lys Tyr Tyr Leu Gly Gly Phe Ala Phe Leu Pro Phe Leu Trp Leu Val
            20                  25                  30

Asn Ile Phe Trp Phe Phe Arg Glu Ala Phe Leu Val Pro Ala Tyr Thr
        35                  40                  45

Glu Gln Ser Gln Ile Lys Gly Tyr Val Trp Arg Ser Ala Val Gly Phe
    50                  55                  60

Leu Phe Trp Val Ile Val Leu Thr Ser Trp Ile Thr Ile Phe Gln Ile
65                  70                  75                  80

Tyr Arg Pro Arg Trp Gly Ala Leu Gly Asp Tyr Leu Ser Phe Thr Ile
                85                  90                  95

Pro Leu Gly Thr Pro
            100
```

<210> SEQ ID NO 63
<211> LENGTH: 5556
<212> TYPE: DNA
<213> ORGANISM: Homo sapiens

<400> SEQUENCE: 63

```
tttctcgctc gctcccgttc cccggacgcg gcggatgagc cggcccccgct ggggaaggct     60

ccgggcggcg gcgggcggcc gggaggaggc tgcgtgctcg gggctggggc tgcgagcggg    120

gtgattttgt attaaaatga ggaggaggaa gaagaggcac ccacagcggc agcggcggcg    180

gcggcggcag cagcagcagg agcagcggcg gagagggctg cagcccgggc ggacgcgcgg    240

agccgagcgg ggcacggcgg cggcagcgac agcggccggg atgagtcaac taataattta    300

atgggggcag agacggcagc gaggggtaga gctagcgagg gagagagcga gagaagcagc    360

cccgtccggg gactcgcgct cacactcacg cacacacaca aacacacaca cacctctccc    420

tgtgccaccc agcaacaccc ggcctcgtca caacaacaac agccgcggcc gccctctatc    480

ctgcccgggg gcccagccga aagccagggc gactctagag gacgctgccc gcccccctct    540

ttcatttcgg gaaactcctg atcagttttg tcggggtttc tgggtttctt ttcccccaaa    600

gtcctagtgc cattgtggtg ctcgttgttt acctcggact ctggacgagt gagagcttgg    660

cgactttttg gggggagggg gcggggagtt tgtcgctgcc taggcggtgg aggtggctgg    720

gggtgccttc tgatcttcct cctcctcccc ctccccccga acctcttctc tcctcacttg    780

ctgggacccc agacgctcac agccccgcgt caatgggcag ggagagggtc cttgcggctg    840

ttgtcagcga gggcagaatc aaaagtggca ttttagtgcc tttccggggc ttttctcgcg    900

acccccctgcc ccccaccctc gctgtccccc gctagatgcc ctcgttgggg gtgcgaggct    960
```

```
gtggggaaaa gtttaaggtt tgttaatatt agtcgcgatt gttggcgagg ggggtggggg   1020
tgattggaag ggaggcgagg tggccttccc aatgcgcgtt attcggggtt attgaagaat   1080
aatattgcaa gtgacagcca gaagtagact ttctgtcctc acaccgaaga acccgagtga   1140
gcaggaggga gggagagacg cgaagagacc ttttttcctt tttggagacc ttgtccgcag   1200
tgattttttt ttttttaaga gaatcctcag tcaccacgtc gtttccccag caccatcaca   1260
gtgtacagct cataacgggt tttgctttgt ttttacgatt tccccccaac gaatcacttg   1320
tcagatcaat tttatcttct tcctcctccc tgcttcccac tctcccctcc tccccatcgc   1380
aaaccctgtt ctctgaggtt agacatttta caaaccccta tatgttggtt ttcgaattgt   1440
gatttttttt ttaaacccct ttctcatggc tactcttcta gacgtttatt tctgcccttc   1500
ccccgcttag gggggcgggg gtaggggaaa ggaaaataat acaatttcag gggaagtcgc   1560
cttcaggtct gctgcttttt tatttttttt tttttaatta aaaaaaaaaa ggacatagaa   1620
aacatcagtc ttgaacttct cttcaagaac ccgggctgca aaggaaatct cctttgtttt   1680
tgttatttat gtgctgtcaa gttttgaagt ggtgatcttt agacagtgac tgagtatgga   1740
tcatttgaac gaggcaactc aggggaaaga acattcagaa atgtctaaca atgtgagtga   1800
tccgaagggt ccaccagcca agattgcccg cctggagcag aacgggagcc cgctaggaag   1860
aggaaggctt gggagtacag gtgcaaaaat gcagggagtg cctttaaaac actcgggcca   1920
tctgatgaaa accaacctta ggaaaggaac catgctgcca gttttctgtg tggtggaaca   1980
ttatgaaaac gccattgaat atgattgcaa ggaggagcat gcagaatttg tgctggtgag   2040
aaaggatatg cttttcaacc agctgatcga aatggcattg ctgtctctag gttattcaca   2100
tagctctgct gcccaggcca aagggctaat ccaggttgga aagtggaatc cagttccact   2160
gtcttacgtg acagatgccc ctgatgctac agtagcagat atgcttcaag atgtgtatca   2220
tgtggtcaca ttgaaaattc agttacacag ttgccccaaa ctagaagact tgcctcccga   2280
acaatggtcg cacaccacag tgaggaatgc tctgaaggac ttactgaaag atatgaatca   2340
gagttcattg gccaaggagt gccccctttc acagagtatg atttcttcca ttgtgaacag   2400
tacttactat gcaaatgtct cagcagcaaa atgtcaagaa tttggaaggt ggtacaaaca   2460
tttcaagaag acaaaaagata tgatggttga aatggatagt ctttctgagc tatcccagca   2520
aggcgccaat catgtcaatt ttggccagca accagttcca gggaacacag ccgagcagcc   2580
tccatcccct gcgcagctct cccatggcag ccagccctct gtccggacac ctcttccaaa   2640
cctgcaccct gggctcgtat caacacctat cagtcctcaa ttggtcaacc agcagctggt   2700
gatggctcag ctgctgaacc agcagtatgc agtgaataga cttttagccc agcagtcctt   2760
aaaccaacaa tacttgaacc accctccccc tgtcagtaga tctatgaata agcctttgga   2820
gcaacaggtt tcgaccaaca cagaggtgtc ttccgaaatc taccagtggg tacgcgatga   2880
actgaaacga gcaggaatct cccaggcggt atttgcacgt gtggctttta acagaactca   2940
gggcttgctt tcagaaatcc tccgaaagga agaggacccc aagactgcat cccagtcttt   3000
gctggtaaac cttcgggcta tgcagaattt cttgcagtta ccggaagctg aaagagaccg   3060
aatataccag gacgaaaggg aaaggagctt gaatgctgcc tcggccatgg gtcctgcccc   3120
cctcatcagc acaccaccca gccgtcctcc ccaggtgaaa acagctacta ttgccactga   3180
aaggaatggg aaaccagaga acaataccat gaacattaat gcttccattt atgatgagat   3240
tcagcaggaa atgaagcgtg ctaaagtgtc tcaagcactg tttgcaaagg ttgcagcaac   3300
caaaagccag ggatggttgt gcgagctgtt acgctggaaa gaagatcctt ctccagaaaa   3360
```

```
cagaaccctg tgggagaacc tctccatgat ccgaaggttc ctcagtcttc ctcagccaga   3420

acgtgatgcc atttatgaac aggagagcaa cgcggtgcat caccatggcg acaggccgcc   3480

ccacattatc catgttccag cagagcagat tcagcaacag cagcagcaac agcaacagca   3540

gcagcagcag cagcaggcac cgccgcctcc acagccacag cagcagccac agacaggccc   3600

tcggctcccc ccacggcaac ccacggtggc ctctccagca gagtcagatg aggaaaaccg   3660

acagaagacc cggccacgaa caaaaatttc agtggaagcc ttgggaatcc tccagagttt   3720

catacaagac gtgggcctgt accctgacga agaggccatc cagactctgt ctgcccagct   3780

cgaccttccc aagtacacca tcatcaagtt ctttcagaac cagcggtact atctcaagca   3840

ccacggcaaa ctgaaggaca attccggttt agaggtcgat gtggcagaat ataaagaaga   3900

ggagctgctg aaggatttgg aagagagtgt ccaagataaa aatactaaca cccttttttc   3960

agtgaaacta gaagaagagc tgtcagtgga aggaaacaca gacattaata ctgatttgaa   4020

agactgagat aaaagtattt gtttcgttca acagtgccac tggtatttac taacaaaatg   4080

aaaagtccac cttgtcttct ctcagaaaac ctttgttgtt cattgtttgg ccaatgaatc   4140

ttcaaaaact tgcacaaaca gaaaagttgg aaaaggataa tacagactgc actaaatgtt   4200

ttcctctgtt ttacaaactg cttggcagcc ccaggtgaag catcaaggat tgtttggtat   4260

taaaatttgt gttcacggga tgcaccaaag tgtgtacccc gtaagcatga aaccagtgtt   4320

ttttgttttt tttttagttc ttattccgga gcctcaaaca agcattatac cttctgtgat   4380

tatgatttcc tctcctataa ttatttctgt agcactccac actgatcttt ggaaacttgc   4440

cccttattta aaaaaaaaaa agaaaaaaaa gagtttgtta ctctattgta tgttacaaaa   4500

gaactataga ctgtggaatg cagtttaaag atgacatatg ccaacaaatg ccttgtatta   4560

tatggcactg ccgtaattca aatttgtttt tattttggaa ataaaagttc actgtacttt   4620

tttttcattc tcattgttac atgatttttt aaaaaaagga aaagaaaatg tgaaacacaa   4680

tttagtcctc attatttatt tgtagatcct gcagcatcat gttgtaatta atttttttgga   4740

agtttccgtt aaatgtaata ttgcttctct tgttaccata ctgattcttt tctatttata   4800

aatgtatttt gatgggcagt aaaacaaagt gtcttaaaag ttttaaatag agaaaatgtg   4860

ctttacacag ttgcctataa aaagtgctct atgttatcca agcaattcat actataagct   4920

tcactcttat tgttgtatgc aatttttact atcatgcaaa taagcttagg taaataaaac   4980

taatagatca ccttagaaaa ttatgcaatt aatgtgaaaa taattgatgt ttgcaatgtg   5040

tcttcctttg gtttacaatc aattttaaag ctacatctgt ataaaatttc tgtataaagg   5100

tgtatttctt ttttatgagt ttatggctat gaaaacagct attttgttac agctggctgt   5160

ttttataagt gtatcacaat tttctttatg cagaaatgtt ctgactagga gtggttattg   5220

actgtaacta cacaattaaa attgtttgta tcgtatgaca tggtagggtt tgtctgctta   5280

tgtgaagtaa ctaaaggagt caaaggatgg ccctctcatt taggtgcatg ttaataactt   5340

gttatttcac tgattttaaa aagagcaatt gacaagttac ttgaaacact gtaaatttaa   5400

atcacaaaca catgctcatt tttaaatagg tatgaaattt cacaatgaaa ataacctgtt   5460

tggttaacat tttgcttaat aagtagagat aggatggtca aaagactctc cgacaaaaac   5520

aaatccagtc tctagcagtt atgttgttag aatgga                             5556
```

<210> SEQ ID NO 64
<211> LENGTH: 763
<212> TYPE: PRT

<213> ORGANISM: Homo sapiens

<400> SEQUENCE: 64

```
Met Asp His Leu Asn Glu Ala Thr Gln Gly Lys Glu His Ser Glu Met
1               5                   10                  15

Ser Asn Asn Val Ser Asp Pro Lys Gly Pro Pro Ala Lys Ile Ala Arg
            20                  25                  30

Leu Glu Gln Asn Gly Ser Pro Leu Gly Arg Gly Arg Leu Gly Ser Thr
        35                  40                  45

Gly Ala Lys Met Gln Gly Val Pro Leu Lys His Ser Gly His Leu Met
    50                  55                  60

Lys Thr Asn Leu Arg Lys Gly Thr Met Leu Pro Val Phe Cys Val Val
65                  70                  75                  80

Glu His Tyr Glu Asn Ala Ile Glu Tyr Asp Cys Lys Glu Glu His Ala
                85                  90                  95

Glu Phe Val Leu Val Arg Lys Asp Met Leu Phe Asn Gln Leu Ile Glu
            100                 105                 110

Met Ala Leu Leu Ser Leu Gly Tyr Ser His Ser Ser Ala Ala Gln Ala
        115                 120                 125

Lys Gly Leu Ile Gln Val Gly Lys Trp Asn Pro Val Pro Leu Ser Tyr
    130                 135                 140

Val Thr Asp Ala Pro Asp Ala Thr Val Ala Asp Met Leu Gln Asp Val
145                 150                 155                 160

Tyr His Val Val Thr Leu Lys Ile Gln Leu His Ser Cys Pro Lys Leu
                165                 170                 175

Glu Asp Leu Pro Pro Glu Gln Trp Ser His Thr Thr Val Arg Asn Ala
            180                 185                 190

Leu Lys Asp Leu Leu Lys Asp Met Asn Gln Ser Ser Leu Ala Lys Glu
        195                 200                 205

Cys Pro Leu Ser Gln Ser Met Ile Ser Ser Ile Val Asn Ser Thr Tyr
    210                 215                 220

Tyr Ala Asn Val Ser Ala Ala Lys Cys Gln Glu Phe Gly Arg Trp Tyr
225                 230                 235                 240

Lys His Phe Lys Lys Thr Lys Asp Met Met Val Glu Met Asp Ser Leu
                245                 250                 255

Ser Glu Leu Ser Gln Gln Gly Ala Asn His Val Asn Phe Gly Gln Gln
            260                 265                 270

Pro Val Pro Gly Asn Thr Ala Glu Gln Pro Pro Ser Pro Ala Gln Leu
        275                 280                 285

Ser His Gly Ser Gln Pro Ser Val Arg Thr Pro Leu Pro Asn Leu His
    290                 295                 300

Pro Gly Leu Val Ser Thr Pro Ile Ser Pro Gln Leu Val Asn Gln Gln
305                 310                 315                 320

Leu Val Met Ala Gln Leu Leu Asn Gln Gln Tyr Ala Val Asn Arg Leu
                325                 330                 335

Leu Ala Gln Gln Ser Leu Asn Gln Gln Tyr Leu Asn His Pro Pro Pro
            340                 345                 350

Val Ser Arg Ser Met Asn Lys Pro Leu Glu Gln Gln Val Ser Thr Asn
        355                 360                 365

Thr Glu Val Ser Ser Glu Ile Tyr Gln Trp Val Arg Asp Glu Leu Lys
    370                 375                 380

Arg Ala Gly Ile Ser Gln Ala Val Phe Ala Arg Val Ala Phe Asn Arg
385                 390                 395                 400
```

```
Thr Gln Gly Leu Leu Ser Glu Ile Leu Arg Lys Glu Glu Asp Pro Lys
                405                 410                 415

Thr Ala Ser Gln Ser Leu Leu Val Asn Leu Arg Ala Met Gln Asn Phe
            420                 425                 430

Leu Gln Leu Pro Glu Ala Glu Arg Asp Arg Ile Tyr Gln Asp Glu Arg
        435                 440                 445

Glu Arg Ser Leu Asn Ala Ala Ser Ala Met Gly Pro Ala Pro Leu Ile
    450                 455                 460

Ser Thr Pro Pro Ser Arg Pro Pro Gln Val Lys Thr Ala Thr Ile Ala
465                 470                 475                 480

Thr Glu Arg Asn Gly Lys Pro Glu Asn Asn Thr Met Asn Ile Asn Ala
                485                 490                 495

Ser Ile Tyr Asp Glu Ile Gln Gln Glu Met Lys Arg Ala Lys Val Ser
            500                 505                 510

Gln Ala Leu Phe Ala Lys Val Ala Ala Thr Lys Ser Gln Gly Trp Leu
        515                 520                 525

Cys Glu Leu Leu Arg Trp Lys Glu Asp Pro Ser Pro Glu Asn Arg Thr
    530                 535                 540

Leu Trp Glu Asn Leu Ser Met Ile Arg Arg Phe Leu Ser Leu Pro Gln
545                 550                 555                 560

Pro Glu Arg Asp Ala Ile Tyr Glu Gln Glu Ser Asn Ala Val His His
                565                 570                 575

His Gly Asp Arg Pro Pro His Ile Ile His Val Pro Ala Glu Gln Ile
            580                 585                 590

Gln Gln Gln Gln Gln Gln Gln Gln Gln Gln Gln Gln Gln Gln Gln Ala
        595                 600                 605

Pro Pro Pro Pro Gln Pro Gln Gln Gln Pro Gln Thr Gly Pro Arg Leu
    610                 615                 620

Pro Pro Arg Gln Pro Thr Val Ala Ser Pro Ala Glu Ser Asp Glu Glu
625                 630                 635                 640

Asn Arg Gln Lys Thr Arg Pro Arg Thr Lys Ile Ser Val Glu Ala Leu
                645                 650                 655

Gly Ile Leu Gln Ser Phe Ile Gln Asp Val Gly Leu Tyr Pro Asp Glu
            660                 665                 670

Glu Ala Ile Gln Thr Leu Ser Ala Gln Leu Asp Leu Pro Lys Tyr Thr
        675                 680                 685

Ile Ile Lys Phe Phe Gln Asn Gln Arg Tyr Tyr Leu Lys His His Gly
    690                 695                 700

Lys Leu Lys Asp Asn Ser Gly Leu Glu Val Asp Val Ala Glu Tyr Lys
705                 710                 715                 720

Glu Glu Glu Leu Leu Lys Asp Leu Glu Glu Ser Val Gln Asp Lys Asn
                725                 730                 735

Thr Asn Thr Leu Phe Ser Val Lys Leu Glu Glu Glu Leu Ser Val Glu
            740                 745                 750

Gly Asn Thr Asp Ile Asn Thr Asp Leu Lys Asp
        755                 760
```

<210> SEQ ID NO 65
<211> LENGTH: 2315
<212> TYPE: DNA
<213> ORGANISM: Homo sapiens

<400> SEQUENCE: 65

```
ccggcgtccc aagtgagtgg aggggggatc ccgactccag tccggggcct tggccagcgg      60
```

```
agccgcgcta ttcggaagcg ggaatcccac tcagagcccg ggcctgtagg ggcggggcgt    120
cccgggcacc cgggattggg gcgtctcccg tcgtgcaccg gggcaccggc gactcacccg    180
gaaggagaag ccgtgatctg gctatatggt ggggcgcggg cggtgtcgct gtggggagct    240
ggtgctgttc tcagatgttt ccttccaatg ggcttttggt gtaggatgtc ggagaaccaa    300
gaacaggagg aggtgattac agtgcgtgtt caggaccccc gagtgcagaa tgagggctcc    360
tggaactctt atgtggatta taagatattc ctccatacca acagcaaagc ctttactgcc    420
aagacttcct gtgtgcggcg ccgctaccgt gagttcgtgt ggctgagaaa gcagctacag    480
agaaatgctg gtttggtgcc tgttcctgaa cttcctggga agtcaacctt cttcggcacc    540
tcagatgagt tcattgagaa gcgacgacaa ggtctgcagc acttccttga aaaggtcctg    600
cagagtgtgg ttctcctgtc agacagccag ttgcacctat tcctgcaaag ccagctctcg    660
gtgcctgaga tagaagcctg tgtccagggc cgaagtacca tgactgtgtc tgatgccatt    720
cttcgatatg ctatgtcaaa ctgtggctgg gcccaggaag agaggcagag ctcttctcac    780
ctggctaaag gagaccagcc taagagttgc tgctttcttc caagatcggg taggaggagc    840
tctccctcac cgcctcccag tgaagaaaag gaccatttag aagtgtgggc tccagttgtt    900
gactctgagg ttccttcctt ggaaagtccc actctcccac ccctctcctc accattatgc    960
tgtgattttg gaagacccaa agagggaacc tccactcttc agtctgtgag gagggctgtg   1020
ggaggagatc atgctgtgcc tttggaccct ggtcagttag aaacagtttt ggaaaagtga   1080
gctctgggtt ctgctctgag atggtcagag aagatgcggg ccaggagact tactcaggtg   1140
ggactgggca cagggcaggt atgtgggagg ctgggctgct tagtgtcttc tagtcacctc   1200
tgcttgggct gattgacaga ggtcagtcat tacagcccct tatgcctctt ccatgggaac   1260
aaatactgtg cagatgtttg taagttaaac ataagacaca ggggctgttg cttttgaaca   1320
gaaccctata ttactctcct gggatctgag tttctgcagg tcatttgtat gtaggaccag   1380
gagtatctcc tcaggtgacc agttttgggg acccgtatgt ggcaaattct aagctgccat   1440
attgaacatc atcccactgg gagtggttat gttgtatccc catcttggct ggcttcagtt   1500
tttgctgtag ccctagagca ctttgtttgt gggaggctgg cctcttgcct acctccttgc   1560
atggacaggg ggatgaatat ttactttccc acctccttgc tttttctttc actgatacca   1620
ctgaatggaa ctggtgctgt gactcctgct gctggggatt tatgtcccga gaccttagcc   1680
tggctgagtg gagcctgaga cctgcacaac agctcatggt catgcatgag agagaagtgg   1740
ctggccacag ccagagggaa cagtaacagc ccaggggcct ttattttggg aaaggctgtc   1800
ccgggctgtt actgtctctt ctggttataa agcagacatg tggccatctt ttccgcaggg   1860
ttagagtggg ctcctttctt tttggaatcc ttttcttctc ctttggtagc agctccctgc   1920
ctccagggct tccgccacca gcgtctctgc tgtgttgcgc agtgcagtgg ggtgcaaggg   1980
ctttgtttct gcctgcctga aagagagggc tctggggatg gagatgagaa acaacacgct   2040
ctccttcaga caatgaggca ttctgtcctc ctgctgccat tcttcatctc cactgagagc   2100
cagagctggt aggagccgag tgccacaggc attctgcatt gctctactct taggtttgtg   2160
tgtgtgatcc ttcccctccc tgtcgcccac tcctccctcc tctggctatc ctaccctgtc   2220
tgtgggctct tttactacca gcctatgctg tgggactgtc atggcattta gttcagagtg   2280
gaggggcttt ggcctgaaat aaaatgcaag tattt                              2315
```

<210> SEQ ID NO 66
<211> LENGTH: 270

<212> TYPE: PRT
<213> ORGANISM: Homo sapiens

<400> SEQUENCE: 66

```
Met Gly Phe Trp Cys Arg Met Ser Glu Asn Gln Glu Gln Glu Glu Val
1               5                   10                  15

Ile Thr Val Arg Val Gln Asp Pro Arg Val Gln Asn Glu Gly Ser Trp
            20                  25                  30

Asn Ser Tyr Val Asp Tyr Lys Ile Phe Leu His Thr Asn Ser Lys Ala
        35                  40                  45

Phe Thr Ala Lys Thr Ser Cys Val Arg Arg Arg Tyr Arg Glu Phe Val
    50                  55                  60

Trp Leu Arg Lys Gln Leu Gln Arg Asn Ala Gly Leu Val Pro Val Pro
65                  70                  75                  80

Glu Leu Pro Gly Lys Ser Thr Phe Phe Gly Thr Ser Asp Glu Phe Ile
                85                  90                  95

Glu Lys Arg Arg Gln Gly Leu Gln His Phe Leu Glu Lys Val Leu Gln
            100                 105                 110

Ser Val Val Leu Leu Ser Asp Ser Gln Leu His Leu Phe Leu Gln Ser
        115                 120                 125

Gln Leu Ser Val Pro Glu Ile Glu Ala Cys Val Gln Gly Arg Ser Thr
    130                 135                 140

Met Thr Val Ser Asp Ala Ile Leu Arg Tyr Ala Met Ser Asn Cys Gly
145                 150                 155                 160

Trp Ala Gln Glu Glu Arg Gln Ser Ser Ser His Leu Ala Lys Gly Asp
                165                 170                 175

Gln Pro Lys Ser Cys Cys Phe Leu Pro Arg Ser Gly Arg Arg Ser Ser
            180                 185                 190

Pro Ser Pro Pro Pro Ser Glu Glu Lys Asp His Leu Glu Val Trp Ala
        195                 200                 205

Pro Val Val Asp Ser Glu Val Pro Ser Leu Glu Ser Pro Thr Leu Pro
    210                 215                 220

Pro Leu Ser Ser Pro Leu Cys Cys Asp Phe Gly Arg Pro Lys Glu Gly
225                 230                 235                 240

Thr Ser Thr Leu Gln Ser Val Arg Arg Ala Val Gly Gly Asp His Ala
                245                 250                 255

Val Pro Leu Asp Pro Gly Gln Leu Glu Thr Val Leu Glu Lys
            260                 265                 270
```

<210> SEQ ID NO 67
<211> LENGTH: 8017
<212> TYPE: DNA
<213> ORGANISM: Homo sapiens

<400> SEQUENCE: 67

```
tatgtcttct aaagataatg tcgattgtgt atggctgatg ggattctagg accaagcaag      60

aggtttttt ttttccccca catacttaac gtttctatat ttctatttga attcgactgg     120

acagttccat ttgaattatt tctctctctc tctctctctg acacatttta tcttgccagg     180

ttctaaacct ttaggaaaaa tggagcaatt tccaaaggaa accgttgtgg agagcagtgg     240

gccaaaggtt ttggaaacag cagaagagat ccaggagagg cgtcaggaag tgttgactcg     300

gtatcaaagt ttcaaggagc gggtcgctga gaggggtcag aagcttgagg attcctatca     360

cttacaagtt ttcaagcgag atgcagatga tctggggaag tggatcatgg agaaagtcaa     420

tatcttaacc gataagagct atgaagaccc aactaatata caggggaaat atcagaagca     480
```

```
tcaatccctt gaagcagagg tgcaaacaaa atcaagactc atgtctgaac tggaaaaaac    540
aagggaagaa cgatttacca tgggtcattc tgcccacgaa gaaacgaagg cccatataga    600
ggagctacgc cacctgtggg acctgctgtt agagctgacc ctggagaagg gtgaccagtt    660
gctgcgggcc ctgaagttcc agcagtatgt acaggagtgt gctgacatct tagagtggat    720
tggagacaag gaggctatag cgacatcagt ggagctaggt gaagactggg agcgcaccga    780
agttctgcat aagaaatttg aagacttcca agtggagctg gtagctaaag aagggagagt    840
tgttgaagtg aaccaatatg ccaatgagtg tgccgaggaa aaccatcctg acctaccctt    900
aattcagtct aagcaaaatg aggtgaatgc tgcctgggag cgccttcgtg gtttggctct    960
ccagagacag aaagctctgt ccaatgctgc aaacttacaa cgattcaaaa gggatgtgac   1020
tgaagccatc cagtggatca aggagaagga acctgtactc acctctgagg actatggcaa   1080
agaccttgtt gcctctgaag gactgtttca cagtcacaag ggacttgaga gaaatcttgc   1140
tgtcatgagt gacaaggtga aggagttatg tgctaaagca gagaagctga cactttccca   1200
tccttcagat gcacctcaga tccaggagat gaaagaagat ctggtctcca gctgggagca   1260
tattcgtgcc ctggccacca gcagatatga aaaactgcag gctacttatt ggtaccatcg   1320
attttcatct gactttgatg aactctcagg ctggatgaac gagaagactg ctgcgatcaa   1380
tgctgatgag ctgccaacag atgtggctgg tggagaagtt ctgctggaca ggcatcagca   1440
gcataagcat gagattgact cttacgatga ccgatttcaa tctgctgatg agactggtca   1500
agacctcgtg aatgccaatc atgaagcctc tgatgaagtt cgggaaaaga tggaaatact   1560
tgacaacaac tggactgccc tgctggaact gtgggacgag cgtcatcgtc agtatgagca   1620
gtgcttggac tttcatctct tctacagaga cagtgagcaa gtggacagtt ggatgagtag   1680
acaagaggcc ttcctggaaa acgaggatct gggaaactca ctgggcagtg cagaagccct   1740
tcttcagaag catgaagact ttgaggaagc ctttactgcc caggaagaga agatcataac   1800
tgtagacaag actgcaacca aattgattgg tgatgaccat tatgattcag agaacatcaa   1860
ggctatccgt gacgggctgt tagcccggcg ggatgcccta cgtgaaaagg ctgccactag   1920
acgtagattg ctgaaggagt cattgcttct gcaaaaactg tatgaggact cagatgacct   1980
aaagaactgg atcaacaaga agaaaaagtt ggcagatgat gaagattaca aggacataca   2040
gaacttgaag agcagggttc aaaagcagca agtctttgaa aaggagttgg cagttaataa   2100
gacccagctg gaaaacatac agaaaactgg ccaagagatg attgagggtg gtcactatgc   2160
ctctgacaat gtgaccactc gtctgagtga agttgccagc ctctgggagg agttgctgga   2220
ggctacaaaa cagaaaggga cccagttgca tgaggccaac cagcagctgc aatttgaaaa   2280
taatgcagaa gatttgcagc gctggctgga ggatgttgag tggcaagtca cctctgagga   2340
ttatgggaaa ggcctggccg aggtacagaa tcgactcagg aaacacggcc tcctggagtc   2400
ggctgtggct gctcgtcagg atcaggtgga tatccttaca gacctggctg catattttga   2460
agaaataggc catcctgatt ctaaggatat aagggcaagg caagagtcct tggtatgccg   2520
atttgaagct ctgaaagagc cactggccac ccgaaagaag aagctcttag accttctcca   2580
tctgcagctg atttgtagag acacagagga tgaggaggcc tggatccaag agactgaacc   2640
ctcagctact tccacctacc ttggaaagga cctgattgct tccaaaaagc ttctgaatag   2700
gcatagagtc atcctggaga acattgccag ccatgaacca cgcattcaag agataacaga   2760
aaggggaaac aaaatggtag aggaaggaca ctttgctgca gaagatgtgg cctctagggt   2820
```

```
caagagtttg aaccagaata tggagtctct ccgtgctcga gctgctaggc gacaaaatga   2880
tcttgaagcc aatgtccagt tccagcagta cctggctgac ctgcatgaag cagaaacatg   2940
gatcagagag aaggaaccta ttgtagataa tactaactat ggtgctgatg aagaagcagc   3000
tggggctctt ctaaagaagc atgaggcctt tctattagat ctcaattcat ttggagacag   3060
tatgaaagct ctgcggaatc aggcaaacgc ctgccagcaa caacaggctg caccagtgga   3120
gggagttgct ggagaacaaa gggtcatggc tttatatgac ttccaggccc gcagcccccg   3180
agaagtcacc atgaagaaag gtgatgtctt aacgctgctc agttccatca ataaggactg   3240
gtggaaggtg gaagctgctg atcatcaggg cattgtccca gctgtctatg tcagaagact   3300
ggcccacgat gagttcccga tgctcccaca gcggcgacga gaagagccag gaaacatcac   3360
ccagcgccag gagcagattg agaaccaata ccgctccctc ttggatcggg cagaagaacg   3420
cagacgtcgt ctattgcaac gttataatga atttttattg gcctatgagg caggagacat   3480
gctggaatgg attcaagaga aaaaggcaga aaacactgga gtggaactag atgatgtttg   3540
ggagctgcag aaaaagtttg atgagttcca aaaggatttg aataccaatg agcctcggct   3600
aagggatatc aacaaggtag ctgatgatct actatttgaa ggacttctaa caccagaagg   3660
agctcaaatc cggcaggaat tgaattcccg ctggggttct ttgcagaggc ttgcagatga   3720
acagcggcag ctgctgggca gtgcccatgc tgttgaagtg tttcacagag aagcagatga   3780
cacgaaggag cagattgaga agaaatgcca ggccctcagt gctgcagacc ctggctcaga   3840
tctgttcagt gttcaggctc ttcagcgacg gcatgagggc tttgaaaggg acctcgtacc   3900
cctgggagat aaggtgacca tactggggga gacagcagag cggctcagtg agtcccatcc   3960
agatgccact gaggacctgc agagacagaa aatggagctg aatgaggcct gggaagacct   4020
gcaggggcgt acaaaggatc gtaaggagag cctaaatgag gcccagaaat tctacctgtt   4080
cctcagcaag gccagggatc tgcagaactg gatcagtagc attggtggca tggtatcatc   4140
acaggagctg gccgaagact taactggcat agagatcttg ctggagagac atcaggagca   4200
ccgtgctgac atggaggcag aggctcccac cttccaggcc ttagaggact tcagtgcaga   4260
acttatcgac agtgggcacc atgctagccc tgaaattgaa aaaaagcttc aagctgtcaa   4320
gctagagaga gatgatttgg agaaggcttg ggaaaaacgc aagaagatcc tagaccagtg   4380
cctggagttg cagatgttcc aggggaactg tgatcaagtt gagagctgga tggtggcacg   4440
tgagaattcc ctgaggtcag atgacaaaag ttccttagac agtctggagg ctttgatgaa   4500
gaaacgggac gatttggaca aagcaatcac tgcccaggaa gggaagatca ctgacctaga   4560
acattttgct gagagcctca ttgctgatga acactatgcc aaagaagaga ttgctacgcg   4620
gctccaacgt gtactagaca ggtggaaggc tctcaaagca caactgattg atgagcggac   4680
aaagcttgga gactatgcca acctaaaaca attctaccga gaccttgagg agctggaaga   4740
atggatcagt gagatgctgc ccacagcctg tgatgaatcc tacaaagacg ccactaacat   4800
tcagaggaaa tacctgaaac accagacctt tgcacatgaa gtcgatggcc gatctgagca   4860
ggtgcatggc gtcatcaacc tggggaactc cctgattgag tgtagcgctt gtgatggcaa   4920
tgaagaggcc atgaaggagc aactggaaca gctgaaggaa cattgggatc atctgcttga   4980
gagaacaaat gacaaaggga agaagctcaa tgaggccagt cgtcaacaga ggttcaacac   5040
aagcatccgg gactttgagt tctggctctc agaggcagag acattgctgg ccatgaaaga   5100
tcaggccagg gacttggctt cagcaggaaa cctactcaag aagcatcagc tattggagag   5160
agagatgttg gctcgagagg atgcactcaa ggacctgaat acattggctg aagatttgct   5220
```

```
ctccagcggg actttcaacg ttgatcagat tgtgaagaaa aaagataatg tcaacaagcg   5280
tttcctgaat gtccaagaat tggcagctgc acaccacgaa aaattgaaag aggcctatgc   5340
cttgttccag ttcttccagg atctagatga tgaggaatcc tggatagagg agaagttgat   5400
acgagtgagc tcccaggact atgggagaga tcttcagggg gttcagaact tgctgaagaa   5460
gcacaaacgc ctagaggggg agctggtggc ccatgagcct gccatccaga atgtgctgga   5520
tatggcagag aagctgaaag acaaggctgc tgtggggcaa gaggagatcc agttgcggct   5580
ggctcagttt gttgaacact gggagaagct caaagagttg gccaaggccc gaggacttaa   5640
gttggaagaa tccctagaat acttgcaatt catgcagaat gctgaggaag aggaagcttg   5700
gatcaatgaa aagaatgctt tggctgtccg aggagattgt ggagatacat tagctgctac   5760
tcagagcttg ctaatgaagc atgaagcttt ggaaaatgac tttgctgtcc atgagacccg   5820
agtacaaaat gtgtgtgcac aaggagaaga catcctaaat aaggtgttgc aggaggaaag   5880
tcagaacaaa gagatttctt ccaagataga ggctctgaat gaaaagaccc cttctctggc   5940
taaggcaata gctgcttgga agttgcaatt ggaagacgat tatgcctttc aggaattcaa   6000
ctggaaggct gatgtggtag aggcttggat agctgataag gaaacaagcc taaagaccaa   6060
tggcaatggt gcagaccttg gtgacttcct cactcttctg gcaaaacagg acactctgga   6120
tgccagtctg cagagtttcc agcaagagag acttcccgag atcactgacc tgaaggacaa   6180
actgatttct gctcaacaca accagtctaa agccattgaa gagcgttatg ccgctctgct   6240
gaagcgctgg gaacagttgc tggaagcctc ggcagtccac agacagaaat tgctggagaa   6300
acagctgcct ctacagaagg ctgaggacct gttcgtggaa tttgcacata aggcttcagc   6360
tttgaacaac tggtgtgaaa agatggaaga aaacttgtca gagcctgtgc actgtgtctc   6420
cctgaatgaa attcggcagc tgcagaaaga ccatgaggac ttcttggcct ccctggctag   6480
ggctcaagca gactttaaat gtttgctgga gctagaccag cagattaagg ccttaggtgt   6540
gccttccagc ccttatacct ggttaacagt ggaggtgctg gaaaggacct ggaagcacct   6600
atctgacatc attgaggaac gggagcagga gctgcaaaag gaagaggcaa gacaggtcaa   6660
gaactttgag atgtgtcagg agtttgaaca gaatgccagt accttccttc aatggatcct   6720
ggaaaccagg gcttactttc tggatggatc attgctcaaa gaaacaggaa ctctggaatc   6780
tcagctggaa gcaaataaaa gaaaacagaa ggagatccag gcgatgaagc gtcaactaac   6840
caagattgtg gacctggggg acaacttgga agacgctctg atccttgata tcaaatacag   6900
caccattgga ttggctcagc agtgggacca gctctaccag cttgggttgc ggatgcaaca   6960
caacctggag caacagatcc aggccaagga catcaaaggt gtgagtgaag agactctaaa   7020
ggaatttagc acaatctata aacactttga tgagaatttg acagggcgcc tgactcacaa   7080
agagttccgg tcctgcctga gaggactcaa ttactacttg cccatggtgg aggaggatga   7140
acatgagccc aagtttgaga agttcctgga tgctgtggat ccagggagga agggctatgt   7200
ctcactggag gactatactg ctttcctgat tgacaaggag tcagaaaaca tcaagtccag   7260
tgatgaaata gagaatgcct tccaagccct ggcagagggc aagtcatata ttaccaaaga   7320
agacatgaag caggccctta ccccagagca agtgtcattc tgtgccacac atatgcagca   7380
atatatggac ccacggggtc gaagccatct ctctggctat gactacgttg gcttcaccaa   7440
ttcctacttt ggcaactaat aagcagctcc tcgtggatcg tagaaaatct tagtgtcgtg   7500
ggaaatttac tggggggcaa agagtacagg caaatgtgga agataaagat ggcctcgtgt   7560
```

```
gtgtgtgtgt gtgtgtgtgt gtgtgtgtgt gcttgtgttt gtgtgcatat tacatttatt   7620

gtaggatctt aaaaaatctc aagggtggga gatagaaagg ttaatagagt tggaggagtg   7680

gaagctattt tgtatgcaac tagtcactgc tgaggggtgt caaagtttct atttttattt   7740

gttctgtttt gcacgtcttt atcattttgc tttattccga ttatagaata aagtaattct   7800

ttttaaaaat attttttggg gcaaagttaa gtaaaatgtt gagcttctat atttctggga   7860

actgtactca tataagagtg ggcagctaat tttactgtaa agaagggcca tggtatagta   7920

gataaataaa atccaaggca attttcaaac aattttttta aactttggaa tgtgtttaaa   7980

tttaaatttg aaaataaaga tatttgattt tctgggg                            8017


<210> SEQ ID NO 68
<211> LENGTH: 2419
<212> TYPE: PRT
<213> ORGANISM: Homo sapiens

<400> SEQUENCE: 68

Met Glu Gln Phe Pro Lys Glu Thr Val Val Glu Ser Ser Gly Pro Lys
1               5                   10                  15

Val Leu Glu Thr Ala Glu Glu Ile Gln Glu Arg Arg Gln Glu Val Leu
            20                  25                  30

Thr Arg Tyr Gln Ser Phe Lys Glu Arg Val Ala Glu Arg Gly Gln Lys
        35                  40                  45

Leu Glu Asp Ser Tyr His Leu Gln Val Phe Lys Arg Asp Ala Asp Asp
    50                  55                  60

Leu Gly Lys Trp Ile Met Glu Lys Val Asn Ile Leu Thr Asp Lys Ser
65                  70                  75                  80

Tyr Glu Asp Pro Thr Asn Ile Gln Gly Lys Tyr Gln Lys His Gln Ser
                85                  90                  95

Leu Glu Ala Glu Val Gln Thr Lys Ser Arg Leu Met Ser Glu Leu Glu
            100                 105                 110

Lys Thr Arg Glu Glu Arg Phe Thr Met Gly His Ser Ala His Glu Glu
        115                 120                 125

Thr Lys Ala His Ile Glu Glu Leu Arg His Leu Trp Asp Leu Leu Leu
    130                 135                 140

Glu Leu Thr Leu Glu Lys Gly Asp Gln Leu Leu Arg Ala Leu Lys Phe
145                 150                 155                 160

Gln Gln Tyr Val Gln Glu Cys Ala Asp Ile Leu Glu Trp Ile Gly Asp
                165                 170                 175

Lys Glu Ala Ile Ala Thr Ser Val Glu Leu Gly Glu Asp Trp Glu Arg
            180                 185                 190

Thr Glu Val Leu His Lys Lys Phe Glu Asp Phe Gln Val Glu Leu Val
        195                 200                 205

Ala Lys Glu Gly Arg Val Val Glu Val Asn Gln Tyr Ala Asn Glu Cys
    210                 215                 220

Ala Glu Glu Asn His Pro Asp Leu Pro Leu Ile Gln Ser Lys Gln Asn
225                 230                 235                 240

Glu Val Asn Ala Ala Trp Glu Arg Leu Arg Gly Leu Ala Leu Gln Arg
                245                 250                 255

Gln Lys Ala Leu Ser Asn Ala Ala Asn Leu Gln Arg Phe Lys Arg Asp
            260                 265                 270

Val Thr Glu Ala Ile Gln Trp Ile Lys Glu Lys Glu Pro Val Leu Thr
        275                 280                 285

Ser Glu Asp Tyr Gly Lys Asp Leu Val Ala Ser Glu Gly Leu Phe His
```

```
    290                 295                 300

Ser His Lys Gly Leu Glu Arg Asn Leu Ala Val Met Ser Asp Lys Val
305                 310                 315                 320

Lys Glu Leu Cys Ala Lys Ala Glu Lys Leu Thr Leu Ser His Pro Ser
                325                 330                 335

Asp Ala Pro Gln Ile Gln Glu Met Lys Glu Asp Leu Val Ser Ser Trp
            340                 345                 350

Glu His Ile Arg Ala Leu Ala Thr Ser Arg Tyr Glu Lys Leu Gln Ala
        355                 360                 365

Thr Tyr Trp Tyr His Arg Phe Ser Ser Asp Phe Asp Glu Leu Ser Gly
    370                 375                 380

Trp Met Asn Glu Lys Thr Ala Ala Ile Asn Ala Asp Glu Leu Pro Thr
385                 390                 395                 400

Asp Val Ala Gly Gly Glu Val Leu Leu Asp Arg His Gln Gln His Lys
                405                 410                 415

His Glu Ile Asp Ser Tyr Asp Asp Arg Phe Gln Ser Ala Asp Glu Thr
            420                 425                 430

Gly Gln Asp Leu Val Asn Ala Asn His Glu Ala Ser Asp Glu Val Arg
        435                 440                 445

Glu Lys Met Glu Ile Leu Asp Asn Asn Trp Thr Ala Leu Leu Glu Leu
    450                 455                 460

Trp Asp Glu Arg His Arg Gln Tyr Glu Gln Cys Leu Asp Phe His Leu
465                 470                 475                 480

Phe Tyr Arg Asp Ser Glu Gln Val Asp Ser Trp Met Ser Arg Gln Glu
                485                 490                 495

Ala Phe Leu Glu Asn Glu Asp Leu Gly Asn Ser Leu Gly Ser Ala Glu
            500                 505                 510

Ala Leu Leu Gln Lys His Glu Asp Phe Glu Glu Ala Phe Thr Ala Gln
        515                 520                 525

Glu Glu Lys Ile Ile Thr Val Asp Lys Thr Ala Thr Lys Leu Ile Gly
    530                 535                 540

Asp Asp His Tyr Asp Ser Glu Asn Ile Lys Ala Ile Arg Asp Gly Leu
545                 550                 555                 560

Leu Ala Arg Arg Asp Ala Leu Arg Glu Lys Ala Ala Thr Arg Arg Arg
                565                 570                 575

Leu Leu Lys Glu Ser Leu Leu Leu Gln Lys Leu Tyr Glu Asp Ser Asp
            580                 585                 590

Asp Leu Lys Asn Trp Ile Asn Lys Lys Lys Lys Leu Ala Asp Asp Glu
        595                 600                 605

Asp Tyr Lys Asp Ile Gln Asn Leu Lys Ser Arg Val Gln Lys Gln Gln
    610                 615                 620

Val Phe Glu Lys Glu Leu Ala Val Asn Lys Thr Gln Leu Glu Asn Ile
625                 630                 635                 640

Gln Lys Thr Gly Gln Glu Met Ile Glu Gly Gly His Tyr Ala Ser Asp
                645                 650                 655

Asn Val Thr Thr Arg Leu Ser Glu Val Ala Ser Leu Trp Glu Glu Leu
            660                 665                 670

Leu Glu Ala Thr Lys Gln Lys Gly Thr Gln Leu His Glu Ala Asn Gln
        675                 680                 685

Gln Leu Gln Phe Glu Asn Asn Ala Glu Asp Leu Gln Arg Trp Leu Glu
    690                 695                 700

Asp Val Glu Trp Gln Val Thr Ser Glu Asp Tyr Gly Lys Gly Leu Ala
705                 710                 715                 720
```

```
Glu Val Gln Asn Arg Leu Arg Lys His Gly Leu Leu Glu Ser Ala Val
                725                 730                 735

Ala Ala Arg Gln Asp Gln Val Asp Ile Leu Thr Asp Leu Ala Ala Tyr
            740                 745                 750

Phe Glu Glu Ile Gly His Pro Asp Ser Lys Asp Ile Arg Ala Arg Gln
        755                 760                 765

Glu Ser Leu Val Cys Arg Phe Glu Ala Leu Lys Glu Pro Leu Ala Thr
    770                 775                 780

Arg Lys Lys Lys Leu Leu Asp Leu Leu His Leu Gln Leu Ile Cys Arg
785                 790                 795                 800

Asp Thr Glu Asp Glu Glu Ala Trp Ile Gln Glu Thr Glu Pro Ser Ala
                805                 810                 815

Thr Ser Thr Tyr Leu Gly Lys Asp Leu Ile Ala Ser Lys Lys Leu Leu
            820                 825                 830

Asn Arg His Arg Val Ile Leu Glu Asn Ile Ala Ser His Glu Pro Arg
        835                 840                 845

Ile Gln Glu Ile Thr Glu Arg Gly Asn Lys Met Val Glu Glu Gly His
    850                 855                 860

Phe Ala Ala Glu Asp Val Ala Ser Arg Val Lys Ser Leu Asn Gln Asn
865                 870                 875                 880

Met Glu Ser Leu Arg Ala Arg Ala Ala Arg Arg Gln Asn Asp Leu Glu
                885                 890                 895

Ala Asn Val Gln Phe Gln Gln Tyr Leu Ala Asp Leu His Glu Ala Glu
            900                 905                 910

Thr Trp Ile Arg Glu Lys Glu Pro Ile Val Asp Asn Thr Asn Tyr Gly
        915                 920                 925

Ala Asp Glu Glu Ala Ala Gly Ala Leu Leu Lys Lys His Glu Ala Phe
    930                 935                 940

Leu Leu Asp Leu Asn Ser Phe Gly Asp Ser Met Lys Ala Leu Arg Asn
945                 950                 955                 960

Gln Ala Asn Ala Cys Gln Gln Gln Gln Ala Ala Pro Val Glu Gly Val
                965                 970                 975

Ala Gly Glu Gln Arg Val Met Ala Leu Tyr Asp Phe Gln Ala Arg Ser
            980                 985                 990

Pro Arg Glu Val Thr Met Lys Lys  Gly Asp Val Leu Thr  Leu Leu Ser
        995                 1000                1005

Ser Ile  Asn Lys Asp Trp Trp  Lys Val Glu Ala Ala  Asp His Gln
    1010                1015                1020

Gly Ile  Val Pro Ala Val Tyr  Val Arg Arg Leu Ala  His Asp Glu
    1025                1030                1035

Phe Pro  Met Leu Pro Gln Arg  Arg Arg Glu Glu Pro  Gly Asn Ile
    1040                1045                1050

Thr Gln  Arg Gln Glu Gln Ile  Glu Asn Gln Tyr Arg  Ser Leu Leu
    1055                1060                1065

Asp Arg  Ala Glu Glu Arg Arg  Arg Arg Leu Leu Gln  Arg Tyr Asn
    1070                1075                1080

Glu Phe  Leu Leu Ala Tyr Glu  Ala Gly Asp Met Leu  Glu Trp Ile
    1085                1090                1095

Gln Glu  Lys Lys Ala Glu Asn  Thr Gly Val Glu Leu  Asp Asp Val
    1100                1105                1110

Trp Glu  Leu Gln Lys Lys Phe  Asp Glu Phe Gln Lys  Asp Leu Asn
    1115                1120                1125
```

```
Thr Asn  Glu Pro Arg Leu Arg  Asp Ile Asn Lys Val  Ala Asp Asp
    1130                 1135                 1140

Leu Leu  Phe Glu Gly Leu Leu  Thr Pro Glu Gly Ala  Gln Ile Arg
    1145                 1150                 1155

Gln Glu  Leu Asn Ser Arg Trp  Gly Ser Leu Gln Arg  Leu Ala Asp
    1160                 1165                 1170

Glu Gln  Arg Gln Leu Leu Gly  Ser Ala His Ala Val  Glu Val Phe
    1175                 1180                 1185

His Arg  Glu Ala Asp Asp Thr  Lys Glu Gln Ile Glu  Lys Lys Cys
    1190                 1195                 1200

Gln Ala  Leu Ser Ala Ala Asp  Pro Gly Ser Asp Leu  Phe Ser Val
    1205                 1210                 1215

Gln Ala  Leu Gln Arg Arg His  Glu Gly Phe Glu Arg  Asp Leu Val
    1220                 1225                 1230

Pro Leu  Gly Asp Lys Val Thr  Ile Leu Gly Glu Thr  Ala Glu Arg
    1235                 1240                 1245

Leu Ser  Glu Ser His Pro Asp  Ala Thr Glu Asp Leu  Gln Arg Gln
    1250                 1255                 1260

Lys Met  Glu Leu Asn Glu Ala  Trp Glu Asp Leu Gln  Gly Arg Thr
    1265                 1270                 1275

Lys Asp  Arg Lys Glu Ser Leu  Asn Glu Ala Gln Lys  Phe Tyr Leu
    1280                 1285                 1290

Phe Leu  Ser Lys Ala Arg Asp  Leu Gln Asn Trp Ile  Ser Ser Ile
    1295                 1300                 1305

Gly Gly  Met Val Ser Ser Gln  Glu Leu Ala Glu Asp  Leu Thr Gly
    1310                 1315                 1320

Ile Glu  Ile Leu Leu Glu Arg  His Gln Glu His Arg  Ala Asp Met
    1325                 1330                 1335

Glu Ala  Glu Ala Pro Thr Phe  Gln Ala Leu Glu Asp  Phe Ser Ala
    1340                 1345                 1350

Glu Leu  Ile Asp Ser Gly His  His Ala Ser Pro Glu  Ile Glu Lys
    1355                 1360                 1365

Lys Leu  Gln Ala Val Lys Leu  Glu Arg Asp Asp Leu  Glu Lys Ala
    1370                 1375                 1380

Trp Glu  Lys Arg Lys Lys Ile  Leu Asp Gln Cys Leu  Glu Leu Gln
    1385                 1390                 1395

Met Phe  Gln Gly Asn Cys Asp  Gln Val Glu Ser Trp  Met Val Ala
    1400                 1405                 1410

Arg Glu  Asn Ser Leu Arg Ser  Asp Asp Lys Ser Ser  Leu Asp Ser
    1415                 1420                 1425

Leu Glu  Ala Leu Met Lys Lys  Arg Asp Asp Leu Asp  Lys Ala Ile
    1430                 1435                 1440

Thr Ala  Gln Glu Gly Lys Ile  Thr Asp Leu Glu His  Phe Ala Glu
    1445                 1450                 1455

Ser Leu  Ile Ala Asp Glu His  Tyr Ala Lys Glu Glu  Ile Ala Thr
    1460                 1465                 1470

Arg Leu  Gln Arg Val Leu Asp  Arg Trp Lys Ala Leu  Lys Ala Gln
    1475                 1480                 1485

Leu Ile  Asp Glu Arg Thr Lys  Leu Gly Asp Tyr Ala  Asn Leu Lys
    1490                 1495                 1500

Gln Phe  Tyr Arg Asp Leu Glu  Glu Leu Glu Glu Trp  Ile Ser Glu
    1505                 1510                 1515

Met Leu  Pro Thr Ala Cys Asp  Glu Ser Tyr Lys Asp  Ala Thr Asn
```

```
    1520                1525                1530

Ile Gln  Arg Lys Tyr Leu Lys  His Gln Thr Phe Ala  His Glu Val
    1535                1540                1545

Asp Gly  Arg Ser Glu Gln Val  His Gly Val Ile Asn  Leu Gly Asn
    1550                1555                1560

Ser Leu  Ile Glu Cys Ser Ala  Cys Asp Gly Asn Glu  Glu Ala Met
    1565                1570                1575

Lys Glu  Gln Leu Glu Gln Leu  Lys Glu His Trp Asp  His Leu Leu
    1580                1585                1590

Glu Arg  Thr Asn Asp Lys Gly  Lys Lys Leu Asn Glu  Ala Ser Arg
    1595                1600                1605

Gln Gln  Arg Phe Asn Thr Ser  Ile Arg Asp Phe Glu  Phe Trp Leu
    1610                1615                1620

Ser Glu  Ala Glu Thr Leu Leu  Ala Met Lys Asp Gln  Ala Arg Asp
    1625                1630                1635

Leu Ala  Ser Ala Gly Asn Leu  Leu Lys Lys His Gln  Leu Leu Glu
    1640                1645                1650

Arg Glu  Met Leu Ala Arg Glu  Asp Ala Leu Lys Asp  Leu Asn Thr
    1655                1660                1665

Leu Ala  Glu Asp Leu Leu Ser  Ser Gly Thr Phe Asn  Val Asp Gln
    1670                1675                1680

Ile Val  Lys Lys Lys Asp Asn  Val Asn Lys Arg Phe  Leu Asn Val
    1685                1690                1695

Gln Glu  Leu Ala Ala Ala His  His Glu Lys Leu Lys  Glu Ala Tyr
    1700                1705                1710

Ala Leu  Phe Gln Phe Phe Gln  Asp Leu Asp Asp Glu  Glu Ser Trp
    1715                1720                1725

Ile Glu  Glu Lys Leu Ile Arg  Val Ser Ser Gln Asp  Tyr Gly Arg
    1730                1735                1740

Asp Leu  Gln Gly Val Gln Asn  Leu Leu Lys Lys His  Lys Arg Leu
    1745                1750                1755

Glu Gly  Glu Leu Val Ala His  Glu Pro Ala Ile Gln  Asn Val Leu
    1760                1765                1770

Asp Met  Ala Glu Lys Leu Lys  Asp Lys Ala Ala Val  Gly Gln Glu
    1775                1780                1785

Glu Ile  Gln Leu Arg Leu Ala  Gln Phe Val Glu His  Trp Glu Lys
    1790                1795                1800

Leu Lys  Glu Leu Ala Lys Ala  Arg Gly Leu Lys Leu  Glu Glu Ser
    1805                1810                1815

Leu Glu  Tyr Leu Gln Phe Met  Gln Asn Ala Glu Glu  Glu Glu Ala
    1820                1825                1830

Trp Ile  Asn Glu Lys Asn Ala  Leu Ala Val Arg Gly  Asp Cys Gly
    1835                1840                1845

Asp Thr  Leu Ala Ala Thr Gln  Ser Leu Leu Met Lys  His Glu Ala
    1850                1855                1860

Leu Glu  Asn Asp Phe Ala Val  His Glu Thr Arg Val  Gln Asn Val
    1865                1870                1875

Cys Ala  Gln Gly Glu Asp Ile  Leu Asn Lys Val Leu  Gln Glu Glu
    1880                1885                1890

Ser Gln  Asn Lys Glu Ile Ser  Ser Lys Ile Glu Ala  Leu Asn Glu
    1895                1900                1905

Lys Thr  Pro Ser Leu Ala Lys  Ala Ile Ala Ala Trp  Lys Leu Gln
    1910                1915                1920
```

```
Leu Glu  Asp Asp Tyr Ala Phe  Gln Glu Phe Asn Trp  Lys Ala Asp
    1925                 1930                 1935

Val Val  Glu Ala Trp Ile Ala  Asp Lys Glu Thr Ser  Leu Lys Thr
    1940                 1945                 1950

Asn Gly  Asn Gly Ala Asp Leu  Gly Asp Phe Leu Thr  Leu Leu Ala
    1955                 1960                 1965

Lys Gln  Asp Thr Leu Asp Ala  Ser Leu Gln Ser Phe  Gln Gln Glu
    1970                 1975                 1980

Arg Leu  Pro Glu Ile Thr Asp  Leu Lys Asp Lys Leu  Ile Ser Ala
    1985                 1990                 1995

Gln His  Asn Gln Ser Lys Ala  Ile Glu Glu Arg Tyr  Ala Ala Leu
    2000                 2005                 2010

Leu Lys  Arg Trp Glu Gln Leu  Leu Glu Ala Ser Ala  Val His Arg
    2015                 2020                 2025

Gln Lys  Leu Leu Glu Lys Gln  Leu Pro Leu Gln Lys  Ala Glu Asp
    2030                 2035                 2040

Leu Phe  Val Glu Phe Ala His  Lys Ala Ser Ala Leu  Asn Asn Trp
    2045                 2050                 2055

Cys Glu  Lys Met Glu Glu Asn  Leu Ser Glu Pro Val  His Cys Val
    2060                 2065                 2070

Ser Leu  Asn Glu Ile Arg Gln  Leu Gln Lys Asp His  Glu Asp Phe
    2075                 2080                 2085

Leu Ala  Ser Leu Ala Arg Ala  Gln Ala Asp Phe Lys  Cys Leu Leu
    2090                 2095                 2100

Glu Leu  Asp Gln Gln Ile Lys  Ala Leu Gly Val Pro  Ser Ser Pro
    2105                 2110                 2115

Tyr Thr  Trp Leu Thr Val Glu  Val Leu Glu Arg Thr  Trp Lys His
    2120                 2125                 2130

Leu Ser  Asp Ile Ile Glu Glu  Arg Glu Gln Glu Leu  Gln Lys Glu
    2135                 2140                 2145

Glu Ala  Arg Gln Val Lys Asn  Phe Glu Met Cys Gln  Glu Phe Glu
    2150                 2155                 2160

Gln Asn  Ala Ser Thr Phe Leu  Gln Trp Ile Leu Glu  Thr Arg Ala
    2165                 2170                 2175

Tyr Phe  Leu Asp Gly Ser Leu  Leu Lys Glu Thr Gly  Thr Leu Glu
    2180                 2185                 2190

Ser Gln  Leu Glu Ala Asn Lys  Arg Lys Gln Lys Glu  Ile Gln Ala
    2195                 2200                 2205

Met Lys  Arg Gln Leu Thr Lys  Ile Val Asp Leu Gly  Asp Asn Leu
    2210                 2215                 2220

Glu Asp  Ala Leu Ile Leu Asp  Ile Lys Tyr Ser Thr  Ile Gly Leu
    2225                 2230                 2235

Ala Gln  Gln Trp Asp Gln Leu  Tyr Gln Leu Gly Leu  Arg Met Gln
    2240                 2245                 2250

His Asn  Leu Glu Gln Gln Ile  Gln Ala Lys Asp Ile  Lys Gly Val
    2255                 2260                 2265

Ser Glu  Glu Thr Leu Lys Glu  Phe Ser Thr Ile Tyr  Lys His Phe
    2270                 2275                 2280

Asp Glu  Asn Leu Thr Gly Arg  Leu Thr His Lys Glu  Phe Arg Ser
    2285                 2290                 2295

Cys Leu  Arg Gly Leu Asn Tyr  Tyr Leu Pro Met Val  Glu Glu Asp
    2300                 2305                 2310
```

```
Glu His  Glu Pro Lys Phe Glu  Lys Phe Leu Asp Ala  Val Asp Pro
    2315                 2320                 2325

Gly Arg  Lys Gly Tyr Val Ser  Leu Glu Asp Tyr Thr  Ala Phe Leu
    2330                 2335                 2340

Ile Asp  Lys Glu Ser Glu Asn  Ile Lys Ser Ser Asp  Glu Ile Glu
    2345                 2350                 2355

Asn Ala  Phe Gln Ala Leu Ala  Glu Gly Lys Ser Tyr  Ile Thr Lys
    2360                 2365                 2370

Glu Asp  Met Lys Gln Ala Leu  Thr Pro Glu Gln Val  Ser Phe Cys
    2375                 2380                 2385

Ala Thr  His Met Gln Gln Tyr  Met Asp Pro Arg Gly  Arg Ser His
    2390                 2395                 2400

Leu Ser  Gly Tyr Asp Tyr Val  Gly Phe Thr Asn Ser  Tyr Phe Gly
    2405                 2410                 2415

Asn
```

<210> SEQ ID NO 69
<211> LENGTH: 2215
<212> TYPE: DNA
<213> ORGANISM: Homo sapiens

<400> SEQUENCE: 69

```
aggttttgag acacaggtaa agggagggag acagagagaa atacttgcag agccagcagg     60

tagctgggca gctccttccc ggacggacgg atggacagac gctggggacc ctccactcca    120

tatggaaaga tgacatgacc ttgtggtaga tcccagaact gaggccccag gatgacagaa    180

caggagaccc tggccctact ggaagtgaag aggtctgatt ccccagagaa gagctcaccc    240

caggccttgg ttcccaatgg ccggcagcca gaaggggaag gtggggccga atccccggga    300

gctgagtccc tcagagtggg gtcttcagct ggatctccca cagccataga gggggctgag    360

gatggtctag acagcacagt aagtgaggct gccaccttgc cctgggggac tggccctcag    420

cccagtgctc cgttcccgga tccccctggc tggcgggaca ttgaaccaga gccccctgag    480

tcagaaccac ttaccaagct agaggagctg cccgaagacg atgccaacct gctgcctgag    540

aaagcggccc gtgccttcgt gcctattgac ctacagtgca ttgagcggca gccccaagaa    600

gaccttatcg tgcgctgtga ggcaggcgag ggcgagtgcc gaaccttcat gcccccccgg    660

gtcacccacc ccgaccccac tgagcgcaag tgggctgagg cagtggtgag gccgcctggc    720

tgttcctgtg ggggctgcgg gagctgtgga gaccgtgagt ggctaagggc tgtggcctcc    780

gtgggagccg cactcattct cttcccttgc ctactatacg ggcatatgc cttcctgccg     840

tttgatgtcc cacggctgcc caccatgagt tcccgcctga tctacacact gcgctgcggg    900

gtctttgcca ccttccccat tgtgctgggg atcctggtgt acgggctgag cctgttatgc    960

ttttctgccc ttcggccctt tggggagcca cggcgggagg tggagatcca ccggcgatat   1020

gtggcccagt cggtccagct ctttattctc tacttcttca acctggccgt gctttccact   1080

tacctgcccc aggataccct caaactgctc cctctgctca ctggtctctt tgccgtctcc   1140

cggctgatct actggctgac ctttgccgtg ggccgctcct tccgaggctt cggctacggc   1200

ctgacgtttc tgccactgct gtcgatgctg atgtggaacc tctactacat gttcgtggtg   1260

gagccggagc gcatgctcac tgccaccgag agccgcctgg actacccgga ccacgcccgc   1320

tcggcctccg actacaggcc ccgcccctgg ggctgagcct ctccgccctc gccctcggag   1380

tagggggtag cggcttgggt ctgacacatc tttgaacctt gtggccaggc ctggacttcg   1440
```

```
cccccaggcc taggaccgcg gtgggtggaa ccctgctact gccccaacag ggactccaat   1500

caatcggagt tctccccttg ccggagctgc ccttcacctt tggggcccga gacagtcata   1560

agggatggac ttagttttct tgcagggaaa aaggtggaca gccgtgtttc ttaaggatgc   1620

tgagggcatg gggccaggac caggggagag gcacagctcc ttcctgagca gcctctcacc   1680

actgccacaa ggctccctaa tgctggtctc tgctccactc cccggcttcc cgtgaggcag   1740

gaggcagagc cacagccaag gccctgacca cttctgtgcc agttgtctaa gcagagcgcc   1800

tcagggacgc tggaaatgcc ttaaggatag aggctgggca tcacatcaaa tgggactgtg   1860

gtgtttggtg aaaaccttcc tgaggatctg gattcaggac cctccatgac tggcctattt   1920

actgtttaca gctggccagt gcagagctgc tgctctttta ccttttttagg ccccctgtaac   1980

ttcccacctt taaactgccc agaaggcatg cctctcccac aggaagaggg gagcagacag   2040

ggaaatctgc ctaccaagag gggtgtgtgt gtctttgtgc ccacacgtgg tggctgggga   2100

gtgcctggat ggtgcggtgg ttgatgttaa cctagtgtgt gtgtgtgtgt gtgtgtgtgt   2160

gtgtgtgtgt gtgtgtgtgt aacaataaat tactaccagt caaaaaaaaa aaaaa        2215
```

```
<210> SEQ ID NO 70
<211> LENGTH: 394
<212> TYPE: PRT
<213> ORGANISM: Homo sapiens

<400> SEQUENCE: 70

Met Thr Glu Gln Glu Thr Leu Ala Leu Leu Glu Val Lys Arg Ser Asp
1               5                   10                  15

Ser Pro Glu Lys Ser Ser Pro Gln Ala Leu Val Pro Asn Gly Arg Gln
            20                  25                  30

Pro Glu Gly Glu Gly Gly Ala Glu Ser Pro Gly Ala Glu Ser Leu Arg
        35                  40                  45

Val Gly Ser Ser Ala Gly Ser Pro Thr Ala Ile Glu Gly Ala Glu Asp
    50                  55                  60

Gly Leu Asp Ser Thr Val Ser Glu Ala Ala Thr Leu Pro Trp Gly Thr
65                  70                  75                  80

Gly Pro Gln Pro Ser Ala Pro Phe Pro Asp Pro Pro Gly Trp Arg Asp
                85                  90                  95

Ile Glu Pro Glu Pro Pro Glu Ser Glu Pro Leu Thr Lys Leu Glu Glu
            100                 105                 110

Leu Pro Glu Asp Asp Ala Asn Leu Leu Pro Glu Lys Ala Ala Arg Ala
        115                 120                 125

Phe Val Pro Ile Asp Leu Gln Cys Ile Glu Arg Gln Pro Gln Glu Asp
    130                 135                 140

Leu Ile Val Arg Cys Glu Ala Gly Glu Gly Glu Cys Arg Thr Phe Met
145                 150                 155                 160

Pro Pro Arg Val Thr His Pro Asp Pro Thr Glu Arg Lys Trp Ala Glu
                165                 170                 175

Ala Val Val Arg Pro Pro Gly Cys Ser Cys Gly Gly Cys Gly Ser Cys
            180                 185                 190

Gly Asp Arg Glu Trp Leu Arg Ala Val Ala Ser Val Gly Ala Ala Leu
        195                 200                 205

Ile Leu Phe Pro Cys Leu Leu Tyr Gly Ala Tyr Ala Phe Leu Pro Phe
    210                 215                 220

Asp Val Pro Arg Leu Pro Thr Met Ser Ser Arg Leu Ile Tyr Thr Leu
225                 230                 235                 240
```

```
Arg Cys Gly Val Phe Ala Thr Phe Pro Ile Val Leu Gly Ile Leu Val
                245                 250                 255

Tyr Gly Leu Ser Leu Leu Cys Phe Ser Ala Leu Arg Pro Phe Gly Glu
            260                 265                 270

Pro Arg Arg Glu Val Glu Ile His Arg Arg Tyr Val Ala Gln Ser Val
        275                 280                 285

Gln Leu Phe Ile Leu Tyr Phe Phe Asn Leu Ala Val Leu Ser Thr Tyr
    290                 295                 300

Leu Pro Gln Asp Thr Leu Lys Leu Leu Pro Leu Leu Thr Gly Leu Phe
305                 310                 315                 320

Ala Val Ser Arg Leu Ile Tyr Trp Leu Thr Phe Ala Val Gly Arg Ser
                325                 330                 335

Phe Arg Gly Phe Gly Tyr Gly Leu Thr Phe Leu Pro Leu Leu Ser Met
            340                 345                 350

Leu Met Trp Asn Leu Tyr Tyr Met Phe Val Val Glu Pro Glu Arg Met
        355                 360                 365

Leu Thr Ala Thr Glu Ser Arg Leu Asp Tyr Pro Asp His Ala Arg Ser
    370                 375                 380

Ala Ser Asp Tyr Arg Pro Arg Pro Trp Gly
385                 390


<210> SEQ ID NO 71
<211> LENGTH: 1282
<212> TYPE: DNA
<213> ORGANISM: Homo sapiens

<400> SEQUENCE: 71

ggaagtctgt caactgggag ggggagaggg gggtgatggg ccaggaatgg ggtccccggg      60

catggtgctg ggcctcctgg tgcagatctg ggccctgcaa gaagcctcaa gcctgagcgt     120

gcagcagggg cccaacttgc tgcaggtgag gcagggcagt caggcgaccc tggtctgcca     180

ggtggaccag gccacagcct gggaacggct ccgtgttaag tggacaaagg atggggccat     240

cctgtgtcaa ccgtacatca ccaacggcag cctcagcctg gggtctgcg ggccccaggg      300

acggctctcc tggcaggcac ccagccatct caccctgcag ctggaccctg tgagcctcaa     360

ccacagcggg gcgtacgtgt gctgggcggc cgtagagatt cctgagttgg aggaggctga     420

gggcaacata acaaggctct ttgtggaccc agatgacccc acacagaaca gaaaccggat     480

cgcaagcttc ccaggattcc tcttcgtgct gctgggggtg ggaagcatgg gtgtggctgc     540

gatcgtgtgg ggtgcctggt tctggggccg ccgcagctgc cagcaaaggg actcaggtaa     600

cagcccagga aatgcattct acagcaacgt cctataccgg ccccgggggg ccccaaagaa     660

gagtgaggac tgctctggag aggggaagga ccagaggggc cagagcattt attcaacctc     720

cttcccgcaa ccggcccccc gccagccgca cctggcgtca agaccctgcc ccagcccgag     780

accctgcccc agccccaggc ccggccaccc cgtctctatg gtcagggtct ctcctagacc     840

aagccccacc cagcagccga ggccaaaagg gttccccaaa gtgggagagg agtgagagat     900

cccaggagac ctcaacagga ccccacccat aggtacacac aaaaaagggg ggatcgaggc     960

cagacacggt ggctcacgcc tgtaatccca gcagtttggg aagccgaggc gggtggaaca    1020

cttgaggtca ggggtttgag accagcctgg cttgaacctg ggaggcggag gttgcagtga    1080

gccgagattg cgccactgca ctccagcctg ggcgacagag tgagactccg tctcaaaaaa    1140

aacaaaaagc aggaggattg ggagcctgtc agccccatcc tgagaccccg tcctcatttc    1200

tgtaatgatg gatctcgctc ccactttccc ccaagaacct aataaaggct tgtgaagaaa    1260
```

```
aagcaaaaaa aaaaaaaaaa aa                                              1282


<210> SEQ ID NO 72
<211> LENGTH: 282
<212> TYPE: PRT
<213> ORGANISM: Homo sapiens

<400> SEQUENCE: 72

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
            180                 185                 190

Ser Asn Val Leu Tyr Arg Pro Arg Gly Ala Pro Lys Lys Ser Glu Asp
        195                 200                 205

Cys Ser Gly Glu Gly Lys Asp Gln Arg Gly Gln Ser Ile Tyr Ser Thr
    210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
            260                 265                 270

Pro Lys Gly Phe Pro Lys Val Gly Glu Glu
        275                 280


<210> SEQ ID NO 73
<211> LENGTH: 1843
<212> TYPE: DNA
<213> ORGANISM: Homo sapiens

<400> SEQUENCE: 73

gggcacgagg gcagagccag ttcctagcgc agagccgcgc ccgccatgag ggagatcgtg      60

cacatccagg cgggccagtg cgggaaccag atcggcacca agttttggga agtgatcagc     120

gatgagcacg gcatcgaccc ggccggaggc tacgtgggag actcggcgct gcagctggag     180
```

```
agaatcaacg tctactacaa tgagtcatcg tctcagaaat atgtgcccag ggccgccctg    240

gtggacttag agccaggcac catggacagc gtgcggtctg ggccttttgg gcagcttttc    300

cggcctgaca acttcatctt tggccagacg ggtgcaggga acaactgggc gaaagggcac    360

tacacggagg gcgcggagct ggtggacgca gtgctggacg tggtgcggaa ggagtgcgag    420

cactgcgact gcctgcaggg cttccagctc acgcactcgc tgggcggcgg cacgggctca    480

ggcatgggca cgctgctcat cagcaagatc cgtgaggagt tcccggaccg catcatgaac    540

accttcagcg tcatgccctc gcccaaggtg tcggacacgg tggtggagcc ctacaatgcc    600

acactgtcgg tgcaccagct ggtggagaat acagacgaga cctactgcat cgacaacgag    660

gcgctctatg acatctgctt ccgcactctg aagctgacaa cgcccaccta cggggacctc    720

aaccacctgg tgtccgccac catgagtggg gtcaccacct cgctgcgctt cccgggccag    780

ctcaatgctg acctgcgcaa gctggcggtg aacatggtgc ccttcccgcg cctgcacttc    840

ttcatgcctg gcttcgcgcc gctcaccagc cgcggcagcc agcagtaccg ggccctgacc    900

gtgcccgagc tcacccagca gatgttcgac gccaggaaca tgatggccgc ctgcgatccg    960

cgccatggcc gctacctgac cgtggccacc gtgttccgcg ggcccatgtc catgaaggag   1020

gtggacgagc agatgctggc catccagagt aagaacagca gctacttcgt ggagtggatt   1080

cccaacaacg tgaaggtggc cgtgtgcgac atcccgcccc gcggcctgaa gatggcctcc   1140

accttcatcg gcaacagcac ggccatccag gagctgttca agcgcatctc cgagcagttc   1200

tcagccatgt tccggcgcaa ggccttcctg cactggttca cgggtgaggg catggatgaa   1260

atggagttca ccgaggcgga gagcaacatg aacgacctgg tatccgagta ccagcagtac   1320

caggatgcca ccgccaatga cggggaggaa gcttttgagg atgaggaaga ggagatcgat   1380

ggatagtcgg aatagagccg ccccaactca gatcctacaa cacgcaagtt ccttcttgaa   1440

ccctggtgcc tcctacccta tggccctgaa tggtgcactg gtttaattgt gttggtgtcg   1500

gcccctcaca aatgcagcca agtcatgtaa ttagtcatct ggaacaaaga ctaaaaacag   1560

cagagaattg cgggttctac ccagtcagaa gatcacacca tggagacttt ctactagagg   1620

acttgaaaga gaactgaggg gccacaaaat aaacttcacc ttccattaag tgttcaagca   1680

tgtctgcaaa ttaggaggga gttagaaaca gtctttttca tcctttgtga tgaagcctga   1740

aattgtgccg tgttgcctta tatgaatatg cagtatggga ctttgaaata atgattcata   1800

ataaaatact aaacgtgtgt cttcaaaaaa aaaaaaaaaa aaa                     1843
```

```
<210> SEQ ID NO 74
<211> LENGTH: 446
<212> TYPE: PRT
<213> ORGANISM: Homo sapiens

<400> SEQUENCE: 74

Met Arg Glu Ile Val His Ile Gln Ala Gly Gln Cys Gly Asn Gln Ile
1               5                   10                  15

Gly Thr Lys Phe Trp Glu Val Ile Ser Asp Glu His Gly Ile Asp Pro
            20                  25                  30

Ala Gly Gly Tyr Val Gly Asp Ser Ala Leu Gln Leu Glu Arg Ile Asn
        35                  40                  45

Val Tyr Tyr Asn Glu Ser Ser Ser Gln Lys Tyr Val Pro Arg Ala Ala
    50                  55                  60

Leu Val Asp Leu Glu Pro Gly Thr Met Asp Ser Val Arg Ser Gly Pro
65                  70                  75                  80
```

```
Phe Gly Gln Leu Phe Arg Pro Asp Asn Phe Ile Phe Gly Gln Thr Gly
                85                  90                  95

Ala Gly Asn Asn Trp Ala Lys Gly His Tyr Thr Glu Gly Ala Glu Leu
            100                 105                 110

Val Asp Ala Val Leu Asp Val Val Arg Lys Glu Cys Glu His Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Phe Pro
145                 150                 155                 160

Asp Arg Ile Met Asn Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ala Arg Asn Met Met Ala Ala Cys Asp
    290                 295                 300

Pro Arg His Gly Arg Tyr Leu Thr Val Ala Thr Val Phe Arg Gly Pro
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ala Ser Thr Phe Ile
        355                 360                 365

Gly Asn Ser Thr Ala Ile Gln Glu Leu Phe Lys Arg Ile Ser Glu Gln
    370                 375                 380

Phe Ser Ala Met Phe Arg Arg Lys Ala Phe Leu His Trp Phe Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Asn Asp
            420                 425                 430

Gly Glu Glu Ala Phe Glu Asp Glu Glu Glu Glu Ile Asp Gly
        435                 440                 445


<210> SEQ ID NO 75
<211> LENGTH: 605
<212> TYPE: DNA
<213> ORGANISM: Homo sapiens

<400> SEQUENCE: 75

agacttcctc cttcacttgc ctggacgctg cgccacatcc caccggccct tacactgtgg      60
```

```
tgtccagcag catccggctt catgggggga cttgaaccct gcagcaggct cctgctcctg    120

cctctcctgc tggctgtaag tggtctccgt cctgtccagg cccaggccca gagcgattgc    180

agttgctcta cggtgagccc gggcgtgctg gcagggatcg tgatgggaga cctggtgctg    240

acagtgctca ttgccctggc cgtgtacttc ctgggccggc tggtccctcg gggcgagggg    300

gctgcggagg cgacccggaa acagcgtatc actgagaccg agtcgcctta tcaggagctc    360

cagggtcaga ggtcggatgt ctacagcgac ctcaacacac agaggccgta ttacaaatga    420

gcccgaatca tgacagtcag caacatgata cctggatcca gccattcctg aagcccaccc    480

tgcacctcat tccaactcct accgcgatac agacccacag agtgccatcc ctgagagacc    540

agaccgctcc ccaatactct cctaaaataa acatgaagca caaaaacaaa aaaaaaaaaa    600

aaaaa                                                                605
```

<210> SEQ ID NO 76
<211> LENGTH: 112
<212> TYPE: PRT
<213> ORGANISM: Homo sapiens

<400> SEQUENCE: 76

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln Arg Pro Tyr Tyr Lys
            100                 105                 110
```

<210> SEQ ID NO 77
<211> LENGTH: 3277
<212> TYPE: DNA
<213> ORGANISM: Homo sapiens

<400> SEQUENCE: 77

```
gcgtgcacgc tgacgccgcg cagtctcgtc ccctgccgcc gccgtcgccg ctgctgtcgc     60

cgccgccgcc gccattggag tcgacgcctc ctcagtgcgt ccgcgtcccg ggctcaccgc    120

cgctgccgcc tcgccagggg cccgcgcgcc cagcagccgc cgccgccgcc cggccggcgc    180

ccggggaatt ggcggcgggg cccggggccg cgcgagctag ggtgacaggc ccggcctcta    240

ggggaggccc gagccggcgg gcgccccggc cccgcgtcta gttgttcatg aagcatgtcg    300

gccaccagcg tggacaccca gagaacaaaa ggacaagata ataaagtaca aaatggttcg    360

ttacatcaga aggatacagt tcatgacaat gactttgagc cctaccttac tggacagtca    420

aatcagagta acagttaccc ctcaatgagc gacccctacc tgtccagcta ttacccgccg    480

tccattggat ttccttactc cctcaatgag gctccgtggt ctactgcagg ggaccctccg    540

attccatacc tcaccaccta cggacagctc agtaacggag accatcattt tatgcacgat    600

gctgtttttg ggcagcctgg gggcctgggg aacaacatct atcagcacag gttcaatttt    660
```

```
ttccctgaaa accctgcgtt ctcagcatgg gggacaagtg ggtctcaagg tcagcagacc    720
cagagctccg cgtatgggag cagctacacc tacccccga gctccctggg tggcacggtg    780
gttgatgggc agccaggctt tcacagcgac accctcagca aggcccccgg gatgaacagc    840
ctggagcagg gcatggttgg cctgaagatt ggggacgtca gctcctccgc cgtcaagacg    900
gtgggctctg tcgtcagcag cgtggcactg actggtgtcc tttctggcaa cggtgggaca    960
aatgtgaaca tgccagtttc aaagccgacc tcgtgggctg ccattgccag caagcctgca   1020
aaaccacagc ctaaaatgaa aacaaagagc gggcctgtca tgggggggtgg gctgcccccct   1080
ccacccataa agcataacat ggacattggc acctgggata acaaggggcc tgtgccgaag   1140
gccccagtcc cccagcaggc accctctcca caggctgccc cacagcccca gcaggtggct   1200
cagcctctcc cagcacagcc cccagctttg gctcaaccgc agtatcagag ccctcagcag   1260
ccaccccaga cccgctgggt tgccccacgc aacagaaacg cggcgtttgg gcagagcgga   1320
ggggctggca gcgatagcaa ctctcctgga aacgtccagc ctaattctgc ccccagcgtc   1380
gaatcccacc ccgtccttga aaaactgaag gctgctcaca gctacaaccc gaaagagttt   1440
gagtggaatc tgaaaagcgg gcgtgtgttc atcatcaaga gctactctga ggacgacatc   1500
caccgctcca ttaagtactc catctggtgt agcacagagc acggcaacaa gcgcctggac   1560
agcgccttcc gctgcatgag cagcaagggg cccgtctacc tgctcttcag cgtcaatggg   1620
agtgggcatt tttgtggggt ggccgagatg aagtcccccg tggactacgg caccagtgcc   1680
ggggtctggt ctcaggacaa gtggaagggg aagtttgatg tccagtggat tttgttaag   1740
gatgtaccca ataaccagct ccggcacatc aggctggaga ataacgacaa caaaccggtc   1800
acaaactccc gggacaccca ggaggtgccc ttagaaaaag ccaagcaagt gctgaaaatt   1860
atcagttcct acaagcacac aacctccatc ttcgacgact ttgctcacta cgagaagcgc   1920
caggaggagg aggaggtggt gcgcaaggaa cggcagagtc gaaacaaaca atgagggcga   1980
accagtttct tacatgttct aacgtttgac tttgaaaaca gtttaaaaca cgtgtgcttg   2040
gtcagctcca gtgtgtcgtc ccgtgcgggg gttgagtgtt gcatctttgc ctttcttgtc   2100
gttgattttt gcccagatgg atctgcattt atttgtactt tttctatgta ttataatcct   2160
gtagaagtca ctaataaagg agtatttttt ttgtcagctt atcaatcaga ctgatctaat   2220
gtgaaatgta agtatcctta aaaacaaagc atctattttg gcagaaattg tgttcttaaa   2280
ttcagtcatt tgatattctg tgagacttca tatttctcat ccctttattg ctttttagca   2340
aacataagaa accatgagtc attttgtcat ttagagtatt ctgataaaat ctcttgaaaa   2400
tactgaaatc aaaaggttaa tgattttttg ttcattctga tttgtcattt tattatctgt   2460
tatcggtcta aagtgctaat ttacccattt gatttttctg ctagacagat aacttttaat   2520
ttttcaaatt tggcagacac ttttttttt tttttgaaaa tctttccttc cagatctgtt   2580
gcccactgaa cagccacccg tccctcactg tcctggtgtc cgattgggct ggatggtgtt   2640
ggggcatgat gtgtggagga actggaaggt gctttaggtc tggttcaggg tcgggcattc   2700
tttgttgttt gcacatcttt ttaaatttta caccttttct taagaattct aatgccgtct   2760
taagttttta taccaataat gctgagcttt aagtgtagga tctggtagta cagacagtgt   2820
gatggatgat gctgctggtt gtaaatttca tcgtgtgtgt ctaatttttt ttcctgttga   2880
atgggtaaaa acaaaacaaa actttttta gaagatgaat ttgctgtcat gttttgtgga   2940
atgagggacc gttgagctca ctaccacctg gagtttgagt tgaagcatga aaatggtgcc   3000
catgcctgac gctccagcgc ctggatctgc acgtgccctt gtagaggatc cttaccgtcc   3060
```

```
tagagagcag acgctttctg aaaactactt gctccaaaag accctctgag ttaacgtttc   3120

agctgtatca ttagacttgt atttagagcg tgtcacttcc tctgaactgt tactgcctga   3180

atggagtcct ggacgacatt gggtttttcc tctaggagaa tacaagcctt aataaacaat   3240

actatttagc aaaaaaaaaa aaaaaaaaaa aaaaaaa                            3277


<210> SEQ ID NO 78
<211> LENGTH: 559
<212> TYPE: PRT
<213> ORGANISM: Homo sapiens

<400> SEQUENCE: 78

Met Ser Ala Thr Ser Val Asp Thr Gln Arg Thr Lys Gly Gln Asp Asn
1               5                   10                  15

Lys Val Gln Asn Gly Ser Leu His Gln Lys Asp Thr Val His Asp Asn
            20                  25                  30

Asp Phe Glu Pro Tyr Leu Thr Gly Gln Ser Asn Gln Ser Asn Ser Tyr
        35                  40                  45

Pro Ser Met Ser Asp Pro Tyr Leu Ser Ser Tyr Tyr Pro Pro Ser Ile
    50                  55                  60

Gly Phe Pro Tyr Ser Leu Asn Glu Ala Pro Trp Ser Thr Ala Gly Asp
65                  70                  75                  80

Pro Pro Ile Pro Tyr Leu Thr Thr Tyr Gly Gln Leu Ser Asn Gly Asp
                85                  90                  95

His His Phe Met His Asp Ala Val Phe Gly Gln Pro Gly Gly Leu Gly
            100                 105                 110

Asn Asn Ile Tyr Gln His Arg Phe Asn Phe Phe Pro Glu Asn Pro Ala
        115                 120                 125

Phe Ser Ala Trp Gly Thr Ser Gly Ser Gln Gly Gln Gln Thr Gln Ser
    130                 135                 140

Ser Ala Tyr Gly Ser Ser Tyr Thr Tyr Pro Pro Ser Ser Leu Gly Gly
145                 150                 155                 160

Thr Val Val Asp Gly Gln Pro Gly Phe His Ser Asp Thr Leu Ser Lys
                165                 170                 175

Ala Pro Gly Met Asn Ser Leu Glu Gln Gly Met Val Gly Leu Lys Ile
            180                 185                 190

Gly Asp Val Ser Ser Ser Ala Val Lys Thr Val Gly Ser Val Val Ser
        195                 200                 205

Ser Val Ala Leu Thr Gly Val Leu Ser Gly Asn Gly Gly Thr Asn Val
    210                 215                 220

Asn Met Pro Val Ser Lys Pro Thr Ser Trp Ala Ala Ile Ala Ser Lys
225                 230                 235                 240

Pro Ala Lys Pro Gln Pro Lys Met Lys Thr Lys Ser Gly Pro Val Met
                245                 250                 255

Gly Gly Gly Leu Pro Pro Pro Pro Ile Lys His Asn Met Asp Ile Gly
            260                 265                 270

Thr Trp Asp Asn Lys Gly Pro Val Pro Lys Ala Pro Val Pro Gln Gln
        275                 280                 285

Ala Pro Ser Pro Gln Ala Ala Pro Gln Pro Gln Gln Val Ala Gln Pro
    290                 295                 300

Leu Pro Ala Gln Pro Pro Ala Leu Ala Gln Pro Gln Tyr Gln Ser Pro
305                 310                 315                 320

Gln Gln Pro Pro Gln Thr Arg Trp Val Ala Pro Arg Asn Arg Asn Ala
                325                 330                 335
```

```
Ala Phe Gly Gln Ser Gly Gly Ala Gly Ser Asp Ser Asn Ser Pro Gly
            340                 345                 350

Asn Val Gln Pro Asn Ser Ala Pro Ser Val Glu Ser His Pro Val Leu
        355                 360                 365

Glu Lys Leu Lys Ala Ala His Ser Tyr Asn Pro Lys Glu Phe Glu Trp
    370                 375                 380

Asn Leu Lys Ser Gly Arg Val Phe Ile Ile Lys Ser Tyr Ser Glu Asp
385                 390                 395                 400

Asp Ile His Arg Ser Ile Lys Tyr Ser Ile Trp Cys Ser Thr Glu His
                405                 410                 415

Gly Asn Lys Arg Leu Asp Ser Ala Phe Arg Cys Met Ser Ser Lys Gly
            420                 425                 430

Pro Val Tyr Leu Leu Phe Ser Val Asn Gly Ser Gly His Phe Cys Gly
        435                 440                 445

Val Ala Glu Met Lys Ser Pro Val Asp Tyr Gly Thr Ser Ala Gly Val
    450                 455                 460

Trp Ser Gln Asp Lys Trp Lys Gly Lys Phe Asp Val Gln Trp Ile Phe
465                 470                 475                 480

Val Lys Asp Val Pro Asn Asn Gln Leu Arg His Ile Arg Leu Glu Asn
                485                 490                 495

Asn Asp Asn Lys Pro Val Thr Asn Ser Arg Asp Thr Gln Glu Val Pro
            500                 505                 510

Leu Glu Lys Ala Lys Gln Val Leu Lys Ile Ile Ser Ser Tyr Lys His
        515                 520                 525

Thr Thr Ser Ile Phe Asp Asp Phe Ala His Tyr Glu Lys Arg Gln Glu
    530                 535                 540

Glu Glu Glu Val Val Arg Lys Glu Arg Gln Ser Arg Asn Lys Gln
545                 550                 555
```

```
<210> SEQ ID NO 79
<211> LENGTH: 4607
<212> TYPE: DNA
<213> ORGANISM: Homo sapiens

<400> SEQUENCE: 79

gcggccgcaa gcacgggggc gaatccccgc tgggtcgagg gcctgaacgg gagccaatcg      60

agcagccgag gctactgcca atcacgcggc tccctccaat cccacccgtg ccatttccaa     120

aatctcggtc ccactgtgca gctcaaatgt ggtgttcact ctgccaatcg ctggaggata     180

gagtgggaac aggaataagc agagttaaga ggccaggaca aaagaagtta aagagcgccc     240

aatacataca tgtttttgaa ggcgggcaga gggaataaag tccccccagt gagggtctat     300

gggcctgatt gtgtagttct gatggagccc cctttgagca agaggaaccc gccagcgctg     360

agattagcgg atttggcaac ggctcaggtc cagccgcttc agaatatgac aggcttcccg     420

gcgctggccg gcccgcccgc ccactcccaa ctccgggccg ccgtcgcgca cctccgcctg     480

cgggacctgg gcgctgaccc cggcgtggcc accactccgc tcggacccga gcacatggcc     540

caggcgagca cgctgggcct cagccctccc tcccaggcgt tcccggcaca cccggaggct     600

ccggcagccg ccgcccgtgc tgcagccttg gtcgcgcacc ccggcgcggg cagctacccc     660

tgcggcgggg gcagcagtgg cgcgcagccc tccgcgcccc cgcccccagc ccctcctctt     720

cctcccaccc cttcaccccc tccccctccc ccgcctcctc ctcctcctgc cctctcgggc     780

tacaccacca ccaacagtgg cggcggcggc agcagcggca aaggccacag cagggacttc     840
```

```
gtcctccgga gggacctttc cgccacggcc cccgcggcgg ccatgcacgg ggccccgctc    900
ggaggggagc agcggtccgg caccggctcc ccccagcacc cggccccgcc tccccactcg    960
gccggcatgt tcatctccgc cagcggcacc tacgcgggcc cggacggcag cggcggcccg   1020
gcgctcttcc ccgcgctgca cgacacgccg ggggccccag gcggccaccc gcacccgctc   1080
aacggccaga tgcgcctggg gctggcggcg gcagcggcag ccgcggcggc tgagctgtac   1140
ggccgcgccg aaccgccctt cgcgccgcgc tctggggacg cgcactacgg ggcggttgcg   1200
gccgcagcgg cggccgccct gcacggctac ggagccgtga acttaaacct gaacctggcg   1260
gctgcggcgg ccgcagcagc ggccgggccc gggccccacc tgcagcacca cgcgccgccc   1320
ccggcgccgc cgccgccgcc ggcgcccgcg cagcacccgc accagcacca cccccacctc   1380
ccaggggcgg ctggggcctt cctgcgctac atgcggcagc caatcaagca ggagctcatc   1440
tgcaagtgga tcgaccccga cgagctggcc gggctgccgc cgccgccgcc gccgccgccg   1500
ccgccgccgc caccgccccc ggccggcggc gccaagccct gctccaaaac tttcggcacc   1560
atgcacgagc tggtgaatca cgtcacggtg gagcacgtgg gaggccccga gcagagcagc   1620
cacgtctgct tctgggagga ctgtccgcgc gagggcaagc ccttcaaggc caaatacaag   1680
ctcatcaacc acatccgcgt gcacaccggc gagaagccct ttccctgccc tttccccggc   1740
tgcggcaagg tcttcgcgcg ctccgagaac ctcaagatcc acaagcgtac tcatacaggg   1800
gaaaagcctt tcaaatgtga atttgatggc tgtgacagga agtttgccaa tagcagtgat   1860
cggaagaaac attcccatgt ccacaccagt gacaagccct actactgcaa gattcgaggc   1920
tgtgacaaat cctacactca cccaagctcc ctgaggaagc acatgaagat tcactgcaag   1980
tccccgccac cttctccagg acccccttggt tactcatcag tggggactcc agtgggcgcc   2040
cccttgtccc ctgtgctgga cccagccagg agtcactcca gcactctgtc cctcaggtg   2100
accaacctca atgagtggta cgtttgccag gccagtgggg cccccagcca cctccacacc   2160
ccttccagca acggaaccac ctctgagact gaagatgagg aaatttacgg gaaccctgaa   2220
gttgtgcgga cgatacatta gaatttatta ttaataataa taagtgaaat aataagtggg   2280
agtccttgga ccacatccta acctgagaca atgccgagcc tgagacaaac ccgtgactca   2340
gacttgccac cgggtctaat tagccctatt tattcagtat gaaaccctat ggtgtttgta   2400
catttaatta atttaattaa gatatttggg cttttttttt tttttttctt aaaaaaacaaa   2460
caaaaaacaa ccaagctgga cttgtacatt gcaggaggat ggggctgggg gcaaattgta   2520
ccaaggaaaa tgaatggaga gattagttaa tggcgataca cactgccgat gcaatatata   2580
tatatatata tatatacata tatatatata ttattttttt taaaaggggg agaaaaagag   2640
cattaagtca gaacttaaca cagcaccaag gccctctgca tttcccagag tgcctctcaa   2700
atgcctttga caccatacca tgggctgctt ttgagcctcc ttgttggacc ctaattctgc   2760
caaggcctct tgattgtaaa ccacacacct gctgcattgc caacagatcc tgttccgtac   2820
ctgtgtccaa aaacatttgt aaaaaccctt tgagtttaat atttgtaatt tttaatttcc   2880
actcttttat tactgatctt agcttaatac aatattttta tacaggatta tttcttcagt   2940
atcctactgt gtgattttaa aaaaagatgc agcaacctta atatatctcc atatcttgtg   3000
ctactgtgat tgttcaagca aaagtggaga gaagaaaagc tgctgcaaaa gacaactgtg   3060
aaactgtgat attttataaa atagaagaaa ttcaagtgct ttctttttcc tatatgtttt   3120
ttttttttta tctgaattct cagatactgc ctcctaactg tgtccaaact tcttgtgtaa   3180
taaagagatt ctgttttcga tcctaagttc tttgggatgc caacattcac agtcaagtct   3240
```

```
tgaggaggtg tgatgatggc atcatgccta ttttttttgga aagctgttgt ttttaaaaca   3300

ggccaacacc tcttttatac tgttgtatca gccttttaaa aagtctattt ttcaatgcct   3360

gaaactgcat tttaatgcat tttcttccac ctgagcactg agcacaccaa actggaatcc   3420

atttgaaaat gacagtgtgt gaagtgtatg atttacatta aaagagggga gggagttgcc   3480

atacatatta aaaattttta aaaggtttat agttaccacc aaacactgat gaatgtgtga   3540

cctttgccag agctgtcaag ctaggataaa aaaggtcaag gacctaggac aataactctt   3600

agtcgattta ttttcggttg gtacaacaca tctcctgtgc aaaatgtagt ccatcagaaa   3660

catcctacag atacactaaa gagcactaat ttatccttag agaccccgaa gacaccccct   3720

ccccagggtt tgtagaaatt tgttttgtgt gctgtgagtg gttgatgtag tcttgtcatt   3780

gttaataact tgtatgtgaa cactattatt tgtacagttg aattaattta ttttcagaca   3840

tcatcctttt tttttttctt tcctggaaga gttcaaagca caccaaagaa ttatattata   3900

cattttggtg aaagattgtc atttatgatc catggtttat ttaaaaaaaa aaggaaagaa   3960

aatggaaaaa tatattttta agcttacttg aatgaacaac gtaatgtgaa aaccaagact   4020

cttcctgcat gtctttttttg cattgtgttg ataagattat atatagttta tagatatatt   4080

atattactag tacagtgcat ggtgctgtca cttggaaagc ctttcaatgt tgtcttcaga   4140

ttgttgtgat gaatatgaaa catgcagacc ctcctttata aagaaaaaga ccttaaaact   4200

tgaatatgag ataattttac attttaaaag tttatttgat tttcatatta ttcactttca   4260

aagccctttc aaatagaaaa ggtatgaact tttgggggga taatttatgt atcgtaaact   4320

tattagaaca aaatattcct gatgtataat gagttgtttt atttatacaa ctttttcaat   4380

ggtagtttgc actattcttt attatgctac aggtttattt attatgaaac aaaggaatat   4440

gtattttatg tattttacca tgcataggtt aactctttgc cacagattta ttggttcttg   4500

atacacctaa aataaaaaaa aatgtgtacc tccaatagag agcaagcaag aatgattatg   4560

aagtaacaaa tttaataaag gtattcttgt tattattaaa aaaaaaa                 4607
```

```
<210> SEQ ID NO 80
<211> LENGTH: 663
<212> TYPE: PRT
<213> ORGANISM: Homo sapiens

<400> SEQUENCE: 80

Met Phe Leu Lys Ala Gly Arg Gly Asn Lys Val Pro Pro Val Arg Val
1               5                   10                  15

Tyr Gly Pro Asp Cys Val Val Leu Met Glu Pro Pro Leu Ser Lys Arg
            20                  25                  30

Asn Pro Pro Ala Leu Arg Leu Ala Asp Leu Ala Thr Ala Gln Val Gln
        35                  40                  45

Pro Leu Gln Asn Met Thr Gly Phe Pro Ala Leu Ala Gly Pro Pro Ala
    50                  55                  60

His Ser Gln Leu Arg Ala Ala Val Ala His Leu Arg Leu Arg Asp Leu
65                  70                  75                  80

Gly Ala Asp Pro Gly Val Ala Thr Thr Pro Leu Gly Pro Glu His Met
                85                  90                  95

Ala Gln Ala Ser Thr Leu Gly Leu Ser Pro Pro Ser Gln Ala Phe Pro
            100                 105                 110

Ala His Pro Glu Ala Pro Ala Ala Ala Ala Arg Ala Ala Ala Leu Val
        115                 120                 125
```

```
Ala His Pro Gly Ala Gly Ser Tyr Pro Cys Gly Gly Gly Ser Ser Gly
    130                 135                 140

Ala Gln Pro Ser Ala Pro Pro Pro Pro Ala Pro Pro Leu Pro Pro Thr
145                 150                 155                 160

Pro Ser Pro Pro Pro Pro Pro Pro Pro Pro Pro Pro Pro Ala Leu Ser
                165                 170                 175

Gly Tyr Thr Thr Thr Asn Ser Gly Gly Gly Gly Ser Ser Gly Lys Gly
            180                 185                 190

His Ser Arg Asp Phe Val Leu Arg Arg Asp Leu Ser Ala Thr Ala Pro
        195                 200                 205

Ala Ala Ala Met His Gly Ala Pro Leu Gly Gly Glu Gln Arg Ser Gly
    210                 215                 220

Thr Gly Ser Pro Gln His Pro Ala Pro Pro Pro His Ser Ala Gly Met
225                 230                 235                 240

Phe Ile Ser Ala Ser Gly Thr Tyr Ala Gly Pro Asp Gly Ser Gly Gly
                245                 250                 255

Pro Ala Leu Phe Pro Ala Leu His Asp Thr Pro Gly Ala Pro Gly Gly
            260                 265                 270

His Pro His Pro Leu Asn Gly Gln Met Arg Leu Gly Leu Ala Ala Ala
        275                 280                 285

Ala Ala Ala Ala Ala Ala Glu Leu Tyr Gly Arg Ala Glu Pro Pro Phe
    290                 295                 300

Ala Pro Arg Ser Gly Asp Ala His Tyr Gly Ala Val Ala Ala Ala Ala
305                 310                 315                 320

Ala Ala Ala Leu His Gly Tyr Gly Ala Val Asn Leu Asn Leu Asn Leu
                325                 330                 335

Ala Ala Ala Ala Ala Ala Ala Ala Ala Gly Pro Gly Pro His Leu Gln
            340                 345                 350

His His Ala Pro Pro Pro Ala Pro Pro Pro Pro Pro Ala Pro Ala Gln
        355                 360                 365

His Pro His Gln His His Pro His Leu Pro Gly Ala Ala Gly Ala Phe
    370                 375                 380

Leu Arg Tyr Met Arg Gln Pro Ile Lys Gln Glu Leu Ile Cys Lys Trp
385                 390                 395                 400

Ile Asp Pro Asp Glu Leu Ala Gly Leu Pro Pro Pro Pro Pro Pro Pro
                405                 410                 415

Pro Pro Pro Pro Pro Pro Pro Pro Pro Ala Gly Gly Ala Lys Pro Cys Ser
            420                 425                 430

Lys Thr Phe Gly Thr Met His Glu Leu Val Asn His Val Thr Val Glu
        435                 440                 445

His Val Gly Gly Pro Glu Gln Ser Ser His Val Cys Phe Trp Glu Asp
    450                 455                 460

Cys Pro Arg Glu Gly Lys Pro Phe Lys Ala Lys Tyr Lys Leu Ile Asn
465                 470                 475                 480

His Ile Arg Val His Thr Gly Glu Lys Pro Phe Pro Cys Pro Phe Pro
                485                 490                 495

Gly Cys Gly Lys Val Phe Ala Arg Ser Glu Asn Leu Lys Ile His Lys
            500                 505                 510

Arg Thr His Thr Gly Glu Lys Pro Phe Lys Cys Glu Phe Asp Gly Cys
        515                 520                 525

Asp Arg Lys Phe Ala Asn Ser Ser Asp Arg Lys Lys His Ser His Val
    530                 535                 540
```

-continued

```
His Thr Ser Asp Lys Pro Tyr Tyr Cys Lys Ile Arg Gly Cys Asp Lys
545                 550                 555                 560

Ser Tyr Thr His Pro Ser Ser Leu Arg Lys His Met Lys Ile His Cys
                565                 570                 575

Lys Ser Pro Pro Pro Ser Pro Gly Pro Leu Gly Tyr Ser Ser Val Gly
            580                 585                 590

Thr Pro Val Gly Ala Pro Leu Ser Pro Val Leu Asp Pro Ala Arg Ser
        595                 600                 605

His Ser Ser Thr Leu Ser Pro Gln Val Thr Asn Leu Asn Glu Trp Tyr
    610                 615                 620

Val Cys Gln Ala Ser Gly Ala Pro Ser His Leu His Thr Pro Ser Ser
625                 630                 635                 640

Asn Gly Thr Thr Ser Glu Thr Glu Asp Glu Glu Ile Tyr Gly Asn Pro
                645                 650                 655

Glu Val Val Arg Thr Ile His
            660
```